(12) United States Patent
Fidanze et al.

(10) Patent No.: US 10,035,800 B2
(45) Date of Patent: Jul. 31, 2018

(54) SUBSTITUTED 1,4,10-TRIAZADIBENZO[CD,F]AZULENES, SUBSTITUTED 1,4,5,10-TETRAAZADIBENZO[CD,F]AZULENES AND SUBSTITUTED 1,4,5,7,10-PENTAAZADIBENZO[CD,F]AZULENES AS BROMODOMAIN INHIBITORS

(71) Applicant: AbbVie Inc., North Chicago, IL (US)

(72) Inventors: Steven D. Fidanze, Grayslake, IL (US); Dauchun Liu, Vernon Hills, IL (US); Robert A. Mantei, Franklin, WI (US); Keith F. McDaniel, Wauconda, IL (US); John Pratt, Kenosha, WI (US); George S. Sheppard, Wilmette, IL (US); Le Wang, Vernon Hills, IL (US); Andrew Bogdan, Evanston, IL (US); James H. Holms, Gurnee, IL (US); Justin D. Dietrich, Round Lake, IL (US); Jasmina Marjanovic, Chicago, IL (US); Lisa A. Hasvold, Grayslake, IL (US); Yujia Dai, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/774,866

(22) PCT Filed: Mar. 12, 2014

(86) PCT No.: PCT/CN2014/000258
§ 371 (c)(1),
(2) Date: Sep. 11, 2015

(87) PCT Pub. No.: WO2014/139324
PCT Pub. Date: Sep. 18, 2014

(65) Prior Publication Data
US 2016/0039821 A1    Feb. 11, 2016

Related U.S. Application Data

(60) Provisional application No. 61/928,779, filed on Jan. 17, 2014, provisional application No. 61/777,797, filed on Mar. 12, 2013.

(51) Int. Cl.
*A61K 31/437* (2006.01)
*C07D 471/22* (2006.01)
*C07D 471/16* (2006.01)

(52) U.S. Cl.
CPC ......... *C07D 471/22* (2013.01); *C07D 471/16* (2013.01)

(58) Field of Classification Search
CPC ................ A61K 31/437; C07D 471/22
USPC .......................................... 514/287; 546/64
See application file for complete search history.

(56) References Cited

FOREIGN PATENT DOCUMENTS

| WO | WO-2006129623 A1 | 12/2006 |
|---|---|---|
| WO | WO-2011161031 A1 | 12/2011 |
| WO | WO-2012075383 A2 | 6/2012 |
| WO | WO-2012151512 A2 | 11/2012 |
| WO | WO 14/139324 * | 9/2014 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Banerjee C., et al., "BET Bromodomain Inhibition as a Novel Strategy for Reactivation of HIV-1," Journal of Leukocyte Biology, 2012, vol. 92 (6), pp. 1147-1154.
Berge S.M., et al., "Pharmaceutical Salts," Journal of Pharmaceutical Sciences, 1977, vol. 66 (1), pp. 1-19.
Dawson M.A., et al., "Inhibition of BET Recruitment to Chromatin as an Effective Treatment for MLL-fusion Leukaemia," Nature, 2011, vol. 478 (7370), pp. 529-533.
Delmore J.E., et al., "BET Bromodomain Inhibition as a Therapeutic Strategy to Target c-Myc," Cell, 2011, vol. 146(6), pp. 904-917.
Denis G.V., "Bromodomain Coactivators in Cancer, Obesity, type 2 Diabetes, and Inflammation," Discovery Medicine, 2010, vol. 10 (55), pp. 489-499.
Greene T.W., et al., Protective Groups in Organic Synthesis, 3rd Edition, John Wiley and Sons, Inc., 1999, Preface, Table of Contents, Abbreviations.
Huang B., et al., "Brd4 Coactivates Transcriptional Activation of NF-kappaB via Specific Binding to Acetylated RelA," Molecular and Cellular Biology, 2009, vol. 29 (5), pp. 1375-1387.
Jang M.K., et al., "The Bromodomain Protein Brd4 is a Positive Regulatory Component of P-TEFb and Stimulates RNA Polymerase II-dependent Transcription," Molecular Cell, 2005, vol. 19 (4), pp. 523-534.

(Continued)

*Primary Examiner* — Douglas M Willis
(74) *Attorney, Agent, or Firm* — Michael S. Montgomery

(57) ABSTRACT

The present invention provides for compounds of formula (I) wherein $R^1$, $R^2$, $R^6$, $Y^1$, $Y^3$, $A^1$, $A^2$, $A^3$ and $A^4$ have any of the values defined in the specification, and pharmaceutically acceptable salts thereof, that are useful as agents in the treatment of diseases and conditions, including inflammatory diseases, cancer, and AIDS. Also provided are pharmaceutical compositions comprising one or more compounds of formula (I).

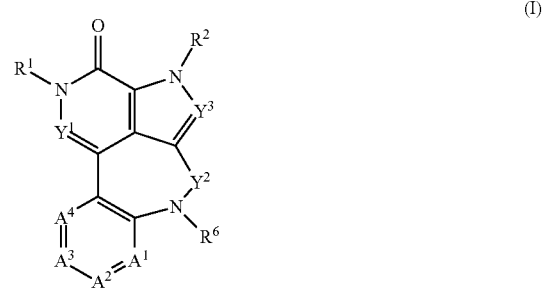

(I)

48 Claims, No Drawings

(56) References Cited

OTHER PUBLICATIONS

Leroy G., et al., "The Double Bromodomain Proteins Brd2 and Brd3 Couple Histone Acetylation to Transcription," Molecular Cell, 2008, vol. 30 (1), pp. 51-60.
Matzuk M.M., et al., "Small-molecule Inhibition of BRDT for Male Contraception," Cell, 2012, vol. 150 (4), pp. 673-684.
Mertz J.A., et al., "Targeting MYC Dependence in Cancer by Inhibiting BET Bromodomains," Proceedings of the National Academy of Sciences, 2011, vol. 108 (40), pp. 16669-16674.
Nicodeme E., et al., "Suppression of Inflammation by a Synthetic Histone Mimic," Nature, 2010, vol. 468 (7327), pp. 1119-1123.
Olson J., et al., "Customization of a Commercially Available Prep Scale SFC System to Provide Enhanced Capabilities," Jala, 2002, vol. 7 (4), pp. 69-74.
Prescott, Ed., Methods in Cell Biology, vol. XIV, Academic Press, New York, 1976, pp. 33.
Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.
Suzuki A., "Recent Advances in the Cross-Coupling Reactions of Organoboron Derivates with Organic Electrophiles, 1995-1998," Journal of Organometallic Chemistry, 1999, vol. 576, pp. 147-168.
Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.
Zhang G. et al., "Down-regulation of NF-κB Transcriptional Activity in HIV-associated Kidney Disease by BRD4 Inhibition," Journal of Biological Chemistry, 2012, vol. 287 (34), pp. 28840-28851.
Zuber J., et al., "RNAi Screen Identifies Brd4 as a Therapeutic Target in Acute Myeloid Leukaemia," Nature, 2011, vol. 478 (7370), pp. 524-528.
Eastwood B.J., et al., "The Minimum Significant Ratio: A Statistical Parameter to Characterize the Reproducibility of Potency Estimates from Concentration-Response Assays and Estimation by Replicate-Experiment Studies," Journal of Biomolecular Screening, 2006, vol. 11 (3), pp. 253-261.
Greene T.W., et al., "Protection for the Amino Group," Protective Groups in Organic Synthesis, 1999, Third Edition, pp. 494-653.
International Search Report and Written Opinion for Application No. PCT/CN2014/000258, dated May 28, 2014, 17 pages.
Miyaura N., et al., "Palladium-Catalyzed Cross-Coupling Reactions of Organoboron Compounds," Chemical Reviews, 1995, vol. 95 (7), pp. 2457-2483.
Supplementary European search report for Application No. EP14762617, dated Sep. 20, 2016, 8 pages.
Suzuki A., et al., "Recent advances in the cross-coupling reactions of organoboron derivatives with organic electrophiles, 1995-1998," Journal of Organometallic. Chemistry, 1999, 576 (1-2), 147-168.

\* cited by examiner

SUBSTITUTED 1,4,10-TRIAZADIBENZO[CD,F]AZULENES, SUBSTITUTED 1,4,5,10-TETRAAZADIBENZO[CD,F]AZULENES AND SUBSTITUTED 1,4,5,7,10-PENTAAZADIBENZO[CD,F]AZULENES AS BROMODOMAIN INHIBITORS

BACKGROUND

Bromodomains refer to conserved protein structural folds which bind to N-acetylated lysine residues that are found in some proteins. The BET family of bromodomain containing proteins is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al, J. Leukocyte Biol. doi:10.1189/jlb.0312165). BRDt has an important role in spermatogenesis that is blocked by BET bromodomain inhibitors (Matzuk, et al., Cell 150: 673-684 (2012)). Thus, compounds that inhibit the binding of BET family bromodomains to their cognate acetylated lysine proteins are being pursued for the treatment of cancer, inflammatory diseases, kidney diseases, diseases involving metabolism or fat accumulation, and some viral infections, as well as for providing a method for male contraception. Accordingly, there is an ongoing medical need to develop new drugs to treat these indications.

SUMMARY

In one aspect the present invention relates to compounds of formula (I) or a salt thereof,

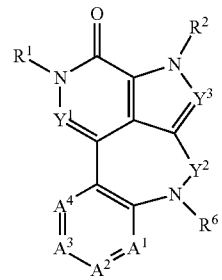

(I)

wherein
$Y^1$ is N or CH;
$R^1$ is $CD_3$, $C_1$-$C_3$ alkyl, or $C_1$-$C_3$ haloalkyl;
$R^2$ is H or $C_1$-$C_3$ alkyl;
$Y^3$ is N or $CR^3$;
$R^3$ is H, $C_1$-$C_6$ alkyl, $C_2$-$C_6$ alkenyl, $C_2$-$C_6$ alkynyl, halogen, $C_1$-$C_6$ haloalkyl, —CN, —C(O)$R^{3a}$, —C(O)O$R^{3a}$, —C(O)N$R^{3b}R^{3c}$, —S(O)$R^{3d}$, —S(O)$_2R^{3a}$, —S(O)$_2$N$R^{3b}R^{3c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —CN, —C(O)$R^{3a}$, —C(O)O$R^{3a}$, —C(O)N$R^{3b}R^{3c}$, —C(O)N($R^{3b}$)N$R^{3b}R^{3c}$, —S(O)$R^{3d}$, —S(O)$_2R^{3a}$, —S(O)$_2$N$R^{3b}R^{3c}$, —O$R^{3a}$, —OC(O)$R^{3d}$, —N$R^{3b}R^{3c}$, N($R^{3b}$)C(O)$R^{3d}$, N($R^{3b}$)SO$_2R^{3d}$, N($R^{3b}$)C(O)O$R^{3d}$, N($R^{3b}$)C(O)N$R^{3b}R^{3c}$, N($R^{3b}$)SO$_2$N$R^{3b}R^{3c}$, and N($R^{3b}$)C(N$R^{3b}R^{3c}$)=N$R^{3b}R^{3c}$;
$Y^2$ is C(O), S(O)$_2$, or $CR^4R^5$;
$R^4$ is H, deuterium, $C_1$-$C_6$ alkyl, halogen, or $C_1$-$C_6$ haloalkyl;
$R^5$ is H, deuterium, $C_1$-$C_6$ alkyl, $C_2$-$C_6$ alkenyl, $C_2$-$C_6$ alkynyl, halogen, $C_1$-$C_6$ haloalkyl, —C(O)$R^{5a}$, —C(O)O$R^{5a}$, —C(O)N$R^{5b}R^{5c}$, —S(O)$R^{5d}$, —S(O)$_2R^{5a}$, —S(O)$_2$ N$R^{5b}R^{5c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —CN, —C(O)$R^{5a}$, —C(O)O$R^{5a}$, —C(O)N$R^{5b}R^{5c}$, —C(O)N($R^{5b}$)N$R^{5b}R^{5c}$, —S(O)$R^{5d}$, —S(O)$_2R^{5a}$, —S(O)$_2$N$R^{5b}R^{5c}$, —O$R^{5a}$, —OC(O)$R^{5d}$, —N$R^{5b}R^{5c}$, N($R^{5b}$)C(O)$R^{5d}$, N($R^{5b}$)SO$_2R^{5d}$, N($R^{5b}$)C(O)O$R^{5d}$, N($R^{5b}$)C(O)N$R^{5b}R^{5c}$, N($R^{5b}$)SO$_2$N$R^{5b}R^{5c}$, and N($R^{5b}$)C(N$R^{5b}R^{5c}$)=N$R^{5b}R^{5c}$;
$R^{3a}$, $R^{3b}$, $R^{3c}$, $R^{5a}$, and $R^{5b}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^1$, or —($C_1$-$C_6$ alkylenyl)-$G^1$;
$R^{5c}$, at each occurrence, is independently H, $C_1$-$C_6$ alkyl, $C_2$-$C_6$ alkenyl, $C_2$-$C_6$ alkynyl, $C_1$-$C_6$ haloalkyl, $G^1$, —($C_1$-$C_6$ alkylenyl)-$G^1$, —($C_1$-$C_6$ alkylenyl)-CN, —($C_1$-$C_6$ alkylenyl)-O$R^a$, or —($C_1$-$C_6$ alkylenyl)-C(O)O$R^a$;
$R^{3d}$, at each occurrence, is independently $C_1$-$C_6$ alkyl, $C_2$-$C_6$ alkenyl, $C_2$-$C_6$ alkynyl, $C_1$-$C_6$ haloalkyl, $G^1$, or —($C_1$-$C_6$ alkylenyl)-$G^1$;
$R^{5d}$, at each occurrence, is independently $C_1$-$C_6$ alkyl, $C_2$-$C_6$ alkenyl, $C_2$-$C_6$ alkynyl, $C_1$-$C_6$ haloalkyl, $G^1$, —($C_1$-$C_6$ alkylenyl)-$G^1$, —($C_1$-$C_6$ alkylenyl)-N$R^cR^d$, or —($C_1$-$C_6$ alkylenyl)-N($R^e$)C(O)O($R^b$);
$G^1$, at each occurrence, is independently aryl, heteroaryl, heterocycle, cycloalkyl, or cycloalkenyl; and each $G^1$ is optionally substituted with 1, 2, 3, 4, or 5 Rig groups;
$R^6$ is H, $C_1$-$C_6$ alkyl, $C_2$-$C_6$ alkenyl, $C_2$-$C_6$ alkynyl, halogen, $C_1$-$C_6$ haloalkyl, —C(O)$R^{6a}$, —C(O)O$R^{6a}$, —C(O)N$R^{6b}R^{6c}$, —S(O)$_2R^{6a}$, —S(O)$_2$N$R^{6b}R^{6c}$, or $G^2$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^2$, —CN, —C(O)$R^{6a}$, —C(O)O$R^{6a}$, —C(O)N$R^{6b}R^{6c}$, —C(O)N($R^{6b}$)N$R^{6b}R^{6c}$, —S(O)$R^{6d}$, —S(O)$_2R^{6a}$, —S(O)$_2$N$R^{6b}R^{6c}$, —O$R^{6a}$, —OC(O)$R^{6d}$, —N$R^{6b}R^{6c}$, N($R^{6b}$)C(O)$R^{6d}$, N($R^{6b}$)SO$_2R^{6d}$, N($R^{6b}$)C(O)O$R^{6d}$, N($R^{6b}$)C(O)N$R^{6b}R^{6c}$, N($R^{6b}$)SO$_2$N$R^{6b}R^{6c}$, and N($R^{6b}$)C(N$R^{6b}R^{6c}$)=N$R^{6b}R^{6c}$;

$R^{6a}$, $R^{6b}$, and $R^{6c}$, at each occurrence, are each independently H, alkyl, $C_2$-$C_6$ alkenyl, $C_2$-$C_6$ alkynyl, haloalkyl, $G^2$, —($C_1$-$C_6$ alkylenyl)-$G^2$, —($C_1$-$C_6$ alkylenyl)-O$R^a$, —($C_1$-$C_6$ alkylenyl)-S(O)$_2R^a$, —($C_1$-$C_6$ alkylenyl)-S(O)$_2$N$R^cR^d$, —($C_1$-$C_6$ alkylenyl)-C(O)$R^a$, —($C_1$-$C_6$ alkylenyl)-C(O)O$R^a$, —($C_1$-$C_6$ alkylenyl)-C(O)N$R^cR^d$, —($C_1$-$C_6$ alkylenyl)-N$R^cR^d$, —($C_1$-$C_6$ alkylenyl)-N($R^e$)C(O)$R^b$, —($C_1$-$C_6$ alkylenyl)-N($R^e$)S(O)$_2R^b$, —($C_1$-$C_6$ alkylenyl)-N($R^e$)C(O)O($R^b$), —($C_1$-$C_6$ alkylenyl)-N($R^e$)C(O)N$R^cR^d$, or —($C_1$-$C_6$ alkylenyl)-N($R^e$)S(O)$_2$N$R^cR^d$;

$R^{6d}$, at each occurrence, is independently alkyl, $C_2$-$C_6$ alkenyl, $C_2$-$C_6$ alkynyl, haloalkyl, $G^2$, —($C_1$-$C_6$ alkylenyl)-$G^2$, —($C_1$-$C_6$ alkylenyl)-O$R^a$, —($C_1$-$C_6$ alkylenyl)-S(O)$_2R^a$, —($C_1$-$C_6$ alkylenyl)-S(O)$_2$N$R^cR^d$, —($C_1$-$C_6$ alkylenyl)-C(O)$R^a$, —($C_1$-$C_6$ alkylenyl)-C(O)O$R^a$, —($C_1$-$C_6$ alkylenyl)-C(O)N$R^cR^d$, —($C_1$-$C_6$ alkylenyl)-N$R^cR^d$, —($C_1$-$C_6$ alkylenyl)-N($R^e$)C(O)$R^b$, —($C_1$-$C_6$ alkylenyl)-N($R^e$)S(O)$_2R^b$, —($C_1$-$C_6$ alkylenyl)-N($R^e$)C(O)O($R^b$), —($C_1$-$C_6$ alkylenyl)-N($R^e$)C(O)N$R^cR^d$, or —($C_1$-$C_6$ alkylenyl)-N($R^e$)S(O)$_2$N$R^cR^d$;

$G^2$, at each occurrence, is independently aryl, heteroaryl, heterocycle, cycloalkyl, or cycloalkenyl; and each $G^2$ is optionally substituted with 1, 2, 3, 4, or 5 $R^{2g}$ groups;

$A^1$ is C($R^7$) or N; $A^2$ is C($R^8$) or N; $A^3$ is C($R^9$) or N; and $A^4$ is C($R^{10}$) or N; wherein zero, one, or two of $A^1$, $A^2$, $A^3$, and $A^4$ are N;

$R^7$, $R^8$, and $R^9$, are each independently H, $C_1$-$C_6$ alkyl, $C_2$-$C_6$ alkenyl, $C_2$-$C_6$ alkynyl, halogen, $C_1$-$C_6$ haloalkyl, —CN, NO$_2$, —O$R^{y1}$, —OC(O)$R^{y2}$, —OC(O)N$R^{y3}R^{y4}$, —S$R^{y1}$, —S(O)$_2R^{y1}$, —S(O)$_2$N$R^{y3}R^{y4}$, —C(O)$R^{y1}$, —C(O)O$R^{y1}$, —C(O)N$R^{y3}R^{y4}$, —N$R^{y3}R^{y4}$, —N($R^{y3}$)C(O)$R^{y2}$, —N($R^{y3}$)S(O)$_2R^{y2}$, —N($R^{y3}$)C(O)O($R^{y2}$), —N($R^{y3}$)C(O)N$R^{y3}R^{y4}$, —N($R^{y3}$)S(O)$_2$N$R^{y3}R^{y4}$, $G^3$, —($C_1$-$C_6$ alkylenyl)-CN, —($C_1$-$C_6$ alkylenyl)-O$R^{y1}$, —($C_1$-$C_6$ alkylenyl)-OC(O)$R^{y2}$, —($C_1$-$C_6$ alkylenyl)-OC(O)N$R^{y3}R^{y4}$, —($C_1$-$C_6$ alkylenyl)-S(O)$_2R^{y1}$, —($C_1$-$C_6$ alkylenyl)-S(O)$_2$N$R^{y3}R^{y4}$, —($C_1$-$C_6$ alkylenyl)-C(O)$R^{y1}$, —($C_1$-$C_6$ alkylenyl)-C(O)O$R^{y1}$, —($C_1$-$C_6$ alkylenyl)-C(O)N$R^{y3}R^{y4}$, —($C_1$-$C_6$ alkylenyl)-N$R^{y3}R^{y4}$, —($C_1$-$C_6$ alkylenyl)-N($R^{y3}$)C(O)$R^{y2}$, —($C_1$-$C_6$ alkylenyl)-N($R^{y3}$)S(O)$_2R^{y2}$, —($C_1$-$C_6$ alkylenyl)-N($R^{y3}$)C(O)O($R^{y2}$), —($C_1$-$C_6$ alkylenyl)-N($R^{y3}$)C(O)N$R^{y3}R^{y4}$, —($C_1$-$C_6$ alkylenyl)-N($R^{y3}$)S(O)$_2$N$R^{y3}R^{y4}$, —($C_1$-$C_6$ alkylenyl)-CN, or —($C_1$-$C_6$ alkylenyl)-$G^3$;

$R^{y1}$, $R^{y3}$, and $R^{y4}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^3$, —($C_1$-$C_6$ alkylenyl)-$G^3$, —($C_1$-$C_6$ alkylenyl)-O$R^a$, —($C_1$-$C_6$ alkylenyl)-S(O)$_2R^a$, —($C_1$-$C_6$ alkylenyl)-S(O)$_2$N$R^cR^d$, —($C_1$-$C_6$ alkylenyl)-C(O)$R^a$, —($C_1$-$C_6$ alkylenyl)-C(O)O$R^a$, —($C_1$-$C_6$ alkylenyl)-C(O)N$R^cR^d$, —($C_1$-$C_6$ alkylenyl)-N$R^cR^d$, —($C_1$-$C_6$ alkylenyl)-N($R^e$)C(O)$R^b$, —($C_1$-$C_6$ alkylenyl)-N($R^e$)S(O)$_2R^b$, —($C_1$-$C_6$ alkylenyl)-N($R^e$)C(O)O($R^b$), —($C_1$-$C_6$ alkylenyl)-N($R^e$)C(O)N$R^cR^d$, or —($C_1$-$C_6$ alkylenyl)-N($R^e$)S(O)$_2$N$R^cR^d$;

$R^{y2}$, at each occurrence, is independently $C_1$-$C_6$ alkyl, $C_2$-$C_6$ alkenyl, $C_2$-$C_6$ alkynyl, $C_1$-$C_6$ haloalkyl, $G^3$, —($C_1$-$C_6$ alkylenyl)-$G^3$, —($C_1$-$C_6$ alkylenyl)-O$R^a$, —($C_1$-$C_6$ alkylenyl)-S(O)$_2R^a$, —($C_1$-$C_6$ alkylenyl)-S(O)$_2$N$R^cR^d$, —($C_1$-$C_6$ alkylenyl)-C(O)$R^a$, —($C_1$-$C_6$ alkylenyl)-C(O)O$R^a$, —($C_1$-$C_6$ alkylenyl)-C(O)N$R^cR^d$, —($C_1$-$C_6$ alkylenyl)-N$R^cR^d$, —($C_1$-$C_6$ alkylenyl)-N($R^e$)C(O)$R^b$, —($C_1$-$C_6$ alkylenyl)-N($R^e$)S(O)$_2R^b$, —($C_1$-$C_6$ alkylenyl)-N($R^e$)C(O)O($R^b$), —($C_1$-$C_6$ alkylenyl)-N($R^e$)C(O)N$R^cR^d$, or —($C_1$-$C_6$ alkylenyl)-N($R^e$)S(O)$_2$N$R^cR^d$;

$G^3$, at each occurrence, is independently aryl, heteroaryl, cycloalkyl, cycloalkenyl, or heterocycle; and each $G^3$ group is optionally substituted with 1, 2, 3, 4, or 5 $R^{4g}$ groups;

$R^{10}$ is H, $C_1$-$C_3$ alkyl, halogen, $C_1$-$C_3$ haloalkyl, or —CN;

$R^{1g}$, $R^{2g}$, and $R^{4g}$, at each occurrence, is independently selected from the group consisting of oxo, $C_1$-$C_6$ alkyl, $C_2$-$C_6$ alkenyl, $C_2$-$C_6$ alkynyl, halogen, $C_1$-$C_6$ haloalkyl, —CN, NO$_2$, $G^{2a}$, —O$R^a$, —OC(O)$R^b$, —OC(O)N$R^cR^d$, —S$R^a$, —S(O)$_2R^a$, —S(O)$_2$N$R^cR^d$, —C(O)$R^a$, —C(O)O$R^a$, —C(O)N$R^cR^d$, —N$R^cR^d$, —N($R^e$)C(O)$R^b$, —N($R^e$)S(O)$_2R^b$, —N($R^e$)C(O)O($R^b$), —N($R^e$)C(O)N$R^cR^d$, —N($R^e$)S(O)$_2$N$R^cR^d$, —($C_1$-$C_6$ alkylenyl)-CN, —($C_1$-$C_6$ alkylenyl)-$G^{2a}$, —($C_1$-$C_6$ alkylenyl)-O$R^a$, —($C_1$-$C_6$ alkylenyl)-OC(O)$R^b$, —($C_1$-$C_6$ alkylenyl)-OC(O)N$R^cR^d$, —($C_1$-$C_6$ alkylenyl)-S(O)$_2R^a$, —($C_1$-$C_6$ alkylenyl)-S(O)$_2$N$R^cR^d$, —($C_1$-$C_6$ alkylenyl)-C(O)$R^a$, —($C_1$-$C_6$ alkylenyl)-C(O)O$R^a$, —($C_1$-$C_6$ alkylenyl)-C(O)N$R^cR^d$, —($C_1$-$C_6$ alkylenyl)-N$R^cR^d$, —($C_1$-$C_6$ alkylenyl)-N($R^e$)C(O)$R^b$, —($C_1$-$C_6$ alkylenyl)-N($R^e$)S(O)$_2R^b$, —($C_1$-$C_6$ alkylenyl)-N($R^e$)C(O)O($R^b$), —($C_1$-$C_6$ alkylenyl)-N($R^e$)C(O)N$R^cR^d$, —($C_1$-$C_6$ alkylenyl)-N($R^e$)S(O)$_2$N$R^cR^d$, or —($C_1$-$C_6$ alkylenyl)-CN;

$R^a$, $R^c$, $R^d$, and $R^e$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^{2a}$, —($C_1$-$C_6$ alkylenyl)-O$R^{z1}$, —($C_1$-$C_6$ alkylenyl)-N$R^{z3}R^{z4}$, alkylenyl)-C(O)N$R^{z3}R^{z4}$, or —($C_1$-$C_6$ alkylenyl)-$G^{2a}$;

$R^b$, at each occurrence, is independently $C_1$-$C_6$ alkyl, $C_2$-$C_6$ alkenyl, $C_2$-$C_6$ alkynyl, $C_1$-$C_6$ haloalkyl, $G^{2a}$, or —($C_1$-$C_6$ alkylenyl)-$G^{2a}$;

$G^{2a}$, at each occurrence, are each independently aryl, heteroaryl, heterocycle, cycloalkyl, or cycloalkenyl; and each $G^{2a}$ group is optionally substituted with 1, 2, 3, 4, or 5 $R^{3g}$ groups;

$R^{3g}$, at each occurrence, is independently oxo, $C_1$-$C_6$ alkyl, $C_2$-$C_6$ alkenyl, $C_2$-$C_6$ alkynyl, halogen, $C_1$-$C_6$ haloalkyl, —CN, NO$_2$, —O$R^{z1}$, —OC(O)$R^{z2}$, —OC(O)N$R^{z3}R^{z4}$, —S$R^{z1}$, —S(O)$_2R^{z1}$, —S(O)$_2$N$R^{z3}R^{z4}$, —C(O)$R^{z1}$, —C(O)O$R^{z1}$, —C(O)N$R^{z3}R^{z4}$, —N$R^{z3}R^{z4}$, —N($R^{z3}$)C(O)$R^{z2}$, —N($R^{z3}$)S(O)$_2R^{z2}$, —N($R^{z3}$)C(O)O($R^{z2}$), —N($R^{z3}$)C(O)N$R^{z3}R^{z4}$, —N($R^{z3}$)S(O)$_2$N$R^{z3}R^{z4}$, —($C_1$-$C_6$ alkylenyl)-O$R^{z1}$, —($C_1$-$C_6$ alkylenyl)-OC(O)$R^{z2}$, —($C_1$-$C_6$ alkylenyl)-OC(O)N$R^{z3}R^{z4}$, —($C_1$-$C_6$ alkylenyl)-S(O)$_2R^{z1}$, —($C_1$-$C_6$ alkylenyl)-S(O)$_2$N$R^{z3}R^{z4}$, —($C_1$-$C_6$ alkylenyl)-C(O)$R^{z1}$, alkylenyl)-C(O)O$R^{z1}$, —($C_1$-$C_6$ alkylenyl)-C(O)N$R^{z3}R^{z4}$, —($C_1$-$C_6$ alkylenyl)-N$R^{z3}R^{z4}$, —($C_1$-$C_6$ alkylenyl)-N($R^{z3}$)C(O)$R^{z2}$, —($C_1$-$C_6$ alkylenyl)-N($R^{z3}$)S(O)$_2R^{z2}$, —($C_1$-$C_6$ alkylenyl)-N($R^{z3}$)C(O)O($R^{z2}$), alkylenyl)-N($R^{z3}$)C(O)N$R^{z3}R^{z4}$, —($C_1$-$C_6$ alkylenyl)-N($R^{z3}$)S(O)$_2$N$R^{z3}R^{z4}$, or —($C_1$-$C_6$ alkylenyl)-CN;

$R^{z1}$, $R^{z3}$, and $R^{z4}$, at each occurrence, are each independently H, $C_1$-$C_6$ alkyl, $C_2$-$C_6$ alkenyl, $C_2$-$C_6$ alkynyl, or $C_1$-$C_6$ haloalkyl; and $R^{z2}$, at each occurrence, is independently $C_1$-$C_6$ alkyl, $C_2$-$C_6$ alkenyl, $C_2$-$C_6$ alkynyl, or $C_1$-$C_6$ haloalkyl.

In another aspect, the present invention provides for methods for treating or preventing disorders that are ameliorated by inhibition of BET. Such methods comprise of administering to the subject a therapeutically effective amount of a compound of formula (I), alone, or in combination with a pharmaceutically acceptable carrier.

Some of the methods are directed to treating or preventing an inflammatory disease or cancer or AIDS.

In another aspect, the present invention relates to methods of treating cancer in a subject comprising administering a therapeutically effective amount of a compound of formula (I) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is selected from the group consisting of cytarabine, bortezomib, and 5-azacitidine.

In another aspect, the present invention relates to methods of treating a disease or condition in a subject comprising administering a therapeutically effective amount of a compound of formula (I) or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, cardiac myopathy, cardiac hypertrophy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of formula (I) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of formula (I) or a pharmaceutically acceptable salt thereof, to a subject in need thereof, wherein said acute kidney injury or disease or condition is selected from the group consisting of: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, and drug toxicity induced kidney disease. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention provides for contraception in a male subject comprising administering a therapeutically effective amount of a compound of formula (I), or a pharmaceutically acceptable salt thereof, to a subject in need thereof. In certain embodiments, the methods further comprise administering a therapeutically effective amount of at least one additional therapeutic agent.

A further aspect of the invention provides the use of a compound of formula (I), alone or in combination with a second active pharmaceutical agent, in the manufacture of a medicament for treating or preventing conditions and disorders disclosed herein, with or without a pharmaceutically acceptable carrier.

Pharmaceutical compositions comprising a compound of formula (I), or a pharmaceutically acceptable salt, alone or in combination with a second active pharmaceutical agent, are also provided. In certain embodiments, pharmaceutical compositions comprise a therapeutically effective amount of a compound of formula (I), or a pharmaceutically acceptable salt thereof, and a pharmaceutically acceptable carrier.

DETAILED DESCRIPTION

Disclosed herein are compounds of formula (I)

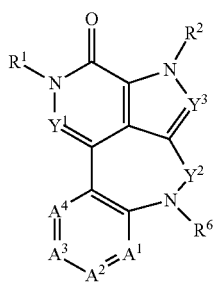

(I)

wherein $R^1$, $R^2$, $R^6$, $Y^1$, $Y^2$, $Y^3$, $A^1$, $A^2$, $A^3$, and $A^4$ are defined above in the Summary of the Invention and below in the Detailed Description. Further, compositions comprising such compounds and methods for treating conditions and disorders using such compounds and compositions are also disclosed.

Compounds disclosed herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

a). Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond, optionally substituted with 1, 2, or 3 halogen atoms. The term "$C_2$-$C_6$ alkenyl" means an alkenyl group containing 2-6 carbon atoms. Non-limiting examples of alkenyl include buta-1,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. Representative examples of alkenylene include, but are not limited to, —CH═CH— and —CH$_2$CH═CH—.

The term "alkyl" as used herein, means a saturated, straight or branched hydrocarbon chain radical. In some instances, the number of carbon atoms in an alkyl moiety is indicated by the prefix "$C_x$-$C_y$," wherein x is the minimum and y is the maximum number of carbon atoms in the substituent. Thus, for example, "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms or of 2 to 3 carbon atoms ($C_2$-$C_3$ alkylenyl). Examples of alkylene and alkylenyl include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon radical containing from 2 to 10 carbon atoms and containing at least one carbon-carbon triple bond, optionally substituted with 1, 2, or 3 halogen atoms. The term "$C_2$-$C_6$ alkynyl" means an alkynyl group of 2 to 6 carbon atoms. Representative examples of alkynyl include, but are not limited, to acetylenyl, 1-propynyl, 2-propynyl, 3-butynyl, 2-pentynyl, 1-butynyl, and but-2-yn-1-yl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl (indanyl), indenyl, naphthyl, dihydronaphthalenyl, and tetrahydronaphthalenyl. The aryls are attached to the parent molecular moiety through any carbon atom contained within the bicyclic ring systems and can be unsubstituted or substituted.

The term "cycloalkyl" as used herein, refers to a radical that is a monocyclic cyclic alkyl, a bicyclic cycloalkyl, or a spiro cycloalkyl. A monocyclic cycloalkyl is a carbocyclic ring system containing three to eight carbon atoms, zero heteroatoms and zero double bonds, i.e., a $C_3$-$C_8$ cycloalkyl. In certain embodiments, a cycloalkyl refers to a monocyclic $C_3$-$C_7$ cycloalkyl. Examples of monocyclic ring systems include cyclopropyl, cyclobutyl, cyclopentyl, cyclohexyl, cycloheptyl, and cyclooctyl. A bicyclic cycloalkyl is a monocyclic cycloalkyl fused to a monocyclic cycloalkyl ring. Monocyclic and the bicyclic cycloalkyl groups may contain one or two alkylene bridges, each consisting of one, two, three, or four carbon atoms in length, and each bridge links two non-adjacent carbon atoms of the ring system. Non-limiting examples of bicyclic ring systems include bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). A spiro cycloalkyl is a monocyclic cycloalkyl wherein two substituents on the same carbon atom of the monocyclic cycloalkyl ring together with said carbon atom form a second monocyclic cycloalkyl ring. Monocyclic, the bicyclic, and the Spiro cycloalkyl groups can be unsubstituted or substituted, and are attached to the parent molecular moiety through any substitutable atom contained within the ring system.

The term "cycloalkenyl" as used herein, refers to a monocyclic or a bicyclic hydrocarbon ring radical. A monocyclic cycloalkenyl has four-, five-, six-, seven- or eight carbon atoms and zero heteroatoms, i.e., a $C_4$-$C_8$ cycloalkenyl. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. A bicyclic cycloalkenyl is a monocyclic cycloalkenyl fused to a monocyclic cycloalkyl group, or a monocyclic cycloalkenyl fused to a monocyclic cycloalkenyl group. Monocyclic or bicyclic cycloalkenyl ring may contain one or two alkylene bridges, each consisting of one, two, or three carbon atoms, and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. Monocyclic and bicyclic cycloalkenyls can be attached to the parent molecular moiety through any substitutable atom contained within the ring systems, and can be unsubstituted or substituted.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, six, or seven hydrogen atoms are replaced by halogen. The term "$C_1$-$C_3$ haloalkyl" means a $C_1$-$C_3$ alkyl group, as defined herein, in which one, two, three, four, five, or six hydrogen atoms are replaced by halogen. Representative examples of haloalkyl include, but are not limited to, chloromethyl, 2-fluoroethyl, 2,2-difluoroethyl, 2,2,2-trifluoroethyl, trifluoromethyl, difluoromethyl, pentafluoroethyl, 4-chlorobutyl, 2-chloro-3-fluoropentyl, trifluorobutyl, trifluoropropyl, 2,2,3,3,3-pentafluoropropyl, and 2,2,3,3,4,4,4-heptafluorobutyl.

The term "heterocycle" or "heterocyclic" as used herein, means a radical of a monocyclic heterocycle, a bicyclic heterocycle, and a Spiro heterocycle. A monocyclic heterocycle is a three-, four-, five-, six-, seven-, or eight-membered carbocyclic ring also containing at least one heteroatom independently selected from the group consisting of O, N, and S. A three- or four-membered ring contains zero or one double bond, and one heteroatom selected from the group consisting of O, N, and S. When two O atoms or one O atom and one S atom are present in a heterocyclic ring, then the two O atoms or one O atom and one S atom are not bonded directly to each other. A five-membered ring contains zero or one double bond and one, two, or three heteroatoms selected from the group consisting of O, N, and S. Examples of five-membered heterocyclic rings include those containing in the ring: 1 O; 1 S; 1 N; 2 N; 3 N; 1 S and 1 N; 1 S, and 2 N; 1 O and 1 N; or 1 O and 2 N. Examples of 5-membered heterocyclic groups include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl. A six-membered ring contains zero, one, or two double bonds and one, two, or three heteroatoms selected from the group consisting of O, N, and S. Examples of six-membered heterocyclic rings include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 Q and 1 N; and 1 O and 2 N. Examples of 6-membered heterocyclic groups include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, 1,1-dioxo-hexahydro-1-thiopyranyl, 1,1-dioxo-1$\lambda^6$-thiomorpholinyl, thiomorpholinyl, thioxanyl, and trithianyl. Seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, 1,3-benzodioxolyl, benzopyranyl, benzothiopyranyl, 2,3-dihydrobenzofuranyl, 2,3-dihydrobenzothienyl, 2,3-dihydro-1H-indolyl, dihydroisoindol-2-yl, isoindolinyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl. The monocyclic heterocycle and the bicyclic heterocycle may contain one or two alkylene bridges or an alkenylene bridge, or mixture thereof, each consisting of no more than four carbon atoms and each linking two non adjacent atoms of the ring system. Examples of such bridged heterocycle include, but are not limited to, azabicyclo[2.2.1]heptyl (including 2-azabicyclo[2.2.1]hept-2-yl), 8-azabicyclo[3.2.1]oct-8-yl, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). A Spiro heterocycle is a monocyclic heterocycle wherein two substituents on the same carbon atom of the monocyclic heterocycle ring together with said carbon atom form a second ring system selected from a monocyclic cycloalkyl, a bicyclic cycloalkyl, a monocyclic heterocycle, or a bicyclic heterocycle. Examples of spiro heterocycle include, but not limited to, 6-azaspiro[2.5]oct-6-yl, 1'H, 4H-spiro[1,3-benzodioxine-2,4'-piperidin]-1'-yl, 1'H, 3H-spiro[2-benzofuran-1,4'-piperidin]-1'-yl, and 1,4-dioxa-8-azaspiro[4.5]dec-8-yl. The monocyclic, the bicyclic, and the spiro heterocycles can be unsubstituted or substituted. The monocyclic, the bicyclic and the spiro heterocycles are connected to the parent molecular moiety through any carbon atom or any nitrogen atom contained within the ring systems. The nitrogen and sulfur heteroatoms in the heterocycle rings may optionally be oxidized (e.g. 1,1-dioxidotetrahydrothienyl, 1,2-dioxido- 1,2-thiazolidinyl, 1,1-dioxidothiomorpholinyl)) and the nitrogen atoms may optionally be quarternized.

The term "$C_4$-$C_6$ heterocycle" or "$C_4$-$C_6$ heterocyclic" as used herein, means a 4, 5, or 6 membered monocyclic heterocycle as defined herein above. Non-limiting examples of $C_4$-$C_6$ heterocycle include azetidinyl, pyrrolidinyl, tetrahydrofuranyl, tetrahydropyranyl, piperazinyl, piperidinyl, and morpholinyl.

The term "heteroaryl" as used herein, means a monocyclic heteroaryl and a bicyclic heteroaryl. The monocyclic heteroaryl is a five- or six-membered monocyclic ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems. The nitrogen atom in the heteroaryl rings may optionally be oxidized and may optionally be quarternized.

The term "heteroatom" as used herein, means a nitrogen, oxygen, and sulfur.

The term "oxo" as used herein, means a =O group.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

b. Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In certain embodiments of formula (I), $Y^1$ is N or CH.

In certain embodiments, $Y^1$ is N.

In certain embodiments, $Y^1$ is CH.

In certain embodiments of formula (I), $R^1$ is $CD_3$, $C_1$-$C_3$ alkyl, or $C_1$-$C_3$ haloalkyl.

In certain embodiments, $R^1$ is $C_1$-$C_3$ alkyl. In some such embodiments, $R^1$ is methyl.

In certain embodiments of formula (I), $R^2$ is H or $C_1$-$C_3$ alkyl.

In certain embodiments, $R^2$ is H or methyl.

In certain embodiments, $R^2$ is H.

In certain embodiments, $R^2$ is $C_1$-$C_3$ alkyl. In some such embodiments, $R^2$ is methyl.

In certain embodiments of formula (I), $Y^3$ is N or $CR^3$.

In certain embodiments, $Y^3$ is N.

In certain embodiments, $Y^3$ is $CR^3$.

In certain embodiments of formula (I), $R^3$ is H, —CN, $C_1$-$C_6$ alkyl, $C_2$-$C_6$ alkenyl, $C_2$-$C_6$ alkynyl, halogen, $C_1$-$C_6$ haloalkyl, —C(O)$R^{3a}$, —C(O)O$R^{3a}$, —C(O)N$R^{3b}R^{3c}$, —S(O)$R^{3d}$, —S(O)$_2R^{3a}$, —S(O)$_2$N$R^{3b}R^{3c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —CN, —C(O)$R^{3a}$, —C(O)O$R^{3a}$, —C(O)N$R^{3b}R^{3c}$, —C(O)N($R^{3b}$)N$R^{3b}R^{3c}$, —S(O)$R^{3d}$, —S(O)$_2R^{3a}$, —S(O)$_2$N$R^{3b}R^{3c}$, —O$R^{3a}$, —OC(O)$R^{3d}$, —N$R^{3b}R^{3c}$, N($R^{3b}$)C(O)$R^{3d}$, N($R^{3b}$)SO$_2R^{3d}$, N($R^{3b}$)C(O)O$R^{3d}$, N($R^{3b}$)C(O)N$R^{3b}R^{3c}$, N($R^{3b}$)SO$_2$N$R^{3b}R^{3c}$, and N($R^{3b}$)C(N$R^{3b}R^{3c}$)=N$R^{3b}R^{3c}$.

In certain embodiments, $R^3$ is H, —CN, —C(O)$R^{3a}$, —C(O)O$R^{3a}$, —C(O)N$R^{3b}R^{3c}$, or $C_1$-$C_6$ alkyl, wherein the $C_1$-$C_6$ alkyl is optionally substituted with a substituent selected from the group consisting of $G^1$, —N$R^{3b}R^{3c}$, N($R^{3b}$)C(O)$R^{3d}$, N($R^{3b}$)SO$_2R^{3d}$, N($R^{3b}$)C(O)O$R^{3d}$, N($R^{3b}$)C(O)N$R^{3b}R^{3c}$, and N($R^{3b}$)SO$_2$N$R^{3b}R^{3c}$. In some such embodiments, the $G^1$ group is optionally substituted heterocycle. In some such embodiments, the $C_1$-$C_6$ alkyl is substituted with a $G^1$ group, wherein the $G^1$ group is piperidinyl, piperazinyl, or morpholinyl, each of which is optionally substituted with 1 or 2 $C_1$-$C_6$ alkyl. In some such embodiments, the $C_1$-$C_6$ alkyl is substituted with a $G^1$ group, wherein the $G^1$ group is piperazinyl or morpholinyl, each of which is optionally substituted with 1 or 2 $C_1$-$C_6$ alkyl.

In certain embodiments, $R^3$ is H, —C(O)N$R^{3b}R^{3c}$, —CN, or $C_1$-$C_6$ alkyl which is substituted with a $G^1$ group. In some such embodiments, the $C_1$-$C_6$ alkyl is substituted with a $G^1$ group, wherein the $G^1$ group is an optionally substituted $C_4$-$C_6$ heterocycle. In some such embodiments, the $C_1$-$C_6$ alkyl is substituted with a $G^1$ group, wherein the $G^1$ group is piperidinyl, piperazinyl, or morpholinyl, each of which is optionally substituted with 1 or 2 $C_1$-$C_6$ alkyl.

In certain embodiments, $R^3$ is H, —C(O)$R^{3a}$, or —C(O)N$R^{3b}R^{3c}$. In some such embodiments, $R^{3a}$ is $G^1$. In some such embodiments, $R^{3a}$ is $G^1$ wherein $G^1$ is optionally substituted heterocycle. In some such embodiments, $R^{3a}$ is $G^1$ wherein $G^1$ is piperidinyl, piperazinyl, or morpholinyl, each of which is optionally substituted with 1 or 2 $C_1$-$C_6$ alkyl. In some such embodiments, $R^{3a}$ is $G^1$ wherein $G^1$ is piperazinyl, optionally substituted with 1 or 2 $C_1$-$C_6$ alkyl.

In certain embodiments, $R^3$ is H or —C(O)N$R^{3b}R^{3c}$. In some such embodiments, $R^{3b}$ and $R^{3c}$ are each independently H or $C_1$-$C_6$ alkyl.

In certain embodiments, $R^3$ is H.

In certain embodiments, $R^3$ is —C(O)N$R^{3b}R^{3c}$. In some such embodiments, $R^{3b}$ and $R^{3c}$ are each independently H or $C_1$-$C_3$ alkyl.

In certain embodiments, $R^3$ is $G^1$. In some such embodiments, $G^1$ is optionally substituted monocyclic heteroaryl. In some such embodiments, $G^1$ is optionally substituted pyrazolyl. In some such embodiments, $G^1$ is pyrazolyl substituted with 1 or 2 $C_1$-$C_6$ alkyl.

In certain embodiments of formula (I), $Y^2$ is C(O), S(O)$_2$, or C$R^4R^5$.

In certain embodiments, $Y^2$ is C(O).

In certain embodiments, $Y^2$ is S(O)$_2$.

In certain embodiments, $Y^2$ is C$R^4R^5$.

In certain embodiments of formula (I), $R^4$ is H, deuterium, $C_1$-$C_6$ alkyl, halogen, or $C_1$-$C_6$ haloalkyl.

In certain embodiments, $R^4$ is H or deuterium.

In certain embodiments, $R^4$ is H.

In certain embodiments of formula (I), $R^5$ is H, deuterium, $C_1$-$C_6$ alkyl, $C_2$-$C_6$ alkenyl, $C_2$-$C_6$ alkynyl, halogen, $C_1$-$C_6$ haloalkyl, —C(O)$R^{5a}$, —C(O)O$R^{5a}$, —C(O)N$R^{5b}R^{5c}$, —S(O)$R^{5d}$, —S(O)$_2R^{5a}$, —S(O)$_2$N$R^{5b}R^{5c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —CN, —C(O)$R^{5a}$, —C(O)O$R^{5a}$, —C(O)N$R^{5b}R^{5b}$, —C(O)N($R^{5b}$)N$R^{5b}R^{5b}$, —S(O)$R^{5d}$, —S(O)$_2R^{5a}$, —S(O)$_2$N$R^{5b}R^{5b}$, —O$R^{5a}$, —OC(O)$R^{5d}$, —N$R^{5b}R^{5b}$, N($R^{5b}$)C(O)$R^{5d}$, N($R^{5b}$)SO$_2R^{5d}$, N($R^{5b}$)C(O)O$R^{5d}$, N($R^{5b}$)C(O)N$R^{5b}R^{5b}$, N($R^{5b}$)SO$_2$N$R^{5b}R^{5c}$, and N($R^{5b}$)C(N$R^{5b}R^{5b}$)=N$R^{5b}R^{5b}$.

In certain embodiments, $R^5$ is H, deuterium, $C_1$-$C_6$ alkyl, $C_2$-$C_6$ alkenyl, $C_2$-$C_6$ alkynyl, $C_1$-$C_6$ haloalkyl, —C(O)$R^{5a}$, —C(O)O$R^{5a}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —C(O)$R^{5a}$, —C(O)O$R^{5a}$, —C(O)N$R^{5b}R^{5b}$, —C(O)N($R^{5b}$)N$R^{5b}R^{5b}$, —O$R^{5a}$, —OC(O)$R^{5d}$, —N$R^{5b}R^{5b}$, N($R^{5b}$)C(O)$R^{5d}$, N($R^{5b}$)SO$_2R^{5d}$, N($R^{5b}$)C(O)O$R^{5d}$, N($R^{5b}$)C(O)N$R^{5b}R^{5b}$, and N($R^{5b}$)SO$_2$N$R^{5b}R^{5b}$.

In certain embodiments, $R^5$ is $C_2$-$C_6$ alkenyl optionally substituted with a $G^1$ group, or $R^5$ is H, deuterium, $C_1$-$C_6$ alkyl, —C(O)$R^{5a}$, —C(O)O$R^{5a}$, or $G^1$; wherein the $C_1$-$C_6$ alkyl is unsubstituted or substituted with a substituent selected from the group consisting of $G^1$, —C(O)$R^{5a}$, —C(O)O$R^{5a}$, —C(O)N$R^{5b}R^{5b}$, —C(O)N($R^{5b}$)N$R^{5b}R^{5b}$, —O$R^{5a}$, —OC(O)$R^{5d}$, —N$R^{5b}R^{5b}$, and N($R^{5b}$)C(N$R^{5b}R^{5b}$)=N$R^{5b}R^{5b}$.

In certain embodiments, $R^5$ is H, deuterium, or $C_1$-$C_6$ alkyl optionally substituted with a substituent selected from the group consisting of —C(O)O$R^{5a}$ and O$R^{5a}$. In some such embodiments, $R^{5a}$ is $C_1$-$C_6$ alkyl.

In certain embodiments, $R^5$ is H.

In certain embodiments of formula (I), $R^6$ is H, $C_1$-$C_6$ alkyl, $C_2$-$C_6$ alkenyl, $C_2$-$C_6$ alkynyl, halogen, $C_1$-$C_6$ haloalkyl, —C(O)$R^{6a}$, —C(O)O$R^{6a}$, —C(O)N$R^{6b}R^{6b}$, —S(O)$_2R^{6a}$, —S(O)$_2$N$R^{6b}R^{6b}$, or $G^2$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^2$, —CN, —C(O)$R^{6a}$, —C(O)O$R^{6a}$, —C(O)N$R^{6b}R^{6c}$, —C(O)N($R^{6b}$)N$R^{6b}R^{6b}$, —S(O)$R^{6d}$, —S(O)$_2R^{6a}$, —S(O)$_2$N$R^{6b}R^{6b}$, —O$R^{6a}$, —OC(O)$R^{6d}$, —N$R^{6b}R^{6b}$, N($R^{6b}$)C(O)$R^{6d}$, N($R^{6b}$)SO$_2R^{6d}$, N($R^{6b}$)C(O)O$R^{6d}$, N($R^{6b}$)C(O)N$R^{6b}R^{6b}$, N($R^{6b}$)SO$_2$N$R^{6b}R^{6c}$, and N($R^{6b}$)C(N$R^{6b}R^{6b}$)=N$R^{6b}R^{6b}$.

In certain embodiments, $R^6$ is H, $C_1$-$C_6$ alkyl, $C_2$-$C_6$ alkenyl, —C(O)$R^{6a}$, —C(O)O$R^{6a}$, —C(O)N$R^{6b}R^{6b}$, —S(O)$_2R^{6a}$, or $G^2$; wherein the $C_1$-$C_6$ alkyl and the $C_2$-$C_6$ alkenyl are each independently unsubstituted or substituted with 1 or 2 substituents independently selected from the group consisting of $G^2$, —CN, —C(O)O$R^{6a}$, —N$R^{6b}R^{6b}$, N($R^{6b}$)C(O)$R^{6d}$, N($R^{6b}$)SO$_2R^{6d}$, N($R^{6b}$)C(O)O$R^{6d}$, N($R^{6b}$)C(O)N$R^{6b}R^{6b}$, and N($R^{6b}$)SO$_2$N$R^{6b}R^{6b}$.

In certain embodiments, $R^6$ is H, $C_1$-$C_6$ alkyl, —C(O)$R^{6a}$, —C(O)O$R^{6a}$, —C(O)—N$R^{6b}R^{6c}$, —S(O)$_2R^{6a}$, or $G^2$; wherein the $C_1$-$C_6$ alkyl is unsubstituted or substituted with a substituent selected from the group consisting of $G^2$ and —C(O)O$R^{6a}$.

In certain embodiments, $R^6$ is —C(O)$R^{6a}$, —C(O)O$R^{6a}$, —C(O)N$R^{6b}R^{6c}$, $G^2$, or $C_1$-$C_6$ alkyl which is unsubstituted or substituted with a $G^2$ group. In certain embodiments, $R^{6a}$ is $G^2$ or unsubstituted $C_1$-$C_6$ alkyl.

In certain embodiments, $R^6$ is —C(O)O$R^{6a}$. In some such embodiments, $R^{6a}$ is $C_1$-$C_6$ alkyl.

In certain embodiments, $R^6$ is $G^2$ or $C_1$-$C_6$ alkyl which is unsubstituted or substituted with a $G^2$ group. In some such embodiments, $R^6$ is optionally substituted aryl, optionally substituted heteroaryl, optionally substituted heterocycle, or optionally substituted cycloalkyl; or $R^6$ is $C_1$-$C_6$ alkyl which is unsubstituted or substituted with a substituent selected from the group consisting of heteroaryl, cycloalkyl, and heterocycle, each of which is optionally substituted. In some such embodiments, $R^6$ is optionally substituted aryl, optionally substituted heteroaryl, or optionally substituted cycloalkyl; or $R^6$ is $C_1$-$C_6$ alkyl which is unsubstituted or substituted with a substituent selected from the group consisting of cycloalkyl and heterocycle, each of which is optionally substituted. In some such embodiments, $R^6$ is phenyl, pyridinyl, pyrimidinyl, pyrazinyl, pyridazinyl, indazolyl, cyclohexyl, tetrahydrofuranyl, tetrahydropyranyl, pyrrolidinyl, piperidinyl, or azepanyl, each of which is optionally substituted; or $R^6$ is $C_1$-$C_6$ alkyl which is unsubstituted or substituted with a $G^1$ group wherein the $G^1$ group is cyclopropyl, cyclohexyl, pyrrolidinyl, piperidinyl, morpholinyl, tetrahydrofuranyl, tetrahydropyranyl, 1, 3 dioxolyl, or pyrazolyl, each of which is optionally substituted. In some such embodiments, $R^6$ is optionally substituted phenyl, optionally substituted pyridinyl, or optionally substituted cyclohexyl; or $R^6$ is $C_1$-$C_6$ alkyl which is unsubstituted or substituted with a substituent selected from the group consisting of cyclopropyl and tetrahydrofuranyl, each of which is optionally substituted. In some such embodiments, said optional substituents are independently selected from the group consisting of halogen, —O($C_1$-$C_3$ alkyl), —O($C_1$-$C_3$ haloalkyl), —N(H)C(O)O($C_1$-$C_6$ alkyl), $C_1$-$C_3$ alkyl, and $C_1$-$C_3$ haloalkyl. In some such embodiments, said optional substituents are halogen. In some such embodiments, said halogen is F or Cl.

In certain embodiments of formula (I), $A^1$ is $C(R^7)$ or N; $A^2$ is $C(R^8)$ or N; $A^3$ is $C(R^9)$ or N; and $A^4$ is $C(R^{10})$ or N; wherein zero, one, or two of $A^1$, $A^2$, $A^3$, and $A^4$ are N.

In certain embodiments, $A^1$ is $C(R^7)$, $A^2$ is $C(R^8)$, $A^3$ is $C(R^9)$, and $A^4$ is $C(R^{10})$.

In certain embodiments, one of $A^1$, $A^2$, $A^3$, and $A^4$ is N. In some such embodiments, $A^1$ is N; $A^2$ is $C(R^8)$; $A^3$ is $C(R^9)$; and $A^4$ is $C(R^{10})$.

In certain embodiments, two of $A^1$, $A^2$, $A^3$, and $A^4$ are N. In some such embodiments, $A^1$ is N; $A^2$ is $C(R^8)$; $A^3$ is N; and $A^4$ is $C(R^{10})$.

In certain embodiments, $A^1$ is $C(R^7)$, $A^2$ is $C(R^8)$, $A^3$ is $C(R^9)$, and $A^4$ is $C(R^{10})$; or $A^1$ is N; $A^2$ is $C(R^8)$; $A^3$ is $C(R^9)$; and $A^4$ is $C(R^{10})$; or $A^1$ is N; $A^2$ is $C(R^8)$; $A^3$ is N; and $A^4$ is $C(R^{10})$.

In certain embodiments of formula (I), $R^7$, $R^8$, and $R^9$, are each independently H, $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{y1}$, —$OC(O)R^{y2}$, —$OC(O)NR^{y3}R^{y4}$, —$S(O)_2R^{y1}$, —$S(O)_2NR^{y3}R^{y4}$, —$C(O)R^{y1}$, —$C(O)OR^{y1}$, —$C(O)NR^{y3}R^{y4}$, —$NR^{y3}R^{y4}$, —$N(R^{y3})C(O)R^{y2}$, —$N(R^{y3})S(O)_2R^{y1}$, —$N(R^{y3})C(O)O(R^{y2})$, —$N(R^{y3})C(O)NR^{y3}R^{y4}$, —$N(R^{y3})S(O)_2NR^{y3}R^{y4}$, $G^3$, —($C_1$-$C_6$ alkylenyl)-CN, —($C_1$-$C_6$ alkylenyl)-$OR^{y1}$, —($C_1$-$C_6$ alkylenyl)-$OC(O)R^{y2}$, —($C_1$-$C_6$ alkylenyl)-$OC(O)NR^{y3}R^{y4}$, —($C_1$-$C_6$ alkylenyl)-$S(O)_2R^{y1}$, —($C_1$-$C_6$ alkylenyl)-$S(O)_2NR^{y3}R^{y4}$, alkylenyl)-$C(O)R^{y1}$, —($C_1$-$C_6$ alkylenyl)-$C(O)OR^{y1}$, —($C_1$-$C_6$ alkylenyl)-$C(O)NR^{y3}R^{y4}$, —($C_1$-$C_6$ alkylenyl)-$NR^{y3}R^{y4}$, —($C_1$-$C_6$ alkylenyl)-$N(R^{y3})C(O)R^{y2}$, —($C_1$-$C_6$ alkylenyl)-$N(R^{y3})S(O)_2R^{y2}$, —($C_1$-$C_6$ alkylenyl)-$N(R^{y3})C(O)O(R^{y2})$, alkylenyl)-$N(R^{y3})C(O)NR^{y3}R^{y4}$, —($C_1$-$C_6$ alkylenyl)-$N(R^{y3})S(O)_2NR^{y3}R^{y4}$, alkylenyl)-CN, or —($C_1$-$C_6$ alkylenyl)-$G^3$.

In certain embodiments, $R^7$ is H, halogen, —CN, $C_1$-$C_3$ alkyl, or optionally substituted cyclopropyl.

In certain embodiments, $R^7$ is H, halogen, $C_1$-$C_3$ alkyl, or optionally substituted cyclopropyl. In some such embodiments, the cyclopropyl is optionally substituted with 1, 2, 3, 4, or 5 $R^{4g}$ groups, wherein $R^{4g}$ is $C_1$-$C_3$ alkyl, halogen, or $C_1$-$C_3$ haloalkyl.

In certain embodiments, $R^7$ is H or halogen. In some such embodiments, the halogen is F or Cl. In some such embodiments, the halogen is F.

In certain embodiments, $R^8$ is H, $C_1$-$C_6$ alkyl, halogen, $C_1$-$C_6$ haloalkyl, —CN, optionally substituted heterocycle, —$C(O)NR^{y3}R^{y4}$, alkylenyl)-$NR^{y3}R^{y4}$, —($C_1$-$C_6$ alkylenyl)-$N(R^{y3})C(O)R^{y2}$, —($C_1$-$C_6$ alkylenyl)-$N(R^{y3})S(O)_2R^{y2}$, —($C_1$-$C_6$ alkylenyl)-$N(R^{y3})C(O)O(R^{y2})$, —($C_1$-$C_6$ alkylenyl)-$N(R^{y3})C(O)NR^{y3}R^{y4}$, —($C_1$-$C_6$ alkylenyl)-$N(R^{y3})S(O)_2 NR^{y3}R^{y4}$, or —($C_1$-$C_6$ alkylenyl)-$G^3$ wherein $G^3$ is optionally substituted heterocycle.

In certain embodiments, $R^8$ is H.

In certain embodiments, $R^9$ is H, $C_1$-$C_6$ alkyl, halogen, $C_1$-$C_6$ haloalkyl, —CN, —$S(O)_2R^{y1}$, —$S(O)_2NR^{y3}R^{y4}$, —$C(O)NR^{y3}R^{y4}$, —$NR^{y3}R^{y4}$, —$N(R^{y3})C(O)R^{y2}$, —$N(R^{y3})S(O)_2R^{y2}$, —$N(R^{y3})C(O)O(R^{y2})$, —$N(R^{y3})C(O)NR^{y3}R^{y4}$, —$N(R^{y3})S(O)_2NR^{y3}R^{y4}$, —($C_1$-$C_6$ alkylenyl)-CN, —($C_1$-$C_6$ alkylenyl)-$S(O)_2R^{y1}$, —($C_1$-$C_6$ alkylenyl)-$S(O)_2 NR^{y3}R^{y4}$, —($C_1$-$C_6$ alkylenyl)-$C(O)NR^{y3}R^{y4}$, —($C_1$-$C_6$ alkylenyl)-$NR^{y3}R^{y4}$, —($C_1$-$C_6$ alkylenyl)-$N(R^{y3})C(O)R^{y2}$, —($C_1$-$C_6$ alkylenyl)-$N(R^{y3})S(O)_2R^{y2}$, —($C_1$-$C_6$ alkylenyl)-$N(R^{y3})C(O)O(R^{y2})$, —($C_1$-$C_6$ alkylenyl)-$N(R^{y3})C(O) NR^{y3}R^{y4}$, or —($C_1$-$C_6$ alkylenyl)-$N(R^{y3})S(O)_2NR^{y3}R^{y4}$.

In certain embodiments, $R^9$ is H, $C_1$-$C_6$ alkyl, halogen, —$S(O)_2R^{y1}$, —$S(O)_2NR^{y3}R^{y4}$, —$NR^{y3}R^{y4}$, —$N(R^{y3})S(O)_2R^{y2}$, —($C_1$-$C_6$ alkylenyl)-CN, or —($C_1$-$C_6$ alkylenyl)-$S(O)_2R^{y1}$.

In certain embodiments, $R^9$ is H, $C_1$-$C_6$ alkyl, halogen, —$S(O)_2R^{y1}$, —$S(O)_2NR^{y3}R^{y4}$, —$NR^{y3}R^{y4}$, —$N(R^{y3})S(O)_2R^{y2}$, or —($C_1$-$C_6$ alkylenyl)-$S(O)_2R^{y1}$. In some such embodiments, $R^{y1}$, $R^{y3}$, and $R^{y4}$, at each occurrence, are each independently H or $C_1$-$C_6$ alkyl, and $R^{y2}$ is $C_1$-$C_6$ alkyl. In some such embodiments, $R^{y1}$ and $R^{y2}$ are $C_1$-$C_3$ alkyl, and $R^{y3}$ and $R^{y4}$ are hydrogen.

In certain embodiments, $R^9$ is halogen, —$NR^{y3}R^{y4}$, —$N(R^{y3})C(O)R^{y2}$, —$N(R^{y3})S(O)_2R^{y2}$, or —($C_1$-$C_6$ alkylenyl)-$S(O)_2R^{y1}$.

In certain embodiments, $R^9$ is halogen, —$N(R^{y3})S(O)_2R^{y2}$, or —($C_1$-$C_6$ alkylenyl)-$S(O)_2R^{y1}$. In some such embodiments, $R^{y1}$ and $R^{y2}$ are $C_1$-$C_6$ alkyl, and $R^{y3}$ is H.

In some such embodiments, the halogen is F. In some such embodiments, $R^{y1}$ and $R^{y2}$ are each independently methyl or ethyl, and $R^{y3}$ is H.

In certain embodiments, $R^9$ is —($CH_2$)—$S(O)_2R^{y1}$. In some such embodiments, $R^{y1}$ is $C_1$-$C_6$ alkyl. In some such embodiments, $R^{y1}$ is methyl.

In certain embodiments of formula (I), $R^{10}$ is H, $C_1$-$C_3$ alkyl, halogen, $C_1$-$C_3$ haloalkyl, or —CN.

In certain embodiments, $R^{10}$ is H, $C_1$-$C_3$ alkyl, or halogen.

In certain embodiments, $R^{10}$ is H.

Various embodiments of substituents $R^1$, $R^2$, $R^6$, $Y^1$, $Y^2$, $Y^3$, $A^1$, $A^2$, $A^3$, and $A^4$ have been discussed above. These substituents embodiments can be combined to form various embodiments of compounds of formula (I). All embodiments of compounds of formula (I), formed by combining the substituent embodiments discussed above are within the scope of Applicant's invention, and some illustrative embodiments of the compounds of formula (I) are provided below.

In certain embodiments,
$Y^1$ is CH;
$Y^3$ is $CR^3$; and
$Y^2$ is $CR^4R^5$.

In certain embodiments,
$Y^1$ is CH;
$Y^3$ is $CR^3$;
$Y^2$ is $CR^4R^5$; and

R³ is H, —CN, —C(O)R$^{3a}$, —C(O)OR$^{3a}$, —C(O)NR$^{3b}$R$^{3c}$, or C$_1$-C$_6$ alkyl, wherein the C$_1$-C$_6$ alkyl is optionally substituted with a substituent selected from the group consisting of
G¹, —NR$^{3b}$R$^{3c}$, N(R$^{3b}$)C(O)R$^{3d}$, N(R$^{3b}$)SO$_2$R$^{3d}$, N(R$^{3b}$)C(O)OR$^{3d}$, N(R$^{3b}$)C(O)NR$^{3b}$R$^{3c}$, and N(R$^{3b}$)SO$_2$NR$^{3b}$R$^{3c}$.

In some further embodiments, A¹ is C(R⁷), A² is C(R⁸), A³ is C(R⁹), and A⁴ is C(R¹⁰); or A¹ is N, A² is C(R⁸), A³ is C(R⁹), and A⁴ is C(R¹⁰); or A¹ is N, A² is C(R⁸), A³ is N, and A⁴ is C(R¹⁰).

In some further embodiments, A¹ is C(R⁷), A² is C(R⁸), A³ is C(R⁹), and A⁴ is C(R¹⁰).

In some further embodiments, A¹ is N, A² is C(R⁸), A³ is C(R⁹), and A⁴ is C(R¹⁰).

In some further embodiments, A¹ is N, A² is C(R⁸), A³ is N, and A⁴ is C(R¹⁰).

In certain embodiments,
Y¹ is CH;
Y³ is CR³;
Y² is CR⁴R⁵;
R⁴ is H or deuterium; and
R⁵ is H, deuterium, C$_1$-C$_6$ alkyl, C$_2$-C$_6$ alkenyl, C$_2$-C$_6$ alkynyl, C$_1$-C$_6$ haloalkyl, —C(O)R$^{5a}$, —C(O)OR$^{5a}$, or G¹; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G¹, —C(O)R$^{5a}$, —C(O)OR$^{5a}$, —C(O)NR$^{5b}$R$^{5c}$, —C(O)N(R$^{5b}$)NR$^{5b}$R$^{5c}$, —OR$^{5a}$, —OC(O)R$^{5d}$, —NR$^{5b}$R$^{5c}$, N(R$^{5b}$)C(O)R$^{5d}$, N(R$^{5b}$)SO$_2$R$^{5d}$, N(R$^{5b}$)C(O)OR$^{5d}$, N(R$^{5b}$)C(O)NR$^{5b}$R$^{5c}$, and N(R$^{5b}$)SO$_2$NR$^{5b}$R$^{5c}$.

In some further embodiments, A¹ is C(R⁷), A² is C(R⁸), A³ is C(R⁹), and A⁴ is C(R¹⁰); or A¹ is N, A² is C(R⁸), A³ is C(R⁹), and A⁴ is C(R¹⁰); or A¹ is N, A² is C(R⁸), A³ is N, and A⁴ is C(R¹⁰).

In some further embodiments, A¹ is C(R⁷), A² is C(R⁸), A³ is C(R⁹), and A⁴ is C(R¹⁰).

In some further embodiments, A¹ is N, A² is C(R⁸), A³ is C(R⁹), and A⁴ is C(R¹⁰).

In some further embodiments, A¹ is N, A² is C(R⁸), A³ is N, and A⁴ is C(R¹⁰).

In certain embodiments,
Y¹ is CH;
Y³ is CR³;
Y² is CR⁴R⁵; and
R⁶ is H, C$_1$-C$_6$ alkyl, C$_2$-C$_6$ alkenyl, —C(O)R$^{6a}$, —C(O)OR$^{6a}$, —C(O)NR$^{6b}$R$^{6c}$, —S(O)$_2$R$^{6a}$, or G²; wherein the C$_1$-C$_6$ alkyl and the C$_2$-C$_6$ alkenyl are each independently unsubstituted or substituted with 1 or 2 substituents independently selected from the group consisting of G², —CN, —C(O)OR$^{6a}$, —NR$^{6b}$R$^{6c}$, N(R$^{6b}$)C(O)R$^{6d}$, N(R$^{6b}$)SO$_2$R$^{6d}$, N(R$^{6b}$)C(O)OR$^{6d}$, N(R$^{6b}$)C(O)NR$^{6b}$R$^{6c}$, and N(R$^{6b}$)SO$_2$NR$^{6b}$R$^{6c}$.

In some further embodiments, A¹ is C(R⁷), A² is C(R⁸), A³ is C(R⁹), and A⁴ is C(R¹⁰); or A¹ is N, A² is C(R⁸), A³ is C(R⁹), and A⁴ is C(R¹⁰); or A¹ is N, A² is C(R⁸), A³ is N, and A⁴ is C(R¹⁰).

In some further embodiments, A¹ is C(R⁷), A² is C(R⁸), A³ is C(R⁹), and A⁴ is C(R¹⁰).

In some further embodiments, A¹ is N, A² is C(R⁸), A³ is C(R⁹), and A⁴ is C(R¹⁰).

In some further embodiments, A¹ is N, A² is C(R⁸), A³ is N, and A⁴ is C(R¹⁰).

In certain embodiments,
Y¹ is CH;
Y³ is CR³;
Y² is CR⁴R⁵; and
R⁹ is H, C$_1$-C$_6$ alkyl, halogen, C$_1$-C$_6$ haloalkyl, —CN, —S(O)$_2$R$^{y1}$, —S(O)$_2$NR$^{y3}$R$^{y4}$, —C(O)NR$^{y3}$R$^{y4}$, —NR$^{y3}$R$^{y4}$, —N(R$^{y3}$)C(O)R$^{y2}$, —N(R$^{y3}$)S(O)$_2$R$^{y2}$, —N(R$^{y3}$)C(O)O(R$^{y2}$), —N(R$^{y3}$)C(O)NR$^{y3}$R$^{y4}$, —N(R$^{y3}$)S(O)$_2$NR$^{y3}$R$^{y4}$, —(C$_1$-C$_6$ alkylenyl)-S(O)$_2$R$^{y1}$, —(C$_1$-C$_6$ alkylenyl)-S(O)$_2$NR$^{y3}$R$^{y4}$, —(C$_1$-C$_6$ alkylenyl)-C(O)NR$^{y3}$R$^{y4}$, —(C$_1$-C$_6$ alkylenyl)-NR$^{y3}$R$^{y4}$, —(C$_1$-C$_6$ alkylenyl)-N(R$^{y3}$)C(O)R$^{y2}$, —(C$_1$-C$_6$ alkylenyl)-N(R$^{y3}$)S(O)$_2$R$^{y2}$, —(C$_1$-C$_6$ alkylenyl)-N(R$^{y3}$)C(O)O(R$^{y2}$), —(C$_1$-C$_6$ alkylenyl)-N(R$^{y3}$)C(O)NR$^{y3}$R$^{y4}$, or —(C$_1$-C$_6$ alkylenyl)-N(R$^{y3}$)S(O)$_2$NR$^{y3}$R$^{y4}$.

In some further embodiments, A¹ is C(R⁷), A² is C(R⁸), A³ is C(R⁹), and A⁴ is C(R¹⁰); or A¹ is N, A² is C(R⁸), A³ is C(R⁹), and A⁴ is C(R¹⁰); or A¹ is N, A² is C(R⁸), A³ is N, and A⁴ is C(R¹⁰).

In some further embodiments, A¹ is C(R⁷), A² is C(R⁸), A³ is C(R⁹), and A⁴ is C(R¹⁰).

In some further embodiments, A¹ is N, A² is C(R⁸), A³ is C(R⁹), and A⁴ is C(R¹⁰).

In some further embodiments, A¹ is N, A² is C(R⁸), A³ is N, and A⁴ is C(R¹⁰).

In certain embodiments,
Y¹ is CH;
Y³ is CR³;
Y² is CR⁴R⁵; and
A¹ is C(R⁷), A² is C(R⁸), A³ is C(R⁹), and A⁴ is C(R¹⁰); or
A¹ is N, A² is C(R⁸), A³ is C(R⁹), and A⁴ is C(R¹⁰); or
A¹ is N, A² is C(R⁸), A³ is N, and A⁴ is C(R¹⁰).

In some further embodiments, A¹ is C(R⁷), A² is C(R⁸), A³ is C(R⁹), and A⁴ is C(R¹⁰).

In some further embodiments, A¹ is N, A² is C(R⁸), A³ is C(R⁹), and A⁴ is C(R¹⁰).

In some further embodiments, A¹ is N, A² is C(R⁸), A³ is N, and A⁴ is C(R¹⁰).

In certain embodiments,
R¹ is C$_1$-C$_3$ alkyl;
R² is H;
Y¹ is CH;
Y³ is CR³; and
Y² is CR⁴R⁵.

In some further embodiments, R¹ is methyl.

In certain embodiments,
R¹ is C$_1$-C$_3$ alkyl;
R² is H;
Y¹ is CH;
Y³ is CR³;
Y² is CR⁴R⁵;
R⁴ is H or deuterium; and
R⁵ is C$_2$-C$_6$ alkenyl optionally substituted with a G¹ group, or R⁵ is H, deuterium, C$_1$-C$_6$ alkyl, —C(O)R$^{5a}$, —C(O)OR$^{5a}$, or G¹; wherein the C$_1$-C$_6$ alkyl is unsubstituted or substituted with a substituent selected from the group consisting of G¹, —C(O)R$^{5a}$, —C(O)OR$^{5a}$, —C(O)NR$^{5b}$R$^{5c}$, —C(O)N(R$^{5b}$)NR$^{5b}$R$^{5c}$, —OR$^{5a}$, —OC(O)R$^{5d}$, —NR$^{5b}$R$^{5c}$, and N(R$^{5b}$)C(NR$^{5b}$R$^{5c}$)=NR$^{5b}$R$^{5c}$.

In some further embodiments, R¹ is methyl.

In some further embodiments, A¹ is C(R⁷), A² is C(R⁸), A³ is C(R⁹), and A⁴ is C(R¹⁰); or A¹ is N, A² is C(R⁸), A³ is C(R⁹), and A⁴ is C(R¹⁰); or A¹ is N, A² is C(R⁸), A³ is N, and A⁴ is C(R¹⁰).

In some further embodiments, A¹ is C(R⁷), A² is C(R⁸), A³ is C(R⁹), and A⁴ is C(R¹⁰).

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments,
$R^1$ is $C_1$-$C_3$ alkyl;
$R^2$ is H;
$Y^1$ is CH;
$Y^3$ is $CR^3$;
$Y^2$ is $CR^4R^5$; and
$R^3$ is H, —C(O)$R^{3a}$, or —C(O)NR$^{3b}$R$^{3c}$.

In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.

In some further embodiments, $A^1$ is $C(R^7)$, $A^2$ is $C(R^8)$, $A^3$ is $C(R^9)$, and $A^4$ is $C(R^{10})$.

In some further embodiments, A1 is N, A2 is C(R8), A3 is C(R9), and A4 is C(R10).

In some further embodiments, $A^1$ is N, $A^2$ is $C(R^8)$, $A^3$ is N, and $A^4$ is $C(R^{10})$.

In some further embodiments, $R^1$ is methyl.

In some further embodiments, $R^1$ is methyl, and $R^{3a}$ is $G^1$.

In yet some further embodiments, $R^1$ is methyl, $R^{3a}$ is $G^1$ wherein $G^1$ is optionally substituted heterocycle.

In certain embodiments,
$R^1$ is $C_1$-$C_3$ alkyl;
$R^2$ is H;
$Y^1$ is CH;
$Y^3$ is $CR^3$;
$Y^2$ is $CR^4R^5$; and
$R^6$ is H, $C_1$-$C_6$ alkyl, —C(O)$R^{6a}$, —C(O)OR$^{6a}$, —C(O)NR$^{6b}$R$^{6c}$, —S(O)$_2$R$^{6a}$, or $G^2$; wherein the $C_1$-$C_6$ alkyl is unsubstituted or substituted with a substituent selected from the group consisting of $G^2$ and —C(O)OR$^{6a}$.

In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.

In some further embodiments, $R^1$ is methyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments,
$R^1$ is $C_1$-$C_3$ alkyl;
$R^2$ is H;
$Y^1$ is CH;
$Y^3$ is $CR^3$;
$Y^2$ is $CR^4R^5$; and
$R^9$ is H, $C_1$-$C_6$ alkyl, halogen, —S(O)$_2$R$^{y1}$, —S(O)$_2$NR$^{y3}$R$^{y4}$, —NR$^{y3}$R$^{y4}$, —N(R$^{y3}$)S(O)$_2$R$^{y2}$, or —(C$_1$-C$_6$ alkylenyl)-S(O)$_2$R$^{y1}$.

In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^1$ is methyl.

In certain embodiments,
$R^1$ is $C_1$-$C_3$ alkyl;
$R^2$ is H;
$Y^1$ is CH;
$Y^3$ is $CR^3$;
$Y^2$ is $CR^4R^5$; and
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In yet some further embodiments, $R^1$ is methyl.

In certain embodiments,
$R^1$ is methyl;
$R^2$ is H;
$Y^1$ is CH;
$Y^3$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^4$ is H or deuterium;
$R^7$ is H, halogen, $C_1$-$C_3$ alkyl, or optionally substituted cyclopropyl;
$R^8$ is H, $C_1$-$C_6$ alkyl, halogen, $C_1$-$C_6$ haloalkyl, —CN, optionally substituted heterocycle, —C(O)NR$^{y3}$R$^{y4}$, —(C$_1$-C$_6$ alkylenyl)-NR$^{y3}$R$^{y4}$, —(C$_1$-C$_6$ alkylenyl)-N(R$^{y3}$)C(O)R$^{y2}$, —(C$_1$-C$_6$ alkylenyl)-N(R$^{y3}$)S(O)$_2$R$^{y2}$, —(C$_1$-C$_6$ alkylenyl)-N(R$^{y3}$)C(O)O(R$^{y2}$), alkylenyl)-N(R$^{y3}$)C(O)NR$^{y3}$R$^{y4}$, —(C$_1$-C$_6$ alkylenyl)-N(R$^{y3}$)S(O)$_2$NR$^{y3}$R$^{y4}$, or —(C$_1$-C$_6$ alkylenyl)-G$^3$ wherein G$^3$ is optionally substituted heterocycle; and
$R^{10}$ is H, $C_1$-$C_3$ alkyl, or halogen.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In one embodiment, the invention is directed to compounds of formula (I), wherein
$R^1$ is methyl;
$R^2$ is H;
$Y^1$ is CH;
$Y^3$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^4$ is H or deuterium;
$R^7$ is H, halogen, $C_1$-$C_3$ alkyl, or optionally substituted cyclopropyl;
$R^8$ is H, $C_1$-$C_6$ alkyl, halogen, $C_1$-$C_6$ haloalkyl, —CN, optionally substituted heterocycle, —C(O)NR$^{y3}$R$^{y4}$, —(C$_1$-C$_6$ alkylenyl)-NR$^{y3}$R$^{y4}$, —(C$_1$-C$_6$ alkylenyl)-N(R$^{y3}$)C(O)R$^{y2}$, —(C$_1$-C$_6$ alkylenyl)-N(R$^{y3}$)S(O)$_2$R$^{y2}$, —(C$_1$-C$_6$ alkylenyl)-N(R$^{y3}$)C(O)O(R$^{y2}$), —(C$_1$-C$_6$ alkylenyl)-N(R$^{y3}$)C(O)NR$^{y3}$R$^{y4}$, —(C$_1$-C$_6$ alkylenyl)-N(R$^{y3}$)S(O)$_2$NR$^{y3}$R$^{y4}$, or —(C$_1$-C$_6$ alkylenyl)-G$^3$ wherein G$^3$ is optionally substituted heterocycle;

$R^{10}$ is H, $C_1$-$C_3$ alkyl, or halogen; and
$R^3$ is H or —C(O)NR$^{3b}$R$^{3c}$.

In some further embodiments, $R^{3b}$ and $R^{3c}$ are each independently H or $C_1$-$C_6$ alkyl.

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In one embodiment, the invention is directed to compounds of formula (I), wherein
$R^1$ is methyl;
$R^2$ is H;
$Y^1$ is CH;
$Y^3$ is CR$^3$;
$Y^2$ is CR$^4$R$^5$;
$A^1$ is C($R^7$), $A^2$ is C($R^8$), $A^3$ is C($R^9$), and $A^4$ is C($R^{10}$); or
$A^1$ is N, $A^2$ is C($R^8$), $A^3$ is C($R^9$), and $A^4$ is C($R^{10}$); or
$A^1$ is N, $A^2$ is C($R^8$), $A^3$ is N, and $A^4$ is C($R^{10}$);
$R^4$ is H or deuterium;
$R^7$ is H, halogen, $C_1$-$C_3$ alkyl, or optionally substituted cyclopropyl;
$R^8$ is H, $C_1$-$C_6$ alkyl, halogen, $C_1$-$C_6$ haloalkyl, —CN, optionally substituted heterocycle, —C(O)NR$^{y3}$R$^{y4}$, —($C_1$-$C_6$ alkylenyl)-NR$^{y3}$R$^{y4}$, —($C_1$-$C_6$ alkylenyl)-N(R$^{y3}$)C(O)R$^{y2}$, —($C_1$-$C_6$ alkylenyl)-N(R$^{y3}$)S(O)$_2$R$^{y2}$, —($C_1$-$C_6$ alkylenyl)-N(R$^{y3}$)C(O)O(R$^{y2}$), —($C_1$-$C_6$ alkylenyl)-N(R$^{y3}$)C(O)NR$^{y3}$R$^{y4}$, —($C_1$-$C_6$ alkylenyl)-N(R$^{y3}$)S(O)$_2$NR$^{y3}$R$^{y4}$, or —($C_1$-$C_6$ alkylenyl)-G$^3$ wherein G$^3$ is optionally substituted heterocycle;
$R^{10}$ is H, $C_1$-$C_3$ alkyl, or halogen; and
$R^5$ is H, deuterium, or $C_1$-$C_6$ alkyl optionally substituted with a substituent selected from the group consisting of —C(O)OR$^{5a}$ and OR$^{5a}$.

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In yet some further embodiments, $R^{5a}$ is $C_1$-$C_6$ alkyl.

In one embodiment, the invention is directed to compounds of formula (I), wherein
$R^1$ is methyl;
$R^2$ is H;
$Y^1$ is CH;
$Y^3$ is CR$^3$;
$Y^2$ is CR$^4$R$^5$;
$A^1$ is C($R^7$), $A^2$ is C($R^8$), $A^3$ is C($R^9$), and $A^4$ is C($R^{10}$); or
$A^1$ is N, $A^2$ is C($R^8$), $A^3$ is C($R^9$), and $A^4$ is C($R^{10}$); or
$A^1$ is N, $A^2$ is C($R^8$), $A^3$ is N, and $A^4$ is C($R^{10}$);
$R^4$ is H or deuterium;
$R^7$ is H, halogen, $C_1$-$C_3$ alkyl, or optionally substituted cyclopropyl;
$R^8$ is H, $C_1$-$C_6$ alkyl, halogen, $C_1$-$C_6$ haloalkyl, —CN, optionally substituted heterocycle, —C(O)NR$^{y3}$R$^{y4}$, —($C_1$-$C_6$ alkylenyl)-NR$^{y3}$R$^{y4}$, —($C_1$-$C_6$ alkylenyl)-N(R$^{y3}$)C(O)R$^{y2}$, —($C_1$-$C_6$ alkylenyl)-N(R$^{y3}$)S(O)$_2$R$^{y2}$, —($C_1$-$C_6$ alkylenyl)-N(R$^{y3}$)C(O)O(R$^{y2}$), —($C_1$-$C_6$ alkylenyl)-N(R$^{y3}$)C(O)NR$^{y3}$R$^{y4}$, —($C_1$-$C_6$ alkylenyl)-N(R$^{y3}$)S(O)$_2$NR$^{y3}$R$^{y4}$, or —($C_1$-$C_6$ alkylenyl)-G$^3$ wherein G$^3$ is optionally substituted heterocycle;
$R^{10}$ is H, $C_1$-$C_3$ alkyl, or halogen; and
$R^6$ is —C(O)R$^{6a}$, —C(O)OR$^{6a}$, —C(O)NR$^{6b}$R$^{6c}$, G$^2$, or $C_1$-$C_6$ alkyl which is unsubstituted or substituted with a G$^2$ group.

In some further embodiments, $R^{6a}$ is G$^2$ or unsubstituted $C_1$-$C_6$ alkyl.

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In one embodiment, the invention is directed to compounds of formula (I), wherein
$R^1$ is methyl;
$R^2$ is H;
$Y^1$ is CH;
$Y^3$ is CR$^3$;
$Y^2$ is CR$^4$R$^5$;
$A^1$ is C($R^7$), $A^2$ is C($R^8$), $A^3$ is C($R^9$), and $A^4$ is C($R^{10}$); or
$A^1$ is N, $A^2$ is C($R^8$), $A^3$ is C($R^9$), and $A^4$ is C($R^{10}$); or
$A^1$ is N, $A^2$ is C($R^8$), $A^3$ is N, and $A^4$ is C($R^{10}$);
$R^4$ is H or deuterium;
$R^7$ is H, halogen, $C_1$-$C_3$ alkyl, or optionally substituted cyclopropyl;
$R^8$ is H, $C_1$-$C_6$ alkyl, halogen, $C_1$-$C_6$ haloalkyl, —CN, optionally substituted heterocycle, —C(O)NR$^{y3}$R$^{y4}$, —($C_1$-$C_6$ alkylenyl)-NR$^{y3}$R$^{y4}$, —($C_1$-$C_6$ alkylenyl)-N(R$^{y3}$)C(O)R$^{y2}$, —($C_1$-$C_6$ alkylenyl)-N(R$^{y3}$)S(O)$_2$R$^{y2}$, —($C_1$-$C_6$ alkylenyl)-N(R$^{y3}$)C(O)O(R$^{y2}$), —($C_1$-$C_6$ alkylenyl)-N(R$^{y3}$)C(O)NR$^{y3}$R$^{y4}$, —($C_1$-$C_6$ alkylenyl)-N(R$^{y3}$)S(O)$_2$NR$^{y3}$R$^{y4}$, or —($C_1$-$C_6$ alkylenyl)-G$^3$ wherein G$^3$ is optionally substituted heterocycle;
$R^{10}$ is H, $C_1$-$C_3$ alkyl, or halogen; and
$R^9$ is halogen, —NR$^{y3}$R$^{y4}$, —N(R$^{y3}$)C(O)R$^{y2}$, —N(R$^{y3}$)S(O)$_2$R$^{y2}$, or —($C_1$-$C_6$ alkylenyl)-S(O)$_2$R$^{y1}$.

In some further embodiments, $A^1$ is C($R^7$), $A^2$ is C($R^8$), $A^3$ is C($R^9$), and $A^4$ is C($R^{10}$);

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In certain embodiments,
$R^1$ is methyl;
$R^2$ is H;
$Y^1$ is CH;
$Y^3$ is CR$^3$;
$Y^2$ is CR$^4$R$^5$;
$A^1$ is C($R^7$), $A^2$ is C($R^8$), $A^3$ is C($R^9$), and $A^4$ is C($R^{10}$); or
$A^1$ is N, $A^2$ is C($R^8$), $A^3$ is C($R^9$), and $A^4$ is C($R^{10}$); or
$A^1$ is N, $A^2$ is C($R^8$), $A^3$ is N, and $A^4$ is C($R^{10}$);
$R^4$ is H or deuterium;
$R^7$ is H or halogen;
$R^8$ is H; and
$R^{10}$ is H.

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In certain embodiments,
$R^1$ is methyl;
$R^2$ is H;
$Y^1$ is CH;
$Y^3$ is CR$^3$;

$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$; and
$R^4$ is H or deuterium;
$R^7$ is H or halogen;
$R^8$ is H;
$R^{10}$ is H; and
$R^9$ is halogen, $-N(R^{y3})S(O)_2R^{y2}$, or $-(C_1\text{-}C_6$ alkylenyl)-$S(O)_2R^{y1}$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{y1}$ and $R^{y2}$ are $C_1\text{-}C_6$ alkyl, and $R^{y3}$ is H.

In certain embodiments,
$R^1$ is methyl;
$R^2$ is H;
$Y^1$ is CH;
$Y^3$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^4$ is H or deuterium;
$R^7$ is H or halogen;
$R^8$ is H;
$R^{10}$ is H;
$R^9$ is halogen, $-N(R^{y3})S(O)_2R^{y2}$, or $-(C_1\text{-}C_6$ alkylenyl)-$S(O)_2R^{y1}$; and
$R^6$ is $-C(O)R^{6a}$, $-C(O)OR^{6a}$, $-C(O)NR^{6b}R^{6c}$, $G^2$, or $C_1\text{-}C_6$ alkyl which is unsubstituted or substituted with a $G^2$ group.

In some further embodiments, $R^{6a}$ is $G^2$ or unsubstituted $C_1\text{-}C_6$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{y1}$ and $R^{y2}$ are $C_1\text{-}C_6$ alkyl, and $R^{y3}$ is H.

In certain embodiments,
$R^1$ is methyl;
$R^2$ is H;
$Y^1$ is CH;
$Y^3$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^4$ is H or deuterium;
$R^7$ is H or halogen;
$R^8$ is H;
$R^{10}$ is H;
$R^9$ is halogen, $-N(R^{y3})S(O)_2R^{y2}$, or $-(C_1\text{-}C_6$ alkylenyl)-$S(O)_2R^{y1}$;
$R^6$ is $-C(O)R^{6a}$, $-C(O)OR^{6a}$, $-C(O)NR^{6b}R^{6c}$, $G^2$, or $C_1\text{-}C_6$ alkyl which is unsubstituted or substituted with a $G^2$ group;
$R^5$ is H, deuterium, or $C_1\text{-}C_6$ alkyl optionally substituted with a substituent selected from the group consisting of $-C(O)OR^{5a}$ and $OR^{5a}$; and
$R^3$ is H or $-C(O)NR^{3b}R^{3c}$.

In some further embodiments, $R^{6a}$ is $G^2$ or unsubstituted $C_1\text{-}C_6$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments,
$R^1$ is methyl;
$R^2$ is H;
$Y^1$ is CH;
$Y^3$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^4$ is H or deuterium;
$R^7$ is H or halogen;
$R^8$ is H;
$R^{10}$ is H;
$R^9$ is halogen, $-N(R^{y3})S(O)_2R^{y2}$, or $-(C_1\text{-}C_6$ alkylenyl)-$S(O)_2R^{y1}$;
$R^6$ is $-C(O)R^{6a}$, $-C(O)OR^{6a}$, $-C(O)NR^{6b}R^{6c}$, $G^2$, or $C_1\text{-}C_6$ alkyl which is unsubstituted or substituted with a $G^2$ group;
$R^5$ is H, deuterium, or $C_1\text{-}C_6$ alkyl optionally substituted with a substituent selected from the group consisting of $-C(O)OR^{5a}$ and $OR^{5a}$;
$R^3$ is H or $-C(O)NR^{3b}R^{3c}$;

$R^{3b}$ and $R^{3c}$ are each independently H or $C_1$-$C_6$ alkyl;
$R^{5a}$ is $C_1$-$C_6$ alkyl;
$R^{y1}$ and $R^{y2}$ are $C_1$-$C_6$ alkyl; and
$R^{y3}$ is H.

In some further embodiments, $R^{6a}$ is $G^2$ or unsubstituted $C_1$-$C_6$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments,
$R^1$ is methyl;
$R^2$ is H;
$Y^1$ is CH;
$Y^3$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^4$ is H or deuterium;
$R^7$ is H or halogen;
$R^8$ is H;
$R^{10}$ is H;
$R^9$ is halogen, —$N(R^{y3})S(O)_2R^{y2}$, or —($C_1$-$C_6$ alkylenyl)-$S(O)_2R^{y1}$;
$R^6$ is $G^2$ or $C_1$-$C_6$ alkyl which is unsubstituted or substituted with a $G^2$ group;
$R^5$ is H, deuterium, or $C_1$-$C_6$ alkyl optionally substituted with a substituent selected from the group consisting of —$C(O)OR^{5a}$ and $OR^{5a}$;
$R^3$ is H or —$C(O)NR^{3b}R^{3c}$;
$R^{3b}$ and $R^{3c}$ are each independently H or $C_1$-$C_6$ alkyl;
$R^{y1}$ is $C_1$-$C_6$ alkyl;
$R^{y1}$ and $R^{y2}$ are $C_1$-$C_6$ alkyl; and
$R^{y3}$ is H.

In some further embodiments, $R^6$ is optionally substituted aryl, optionally substituted heteroaryl, or optionally substituted cycloalkyl; or $R^6$ is $C_1$-$C_6$ alkyl which is unsubstituted or substituted with a substituent selected from the group consisting of cycloalkyl and heterocycle, each of which is optionally substituted.

In some further embodiments, $R^6$ is optionally substituted phenyl, optionally substituted cyclohexyl, optionally substituted pyridinyl, or $C_1$-$C_6$ alkyl which is unsubstituted or substituted with a $G^2$ group wherein $G^2$ is cyclopropyl or tetrahydrofuranyl, each of which is optionally substituted.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments,
$R^1$ is methyl;
$R^2$ is H;
$Y^1$ is CH;
$Y^3$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^3$ is H, —$C(O)NR^{3b}R^{3c}$, —CN, or $C_1$-$C_6$ alkyl which is substituted with a $G^1$ group;
wherein $G^1$ is an optionally substituted $C_4$-$C_6$ heterocycle;
$R^4$ is H or deuterium;
$R^7$ is H, halogen, —CN, $C_1$-$C_3$ alkyl, or optionally substituted cyclopropyl;
$R^8$ is H;
$R^9$ is halogen, —$N(R^{y3})S(O)_2R^{y2}$, or —($C_1$-$C_6$ alkylenyl)-$S(O)_2R^{y1}$; and
$R^{10}$ is H.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{3b}$ is H or $C_1$-$C_6$ alkyl; and $R^{3c}$ is H, $C_1$-$C_6$ alkyl, $C_1$-$C_6$ haloalkyl, $G^1$, or —($C_1$-$C_6$ alkylenyl)-$G^1$.

In some further embodiments, $R^{3b}$ and $R^{3c}$ are each independently H or $C_1$-$C_6$ alkyl.

In some further embodiments, $R^{y1}$ and $R^{y2}$ are $C_1$-$C_6$ alkyl; and $R^{y3}$ is H.

In certain embodiments,
$R^1$ is methyl;
$R^2$ is H;
$Y^1$ is CH;
$Y^3$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^3$ is H, —$C(O)NR^{3b}R^{3c}$, —CN, or $C_1$-$C_6$ alkyl which is substituted with a $G^1$ group;
wherein $G^1$ is an optionally substituted $C_4$-$C_6$ heterocycle;
$R^4$ is H or deuterium;
$R^7$ is H, halogen, —CN, $C_1$-$C_3$ alkyl, or optionally substituted cyclopropyl;
$R^8$ is H;
$R^9$ is halogen, —$N(R^{y3})S(O)_2R^{y2}$, or —($C_1$-$C_6$ alkylenyl)-$S(O)_2R^{y1}$;
$R^{10}$ is H; and
$R^5$ is H.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{3b}$ and $R^{3c}$ are each independently H or $C_1$-$C_6$ alkyl.

In some further embodiments, $R^{y1}$ and $R^{y2}$ are $C_1$-$C_6$ alkyl; and $R^{y3}$ is H.

In certain embodiments,
$R^1$ is methyl;
$R^2$ is H;
$Y^1$ is CH;
$Y^3$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^3$ is H, —$C(O)NR^{3b}R^{3b}$, —CN, or $C_1$-$C_6$ alkyl which is substituted with a $G^1$ group; wherein $G^1$ is an optionally substituted $C_4$-$C_6$ heterocycle;

R⁴ is H or deuterium;
R⁷ is H, halogen, —CN, $C_1$-$C_3$ alkyl, or optionally substituted cyclopropyl;
R⁸ is H;
R⁹ is halogen, —N($R^{y3}$)S(O)$_2$$R^{y2}$, or —($C_1$-$C_6$ alkylenyl)-S(O)$_2$$R^{y1}$;
R¹⁰ is H;
R⁵ is H; and
R⁶ is phenyl, pyridinyl, or cyclohexyl; each of which is optionally substituted; or R⁶ is —C(O)O($C_1$-$C_6$ alkyl); or R⁶ is —CH$_2$-(optionally substituted tetrahydropyranyl).

In some further embodiments, A¹ is C(R⁷), A² is C(R⁸), A³ is C(R⁹), and A⁴ is C(R¹⁰).
In some further embodiments, A¹ is N, A² is C(R⁸), A³ is C(R⁹), and A⁴ is C(R¹⁰).
In some further embodiments, A¹ is N, A² is C(R⁸), A³ is N, and A⁴ is C(R¹⁰).
In some further embodiments, $R^{3b}$ and $R^{3c}$ are each independently H or $C_1$-$C_6$ alkyl.
In some further embodiments, $R^{y1}$ and $R^{y2}$ are $C_1$-$C_6$ alkyl; and $R^{y3}$ is H.

In certain embodiments,
R¹ is methyl;
R² is H;
Y¹ is CH;
Y³ is CR³;
Y² is CR⁴R⁵;
A¹ is C(R⁷), A² is C(R⁸), A³ is C(R⁹), and A⁴ is C(R¹⁰); or
A¹ is N, A² is C(R⁸), A³ is C(R⁹), and A⁴ is C(R¹⁰); or
A¹ is N, A² is C(R⁸), A³ is N, and A⁴ is C(R¹⁰);
R³ is G¹;
R⁴ is H or deuterium;
R⁷ is H, halogen, —CN, $C_1$-$C_3$ alkyl, or optionally substituted cyclopropyl;
R⁸ is H;
R⁹ is —S(O)$_2$$R^{y1}$, —N($R^{y3}$)S(O)$_2$$R^{y2}$, or —($C_1$-$C_6$ alkylenyl)-S(O)$_2$$R^{y1}$; and
R¹⁰ is H.

In some further embodiments, A¹ is C(R⁷), A² is C(R⁸), A³ is C(R⁹), and A⁴ is C(R¹⁰).
In some further embodiments, A¹ is N, A² is C(R⁸), A³ is C(R⁹), and A⁴ is C(R¹⁰).
In some further embodiments, A¹ is N, A² is C(R⁸), A³ is N, and A⁴ is C(R¹⁰).
In some further embodiments, $R^{y1}$ and $R^{y2}$ are $C_1$-$C_6$ alkyl; and $R^{y3}$ is H.

In certain embodiments,
R¹ is methyl;
R² is H;
Y¹ is CH;
Y³ is CR³;
Y² is CR⁴R⁵;
A¹ is C(R⁷), A² is C(R⁸), A³ is C(R⁹), and A⁴ is C(R¹⁰); or
A¹ is N, A² is C(R⁸), A³ is C(R⁹), and A⁴ is C(R¹⁰); or
A¹ is N, A² is C(R⁸), A³ is N, and A⁴ is C(R¹⁰);
R³ is G¹; wherein G¹ is optionally substituted heteroaryl;
R⁴ is H or deuterium;
R⁷ is H, halogen, —CN, $C_1$-$C_3$ alkyl, or optionally substituted cyclopropyl;
R⁸ is H;
R⁹ is —S(O)$_2$$R^{y1}$, —N($R^{y3}$)S(O)$_2$$R^{y2}$, or —($C_1$-$C_6$ alkylenyl)-S(O)$_2$$R^{y1}$;
R¹⁰ is H; and
R⁵ is H.

In some further embodiments, A¹ is C(R⁷), A² is C(R⁸), A³ is C(R⁹), and A⁴ is C(R¹⁰).
In some further embodiments, A¹ is N, A² is C(R⁸), A³ is C(R⁹), and A⁴ is C(R¹⁰).
In some further embodiments, A¹ is N, A² is C(R⁸), A³ is N, and A⁴ is C(R¹⁰).
In some further embodiments, $R^{y1}$ and $R^{y2}$ are $C_1$-$C_6$ alkyl; and $R^{y3}$ is H.

In certain embodiments,
R¹ is methyl;
R² is H;
Y¹ is CH;
Y³ is CR³;
Y² is CR⁴R⁵;
A¹ is C(R⁷), A² is C(R⁸), A³ is C(R⁹), and A⁴ is C(R¹⁰); or
A¹ is N, A² is C(R⁸), A³ is C(R⁹), and A⁴ is C(R¹⁰); or
A¹ is N, A² is C(R⁸), A³ is N, and A⁴ is C(R¹⁰);
R³ is G¹; wherein G¹ is optionally substituted pyrazolyl;
R⁴ is H or deuterium;
R⁷ is H, halogen, —CN, $C_1$-$C_3$ alkyl, or optionally substituted cyclopropyl;
R⁸ is H;
R⁹ is —S(O)$_2$$R^{y1}$;
R¹⁰ is H;
R⁵ is H; and
R⁶ is phenyl, pyridinyl, or cyclohexyl; each of which is optionally substituted; or R⁶ is —C(O)O($C_1$-$C_6$ alkyl); or R⁶ is —CH$_2$-(optionally substituted tetrahydropyranyl).

In some further embodiments, A¹ is C(R⁷), A² is C(R⁸), A³ is C(R⁹), and A⁴ is C(R¹⁰).
In some further embodiments, A¹ is N, A² is C(R⁸), A³ is C(R⁹), and A⁴ is C(R¹⁰).
In some further embodiments, A¹ is N, A² is C(R⁸), A³ is N, and A⁴ is C(R¹⁰).
In some further embodiments, $R^{y1}$ is $C_1$-$C_6$ alkyl.

In certain embodiments,
Y¹ is N or CH;
R¹ is CD$_3$, $C_1$-$C_3$ alkyl, or $C_1$-$C_3$ haloalkyl;
R² is H or $C_1$-$C_3$ alkyl;
Y³ is N or CR³;
R³ is H, $C_1$-$C_6$ alkyl, $C_2$-$C_6$ alkenyl, $C_2$-$C_6$ alkynyl, halogen, $C_1$-$C_6$ haloalkyl, —C(O)$R^{3a}$, —C(O)O$R^{3a}$, —C(O)N$R^{3b}R^{3c}$, —S(O)$R^{3d}$, —S(O)$_2$$R^{3a}$, —S(O)$_2$N$R^{3b}R^{3c}$, or G¹; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of G¹, —C(O)$R^{3a}$, —C(O)O$R^{3a}$, —C(O)N$R^{3b}R^{3c}$, —C(O)N($R^{3b}$)N$R^{3b}R^{3c}$, —S(O)$R^{3d}$, —S(O)$_2$$R^{3a}$, —S(O)$_2$N$R^{3b}R^{3c}$, —O$R^{3a}$, —OC(O)$R^{3d}$, —N$R^{3b}R^{3c}$, N($R^{3b}$)C(O)$R^{3d}$, N($R^{3b}$)SO$_2$$R^{3d}$, N($R^{3b}$)C(O)O$R^{3d}$, N($R^{3b}$)C(O)N$R^{3b}R^{3c}$, N($R^{3b}$)SO$_2$N$R^{3b}R^{3c}$, and N($R^{3b}$)C(N$R^{3b}R^{3c}$)=N$R^{3b}R^{3c}$;
Y² is C(O), S(O)$_2$, or CR⁴R⁵;
R⁴ is H, deuterium, $C_1$-$C_6$ alkyl, halogen, or $C_1$-$C_6$ haloalkyl;
R⁵ is H, deuterium, $C_1$-$C_6$ alkyl, $C_2$-$C_6$ alkenyl, $C_2$-$C_6$ alkynyl, halogen, $C_1$-$C_6$ haloalkyl, —C(O)$R^{5a}$, —C(O)O$R^{5a}$, —C(O)N$R^{5b}R^{5c}$, —S(O)$R^{5d}$, —S(O)$_2$$R^{5a}$, —S(O)$_2$N$R^{5b}R^{5c}$, or G¹; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of G¹, —C(O)$R^{5a}$, —C(O)O$R^{5a}$, —C(O)N$R^{5b}R^{5c}$, —C(O)N($R^{5b}$)N$R^{5b}R^{5c}$, —S(O)$R^{5d}$, —S(O)$_2$$R^{5a}$, —S(O)$_2$NR$^{5b}$R$^{5c}$, —OR$^{5a}$, —OC(O)R$^{5d}$, —NR$^{5b}$R$^{5c}$, N(R$^{5b}$)C(O)R$^{5d}$, N(R$^{5b}$)SO$_2$R$^{5d}$, N(R$^{5b}$)C(O)OR$^{5d}$, N(R$^{5b}$)C(O)NR$^{5b}$R$^{5c}$, N(R$^{5b}$)SO$_2$NR$^{5b}$R$^{5c}$, and N(R$^{5b}$)C(NR$^{5b}$R$^{5c}$)=NR$^{5b}$R$^{5c}$;

R$^{3a}$, R$^{3b}$, R$^{3c}$, R$^{5a}$, R$^{5b}$, and R$^{5c}$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^1$, or —(C$_1$-C$_6$ alkylenyl)-G$^1$;

R$^{3d}$ and R$^{5d}$, at each occurrence, are each independently C$_1$-C$_6$ alkyl, C$_2$-C$_6$ alkenyl, C$_2$-C$_6$ alkynyl, C$_1$-C$_6$ haloalkyl, G$^1$, or —(C$_1$-C$_6$ alkylenyl)-G$^1$;

G$^1$, at each occurrence, is independently aryl, heteroaryl, heterocycle, cycloalkyl, or cycloalkenyl; and each G$^1$ is optionally substituted with 1, 2, 3, 4, or 5 Rig groups;

R$^6$ is H, C$_1$-C$_6$ alkyl, C$_2$-C$_6$ alkenyl, C$_2$-C$_6$ alkynyl, halogen, C$_1$-C$_6$ haloalkyl, —C(O)R$^{6a}$, —C(O)OR$^{6a}$, —C(O)NR$^{6b}$R$^{6c}$, —S(O)$_2$R$^{6a}$, —S(O)$_2$NR$^{6b}$R$^{6c}$, or G$^2$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^2$, —C(O)R$^{6a}$, —C(O)OR$^{6a}$, —C(O)NR$^{6b}$R$^{6c}$, —C(O)N(R$^{6b}$)NR$^{6b}$R$^{6c}$, —S(O)R$^{6d}$, —S(O)$_2$R$^{6a}$, —S(O)$_2$NR$^{6b}$R$^{6c}$, —OR$^{6a}$, —OC(O)R$^{6d}$, —NR$^{6b}$R$^{6c}$, N(R$^{6b}$)C(O)R$^{6d}$, N(R$^{6b}$)SO$_2$R$^{6d}$, N(R$^{6b}$)C(O)OR$^{6d}$, N(R$^{6b}$)C(O)NR$^{6b}$R$^{6c}$, N(R$^{6b}$)SO$_2$NR$^{6b}$R$^{6c}$, and N(R$^{6b}$)C(NR$^{6b}$R$^{6c}$)=NR$^{6b}$R$^{6c}$;

R$^{6a}$, R$^{6b}$, and R$^{6c}$, at each occurrence, are each independently H, alkyl, C$_2$-C$_6$ alkenyl, C$_2$-C$_6$ alkynyl, haloalkyl, G$^2$, —(C$_1$-C$_6$ alkylenyl)-G$^2$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, or —(C$_1$-C$_6$ alkylenyl)-N(R$^e$)S(O)$_2$NR$^c$R$^d$;

R$^{6d}$, at each occurrence, is independently alkyl, C$_2$-C$_6$ alkenyl, C$_2$-C$_6$ alkynyl, haloalkyl, G$^2$, —(C$_1$-C$_6$ alkylenyl)-G$^2$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, or —(C$_1$-C$_6$ alkylenyl)-N(R$^e$)S(O)$_2$NR$^c$R$^d$;

G$^2$, at each occurrence, is independently aryl, heteroaryl, heterocycle, cycloalkyl, or cycloalkenyl; and each G$^2$ is optionally substituted with 1, 2, 3, 4, or 5 R$^{2g}$ groups;

A$^1$ is C(R$^7$) or N; A$^2$ is C(R$^8$) or N; A$^3$ is C(R$^9$) or N; and A$^4$ is C(R$^{10}$) or N; wherein zero, one, or two of A$^1$, A$^2$, A$^3$, and A$^4$ are N;

R$^7$, R$^8$, and R$^9$, are each independently H, C$_1$-C$_6$ alkyl, C$_2$-C$_6$ alkenyl, C$_2$-C$_6$ alkynyl, halogen, C$_1$-C$_6$ haloalkyl, —CN, NO$_2$, —OR$^{y1}$, —OC(O)R$^{y2}$, —OC(O)NR$^{y3}$R$^{y4}$, —SR$^{y1}$, —S(O)$_2$R$^{y1}$, —S(O)$_2$NR$^{y3}$R$^{y4}$, —C(O)R$^{y1}$, —C(O)OR$^{y1}$, —C(O)NR$^{y3}$R$^{y4}$, —NR$^{y3}$R$^{y4}$, —N(R$^{y3}$)C(O)R$^{y2}$, —N(R$^{y3}$)S(O)$_2$R$^{y2}$, —N(R$^{y3}$)C(O)O(R$^{y2}$), —N(R$^{y3}$)C(O)NR$^{y3}$R$^{y4}$, —N(R$^{y3}$)S(O)$_2$NR$^{y3}$R$^{y4}$, G$^3$, —(C$_1$-C$_6$ alkylenyl)-CN, —(C$_1$-C$_6$ alkylenyl)-OR$^{y1}$, —(C$_1$-C$_6$ alkylenyl)-OC(O)R$^{y2}$, —(C$_1$-C$_6$ alkylenyl)-OC(O)NR$^{y3}$R$^{y4}$, —(C$_1$-C$_6$ alkylenyl)-S(O)$_2$R$^{y1}$, —(C$_1$-C$_6$ alkylenyl)-S(O)$_2$NR$^{y3}$R$^{y4}$, —(C$_1$-C$_6$ alkylenyl)-C(O)R$^{y1}$, —(C$_1$-C$_6$ alkylenyl)-C(O)OR$^{y1}$, —(C$_1$-C$_6$ alkylenyl)-C(O)NR$^{y3}$R$^{y4}$, —(C$_1$-C$_6$ alkylenyl)-NR$^{y3}$R$^{y4}$, —(C$_1$-C$_6$ alkylenyl)-N(R$^{y3}$)C(O)R$^{y2}$, —(C$_1$-C$_6$ alkylenyl)-N(R$^{y3}$)S(O)$_2$R$^{y2}$, —(C$_1$-C$_6$ alkylenyl)-N(R$^{y3}$)C(O)O(R$^{y2}$), —(C$_1$-C$_6$ alkylenyl)-N(R$^{y3}$)C(O)NR$^{y3}$R$^{y4}$, —(C$_1$-C$_6$ alkylenyl)-N(R$^{y3}$)S(O)$_2$NR$^{y3}$R$^{y4}$, —(C$_1$-C$_6$ alkylenyl)-CN, or —(C$_1$-C$_6$ alkylenyl)-G$^3$;

R$^{y1}$, R$^{y3}$, and R$^{y4}$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^3$, —(C$_1$-C$_6$ alkylenyl)-G$^3$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, or —(C$_1$-C$_6$ alkylenyl)-N(R$^e$)S(O)$_2$NR$^c$R$^d$;

R$^{y2}$, at each occurrence, is independently C$_1$-C$_6$ alkyl, C$_2$-C$_6$ alkenyl, C$_2$-C$_6$ alkynyl, C$_1$-C$_6$ haloalkyl, G$^3$, —(C$_1$-C$_6$ alkylenyl)-G$^3$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, or —(C$_1$-C$_6$ alkylenyl)-N(R$^e$)S(O)$_2$NR$^c$R$^d$;

G$^3$, at each occurrence, is independently aryl, heteroaryl, cycloalkyl, cycloalkenyl, or heterocycle; and each G$^3$ group is optionally substituted with 1, 2, 3, 4, or 5 R$^{4g}$ groups;

R$^{10}$ is H, C$_1$-C$_3$ alkyl, halogen, C$_1$-C$_3$ haloalkyl, or —CN;

R$^{1g}$, R$^{2g}$, and R$^{4g}$, at each occurrence, is independently selected from the group consisting of oxo, C$_1$-C$_6$ alkyl, C$_2$-C$_6$ alkenyl, C$_2$-C$_6$ alkynyl, halogen, C$_1$-C$_6$ haloalkyl, —CN, NO$_2$, G$^{2a}$, —OR$^a$, —OC(O)R$^b$, —OC(O)NR$^c$R$^d$, —SR$^a$, —S(O)$_2$R$^a$, —S(O)$_2$NR$^c$R$^d$, —C(O)R$^a$, —C(O)OR$^a$, —C(O)NR$^c$R$^d$, —NR$^c$R$^d$, —N(R$^e$)C(O)R$^b$, —N(R$^e$)S(O)$_2$R$^b$, —N(R$^e$)C(O)O(R$^b$), —N(R$^e$)C(O)NR$^c$R$^d$, —N(R$^e$)S(O)$_2$NR$^c$R$^d$, —(C$_1$-C$_6$ alkylenyl)-CN, —(C$_1$-C$_6$ alkylenyl)-G$^{2a}$, —(C$_1$-C$_6$ alkylenyl)-OR$^a$, —(C$_1$-C$_6$ alkylenyl)-OC(O)R$^b$, —(C$_1$-C$_6$ alkylenyl)-OC(O)NR$^c$R$^d$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, —(C$_1$-C$_6$ alkylenyl)-N(R$^e$)S(O)$_2$NR$^c$R$^d$, or —(C$_1$-C$_6$ alkylenyl)-CN;

R$^a$, R$^c$, R$^d$, and R$^e$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^{2a}$, or —(C$_1$-C$_6$ alkylenyl)-G$^{2a}$;

R$^b$, at each occurrence, is independently C$_1$-C$_6$ alkyl, C$_2$-C$_6$ alkenyl, C$_2$-C$_6$ alkynyl, C$_1$-C$_6$ haloalkyl, G$^{2a}$, or —(C$_1$-C$_6$ alkylenyl)-G$^{2a}$;

G$^{2a}$, at each occurrence, are each independently aryl, heteroaryl, heterocycle, cycloalkyl, or cycloalkenyl; and each G$^{2a}$ group is optionally substituted with 1, 2, 3, 4, or 5 R$^{3g}$ groups;

R$^{3g}$, at each occurrence, is independently oxo, C$_1$-C$_6$ alkyl, C$_2$-C$_6$ alkenyl, C$_2$-C$_6$ alkynyl, halogen, C$_1$-C$_6$ haloalkyl, —CN, NO$_2$, —OR$^{z1}$, —OC(O)R$^{z2}$, —OC(O)NR$^{z3}$R$^{z4}$, —SR$^{z1}$, —S(O)$_2$R$^{z1}$, —S(O)$_2$NR$^{z3}$R$^{z4}$, —C(O)R$^{z1}$, —C(O)OR$^{z1}$, —C(O)NR$^{z3}$R$^{z4}$, —NR$^{z3}$R$^{z4}$, —N(R$^{z3}$)C(O)R$^{z2}$, —N(R$^{z3}$)S(O)$_2$R$^{z2}$, —N(R$^{z3}$)C(O)O(R$^{z2}$), —N(R$^{z3}$)C(O)NR$^{z3}$R$^{z4}$, —N(R$^{z3}$)S(O)$_2$NR$^{z3}$R$^{z4}$, —(C$_1$-C$_6$ alkylenyl)-OR$^{z1}$, —(C$_1$-C$_6$ alkylenyl)-OC(O)R$^{z2}$, —(C$_1$-C$_6$ alkylenyl)-OC(O)NR$^{z3}$R$^{z4}$, —(C$_1$-C$_6$ alkylenyl)-S(O)$_2$R$^{z1}$, —(C$_1$-C$_6$ alkylenyl)-S(O)$_2$NR$^{z3}$R$^{z4}$, —(C$_1$-C$_6$ alkylenyl)-C(O)R$^{z1}$, —(C$_1$-C$_6$ alkylenyl)-C(O)OR$^{z1}$, —(C$_1$-C$_6$ alkylenyl)-C(O)NR$^{z3}$R$^{z4}$, —(C$_1$-C$_6$ alkylenyl)-NR$^{z3}$R$^{z4}$, —(C$_1$-C$_6$ alkylenyl)-N(R$^{z3}$)C(O)R$^{z2}$, —(C$_1$-C$_6$ alkylenyl)-N(R$^{z3}$)S(O)$_2$R$^{z2}$, —(C$_1$-C$_6$ alkylenyl)-N(R$^{z3}$)C(O)O(R$^{z2}$), —(C$_1$-C$_6$ alkylenyl)-N(R$^{z3}$)C(O)NR$^{z3}$R$^{z4}$, —(C$_1$-C$_6$ alkylenyl)-N(R$^{z3}$)S(O)$_2$NR$^{z3}$R$^{z4}$, or —(C$_1$-C$_6$ alkylenyl)-CN;

R$^{z1}$, R$^{z3}$, and R$^{z4}$, at each occurrence, are each independently H, C$_1$-C$_6$ alkyl, C$_2$-C$_6$ alkenyl, C$_2$-C$_6$ alkynyl, or C$_1$-C$_6$ haloalkyl; and R$^{z2}$, at each occurrence, is independently C$_1$-C$_6$ alkyl, C$_2$-C$_6$ alkenyl, C$_2$-C$_6$ alkynyl, or C$_1$-C$_6$ haloalkyl.

In certain embodiments,

Y$^1$ is N or CH;

R$^1$ is CD$_3$, C$_1$-C$_3$ alkyl, or C$_1$-C$_3$ haloalkyl;

R$^2$ is H or C$_1$-C$_3$ alkyl;

Y$^3$ is N or CR$^3$;

R$^3$ is H, C$_1$-C$_6$ alkyl, C$_2$-C$_6$ alkenyl, C$_2$-C$_6$ alkynyl, halogen, C$_1$-C$_6$ haloalkyl, —CN, —C(O)R$^{3a}$, —C(O)OR$^{3a}$, —C(O)NR$^{3b}$R$^{3c}$, —S(O)R$^{3d}$, —S(O)$_2$R$^{3a}$, —S(O)$_2$NR$^{3b}$R$^{3c}$, or G$^1$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^1$, —CN, —C(O)R$^{3a}$, —C(O)OR$^{3a}$, —C(O)NR$^{3b}$R$^{3c}$, —C(O)N(R$^{3b}$)NR$^{3b}$R$^{3c}$, —S(O)R$^{3d}$, —S(O)$_2$R$^{3a}$, —S(O)$_2$NR$^{3b}$R$^{3c}$, —OR$^{3a}$, —OC(O)R$^{3d}$, —NR$^{3b}$R$^{3c}$, N(R$^{3b}$)C(O)R$^{3d}$, N(R$^{3b}$)S(O)$_2$R$^{3d}$, N(R$^{3b}$)C(O)OR$^{3d}$, N(R$^{3b}$)C(O)NR$^{3b}$R$^{3c}$, N(R$^{3b}$)S(O)$_2$NR$^{3b}$R$^{3c}$, and N(R$^{3b}$)C(NR$^{3b}$R$^{3c}$)=NR$^{3b}$R$^{3c}$;

Y$^2$ is C(O), S(O)$_2$, or CR$^4$R$^5$;

R$^4$ is H, deuterium, C$_1$-C$_6$ alkyl, halogen, or C$_1$-C$_6$ haloalkyl;

R$^5$ is H, deuterium, C$_1$-C$_6$ alkyl, C$_2$-C$_6$ alkenyl, C$_2$-C$_6$ alkynyl, halogen, C$_1$-C$_6$ haloalkyl, —C(O)R$^{5a}$, —C(O)OR$^{5a}$, —C(O)NR$^{5b}$R$^{5c}$, —S(O)R$^{5d}$, —S(O)$_2$R$^{5a}$, —S(O)$_2$NR$^{5b}$R$^{5c}$, or G$^1$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^1$, —C(O)R$^{5a}$, —C(O)OR$^{5a}$, —C(O)NR$^{5b}$R$^{5c}$, —C(O)N(R$^{5b}$)NR$^{5b}$R$^{5c}$, —S(O)R$^{5d}$, —S(O)$_2$R$^{5a}$, —S(O)$_2$NR$^{5b}$R$^{5c}$, —OR$^{5a}$, —OC(O)R$^{5d}$, —NR$^{5b}$R$^{5c}$, N(R$^{5b}$)C(O)R$^{5d}$, N(R$^{5b}$)S(O)$_2$R$^{5d}$, N(R$^{5b}$)C(O)OR$^{5d}$, N(R$^{5b}$)C(O)NR$^{5b}$R$^{5c}$, N(R$^{5b}$)S(O)$_2$NR$^{5b}$R$^{5c}$, and N(R$^{5b}$)C(NR$^{5b}$R$^{5c}$)=NR$^{5b}$R$^{5c}$;

R$^{3a}$, R$^{3b}$, R$^{3c}$, R$^{5a}$, and R$^{5b}$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^1$, or —(C$_1$-C$_6$ alkylenyl)-G$^1$;

R$^{5c}$, at each occurrence, is independently H, C$_1$-C$_6$ alkyl, C$_2$-C$_6$ alkenyl, C$_2$-C$_6$ alkynyl, C$_1$-C$_6$ haloalkyl, G$^1$, —(C$_1$-C$_6$ alkylenyl)-G$^1$, —(C$_1$-C$_6$ alkylenyl)-CN, —(C$_1$-C$_6$ alkylenyl)-OR$^a$, or —(C$_1$-C$_6$ alkylenyl)-C(O)OR$^a$;

R$^{3d}$, at each occurrence, is independently C$_1$-C$_6$ alkyl, C$_2$-C$_6$ alkenyl, C$_2$-C$_6$ alkynyl, C$_1$-C$_6$ haloalkyl, G$^1$, or —(C$_1$-C$_6$ alkylenyl)-G$^1$;

R$^{5d}$, at each occurrence, is independently C$_1$-C$_6$ alkyl, C$_2$-C$_6$ alkenyl, C$_2$-C$_6$ alkynyl, C$_1$-C$_6$ haloalkyl, G$^1$, —(C$_1$-C$_6$ alkylenyl)-G$^1$, —(C$_1$-C$_6$ alkylenyl)-NR$^c$R$^d$, or —(C$_1$-C$_6$ alkylenyl)-N(R$^e$)C(O)O(R$^b$);

G$^1$, at each occurrence, is independently aryl, heteroaryl, heterocycle, cycloalkyl, or cycloalkenyl; and each G$^1$ is optionally substituted with 1, 2, 3, 4, or 5 Rig groups;

R$^6$ is H, C$_1$-C$_6$ alkyl, C$_2$-C$_6$ alkenyl, C$_2$-C$_6$ alkynyl, halogen, C$_1$-C$_6$ haloalkyl, —C(O)R$^{6a}$, —C(O)OR$^{6a}$, —C(O)NR$^{6b}$R$^{6c}$, —S(O)$_2$R$^{6a}$, —S(O)$_2$NR$^{6b}$R$^{6c}$, or G$^2$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^2$, —C(O)R$^{6a}$, —C(O)OR$^{6a}$, —C(O)NR$^{6b}$R$^{6c}$, —C(O)N(R$^{6b}$)NR$^{6b}$R$^{6c}$, —S(O)R$^{6d}$, —S(O)$_2$R$^{6a}$, —S(O)$_2$NR$^{6b}$R$^{6c}$, —OR$^{6a}$, —OC(O)R$^{6d}$, —NR$^{6b}$R$^{6c}$, N(R$^{6b}$)C(O)R$^{6d}$, N(R$^{6b}$)SO$_2$R$^{6d}$, N(R$^{6b}$)C(O)OR$^{6d}$, N(R$^{6b}$)C(O)NR$^{6b}$R$^{6c}$, N(R$^{6b}$)SO$_2$NR$^{6b}$R$^{6c}$, and N(R$^{6b}$)C(NR$^{6b}$R$^{6c}$)=NR$^{6b}$R$^{6c}$;

R$^{6a}$, R$^{6b}$, and R$^{6c}$, at each occurrence, are each independently H, alkyl, C$_2$-C$_6$ alkenyl, C$_2$-C$_6$ alkynyl, haloalkyl, G$^2$, —(C$_1$-C$_6$ alkylenyl)-G$^2$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, alkylenyl-NR$^c$R$^d$, —(C$_1$-C$_6$ alkylenyl)-N(R$^e$)C(O)R$^b$, alkylenyl-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, or —(C$_1$-C$_6$ alkylenyl)-N(R$^e$)S(O)$_2$NR$^c$R$^d$;

R$^{6d}$, at each occurrence, is independently alkyl, C$_2$-C$_6$ alkenyl, C$_2$-C$_6$ alkynyl, haloalkyl, G$^2$, —(C$_1$-C$_6$ alkylenyl)-G$^2$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, or —(C$_1$-C$_6$ alkylenyl)-N(R$^e$)S(O)$_2$NR$^c$R$^d$;

G$^2$, at each occurrence, is independently aryl, heteroaryl, heterocycle, cycloalkyl, or cycloalkenyl; and each G$^2$ is optionally substituted with 1, 2, 3, 4, or 5 R$^{2g}$ groups;

A$^1$ is C(R$^7$) or N; A$^2$ is C(R$^8$) or N; A$^3$ is C(R$^9$) or N; and A$^4$ is C(R$^{10}$) or N; wherein zero, one, or two of A$^1$, A$^2$, A$^3$, and A$^4$ are N;

R$^7$, R$^8$, and R$^9$, are each independently H, C$_1$-C$_6$ alkyl, C$_2$-C$_6$ alkenyl, C$_2$-C$_6$ alkynyl, halogen, C$_1$-C$_6$ haloalkyl, —CN, NO$_2$, —OR$^{y1}$, —OC(O)R$^{y2}$, —OC(O)NR$^{y3}$R$^{y4}$, —S(O)$_2$R$^{y1}$, —S(O)$_2$NR$^{y3}$R$^{y4}$, —C(O)R$^{y1}$, —C(O)OR$^{y1}$, —C(O)NR$^{y3}$R$^{y4}$, —NR$^{y3}$R$^{y4}$, —N(R$^{y3}$)C(O)R$^{y2}$, —N(R$^{y3}$)S(O)$_2$R$^{y2}$, —N(R$^{y3}$)C(O)O(R$^{y2}$), —N(R$^{y3}$)C(O)NR$^{y3}$R$^{y4}$, —N(R$^{y3}$)S(O)$_2$NR$^{y3}$R$^{y4}$, G$^3$, —(C$_1$-C$_6$ alkylenyl)-CN, —(C$_1$-C$_6$ alkylenyl)-OR$^{y1}$, —(C$_1$-C$_6$ alkylenyl)-OC(O)R$^{y2}$, —(C$_1$-C$_6$ alkylenyl)-OC(O)NR$^{y3}$R$^{y4}$, —(C$_1$-C$_6$ alkylenyl)-S(O)$_2$R$^{y1}$, —(C$_1$-C$_6$ alkylenyl)-S(O)$_2$NR$^{y3}$R$^{y4}$, —(C$_1$-C$_6$ alkylenyl)-C(O)R$^{y1}$, —(C$_1$-C$_6$ alkylenyl)-C(O)OR$^{y1}$, —(C$_1$-C$_6$ alkylenyl)-C(O)NR$^{y3}$R$^{y4}$, —(C$_1$-C$_6$ alkylenyl)-NR$^{y3}$R$^{y4}$, —(C$_1$-C$_6$ alkylenyl)-N(R$^{y3}$)C(O)R$^{y2}$, —(C$_1$-C$_6$ alkylenyl)-N(R$^{y3}$)S(O)$_2$R$^{y2}$, —(C$_1$-C$_6$ alkylenyl)-N(R$^{y3}$)C(O)O(R$^{y2}$), —(C$_1$-C$_6$ alkylenyl)-N(R$^{y3}$)C(O)NR$^{y3}$R$^{y4}$, —(C$_1$-C$_6$ alkylenyl)-N(R$^{y3}$)S(O)$_2$NR$^{y3}$R$^{y4}$, —(C$_1$-C$_6$ alkylenyl)-CN, or —(C$_1$-C$_6$ alkylenyl)-G$^3$;

R$^{y1}$, R$^{y3}$, and R$^{y4}$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^3$, —(C$_1$-C$_6$ alkylenyl)-G$^3$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —($C_1$-$C_6$ alkylenyl)-N($R^e$)C(O)O($R^b$), —($C_1$-$C_6$ alkylenyl)-N($R^e$)C(O)NR$^c$R$^d$, or —($C_1$-$C_6$ alkylenyl)-N($R^e$)S(O)$_2$NR$^c$R$^d$;

$R^{y2}$, at each occurrence, is independently $C_1$-$C_6$ alkyl, $C_2$-$C_6$ alkenyl, $C_2$-$C_6$ alkynyl, $C_1$-$C_6$ haloalkyl, $G^3$, —($C_1$-$C_6$ alkylenyl)-$G^3$, —($C_1$-$C_6$ alkylenyl)-OR$^a$, —($C_1$-$C_6$ alkylenyl)-S(O)$_2$R$^a$, —($C_1$-$C_6$ alkylenyl)-S(O)$_2$NR$^c$R$^d$, —($C_1$-$C_6$ alkylenyl)-C(O)R$^a$, —($C_1$-$C_6$ alkylenyl)-C(O)OR$^a$, —($C_1$-$C_6$ alkylenyl)-C(O)NR$^c$R$^d$, —($C_1$-$C_6$ alkylenyl)-NR$^c$R$^d$, —($C_1$-$C_6$ alkylenyl)-N(R$^e$)C(O)R$^b$, —($C_1$-$C_6$ alkylenyl)-N(R$^e$)S(O)$_2$R$^b$, —($C_1$-$C_6$ alkylenyl)-N(R$^e$)C(O)O(R$^b$), —($C_1$-$C_6$ alkylenyl)-N(R$^e$)C(O)NR$^c$R$^d$, or —($C_1$-$C_6$ alkylenyl)-N(R$^e$)S(O)$_2$NR$^c$R$^d$;

$G^3$, at each occurrence, is independently aryl, heteroaryl, cycloalkyl, cycloalkenyl, or heterocycle; and each $G^3$ group is optionally substituted with 1, 2, 3, 4, or 5 $R^{4g}$ groups;

$R^{10}$ is H, $C_1$-$C_3$ alkyl, halogen, $C_1$-$C_3$ haloalkyl, or —CN;

$R^{1g}$, $R^{2g}$, and $R^{4g}$, at each occurrence, is independently selected from the group consisting of oxo, $C_1$-$C_6$ alkyl, $C_2$-$C_6$ alkenyl, $C_2$-$C_6$ alkynyl, halogen, $C_1$-$C_6$ haloalkyl, —CN, NO$_2$, $G^{2a}$, —OR$^a$, —OC(O)R$^b$, —OC(O)NR$^c$R$^d$, —SR$^a$, —S(O)$_2$R$^a$, —S(O)$_2$NR$^c$R$^d$, —C(O)R$^a$, —C(O)OR$^a$, —C(O)NR$^c$R$^d$, —NR$^c$R$^d$, —N(R$^e$)C(O)R$^b$, —N(R$^e$)S(O)$_2$R$^b$, —N(R$^e$)C(O)O(R$^b$), —N(R$^e$)C(O)NR$^c$R$^d$, —N(R$^e$)S(O)$_2$NR$^c$R$^d$, —($C_1$-$C_6$ alkylenyl)-CN, —($C_1$-$C_6$ alkylenyl)-$G^{2a}$, —($C_1$-$C_6$ alkylenyl)-OR$^a$, —($C_1$-$C_6$ alkylenyl)-OC(O)R$^b$, —($C_1$-$C_6$ alkylenyl)-OC(O)NR$^c$R$^d$, —($C_1$-$C_6$ alkylenyl)-S(O)$_2$R$^a$, —($C_1$-$C_6$ alkylenyl)-S(O)$_2$NR$^c$R$^d$, —($C_1$-$C_6$ alkylenyl)-C(O)R$^a$, —($C_1$-$C_6$ alkylenyl)-C(O)OR$^a$, —($C_1$-$C_6$ alkylenyl)-C(O)NR$^c$R$^d$, —($C_1$-$C_6$ alkylenyl)-NR$^c$R$^d$, —($C_1$-$C_6$ alkylenyl)-N(R$^e$)C(O)R$^b$, —($C_1$-$C_6$ alkylenyl)-N(R$^e$)S(O)$_2$R$^b$, —($C_1$-$C_6$ alkylenyl)-N(R$^e$)C(O)O(R$^b$), —($C_1$-$C_6$ alkylenyl)-N(R$^e$)C(O)NR$^c$R$^d$, —($C_1$-$C_6$ alkylenyl)-N(R$^e$)S(O)$_2$NR$^c$R$^d$, or —($C_1$-$C_6$ alkylenyl)-CN;

$R^a$, $R^c$, $R^d$, and $R^e$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^{2a}$, or —($C_1$-$C_6$ alkylenyl)-$G^{2a}$;

$R^b$, at each occurrence, is independently $C_1$-$C_6$ alkyl, $C_2$-$C_6$ alkenyl, $C_2$-$C_6$ alkynyl, $C_1$-$C_6$ haloalkyl, $G^{2a}$, or —($C_1$-$C_6$ alkylenyl)-$G^{2a}$;

$G^{2a}$, at each occurrence, are each independently aryl, heteroaryl, heterocycle, cycloalkyl, or cycloalkenyl; and each $G^{2a}$ group is optionally substituted with 1, 2, 3, 4, or 5 $R^{3g}$ groups;

$R^{3g}$, at each occurrence, is independently oxo, $C_1$-$C_6$ alkyl, $C_2$-$C_6$ alkenyl, $C_2$-$C_6$ alkynyl, halogen, $C_1$-$C_6$ haloalkyl, —CN, NO$_2$, —OR$^{z1}$, —OC(O)R$^{z2}$, —OC(O)NR$^{z3}$R$^{z4}$, —SR$^{z1}$, —S(O)$_2$R$^{z1}$, —S(O)$_2$NR$^{z3}$R$^{z4}$, —C(O)R$^{z1}$, —C(O)OR$^{z1}$, —C(O)NR$^{z3}$R$^{z4}$, —NR$^{z3}$R$^{z4}$, —N(R$^{z3}$)C(O)R$^{z2}$, —N(R$^{z3}$)S(O)$_2$R$^{z2}$, —N(R$^{z3}$)C(O)O(R$^{z2}$), —N(R$^{z3}$)C(O)NR$^{z3}$R$^{z4}$, —N(R$^{z3}$)S(O)$_2$NR$^{z3}$R$^{z4}$, —($C_1$-$C_6$ alkylenyl)-OR$^{z1}$, —($C_1$-$C_6$ alkylenyl)-OC(O)R$^{z2}$, —($C_1$-$C_6$ alkylenyl)-OC(O)NR$^{z3}$R$^{z4}$, —($C_1$-$C_6$ alkylenyl)-S(O)$_2$R$^{z1}$, —($C_1$-$C_6$ alkylenyl)-S(O)$_2$NR$^{z3}$R$^{z4}$, —($C_1$-$C_6$ alkylenyl)-C(O)R$^{z1}$, —($C_1$-$C_6$ alkylenyl)-C(O)OR$^{z1}$, —($C_1$-$C_6$ alkylenyl)-C(O)NR$^{z3}$R$^{z4}$, —($C_1$-$C_6$ alkylenyl)-NR$^{z3}$R$^{z4}$, —($C_1$-$C_6$ alkylenyl)-N(R$^{z3}$)C(O)R$^{z2}$, —($C_1$-$C_6$ alkylenyl)-N(R$^{z3}$)S(O)$_2$R$^{z2}$, —($C_1$-$C_6$ alkylenyl)-N(R$^{z3}$)C(O)O(R$^{z2}$), —($C_1$-$C_6$ alkylenyl)-N(R$^{z3}$)C(O)NR$^{z3}$R$^{z4}$, —($C_1$-$C_6$ alkylenyl)-N(R$^{z3}$)S(O)$_2$NR$^{z3}$R$^{z4}$, or —($C_1$-$C_6$ alkylenyl)-CN;

$R^{z1}$, $R^{z3}$, and $R^{z4}$, at each occurrence, are each independently H, $C_1$-$C_6$ alkyl, $C_2$-$C_6$ alkenyl, $C_2$-$C_6$ alkynyl, or $C_1$-$C_6$ haloalkyl; and $R^{z2}$, at each occurrence, is independently $C_1$-$C_6$ alkyl, $C_2$-$C_6$ alkenyl, $C_2$-$C_6$ alkynyl, or $C_1$-$C_6$ haloalkyl.

Compounds of formula (I) may contain one or more asymmetrically substituted atoms. Compounds of formula (I) may also exist as individual stereoisomers (including enantiomers and diastereomers) and mixtures thereof. Individual stereoisomers of compounds of formula (I) may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Compounds of formula (I) may also include the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of the invention are named using ChemDraw Ultra Version 12.0.

Exemplary compounds of formula (I) include, but are not limited to:

4-(cyclopropylmethyl)-7-(isopropylsulfonyl)-10-methyl-3,4-dihydro-1H-1,4,10-triazadibenzo[cd,f]azulen-11(10H)-one;

4-(cyclopropylmethyl)-7-(ethylsulfonyl)-10-methyl-3,4-dihydro-1H-1,4,10-triazadibenzo[cd,f]azulen-11(10H)-one;

4-(cyclopropylmethyl)-3-ethyl-7-(ethylsulfonyl)-10-methyl-3,4-dihydro-1H-1,4,10-triazadibenzo[cd,f]azulen-11(10H)-one;

10-methyl-7-(methylsulfonyl)-3,4-dihydro-1H-1,4,10-triazadibenzo[cd,f]azulen-11(10H)-one;

10-methyl-7-((methylsulfonyl)methyl)-3,4-dihydro-1H-1,4,10-triazadibenzo[cd,f]azulen-11(10H)-one;

4-(cyclopropylmethyl)-10-methyl-7-((methylsulfonyl)methyl)-3,4-dihydro-1H-1,4,10-triazadibenzo[cd,f]azulen-11(10H)-one;

ethyl 4-(cyclopropylmethyl)-10-methyl-7-((methylsulfonyl)methyl)-11-oxo-3,4,10,11-tetrahydro-1H-1,4,10-triazadibenzo[cd,f]azulene-3-carboxylate;

4-(4-fluorophenyl)-10-methyl-7-(methylsulfonyl)-3,4-dihydro-1H-1,4,10-triazadibenzo[cd,f]azulen-11(10H)-one;

4-(4-fluorophenyl)-10-methyl-7-((methylsulfonyl)methyl)-3,4-dihydro-1H-1,4,10-triazadibenzo[cd,f]azulen-11(10H)-one;

4-(cyclopropylmethyl)-10-methyl-11-oxo-3,4,10,11-tetrahydro-1H-1,4,5,10-tetraazadibenzo[cd,f]azulene-7-sulfonamide;

4-(4-fluorophenyl)-7,10-dimethyl-3,4-dihydro-1H-1,4,5,10-tetraazadibenzo[cd,f]azulen-11(10H)-one;

4-(2,4-difluorophenyl)-10-methyl-7-((methylsulfonyl)methyl)-3,4-dihydro-1H-1,4,10-triazadibenzo[cd,f]azulen-11(10H)-one;

4-(cyclopropylmethyl)-10-methyl-3,4-dihydro-1H-1,4,10-triazadibenzo[cd,f]azulen-11(10H)-one;

methyl 3-(4-(cyclopropylmethyl)-10-methyl-7-((methylsulfonyl)methyl)-11-oxo-3,4,10,11-tetrahydro-1H-1,4,10-triazadibenzo[cd,f]azulen-3-yl)propanoate;

4-(cyclopropylmethyl)-3-(2-methoxyethyl)-10-methyl-7-((methylsulfonyl)methyl)-3,4-dihydro-1H-1,4,10-triazadibenzo[cd,f]azulen-11(10H)-one;

3-benzyl-10-methyl-7-((methylsulfonyl)methyl)-3,4-dihydro-1H-1,4,10-triazadibenzo[cd,f]azulen-11(10H)-one;

methyl 3-(10-methyl-7-((methylsulfonyl)methyl)-11-oxo-3,4,10,11-tetrahydro-1H-1,4,10-triazadibenzo[cd,f]azulen-3-yl)propanoate;

10-methyl-7-((methylsulfonyl)methyl)-3-phenethyl-3,4-dihydro-1H-1,4,10-triazadibenzo[cd,f]azulen-11(10H)-one;

3-isobutyl-10-methyl-7-((methylsulfonyl)methyl)-3,4-dihydro-1H-1,4,10-triazadibenzo[cd,f]azulen-11(10H)-one;

(E)-3-(4-fluorostyryl)-10-methyl-7-((methylsulfonyl)methyl)-3,4-dihydro-1H-1,4,10-triazadibenzo[cd,f]azulen-11(10H)-one;

7-amino-4-(4-fluorophenyl)-10-methyl-3,4-dihydro-1H-1,4,5,10-tetraazadibenzo[cd,f]azulen-11(10H)-one;

N-(4-(4-fluorophenyl)-10-methyl-11-oxo-3,4,10,11-tetrahydro-1H-1,4,5,10-tetraazadibenzo[cd,f]azulen-7-yl)ethanesulfonamide;

N-(4-(2,4-difluorophenyl)-10-methyl-11-oxo-3,4,10,11-tetrahydro-1H-1,4,5,10-tetraazadibenzo[cd,f]azulen-7-yl)ethanesulfonamide;

4-butyl-10-methyl-7-((methylsulfonyl)methyl)-3,4-dihydro-1H-1,4,10-triazadibenzo[cd,f]azulen-11(10H)-one;

tert-butyl 3-((10-methyl-7-((methylsulfonyl)methyl)-11-oxo-10,11-dihydro-1H-1,4,10-triazadibenzo[cd,f]azulen-4(3H)-yl)methyl)pyrrolidine-1-carboxylate;

10-methyl-7-((methylsulfonyl)methyl)-4-((tetrahydrofuran-3-yl)methyl)-3,4-dihydro-1H-1,4,10-triazadibenzo[cd,f]azulen-11(10H)-one;

4-((4,4-difluorocyclohexyl)methyl)-10-methyl-7-((methylsulfonyl)methyl)-3,4-dihydro-1H-1,4,10-triazadibenzo[cd,f]azulen-11(10H)-one;

tert-butyl 4-((10-methyl-7-((methylsulfonyl)methyl)-11-oxo-10,11-dihydro-1H-1,4,10-triazadibenzo[cd,f]azulen-4(3H)-yl)methyl)piperidine-1-carboxylate;

10-methyl-7-((methylsulfonyl)methyl)-4-((tetrahydro-2H-pyran-3-yl)methyl)-3,4-dihydro-1H-1,4,10-triazadibenzo[cd,f]azulen-11(10H)-one;

4-(4,4-difluorocyclohexyl)-10-methyl-7-((methylsulfonyl)methyl)-3,4-dihydro-1H-1,4,10-triazadibenzo[cd,f]azulen-11(10H)-one;

4-(4-fluorophenyl)-(3,3-$^2$H$_2$)-10-methyl-7-((methylsulfonyl)methyl)-3,4-dihydro-1H-1,4,10-triazadibenzo[cd,f]azulen-11(10H)-one;

7-fluoro-4-(4-fluorophenyl)-10-methyl-3,4-dihydro-1H-1,4,5,10-tetraazadibenzo[cd,f]azulen-11(10H)-one;

4-(4-fluorophenyl)-7,10-dimethyl-3-phenyl-3,4-dihydro-1H-1,4,5,10-tetraazadibenzo[cd,f]azulen-11(10H)-one;

ethyl 4-(4-fluorophenyl)-10-methyl-7-((methylsulfonyl)methyl)-11-oxo-3,4,10,11-tetrahydro-1H-1,4,10-triazadibenzo[cd,f]azulene-3-carboxylate;

tert-butyl 4-(4-(4-fluorophenyl)-10-methyl-7-((methylsulfonyl)methyl)-11-oxo-3,4,10,11-tetrahydro-1H-1,4,10-triazadibenzo[cd,f]azulene-3-carbonyl)piperazine-1-carboxylate;

10-methyl-7-((methylsulfonyl)methyl)-4-(pyrrolidin-3-ylmethyl)-3,4-dihydro-1H-1,4,10-triazadibenzo[cd,f]azulen-11(10H)-one;

10-methyl-7-((methylsulfonyl)methyl)-4-(piperidin-4-ylmethyl)-3,4-dihydro-1H-1,4,10-triazadibenzo[cd,f]azulen-11(10H)-one;

7-fluoro-10-methyl-3,4-dihydro-1H-1,4,5,10-tetraazadibenzo[cd,f]azulen-11(10H)-one;

ethyl 7-fluoro-10-methyl-11-oxo-3,4,10,11-tetrahydro-1H-1,4,5,10-tetraazadibenzo[cd,f]azulene-3-carboxylate;

4-(4-fluorophenyl)-3-(4-methoxypiperidine-1-carbonyl)-10-methyl-7-((methylsulfonyl)methyl)-3,4-dihydro-1H-1,4,10-triazadibenzo[cd,f]azulen-11(10H)-one;

4-(4-fluorophenyl)-10-methyl-3-(4-methylpiperazine-1-carbonyl)-7-((methylsulfonyl)methyl)-3,4-dihydro-1H-1,4,10-triazadibenzo[cd,f]azulen-11(10H)-one;

5,7-difluoro-10-methyl-4-((tetrahydrofuran-3-yl)methyl)-3,4-dihydro-1H-1,4,10-triazadibenzo[cd,f]azulen-11(10H)-one;

ethyl 4-(4-fluorophenyl)-7,10-dimethyl-11-oxo-3,4,10,11-tetrahydro-1H-1,4,5,10-tetraazadibenzo[cd,f]azulene-3-carboxylate;

N-cyclopentyl-10-methyl-7-((methylsulfonyl)methyl)-11-oxo-10,11-dihydro-1H-1,4,10-triazadibenzo[cd,f]azulene-4(3H)-carboxamide;

N-ethyl-10-methyl-7-((methylsulfonyl)methyl)-11-oxo-10,11-dihydro-1H-1,4,10-triazadibenzo[cd,f]azulene-4(3H)-carboxamide;

N-(4-fluorophenyl)-10-methyl-7-((methylsulfonyl)methyl)-11-oxo-10,11-dihydro-1H-1,4,10-triazadibenzo[cd,f]azulene-4(3H)-carboxamide;

4-butyl-5,7-difluoro-10-methyl-3,4-dihydro-1H-1,4,10-triazadibenzo[cd,f]azulen-11(10H)-one;

5,7-difluoro-10-methyl-4-propyl-3,4-dihydro-1H-1,4,10-triazadibenzo[cd,f]azulen-11(10H)-one;

4-(cyclopropylmethyl)-5,7-difluoro-10-methyl-3,4-dihydro-1H-1,4,10-triazadibenzo[cd,f]azulen-11(10H)-one;

methyl 4-(5,7-difluoro-10-methyl-11-oxo-10,11-dihydro-1H-1,4,10-triazadibenzo[cd,f]azulen-4(3H)-yl)butanoate;

5,7-difluoro-10-methyl-4-(3-phenylpropyl)-3,4-dihydro-1H-1,4,10-triazadibenzo[cd,f]azulen-11(10H)-one;

10-methyl-7-((methylsulfonyl)methyl)-11-oxo-N-(o-tolyl)-10,11-dihydro-1H-1,4,10-triazadibenzo[cd,f]azulene-4(3H)-carboxamide;

2-ethylhexyl 10-methyl-7-((methylsulfonyl)methyl)-11-oxo-10,11-dihydro-1H-1,4,10-triazadibenzo[cd,f]azulene-4(3H)-carboxylate;

4-isobutyryl-10-methyl-7-((methylsulfonyl)methyl)-3,4-dihydro-1H-1,4,10-triazadibenzo[cd,f]azulen-11(10H)-one;

5,7-difluoro-10-methyl-4-phenethyl-3,4-dihydro-1H-1,4,10-triazadibenzo[cd,f]azulen-11(10H)-one;

4-(2-(benzo[d][1,3]dioxol-5-yl)ethyl)-5,7-difluoro-10-methyl-3,4-dihydro-1H-1,4,10-triazadibenzo[cd,f]azulen-11(10H)-one;

4-((1Z,3E)-2,4-diphenylbuta-1,3-dien-1-yl)-5,7-difluoro-10-methyl-3,4-dihydro-1H-1,4,10-triazadibenzo[cd,f]azulen-11(10H)-one;

4-(4-chlorophenyl)-10-methyl-7-((methylsulfonyl)methyl)-11-oxo-3,4,10,11-tetrahydro-1H-1,4,10-triazadibenzo[cd,f]azulene-2-carboxamide;

4-(4-chlorophenyl)-N-ethyl-10-methyl-7-((methylsulfonyl)methyl)-11-oxo-3,4,10,11-tetrahydro-1H-1,4,10-triazadibenzo[cd,f]azulene-2-carboxamide;

4-(4-chlorophenyl)-10-methyl-2-(4-methylpiperazine-1-carbonyl)-7-((methylsulfonyl)methyl)-3,4-dihydro-1H-1,4,10-triazadibenzo[cd,f]azulen-11(10H)-one;

N-(2,6-dimethylphenyl)-10-methyl-7-((methylsulfonyl)methyl)-11-oxo-10,11-dihydro-1H-1,4,10-triazadibenzo[cd,f]azulene-4(3H)-carboxamide;

N-(4-methoxyphenyl)-10-methyl-7-((methylsulfonyl)methyl)-11-oxo-10,11-dihydro-1H-1,4,10-triazadibenzo[cd,f]azulene-4(3H)-carboxamide;

N-(4-ethylphenethyl)-10-methyl-7-((methylsulfonyl)methyl)-11-oxo-10,11-dihydro-1H-1,4,10-triazadibenzo[cd,f]azulene-4(3H)-carboxamide;

10-methyl-7-((methylsulfonyl)methyl)-11-oxo-N-propyl-10,11-dihydro-1H-1,4,10-triazadibenzo[cd,f]azulene-4(3H)-carboxamide;

N-(3-methoxybenzyl)-10-methyl-7-((methylsulfonyl)methyl)-11-oxo-10,11-dihydro-1H-1,4,10-triazadibenzo[cd,f]azulene-4(3H)-carboxamide;

N-(2-chloroethyl)-10-methyl-7-((methylsulfonyl)methyl)-11-oxo-10,11-dihydro-1H-1,4,10-triazadibenzo[cd,f]azulene-4(3H)-carboxamide;

N-(cyclohexylmethyl)-10-methyl-7-((methylsulfonyl)methyl)-11-oxo-10,11-dihydro-1H-1,4,10-triazadibenzo[cd,f]azulene-4(3H)-carboxamide;

N-(2,4-difluorophenyl)-10-methyl-7-((methylsulfonyl)methyl)-11-oxo-10,11-dihydro-1H-1,4,10-triazadibenzo[cd,f]azulene-4(3H)-carboxamide;

N-(4-isopropylphenyl)-10-methyl-7-((methylsulfonyl)methyl)-11-oxo-10,11-dihydro-1H-1,4,10-triazadibenzo[cd,f]azulene-4(3H)-carboxamide;

N-(2,6-difluorophenyl)-10-methyl-7-((methylsulfonyl)methyl)-11-oxo-10,11-dihydro-1H-1,4,10-triazadibenzo[cd,f]azulene-4(3H)-carboxamide;

N-(4-fluoro-3-(trifluoromethyl)phenyl)-10-methyl-7-((methylsulfonyl)methyl)-11-oxo-10,11-dihydro-1H-1,4,10-triazadibenzo[cd,f]azulene-4(3H)-carboxamide;

ethyl 4-((10-methyl-7-((methylsulfonyl)methyl)-11-oxo-3,4,10,11-tetrahydro-1H-1,4,10-triazadibenzo[cd,f]azulene-4-carboxamido)methyl)cyclohexanecarboxylate;

N-(3-methoxypropyl)-10-methyl-7-((methylsulfonyl)methyl)-11-oxo-10,11-dihydro-1H-1,4,10-triazadibenzo[cd,f]azulene-4(3H)-carboxamide;

10-methyl-7-((methylsulfonyl)methyl)-4-tosyl-3,4-dihydro-1H-1,4,10-triazadibenzo[cd,f]azulen-11(10H)-one;

4-([1,1'-biphenyl]-4-ylsulfonyl)-10-methyl-7-((methylsulfonyl)methyl)-3,4-dihydro-1H-1,4,10-triazadibenzo[cd,f]azulen-11(10H)-one;

4-((4-methoxyphenyl)sulfonyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(phenylsulfonyl)-3,4-dihydro-1H-1,4,10-triazadibenzo[cd,f]azulen-11(10H)-one;

4-((2-methoxyphenyl)sulfonyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-((4-phenoxyphenyl)sulfonyl)-3,4-dihydro-1H-1,4,10-triazadibenzo[cd,f]azulen-11(10H)-one;

4-((4-fluorophenyl)sulfonyl)-10-methyl-7-((methylsulfonyl)methyl)-3,4-dihydro-1H-1,4,10-triazadibenzo[cd,f]azulen-11(10H)-one;

4-(2-naphthoyl)-10-methyl-7-((methylsulfonyl)methyl)-3,4-dihydro-1H-1,4,10-triazadibenzo[cd,f]azulen-11(10H)-one;

methyl 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoate;

4-(2,4-difluorophenyl)-10-methyl-3,4-dihydro-1H-1,4,5,7,10-pentaazadibenzo[cd,f]azulen-11(10H)-one;

(R)-ethyl 4-(4-fluorophenyl)-10-methyl-7-((methylsulfonyl)methyl)-11-oxo-3,4,10,11-tetrahydro-1H-1,4,10-triazadibenzo[cd,f]azulene-3-carboxylate;

(S)-ethyl 4-(4-fluorophenyl)-10-methyl-7-((methylsulfonyl)methyl)-11-oxo-3,4,10,11-tetrahydro-1H-1,4,10-triazadibenzo[cd,f]azulene-3-carboxylate;

2-methoxyethyl 10-methyl-7-((methylsulfonyl)methyl)-11-oxo-10,11-dihydro-1H-1,4,10-triazadibenzo[cd,f]azulene-4(3H)-carboxylate;

ethyl 10-methyl-7-((methylsulfonyl)methyl)-11-oxo-10,11-dihydro-1H-1,4,10-triazadibenzo[cd,f]azulene-4(3H)-carboxylate;

pentyl 10-methyl-7-((methylsulfonyl)methyl)-11-oxo-10,11-dihydro-1H-1,4,10-triazadibenzo[cd,f]azulene-4(3H)-carboxylate;

4-chlorobutyl 10-methyl-7-((methylsulfonyl)methyl)-11-oxo-10,11-dihydro-1H-1,4,10-triazadibenzo[cd,f]azulene-4(3H)-carboxylate;

naphthalen-2-yl 10-methyl-7-((methylsulfonyl)methyl)-11-oxo-10,11-dihydro-1H-1,4,10-triazadibenzo[cd,f]azulene-4(3H)-carboxylate;

p-tolyl 10-methyl-7-((methylsulfonyl)methyl)-11-oxo-10,11-dihydro-1H-1,4,10-triazadibenzo[cd,f]azulene-4(3H)-carboxylate;

neopentyl 10-methyl-7-((methylsulfonyl)methyl)-11-oxo-10,11-dihydro-1H-1,4,10-triazadibenzo[cd,f]azulene-4(3H)-carboxylate;

phenyl 10-methyl-7-((methylsulfonyl)methyl)-11-oxo-10,11-dihydro-1H-1,4,10-triazadibenzo[cd,f]azulene-4(3H)-carboxylate;

4-fluorophenyl 10-methyl-7-((methylsulfonyl)methyl)-11-oxo-10,11-dihydro-1H-1,4,10-triazadibenzo[cd,f]azulene-4(3H)-carboxylate;

2-methoxyphenyl 10-methyl-7-((methylsulfonyl)methyl)-11-oxo-10,11-dihydro-1H-1,4,10-triazadibenzo[cd,f]azulene-4(3H)-carboxylate;

2-fluoroethyl 10-methyl-7-((methylsulfonyl)methyl)-11-oxo-10,11-dihydro-1H-1,4,10-triazadibenzo[cd,f]azulene-4(3H)-carboxylate;

4-methoxyphenyl 10-methyl-7-((methylsulfonyl)methyl)-11-oxo-10,11-dihydro-1H-1,4,10-triazadibenzo[cd,f]azulene-4(3H)-carboxylate;

but-2-yn-1-yl 10-methyl-7-((methylsulfonyl)methyl)-11-oxo-10,11-dihydro-1H-1,4,10-triazadibenzo[cd,f]azulene-4(3H)-carboxylate;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanamide;

4-(4-fluorobenzoyl)-10-methyl-7-((methylsulfonyl)methyl)-3,4-dihydro-1H-1,4,10-triazadibenzo[cd,f]azulen-11(10H)-one;

4-(3-methoxypropanoyl)-10-methyl-7-((methylsulfonyl)methyl)-3,4-dihydro-1H-1,4,10-triazadibenzo[cd,f]azulen-11(10H)-one;

4-([1,1'-biphenyl]-4-carbonyl)-10-methyl-7-((methylsulfonyl)methyl)-3,4-dihydro-1H-1,4,10-triazadibenzo[cd,f]azulen-11(10H)-one;

4-(3-cyclopentylpropanoyl)-10-methyl-7-((methylsulfonyl)methyl)-3,4-dihydro-1H-1,4,10-triazadibenzo[cd,f]azulen-11(10H)-one;

4-(2-(3-methoxyphenyl)acetyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-propionyl-3,4-dihydro-1H-1,4,10-triazadibenzo[cd,f]azulen-11(10H)-one;

10-methyl-4-(3-methylbutanoyl)-7-((methylsulfonyl)methyl)-3,4-dihydro-1H-1,4,10-triazadibenzo[cd,f]azulen-11(10H)-one;

4-(3,3-dimethylbutanoyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(2-phenylacetyl)-3,4-dihydro-1H-1,4,10-triazadibenzo[cd,f]azulen-11(10H)-one;

4-benzoyl-10-methyl-7-((methylsulfonyl)methyl)-3,4-dihydro-1H-1,4,10-triazadibenzo[cd,f]azulen-11(10H)-one;

4-(4-methoxybenzoyl)-10-methyl-7-((methylsulfonyl)methyl)-3,4-dihydro-1H-1,4,10-triazadibenzo[cd,f]azulen-11(10H)-one;

methyl 4-(10-methyl-7-((methylsulfonyl)methyl)-11-oxo-10,11-dihydro-1H-1,4,10-triazadibenzo[cd,f]azulen-4(3H)-yl)-4-oxobutanoate;

4-(2,4-difluorobenzoyl)-10-methyl-7-((methylsulfonyl)methyl)-3,4-dihydro-1H-1,4,10-triazadibenzo[cd,f]azulen-11(10H)-one;

4-(2-fluorobenzoyl)-10-methyl-7-((methylsulfonyl)methyl)-3,4-dihydro-1H-1,4,10-triazadibenzo[cd,f]azulen-11(10H)-one;

4-(1-naphthoyl)-10-methyl-7-((methylsulfonyl)methyl)-3,4-dihydro-1H-1,4,10-triazadibenzo[cd,f]azulen-11(10H)-one;

4-(cyclopropanecarbonyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(3-phenylpropanoyl)-3,4-dihydro-1H-1,4,10-triazadibenzo[cd,f]azulen-11(10H)-one;

2-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)isoindoline-1,3-dione;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-methylpropanamide;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N,N-dimethylpropanamide;

4-(2,4-difluorophenyl)-10-methyl-7-((methylsulfonyl)methyl)-3-(3-morpholino-3-oxopropyl)-3,4-dihydro-1H-1,4,10-triazadibenzo[cd,f]azulen-11(10H)-one;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-(tetrahydro-2H-pyran-4-yl)propanamide;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N'-methyl-N'-phenylpropanehydrazide;

N-benzyl-3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanamide;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-(1,1-dioxidotetrahydrothiophen-3-yl)propanamide;

tert-butyl 4-(3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoyl)piperazine-1-carboxylate;

tert-butyl 4-(3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanamido)piperidine-1-carboxylate;

4-(4-chlorophenyl)-N-ethyl-10-methyl-11-oxo-3,4,10,11-tetrahydro-1H-1,4,10-triazadibenzo[cd,f]azulene-2-carboxamide;

6-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)hexyl acetate;

3-(aminomethyl)-4-(2,4-difluorophenyl)-10-methyl-7-((methylsulfonyl)methyl)-3,4-dihydro-1H-1,4,10-triazadibenzo[cd,f]azulen-11(10H)-one;

N-((((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)amino)(dimethylamino)methylene)-N-methylmethanaminium;

4-(2,4-difluorophenyl)-10-methyl-7-((methylsulfonyl)methyl)-3-(3-oxo-3-(piperazin-1-yl)propyl)-3,4-dihydro-1H-1,4,10-triazadibenzo[cd,f]azulen-11(10H)-one;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-(piperidin-4-yl)propanamide;

4-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)butane-1,2-diyl diacetate;

methyl 5-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)pentanoate;

tert-butyl (2-(((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)amino)-2-oxoethyl)carbamate;

4-(2,4-difluorophenyl)-3-(6-hydroxyhexyl)-10-methyl-7-((methylsulfonyl)methyl)-3,4-dihydro-1H-1,4,10-triazadibenzo[cd,f]azulen-11(10H)-one;

N-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)benzamide;

1-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)-3-phenylurea;

2-amino-N-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)acetamide;

4-(2,4-difluorophenyl)-3-(3,4-dihydroxybutyl)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-3-(3-hydroxypropyl)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-3-(3-phenoxypropyl)-3,4-dihydro-1H-1,4,10-triazadibenzo[cd,f]azulen-11(10H)-one;

(S)-4-(2,4-difluorophenyl)-10-methyl-7-((methylsulfonyl)methyl)-3-(3-phenoxypropyl)-3,4-dihydro-1H-1,4,10-triazadibenzo[cd,f]azulen-11(10H)-one;

(R)-4-(2,4-difluorophenyl)-10-methyl-7-((methylsulfonyl)methyl)-3-(3-phenoxypropyl)-3,4-dihydro-1H-1,4,10-triazadibenzo[cd,f]azulen-11(10H)-one;

4-(4-chlorophenyl)-10-methyl-2-((4-methylpiperazin-1-yl)methyl)-3,4-dihydro-1H-1,4,10-triazadibenzo[cd,f]azulen-11(10H)-one;

4-(2,4-difluorophenyl)-3-(3-methoxypropyl)-10-methyl-7-((methylsulfonyl)methyl)-3,4-dihydro-1H-1,4,10-triazadibenzo[cd,f]azulen-11(10H)-one;

4-(2,4-difluorophenyl)-3-(3-ethoxypropyl)-10-methyl-7-((methylsulfonyl)methyl)-3,4-dihydro-1H-1,4,10-triazadibenzo[cd,f]azulen-11(10H)-one;

4-isobutyl-10-methyl-7-((methylsulfonyl)methyl)-3,4-dihydro-1H-1,4,10-triazadibenzo[cd,f]azulen-11(10H)-one;

4-((1-ethylpiperidin-3-yl)methyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(tetrahydro-2H-pyran-4-yl)-3,4-dihydro-1H-1,4,10-triazadibenzo[cd,f]azulen-11(10H)-one;

4-((2,2-dimethyltetrahydro-2H-pyran-4-yl)methyl)-10-methyl-7-((methylsulfonyl)methyl)-3,4-dihydro-1H-1,4,10-triazadibenzo[cd,f]azulen-11(10H)-one;

4-(4-ethoxybutan-2-yl)-10-methyl-7-((methylsulfonyl)methyl)-3,4-dihydro-1H-1,4,10-triazadibenzo[cd,f]azulen-11(10H)-one;

N-(2-cyanoethyl)-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

methyl 2-(4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamido)acetate;

4-(2,4-difluorophenyl)-10-methyl-7-((methylsulfonyl)methyl)-11-oxo-N-phenethyl-3,4,10,11-tetrahydro-1H-1,4,10-triazadibenzo[cd,f]azulene-3-carboxamide;

N-butyl-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

N-cyclohexyl-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

N-benzyl-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-10-methyl-7-((methylsulfonyl)methyl)-11-oxo-N-(3-phenylpropyl)-3,4,10,11-tetrahydro-1H-1,4,10-triazadibenzo[cd,f]azulene-3-carboxamide;

4-(2,4-difluorophenyl)-N-isobutyl-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-N-(2-hydroxyethyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-10-methyl-7-((methylsulfonyl)methyl)-N-(oxazol-4-ylmethyl)-11-oxo-3,4,10,11-tetrahydro-1H-1,4,10-triazadibenzo[cd,f]azulene-3-carboxamide;

N-(cyclopropylmethyl)-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-N-(2-hydroxy-2-methylpropyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-N-(1-(hydroxymethyl)cyclopropyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-10-methyl-N-(1-methylcyclopropyl)-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-10-methyl-7-((methylsulfonyl)methyl)-11-oxo-N-(4-phenylbutyl)-3,4,10,11-tetrahydro-1H-1,4,10-triazadibenzo[cd,f]azulene-3-carboxamide;

4-(3,3-dimethylbutanoyl)-5,7-difluoro-10-methyl-3,4-dihydro-1H-1,4,10-triazadibenzo[cd,f]azulen-11(10H)-one;

tert-butyl ((trans)-4-(10-methyl-7-(methylsulfonyl)-11-oxo-10,11-dihydro-1H-1,4,10-triazadibenzo[cd,f]azulen-4(3H)-yl)cyclohexyl)carbamate;

4-((trans)-4-aminocyclohexyl)-10-methyl-7-(methylsulfonyl)-3,4-dihydro-1H-1,4,10-triazadibenzo[cd,f]azulen-11(10H)-one;

4-(cyclopropylsulfonyl)-10-methyl-7-((methylsulfonyl)methyl)-3,4-dihydro-1H-1,4,10-triazadibenzo[cd,f]azulen-11(10H)-one;

ethyl 5,7-difluoro-10-methyl-11-oxo-10,11-dihydro-1H-1,4,10-triazadibenzo[cd,f]azulene-4(3H)-carboxylate;

4-(2,4-difluorophenyl)-10-methyl-3-(3-(methylamino)propyl)-7-((methylsulfonyl)methyl)-3,4-dihydro-1H-1,4,10-triazadibenzo[cd,f]azulen-11(10H)-one;

4-(2,4-difluorophenyl)-3-(3-(dimethylamino)propyl)-10-methyl-7-((methylsulfonyl)methyl)-3,4-dihydro-1H-1,4,10-triazadibenzo[cd,f]azulen-11(10H)-one;

4-(4-chlorophenyl)-10-methyl-2-((4-methylpiperazin-1-yl)methyl)-7-((methylsulfonyl)methyl)-3,4-dihydro-1H-1,4,10-triazadibenzo[cd,f]azulen-11(10H)-one;

2-(4-(4-fluorophenyl)-10-methyl-11-oxo-3,4,10,11-tetrahydro-1H-1,4,10-triazadibenzo[cd,f]azulen-7-yl)acetonitrile;

4-(2,2-dimethyl-3-(pyrrolidin-1-yl)propyl)-10-methyl-7-((methylsulfonyl)methyl)-3,4-dihydro-1H-1,4,10-triazadibenzo[cd,f]azulen-11(10H)-one;

2-(3-(10-methyl-7-((methylsulfonyl)methyl)-11-oxo-10,11-dihydro-1H-1,4,10-triazadibenzo[cd,f]azulen-4(3H)-yl)pyrrolidin-1-yl)acetic acid;

10-methyl-7-((methylsulfonyl)methyl)-4-(2-methyltetrahydrofuran-3-yl)-3,4-dihydro-1H-1,4,10-triazadibenzo[cd,f]azulen-11(10H)-one;

10-methyl-4-(1-methylpiperidin-4-yl)-7-((methylsulfonyl)methyl)-3,4-dihydro-1H-1,4,10-triazadibenzo[cd,f]azulen-11(10H)-one;

10-methyl-7-((methylsulfonyl)methyl)-4-(tetrahydro-2H-pyran-3-yl)-3,4-dihydro-1H-1,4,10-triazadibenzo[cd,f]azulen-11(10H)-one;

4-((1-isopropylpiperidin-4-yl)methyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(1-(2-oxotetrahydrofuran-3-yl)ethyl)-3,4-dihydro-1H-1,4,10-triazadibenzo[cd,f]azulen-11(10H)-one;

4-(1-methoxypropan-2-yl)-10-methyl-7-((methylsulfonyl)methyl)-3,4-dihydro-1H-1,4,10-triazadibenzo[cd,f]azulen-11(10H)-one;

4-(4-methoxybutan-2-yl)-10-methyl-7-((methylsulfonyl)methyl)-3,4-dihydro-1H-1,4,10-triazadibenzo[cd,f]azulen-11(10H)-one;

10-methyl-4-(1-methylpyrrolidin-3-yl)-7-((methylsulfonyl)methyl)-3,4-dihydro-1H-1,4,10-triazadibenzo[cd,f]azulen-11(10H)-one;

10-methyl-7-((methylsulfonyl)methyl)-4-(1-(tetrahydro-2H-pyran-4-yl)ethyl)-3,4-dihydro-1H-1,4,10-triazadibenzo[cd,f]azulen-11(10H)-one;

10-methyl-4-(1-methylazepan-4-yl)-7-((methylsulfonyl)methyl)-3,4-dihydro-1H-1,4,10-triazadibenzo[cd,f]azulen-11(10H)-one;

4-(1-ethylpiperidin-3-yl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(2-(tetrahydro-2H-pyran-4-yl)ethyl)-3,4-dihydro-1H-1,4,10-triazadibenzo[cd,f]azulen-11(10H)-one;

4-(10-methyl-7-((methylsulfonyl)methyl)-11-oxo-10,11-dihydro-1H-1,4,10-triazadibenzo[cd,f]azulen-4(3H)-yl)benzonitrile;

4-(4-chlorophenyl)-10-methyl-7-((methylsulfonyl)methyl)-2-(morpholinomethyl)-3,4-dihydro-1H-1,4,10-triazadibenzo[cd,f]azulen-11(10H)-one;

N-ethyl-4-(4-fluorophenyl)-10-methyl-7-((methylsulfonyl)methyl)-11-oxo-3,4,10,11-tetrahydro-1H-1,4,10-triazadibenzo[cd,f]azulene-2-carboxamide;

5-cyclopropyl-4-(2,4-difluorophenyl)-10-methyl-7-((methylsulfonyl)methyl)-3,4-dihydro-1H-1,4,10-triazadibenzo[cd,f]azulen-11(10H)-one;

tert-butyl (4-(10-methyl-7-((methylsulfonyl)methyl)-11-oxo-10,11-dihydro-1H-1,4,10-triazadibenzo[cd,f]azulen-4(3H)-yl)cyclohexyl)carbamate;

tert-butyl ((trans)-4-(10-methyl-7-((methylsulfonyl)methyl)-11-oxo-10,11-dihydro-1H-1,4,10-triazadibenzo[cd,f]azulen-4(3H)-yl)cyclohexyl)carbamate;

4-(4-chlorophenyl)-10-methyl-7-((methylsulfonyl)methyl)-3,4-dihydro-1H-1,4,10-triazadibenzo[cd,f]azulen-11(10H)-one;

4-(4-chlorophenyl)-10-methyl-7-((methylsulfonyl)methyl)-11-oxo-3,4,10,11-tetrahydro-1H-1,4,10-triazadibenzo[cd,f]azulene-2-carbonitrile;

4-(2,4-difluorophenyl)-3-(hydroxymethyl)-10-methyl-7-((methylsulfonyl)methyl)-3,4-dihydro-1H-1,4,10-triazadibenzo[cd,f]azulen-11(10H)-one;

4-(4-chlorophenyl)-10-methyl-11-oxo-3,4,10,11-tetrahydro-1H-1,4,10-triazadibenzo[cd,f]azulene-2-carbonitrile;

4-(2,4-difluorophenyl)-N-ethyl-10-methyl-7-((methylsulfonyl)methyl)-11-oxo-3,4,10,11-tetrahydro-1H-1,4,10-triazadibenzo[cd,f]azulene-2-carboxamide;

4-(4-cyanophenyl)-N-ethyl-10-methyl-7-((methylsulfonyl)methyl)-11-oxo-3,4,10,11-tetrahydro-1H-1,4,10-triazadibenzo[cd,f]azulene-2-carboxamide;

(S)-2-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)isoindoline-1,3-dione;

(R)-2-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)isoindoline-1,3-dione;

4-(2,4-difluorophenyl)-10-methyl-7-((methylsulfonyl)methyl)-11-oxo-3,4,10,11-tetrahydro-1H-1,4,10-triazadibenzo[cd,f]azulene-5-carbonitrile;

10-methyl-7-((methylsulfonyl)methyl)-4-(pyridin-2-yl)-3,4-dihydro-1H-1,4,10-triazadibenzo[cd,f]azulen-11(10H)-one;

ethyl 4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxylate;

4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxamide;

4-(2,4-difluorophenyl)-10-methyl-7-((methylsulfonyl)methyl)-11-oxo-3,4,10,11-tetrahydro-1H-1,4,10-triazadibenzo[cd,f]azulene-2-carbonitrile;

10-methyl-7-((methylsulfonyl)methyl)-4-(3,4,5-trimethoxyphenyl)-3,4-dihydro-1H-1,4,10-triazadibenzo[cd,f]azulen-11(10H)-one;

4-(4-aminocyclohexyl)-10-methyl-7-((methylsulfonyl)methyl)-3,4-dihydro-1H-1,4,10-triazadibenzo[cd,f]azulen-11(10H)-one;

4-(3,5-difluoropyridin-2-yl)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-3-phenyl-3,4-dihydro-1H-1,4,10-triazadibenzo[cd,f]azulen-11(10H)-one;

(R)-4-(2,4-difluorophenyl)-10-methyl-7-((methylsulfonyl)methyl)-3-phenyl-3,4-dihydro-1H-1,4,10-triazadibenzo[cd,f]azulen-11(10H)-one;

(S)-4-(2,4-difluorophenyl)-10-methyl-7-((methylsulfonyl)methyl)-3-phenyl-3,4-dihydro-1H-1,4,10-triazadibenzo[cd,f]azulen-11(10H)-one;

4-(2,4-difluorophenyl)-10-methyl-7-((methylsulfonyl)methyl)-3-(naphthalen-1-yl)-3,4-dihydro-1H-1,4,10-triazadibenzo[cd,f]azulen-11(10H)-one;

4-(2,4-difluorophenyl)-(3,3-$^2H_2$)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-3-neopentyl-3,4-dihydro-1H-1,4,10-triazadibenzo[cd,f]azulen-11(10H)-one;

4-(2,4-difluorophenyl)-10-methyl-7-((methylsulfonyl)methyl)-3-((1-oxoisoindolin-2-yl)methyl)-3,4-dihydro-1H-1,4,10-triazadibenzo[cd,f]azulen-11(10H)-one;

4-(2,4-difluorophenyl)-3-(2,6-dimethoxyphenyl)-10-methyl-7-((methylsulfonyl)methyl)-3,4-dihydro-1H-1,4,10-triazadibenzo[cd,f]azulen-11(10H)-one;

4-(2,4-difluorophenyl)-3-(3,5-dimethoxyphenyl)-10-methyl-7-((methylsulfonyl)methyl)-3,4-dihydro-1H-1,4,10-triazadibenzo[cd,f]azulen-11(10H)-one;

3-(3,5-di-tert-butylphenyl)-4-(2,4-difluorophenyl)-10-methyl-7-((methylsulfonyl)methyl)-3,4-dihydro-1H-1,4,10-triazadibenzo[cd,f]azulen-11(10H)-one;

methyl (4-(10-methyl-7-((methylsulfonyl)methyl)-11-oxo-10,11-dihydro-1H-1,4,10-triazadibenzo[cd,f]azulen-4(3H)-yl)cyclohexyl)carbamate;

methyl ((trans)-4-(10-methyl-7-((methylsulfonyl)methyl)-11-oxo-10,11-dihydro-1H-1,4,10-triazadibenzo[cd,f]azulen-4(3H)-yl)cyclohexyl)carbamate;

methyl ((cis)-4-(10-methyl-7-((methylsulfonyl)methyl)-11-oxo-10,11-dihydro-1H-1,4,10-triazadibenzo[cd,f]azulen-4(3H)-yl)cyclohexyl)carbamate;

2-(2-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)ethyl)isoindoline-1,3-dione;

4-(2,4-difluorophenyl)-10-methyl-7-((methylsulfonyl)methyl)-3-(tetrahydro-2H-pyran-4-yl)-3,4-dihydro-1H-1,4,10-triazadibenzo[cd,f]azulen-11(10H)-one;

benzyl (2-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)ethyl)carbamate;

3-([1,1'-biphenyl]-2-yl)-4-(2,4-difluorophenyl)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-3-(quinolin-8-yl)-3,4-dihydro-1H-1,4,10-triazadibenzo[cd,f]azulen-11(10H)-one;

4-(2,4-difluorophenyl)-10-methyl-7-((methylsulfonyl)methyl)-3-(pyridin-2-yl)-3,4-dihydro-1H-1,4,10-triazadibenzo[cd,f]azulen-11(10H)-one;
3-(4-(1H-imidazol-1-yl)phenyl)-4-(2,4-difluorophenyl)-10-methyl-7-((methylsulfonyl)methyl)-3,4-dihydro-1H-1,4,10-triazadibenzo[cd,f]azulen-11(10H)-one;
4-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)benzonitrile;
4-(2,4-difluorophenyl)-10-methyl-7-((methylsulfonyl)methyl)-3-(3-(pyridin-2-yl)phenyl)-3,4-dihydro-1H-1,4,10-triazadibenzo[cd,f]azulen-11(10H)-one;
3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)benzonitrile;
4-(2,4-difluorophenyl)-10-methyl-7-((methylsulfonyl)methyl)-3-((2-oxopyridin-1(2H)-yl)methyl)-3,4-dihydro-1H-1,4,10-triazadibenzo[cd,f]azulen-11(10H)-one;
ethyl 4-(2,4-difluorophenyl)-2-(ethylcarbamoyl)-10-methyl-7-((methylsulfonyl)methyl)-11-oxo-3,4,10,11-tetrahydro-1H-1,4,10-triazadibenzo[cd,f]azulene-3-carboxylate;
4-(2,4-difluorophenyl)-10-methyl-7-((methylsulfonyl)methyl)-11-oxo-3,4,10,11-tetrahydro-1H-1,4,10-triazadibenzo[cd,f]azulene-5-carboxamide;
4-(2,4-difluorophenyl)-N,10-dimethyl-7-((methylsulfonyl)methyl)-11-oxo-3,4,10,11-tetrahydro-1H-1,4,10-triazadibenzo[cd,f]azulene-5-carboxamide;
4-(2,4-difluorophenyl)-N,N,10-trimethyl-7-((methylsulfonyl)methyl)-11-oxo-3,4,10,11-tetrahydro-1H-1,4,10-triazadibenzo[cd,f]azulene-5-carboxamide;
N-(4-(10-methyl-7-((methylsulfonyl)methyl)-11-oxo-10,11-dihydro-1H-1,4,10-triazadibenzo[cd,f]azulen-4(3H)-yl)cyclohexyl)acetamide;
10-methyl-7-((methylsulfonyl)methyl)-4-(pyridin-3-yl)-3,4-dihydro-1H-1,4,10-triazadibenzo[cd,f]azulen-11(10H)-one;
4-(5-chloropyridin-2-yl)-10-methyl-7-((methylsulfonyl)methyl)-3,4-dihydro-1H-1,4,10-triazadibenzo[cd,f]azulen-11(10H)-one;
4-(1H-indazol-5-yl)-10-methyl-7-((methylsulfonyl)methyl)-3,4-dihydro-1H-1,4,10-triazadibenzo[cd,f]azulen-11(10H)-one;
4-benzyl-10-methyl-7-((methylsulfonyl)methyl)-3,4-dihydro-1H-1,4,10-triazadibenzo[cd,f]azulen-11(10H)-one;
10-methyl-7-((methylsulfonyl)methyl)-4-(pyrimidin-5-yl)-3,4-dihydro-1H-1,4,10-triazadibenzo[cd,f]azulen-11(10H)-one;
10-methyl-7-((methylsulfonyl)methyl)-4-(pyridin-2-ylmethyl)-3,4-dihydro-1H-1,4,10-triazadibenzo[cd,f]azulen-11(10H)-one;
10-methyl-7-((methylsulfonyl)methyl)-4-(pyridazin-3-ylmethyl)-3,4-dihydro-1H-1,4,10-triazadibenzo[cd,f]azulen-11(10H)-one;
(S)-4-(2,4-difluorophenyl)-10-methyl-7-((methylsulfonyl)methyl)-3-((2-oxopyridin-1(2H)-yl)methyl)-3,4-dihydro-1H-1,4,10-triazadibenzo[cd,f]azulen-11(10H)-one;
(R)-4-(2,4-difluorophenyl)-10-methyl-7-((methylsulfonyl)methyl)-3-((2-oxopyridin-1(2H)-yl)methyl)-3,4-dihydro-1H-1,4,10-triazadibenzo[cd,f]azulen-11(10H)-one;
10-methyl-7-((methylsulfonyl)methyl)-4-(5-(trifluoromethyl)pyridin-2-yl)-3,4-dihydro-1H-1,4,10-triazadibenzo[cd,f]azulen-11(10H)-one;
4-(2-fluoropyridin-4-yl)-10-methyl-7-((methylsulfonyl)methyl)-3,4-dihydro-1H-1,4,10-triazadibenzo[cd,f]azulen-11(10H)-one;
10-methyl-4-((1-methyl-1H-pyrazol-3-yl)methyl)-7-((methylsulfonyl)methyl)-3,4-dihydro-1H-1,4,10-triazadibenzo[cd,f]azulen-11(10H)-one;
4-(6-methoxypyridin-2-yl)-10-methyl-7-((methylsulfonyl)methyl)-3,4-dihydro-1H-1,4,10-triazadibenzo[cd,f]azulen-11(10H)-one;
4-(2,2-dimethyl-3-morpholinopropyl)-10-methyl-7-((methylsulfonyl)methyl)-3,4-dihydro-1H-1,4,10-triazadibenzo[cd,f]azulen-11(10H)-one;
4-(5-fluoropyrimidin-2-yl)-10-methyl-7-((methylsulfonyl)methyl)-3,4-dihydro-1H-1,4,10-triazadibenzo[cd,f]azulen-11(10H)-one;
10-methyl-7-((methylsulfonyl)methyl)-4-(pyrimidin-4-yl)-3,4-dihydro-1H-1,4,10-triazadibenzo[cd,f]azulen-11(10H)-one;
4-(2-(3-(dimethylamino)propoxy)benzyl)-10-methyl-7-((methylsulfonyl)methyl)-3,4-dihydro-1H-1,4,10-triazadibenzo[cd,f]azulen-11(10H)-one;
2-(10-methyl-7-((methylsulfonyl)methyl)-11-oxo-10,11-dihydro-1H-1,4,10-triazadibenzo[cd,f]azulen-4(3H)-yl)-2-phenylacetonitrile;
2-(2-((10-methyl-7-((methylsulfonyl)methyl)-11-oxo-10,11-dihydro-1H-1,4,10-triazadibenzo[cd,f]azulen-4(3H)-yl)methyl)phenoxy)acetamide;
4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxylic acid;
10-methyl-7-((methylsulfonyl)methyl)-4-(2-(pyridin-2-ylmethoxy)benzyl)-3,4-dihydro-1H-1,4,10-triazadibenzo[cd,f]azulen-11(10H)-one;
(R)-7-(ethylsulfonyl)-10-methyl-4-(1-phenylethyl)-3,4-dihydro-1H-1,4,10-triazadibenzo[cd,f]azulen-11(10H)-one;
10-methyl-4-(pyridin-2-yl)-7-(pyrrolidin-1-ylsulfonyl)-3,4-dihydro-1H-1,4,5,10-tetraazadibenzo[cd,f]azulen-11(10H)-one;
(S)-7-(ethylsulfonyl)-10-methyl-4-(1-phenylethyl)-3,4-dihydro-1H-1,4,10-triazadibenzo[cd,f]azulen-11(10H)-one;
(R)-methyl 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoate;
(S)-methyl 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoate;
4-(2,4-difluorophenyl)-10-methyl-2-(1-methyl-1H-pyrazol-4-yl)-7-(methylsulfonyl)-3,4-dihydro-1H-1,4,10-triazadibenzo[cd,f]azulen-11(10H)-one;
4-(4-chlorophenyl)-10-methyl-2-(1-methyl-1H-pyrazol-4-yl)-7-(methylsulfonyl)-3,4-dihydro-1H-1,4,10-triazadibenzo[cd,f]azulen-11(10H)-one;
(R)—N-ethyl-7-(ethylsulfonyl)-10-methyl-11-oxo-4-(1-phenylpropyl)-3,4,10,11-tetrahydro-1H-1,4,10-triazadibenzo[cd,f]azulene-2-carboxamide;
10-methyl-2-(1-methyl-1H-pyrazol-4-yl)-7-((methylsulfonyl)methyl)-4-(pyridin-2-yl)-3,4-dihydro-1H-1,4,10-triazadibenzo[cd,f]azulen-11(10H)-one;
10-methyl-2-(1-methyl-1H-pyrazol-4-yl)-7-(methylsulfonyl)-4-phenyl-3,4-dihydro-1H-1,4,10-triazadibenzo[cd,f]azulen-11(10H)-one;
10-methyl-2-(1-methyl-1H-pyrazol-4-yl)-7-(methylsulfonyl)-4-(pyridin-2-yl)-3,4-dihydro-1H-1,4,10-triazadibenzo[cd,f]azulen-11(10H)-one; and 4-(4-fluorophenyl)-10-methyl-2-(1-methyl-1H-pyrazol-4-yl)-7-((methylsulfonyl)methyl)-3,4-dihydro-1H-1,4,10-triazadibenzo[cd,f]azulen-11(10H)-one;
or pharmaceutically acceptable salts thereof.

Compounds of formula I can be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds described herein, including compounds of general formula (I) and specific examples, may be prepared, for example, through the reaction routes depicted in schemes 1-6. The variables $A^1$, $A^2$, $A^3$, $A^4$, $Y^1$, $Y^2$, $Y^3$, $R^1$, $R^2$, $R^3$, $R^4$, $R^5$, $R^6$, $R^{3b}$, $R^{3c}$, $R^{6a}$, $R^{6b}$, and $R^{6c}$ used in the following schemes have the meanings as set forth in the summary and detailed description sections unless otherwise noted.

Abbreviations used in the descriptions of the schemes and the specific examples have the following meanings: DMF for dimethylformamide, DMSO for dimethyl sulfoxide, mCPBA for 3-chloroperbenzoic acid, $Pd(OAc)_2$ for palladium(II) acetate, SFC for Supercritical Fluid Chromatography, THF for tetrahydrofuran, TFA for trifluoroacetic acid, and HPLC for high performance liquid chromatography.

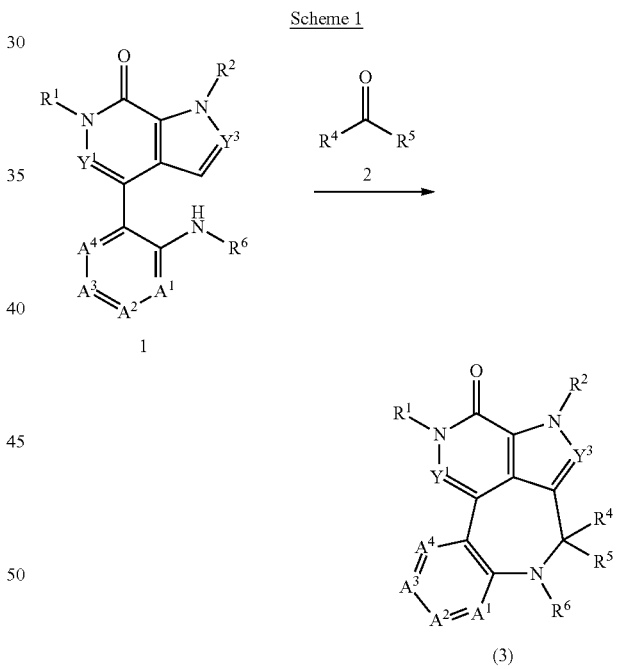

Compounds of general formula (I) wherein $Y^2$ is $CR^4R^5$ may be prepared by treating compounds of general formula (1) with an aldehyde or ketone (2) under acidic conditions, as illustrated in Scheme 1. Generally this cyclization reaction may be effected in the presence of a reagent such as titanium tetrachloride in a solvent such as, but not limited to, tetrahydrofuran or dichloromethane, at a temperature ranging from 0° C. to 50° C. Alternatively, this cyclization reaction may also be effected in the presence of an acid, such as acetic acid or hydrochloric acid, in the absence or presence of a solvent such as, but not limited to, methanol or ethanol, at a temperature ranging from 50° C. to 150° C.

Scheme 2

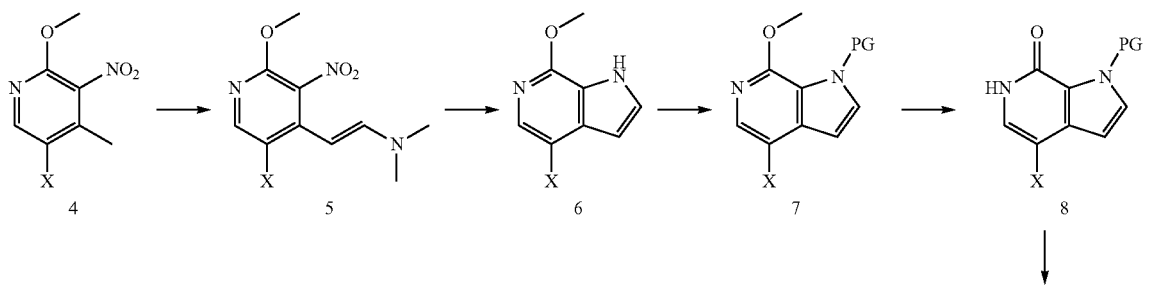

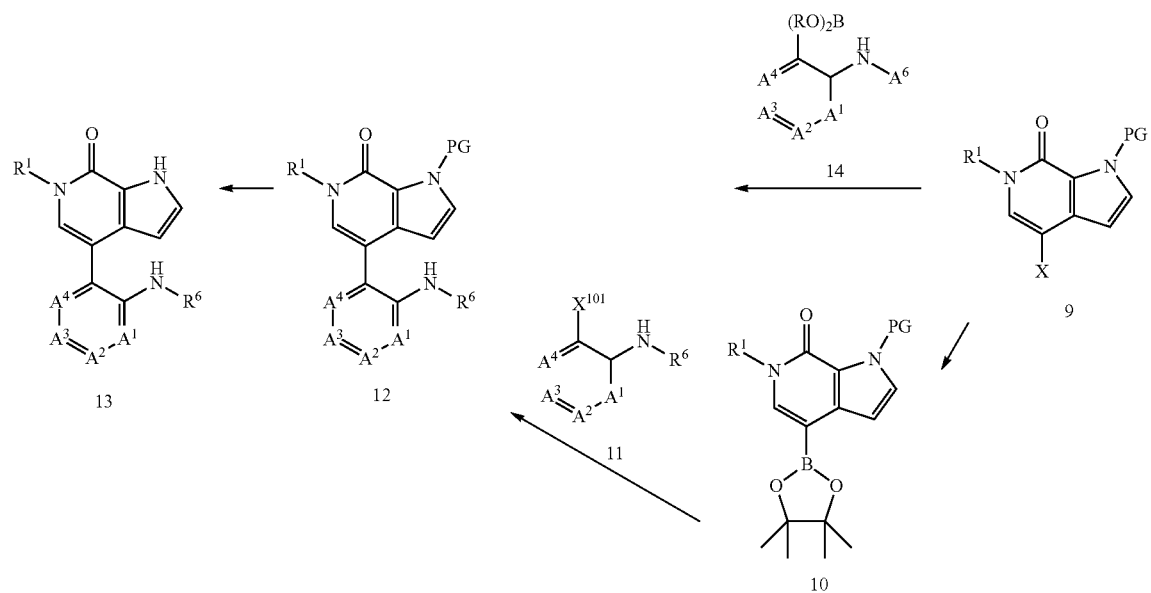

Compounds of formula (1) wherein $Y^1$ and $Y^3$ are CH and $R^2$ is H may be prepared by general synthetic methods as shown in Scheme 2. Treatment of compounds of formula (4) wherein X is Br, Cl, or I, with 1,1-dimethoxy-N,N-dimethylmethanamine at elevated temperature (e.g. about 60° C. to about 100° C.), in the absence or presence of a base, and in a solvent such as, but not limited to, DMF, provide compounds of formula (5). Examples of suitable bases include, but are not limited to, lithium or sodium methanolate. Catalytic hydrogenation of (5) in the presence of a catalyst such as, but not limited to, Raney-Nickel and under hydrogen atmosphere (about 30 psi) and in a solvent such as, but not limited to, ethyl acetate, at about room temperature generally affords compounds of formula (6). Protection of the nitrogen atom with protecting group such as, but not limited to, benzyl, tosyl, or (trimethylsilyl)ethoxy)methyl group may be derived from reaction with an appropriate halide in the presence of a strong base such as, but not limited to, sodium hydride, to provide compounds of formula (7).

Treatment of (7) with an acid such as, but not limited to, hydrochloric acid or hydrobromic acid and in a solvent such as, but not limited to, dioxane or water, at about 40° C. to about 100° C., typically provides compounds of formula (8).

Alkylation of (8) with an halide or mesylate, in the presence of a base such as, but not limited to, sodium hydride, cesium carbonate, or potassium carbonate, and in a solvent such as, but not limited to, dimethylformamide or dimethylsulfoxide at a temperature of about 0° C. to about 50° C. provides compounds of formula (9).

Treatment of the compounds of formula (9) with 4,4,4', 4',5,5,5',5'-octamethyl-2,2'-bi(1,3,2-dioxaborolane) affords compounds of formula (10). In general, the conversion may be facilitated by a palladium catalyst such as, but not limited to, tetrakis(triphenylphosphine)palladium(0), tris(dibenzylideneacetone)dipalladium(0), or palladium(II)acetate, an optional ligand such as, but not limited to, 2-dicyclohexylphosphino-2',4',6'-triisopropylbiphenyl (X-phos), or 1,1'-bis(diphenylphosphanyl) ferrocene, and a base such as, but not limited to, carbonates, acetates, or phosphates. of sodium, potassium, and cesium; and cesium fluoride. Non-limiting examples of suitable solvents include methanol, dimethoxyethane, N,N-dimethylformamide, dimethylsulfoxide, dioxane, tetrahydrofuran, and water, or a mixture thereof. Compounds of formula (13) may be prepared by (a) treating compounds of formula (10) with compounds of formula (11) wherein $X^{101}$ is halide, mesylate, or triflate, under Suzuki coupling conditions (N. Miyama and A. Suzuki, Chem. Rev. 1995, 95:2457-2483, J. Organomet. Chem. 1999, 576:147-148), to provide compounds of formula (12), and (b) removal of the protecting group (PG), as illustrated in Scheme 2. Removal of the protecting group may also occur in situ under the Suzuki reaction conditions. Generally, the coupling reaction is effected in the presence of a palladium catalyst and a base, and optionally in the presence of a ligand, and in a suitable solvent at elevated temperature (for example, at about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), and palladium(II)acetate. Examples of suitable bases that may be employed include, but not limited to, carbonates or phosphates of sodium, potassium, and cesium; and cesium fluoride. Examples of suitable ligands include, but not limited to, 1,3,5,7-tetramethyl-6-phenyl-2,4,8-trioxa-6-phosphaadamante, 2-dicyclohexylphosphino-2',4',6'-triisopropylbiphenyl (X-phos), and 1,1'-bis(diphenylphosphanyl) ferrocene. Non-limiting examples of suitable solvent include methanol, dimethoxyethane, N,N-dimethylformamide, dimethylsulfoxide, dioxane, tetrahydrofuran, and water, or a mixture thereof.

Alternatively, treatment of compounds of formula (9) wherein X is I, Br, Cl, or triflate with boronic acid or derivatives thereof (e.g. boronic esters) of formula (14), under Suzuki coupling conditions as described above, may also afford compounds of formula (12). Removal of the protecting group may take place under the Suzuki reaction conditions to provide compounds of formula (13).

Scheme 3

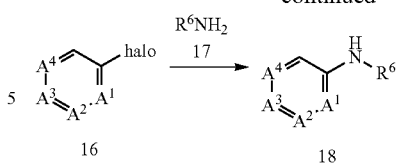

Compounds of formula (11) wherein $X^{101}$ is I, Br, or Cl and formula (14) may be prepared according to the synthesis outlined in Scheme 3. Reductive amination of amines (15) wherein $X^{101}$ is I, Br, or Cl with a suitable aldehyde or ketone in the presence of a reducing agent such as, for example, sodium triacetoxyhydroborate, sodium borohydride, or sodium cyanoborohydride, and an acid (e.g. acetic acid), provides compounds (11) wherein $R^6$ is $C_1$-$C_6$ alkyl, $C_2$-$C_6$ alkenyl, or $C_2$-$C_6$ alkynyl, each of which is optionally substituted, or $R^6$ is $C_1$-$C_6$ haloalkyl. The reaction is generally conducted in a solvent such as, for example, dichloromethane, methanol, or ethanol, at a temperature of about 0° C. to about 100° C. Compounds of formula (14) may be prepared from compounds of formula (11) under Suzuki coupling conditions as described in Scheme 2.

Alternatively, compounds of formula (11) may be prepared using Buchwald reaction conditions. Halides (16) may be treated with a suitable amine (17) in the presence of a catalyst, a ligand, a base, and in a solvent to provide compounds of formula (18). Examples of catalysts that may be employed include, but are not limited to, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamante, 2-dicyclohexylphosphino-2',4',6'-triisopropylbiphenyl (X-phos), and 1,1'-bis(diphenylphosphanyl) ferrocene. Non-limiting examples of suitable solvent include toluene, tert-butanol, methanol, ethanol, dimethoxyethane, N,N-dimethylformamide, dimethylsulfoxide, dioxane, tetrahydrofuran, and water, or a mixture thereof. Halogenation of compounds of formula (18) by reaction with a reagent such as, but not limited to, N-bromosuccinimide or N-iodosuccinimide, in a solvent such as, but not limited to, acetic acid, at temperatures from about 0° C. to about 50° C., provides compounds of formula (11) wherein $X^{101}$ is I or Br.

Scheme 4

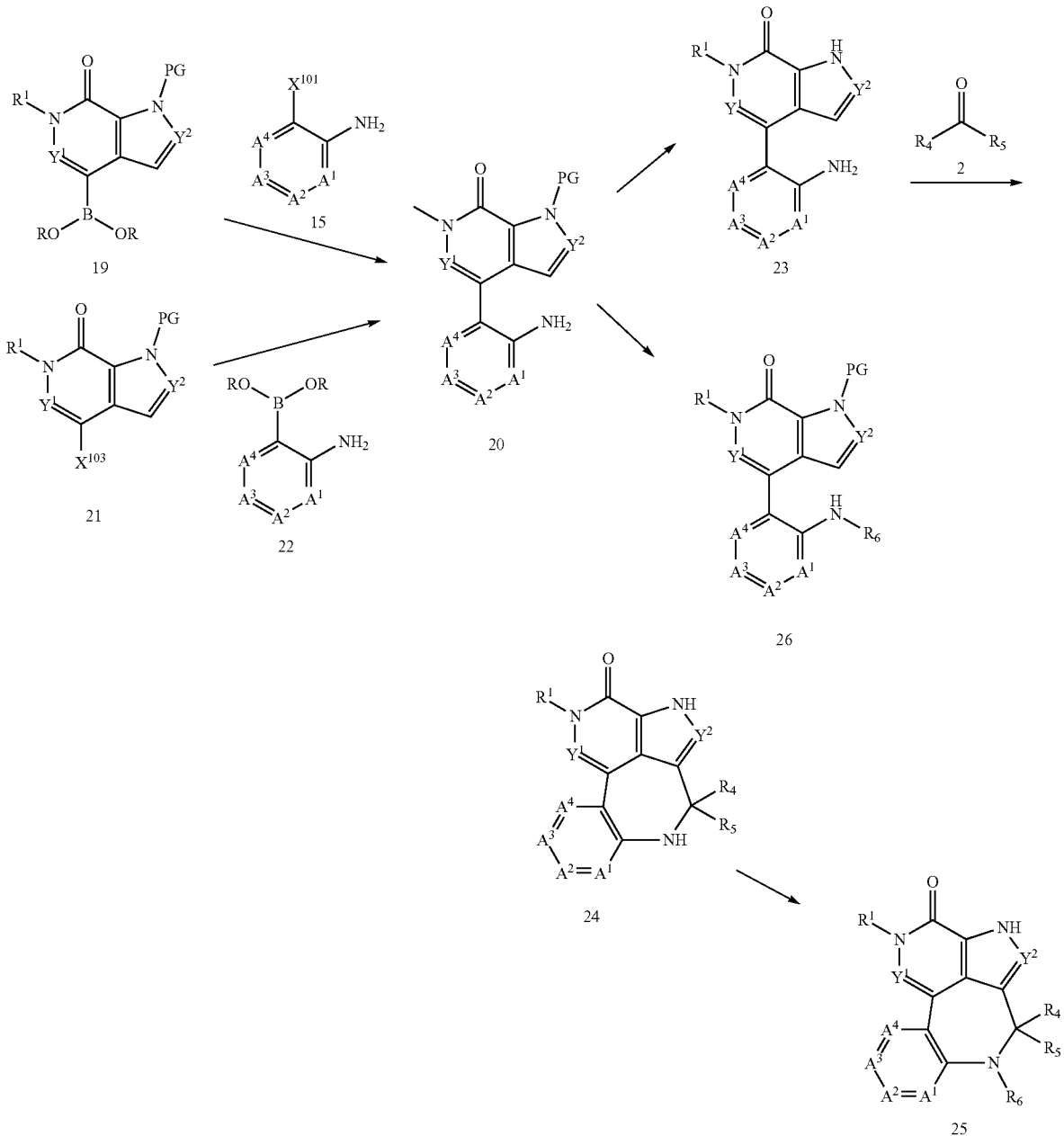

Compounds of general formula (3) wherein R² is H may be prepared according to the synthesis outlined in Scheme 4. Compounds of formula (20) may be prepared by treating compounds of formula (18) with (15) wherein $X^{101}$ is halide, mesylate, or triflate under Suzuki coupling conditions as described in Scheme 2. Compounds of formula (20) may also be prepared by treating compounds of formula (21), wherein $X^{103}$ is halide, mesylate, or triflate, with a boronic acid (or a boronic acid derivative) (22) under Suzuki coupling conditions. Deprotection of compound (20) under suitable conditions provides compounds of formula (23). Compounds of formula (24) may be prepared by treating compounds of the formula (23) with an aldehyde or ketone (2) using conditions described in Scheme 1. Compounds of formula (25) wherein $R^6$ is optionally substituted $C_1$-$C_6$ alkyl, $C_2$-$C_6$ alkenyl, or $C_2$-$C_6$ alkynyl, or $R^6$ is $C_1$-$C_6$ haloalkyl may be prepared by the reductive amination reaction of compounds of formula (24) with suitable aldehydes or ketones, employing reaction conditions described in Scheme 3. Similarly, reductive amination of compounds of formula (20) with suitable aldehydes or ketones provides compounds of formula (26). Compounds of general formula (25) wherein $R^6$ is $C(O)OR^{6a}$, $C(O)R^{6a}$, $S(O)_2R^{6a}$, and $C(O)NR^{6b}R^{6c}$ may be prepared by the reaction of compounds of formula (24) with chloroformates, acid chlorides, sulfonyl chlorides or isocyanates in the presence of a base such as, but not limited to, diisopropylethylamine, triethylamine, or cesium carbonate, in a solvent such as dimethylformamide, dimethylacetamide, 1,2-dichloroethane, or dichloromethane, at temperatures ranging from ambient temperature to about 100° C. for about 2 to about 72 hours.

Scheme 5

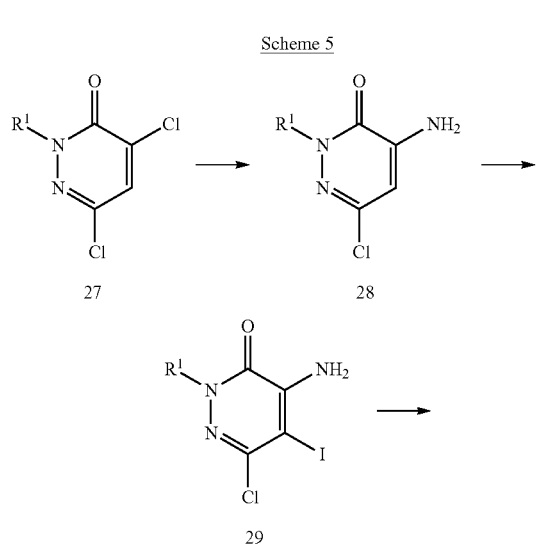

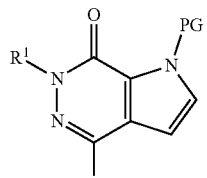

Compounds of formula (21) wherein $X^{103}$ is Cl, $Y^1$ is N and $Y^3$ is CH may be prepared according to the synthesis described in Scheme 5. Treatment of (27) with ammonium hydroxide at about 100° C. to about 150° C. affords amines of formula (28).

Iodination of (28) with N-iodosuccinimide in a solvent such as, but not limited to, acetonitrile or acetone, at a temperature of about 40° C. to about 85° C., yields compounds of formula (29). Subsequent coupling with (E)-2-(2-ethoxyvinyl)-4,4,5,5-tetramethyl-1,3,2-dioxaborolane utilizing Suzuki coupling reaction conditions as described above provides compounds of formula (30). Cyclization of (30) followed by protection of the nitrogen atom affords compounds of formula (31).

Cyclization of (30) may be accomplished in the presence of an acid such as, but not limited to, acetic acid or hydrochloric acid and at an elevated temperature (e.g. about 50° C. to about 100° C.).

Scheme 6

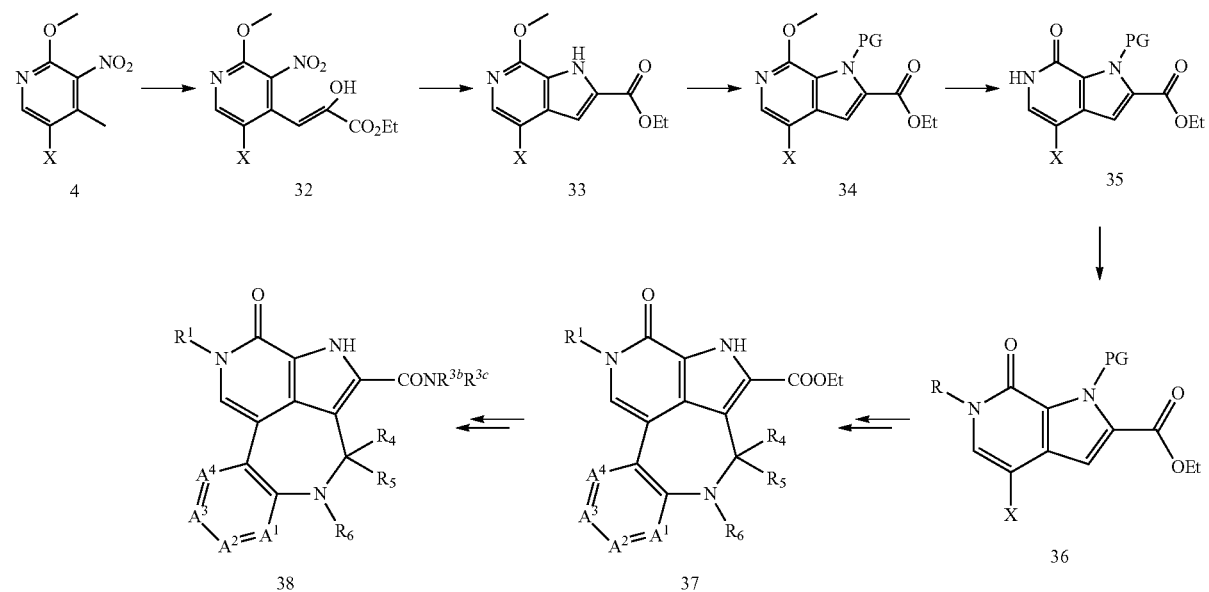

Compounds of formula (38) may be prepared according to Scheme 6. Esters of formula (33) may be obtained from (a) treatment of formula (4) with diethyl oxalate in the presence of a base such as, but not limited to, potassium ethoxide or sodium ethoxide, in a solvent such as, but not limited to, ethanol, dioxane, and diethyl ether, and at a temperature of about 40° C. to about 80° C.; and (b) cyclization of the resulting intermediate (32) in the presence of iron and in ethanol and acetic acid, at a temperature of about 80° C. to about 100° C. Conversion of (33) to (36) may be accomplished by employing reaction conditions discussed above.

Utilizing reaction conditions described in Schemes 1-5, intermediates (36) may be transformed to compounds (37). Hydrolysis of the ester function of (37), followed by coupling of the resulting acids with a suitable amines of formula NHR$^{3b}$R$^{3c}$ provides compounds of formula (38).

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a bromodomain-mediated disorder or condition. The term "administering" refers to the method of contacting a compound with a subject. Thus, the compounds of formula I can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. Bromodomain-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, compounds of formula I may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Further, compounds of formula I may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, cardiac myopathy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Compounds of formula I, or pharmaceutically acceptable salts thereof, may be used to treat AIDS.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPB), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-

((trifluoromethyl)sulfonyl)benzenesulfonamide (ABT-263), GX-070 (obatoclax), ABT-199, and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like.

Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combreastatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-*pseudomonas* exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVACkVF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The compounds of the invention can also be co-administered with a therapeutically effective amount of one or more agents to treat an inflammatory disease or condition, or autoimmune disease, where examples of the agents include, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

A compound of Formula (I) may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®).

Non-limiting examples of therapeutic agents for asthma with which a compound of Formula (I) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of Formula (I) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Preferred examples of therapeutic agents for SLE (Lupus) with which a compound of Formula (I) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, lamivudine, nevirapine, stavudine zalcitabine, and zidovudine. Examples of protease inhibitors include, but are not limited to, amprenavir, indinavir, lopinavir, nelfinavir, ritonavir, and saquinavir.

A compound of Formula (I) may also be co-administered with insulin for the treatment of type I diabetes.

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

The compounds of the invention can also be co-administered with a therapeutically effective amount of one or more agents used in the treatment of obesity, where examples of the agents include orlistat.

The compounds of the invention can also be co-administered with a therapeutically effective amount of one or more agents used in the treatment of type II diabetes, where examples of the agents include, alpha glucosidase inhibitors, insulin, metformin, sulfonylureas (e.g., carbutamide, acetohexamide, chlorpropamide, glibenclamide, glibornuride, gliclazide, glimepiride, glipizide, gliquidone, glisoxepide, glyclopyramide, tolbutamide, and tolazamide), nonsulfonylureas (e.g., nateglinide, and repaglinide), and thiazolidinediones (e.g., pioglitazone).

The compounds of the invention can be co-administered with a therapeutically effective amount of one or more agents to prevent or treat type II diabetes, hepatic steatosis, insulin resistance, metabolic syndrome and related disorders, where examples of the agents include, but are not limited to, insulin and insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide and tolbutamide; agents that are glucagon-like peptide agonists such as exanatide, liraglutide and taspoglutide; agents that inhibit dipeptidyl-peptidase IV such as vildagliptin, sitagliptin, saxagliptin, linagliptin, allogliptin and septagliptin; agents that bind to the peroxisome proliferator-activated receptor gamma such as rosiglitazone and pioglitazone; agents that decrease insulin resistance such as metformin; agents that reduce glucose absorbance in the small intestine such as acarbose, miglitol and voglibose.

The compounds of the invention can be co-administered with a therapeutically effective amount of one or more agents to prevent or treat acute kidney disorders and chronic kidney diseases, where examples of the agents include, but are not limited to, dopamine, diuretics such as furosemide, bumetanide, thiazide and the like, mannitol, calcium gluconate, sodium bicarbonate, albuterol, paricalcitol, doxercalciferol, and cinacalcet.

The following Examples may be used for illustrative purposes and should not be deemed to narrow the scope of the invention.

EXAMPLES

Example 1

4-(cyclopropylmethyl)-7-(isopropylsulfonyl)-10-methyl-3,4-dihydro-1H-1,4,10-triazadibenzo[cd,f]azulen-11(10H)-one

Example 1a (E)-2-(5-bromo-2-methoxy-3-nitropyridin-4-yl)-N,N-dimethylethenamine 5-Bromo-2-methoxy-4-methyl-3-nitropyridine (15.0 g, 60.7 mmol) was dissolved in dimethylformamide (300 mL), and lithium methanolate (6.07 mL, 6.07 mmol, 1 M) was added. The reaction mixture was heated at 100° C. To this mixture was added 1,1-dimethoxy-N,N-dimethylmethanamine (64.5 mL, 486 mmol) over 10 minutes. The reaction mixture was stirred at 95° C. for 16 hours. The reaction mixture was cooled to ambient temperature and water was added carefully (300 mL, exothermic). The resulting precipitate was collected by vacuum filtration, washed with water, and dried to provide the title compound (13.9 g, 45.9 mmol, 76% yield).

Example 1b 4-bromo-7-methoxy-1H-pyrrolo[2,3-c]pyridine

Example 1a (13.9 g, 45.8 mmol) and ethyl acetate (150 mL) were added to Ra—Ni 2800 (pre-washed with ethanol), water slurry (6.9 g, 118 mmol) in a stainless steel pressure bottle and stirred for 30 minutes at 30 psi and ambient temperature. The reaction mixture was filtered, and concentrated. The residue was triturated with dichloromethane, and the solid filtered to provide the title compound (5.82 g). The mother liquor was concentrated and the residue triturated again with dichloromethane and filtered to provide an additional 1.63 g of the title compound. Total yield=7.45 g, 72% yield

Example 1c 4-bromo-7-methoxy-1-tosyl-1H-pyrrolo[2,3-c]pyridine

A solution of Example 1b (7.42 g, 32.7 mmol) in dimethylformamide (235 mL) was stirred at ambient temperature. To this solution was added sodium hydride (1.18 g, 1.96 g of 60% dispersion in oil, 49.0 mmol), and the reaction mixture was stirred for 10 minutes. P-toluenesulfonyl chloride (9.35 g, 49.0 mmol) was then added portion-wise, and the mixture was stirred at ambient temperature under nitrogen for 16 hours. The reaction mixture was quenched carefully with water and the resulting beige solid collected by vacuum filtration on a Buchner funnel, and washed with water. The solid was collected and dried in a vacuum oven at 50° C. to provide 12.4 g (100%) of the title compound.

Example 1d 4-bromo-1-tosyl-1H-pyrrolo[2,3-c]pyridin-7(6H)-one

A solution of Example 1c (12.4 g, 32.6 mmol) in dioxane (140 mL) was stirred at ambient temperature. To this solution was added 4M HCl in dioxane (140 mL). The reaction mixture was stirred at 40° C. for 16 hours. The reaction mixture was cooled to ambient temperature and concentrated. The residue was triturated with diethylether, filtered, and rinsed with additional diethylether and dried to provide the title compound (11.23 g, 30.6 mmol, 94% yield) as a beige solid.

Example 1e 4-bromo-6-methyl-1-tosyl-1H-pyrrolo[2,3-c]pyridin-7(6H)-one

Sodium hydride (0.875 g, 36.5 mmol, 1.46 g of a 60% in oil dispersion) was added to a stirring solution of Example 1d (11.2 g, 30.4 mmol) in dimethylformamide (217 mL) under nitrogen. After 30 minutes, iodomethane (2.27 mL, 36.5 mmol) was added and the solution was stirred at ambient temperature for 3 hours. Upon addition of water (250 mL) a precipitate formed. The precipitate was collected by vacuum filtration, rinsed with water (50 mL) and dried in a vacuum oven at 55° C. overnight to provide 11.2 g of the title compound (96%).

Example 1f 6-methyl-4-(4,4,5,5-tetramethyl-1,3,2-dioxaborolan-2-yl)-1-tosyl-1H-pyrrolo[2,3-c]pyridin-7(6H)-one Example 1e (6.55 g, 17.2 mmol), 4,4,4',4',5,5,5',5'-octamethyl-2,2'-bi(1,3,2-dioxaborolane) (8.73 g, 34.4 mmol), potassium acetate (3.71 g, 37.8 mmol), tris(dibenzylideneacetone)dipalladium(0) (0.393 g, 0.430 mmol) and 2-dicyclohexylphosphino-2',4',6'-triisopropylbiphenyl (X-PHOS, 0.819 g, 1.72 mmol) were combined and sparged with argon for 1 hour with stirring. Dioxane (86 mL) was sparged with nitrogen for 1 hour, transferred via cannula under nitrogen to the solid components, and the mixture was heated under argon at 80° C. for 5 hours. The reaction mixture was cooled to ambient temperature, partitioned between ethyl acetate and water, and filtered through Celite. The ethyl acetate layer was washed twice with saturated aqueous sodium chloride, dried (anhydrous sodium sulfate), filtered and concentrated. The residue was purified by chromatography (silica gel, 25-80% ethyl acetate in hexane). The resulting material from chromatography was triturated with a minimal amount of hexanes (30 mL) and the particulate solid was collected by filtration, rinsed with a minimal amount of hexanes and dried to constant mass to afford the title compound (5.4 g, 73%).

Example 1g (3-bromo-4-fluorophenyl)(isopropyl)sulfane

A 250 mL round bottomed flask was charged with 3-bromo-4-fluorobenzenethiol (3.89 g, 18.79 mmol), sodium hydroxide (3.95 mL, 19.73 mmol) and methanol. The reaction mixture was stirred at 0° C. for 10 minutes. To this solution was added 2-iodopropane (3.83 g, 22.54 mmol). The reaction mixture was stirred at ambient temperature for 6 hours. The solvent was removed, and the residue was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated to provide the title compound.

Example 1h 2-bromo-1-fluoro-4-(isopropylsulfonyl)benzene

A 500 mL round bottomed flask was charged with Example 1g (4.0 g, 16.06 mmol) and dichloromethane (200 mL). mCPBA (8.71 g, 35.3 mmol) was added. The reaction mixture was stirred at ambient temperature for 6 hours. The reaction mixture was filtered, and the solids were washed by additional dichloromethane. The filtrate was washed with 10% NaOH (50 mL, twice), then saturated sodium bicarbonate. The organic layer was concentrated, and the residue was purified by flash chromatography on silica gel (15% ethyl acetate in heptanes) to provide the title compound.

Example 1i 2-bromo-N-(cyclopropylmethyl)-4-(isopropylsulfonyl)aniline

A mixture of Example 1h (0.562 g, 2 mmol) and cyclopropylmethanamine (0.427 g, 6.00 mmol) in dioxane (10 mL) was heated at 100° C. overnight. The solvent was removed, and the residue was purified by flash chromatography (50% ethyl acetate in heptanes) to provide the title compound.

Example 1j 4-(2-((cyclopropylmethyl)amino)-5-(isopropylsulfonyl)phenyl)-6-methyl-1H-pyrrolo[2,3-c]pyridin-7(6H)-one A mixture of Example 1f (0.086 g, 0.2 mmol), Example 1i (0.066 g, 0.2 mmol), cesium fluoride (0.091 g, 0.600 mmol), and tetrakistriphenylphosphine palladium (0.012 g, 10.00 µmol) in dimethoxyethane (2 mL) and methanol (1 mL) was heated under microwave conditions (120 C, 40 min). The reaction mixture was partitioned between ethyl acetate and water. The organic layer was washed with saturated aqueous sodium chloride, dried over anhydrous magnesium sulfate, filtered and concentrated. The residue was purified by reverse phase HPLC (C18, CH$_3$CN/water (0.1% TFA), 0-100% gradient) to provide the title compound.

Example 1k 4-(cyclopropylmethyl)-7-(isopropylsulfonyl)-10-methyl-3,4-dihydro-1H-1,4,10-triazadibenzo[cd,f]azulen-11(10H)-one A 4 mL vial was charged with Example 1j (0.0106 g, 0.027 mmol), paraformaldehyde (3.98 mg, 0.133 mmol) and methanol (0.265 mL) to give a white suspension. Hydrochloric acid (4N in dioxane, 0.133 mL, 0.531 mmol) was added. The vial was closed and the reaction mixture was heated at 90° C. for 1 hour. The reaction mixture was cooled to ambient temperature and diluted with ether. The resulting suspension was filtered, and the solid was rinsed with ether, collected, and dried in a 60° C. vacuum oven overnight to provide a white solid. $^1$H NMR (300 MHz, DMSO-$d_6$) δ 11.83 (s, 1H), 8.04 (d, J=2.04 Hz, 1H), 7.65 (m, 2H), 7.41 (d, J=8.82 Hz, 1H), 7.18 (d, J=2.03 Hz, 1H), 4.26 (s, 2H), 3.64 (s, 3H), 3.49 (m, 1H), 3.03 (d, J=6.1 Hz, 2H), 1.20 (d, J=6.78 Hz, 6H), 0.90 (m, 1H), 0.41 (m, 2H), 0.09 (q, J=4.63 Hz, 2H). MS (ESI+) m/z 412.1 (M+H)$^+$.

Example 2

4-(cyclopropylmethyl)-7-(ethylsulfonyl)-10-methyl-3,4-dihydro-1H-1,4,10-triazadibenzo[cd,f]azulen-11(10H)-one Example 2a (3-bromo-4-fluorophenyl)(ethyl)sulfane A mixture of 3-bromo-4-fluorobenzenethiol (3.89 g, 18.79 mmol) and sodium hydroxide (3.95 mL, 19.73 mmol) in methanol was stirred at 0° C. for 10 minutes. To this solution was added iodoethane (1.803 mL, 22.54 mmol). The reaction mixture was stirred at ambient temperature for 6 hours. The solvent was removed, and the residue was partitioned between water and ethyl acetate. The aqueous layer was extracted with addition ethyl acetate three times. The combined organic layers were washed with saturated aqueous sodium chloride, dried over anhydrous magnesium sulfate, filtered, and concentrated to give the title compound (4.35 g, 18.50 mmol, 98% yield).

Example 2b 2-bromo-4-(ethylsulfonyl)-1-fluorobenzene

Example 2a (4.4 g, 18.71 mmol) in dichloromethane (250 mL) was cooled to 0° C. To this solution was treated with mCPBA (10.15 g, 41.2 mmol) portionwise. The reaction mixture was stirred at ambient temperature for 6 hours. The solid from the reaction mixture was removed by filtration. The filtrate was washed with saturated aqueous sodium bicarbonate several times. The aqueous layer was then extracted with additional dichloromethane three times. The combined organic layers were washed with saturated aqueous sodium chloride, dried over anhydrous magnesium sulfate, filtered, and concentrated. The residue was purified by flash chromatography on silica gel eluting with 15% ethyl acetate/hexanes to afford the title compound (4.4 g, 16.47 mmol, 88% yield).

Example 2c 2-bromo-N-(cyclopropylmethyl)-4-(ethylsulfonyl)aniline

Example 2c was prepared according to the procedure used for the preparation of Example 1i, substituting Example 2b for Example 1h, to provide the title compound.

Example 2d

4-{2-[(cyclopropylmethyl)amino]-5-(ethylsulfonyl)phenyl}-6-methyl-1,6-dihydro-7H-pyrrolo[2,3-c]pyridin-7-one Example 2d was prepared according to the procedure used for the preparation of Example 1j, substituting Example 2c for Example 1i, to provide the title compound.

Example 2e 4-(cyclopropylmethyl)-7-(ethylsulfonyl)-10-methyl-3,4-dihydro-1H-1,4,10-triazadibenzo[cd,f]azulen-11(10H)-one A mixture of Example 2d (0.03 g, 0.078 mmol) and paraformaldehyde (0.012 g, 0.389 mmol) in methanol (0.778 mL) was treated with 4M hydrogen chloride (0.389 mL, 1.557 mmol). The mixture was heated at 90° C. for 1 hour, cooled, and concentrated. Purification by chromatography (silica gel, 1-5% methanol in dichloromethane) afforded the title compound (0.022 g, 71%). $^1$H NMR (400 MHz, DMSO-$d_6$) δ 11.51 (s, 1H), 8.08 (d, J=2.14 Hz, 1H), 7.66 (dd, J=8.54, 2.14 Hz, 1H), 7.58 (s, 1H), 7.44 (d, J=8.54 Hz, 1H), 7.12 (d, J=2.75 Hz, 1H), 4.27 (s, 2H), 3.64 (s, 3H), 3.28 (d, J=7.32 Hz, 2H), 3.03 (d, J=6.10 Hz, 2H), 1.18 (t, J=7.32 Hz, 3H), 0.83-0.98 (m, 1H), 0.33-0.43 (m, 2H), 0.04-0.11 (m, 2H). MS (ESI+) m/z 398 (M+H)$^+$.

Example 3

4-(cyclopropylmethyl)-3-ethyl-7-(ethylsulfonyl)-10-methyl-3,4-dihydro-1H-1,4,10-triazadibenzo[cd,f]azulen-11(10H)-one A mixture of Example 2d (0.045 g, 0.117 mmol) and propionaldehyde (0.136 g, 2.335 mmol) in methanol (1.167 mL) was treated with 4M hydrogen chloride (0.584 mL, 2.34 mmol). The mixture was heated at 90° C. for 3 hours, cooled and concentrated. The residue was dissolved in ethyl acetate, washed with 5% aqueous sodium bicarbonate, saturated aqueous sodium chloride, dried (anhydrous Na$_2$SO$_4$), filtered and concentrated. Purification by chromatography (silica gel, 0-5% methanol in dichloromethane) afforded a solid that was triturated in a minimal amount of 30% ethyl acetate in heptanes to afford the title compound (0.017 g, 34%). $^1$H NMR (300 MHz, DMSO-$d_6$) δ 11.83 (s, 1H), 8.05 (s, 1H), 7.70 (s, 1H), 7.65 (dd, J=8.31, 2.20 Hz, 1H), 7.41 (d, J=8.48 Hz, 1H), 7.14 (d, J=2.37 Hz, 1H), 4.37 (s, 1H), 3.64 (s, 3H), 3.37 (q, J=7.29 Hz, 2H), 3.13 (s, 1H), 2.93 (s, 1H), 1.41-1.59 (m, 1H), 1.14 (t, J=7.29 Hz, 3H), 1.03-1.09 (m, 1H), 0.86 (t, J=6.78 Hz, 3H), 0.77-0.88 (m, 1H), 0.36 (d, J=8.14 Hz, 2H), 0.03-0.10 (m, 2H). MS (ESI+) m/z 426 (M+H)$^+$.

Example 4

10-methyl-7-(methylsulfonyl)-3,4-dihydro-1H-1,4,10-triazadibenzo[cd,f]azulen-11(10H)-one Example 4a 4-(2-amino-5-(methylsulfonyl)phenyl)-6-methyl-1-tosyl-1H-pyrrolo[2,3-c]pyridin-7(6H)-one 2-bromo-4-(methylsulfonyl)aniline (1.0 g, 4.00 mmol), Example 1f (1.712 g, 4.00 mmol), tris(dibenzylideneacetone)dipalladium (0) (0.110 g, 0.120 mmol), 1,3,5,7-tetramethyl-6-phenyl-2,4,8-trioxa-6-phosphaadamantane (0.117 g, 0.400 mmol) and sodium carbonate (1.483 g, 13.99 mmol) were combined and sparged with argon for 15 minutes. Meanwhile a solution of 4:1 dioxane/water (26 mL) was sparged with nitrogen for 15 minutes and transferred by syringe into the reaction vessel under argon. The mixture was stirred for 3 hours at 60° C., cooled, diluted into 100 mL of water and the resulting solid was collected by filtration, washed with water and dried to constant mass to afford the title compound (2.05 g, 100%).

Example 4b 4-(2-amino-5-(methylsulfonyl)phenyl)-6-methyl-1H-pyrrolo[2,3-c]pyridin-7(6H)-one Example 4b was prepared according to the procedure used for the preparation of Example 5e, substituting Example 4a for Example 5d. Purification by trituration in dichloromethane afforded the title compound (0.55 g, 82%).

Example 4c 10-methyl-7-(methylsulfonyl)-3,4-dihydro-1H-1,4,10-triazadibenzo[cd,f]azulen-11(10H)-one Example 4c was prepared according to the procedure used for the preparation of Example 1k, substituting Example 4b for Example 1j, to afford the title compound as the HCl salt (0.046 g, 98%). $^1$H NMR (400 MHz, DMSO-$d_6$) δ 11.53 (s, 1H), 8.14 (d, J=2.14 Hz, 1H), 7.63 (s, 1H), 7.56 (dd, J=8.39, 2.29 Hz, 1H), 7.23 (d, J=8.54 Hz, 1H), 7.13 (d, J=2.44 Hz, 1H), 4.23 (s, 2H), 3.65 (s, 3H), 3.17 (s, 3H). MS (ESI+) m/z 330 (M+H)$^+$.

Example 5

10-methyl-7-((methylsulfonyl)methyl)-3,4-dihydro-1H-1,4,10-triazadibenzo[cd,f]azulen-11(10H)-one Example 5a 1-((methylsulfonyl)methyl)-4-nitrobenzene To a solution of 4-nitrobenzyl bromide (10.02 g, 46.4 mmol) in N,N-dimethylformamide (25 mL) was added sodium methanesulfinate (7.10 g, 69.6 mmol). The reaction mixture was stirred at 65° C. for 1 hour. The reaction mixture was cooled to ambient temperature and diluted with water. The resulting suspension was stirred 10 minutes and filtered through a medium fit to provide the title compound.

Example 5b 4-((methylsulfonyl)methyl)aniline

Example 5a (8.2 g, 38.1 mmol) and tetrahydrofuran (200 mL) were added to 5% Pd/C, wet (1.6 g, 0.376 mmol) in a 50 mL pressure bottle and stirred for 2 hours at 30 psi and 50° C. The mixture was filtered through a nylon membrane and washed with a small amount of tetrahydrofuran and methanol. The solvent was removed to provide the title compound.

Example 5c 2-iodo-4-((methylsulfonyl)methyl)aniline

To a solution of Example 5b (3.80 g, 20.51 mmol) in N,N-dimethylformamide (103 mL) was added N-iodosuccinimide (5.08 g, 22.56 mmol). The reaction mixture was stirred at ambient temperature for 1 hour. The reaction mixture was quenched with 150 mL 10% sodium thiosulfate and 100 mL saturated sodium bicarbonate. The reaction mixture was extracted 3× with ethyl acetate. The combined organic layers were washed with saturated aqueous sodium chloride and concentrated. Water was added, and the resulting suspension was stirred at ambient temperature for 10 minutes. The suspension was filtered and dried overnight to provide the title compound.

Example 5d 4-(2-amino-5-((methylsulfonyl)methyl)phenyl)-6-methyl-1-tosyl-1H-pyrrolo[2,3-c]pyridin-7(6H)-one A 100 mL round-bottomed flask was charged with Example 5c (0.160 g, 0.514 mmol), Example 1f (0.200 g, 0.467 mmol), potassium phosphate (0.446 g, 2.101 mmol), tris(dibenzylideneacetone)dipalladium (II) (0.021 g, 0.023 mmol), and 1,3,5,7-tetramethyl-6-phenyl-2,4,8-trioxa-6-phosphaadamantane (0.023 g, 0.079 mmol). The solids were flow purged with nitrogen for 30 minutes. Degassed dioxane (3.74 mL) and water (0.934 mL) were added. The reaction mixture was heated at 60° C. for 3 hours. The reaction mixture was cooled to ambient temperature and diluted with water. The resulting suspension was filtered, and the brown solid was collected.

Example 5e 4-(2-amino-5-((methylsulfonyl)methyl)phenyl)-6-methyl-1H-pyrrolo[2,3-c]pyridin-7(6H)-one A 250 mL round-bottomed flask was charged with Example 5d (0.230 g, 0.474 mmol), potassium hydroxide (0.691 g, 12.32 mmol), N,N,N-trimethylhexadecan-1-aminium bromide (8.63 mg, 0.024 mmol), dioxane (3.55 mL) and water (1.18 mL) to give a light yellow solution. The reaction mixture was heated at 90° C. overnight. The reaction mixture was cooled to ambient temperature and treated with 1N hydrochloric acid to achieve a pH of 1. The reaction mixture was extracted with twice with ethyl acetate. The combined organic layers were washed with saturated aqueous sodium chloride, dried over anhydrous magnesium sulfate, filtered and concentrated. The residue was purified by flash chromatography (0%-10% methanol in dichloromethane) to provide the title compound.

Example 5f 10-methyl-7-((methylsulfonyl)methyl)-3,4-dihydro-1H-1,4,10-triazadibenzo[cd,f]azulen-11(10H)-one A 20 mL microwave tube was charged with Example 5e (0.0397 g, 0.120 mmol), paraformaldehyde (0.018 g, 0.599 mmol) and methanol (1.198 mL) to give a white suspension.

Hydrochloric acid (4N in dioxane 0.599 mL, 2.396 mmol) was added. The reaction mixture was heated at 90° C. for 1 hour. The reaction mixture was cooled to ambient temperature and diluted with ether and ethyl acetate. The reaction mixture was washed with saturated sodium bicarbonate and saturated aqueous sodium chloride, dried over anhydrous magnesium sulfate, filtered and concentrated. The residue was purified by flash chromatography (0%-10% methanol in dichloromethane) to provide the title compound. $^1$H NMR (300 MHz, DMSO-$d_6$) δ 11.75 (s, 1H), 7.68 (d, J=1.8 Hz, 1H), 7.50 (s, 1H), 7.07-7.15 (m, 2H), 7.00 (d, J=8.2 Hz, 1H), 4.37 (s, 2H), 4.11 (d, J=3.2 Hz, 2H), 3.61 (s, 3H), 2.90 (s, 3H). MS (ESI+) m/z 344.4 (M+H)$^+$.

Example 6

4-(cyclopropylmethyl)-10-methyl-7-((methylsulfonyl)methyl)-3,4-dihydro-1H-1,4,10-triazadibenzo[cd,f]azulen-11(10H)-one Example 6a N-(cyclopropylmethyl)-2-iodo-4-((methylsulfonyl)methyl)aniline Example 5c (0.200 g, 0.643 mmol) and cyclopropanecarbaldehyde (0.062 mL, 0.836 mmol) were suspended in dichloromethane (3.21 mL) and methanol (3.21 mL). Acetic acid (0.368 mL, 6.43 mmol) was added. The reaction mixture was heated at 50° C. for 30 minutes, then cooled to ambient temperature. Polymer supported cyanoborohydride (0.817 g, 1.928 mmol) was added. The reaction mixture was stirred at ambient temperature overnight. Cyclopropanecarbaldehyde (0.062 mL, 0.836 mmol) was added, and the reaction mixture was stirred at ambient temperature for 2 hours. The reaction mixture was filtered, thoroughly rinsed with dichloromethane, and concentrated. The residue was purified by flash chromatography (20-100% ethyl acetate/heptane) to provide the title compound.

Example 6b 4-(2-((cyclopropylmethyl)amino)-5-((methylsulfonyl)methyl)phenyl)-6-methyl-1-tosyl-1H-pyrrolo[2,3-c]pyridin-7(6H)-one A 250 mL round-bottomed flask was charged with Example 6a (0.1546 g, 0.423 mmol), Example 1f (0.404 g, 1.905 mmol), tris(dibenzylideneacetone)dipalladium (II) (0.019 g, 0.021 mmol), and 1,3,5,7-tetramethyl-6-phenyl-2,4,8-trioxa-6-phosphaadamantane (0.021 g, 0.072 mmol). The solids were sparged with nitrogen for 30 minutes. Degassed dioxane (3.40 mL) and water (0.850 mL) were added. The reaction was heated at 60° C. for 3 hours. The reaction was cooled to room temperature and partitioned between ethyl acetate and water. The organic layer was washed with saturated aqueous sodium chloride solution, dried over magnesium sulfate, filtered and concentrated. The residue was purified by flash chromatography (0-5% methanol/dichloromethane) to provide the title compound (0.211 g, 92% yield).

Example 6c

4-{2-[(cyclopropylmethyl)amino]-5-[(methylsulfonyl)methyl]phenyl}-6-methyl-1,6-dihydro-7H-pyrrolo[2,3-c]pyridin-7-one A 250 mL round-bottomed flask was charged with Example 6b (0.211 g, 0.391 mmol), potassium hydroxide (0.570 g, 10.17 mmol), and N,N,N-trimethylhexadecan-1-aminium bromide (7.12 mg, 0.020 mmol), dioxane (2.93 mL) and water (0.977 mL). The reaction mixture was heated at 90° C. for 2.5 hours. The reaction mixture was cooled to ambient temperature and treated with 1N HCl to achieve a pH of about 7. The reaction mixture was extracted with ethyl acetate (2×). The combined organic extracts were washed with saturated aqueous sodium chloride solution, dried over anhydrous magnesium sulfate, filtered and concentrated to provide the title compound (0.0886 g, 59% yield).

Example 6d 4-(cyclopropylmethyl)-10-methyl-7-((methylsulfonyl)methyl)-3,4-dihydro-1H-1,4,10-triazadibenzo[cd,f]azulen-11(10H)-one A 5 mL microwave tube was charged with Example 6c (0.027 g, 0.070 mmol), paraformaldehyde (0.032 g, 0.350 mmol) and methanol (0.700 mL) to give a white suspension. 4N HCl in dioxane (0.350 mL, 1.401 mmol) was added. The tube was closed and the reaction was heated at 90° C. for 1 hour. The reaction was cooled to room temperature and diluted with ether. The resulting suspension was filtered, and the solid was rinsed with ether, collected, and dried in a 60° C. vacuum oven overnight to provide the title compound. $^1$H NMR (400 MHz, DMSO-$d_6$ 90° C.) δ 11.64 (m, 1H), 7.79 (s, 1H), 7.57 (s, 1H), 7.39-7.52 (m, 1H), 7.32 (d, J=7.1 Hz, 1H), 7.19 (s, 1H), 4.44 (s, 2H), 4.40 (s, 2H), 3.55 (s, 1H), 2.84-2.92 (m, 5H), 0.85 (s, 1H), 0.35 (dd, J=7.9, 1.1 Hz, 2H), −0.02-0.04 (m, 2H). MS (ESI+) m/z 398.0 (M+H)$^+$.

Example 7 ethyl 4-(cyclopropylmethyl)-10-methyl-7-((methylsulfonyl)methyl)-11-oxo-3,4,10,11-tetrahydro-1H-1,4,10-triazadibenzo[cd,f]azulene-3-carboxylate A 5 mL microwave tube was charged with Example 6c (0.027 g, 0.070 mmol), ethyl glyoxalate (0.069 mL, 0.350 mmol) and ethanol (0.700 mL) to give a white suspension. Hydrochloric acid (4N in dioxane, 0.350 mL, 1.401 mmol) was added. The suspension became a colorless solution. The vial was closed and the reaction mixture was heated at 90° C. for 1 hour. The reaction mixture was cooled to ambient temperature and diluted with ether. A white precipitate formed. The resulting suspension was filtered, and the solid was rinsed with ether, collected, and dried in a 60° C. vacuum oven overnight. The residue was purified by reverse phase HPLC (C18, CH$_3$CN/water (0.1% TFA), 0-100% gradient) to afford the title compound (0.0090 g, 27%). $^1$H NMR (300 MHz, DMSO-$d_6$) δ 11.91 (s, 1H), 7.64 (s, 1H), 7.52 (s, 1H), 7.21 (dd, J=13.0, 5.3 Hz, 4H), 5.39 (s, 1H), 4.42 (m, 2H), 3.83 (s, 2H), 3.83 (s, 2H), 3.63 (s, 3H), 2.86 (s, 3H), 0.93 (t, J=7.2 Hz, 3H), 0.83 (m, 1H), 0.29-0.46 (m, 2H), 0.07 (m, 2H). MS (ESI+) m/z 470.0 (M+H)$^+$.

Example 8

4-(4-fluorophenyl)-10-methyl-7-(methylsulfonyl)-3,4-dihydro-1H-1,4,10-triazadibenzo[cd,f]azulen-11(10H)-one Example 8a 4-(2-amino-5-(methylsulfonyl)phenyl)-6-methyl-1-tosyl-1H-pyrrolo[2,3-c]pyridin-7(6H)-one Example 1f (1.71 g, 4.00 mmol), 2-bromo-4-(methylsulfonyl)aniline (1.00 g, 4.00 mmol), tris(dibenzylideneacetone)dipalladium (0.110 g, 0.120 mmol), 1,3,5,7-tetramethyl-6-phenyl-2,4,8-trioxa-6-phosphaadamante (0.117 g, 0.400 mmol) and sodium carbonate (1.48 g, 14.0 mmol) were combined and purged with argon for 15 minutes. A mixture of dioxane (21.3 mL) and water (5.3 mL) was purged with nitrogen for 15 minutes and transferred to the reaction vessel. The reaction mixture was heated at 60° C. for 3 hours, cooled to ambient temperature and diluted with water. The resulting solid was filtered, washed with water and dried to afford the title compound (2.06 g, quantitative yield).

Example 8b 4-(2-((4-fluorophenyl)amino)-5-(methylsulfonyl) phenyl)-6-methyl-1-tosyl-1H-pyrrolo[2,3-c]pyridin-7(6H)-one Example 8a (47.2 mg, 0.100 mmol), 1-bromo-4-fluorobenzene (17.5 mg, 0.100 mmol), diacetoxypalladium (0.9 mg, 4 µmol), dicyclohexyl(2',4',6'-triisopropyl-[1,1'-biphenyl]-2-yl)phosphine (3.8 mg, 8.0 µmol) and cesium carbonate (45.6 mg, 0.140 mmol) were combined in a mixture of toluene (1.6 mL) and tert-butanol (0.4 mL). The reaction mixture was heated in a microwave reactor at 150° C. for 15 minutes. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 2-4% methanol in dichloromethane) to provide the title compound (30 mg, 53%).

Example 8c

4-{2-[(4-fluorophenyl)amino]-5-(methylsulfonyl) phenyl}-6-methyl-1,6-dihydro-7H-pyrrolo[2,3-c] pyridin-7-one Example 8b (28 mg, 0.050 mmol), potassium hydroxide (41.7 mg, 0.743 mmol) and cetyltrimethylammonium bromide (0.90 mg, 2.5 µmol) were combined in a mixture of tetrahydrofuran (2 mL) and water (1 mL). The reaction mixture was heated at 100° C. for 20 hours and then cooled to ambient temperature. To this mixture was added water, and the pH was adjusted to pH 7 by the addition of 1M HCl. The mixture was extracted with ethyl acetate and the organic layer was washed with saturated aqueous sodium chloride twice, dried with anhydrous sodium sulfate, filtered, and concentrated. The residue was purified by flash chromatography (silica gel, 2-4% methanol in dichloromethane) to provide the title compound (13 mg, 64%).

Example 8d 4-(4-fluorophenyl)-10-methyl-7-(methylsulfonyl)-3,4-dihydro-1H-1,4,10-triazadibenzo[cd,f]azulen-11(10H)-one A 2 mL vial was charged with Example 8c (8.0 mg, 0.019 mmol), paraformaldehyde (5.8 mg, 0.19 mmol) and methanol (0.5 mL). To this suspension was added 4M HCl in dioxane (0.097 mL, 0.39 mmol). The vial was closed and stirred at 90° C. for 4 hours. The reaction mixture was cooled to ambient temperature and concentrated. To this residue was added water, and the pH was adjusted to pH 7 by addition of saturated aqueous sodium bicarbonate. The residue was sonicated for 5 minutes and filtered to afford the title compound (7.0 mg, 85%). $^1$H NMR (300 MHz, DMSO-d$_6$) δ 11.88 (d, J=1.70 Hz, 1H) 8.37 (d, J=2.37 Hz, 1H) 7.88 (dd, J=8.14, 2.37 Hz, 1H) 7.85 (s, 1H) 7.53 (d, J=8.14 Hz, 1H) 7.35 (d, J=2.37 Hz, 1H) 6.75-6.91 (m, 2H) 6.43-6.51 (m, 2H) 4.80 (s, 2H) 3.59 (s, 3H) 3.36 (s, 3H). MS (ESI+) m/z 424 (M+H)$^+$.

Example 9

4-(4-fluorophenyl)-10-methyl-7-((methylsulfonyl) methyl)-3,4-dihydro-1H-1,4,10-triazadibenzo[cd,f] azulen-11(10H)-one

Example 9a 1-bromo-4-((methylsulfonyl)methyl)benzene

A 250 mL round-bottomed flask was charged with 4-bromobenzyl bromide (5.000 g, 20.01 mmol) and N,N-dimethylformamide (10.81 mL) to give a colorless solution. Sodium methanesulfinate (3.06 g, 30.0 mmol) was added. The reaction mixture was stirred at 65° C. for 1 hour. The reaction mixture was cooled to room temperature and diluted with water. The resulting suspension was stirred for 10 minutes and filtered. The solid was rinsed with water and dried under house vacuum over the weekend to provide the title compound (4.75 g, 95% yield).

Example 9b 4-fluoro-N-(4-((methylsulfonyl)methyl)phenyl)aniline

A 100 mL microwave tube was charged with 4-fluoroaniline (0.388 mL, 4.04 mmol), Example 9a (1.0065 g, 4.04 mmol), diacetoxypalladium (0.036 g, 0.162 mmol), dicyclohexyl(2',4',6'-triisopropyl-[1,1'-biphenyl]-2-yl)phosphine (0.154 g, 0.323 mmol), cesium carbonate (1.843 g, 5.66 mmol), toluene (20.20 mL) and t-butanol (4.04 mL) to give a yellow suspension. The tube was sealed, and the reaction mixture was heated in a Milestone Ethos microwave reactor to 150° C. for 15 minutes fixed hold time. The reaction mixture was filtered through a 10 g Celite SPE column and rinsed with ethyl acetate. The filtrate was washed with saturated aqueous sodium chloride, dried over anhydrous magnesium sulfate, filtered and concentrated onto silica gel. The crude product was purified by flash chromatography (20-100% ethyl acetate in heptanes) to provide the title compound as an off white solid.

Example 9c 2-bromo-N-(4-fluorophenyl)-4-((methylsulfonyl) methyl)aniline

A 250 mL round-bottomed flask was charged with Example 9b (1.32 g, 4.73 mmol) and acetic acid (47.3 mL) to give a white suspension. The reaction mixture was cooled in a water bath. N-bromosuccinimide (0.807 g, 4.54 mmol) was added in two portions 10 minutes apart. The reaction mixture was stirred at ambient temperature for 1.5 hours. The reaction mixture was quenched with 10% sodium thiosulfate (40 mL) and diluted with 2N sodium hydroxide and ethyl acetate. The layers were separated, and the organic layer was washed with saturated aqueous sodium chloride, dried over anhydrous magnesium sulfate, filtered and concentrated onto silica gel. The crude product was purified by flash chromatography (20-70% ethyl acetate in heptanes) to provide the title compound as a white solid.

Example 9d 4-(2-((4-fluorophenyl)amino)-5-((methylsulfonyl)methyl)phenyl)-6-methyl-1-tosyl-1H-pyrrolo[2,3-c]pyridin-7(6H)-one A 250 mL round-bottomed flask was charged with Example 9c (1.9175 g, 5.35 mmol), Example 1f (2.084 g, 4.87 mmol), sodium carbonate (1.805 g, 17.03 mmol), tris(dibenzylideneacetone)dipalladium (II) (0.223 g, 0.243 mmol), and 1,3,5,7-tetramethyl-6-phenyl-2,4,8-trioxa-6-phosphaadamantane (0.242 g, 0.827 mmol). The solids were sparged with nitrogen for 30 minutes. Degassed dioxane (38.9 mL) and water (9.73 mL) were added. The reaction mixture was heated at 60° C. for 3 hours. The reaction mixture was cooled to room temperature and partitioned between ethyl acetate and water. The organic layer was washed with saturated aqueous sodium chloride solution, dried over anhydrous magnesium sulfate and mercaptopropyl silica gel, filtered and concentrated. The residue was taken up into dichloromethane, triturated with ether, and filtered to provide the title compound (2.13 g, 75% yield).

Example 9e 4-(2-((4-fluorophenyl)amino)-5-((methylsulfonyl)methyl)phenyl)-6-methyl-1H-pyrrolo[2,3-c]pyridin-7(6H)-one A 250 mL round-bottomed flask was charged with Example 9d (2.1251 g, 3.67 mmol), potassium hydroxide (5.35 g, 95 mmol), and N,N,N-trimethylhexadecan-1-aminium bromide (0.067 g, 0.183 mmol), dioxane (55.0 mL) and water (18.33 mL). The reaction mixture was heated at 90° C. for 2.5 hours. The reaction mixture was cooled to room temperature and diluted to 500 mL (total volume) with water. The resulting suspension was filtered, and the solid was rinsed with water and allowed to dry on the frit for 1.5 hours. The solid was collected and dried in a 60° C. vacuum oven overnight to provide the title compound (1.24 g, 80% yield).

Example 9f 4-(4-fluorophenyl)-10-methyl-7-((methylsulfonyl)methyl)-3,4-dihydro-1H-1,4,10-triazadibenzo[cd,f]azulen-11(10H)-one A 20 mL microwave tube was charged with Example 9e (0.5195 g, 1.221 mmol), paraformaldehyde (0.550 g, 6.10 mmol) and methanol (12.21 mL) to give a white suspension. Hydrochloric acid (4N in dioxane, 6.10 mL, 24.42 mmol) was added. The vial was closed and the reaction mixture was heated at 90° C. for 1 hour. The reaction mixture was cooled to ambient temperature. The reaction mixture was partitioned between dichloromethane and saturated sodium bicarbonate. The aqueous layer was extracted 3× with dichloromethane. The combined organic layers were washed with saturated aqueous sodium chloride, dried over anhydrous magnesium sulfate, filtered and concentrated. The residue was taken up into dichloromethane and triturated with ether. The resulting slurry was stirred for 10 minutes, and filtered. The white solid was rinsed with ether, collected, and dried in a 60° C. vacuum oven overnight to provide the title compound. $^1$H NMR (300 MHz, DMSO-$d_6$) δ 11.90-11.84 (m, 1H), 7.91 (d, J=1.9 Hz, 1H), 7.61 (s, 1H), 7.44 (dd, J=8.0, 1.9 Hz, 1H), 7.33 (d, J=4.9 Hz, 2H), 6.80 (t, J=8.8 Hz, 2H), 6.35-6.46 (m, 2H), 4.56 (m, 2H), 3.55 (s, 3H), 3.00 (s, 3H). MS (ESI+) m/z 438.2 (M+H)$^+$.

Example 10

4-(cyclopropylmethyl)-10-methyl-11-oxo-3,4,10,11-tetrahydro-1H-1,4,5,10-tetraazadibenzo[cd,f]azulene-7-sulfonamide Example 10a 5-bromo-6-((cyclopropylmethyl)amino)pyridine-3-sulfonamide A mixture of 5-bromo-6-chloropyridine-3-sulfonamide (0.272 g, 1 mmol) and cyclopropylmethanamine (0.213 g, 3.00 mmol) in dioxane (5 mL) was heated at 100° C. overnight. The reaction mixture was partitioned between water and ethyl acetate. The organic layer was separated, and the aqueous layer was extracted with additional ethyl acetate twice. The combined organic layers were washed with saturated aqueous sodium chloride, dried over anhydrous magnesium sulfate, filtered, and concentrated under reduced pressure. The residue was purified by flash column chromatography on silica gel, eluting with 60% ethyl acetate in hexanes to give 0.298 g (97%) of the title compound.

Example 10b

6-[(cyclopropylmethyl)amino]-5-(6-methyl-7-oxo-6,7-dihydro-1H-pyrrolo[2,3-c]pyridin-4-yl)pyridine-3-sulfonamide Example 10b was prepared according to the procedure used for the preparation of Example 1j, substituting Example 10a for Example 1i, to provide the title compound.

Example 10c 4-(cyclopropylmethyl)-10-methyl-11-oxo-3,4,10,11-tetrahydro-1H-1,4,5,10-tetraazadibenzo[cd,f]azulene-7-sulfonamide Example 10c was prepared according to the procedure used for the preparation of Example 1k, substituting Example 10b for Example 1j, to provide the title compound. $^1$H NMR (500 MHz, DMSO-$d_6$) δ 11.90 (s, 1H), 8.46 (d, J=2.44 Hz, 1H), 8.31 (d, J=2.44 Hz, 1H), 7.51 (s, 1H), 7.31 (s, 2H), 7.22 (d, J=2.44 Hz, 1H), 4.39 (s, 2H), 3.63 (s, 3H), 3.48 (d, J=6.41 Hz, 2H), 0.45 (dd, J=8.09, 1.68 Hz, 2H), 0.25 (dd, J=4.88 Hz, 2H). MS (ESI+) m/z 386.1 (M+H)$^+$.

Example 11

4-(4-fluorophenyl)-7,10-dimethyl-3,4-dihydro-1H-1,4,5,10-tetraazadibenzo[cd,f]azulen-11(10H)-one Example 11a 3-bromo-N-(4-fluorophenyl)-5-methylpyridin-2-amine 2-Amino-3-bromo-5-methylpyridine (0.468 g, 2.5 mmol), 4-fluoroiodobenzene (0.555 g, 2.500 mmol), diacetoxypalladium (0.017 g, 0.075 mmol), (9,9-dimethyl-9H-xanthene-4,5-diyl)bis(diphenylphosphine) (0.043 g, 0.075 mmol) and sodium 2-methylpropan-2-olate (0.336 g, 3.50 mmol) were combined in t-butanol (10.00 mL) and sparged with argon for 10 minutes. The mixture was heated for 60 minutes at 85° C., cooled, diluted with 50 mL ethanol and filtered through Celite to remove solids. The filtrate was concentrated and diluted with ethyl acetate. The organic layer was washed with water, saturated aqueous sodium chloride, dried (anhydrous sodium sulfate), treated with 3-mercaptopropyl functionalized silica, filtered and concentrated. Purification by chromatography (silica gel, 0-25% ethyl acetate in heptanes) afforded the title compound (0.317 g, 45%).

Example 11b 4-(2-((4-fluorophenyl)amino)-5-methylpyridin-3-yl)-6-methyl-1-tosyl-1H-pyrrolo[2,3-c]pyridin-7(6H)-one Example 11a (0.3 g, 1.067 mmol), Example 1 f (0.457 g, 1.067 mmol), tris(dibenzylideneacetone)dipalladium (0) (0.029 g, 0.032 mmol), 1,3,5,7-tetramethyl-6-phenyl-2,4,8-trioxa-6-phosphaadamantane (0.031 g, 0.107 mmol) and sodium carbonate (0.396 g, 3.74 mmol) were combined and sparged with argon for 15 minutes. A solution of 4:1 dioxane/water (12 mL) was sparged with nitrogen for 15 minutes and transferred by syringe into the reaction vessel under argon. The mixture was stirred for 1 hour at 60° C., cooled and partitioned into 100 mL of water and 120 mL of dichloromethane. The organic layer was washed with water, saturated aqueous sodium chloride, dried (anhydrous sodium sulfate), treated with 3-mercaptopropyl functionalized silica, filtered and concentrated. Purification by trituration in 9:1 heptane/ethyl acetate afforded the title compound (0.46 g, 86%).

Example 11c 4-(2-((4-fluorophenyl)amino)-5-methylpyridin-3-yl)-6-methyl-1H-pyrrolo[2,3-c]pyridin-7(6H)-one Example 11c was prepared according to the procedure used for the preparation of Example 5e, substituting Example 11b for Example 5d. Purification by trituration in dichloromethane afforded the title compound (0.20 g, 63%).

Example 11d 4-(4-fluorophenyl)-7,10-dimethyl-3,4-dihydro-1H-1,4,5,10-tetraazadibenzo[cd,f]azulen-11(10H)-one A mixture of Example 11c (0.05 g, 0.144 mmol), paraformaldehyde (0.043 g, 1.435 mmol) and 4M hydrogen chloride (1.076 mL, 4.31 mmol) in methanol (1.435 mL) in a sealed microwave tube was heated by microwave at 130° C. for 2 hours. The mixture was concentrated and the residue was partitioned between ethyl acetate and 5% aqueous sodium bicarbonate. The organic layer was washed with saturated aqueous sodium chloride, dried (anhydrous sodium sulfate), filtered and concentrated. Purification by chromatography (silica gel, 1-4% methanol in dichloromethane) afforded the title compound (0.008 g, 14%). $^1$H NMR (400 MHz, DMSO-d$_6$) δ 11.48 (s, 1H), 8.23 (s, 1H), 8.08 (s, 1H), 7.63 (s, 1H), 7.27 (s, 1H), 6.78 (t, J=9.00 Hz, 2H), 6.49-6.55 (m, 2H), 4.74 (s, 2H), 3.57 (s, 3H), 2.39 (s, 3H). MS (ESI+) m/z 361 (M+H)$^+$.

Example 12

4-(2,4-difluorophenyl)-10-methyl-7-((methylsulfonyl)methyl)-3,4-dihydro-1H-1,4,10-triazadibenzo[cd,f]azulen-11(10H)-one Example 12a 2,4-difluoro-N-(4-((methylsulfonyl)methyl)phenyl)aniline A 100 mL microwave tube was charged with 2,4-difluoroaniline (1.235 mL, 12.26 mmol), Example 9a (3.0539 g, 12.26 mmol), diacetoxypalladium (0.055 g, 0.245 mmol), dicyclohexyl(2',4',6'-triisopropyl-[1,1'-biphenyl]-2-yl)phosphine (0.234 g, 0.490 mmol), cesium carbonate (5.59 g, 17.16 mmol), toluene (40.9 mL) and tert-butanol (8.17 mL). The tube was sealed, and the reaction mixture was heated in a Milestone Ethos microwave, 5 minute ramp to 150° C., then 10 minutes fixed hold time. The reaction mixture was filtered through a 10 g Celite SPE column and rinsed with ethyl acetate. The filtrate was concentrated, and the residue was purified by flash chromatography (20-100% ethyl acetate/heptanes) to provide the title compound (3.44 g, 94% yield).

Example 12b 2-bromo-N-(2,4-difluorophenyl)-4-((methylsulfonyl)methyl)aniline

A 500 mL round-bottomed flask was charged with Example 12a (3.4409 g, 11.57 mmol) and acetic acid (116 mL). The reaction mixture was placed into a water bath. N-bromosuccinimide (2.060 g, 11.57 mmol) was added in 2 portions, 10 minutes apart. The reaction mixture was stirred at ambient temperature for 1.5 hours. The reaction mixture was quenched with 200 mL 10% sodium thiosulfate and diluted with water. The reaction mixture was extracted 2× with ethyl acetate. The combined organic layers were washed 2× with 2N NaOH (until the pH of the aqueous was >7) and 1× with saturated aqueous sodium chloride solution, dried over anhydrous magnesium sulfate, filtered and concentrated. The residue was taken up into ethyl acetate, then treated with heptanes. The resulting slurry was stirred for 30 minutes and filtered. to provide the title compound 3.82 g, 88% yield).

Example 12c 4-(2-((2,4-difluorophenyl)amino)-5-((methylsulfonyl)methyl)phenyl)-6-methyl-1-tosyl-1H-pyrrolo[2,3-c]pyridin-7(6H)-one A 250 mL round-bottomed flask was charged with Example 12b (1.9813 g, 5.27 mmol), Example 1f (2.051 g, 4.79 mmol), sodium carbonate (1.776 g, 16.76 mmol), tris(dibenzylideneacetone)dipalladium (II) (0.219 g, 0.239 mmol), and 1,3,5,7-tetramethyl-6-phenyl-2,4,8-trioxa-6-phosphaadamantane (0.238 g, 0.814 mmol). The solids were sparged with nitrogen for 30 minutes. Degassed dioxane (38.3 mL) and water (9.58 mL) were added. The reaction was heated at 60° C. for 3 hours. The reaction mixture was cooled to room temperature and partitioned between ethyl acetate and water. The organic layer was washed with saturated aqueous sodium chloride solution, dried over magnesium sulfate, filtered, and concentrated. The residue

89 was taken up into dichloromethane, triturated with ether, and filtered to provide the title compound (2.30 g, 80% yield).

Example 12d 4-(2-((2,4-difluorophenyl)amino)-5-((methylsulfonyl)methyl)phenyl)-6-methyl-1H-pyrrolo[2,3-c]pyridin-7(6H)-one A 20 mL microwave tube was charged with Example 12c (1.9830 g, 3.32 mmol), lithium hydroxide monohydrate (1.392 g, 33.2 mmol), dioxane (16 mL) and water (5.33 mL) to give a white suspension. The reaction mixture was heated at 50° C. for 72 hours. The reaction mixture was cooled to ambient temperature and diluted with water. The resulting suspension was filtered, and the solid was rinsed with water and dried under vacuum overnight (1.25 g, 85% yield).

Example 12e 4-(2,4-difluorophenyl)-10-methyl-7-((methylsulfonyl)methyl)-3,4-dihydro-1H-1,4,10-triazadibenzo[cd,f]azulen-11(10H)-one A 5 mL microwave tube was charged with Example 12d (0.0504 g, 0.114 mmol), paraformaldehyde (0.051 g, 0.568 mmol) and methanol (1.137 mL). 4N HCl in dioxane (0.568 mL, 2.273 mmol) was added. The tube was closed and the reaction mixture was heated at 90° C. for 1 hour. The reaction mixture was cooled to room temperature and diluted with ether. The resulting suspension was filtered, and the solid was rinsed with ether and collected. The solid and the filtrate were combined and purified by flash chromatography (0-5% methanol/dichloromethane) to provide the title compound (0.0234 g, 45% yield). $^1$H NMR (300 MHz, DMSO-$d_6$) δ 11.83 (s, 1H), 7.85 (d, J=2.0 Hz, 1H), 7.66 (s, 1H), 7.26 (d, J=10.2 Hz, 1H), 6.99-7.19 (m, 3H), 6.81 (s, 1H), 4.72-4.78 (m, 2H), 4.49 (d, J=1.1 Hz, 3H), 4.01 (m, 1H), 3.62 (s, 3H), 2.95 (s, 3H). MS (ESI+) m/z 456.3 (M+H)$^+$.

Example 13

4-(cyclopropylmethyl)-10-methyl-3,4-dihydro-1H-1,4,10-triazadibenzo[cd,f]azulen-11(10H)-one Example 13a 2-bromo-N-(cyclopropylmethyl)aniline A 100 mL flask was charged with 2-bromoaniline (1.72 g, 10.0 mmol), cyclopropanecarbaldehyde (0.374 mL, 5.00 mmol), acetic acid (2.86 mL, 50.0 mmol) and dichloromethane (50 mL). The resulting solution was heated at 50° C. for 1 hour. The solution was cooled in an ice bath and the sodium triacetoxyborohydride (2.119 g, 10.0 mmol) was added portionwise over a few minutes. After 15 minutes, the ice bath was removed and the solution was stirred for 2 hours while warming to ambient temperature. The reaction mixture was quenched with 2.5 M sodium hydroxide (about 15 mL) and partitioned between saturated aqueous sodium bicarbonate solution (100 mL) and ethyl acetate (100 mL). The layers were separated and the organic layer was dried over anhydrous sodium sulfate, filtered and concentrated. The residue was purified by flash chromatography (silica gel, 0-10% ethyl acetate in heptanes) to provide the title compound (1.05 g, 93%).

90

Example 13b 4-(2-((cyclopropylmethyl)amino)phenyl)-6-methyl-1-tosyl-1H-pyrrolo[2,3-c]pyridin-7(6H)-one A 25 mL vial was charged with Example 1f (244 mg, 0.570 mmol), tris(dibenzylideneacetone)dipalladium (0) (15.66 mg, 0.017 mmol), Example 13a (132.1 mg, 0.584 mmol), 1,3,5,7-tetramethyl-8-phenyl-2,4,6-trioxa-8-phosphaadamantane (18.33 mg, 0.063 mmol) and potassium phosphate (363 mg, 1.710 mmol). This mixture was sparged with argon for 30 minutes. To this vial was added a mixture of dioxane (4 mL) and water (1 mL) [that had been degassed with argon for 30 minutes]. The mixture was heated at 75° C. for 2.5 hours. Upon cooling the reaction mixture was partitioned between ethyl acetate (75 mL) and 50% saturated aqueous sodium chloride (100 mL). The layers were separated and the organic layer was treated with 3-mercaptopropyl functionalized silica gel (Aldrich), dried over anhydrous sodium sulfate, filtered and concentrated. The residue was purified by flash chromatography (silica gel, 0-3% methanol in dichloromethane) to provide the title compound (266 mg, 100%).

Example 13c 4-(2-((cyclopropylmethyl)amino)phenyl)-6-methyl-1H-pyrrolo[2,3-c]pyridin-7(6H)-one A 25 mL flask was charged with Example 13b (255 mg, 0.570 mmol), cetyltrimethylammonium bromide (10.38 mg, 0.028 mmol), potassium hydroxide (615 mg, 10.96 mmol), dioxane (9 mL) and water (3 mL). The mixture was heated at 90° C. for 2.5 hours. Upon cooling, the mixture was neutralized with 1M aqueous hydrogen chloride solution and partitioned between ethyl acetate (80 mL) and 50% saturated aqueous sodium chloride (75 mL). The layers were separated and the aqueous layer was extracted with ethyl acetate (2×40 mL). The combined organics were dried over anhydrous sodium sulfate, filtered and concentrated. The residue was purified by flash chromatography (silica gel, 0-5% methanol in dichloromethane) to provide the title compound (120 mg, 72%).

Example 13d 4-(cyclopropylmethyl)-10-methyl-3,4-dihydro-1H-1,4,10-triazadibenzo[cd,f]azulen-11(10H)-one A 5 mL microwave vial was charged with Example 13c (60 mg, 0.205 mmol), paraformaldehyde (92 mg, 1.023 mmol), methanol (2 mL) and hydrogen chloride (4M in dioxane, 1.023 mL, 4.09 mmol). The vial was sealed and the reaction mixture was heated at 90° C. for 1 hour. Upon cooling, the reaction mixture was partitioned between 50% saturated bicarbonate solution (100 mL) and ethyl acetate (75 mL). The layers were separated and the aqueous layer was extracted with ethyl acetate (50 mL). The combined organic layers were dried over anhydrous sodium sulfate, filtered and concentrated. The residue was purified by flash chromatography (silica gel, 0-5% methanol in dichloromethane) to provide the title compound (52 mg, 83%). 1H NMR (400 MHz, DMSO-$d_6$) δ 11.74 (s, 1H), 7.63-7.67 (m, 1H), 7.59 (s, 1H), 7.10-7.25 (m, 4H), 4.19 (s, 2H), 3.60 (s, 3H), 2.68 (d, J=6.41 Hz, 2H), 0.74-0.87 (m, 1H), 0.45-0.36 (m, 2H), −0.07 (q, J=4.78 Hz, 2H).). MS (ESI+) m/z 306.0 (M+H)$^+$.

Example 14 methyl 3-(4-(cyclopropylmethyl)-10-methyl-7-((methylsulfonyl)methyl)-11-oxo-3,4,10,11-tetrahydro-1H-1,4,10-triazadibenzo[cd,f]azulen-3-yl)propanoate A stock solution of Example 6c (0.086 M in methanol, 455 µL, 0.040 mmol, 1.0 equivalent), HCl (4.0 M in dioxane, 195 µL, 0.78 mmol, 20 eq), and methyl 4-oxobutanoate (0.40 M in methanol, 243 µL, 0.19 mmol, 5 equivalents) were combined and heated under microwave conditions at 90° C. for 99 minutes. The reaction mixture was concentrated and purified by reverse phase HPLC (C8 column, $CH_3CN$/water (0.1% ammonium acetate), 5-100% gradient) to afford the title compound (5.1 mg, 27% yield). $^1$H NMR (400 MHz, DMSO-$d_6$-$D_2O$) δ 7.70 (s, 1H), 7.52 (s, 1H), 7.22-7.33 (m, 2H), 7.12 (s, 1H), 4.43 (bs, 1H), 3.63 (s, 2H), 3.55 (m, 4H), 2.89 (s, 3H), 1.71 (m, 2H), 0.74 (s, 1H), 0.02-0.37 (m, 2H), −0.13 (s, 2H). MS (APCI) m/z 484.1 $(M+H)^+$.

Example 15

4-(cyclopropylmethyl)-3-(2-methoxyethyl)-10-methyl-7-((methylsulfonyl)methyl)-3,4-dihydro-1H-1,4,10-triazadibenzo[cd,f]azulen-11(10H)-one A stock solution of Example 6c (0.086 M in methanol, 455 µl, 0.040 mmol, 1.0 equivalent), HCl (4.0 M in dioxane, 195 µL, 0.78 mmol, 20 eq), and 3-methoxypropanal (0.40 M in methanol, 243 µL, 0.19 mmol, 5 equivalents) were combined and heated under microwave conditions at 90° C. for 99 minutes. The reaction mixture was concentrated and purified by reverse phase HPLC (C8 column, $CH_3CN$/water (0.1% ammonium acetate), 5-100% gradient) to afford the title compound. $^1$H NMR (400 MHz, DMSO-$d_6$-$D_2O$) δ 7.69 (bs, 1H), 7.51 (s, 1H), 7.19-7.32 (m, 2H), 7.10 (s, 1H), 4.42 (bs, 2H), 3.63 (s, 3H), 2.74-2.93 (m, 5H), 1.77 (s, 2H), 1.08-1.43 (m, 1H), 0.70-0.83 (m, 1H), 0.02-0.40 (m, 2H), −0.11 (s, 2H). MS (APCI) m/z 456.1 $(M+H)^+$.

Example 16

3-benzyl-10-methyl-7-((methylsulfonyl)methyl)-3,4-dihydro-1H-1,4,10-triazadibenzo[cd,f]azulen-11(10H)-one A stock solution of Example 5e (0.11 M in methanol, 417 µL, 0.045 mmol, 1.0 equivalent), HCl (4.0 M in dioxane, 226 µL, 0.90 mmol, 20 equivalents), and 2-phenylacetaldehyde (0.40 M in methanol, 189 µL, 0.225 mmol, 5 equivalents) were aspirated from their respective source vials, mixed through a perfluoroalkoxy mixing tube (0.2 mm inner diameter), and loaded into an injection loop. The reaction segment was injected into a flow reactor (Hastelloy coil, 0.75 mm inner diameter, 1.8 mL internal volume) set at 100° C., and passed through the reactor at 180 µL per minute (10 minute residence time). Upon exiting the reactor, the reaction mixture was loaded directly into an injection loop and purified by reverse phase HPLC (C8, $CH_3CN$/water (0.1% ammonium acetate), 5-100% gradient) to afford the title compound. (3.4 mg, 17% yield). $^1$H NMR (400 MHz, DMSO-$d_6$-$D_2O$) δ 7.70 (d, J=2.0 Hz, 1H), 7.51 (s, 1H), 7.27 (t, J=7.2 Hz, 1H), 7.21 (dd, J=8.3, 6.1 Hz, 1H), 7.10 (dd, J=10.1, 4.3 Hz, 3H), 6.78 (d, J=0.4 Hz, 1H), 6.72 (d, J=8.1 Hz, 1H), 4.54 (t, J=7.2 Hz, 1H), 4.36 (bs, 2H), 3.64 (s, 3H), 2.91-3.01 (m, 2H), 2.88 (s, 3H). MS (APCI) m/z 434.0 $(M+H)^+$.

Example 17 methyl 3-(10-methyl-7-((methylsulfonyl)methyl)-11-oxo-3,4,10,11-tetrahydro-1H-1,4,10-triazadibenzo[cd,f]azulen-3-yl)propanoate Example 17 was prepared according to the procedure used for the preparation of Example 16, substituting methyl 4-oxobutanoate for 2-phenylacetaldehyde to provide the title compound (8.7 mg, 45% yield). $^1$H NMR (400 MHz, DMSO-$d_6$-$D_2O$) δ 7.68 (d, J=2.0 Hz, 1H), 7.49 (s, 1H), 7.14 (dd, J=8.2, 1.8 Hz, 1H), 7.11 (s, 1H), 7.03 (d, J=8.0 Hz, 1H), 4.36 (bs, 2H), 4.27 (t, J=6.8 Hz, 1H), 3.63 (s, 3H), 3.55 (s, 3H), 2.87 (s, 3H), 2.26-2.46 (m, 2H), 1.75-1.97 (m, 2H). MS (APCI) m/z 430.0 $(M+H)^+$.

Example 18

10-methyl-7-((methylsulfonyl)methyl)-3-phenethyl-3,4-dihydro-1H-1,4,10-triazadibenzo[cd,f]azulen-11(10H)-one Example 18 was prepared according to the procedure used for the preparation of Example 16, substituting 3-phenylpropanal for 2-phenylacetaldehyde to provide the title compound (5.1 mg, 25% yield). $^1$H NMR (400 MHz, DMSO-$d_6$-$D_2O$) δ 7.67 (d, J=2.0 Hz, 1H), 7.49 (s, 1H), 7.21 (t, J=7.4 Hz, 2H), 7.01-7.19 (m, 6H), 4.36 (bs, 2H), 4.23-4.30 (m, 1H), 3.63 (s, 3H), 2.86 (s, 3H), 2.72-2.84 (m, 1H), 2.58-2.71 (m, 1H), 1.65-1.98 (m, 2H). MS (APCI) m/z 448.1 $(M+H)^+$.

Example 19

3-isobutyl-10-methyl-7-((methylsulfonyl)methyl)-3,4-dihydro-1H-1,4,10-triazadibenzo[cd,f]azulen-11(10H)-one Example 19 was prepared according to the procedure used for the preparation of Example 16, substituting 3-methylbutanal for 2-phenylacetaldehyde to provide the title compound (4.4 mg, 24% yield). $^1$H NMR (400 MHz, DMSO-$d_6$-$D_2O$) δ 7.67 (d, J=2.0 Hz, 1H), 7.48 (s, 1H), 7.13 (dd, J=8.1, 2.0 Hz, 1H), 7.09 (s, 1H), 7.00 (d, J=8.0 Hz, 1H), 4.35 (bs, 2H), 4.27 (t, J=7.0 Hz, 1H), 3.63 (s, 3H), 2.87 (s, 3H), 1.63-1.79 (m, 1H), 1.54 (ddd, J=13.6, 7.7, 6.0 Hz, 1H), 1.33-1.48 (m, 1H), 0.89 (t, J=6.6 Hz, 6H). MS (APCI) m/z 400.0 $(M+H)^+$.

Example 20

(E)-3-(4-fluorostyryl)-10-methyl-7-((methylsulfonyl)methyl)-3,4-dihydro-1H-1,4,10-triazadibenzo[cd,f]azulen-11(10H)-one Example 20 was prepared according to the procedure used for the preparation of Example 16, substituting (E)-3-(4-fluorophenyl)acrylaldehyde for 2-phenylacetaldehyde to provide the title compound (4.8 mg, 23% yield). $^1$H NMR (400 MHz, DMSO_$D_2O$) δ 7.67 (s, 1H), 7.52 (s, 1H), 7.31 (dd, J=8.7, 5.6 Hz, 2H), 7.11-7.17 (m, 1H), 7.01-7.11 (m, 4H), 6.45 (d, J=15.8 Hz, 1H), 6.29 (dd, J=15.9, 6.9 Hz, 1H), 5.00 (d, J=6.7 Hz, 1H), 4.35 (s, 2H), 3.65 (s, 3H), 2.82 (s, 3H). MS (APCI) m/z 464.0 (M+H)$^+$.

Example 21

7-amino-4-(4-fluorophenyl)-10-methyl-3,4-dihydro-1H-1,4,5,10-tetraazadibenzo[cd,f]azulen-11(10H)-one

Example 21a

3-Bromo-2-chloro-5-nitropyridine (3.936 g, 16.58 mmol), 4-fluoroaniline (5.53 g, 49.7 mmol) and dimethyl sulfoxide (DMSO) (33.2 mL) were combined and stirred at 120° C. for 1 hour. The reaction mixture was cooled to ambient temperature, producing a solid. Precipitation was induced further by the addition of 150 mL of water. The solid was collected by filtration and rinsed with 600 mL of water. The solid was purified by flash chromatography (silica gel, 0 to 20% ethyl acetate in heptanes) and then triturated with 15% ethyl acetate in heptanes to provide 4.2 g (81%) of the title compound.

Example 21b 4-(2-((4-fluorophenyl)amino)-5-nitropyridin-3-yl)-6-methyl-1H-pyrrolo[2,3-c]pyridin-7(6H)-one Example 21b was prepared according to the procedure used for the preparation of Example 1j, substituting Example 21a for Example 1i, to provide the title compound.

Example 21c 4-(4-fluorophenyl)-10-methyl-7-nitro-3,4-dihydro-1H-1,4,5,10-tetraazadibenzo[cd,f]azulen-11(10H)-one Example 21c was prepared according to the procedure used for the preparation of Example 1k, substituting Example 21b for Example 1j, to provide the title compound.

Example 21d 7-amino-4-(4-fluorophenyl)-10-methyl-3,4-dihydro-1H-1,4,5,10-tetraazadibenzo[cd,f]azulen-11(10H)-one A mixture of Example 21c (0.06 g, 0.153 mmol), and Pd/C (0.033 g, 0.031 mmol) in ethyl acetate (10 mL) was treated with a balloon of hydrogen. The reaction mixture was stirred overnight. The solvent was removed, and residue was purified by reverse phase HPLC (C18, CH$_3$CN/water (0.1% TFA), 0-100% gradient) to afford the title compound (0.0351 g, 63%) as the bis TFA salt. $^1$H NMR (500 MHz, DMSO-d$_6$) δ 11.92 (s, 1H), 7.85 (d, J=2.44 Hz, 1H), 7.79 (s, 1H), 7.68 (s, 1H), 7.36 (d, J=2.44 Hz, 1H), 6.84 (t, J=8.85 Hz, 1H), 6.44-6.47 (m, 2H), 4.81 (s, 2H), 3.56 (s, 3H). MS (ESI+) m/z 362.1 (M+H)$^+$.

Example 22

N-(4-(4-fluorophenyl)-10-methyl-11-oxo-3,4,10,11-tetrahydro-1H-1,4,5,10-tetraazadibenzo[cd,f]azulen-7-yl)ethanesulfonamide A mixture of Example 21d (0.025 g, 0.069 mmol), ethanesulfonyl chloride (0.027 g, 0.208 mmol), and triethylamine (0.042 g, 0.415 mmol) in dichloromethane (2 mL) was stirred at ambient temperature for 2 hours. The solvent was removed, and residue was treated with dioxane (2 mL) and 2.0 N NaOH (1 mL). The reaction mixture was heated at 85° C. for 2 hours. The reaction mixture was partitioned between water and ethyl acetate. The organic layer was separated. The aqueous layer was neutralized to pH=7, and extracted with additional ethyl acetate twice. The combined organic layers were washed with saturated aqueous sodium chloride, dried over anhydrous magnesium sulfate, filtered, and concentrated under reduced pressure. The residue was purified by reverse phase HPLC (C18, CH$_3$CN/water (0.1% TFA), 0-100% gradient) to afford the title compound (0.022 g, 0.049 mmol, 70.1% yield) as mono TFA salt. $^1$H NMR (500 MHz, DMSO-d$_6$) δ 11.89 (s, 1H), 10.12 (s, 1H), 8.28 (s, 1H), 8.01 (s, 1H), 7.59 (s, 1H), 7.35 (s, 1H), 6.83 (t, J=8.39 Hz, 1H), 6.49-6.50 (m, 2H), 4.76 (s, 2H), 3.57 (s, 3H), 3.27 (q, J=7.17 Hz, 2H), 1.29 (t, J=7.17 Hz, 3H). MS (ESI+) m/z 451.1 (M+H)$^+$.

Example 23

N-(4-(2,4-difluorophenyl)-10-methyl-11-oxo-3,4,10,11-tetrahydro-1H-1,4,5,10-tetraazadibenzo[cd,f]azulen-7-yl)ethanesulfonamide

Example 23a 3-bromo-N-(2,4-difluorophenyl)-5-nitropyridin-2-amine

A mixture of 3-bromo-2-chloro-5-nitropyridine (2.374 g, 10 mmol) and 2,4-difluoroaniline (2.58 g, 20 mmol) in DMSO (20 mL) was heated at 100° C. for 2 hours. After cooling, the reaction mixture was partitioned between water and ethyl acetate. The organic layer was separated, and the aqueous layer was extracted with additional ethyl acetate twice. The combined organic layers were washed with saturated aqueous sodium chloride solution, dried over anhydrous magnesium sulfate, filtered, and concentrated. The residue was purified by flash chromatography on silica gel, eluting with 1:20 ethyl acetate/heptans to give the title compound (1.75 g, 5.30 mmol, 53.0% yield) as yellow crystals.

Example 23b 4-(2-((2,4-difluorophenyl)amino)-5-nitropyridin-3-yl)-6-methyl-1H-pyrrolo[2,3-c]pyridin-7(6H)-one A mixture of 3 Example 23a (0.330 g, 1 mmol), Example 1f (0.471 g, 1.100 mmol), 1,3,5,7-tetramethyl-8-phenyl-2,4,6-trioxa-8-phosphaadamantane (0.034 g, 0.117 mmol), tris(dibenzylideneacetone)dipalladium(0) (0.027 g, 0.030 mmol), and potassium phosphate (0.531 g, 2.500 mmol) in dioxane (4 mL) and water (1 mL) was degassed and back-filled with nitrogen several times. The reaction mixture was heated at 60° C. overnight. To this reaction mixture were added dioxane (5 mL) and 2.0 N NaOH (5 mL). The reaction was heated at 90° C. for 2 hours. After cooling, the reaction mixture was partitioned between 0.1 N HCl and ethyl acetate. The aqueous pH appeared around 5. The organic layer was separated, and the aqueous layer was extracted with additional ethyl acetate twice. The combined organic layers were washed with saturated aqueous sodium chloride solution, dried over anhydrous magnesium sulfate, filtered, and concentrated. The residue was triturated with 3:7 ethyl acetate/heptanes to give the title compound (0.365 g, 0.919 mmol, 92% yield).

Example 23c 4-(2,4-difluorophenyl)-10-methyl-7-nitro-3,4-dihydro-1H-1,4,5,10-tetraazadibenzo[cd,f]azulen-11(10H)-one A mixture of Example 23b (0.17 g, 0.428 mmol), 4 N hydrogen chloride in dioxane (3.21 mL, 12.84 mmol) and formaldehyde (0.128 g, 4.28 mmol) in methanol (2) was heated at 130° C. under microwave conditions for 2 hours. After cooling, the reaction mixture was partitioned between water and ethyl acetate. The organic layer was separated, and the aqueous layer was extracted with additional ethyl acetate three times. The combined organic layers were washed with saturated aqueous sodium chloride solution, dried over anhydrous magnesium sulfate, filtered, and concentrated. The residue was used for the next reaction without additional purification.

Example 23d 7-amino-4-(2,4-difluorophenyl)-10-methyl-3,4-dihydro-1H-1,4,5,10-tetraazadibenzo[cd,f]azulen-11(10H)-one A mixture of 23c (0.18 g, 0.440 mmol), iron (0.123 g, 2.199 mmol), and ammonium hydrochloride (0.047 g, 0.879 mmol) in tetrahydrofuran (5 mL), water (1 mL) and ethanol (5 mL) was heated at 90° C. for 2 hours. The solid was filtered off, and washed with ethyl acetate several times. It was then poured into water. Organic layer was separated, and the aqueous layer was extracted with ethyl acetate several times. The combined organic layers were washed with saturated aqueous sodium chloride, dried over anhydrous magnesium sulfate, filtered, and concentrated. The residue was purified by reverse phase HPLC (C18, CH$_3$CN/water (0.1% TFA), 0-100% gradient) to give 0.05 g (23.1%) of the title compound as a bis TFA salt.

Example 23e

N-(4-(2,4-difluorophenyl)-10-methyl-11-oxo-3,4,10,11-tetrahydro-1H-1,4,5,10-tetraazadibenzo[cd,f]azulen-7-yl)ethanesulfonamide A mixture of Example 23d (0.05 g, 0.132 mmol), ethanesulfonyl chloride (0.017 g, 0.132 mmol), and triethylamine (0.013 g, 0.132 mmol) in dichloromethane (5 mL) was stirred at ambient temperature for 2 hours. The solvent was removed, and residue was treated with dioxane (2 mL) and 2.0 N NaOH (1 mL). The reaction mixture was heated at 85° C. for 2 hours. The reaction mixture was partitioned between water and ethyl acetate. The organic layer was separated. The aqueous layer was neutralized to pH=7, and extracted with additional ethyl acetate twice. The combined organic layers were washed with saturated aqueous sodium chloride, dried over anhydrous magnesium sulfate, filtered, and concentrated under reduced pressure. The residue was purified by reverse phase HPLC (C18, CH$_3$CN/water (0.1% TFA), 0-100% gradient) to afford the title compound (0.048 g, 0.77 mmol, 58.3% yield) as mono TFA salt. $^1$H NMR (500 MHz, DMSO-d$_6$) δ 11.92 (s, 1H), 9.76 (s, 1H), 7.91-7.93 (m, 2H), 7.62 (s, 1H), 7.29-7.35 (m, 1H), 7.20 (d, J=2.75 Hz, 1H), 7.07-7.13 (m, 1H), 7.00-7.06 (m, 1H), 4.76 (s, 2H), 3.65 (s, 3H), 3.14 (q, J=7.32 Hz, 2H), 1.25 (t, J=7.32 Hz, 3H). MS (ESI+) m/z 472.2 (M+H)$^+$.

Example 24

4-butyl-10-methyl-7-((methylsulfonyl)methyl)-3,4-dihydro-1H-1,4,10-triazadibenzo[cd,f]azulen-11(10H)-one A 5 mL vial was charged with Example 5f (75 mg, 0.218 mmol), butyraldehyde (0.039 mL, 0.437 mmol), acetic acid (0.125 mL, 2.184 mmol) and dichloromethane (2.5 mL). The vial was sealed and the mixture was heated at 60° C. for 1 hour. The reaction mixture was cooled in an ice bath and sodium triacetoxyborohydride (93 mg, 0.437 mmol) was added portionwise over a few minutes. Stirring was continued overnight while warming to ambient temperature. The reaction mixture was quenched with 1 M sodium hydroxide (2 mL) and partitioned between saturated sodium bicarbonate solution (50 mL) and ethyl acetate (50 mL). The layers were separated and the aqueous layer was extracted with ethyl acetate (2×25 mL). The combined organic layers were dried over anhydrous sodium sulfate, filtered and concentrated. The residue was purified by flash chromatography (silica gel, 0-10% methanol in dichloromethane) to provide the title compound (74 mg, 85%). $^1$H NMR (400 MHz, DMSO-d$_6$) δ 11.76 (s, 1H), 7.68 (d, J=1.83 Hz, 1H), 7.50 (s, 1H), 7.23-7.29 (m, 1H), 7.17-7.21 (m, 1H), 7.14 (d, J=2.14 Hz, 1H), 4.44 (s, 2H), 4.08 (s, 2H), 3.62 (s, 3H), 2.90-2.98 (m, 5H), 1.32-1.43 (m, 2H), 1.14-1.25 (m, 2H), 0.77 (t, J=7.32 Hz, 3H). MS (ESI+) m/z 400.1 (M+H)$^+$.

Example 25 tert-butyl 3-((10-methyl-7-((methylsulfonyl)methyl)-11-oxo-10,11-dihydro-1H-1,4,10-triazadibenzo[cd,f]azulen-4(3H)-yl)methyl)pyrrolidine-1-carboxylate Example 25 was prepared according to the procedure used for the preparation of Example 24, substituting tert-butyl 3-formylpyrrolidine-1-carboxylate for butyraldehyde to provide the title compound. $^1$H NMR (400 MHz, DMSO-d$_6$) δ 11.79 (d, J=2.14 Hz, 1H), 7.70 (d, J=1.83 Hz, 1H), 7.53 (s, 1H), 7.24-7.29 (m, 1H), 7.18-7.24 (m, 1H), 7.14 (d, J=2.44 Hz, 1H), 4.44 (s, 2H), 4.12 (s, 2H), 3.62 (s, 3H), 3.13-3.24 (m, 2H), 3.03-3.12 (m, 1H), 2.75-2.97 (m, 6H), 2.18-2.30 (m, 1H), 1.73 (d, J=6.71 Hz, 1H), 1.26-1.49 (m, 10H). MS (ESI+) m/z 526.9 (M+H)$^+$.

Example 26

10-methyl-7-((methylsulfonyl)methyl)-4-((tetrahydrofuran-3-yl)methyl)-3,4-dihydro-1H-1,4,10-triazadibenzo[cd,f]azulen-11(10H)-one A 5 mL vial was charged with Example 5f (75 mg, 0.218 mmol), tetrahydrofuran-3-carbaldehyde (50% weight in water, 131 mg, 0.655 mmol), acetic acid (0.125 mL, 2.184 mmol) and dichloromethane (2.5 mL). The vial was sealed and the mixture was heated at 60° C. for 1 hour. The reaction mixture was cooled in an ice bath and sodium triacetoxyborohydride (93 mg, 0.437 mmol) was added portionwise over several minutes. Stirring was continued overnight while warming to ambient temperature. The reaction mixture was quenched with 1 M sodium hydroxide (2 mL) and partitioned between saturated sodium bicarbonate solution (50 mL) and ethyl acetate (50 mL). The layers were separated and the aqueous layer was extracted with ethyl acetate (2×25 mL). The combined organic layers were dried over anhydrous sodium sulfate, filtered and concentrated. The residue was purified by flash chromatography (silica gel, 0-10% methanol in dichloromethane) to provide the title compound (79.6 mg, 85%). NMR (400 MHz, DMSO-$d_6$) δ 11.79 (s, 1H), 7.70 (d, J=1.83 Hz, 1H), 7.54 (s, 1H), 7.24-7.30 (m, 1H), 7.18-7.23 (m, 1H), 7.15 (d, J=2.44 Hz, 1H), 4.45 (s, 2H), 4.13 (s, 2H), 3.45-3.66 (m, H), 3.25-3.30 (m, 1H), 2.94 (s, 3H), 2.84-2.92 (m, 1H), 2.77 (dd, J=12.36, 8.70 Hz, 1H), 2.20-2.35 (m, 1H), 1.65-1.85 (m, 1H), 1.33-1.46 (m, 1H). MS (ESI+) m/z 428.1 (M+H)$^+$.

Example 27

4-((4,4-difluorocyclohexyl)methyl)-10-methyl-7-((methylsulfonyl)methyl)-3,4-dihydro-1H-1,4,10-triazadibenzo[cd,f]azulen-11(10H)-one Example 27 was prepared according to the procedure used for the preparation of Example 24, substituting 4,4-difluorocyclohexanecarbaldehyde for butyraldehyde, to provide the title compound. $^1$H NMR (400 MHz, DMSO-$d_6$) δ 11.77 (d, J=1.83 Hz, 1H), 7.69 (d, J=1.83 Hz, 1H), 7.51 (s, 1H), 7.24-7.29 (m, 1H), 7.19-7.23 (m, 1H), 7.13 (d, J=2.44 Hz, 1H), 4.44 (s, 2H), 4.08 (s, 2H), 3.62 (s, 3H), 2.94 (s, 3H), 2.82 (d, J=7.02 Hz, 2H), 1.82-1.96 (m, 2H), 1.48-1.76 (m, 5H), 0.94-1.10 (m, 2H). MS (ESI+) m/z 428.1 (M+H)$^+$.

Example 28 tert-butyl 4-((10-methyl-7-((methylsulfonyl)methyl)-11-oxo-10,11-dihydro-1H-1,4,10-triazadibenzo[cd,f]azulen-4(3H)-yl)methyl)piperidine-1-carboxylate Example 28 was prepared according to the procedure used for the preparation of Example 24, substituting tert-butyl 4-formylpiperidine-1-carboxylate for butyraldehyde, to provide the title compound. $^1$H NMR (400 MHz, DMSO-$d_6$) δ 11.77 (d, J=2.44 Hz, 1H), 7.68 (d, J=1.83 Hz, 1H), 7.51 (s, 1H), 7.23-7.28 (m, 1H), 7.18-7.23 (m, 1H), 7.13 (d, J=2.44 Hz, 1H), 4.44 (s, 2H), 4.08 (s, 2H), 3.81 (d, J=11.90 Hz, 2H), 3.62 (s, 3H), 2.94 (s, 3H), 2.80 (d, J=6.10 Hz, 2H), 2.51 (s, 2H), 1.56 (d, J=10.68 Hz, 3H), 1.34 (s, 9H), 0.76-0.92 (m, 2H). MS (ESI+) m/z 540.9 (M+H)$^+$.

Example 29

10-methyl-7-((methylsulfonyl)methyl)-4-((tetrahydro-2H-pyran-3-yl)methyl)-3,4-dihydro-1H-1,4,10-triazadibenzo[cd,f]azulen-11(10H)-one Example 29 was prepared according to the procedure used for the preparation of Example 24, substituting tetrahydro-2H-pyran-3-carbaldehyde for butyraldehyde, to provide the title compound. $^1$H NMR (400 MHz, DMSO-$d_6$) δ 11.77 (d, J=1.83 Hz, 1H), 7.68 (d, J=2.14 Hz, 1H), 7.51 (s, 1H), 7.23-7.29 (m, 1H), 7.18-7.23 (m, 1H), 7.15 (d, J=2.75 Hz, 1H), 4.44 (s, 2H), 4.00-4.13 (m, 2H), 3.56-3.70 (m, 5H), 3.16-3.25 (m, 1H), 2.91-3.00 (m, 4H), 2.83-2.91 (m, 1H), 2.73-2.81 (m, 1H), 1.57-1.72 (m, 2H), 1.28-1.50 (m, 2H), 1.07 (t, J=9.61 Hz, 1H). MS (ESI+) m/z 540.9 (M+H)$^+$.

Example 30

4-(4,4-difluorocyclohexyl)-10-methyl-7-((methylsulfonyl)methyl)-3,4-dihydro-1H-1,4,10-triazadibenzo[cd,f]azulen-11(10H)-one Example 30 was prepared according to the procedure used for the preparation of Example 24, substituting 4,4-difluorocyclohexanone for butyraldehyde, to provide the title compound. NMR (300 MHz, DMSO-$d_6$) δ 11.84 (d, J=1.70 Hz, 1H), 7.72 (s, 1H), 7.59 (s, 1H), 7.25 (s, 2H), 7.19 (d, J=2.71 Hz, 1H), 4.46 (s, 2H), 4.08 (s, 2H), 3.62 (s, 3H), 2.94 (s, 3H), 2.88 (s, 1H), 1.96 (d, J=12.55 Hz, 2H), 1.19-1.86 (m, 6H). MS (ESI+) m/z 462.1 (M+H)$^+$.

Example 31

4-(4-fluorophenyl)-(3,3-$^2$H$_2$)-10-methyl-7-((methylsulfonyl)methyl)-3,4-dihydro-1H-1,4,10-triazadibenzo[cd,f]azulen-11(10H)-one A 20 mL microwave tube was charged Example 9e (0.0506 g, 0.119 mmol), formaldehyde-$d_2$ (0.095 mL, 0.595 mmol) and methanol (1.189 mL). 4N HCl in dioxane (0.595 mL, 2.379 mmol) was added. The tube was closed and the reaction was heated to 90° C. for 2 hours. The reaction was cooled to room temperature. The reaction was partitioned between dichloromethane and saturated aqueous sodium bicarbonate. The aqueous layer was extracted with dichloromethane. The combined organic layers were washed with saturated aqueous sodium chloride solution, dried over anhydrous magnesium sulfate, filtered, and concentrated. The residue was taken up into dichloromethane and triturated with ether. The resulting slurry was stirred for 10 minutes and filtered. The white solid was rinsed with ether, collected, and dried in a 60° C. vacuum oven to provide the title compound. $^1$H NMR (400 MHz, DMSO-$d_6$) δ11.80-11.85 (m, 1H), 7.91 (d, J=2.0 Hz, 1H), 7.60 (s, 1H), 7.40-7.51 (m, 1H), 7.33 (d, J=4.5 Hz, 2H), 6.72-6.85 (m, 2H), 6.36-6.46 (m, 2H), 4.53-4.59 (m, 2H), 3.56 (s, 3H), 3.00 (s, 3H). MS (ESI+) m/z 440.1 (M+H)$^+$.

Example 32

7-fluoro-4-(4-fluorophenyl)-10-methyl-3,4-dihydro-1H-1,4,5,10-tetraazadibenzo[cd,f]azulen-11(10H)-one Example 32a 4-(2-amino-5-fluoropyridin-3-yl)-6-methyl-1-tosyl-1H-pyrrolo[2,3-c]pyridin-7(6H)-one 3-Bromo-5-fluoropyridin-2-amine (0.3 g, 1.571 mmol), Example 1f (0.673 g, 1.571 mmol), tris(dibenzylideneacetone)dipalladium (0) (0.043 g, 0.047 mmol), 1,3,5,7-tetramethyl-6-phenyl-2,4,8-trioxa-6-phosphaadamantane (0.046 g, 0.157 mmol) and potassium phosphate (1.167 g, 5.50 mmol) were combined and sparged with argon for 15 minutes. Meanwhile a solution of 4:1 dioxane/water (8 mL) was sparged with nitrogen for 15 minutes and then transferred by syringe into the reaction vessel under argon. The mixture was stirred for 2 hours at 60° C., cooled, diluted with 50 mL of water and the crude solid was collected by filtration, washed with additional water and dried to afford the title compound (0.648 g, 100%).

Example 32b

4-(5-fluoro-2-((4-fluorophenyl)amino)pyridin-3-yl)-6-methyl-1H-pyrrolo[2,3-c]pyridin-7(6H)-one 1-Bromo-4-fluorobenzene (0.424 g, 2.425 mmol), Example 32a (0.5 g, 1.212 mmol), diacetoxypalladium (10.89 mg, 0.048 mmol), dicyclohexyl(2',4',6'-triisopropyl-[1,1'-biphenyl]-2-yl)phosphine (0.046 g, 0.097 mmol) and cesium carbonate (0.790 g, 2.425 mmol) were combined in a mixture of t-butanol (2.021 mL) and toluene (10.10 mL) and heated by microwave at 150° C. for 2 hours. The mixture was cooled and partitioned between ethyl acetate and water. The organic layer was washed with saturated aqueous sodium chloride, dried (anhydrous sodium sulfate), treated with 3-mercaptopropyl functionalized silica, filtered and concentrated. Purification by chromatography (silica gel, 1-5% methanol in dichloromethane) afforded the title compound (0.065 g, 15%).

Example 32c

7-fluoro-4-(4-fluorophenyl)-10-methyl-3,4-dihydro-1H-1,4,5,10-tetraazadibenzo[cd,f]azulen-11(10H)-one Example 32b (0.055 g, 0.156 mmol), paraformaldehyde (0.141 g, 4.68 mmol) and hydrogen chloride (4M in 1,4-dioxane, 1 mL, 4.00 mmol) were combined in methanol (1 mL) in a sealed tube and heated by microwave at 130° C. for 2 hours, cooled and concentrated. Purification by reverse phase HPLC (C18, $CH_3CN$/water (0.1% TFA), 0-100% gradient) afforded the title compound as the TFA salt (0.009 g, 12%). $^1$H NMR (500 MHz, DMSO-$d_6$) δ 11.91 (s, 1H), 8.43 (d, J=2.75 Hz, 1H), 8.27 (dd, J=9.92, 2.90 Hz, 1H), 7.85 (s, 1H), 7.36 (d, J=2.44 Hz, 1H), 6.78-6.92 (m, 2H), 6.43-6.53 (m, 2H), 4.78 (s, 2H), 3.56 (s, 3H). MS (ESI+) m/z 365 $(M+H)^+$.

Example 33

4-(4-fluorophenyl)-7,10-dimethyl-3-phenyl-3,4-dihydro-1H-1,4,5,10-tetraazadibenzo[cd,f]azulen-11(10H)-one A mixture of Example 11c and benzaldehyde (0.116 mL, 1.148 mmol) in acetic acid (1 mL) was heated in a sealed tube at 110° C. for 15 hours, cooled and concentrated. Purification by reverse phase HPLC (C18, $CH_3CN$/water (0.1% TFA), 0-100% gradient) afforded the title compound (0.016 g, 25%). $^1$H NMR (400 MHz, DMSO-$d_6$) δ 11.75 (s, 1H), 8.02 (s, 1H), 7.99 (s, 1H), 7.68 (s, 1H), 7.38 (d, J=2.75 Hz, 1H), 6.98-7.12 (m, 5H), 6.81-6.88 (m, 2H), 6.71-6.78 (m, 2H), 6.68 (s, 1H), 3.60 (s, 3H), 2.25 (s, 3H). MS (ESI+) m/z 437 $(M+H)^+$.

Example 34 ethyl 4-(4-fluorophenyl)-10-methyl-7-((methylsulfonyl)methyl)-11-oxo-3,4,10,11-tetrahydro-1H-1,4,10-triazadibenzo[cd,f]azulene-3-carboxylate Example 34 was prepared according to the procedure used for the preparation of Example 7, substituting Example 9e for Example 6c to provide the title compound. $^1$H NMR (300 MHz, DMSO-$d_6$) δ 11.95-12.00 (m, 1H), 7.85 (d, J=2.0 Hz, 1H), 7.62 (s, 1H), 7.37 (d, J=1.9 Hz, 1H), 7.24 (d, J=8.1 Hz, 1H), 6.87 (t, J=8.7 Hz, 2H), 6.46-6.61 (m, 2H), 6.18-6.29 (m, 1H), 4.44-4.62 (m, 2H), 3.70-4.03 (m, 2H), 3.58 (s, 3H), 2.93 (s, 3H), 0.87-1.03 (m, 3H). MS (ESI+) m/z 510.1 $(M+H)^+$.

Example 35 tert-butyl 4-(4-(4-fluorophenyl)-10-methyl-7-((methylsulfonyl)methyl)-11-oxo-3,4,10,11-tetrahydro-1H-1,4,10-triazadibenzo[cd,f]azulene-3-carbonyl)piperazine-1-carboxylate

Example 35a

4-(4-fluorophenyl)-10-methyl-7-((methylsulfonyl)methyl)-11-oxo-3,4,10,11-tetrahydro-1H-1,4,10-triazadibenzo[cd,f]azulene-3-carboxylic acid A 100 mL round-bottomed flask was charged with Example 34 (0.453 g, 0.888 mmol), dioxane (6.66 mL) and water (2.22 mL) to give a yellow solution. Lithium hydroxide hydrate (0.186 g, 4.44 mmol) was added. The reaction mixture was stirred at ambient temperature for 5 hours. The reaction mixture was quenched with 1N hydrochloric acid. The resulting slurry was stirred for 10 minutes and filtered. The solid was rinsed with water, dried on the fit overnight and collected to provide the title compound (0.3664 g, 86% yield).

Example 35b tert-butyl 4-(4-(4-fluorophenyl)-10-methyl-7-((methylsulfonyl)methyl)-11-oxo-3,4,10,11-tetrahydro-1H-1,4,10-triazadibenzo[cd,f]azulene-3-carbonyl)piperazine-1-carboxylate A 2 mL microwave tube was charged with Example 35a (0.0498 g, 0.103 mmol), tert-butyl piperazine-1-carboxylate (0.019 g, 0.103 mmol), polymer supported-carbodiimide (0.248 g, 0.310 mmol), 1H-benzo[d][1,2,3]triazol-1-ol (0.014 g, 0.103 mmol), N-ethyl-N-isopropylpropan-2-amine (0.036 mL, 0.207 mmol) and dimethylacetamide (1.034 mL). The tube was sealed, and the reaction mixture was heated in a Biotage Creator at 110° C. for 10 minutes fixed hold time. The reaction mixture was filtered, and the resin was rinsed thoroughly with ethyl acetate. The filtrate was washed twice with saturated aqueous sodium chloride. The organic layer was dried over anhydrous magnesium sulfate, filtered and concentrated. The residue was purified by flash chromatography (silica gel, 0-10% methanol in dichloromethane) to provide the title compound (0.0133 g, 20% yield). $^1$H NMR (300 MHz, DMSO-$d_6$) δ 11.78-11.89 (m, 1H), 7.77-7.89 (m, 1H), 7.50-7.61 (m, 1H), 7.35-7.45 (m, 1H), 7.20-7.34 (m, 2H), 6.76-6.90 (m, 2H), 6.43-6.57 (m, 2H), 6.33-6.43 (m, 1H), 4.42-4.66 (m, 2H), 3.66-3.81 (m, 2H), 3.40-3.61 (m, 5H), 2.98-3.22 (m, 2H), 2.92 (s, 3H), 2.66-2.85 (m, 2H), 1.47-1.29 (m, 9H). MS (ESI+) m/z 549.8 $(M+H)^+$.

Example 36

10-methyl-7-((methylsulfonyl)methyl)-4-(pyrrolidin-3-ylmethyl)-3,4-dihydro-1H-1,4,10-triazadibenzo[cd,f]azulen-11(10H)-one A 4 mL vial was charged with Example 25 (98 mg, 0.186 mmol) and dichloromethane (2 mL). The mixture was cooled in an ice bath and 2,2,2-trifluoroacetic acid (1 mL, 12.98 mmol) was added. Stirring was continued for 2 hours as the reaction mixture warmed to ambient temperature. The reaction mixture was concentrated under a heated stream of nitrogen and the residue was partitioned between saturated sodium bicarbonate solution (50 mL) and ethyl acetate (50 mL). The layers were separated and the aqueous layer was extracted with 10% methanol in dichloromethane (16×100 mL). The combined organics were also dried over anhydrous sodium sulfate, filtered and concentrated. The residue was purified by reverse phase HPLC (C18, $CH_3CN$/water (0.1% TFA), 0-100% gradient) to afford the title compound (56.6 mg, 56%) as the trifluoroacetic acid salt. 1H NMR (400 MHz, PYRIDINE-$d_5$) δ 13.48 (s, 1H), 11.08-11.34 (m, 1H), 8.06 (d, J=1.83 Hz, 1H), 7.56 (s, 2H), 7.38-7.42 (m, 1H), 7.36 (d, J=8.24 Hz, 1H), 4.76 (s, 2H), 4.25-4.40 (m, 2H), 3.63 (s, 3H), 3.58 (dd, J=11.29, 7.63 Hz, 1H), 3.42-3.52 (m, 1H), 3.30-3.42 (m, 2H), 3.14-3.21 (m, 1H), 3.14 (s, 3H), 3.02 (dd, J=12.51, 9.16 Hz, 1H), 2.59-2.72 (m, 1H), 1.90-2.04 (m, 1H), 1.59-1.73 (m, 1H). MS (ESI+) m/z 427.1 $(M+H)^+$.

Example 37

10-methyl-7-((methylsulfonyl)methyl)-4-(piperidin-4-ylmethyl)-3,4-dihydro-1H-1,4,10-triazadibenzo[cd,f]azulen-11(10H)-one A 4 mL vial was charged with Example 28 (81.5 mg, 0.151 mmol) and dichloromethane (2 mL). The mixture was cooled in an ice bath and 2,2,2-trifluoroacetic acid (1 mL, 13 mmol) was added. Stirring was continued for 2 hours while warming to ambient temperature. The reaction mixture was concentrated under a heated stream of nitrogen and the residue was purified by reverse phase HPLC (C18, $CH_3CN$/water (0.1% TFA), 0-100% gradient) to afford the title compound (76.9 mg, 92%) as the trifluoroacetic acid salt. $^1$H NMR (400 MHz, PYRIDINE-$d_5$) δ 13.45 (d, J=1.53 Hz, 1H), 10.89 (d, 1H), 8.08 (d, J=2.14 Hz, 1H), 7.61 (dd, J=8.24, 1.83 Hz, 2H), 7.41 (d, J=2.44 Hz, 1H), 7.37 (d, J=7.93 Hz, 1H), 4.77 (s, 2H), 4.27 (s, 2H), 3.64 (s, 3H), 3.52 (d, J=12.51 Hz, 2H), 3.13 (s, 3H), 3.00 (d, J=6.41 Hz, 2H), 2.88-2.98 (m, 2H), 1.80-1.99 (m, 3H), 1.55 (d, J=12.82 Hz, 2H). MS (ESI+) m/z 441.1 $(M+H)^+$.

Example 38

7-fluoro-10-methyl-3,4-dihydro-1H-1,4,5,10-tetraazadibenzo[cd,f]azulen-11(10H)-one Example 38a 4-(2-amino-5-fluoropyridin-3-yl)-6-methyl-1-tosyl-1H-pyrrolo[2,3-c]pyridin-7(6H)-one Example 38a was prepared according to the procedure used for the preparation of Example 8a, substituting 3-bromo-5-fluoropyridin-2-amine for 2-bromo-4-(methylsulfonyl)aniline and the reaction time was 4 hours instead of 3 hours, to provide the title compound in quantitative yield.

Example 38b 4-(2-amino-5-fluoropyridin-3-yl)-6-methyl-1H-pyrrolo[2,3-c]pyridin-7(6H)-one Example 38a (825 mg, 2.00 mmol), potassium hydroxide (1.68 g, 30.0 mmol) and cetyltrimethylammonium bromide (36.4 mg, 0.100 mmol) were combined in a mixture of dioxane (20 mL) and water (10 mL). The reaction mixture was heated at 100° C. for 3 hours and then cooled to ambient temperature. To this mixture was added water, and the pH was adjusted to pH 7 by the addition of 1M HCl. The mixture was extracted with ethyl acetate and the organic layer was washed with saturated aqueous sodium chloride twice, dried with anhydrous sodium sulfate, treated with 3-mercaptopropyl functionalized silica gel, filtered, and concentrated. The residue was triturated with dichloromethane to afford the title compound (460 mg, 89%).

Example 38c 7-fluoro-10-methyl-3,4-dihydro-1H-1,4,5,10-tetraazadibenzo[cd,f]azulen-11(10H)-one A 5 mL vial was charged with Example 38b (25.8 mg, 0.100 mmol), paraformaldehyde (30 mg, 1.0 mmol) and methanol (2 mL). To this suspension was added 4M HCl in dioxane (0.50 mL, 2.0 mmol). The vial was closed and heated in a microwave reactor at 120° C. for 2 hours. The reaction mixture was cooled to ambient temperature and concentrated. To this residue was added water, and the pH was adjusted to pH 7 by addition of saturated aqueous sodium bicarbonate. The residue was sonicated for 5 minutes and filtered to afford the title compound (23 mg, 85%). $^1$H NMR (300 MHz, DMSO-$d_6$) δ 11.84 (s, 1H) 7.96-8.06 (m, 2H) 7.79 (s, 1H) 7.18 (d, J=2.71 Hz, 1H) 6.16 (t, J=3.05 Hz, 1H) 4.15 (d, J=3.05 Hz, 2H) 3.61 (s, 3H). MS (ESI+) m/z 271 $(M+H)^+$.

Example 39 ethyl 7-fluoro-10-methyl-11-oxo-3,4,10,11-tetrahydro-1H-1,4,5,10-tetraazadibenzo[cd,f]azulene-3-carboxylate A 5 mL vial was charged with Example 38b (25.8 mg, 0.100 mmol), 50% ethyl 2-oxoacetate in toluene (0.198 mL, 1.00 mmol) and ethanol (2 mL). To this suspension was added 4M HCl in dioxane (0.50 mL, 2.0 mmol). The vial was closed and heated in a microwave reactor at 120° C. for 2 hours. The reaction mixture was cooled to ambient temperature and concentrated. The residue was purified by flash chromatography (silica gel, 2-4% methanol in dichloromethane) to afford the title compound (17 mg, 50%). $^1$H NMR (300 MHz, DMSO-$d_6$) δ 12.10 (s, 1H) 7.96-8.06 (m, 2H) 7.87 (s, 1H) 7.34 (d, J=2.71 Hz, 1H) 6.50 (d, J=5.43 Hz, 1H) 5.11 (d, J=5.43 Hz, 1H) 3.91 (q, J=7.12 Hz, 2H) 3.61 (s, 3H) 0.98 (t, J=7.12 Hz, 3H). MS (ESI+) m/z 343 $(M+H)^+$.

Example 40

4-(4-fluorophenyl)-3-(4-methoxypiperidine-1-carbonyl)-10-methyl-7-((methylsulfonyl)methyl)-3,4-dihydro-1H-1,4,10-triazadibenzo[cd,f]azulen-11(10H)-one Example 40 was prepared according to the procedure used for the preparation of Example 35b, substituting 4-methoxypiperidine for tert-butyl piperazine-1-carboxylate to provide the title compound. $^1$H NMR (300 MHz, DMSO-$d_6$) δ 11.78-11.83 (m, 1H), 7.81-7.86 (m, 1H), 7.55 (s, 1H), 7.33-7.43 (m, 1H), 7.24-7.33 (m, 1H), 7.21 (d, J=7.7 Hz, 1H), 6.79-6.89 (m, 2H), 6.43-6.53 (m, 2H), 6.28-6.40 (m, 1H), 4.46-4.61 (m, 2H), 4.01 (d, J=1.1 Hz, 1H), 3.53-3.41

(m, 1H), 3.56 (s, 3H), 3.41-3.53 (m, 1H), 3.25-3.29 (m, 5H), 2.92 (s, 3H), 1.89-2.14 (m, 1H), 1.69-1.89 (m, 1H), 1.32-1.69 (m, 2H). MS (ESI+) m/z 579.0 (M+H)$^+$

Example 41

4-(4-fluorophenyl)-10-methyl-3-(4-methylpiperazine-1-carbonyl)-7-((methylsulfonyl)methyl)-3,4-dihydro-1H-1,4,10-triazadibenzo[cd,f]azulen-11(10H)-one Example 41 was prepared according to the procedure used for the preparation of Example 35b, substituting 1-methylpiperazine for tert-butyl piperazine-1-carboxylate to provide the title compound. $^1$H NMR (300 MHz, DMSO-d$_6$) δ 11.79-11.85 (m, 1H), 7.84 (d, J=1.7 Hz, 1H), 7.55 (s, 1H), 7.40 (dd, J=8.0, 1.9 Hz, 1H), 7.18-7.32 (m, 2H), 6.78-6.89 (m, 2H), 6.45-6.54 (m, 2H), 6.32-6.40 (m, 1H), 4.47-4.61 (m, 2H), 3.44-3.61 (m, 5H), 2.74-3.04 (m, 5H), 2.15-2.38 (m, 5H). MS (ESI+) m/z 564.1 (M+H)$^+$.

Example 42

5,7-difluoro-10-methyl-4-((tetrahydrofuran-3-yl)methyl)-3,4-dihydro-1H-1,4,10-triazadibenzo[cd,f]azulen-11(10H)-one Example 42a 4-(2-amino-3,5-difluorophenyl)-6-methyl-1-tosyl-1H-pyrrolo[2,3-c]pyridin-7(6H)-one 2-Bromo-4,6-difluoroaniline (1.0 g, 4.81 mmol), Example 1f (2.059 g, 4.81 mmol), tris(dibenzylideneacetone)dipalladium (0), 1,3,5,7-tetramethyl-6-phenyl-2,4,8-trioxa-6-phosphaadamantane (0.141 g, 0.481 mmol) and potassium phosphate (3.57 g, 16.83 mmol) were combined and sparged with argon for 15 minutes. Meanwhile a solution of 4:1 dioxane/water (8 mL) was sparged with nitrogen for 15 minutes and transferred by syringe into the reaction vessel under argon. The mixture was stirred for 2 hours at 60° C., cooled to ambient temperature, and diluted with 100 mL of water. The resulting solid was collected by filtration, washed with additional water and dried to afford the title compound (1.6 g, 77%).

Example 42b 4-(2-amino-3,5-difluorophenyl)-6-methyl-1H-pyrrolo[2,3-c]pyridin-7(6H)-one Example 42a (1.6 g, 3.73 mmol), potassium hydroxide (6.27 g, 112 mmol) and N,N,N-trimethylhexadecan-1-aminium bromide (0.068 g, 0.186 mmol) were combined in dioxane (33.1 mL)/water (16.6 mL) and heated at 100° C. for 3 hours, cooled, diluted with ethyl acetate and water and the pH was adjusted to pH 8 by careful addition of 12 M HCl. The organic layer was washed with saturated aqueous sodium chloride, dried (anhydrous sodium sulfate), filtered and concentrated. Purification by chromatography (silica gel, 0.5-4% methanol in dichloromethane) afforded the title compound (0.80 g, 78%).

Example 42c 5,7-difluoro-10-methyl-3,4-dihydro-1H-1,4,10-triazadibenzo[cd,f]azulen-11(10H)-one A mixture of Example 42b (0.25 g, 0.908 mmol) and paraformaldehyde (0.273 g, 9.08 mmol) in methanol (9.08 mL) was treated with hydrogen chloride (4M in 1,4-dioxane, 6.81 mL, 27.2 mmol). The mixture was heated at 90° C. for 3 hours in a sealed tube, cooled and filtered to collect a solid that was rinsed repeatedly with diethyl ether. The solid was sonicated in 2 mL methanol and 20 mL 5% aqueous sodium bicarbonate for 5 minutes and collected by filtration to afford the title compound (0.2 g, 77%).

Example 42d 5,7-difluoro-10-methyl-4-((tetrahydrofuran-3-yl)methyl)-3,4-dihydro-1H-1,4,10-triazadibenzo[cd,f]azulen-11(10H)-one A mixture of tetrahydrofuran-3-carboxaldehyde (0.131 g, 0.654 mmol) and Example 42c (0.063 g, 0.218 mmol) in dichloromethane (2.5 mL) in a sealed tube was treated with acetic acid (0.125 mL, 2.180 mmol) and heated for 1 hour at 60 C°, cooled to 0° C. and treated portionwise with sodium triacetoxyhydroborate (0.092 g, 0.436 mmol). The reaction mixture was stirred for 18 hours allowing the mixture to warm to ambient temperature. The mixture was partitioned between dichloromethane and 5% aqueous sodium bicarbonate. The organic layer was washed with saturated aqueous sodium chloride, dried (anhydrous sodium sulfate) filtered and concentrated. Purification by reverse phase HPLC (C18, CH$_3$CN/water (0.1% TFA), 0-100% gradient) afforded the title compound as a TFA salt (0.04 g, 38%). $^1$H NMR (300 MHz, DMSO-d$_6$) δ 11.91 (s, 1H), 7.83 (d, J=2.03 Hz, 1H), 7.41-7.46 (m, 1H), 7.06-7.22 (m, 2H), 4.19-4.30 (m, 1H), 4.00-4.10 (m, 1H), 3.61 (s, 3H), 3.25-3.63 (m, 5H), 1.66-2.70 (m, 4H). MS (ESI+) m/z 372 (M+H)$^+$.

Example 43 ethyl 4-(4-fluorophenyl)-7,10-dimethyl-11-oxo-3,4,10,11-tetrahydro-1H-1,4,5,10-tetraazadibenzo[cd,f]azulene-3-carboxylate A mixture of ethyl glyoxalate (0.586 g, 2.87 mmol) and Example 11c (0.1 g, 0.287 mmol) in ethanol (2 mL) was treated with hydrogen chloride (4M in 1,4-dioxane, 2.153 mL, 8.61 mmol). The mixture was heated at 120° C. for 18 hours in a sealed tube, cooled and concentrated. Purification by reverse phase HPLC (C18, CH$_3$CN/water (0.1% TFA), 0-100% gradient) afforded the title compound as a TFA salt (0.01 g, 6%). $^1$H NMR (300 MHz, DMSO-d$_6$) δ 12.06 (d, J=1.70 Hz, 1H), 8.16 (s, 2H), 7.83 (s, 1H), 7.39 (d, J=2.71 Hz, 1H), 6.92-7.00 (m, 2H), 6.74-6.81 (m, 2H), 6.18 (s, 1H), 3.91 (d, J=7.12 Hz, 2H), 3.61 (s, 3H), 2.36 (s, 3H), 0.92 (t, J=7.12 Hz, 3H). MS (ESI+) m/z 433 (M+H)$^+$.

Example 44

N-cyclopentyl-10-methyl-7-((methylsulfonyl)methyl)-11-oxo-10,11-dihydro-1H-1,4,10-triazadibenzo[cd,f]azulene-4(3H)-carboxamide A 5 mL vial was charged with Example 5f (72.5 mg, 0.211 mmol), isocyanatocyclopentane (0.036 mL, 0.317 mmol), N-ethyl-N-isopropylpropan-2-amine (0.110 mL, 0.633 mmol), dichloromethane (2 mL) and N,N-dimethylformamide (2 mL). The reaction mixture was stirred for 18 hours at ambient temperature and then heated at 90° C. for 72 hours. Upon cooling, the reaction mixture was partitioned between 50% saturated aqueous sodium chloride (60 mL)

and dichloromethane (60 mL). The layers were separated and the aqueous layer was extracted with dichloromethane (2×50 mL). The combined extracts were dried over anhydrous sodium sulfate, filtered and concentrated. The residue was purified by flash chromatography (silica gel, 0-10% methanol in dichloromethane) to provide the title compound (59.1 mg, 62%). $^1$H NMR (300 MHz, DMSO-$d_6$) δ 11.85 (d, J=2.37 Hz, 1H), 7.83 (d, J=2.03 Hz, 1H), 7.63 (s, 1H), 7.33-7.40 (m, 1H), 7.25-7.31 (m, 1H), 7.20 (d, J=2.03 Hz, 1H), 5.36 (d, J=15.94 Hz, 1H), 5.24 (d, J=6.78 Hz, 1H), 4.52-4.62 (m, 1H), 4.40-4.51 (m, 1H), 3.96 (d, J=15.60 Hz, 1H), 3.69-3.83 (m, 1H), 3.62 (s, 3H), 2.96 (s, 3H), 1.54-1.72 (m, 2H), 1.31-1.52 (m, 4H), 1.09-1.27 (m, 2H). MS (ESI+) m/z 455.1 (M+H)$^+$.

Example 45

N-ethyl-10-methyl-7-((methylsulfonyl)methyl)-11-oxo-10,11-dihydro-1H-1,4,10-triazadibenzo[cd,f]azulene-4(3H)-carboxamide Example 45 was prepared according to the procedure used for the preparation of Example 44, substituting isocyanatoethane for isocyanatocyclopentane to provide the title compound. $^1$H NMR (300 MHz, DMSO-$d_6$) δ 11.85 (d, J=1.36 Hz, 1H), 7.83 (d, J=1.70 Hz, 1H), 7.62 (s, 1H), 7.34-7.40 (m, 1H), 7.26-7.32 (m, 1H), 7.19 (d, J=2.37 Hz, 1H), 5.59 (s, 1H), 5.35 (d, J=15.94 Hz, 1H), 4.42-4.62 (m, 2H), 3.94 (d, J=15.60 Hz, 1H), 3.59-3.66 (m, 3H), 2.97 (s, 3H), 2.75-2.96 (m, 2H), 0.85 (t, J=7.12 Hz, 3H). MS (ESI+) m/z 415.1 (M+H)$^+$.

Example 46

N-(4-fluorophenyl)-10-methyl-7-((methylsulfonyl)methyl)-11-oxo-10,11-dihydro-1H-1,4,10-triazadibenzo[cd,f]azulene-4(3H)-carboxamide Example 46 was prepared according to the procedure used for the preparation of Example 44, substituting 1-fluoro-4-isocyanatobenzene for isocyanatocyclopentane to provide the title compound. $^1$H NMR (300 MHz, DMSO-$d_6$) δ 11.91 (d, J=2.37 Hz, 1H), 7.87 (s, 2H), 7.66 (s, 1H), 7.38 (s, 2H), 7.28-7.34 (m, 2H), 7.25 (d, J=2.37 Hz, 1H), 6.95-7.02 (m, 2H), 5.52 (d, J=15.60 Hz, 1H), 4.45-4.63 (m, 2H), 4.07 (d, J=16.62 Hz, 1H), 3.63 (s, 3H), 2.98 (s, 3H). MS (ESI+) m/z 481.1 (M+H)$^+$.

Example 47

4-butyl-5,7-difluoro-10-methyl-3,4-dihydro-1H-1,4,10-triazadibenzo[cd,f]azulen-11(10H)-one A mixture of butyraldehyde (0.079 g, 1.097 mmol) and Example 42c (0.063 g, 0.219 mmol) in dichloroethane (1.0 mL) in a sealed tube was treated with acetic acid (0.126 mL, 2.193 mmol) and heated for 2 hours at 60 C°, cooled to 0° C. and treated portionwise with sodium triacetoxyhydroborate (0.139 g, 0.658 mmol). The reaction mixture was stirred for 18 hours allowing the mixture to warm to ambient temperature. The mixture was partitioned between ethyl acetate and 5% aqueous sodium bicarbonate. The organic layer was washed with saturated aqueous sodium chloride, dried (anhydrous sodium sulfate) filtered and concentrated. Purification by chromatography (silica gel, 0.5-3% methanol in dichloromethane) gave a solid that was then triturated in 9:1 hexane/ethyl acetate to afford the title compound (0.057 g, 76%). $^1$H NMR (400 MHz, DMSO-$d_6$) δ 11.89 (s, 1H), 7.81 (s, 1H), 7.40-7.45 (m, 1H), 7.19 (d, J=2.14 Hz, 1H), 7.05-7.14 (m, 1H), 4.19-4.24 (m, 2H), 4.01-4.06 (m, 2H), 3.61 (s, 3H), 1.13-1.33 (m, 4H), 0.76 (t, J=7.02 Hz, 3H). MS (ESI+) m/z 344 (M+H)$^+$.

Example 48

5,7-difluoro-10-methyl-4-propyl-3,4-dihydro-1H-1,4,10-triazadibenzo[cd,f]azulen-11(10H)-one A mixture of propionaldehyde (0.064 g, 1.097 mmol) and Example 42c (0.063 g, 0.219 mmol) in 1,2-dichloroethane (1.0 mL) in a sealed tube was treated with acetic acid (0.126 mL, 2.193 mmol) and stirred for 2 hours at 60° C., cooled to 0° C. and treated portion-wise with sodium triacetoxyhydroborate (0.139 g, 0.658 mmol). The reaction mixture was stirred for 18 hours allowing the mixture to warm to ambient temperature. The mixture was partitioned between ethyl acetate and 5% aqueous sodium bicarbonate. The organic layer was washed with saturated aqueous sodium chloride solution, dried (anhydrous Na$_2$SO$_4$) filtered and concentrated. Purification by flash chromatography (silica gel, 0.5-3% methanol in dichloromethane) gave a solid that was triturated in 9:1 hexane/ethyl acetate to afford the title compound (0.044 g, 60%). $^1$H NMR (400 MHz, DMSO-$d_6$) δ 11.89 (s, 1H), 7.81 (s, 1H), 7.43 (d, J=10.68 Hz, 1H), 7.18 (s, 1H), 7.05-7.13 (m, 1H), 4.17-4.25 (m, 1H), 3.99-4.08 (m, 1H), 3.61 (s, 3H), 2.39-2.64 (m, 2H), 1.07-1.43 (m, 2H), 0.74 (t, J=7.32 Hz, 3H). MS (ESI+) m/z 330 (M+H)$^+$.

Example 49

4-(cyclopropylmethyl)-5,7-difluoro-10-methyl-3,4-dihydro-1H-1,4,10-triazadibenzo[cd,f]azulen-11(10H)-one Example 49 was prepared according to the procedure used for the preparation of Example 47, substituting cyclopropanecarboxaldehyde for butyraldehyde, to afford the title compound (0.054 g, 72%). $^1$H NMR (500 MHz, DMSO-$d_6$) δ 11.90 (s, 1H), 7.80 (s, 1H), 7.38-7.45 (m, 1H), 7.18 (d, J=1.83 Hz, 1H), 7.08-7.13 (m, 1H), 4.35 (d, J=15.87 Hz, 1H), 4.08 (d, J=15.87 Hz, 1H), 3.60 (s, 3H), 2.61 (dd, J=12.51, 6.41 Hz, 1H), 2.25 (dd, J=12.51, 7.02 Hz, 1H), 0.73-0.82 (m, 1H), 0.23-0.36 (m, 1H), 0.10-0.20 (m, 1H), −0.18-−0.08 (m, 1H), −0.42-−0.30 (m, 1H). MS (ESI+) m/z 342 (M+H)$^+$.

Example 50 methyl 4-(5,7-difluoro-10-methyl-11-oxo-10,11-dihydro-1H-1,4,10-triazadibenzo[cd,f]azulen-4(3H)-yl)butanoate Example 50 was prepared according to the procedure used for the preparation of Example 47, substituting 4-oxobutanoic acid methyl ester for butyraldehyde, to afford the title compound (0.064 g, 74%). $^1$H NMR (400 MHz, DMSO-$d_6$) δ 11.90 (s, 1H), 7.82 (s, 1H), 7.43 (d, J=9.77 Hz, 1H), 7.19 (s, 1H), 7.07-7.14 (m, 1H), 4.17-4.23 (m, 1H), 4.01-4.07 (m, 1H), 3.61 (s, 3H), 3.52 (s, 3H), 2.59-2.68 (m, 2H), 2.30 (t, J=7.32 Hz, 2H), 1.46-1.56 (m, 2H). MS (ESI+) m/z 388 (M+H)$^+$.

Example 51

5,7-difluoro-10-methyl-4-(3-phenylpropyl)-3,4-dihydro-1H-1,4,10-triazadibenzo[cd,f]azulen-11(10H)-one Example 51 was prepared according to the procedure used for the preparation of Example 47, substituting 3-phenylpropionaldehyde for butyraldehyde, to afford the title compound (0.062 g, 69%). $^1$H NMR (400 MHz, DMSO-d$_6$) δ 11.89 (s, 1H), 7.81 (s, 1H), 7.43 (dd, J=10.83, 1.37 Hz, 1H), 7.01-7.24 (m, 7H), 4.22-4.27 (m, 1H), 4.04-4.10 (m, 1H), 3.61 (s, 3H), 2.49-2.69 (m, 4H), 1.44-1.67 (m, 2H). MS (ESI+) m/z 406 (M+H)$^+$.

Example 52

10-methyl-7-((methylsulfonyl)methyl)-11-oxo-N-(o-tolyl)-10,11-dihydro-1H-1,4,10-triazadibenzo[cd,f]azulene-4(3H)-carboxamide A 4 mL vial was charged with Example 5f (25 mg, 0.073 mmol), 1-isocyanato-2-methylbenzene (13.39 mg, 0.091 mmol), diisopropylethylamine (38.44, 0.220 mmol) and N,N-dimethylformamide (1 mL). The reaction mixture was heated at 80° C. for 18 hours. The reaction mixture was concentrated and the residue was purified by reverse phase HPLC (C18, CH$_3$CN/water (0.1% TFA), 0-100% gradient) to afford the title compound (5.6 mg, 16%). $^1$H NMR (400 MHz, DMSO-d$_6$/D$_2$O) δ 7.90 (d, J=1.8 Hz, 1H), 7.67 (s, 1H), 7.45-7.53 (m, 2H), 7.31-7.39 (m, 1H), 7.26 (s, 1H), 7.02 (t, J=7.2 Hz, 2H), 6.86-6.94 (m, 1H), 5.40-5.48 (m, 1H), 4.51-4.56 (m, 2H), 4.10-4.19 (m, 1H), 3.64 (s, 3H), 2.96 (s, 3H), 1.76 (s, 3H). MS (ESI+) m/z 477.1 (M+H)$^+$.

Example 53

2-ethylhexyl 10-methyl-7-((methylsulfonyl)methyl)-11-oxo-10,11-dihydro-1H-1,4,10-triazadibenzo[cd,f]azulene-4(3H)-carboxylate A 4 mL vial was charged with Example 5f (15 mg, 0.044 mmol), 2-ethylhexyl carbonochloridate (10.10 mg, 0.05 mmol), diisopropylethylamine (50 μL, 0.287 mmol) and N,N-dimethylacetamide (2 mL). The reaction mixture was heated at 80° C. for 18 hours. To this mixture was added O-(7-azabenzotriazol-1-yl)-N,N,N',N'-tetramethyluronium hexafluorophosphate (19.93 mg, 0.05 mmol) and heating was continued for 18 hours. The reaction mixture was concentrated and the residue was purified by reverse phase HPLC (C18, CH$_3$CN/water (0.1% TFA), 0-100% gradient) to afford the title compound (4.4 mg, 20.2%). $^1$H NMR (400 MHz, DMSO-d$_6$/D$_2$O) δ 7.78-7.81 (m, 1H), 7.59-7.60 (m, 1H), 7.35-7.39 (m, 1H), 7.27-7.31 (m, 1H), 7.20-7.22 (m, 1H), 5.17-5.23 (m, 1H), 4.44-4.54 (m, 1H), 4.12-4.19 (m, 1H), 3.77 (bs, 2H), 3.61-3.64 (m, 3H), 2.90-2.94 (m, 3H), 1.21-1.35 (m, 1H), 0.95-1.18 (m, 9H), 0.65-0.79 (m, 6H). MS (ESI+) m/z 500.1 (M+H)$^+$.

Example 54

4-isobutyryl-10-methyl-7-((methylsulfonyl)methyl)-3,4-dihydro-1H-1,4,10-triazadibenzo[cd,f]azulen-11(10H)-one A 4 mL vial was charged with Example 5f (15 mg, 0.044 mmol), isobutyryl chloride (4.65 mg, 0.044 mmol), diisopropylethylamine (50 μL, 0.287 mmol) and N,N-dimethylacetamide (2 mL). The reaction mixture was heated at 80° C. for 18 hours. To this mixture was added O-(7-azabenzotriazol-1-yl)-N,N,N',N'-tetramethyluronium hexafluorophosphate (19.93 mg, 0.05 mmol) and heating was continued for 18 hours. The reaction mixture was concentrated and the residue was purified by reverse phase HPLC (C18, CH$_3$CN/water (0.1% TFA), 0-100% gradient) to afford the title compound (1.3 mg, 7.2%). $^1$H NMR (400 MHz, DMSO-d$_6$/D$_2$O) δ 7.83-7.87 (m, 1H), 7.65-7.69 (m, 1H), 7.42-7.45 (m, 1H), 7.33-7.41 (m, 1H), 7.20-7.26 (m, 1H), 5.45-5.60 (m, 1H), 4.47-4.58 (m, 2H), 3.89-4.01 (m, 1H), 3.63 (s, 3H), 2.95 (s, 4H), 1.96 (s, 1H), 0.91-1.01 (m, 3H), 0.44-0.55 (m, 2H). MS (ESI+) m/z 414.1 (M+H)$^+$.

Example 55

5,7-difluoro-10-methyl-4-phenethyl-3,4-dihydro-1H-1,4,10-triazadibenzo[cd,f]azulen-11(10H)-one Example 55 was prepared according to the procedure used for the preparation of Example 47, substituting 2-phenylacetaldehyde for butyraldehyde. Purification by reverse phase HPLC (C18, CH$_3$CN/water (0.1% TFA), 0-100% gradient) afforded the title compound (0.034 g, 40%). $^1$H NMR (400 MHz, DMSO-d$_6$) δ 11.91 (d, J=1.22 Hz, 1H), 7.82 (s, 1H), 7.44 (dd, J=10.38, 2.14 Hz, 1H), 7.08-7.21 (m, 5H), 7.02 (d, J=6.71 Hz, 2H), 4.28-4.33 (m, 1H), 4.05-4.10 (m, 1H), 3.60 (s, 3H), 2.67-2.78 (m, 2H), 2.45-2.53 (m, 2H). MS (ESI+) m/z 392 (M+H)$^+$.

Example 56

4-(2-(benzo[d][1,3]dioxol-5-yl)ethyl)-5,7-difluoro-10-methyl-3,4-dihydro-1H-1,4,10-triazadibenzo[cd,f]azulen-11(10H)-one Example 56 was prepared according to the procedure used for the preparation of Example 47, substituting 2-(benzo[d][1,3]dioxol-5-yl)acetaldehyde for butyraldehyde. Purification by reverse phase HPLC (C18, CH$_3$CN/water (0.1% TFA), 0-100% gradient) afforded an impure product that was purified a second time (silica gel, 0.5-3% methanol in dichloromethane) to give the title compound (0.033 g, 32%). $^1$H NMR (400 MHz, DMSO-d$_6$) δ 11.90 (s, 1H), 7.80 (s, 1H), 7.43 (dd, J=8.70, 2.59 Hz, 1H), 7.19 (d, J=2.14 Hz, 1H), 7.08-7.16 (m, 1H), 6.68 (d, J=7.93 Hz, 1H), 6.60 (s, 1H), 6.39-6.49 (m, 1H), 5.89 (s, 2H), 4.28 (d, J=15.87 Hz, 1H), 4.05 (d, J=15.87 Hz, 1H), 3.60 (s, 3H), 2.33-2.88 (m, 4H). MS (ESI+) m/z 436 (M+H)$^+$.

Example 57

4-((1Z,3E)-2,4-diphenylbuta-1,3-dien-1-yl)-5,7-difluoro-10-methyl-3,4-dihydro-1H-1,4,10-triazadibenzo[cd,f]azulen-11(10H)-one Example 57 was prepared according to the procedure used for the preparation of Example 47, substituting 2-phenylacetaldehyde for butyraldehyde. The crude material was triturated in 1 mL of 50/50 DMSO/methanol and filtered to collect a yellow solid (0.013 g, 12%). $^1$H NMR (400 MHz, DMSO-d$_6$) δ 11.62 (s, 1H), 7.60 (s, 1H), 6.95-7.16 (m, 10H), 6.87 (d, J=15.87 Hz, 1H), 6.67 (dd, J=6.56, 2.59 Hz, 2H), 6.59 (s, 1H), 6.50-6.56 (m, 1H), 5.42 (d, J=15.56 Hz, 1H), 4.68 (d, J=15.56 Hz, 1H), 4.26 (d, J=14.95 Hz, 1H), 3.66 (s, 3H). MS (ESI+) m/z 492 (M+H)+.

Example 58

4-(4-chlorophenyl)-10-methyl-7-((methylsulfonyl)methyl)-11-oxo-3,4,10,11-tetrahydro-1H-1,4,10-triazadibenzo[cd,f]azulene-2-carboxamide Example 58a (Z)-ethyl 3-(5-bromo-2-methoxy-3-nitropyridin-4-yl)-2-hydroxyacrylate To a solution of ethanol (15 mL) and ether (150 mL) was added 5-bromo-2-methoxy-4-methyl-3-nitropyridine (14.82 g, 60 mmol), diethyl oxalate (13.15 g, 90 mmol), and potassium ethoxide (6.06 g, 72 mmol). The reaction mixture was heated at 45° C. for 24 hours. During the reaction, the flask was shaken by hand several times. After cooling, the reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by flash chromatography on silica gel eluting with 10-20% ethyl acetate in hexanes to 9.5 g of the title compound (yield 46%).

Example 58b ethyl 4-bromo-7-methoxy-1H-pyrrolo[2,3-c]pyridine-2-carboxylate

A mixture of Example 58a (9.5 g, 27.4 mmol) and iron powder (7.64 g, 137 mmol) in ethanol (60 mL) and acetic acid (60 mL) was heated at 100° C. for 1 hour. The solid was filtered off, and then washed with additional ethyl acetate. The solvents were removed under reduced pressure to 20% of original volume, and the mixture was partitioned between water and ethyl acetate. The aqueous layer was extracted with additional ethyl acetate several times. The combined organic layers were washed with saturated aqueous sodium chloride, dried over anhydrous magnesium sulfate, filtered, and concentrated. The residue was purified by flash chromatography on silica gel eluting with 20-40% ethyl acetate in hexanes to give 6.05 g of the title compound.

Example 58c ethyl 1-benzyl-4-bromo-7-methoxy-1H-pyrrolo[2,3-c]pyridine-2-carboxylate Example 58b (0.88 g, 2.94 mmol) in dimethylformamide (15 mL) was treated with 60% sodium hydride (0.106 g, 4.41 mmol, 0.117 g of a 60% in oil dispersion). The solution was stirred at ambient temperature for 10 minutes. To this solution was added benzyl bromide (0.59 g, 3.45 mmol). The reaction mixture was stirred for another 2 hours and was then partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash chromatography on silica gel eluting with 20-40% ethyl acetate in hexanes to give 1.07 g of the title compound.

Example 58d ethyl 1-benzyl-4-bromo-7-oxo-6,7-dihydro-1H-pyrrolo[2,3-c]pyridine-2-carboxylate The mixture of Example 58c (2, 5.14 mmol) in dioxane (20 mL) was treated with 4.0 M HCl in dioxane (20 mL, 80 mmol). The reaction mixture was stirred at 45° C. for 18 hours. The mixture was concentrated to remove dioxane. The residue was slurry in petroleum ether to obtain the title compound (1.8 g, 4.80 mmol, 93% yield) as gray solid.

Example 58e ethyl 1-benzyl-4-bromo-6-methyl-7-oxo-6,7-dihydro-1H-pyrrolo[2,3-c]pyridine-2-carboxylat To a suspension of Example 58d (5.16 g, 13.75 mmol) in dimethylformamide (100 mL) at ambient temperature was added NaH (0.660 g, 16.50 mmol) and the mixture was stirred at ambient temperature for 30 minutes. Iodomethane (1.032 mL, 16.50 mmol) was added into the reaction mixture. The reaction mixture was stirred at ambient temperature for 2 hours, and was then partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by chromatography on silica gel eluting with 20-40% ethyl acetate in hexanes to give the title compound (4.23 g, 8.91 mmol, 64.8% yield).

Example 58f ethyl 1-benzyl-6-methyl-7-oxo-4-(4,4,5,5-tetramethyl-1,3,2-dioxaborolan-2-yl)-6,7-dihydro-1H-pyrrolo[2,3-c]pyridine-2-carboxylate A mixture of Example 58e (2 g, 5.14 mmol), bis(pinacolato)diboron (2.61 g, 10.3 mmol), potassium acetate (1.11 g, 11.3 mmol tris(dibenzylideneacetone)dipalladium(0) (0.235 g, 0.257 mmol) and 2-dicyclohexylphosphino-2',4',6'-triisopropylbiphenyl (0.245 g, 0.514 mmol) in dioxane (50 mL) was stirred at 90° C. for 16 hour under an argon atmosphere. The mixture was filtered through Celite, washed with ethyl acetate several times and concentrated. The residue was purified by flash chromatography (silica gel, 50-75% ethyl acetate/petroleum ether gradient) to afford the title compound (1.15 g, 40% yield).

Example 58g 2-bromo-4-((methylsulfonyl)methyl)aniline

To a solution of Example 5b (2 g, 10.80 mmol) in DMF (60 mL) was added 1-bromopyrrolidine-2,5-dione (1.922 g, 10.80 mmol) and the reaction mixture was stirred at 15° C. for 1 hour. The reaction mixture was quenched with 150 mL 10% sodium thiosulfate and 100 mL saturated sodium bicarbonate. The reaction mixture was extracted with ethyl acetate three times. The combined organic layers were washed with saturated aqueous sodium chloride and concentrated to a semi-solid. Water was added, and the resulting suspension was stirred at ambient temperature for 10 minutes. The solid was collected by filtration and dried on the frit overnight to give the title compound (2.1 g, 7.85 mmol, 72.7% yield) as a tan solid.

Example 58h 2-bromo-N-(4-chlorophenyl)-4-((methylsulfonyl)methyl)aniline

To a 500 mL flask were added Example 58g (10 g, 37.9 mmol), 1-chloro-4-iodobenzene (18.06 g, 76 mmol), PdOAc$_2$ (0.425 g, 1.893 mmol), xantphos (1.75 g, 3.03 mmol), Cs$_2$CO$_3$ (24.67 g, 76 mmol) and anhydrous dioxane (350 mL) under argon at ambient temperature. The mixture was heated at 110° C. for 18 hours. The reaction mixture was filtered through Celite and washed with ethyl acetate (100 mL). The filtrate was concentrated to remove the solvent and the residue was treated with ethyl acetate (50 mL) and petroleum ether (20 mL) and the mixture was stirred at ambient temperature for 15 min. The resulting solid was collected by filtration, washed with a little petroleum ether and dried under reduced pressure to give the title compound (9.6 g, 24.85 mmol, 65.6% yield) as yellow solid.

Example 58i ethyl 1-benzyl-4-(2-((4-chlorophenyl)amino)-5-((methylsulfonyl)methyl)phenyl)-6-methyl-7-oxo-6,7-dihydro-1H-pyrrolo[2,3-c]pyridine-2-carboxylate Example 58i was prepared according to the procedure used for the preparation of Example 5d, substituting Example 58h for Example 5c, and Example 58f for Example 1f, respectively, to provide the title compound.

Example 58j ethyl 4-(2-((4-chlorophenyl)amino)-5-((methylsulfonyl)methyl)phenyl)-6-methyl-7-oxo-6,7-dihydro-1H-pyrrolo[2,3-c]pyridine-2-carboxylate A mixture of Example 58i (0.5 g, 0.828 mmol), anisole (0.181 mL, 1.655 mmol) and H$_2$SO$_4$ (0.5 mL, 9.38 mmol) in TFA (20 mL, 260 mmol) was heated at 90° C. for 10 hours. Excess TFA was removed under reduced pressure, and the residue was partitioned between water (10 mL) and ethyl acetate (20 mL). The organic layer was separated, and the aqueous layer was extracted with additional ethyl acetate twice (20 mL). The combined organic layers were washed with saturated aqueous sodium bicarbonate (10 mL), followed by saturated aqueous sodium chloride (10 mL), dried over anhydrous magnesium sulfate, filtered, and concentrated to give the title compound (0.38 g, 0.355 mmol, 42.9% yield) as pale solid.

Example 58k ethyl 4-(4-chlorophenyl)-10-methyl-7-((methylsulfonyl)methyl)-11-oxo-3,4,10,11-tetrahydro-1H-1,4,10-triazadibenzo[cd,f]azulene-2-carboxylate A mixture of Example 58j (0.200 g, 0.389 mmol), HCl (4 M in dioxane) (4 mL, 16.00 mmol) and paraformaldehyde (0.234 g, 7.78 mmol) in methanol (2 mL) was heated at 130° C. for 1.5 hours under microwave. The solvent was removed and the residue was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated to give the title compound (0.14 g, 0.130 mmol, 33.5% yield).

Example 58l 4-(4-chlorophenyl)-10-methyl-7-((methylsulfonyl)methyl)-11-oxo-3,4,10,11-tetrahydro-1H-1,4,10-triazadibenzo[cd,f]azulene-2-carboxylic acid A mixture of Example 58k and LiOH (0.646 mL, 1.293 mmol) in dioxane (3 mL) was heated at 65° C. for 18 hours. The solvent was removed and water (20 mL) was added. The aqueous layer was adjusted pH to 3 with 1N HCl. The solid was filtered and dried to give the title compound (0.25 g, 0.487 mmol, 75% yield) as pale solid.

Example 58m 4-(4-chlorophenyl)-10-methyl-7-((methylsulfonyl)methyl)-11-oxo-3,4,10,11-tetrahydro-1H-1,4,10-triazadibenzo[cd,f]azulene-2-carboxamide To a solution of Example 58l (0.1 g, 0.201 mmol) in anhydrous dichloromethane (5 mL) were added oxalyl chloride (0.035 mL, 0.402 mmol) and DMF (0.777 µL, 10.04 µmol) and the reaction mixture was stirred at ambient temperature for 2 hours. The reaction mixture was concentrated to dryness. The residue was redissolved in dichloromethane (5 mL) and was treated with ammonium hydroxide (25% wt/wt in water) (2 mL, 92 mmol) and the reaction mixture was stirred at ambient temperature overnight. The resulting solid was filtered and treated with methanol twice and filtered again to provide the title compound (30 mg, 0.057 mmol, 28.3% yield). $^1$H NMR (400 MHz, DMSO-d$_6$): δ 12.23 (s, 1H), 7.93 (s, 1H), 7.83 (s, 1H), 7.68 (s, 2H), 7.47 (d, J=7.4 Hz, 1H), 7.38 (d, J=7.8 Hz, 1H), 7.00 (d, J=8.4 Hz, 2H), 6.35 (d, J=8.6 Hz, 2H), 5.89 (m, 1H), 4.68-4.35 (m, 3H), 3.59 (s, 3H), 3.01 (s, 3H). MS (ESI+) m/z 497.1 (M+H)$^+$

Example 59

4-(4-chlorophenyl)-N-ethyl-10-methyl-7-((methylsulfonyl)methyl)-11-oxo-3,4,10,11-tetrahydro-1H-1,4,10-triazadibenzo[cd,f]azulene-2-carboxamide Example 59 was prepared according to the procedure used for the preparation of Example 58m, substituting ethylamine for ammonium hydroxide (25% wt/wt in water), to provide the title compound. $^1$H NMR (400 MHz, DMSO-d$_6$-MeOD): δ 8.33 (t, J=5.0 Hz, 1H), 7.93 (d, J=1.6 Hz, 1H), 7.67 (s, 1H), 7.47 (dd, J=8.1, 1.8 Hz, 1H), 7.38 (d, J=8.0 Hz, 1H), 6.99 (d, J=9.1 Hz, 2H), 6.36 (d, J=9.1 Hz, 2H), 6.13-5.82 (m, 2H), 4.50 (dd, J=56.8, 24.0 Hz, 3H), 3.58 (s, 3H), 3.01 (s, 3H), 1.25-1.14 (m, 3H). MS (ESI+) m/z 525.0 (M+H)$^+$

Example 60

4-(4-chlorophenyl)-10-methyl-2-(4-methylpiperazine-1-carbonyl)-7-((methylsulfonyl)methyl)-3,4-dihydro-1H-1,4,10-triazadibenzo[cd,f]azulen-11(10H)-one Example 60 was prepared according to the procedure used for the preparation of Example 58m, substituting 1-methylpiperazine for ammonium hydroxide (25% wt/wt in water), to provide the title compound. ¹H NMR (400 MHz, DMSO-d₆): δ 12.34 (s, 1H), 7.91 (d, J=1.7 Hz, 1H), 7.66 (s, 1H), 7.47 (dd, J=8.1, 1.8 Hz, 1H), 7.37 (d, J=8.0 Hz, 1H), 6.97 (d, J=9.1 Hz, 2H), 6.45 (d, J=9.1 Hz, 2H), 5.10 (d, J=16.8 Hz, 1H), 4.68-4.40 (m, 3H), 3.69-3.40 (m, 7H), 3.00 (s, 3H), 2.36 (s, 4H), 2.21 (s, 3H). MS (ESI+) m/z 580.2 (M+H)⁺

Example 61

N-(2,6-dimethylphenyl)-10-methyl-7-((methylsulfonyl)methyl)-11-oxo-10,11-dihydro-1H-1,4,10-triazadibenzo[cd,f]azulene-4(3H)-carboxamide Example 61 was prepared according to the procedure used for the preparation of Example 52, substituting 2-isocyanato-1,3-dimethylbenzene for 1-isocyanato-2-methylbenzene to provide the title compound. ¹H NMR (400 MHz, DMSO-d₆/D₂O) δ 7.85 (s, 1H), 7.62 (s, 1H), 7.44 (s, 2H), 7.23 (s, 1H), 6.86-6.96 (m, 3H), 5.31-5.40 (m, 1H), 4.48-4.53 (m, 2H), 4.11-4.21 (m, 1H), 3.65 (s, 3H), 2.95 (s, 3H), 1.82 (s, 6H). MS (ESI+) m/z 491.1 (M+H)⁺.

Example 62

N-(4-methoxyphenyl)-10-methyl-7-((methylsulfonyl)methyl)-11-oxo-10,11-dihydro-1H-1,4,10-triazadibenzo[cd,f]azulene-4(3H)-carboxamide Example 62 was prepared according to the procedure used for the preparation of Example 52, substituting 1-isocyanato-4-methoxybenzene for 1-isocyanato-2-methylbenzene to provide the title compound. ¹H NMR (400 MHz, DMSO-d₆/D₂O) δ 7.86 (d, J=1.9 Hz, 1H), 7.63 (s, 1H), 7.43 (dd, J=8.0, 1.9 Hz, 1H), 7.39 (d, J=8.0 Hz, 1H), 7.25 (s, 1H), 7.08-7.15 (m, 1H), 6.70-6.76 (m, 1H), 5.43-5.54 (m, 1H), 4.52 (bs, 2H), 4.02-4.16 (m, 1H), 3.65 (d, J=10.2 Hz, 2H), 2.97 (s, 3H). MS (ESI+) m/z 493.0 (M+H)⁺.

Example 63

N-(4-ethylphenethyl)-10-methyl-7-((methylsulfonyl)methyl)-11-oxo-10,11-dihydro-1H-1,4,10-triazadibenzo[cd,f]azulene-4(3H)-carboxamide Example 63 was prepared according to the procedure used for the preparation of Example 52, substituting 1-ethyl-4-(2-isocyanatoethyl)benzene for 1-isocyanato-2-methylbenzene to provide the title compound. ¹H NMR (400 MHz, DMSO-d₆/D₂O) δ 7.81 (d, J=2.0 Hz, 1H), 7.58 (s, 1H), 7.34 (dd, J=8.1, 2.0 Hz, 1H), 7.16-7.20 (m, 2H), 7.00 (d, J=8.1 Hz, 2H), 6.88 (d, J=8.0 Hz, 2H), 5.27-5.41 (m, 1H), 4.49 (s, 2H), 3.93-4.01 (m, 1H), 3.64 (s, 3H), 3.02-3.20 (m, 2H), 2.95 (s, 3H), 2.53-2.58 (m, 2H), 1.16 (t, J=7.6 Hz, 3H). MS (ESI+) m/z 519.1 (M+H)⁺.

Example 64

10-methyl-7-((methylsulfonyl)methyl)-11-oxo-N-propyl-10,11-dihydro-1H-1,4,10-triazadibenzo[cd,f]azulene-4(3H)-carboxamide Example 64 was prepared according to the procedure used for the preparation of Example 52, substituting 1-isocyanatopropane for 1-isocyanato-2-methylbenzene to provide the title compound. ¹H NMR (400 MHz, DMSO-d₆/D₂O) δ 7.82 (d, J=1.9 Hz, 1H), 7.59 (s, 1H), 7.40 (dd, J=8.1, 2.0 Hz, 1H), 7.30 (d, J=8.0 Hz, 1H), 7.19 (s, 1H), 5.33 (s, 1H), 4.50 (s, 2H), 3.94-4.05 (m, 1H), 3.63 (s, 3H), 2.95 (s, 3H), 2.71-2.92 (m, 2H), 1.25 (h, J=7.3 Hz, 2H), 0.66 (t, J=7.4 Hz, 3H). MS (ESI+) m/z 429.1 (M+H)⁺.

Example 65

N-(3-methoxybenzyl)-10-methyl-7-((methylsulfonyl)methyl)-11-oxo-10,11-dihydro-1H-1,4,10-triazadibenzo[cd,f]azulene-4(3H)-carboxamide Example 65 was prepared according to the procedure used for the preparation of Example 52, substituting 1-(isocyanatomethyl)-3-methoxybenzene for 1-isocyanato-2-methylbenzene to provide the title compound. ¹H NMR (400 MHz, DMSO-d₆/D₂O) δ 7.82 (d, J=1.9 Hz, 1H), 7.59 (s, 1H), 7.40 (dd, J=8.1, 2.0 Hz, 1H), 7.30 (d, J=8.0 Hz, 1H), 7.19 (s, 1H), 5.33 (s, 1H), 4.50 (s, 2H), 3.94-4.05 (m, 1H), 3.63 (s, 3H), 2.95 (s, 3H), 2.71-2.92 (m, 2H), 1.25 (h, J=7.3 Hz, 2H), 0.66 (t, J=7.4 Hz, 3H). MS (ESI+) m/z 507.0 (M+H)⁺.

Example 66

N-(2-chloroethyl)-10-methyl-7-((methylsulfonyl)methyl)-11-oxo-10,11-dihydro-1H-1,4,10-triazadibenzo[cd,f]azulene-4(3H)-carboxamide Example 66 was prepared according to the procedure used for the preparation of Example 52, substituting 1-chloro-2-isocyanatoethane for 1-isocyanato-2-methylbenzene to provide the title compound. ¹H NMR (400 MHz, DMSO-d₆/D₂O) δ 7.95 (d, J=0.4 Hz, 1H), 7.80 (s, 1H), 7.71 (d, J=1.6 Hz, 1H), 7.20 (dd, J=8.2, 1.9 Hz, 1H), 7.04 (d, J=8.1 Hz, 1H), 4.37 (s, 2H), 4.13 (s, 2H), 3.79 (t, J=6.1 Hz, 2H), 3.73 (s, 3H), 3.69 (dt, J=6.4, 3.5 Hz, 2H), 2.89 (s, 3H). MS (ESI+) m/z 449.2 (M+H)⁺.

Example 67

N-(cyclohexylmethyl)-10-methyl-7-((methylsulfonyl)methyl)-11-oxo-10,11-dihydro-1H-1,4,10-triazadibenzo[cd,f]azulene-4(3H)-carboxamide Example 67 was prepared according to the procedure used for the preparation of Example 52, substituting (isocyanatomethyl)cyclohexane for 1-isocyanato-2-methylbenzene to provide the title compound. ¹H NMR (400 MHz, DMSO-d₆/D₂O) δ 7.83 (d, J=2.0 Hz, 1H), 7.59 (s, 1H), 7.40 (dd, J=8.0, 2.0 Hz, 1H), 7.30 (d, J=7.9 Hz, 1H), 7.19 (s, 1H), 5.24-5.37 (m, 1H), 4.50 (s, 1H), 3.96-4.08 (m, 1H), 3.63 (s, 3H), 2.95 (s, 3H), 2.65-2.83 (m, 1H), 1.45-1.58 (m, 3H), 1.34 (dd, J=13.7, 1.1 Hz, 1H), 1.09-1.27 (m, 1H), 0.95-1.10 (m, 3H), 0.56-0.70 (m, 2H). MS (ESI+) m/z 483.1 (M+H)⁺.

Example 68

N-(2,4-difluorophenyl)-10-methyl-7-((methylsulfonyl)methyl)-11-oxo-10,11-dihydro-1H-1,4,10-triazadibenzo[cd,f]azulene-4(3H)-carboxamide Example 68 was prepared according to the procedure used for the preparation of Example 52, substituting 2,4-difluoro-1-isocyanatobenzene for 1-isocyanato-2-methylbenzene to provide the title compound. ¹H NMR (500 MHz, DMSO-d₆) δ 11.90-11.98 (m, 1H), 7.90 (bs, 1H), 7.70 (s, 1H), 7.33-7.52 (m, 4H), 7.26 (d, J=1.0 Hz, 1H), 7.11-7.21 (m, 1H), 6.88-6.97 (m, 1H), 5.46 (d, J=15.6 Hz, 1H), 4.60 (d, J=13.5 Hz, 1H), 4.50 (d, J=13.5 Hz, 1H), 4.10 (d, J=15.1 Hz, 1H), 3.64 (s, 3H), 2.98 (s, 3H). MS (ESI+) m/z 499.1 (M+H)+.

Example 69

N-(4-isopropylphenyl)-10-methyl-7-((methylsulfonyl)methyl)-11-oxo-10,11-dihydro-1H-1,4,10-triazadibenzo[cd,f]azulene-4(3H)-carboxamide Example 69 was prepared according to the procedure used for the preparation of Example 52, substituting 1-isocyanato-4-isopropylbenzene for 1-isocyanato-2-methylbenzene to provide the title compound. $^1$H NMR (400 MHz, DMSO-$d_6$/$D_2O$) δ 7.86 (d, J=1.8 Hz, 1H), 7.63 (s, 1H), 7.43 (dd, J=8.1, 2.0 Hz, 1H), 7.38 (d, J=8.1 Hz, 1H), 7.25 (s, 1H), 7.12 (d, J=8.6 Hz, 2H), 7.01 (d, J=8.5 Hz, 2H), 5.43-5.57 (m, 1H), 4.52 (s, 2H), 4.04-4.14 (m, 1H), 3.64 (s, 3H), 2.97 (s, 3H), 2.77 (dt, J=14.1, 7.0 Hz, 1H), 1.17-1.20 (m, 1H), 1.13 (d, J=6.9 Hz, 6H). MS (ESI+) m/z 505.2 (M+H)+.

Example 70

N-(2,6-difluorophenyl)-10-methyl-7-((methylsulfonyl)methyl)-11-oxo-10,11-dihydro-1H-1,4,10-triazadibenzo[cd,f]azulene-4(3H)-carboxamide Example 70 was prepared according to the procedure used for the preparation of Example 52, substituting 1,3-difluoro-2-isocyanatobenzene for 1-isocyanato-2-methylbenzene to provide the title compound. $^1$H NMR (400 MHz, DMSO-$d_6$/$D_2O$) δ 7.85 (d, J=1.7 Hz, 1H), 7.64 (s, 1H), 7.40-7.45 (m, 2H), 7.15-7.25 (m, 2H), 6.94 (t, J=8.0 Hz, 2H), 5.45 (d, J=15.2 Hz, 1H), 4.50 (d, J=4.0 Hz, 2H), 4.08-4.16 (m, 1H), 3.66 (s, 3H), 2.95 (s, 3H). MS (ESI+) m/z 499.1 (M+H)+.

Example 71

N-(4-fluoro-3-(trifluoromethyl)phenyl)-10-methyl-7-((methylsulfonyl)methyl)-11-oxo-10,11-dihydro-1H-1,4,10-triazadibenzo[cd,f]azulene-4(3H)-carboxamide Example 71 was prepared according to the procedure used for the preparation of Example 52, substituting 1-fluoro-4-isocyanato-2-(trifluoromethyl)benzene for 1-isocyanato-2-methylbenzene to provide the title compound. $^1$H NMR (400 MHz, DMSO-$d_6$/$D_2O$) δ 7.87 (d, J=1.7 Hz, 1H), 7.73 (dd, J=6.5, 2.7 Hz, 1H), 7.64 (s, 1H), 7.58 (ddd, J=8.9, 5.6, 2.4 Hz, 1H), 7.43 (dd, J=8.1, 1.8 Hz, 1H), 7.39 (d, J=8.1 Hz, 1H), 7.25 (s, 1H), 7.21 (d, J=9.6 Hz, 1H), 5.49-5.56 (m, 1H), 4.53 (d, J=3.5 Hz, 2H), 4.08-4.14 (m, 1H), 3.64 (s, 3H), 2.97 (s, 3H). MS (ESI+) m/z 549.0 (M+H)+.

Example 72 ethyl 4-((10-methyl-7-((methylsulfonyl)methyl)-11-oxo-3,4,10,11-tetrahydro-1H-1,4,10-triazadibenzo[cd,f]azulene-4-carboxamido)methyl)cyclohexanecarboxylate Example 72 was prepared according to the procedure used for the preparation of Example 52, substituting ethyl 4-(isocyanatomethyl)cyclohexanecarboxylate for 1-isocyanato-2-methylbenzene to provide the title compound. $^1$H NMR (400 MHz, DMSO-$d_6$/$D_2O$) δ 7.83 (d, J=1.9 Hz, 1H), 7.59 (s, 1H), 7.41 (dd, J=8.1, 2.0 Hz, 1H), 7.31 (d, J=8.0 Hz, 1H), 7.19 (s, 1H), 5.26-5.36 (m, 1H), 4.50 (d, J=1.2 Hz, 2H), 3.95-4.08 (m, 3H), 3.63 (s, 3H), 2.95 (s, 3H), 2.68-2.83 (m, 2H), 2.03 (tt, J=12.2, 3.7 Hz, 1H), 1.75 (dd, J=12.8, 2.2 Hz, 2H), 1.36-1.46 (m, 2H), 1.06-1.19 (m, 6H), 0.60-0.71 (m, 2H). MS (ESI+) m/z 555.1 (M+H)+.

Example 73

N-(3-methoxypropyl)-10-methyl-7-((methylsulfonyl)methyl)-11-oxo-10,11-dihydro-1H-1,4,10-triazadibenzo[cd,f]azulene-4(3H)-carboxamide Example 73 was prepared according to the procedure used for the preparation of Example 52, substituting 1-isocyanato-3-methoxypropane for 1-isocyanato-2-methylbenzene to provide the title compound. $^1$H NMR (400 MHz, DMSO-$d_6$/$D_2O$) δ 7.83 (d, J=1.9 Hz, 1H), 7.60 (s, 1H), 7.41 (dd, J=8.1, 2.0 Hz, 1H), 7.30 (d, J=8.1 Hz, 1H), 7.19 (s, 1H), 5.29-5.38 (m, 1H), 4.50 (d, J=2.0 Hz, 2H), 3.94-4.04 (m, 1H), 3.63 (s, 3H), 3.15 (t, J=5.9 Hz, 2H), 3.06 (s, 3H), 2.98-3.04 (m, 1H), 2.95 (s, 3H), 2.86-2.93 (m, 1H), 1.47 (p, J=6.4 Hz, 2H). MS (ESI+) m/z 555.1 (M+H)+.

Example 74

10-methyl-7-((methylsulfonyl)methyl)-4-tosyl-3,4-dihydro-1H-1,4,10-triazadibenzo[cd,f]azulen-11(10H)-one A 4 mL vial was charged with Example 5f (15 mg, 0.04 mmol), 4-methylbenzene-1-sulfonyl chloride (19 mg, 0.1 mmol), diisopropylethylamine (15 µL, 0.08 mmol) and N,N-dimethylacetamide (0.75 mL). The reaction mixture was heated at 50° C. for 18 hours. The reaction mixture was concentrated and the residue was purified by reverse phase HPLC (C18, $CH_3CN$/water (0.1% TFA), 0-100% gradient) to afford the title compound (1.4 mg, 6%). $^1$H NMR (500 MHz, DMSO-$d_6$/$D_2O$) δ 7.66 (d, J=1.83 Hz, 1H), 7.47-7.49 (m, 1H), 7.41 (dd, J=8.24, 1.83 Hz, 1H), 7.25 (s, 1H), 7.22 (s, 1H), 6.77-6.80 (m, 2H), 6.72-6.75 (m, 2H), 5.21 (d, J=16.48 Hz, 1H), 4.58-4.62 (m, 1H), 4.52 (d, J=4.88 Hz, 1H), 4.49 (s, 1H), 3.51 (s, 3H), 2.98 (s, 3H), 2.15 (s, 3H). MS (APCI+) m/z 498 (M+H)+.

Example 75

4-([1,1'-biphenyl]–4-ylsulfonyl)-10-methyl-7-((methylsulfonyl)methyl)-3,4-dihydro-1H-1,4,10-triazadibenzo[cd,f]azulen-11(10H)-one Example 75 was prepared according to the procedure used for the preparation of Example 74, substituting biphenyl-4-sulfonyl chloride for 4-methylbenzene-1-sulfonyl chloride to provide the title compound. $^1$H NMR (500 MHz, DMSO-$d_6$/$D_2O$) δ 7.66 (d, J=2.14 Hz, 1H) 7.52-7.55 (m, 3H) 7.48 (t, J=7.32 Hz, 2H) 7.42-7.45 (m, 2H) 7.29 (s, 1H) 7.20-7.23 (m, 3H) 6.93 (d, J=8.54 Hz, 2H) 5.29 (d, J=16.48 Hz, 1H) 4.48-4.63 (m, 3H) 3.18 (s, 3H) 2.98 (s, 3H). MS (APCI+) m/z 560 (M+H)+.

Example 76

4-((4-methoxyphenyl)sulfonyl)-10-methyl-7-((methylsulfonyl)methyl)-3,4-dihydro-1H-1,4,10-triazadibenzo[cd,f]azulen-11(10H)-one Example 76 was prepared according to the procedure used for the preparation of Example 74, substituting 4-methoxybenzene-1-sulfonyl chloride for 4-methylbenzene-1-sulfonyl chloride to provide the title compound. $^1$H NMR (500 MHz, DMSO-d$_6$/D$_2$O) δ 7.65 (d, J=2.14 Hz, 1H) 7.47-7.50 (m, 1H) 7.39-7.43 (m, 1H) 7.24 (s, 2H) 6.78 (d, J=9.16 Hz, 2H) 6.44 (d, J=8.85 Hz, 2H) 5.21 (d, J=16.48 Hz, 1H) 4.57-4.62 (m, 1H) 4.50 (s, 1H) 4.46-4.48 (m, J=2.75 Hz, 1H) 3.69 (s, 3H) 3.49 (s, 3H) 2.97 (s, 3H). MS (APCI+) m/z 514 (M+H)$^+$.

Example 77

10-methyl-7-((methylsulfonyl)methyl)-4-(phenylsulfonyl)-3,4-dihydro-1H-1,4,10-triazadibenzo[cd,f]azulen-11(10H)-one Example 77 was prepared according to the procedure used for the preparation of Example 74, substituting benzenesulfonyl chloride for 4-methylbenzene-1-sulfonyl chloride to provide the title compound. $^1$H NMR (500 MHz, DMSO-d$_6$/D$_2$O) δ 7.65 (d, J=1.83 Hz, 1H) 7.47-7.51 (m, 1H) 7.41 (dd, J=8.09, 1.98 Hz, 1H) 7.22-7.26 (m, 2H) 7.21 (s, 1H) 6.93-6.98 (m, 2H) 6.88-6.91 (m, 2H) 5.24 (d, J=16.48 Hz, 1H) 4.58-4.62 (m, 1H) 4.48-4.54 (m, 2H) 3.47 (s, 3H) 2.97 (s, 3H). MS (APCI+) m/z 484 (M+H)$^+$.

Example 78

4-((2-methoxyphenyl)sulfonyl)-10-methyl-7-((methylsulfonyl)methyl)-3,4-dihydro-1H-1,4,10-triazadibenzo[cd,f]azulen-11(10H)-one Example 78 was prepared according to the procedure used for the preparation of Example 74, substituting 2-methoxybenzene-1-sulfonyl chloride for 4-methylbenzene-1-sulfonyl chloride to provide the title compound. $^1$H NMR (500 MHz, DMSO-d$_6$/D$_2$O) δ 7.74 (d, J=1.83 Hz, 1H) 7.50 (s, 1H) 7.33-7.39 (m, 1H) 7.26-7.30 (m, 2H) 7.12-7.16 (m, 2H) 6.81 (d, J=8.24 Hz, 1H) 6.72 (t, J=7.48 Hz, 1H) 5.25 (d, J=16.48 Hz, 1H) 4.54-4.59 (m, 1H) 4.41-4.52 (m, 2H) 3.58 (s, 3H) 3.44 (s, 3H) 2.99 (s, 3H). MS (APCI+) m/z 514 (M+H)$^+$.

Example 79

10-methyl-7-((methylsulfonyl)methyl)-4-((4-phenoxyphenyl)sulfonyl)-3,4-dihydro-1H-1,4,10-triazadibenzo[cd,f]azulen-11(10H)-one Example 79 was prepared according to the procedure used for the preparation of Example 74, substituting 4-phenoxybenzene-1-sulfonyl chloride for 4-methylbenzene-1-sulfonyl chloride to provide the title compound. $^1$H NMR (500 MHz, DMSO-d$_6$/D$_2$O) δ 7.70 (d, J=1.83 Hz, 1H) 7.47-7.52 (m, 3H) 7.41 (dd, J=8.24, 1.83 Hz, 1H) 7.38 (s, 1H) 7.28 (t, J=7.48 Hz, 1H) 7.21 (s, 1H) 7.08 (d, J=7.63 Hz, 2H) 6.91-6.94 (m, 2H) 6.39-6.44 (m, 2H) 5.22 (d, J=16.48 Hz, 1H) 4.58-4.63 (m, 1H) 4.47-4.56 (m, 2H) 3.57 (s, 3H) 2.98 (s, 3H). MS (APCI+) m/z 576 (M+H)$^+$.

Example 80

4-((4-fluorophenyl)sulfonyl)-10-methyl-7-((methylsulfonyl)methyl)-3,4-dihydro-1H-1,4,10-triazadibenzo[cd,f]azulen-11(10H)-one Example 80 was prepared according to the procedure used for the preparation of Example 74, substituting 4-fluorobenzene-1-sulfonyl chloride for 4-methylbenzene-1-sulfonyl chloride to provide the title compound. $^1$H NMR (500 MHz, DMSO-d$_6$/D$_2$O) δ 7.67 (d, J=1.83 Hz, 1H) 7.48-7.51 (m, 1H) 7.42 (dd, J=8.09, 1.68 Hz, 1H) 7.29 (s, 1H) 7.25 (s, 1H) 6.96 (dd, J=8.85, 5.19 Hz, 2H) 6.76 (t, J=8.85 Hz, 2H) 5.23 (d, J=16.48 Hz, 1H) 4.57-4.63 (m, 1H) 4.47-4.56 (m, 2H) 3.51 (s, 3H) 2.98 (s, 3H). MS (APCI+) m/z 502 (M+H)$^+$.

Example 81

4-(2-naphthoyl)-10-methyl-7-((methylsulfonyl)methyl)-3,4-dihydro-1H-1,4,10-triazadibenzo[cd,f]azulen-11(10H)-one Example 81 was prepared according to the procedure used for the preparation of Example 54, substituting 2-naphthoyl chloride for isobutyryl chloride to provide the title compound. $^1$H NMR (400 MHz, DMSO-d$_6$/D$_2$O) δ 7.96-7.99 (m, 1H), 7.93 (s, 1H), 7.86 (s, 1H), 7.80 (d, J=7.02 Hz, 1H), 7.71-7.76 (m, 1H), 7.63-7.67 (m, 2H), 7.57-7.61 (m, 1H), 7.46-7.53 (m, 2H), 7.42 (s, 1H), 7.08 (dd, J=8.39, 1.37 Hz, 1H), 5.93 (d, J=14.95 Hz, 1H), 4.39-4.45 (m, 1H), 4.31-4.38 (m, 1H), 4.20 (d, J=14.65 Hz, 1H), 3.73 (s, 3H), 2.77 (s, 3H). MS (ESI+) m/z 498.1 (M+H)$^+$.

Example 82 methyl 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoate Example 12d (44.3 mg, 0.100 mmol) and methyl 4-oxobutanoate (58.1 mg, 0.500 mmol) were combined in tetrahydrofuran (1 mL). To this suspension was added 1M titanium(IV) chloride in dichloromethane (0.200 mL, 0.200 mmol). The reaction mixture was stirred at ambient temperature for 20 hours, and partitioned with ethyl acetate and water. The organic layer was washed with saturated aqueous sodium chloride, dried with anhydrous sodium sulfate, filtered, and concentrated. The residue was purified by flash chromatography (silica gel, 2-4% methanol in dichloromethane) to afford the title compound (38 mg, 70%). $^1$H NMR (300 MHz, DMSO-d$_6$) δ 11.91 (d, J=2.14 Hz, 1H) 7.85 (d, J=1.83 Hz, 1H) 7.69 (s, 1H) 7.24 (dd, J=8.24, 1.83 Hz, 1H) 7.04-7.13 (m, 2H) 6.81-7.02 (m, 3H) 5.03 (t, J=7.63 Hz, 1H) 4.38-4.63 (m, 2H) 3.64 (s, 3H) 3.55 (s, 3H) 2.93 (s, 3H) 2.35-2.46 (m, 2H) 1.82-2.03 (m, 1H) 1.34-1.61 (m, 1H). MS (ESI+) m/z 542 (M+H)$^+$.

Example 83

4-(2,4-difluorophenyl)-10-methyl-3,4-dihydro-1H-1,4,5,7,10-pentaazadibenzo[cd,f]azulen-11(10H)-one Example 83a 5-chloro-N-(2,4-difluorophenyl)pyrimidin-4-amine A mixture of 2,4-difluoroaniline (0.433 g, 3.36 mmol), 4,5-dichloropyrimidine (0.5 g, 3.36 mmol), cesium carbonate (2.187 g, 6.71 mmol), (9,9-dimethyl-9H-xanthene-4,5-diyl)bis(diphenylphosphine) (0.097 g, 0.168 mmol) and diacetoxypalladium (0.038 g, 0.168 mmol) were combined in toluene (4 mL), sealed, sparged for 15 minutes with argon and heated at 110° C. for 18 hours. The reaction mixture was partitioned between ethyl acetate and water. The organic layer was washed with saturated aqueous sodium chloride, dried (anhydrous sodium sulfate), treated with 3-mercaptopropyl functionalized silica, filtered and concentrated. Purification by chromatography (silica gel, 10-50% ethyl acetate in heptanes) afforded the title compound (0.66 g, 81%).

Example 83b 4-(4-((2,4-difluorophenyl)amino)pyrimidin-5-yl)-6-methyl-1-tosyl-1H-pyrrolo[2,3-c]pyridin-7(6H)-one Example 83a (0.2 g, 0.828 mmol), Example 1f (0.355 g, 0.828 mmol), tris(dibenzylideneacetone)dipalladium (0) (0.038 g, 0.041 mmol), 1,3,5,7-tetramethyl-6-phenyl-2,4,8-trioxa-6-phosphaadamantane (0.041 g, 0.141 mmol) and sodium carbonate (0.307 g, 2.90 mmol) were combined and sparged with argon for 15 minutes. Meanwhile a solution of 4:1 dioxane/water (4 mL) was sparged with nitrogen for 15 minutes and transferred by syringe into the reaction vessel under argon. The mixture was stirred for 18 hour at 80° C., cooled, diluted with 100 mL ethyl acetate and 20 mL of water and filtered through Celite to remove elemental palladium. The filtrate layers were separated. The organic layer was washed with saturated aqueous sodium chloride, dried (anhydrous sodium sulfate), treated with 3-mercaptopropyl functionalized silica gel, filtered and concentrated. Purification by chromatography (silica gel, 0.5-4% methanol in dichloromethane) afforded the title compound (0.272 g, 65%).

Example 83c 4-(4-((2,4-difluorophenyl)amino)pyrimidin-5-yl)-6-methyl-1H-pyrrolo[2,3-c]pyridin-7(6H)-one Example 83b (0.26 g, 0.512 mmol) and lithium hydroxide monohydrate (0.215 g, 5.12 mmol) were combined in dioxane (4 mL) and water (1.333 mL) and heated at 50° C. for 18 hours. The mixture was cooled, diluted with water and the pH was adjusted to pH 9 with 1 M HCl. The resulting solid was collected by filtration, rinsed with water and dried to constant mass affording the title compound (0.171 g, 94%).

Example 83d 4-(2,4-difluorophenyl)-10-methyl-3,4-dihydro-1H-1,4,5,7,10-pentaazadibenzo[cd,f]azulen-11(10H)-one Example 83c (0.03 g, 0.085 mmol) and paraformaldehyde (0.025 g, 0.849 mmol) were combined in methanol (1.0 mL) and treated with hydrogen chloride (4M in 1,4-dioxane, 1.0 mL, 4.00 mmol). The mixture was sealed and heated at 130° C. for 2 hours by microwave. The mixture was cooled, diluted with ether and filtered to collect the HCl salt of the title compound (0.0025 g, 7%). $^1$H NMR (400 MHz, DMSO-d$_6$) δ 12.75 (d, J=2.44 Hz, 1H), 10.45 (s, 1H), 8.48 (s, 1H), 8.45 (s, 1H), 7.77 (d, J=2.75 Hz, 1H), 7.40-7.52 (m, 3H), 7.17 (t, J=8.39 Hz, 1H), 5.58 (d, J=14.95 Hz, 1H), 4.81 (d, J=15.26 Hz, 1H), 3.58 (s, 3H). MS (ESI+) m/z 366 (M+H)$^+$.

Example 84

(R)-ethyl 4-(4-fluorophenyl)-10-methyl-7-((methylsulfonyl)methyl)-11-oxo-3,4,10,11-tetrahydro-1H-1,4,10-triazadibenzo[cd,f]azulene-3-carboxylate Example 34 (13.4 mg, 0.026 mmol) was subjected to SFC purification using a modified Berger Instruments PrepSFC™ system. A manual version of the Berger system was integrated with a Gilson 232 autosampler for sample injection and a Cavro MiniPrep™ pipettor customized for fraction collection at atmospheric pressure (Olson, J.; Pan, J.; Hochlowski, J.; Searle, P.; Blanchard, D. JALA 2002, 7, 69-74). Custom designed collection shoes allowed collection into 18×150 mm tubes and a methanol wash system allows washing of shoes between fractions to maximize recovery and avoid cross-contamination of fractions. The system was controlled using SFC ProNTo™ software (version 1.5.305.15) and an Abbott developed Visual Basic application for autosampler and fraction collector control. The outlet pressure was 100 bar, oven temperature at 35° C., and mobile phase flow rate at 40 mL/min on a ChiralPak OD-H column (21×250 mm, 5 micron). Samples were injected as solutions in 1.5 mL methanol. The preparative SFC system was controlled using SFC ProNTo™ software (version 1.5.305.15) and custom software for autosampler and fraction collector control. Fractions were collected based upon UV signal threshold and on-line Thermo MSQ mass spectrometry was used for molecular mass confirmation, using ESI ionization in positive mode. Mass spectra were acquired using a Navigator4.0 software and an Abbott developed Visual Basic interface to communicate with SFC controlling software to provide two white solids (Example 84, 6.5 mg, 48% yield, and Example 85 (6.0 mg, 44% yield). The first eluting enantiomer was arbitrarily assigned as the R-isomer (Example 84), and the second eluting enantiomer as the S-isomer (Example 85). $^1$H NMR (300 MHz, DMSO-d$_6$) δ 11.95-12.00 (m, 1H), 7.85 (d, J=2.0 Hz, 1H), 7.62 (s, 1H), 7.37 (d, J=1.9 Hz, 1H), 7.24 (d, J=8.1 Hz, 1H), 6.87 (t, J=8.7 Hz, 2H), 6.46-6.61 (m, 2H), 6.18-6.29 (m, 1H), 4.44-4.62 (m, 2H), 3.70-4.03 (m, 2H), 3.58 (s, 3H), 2.93 (s, 3H), 0.87-1.03 (m, 3H). MS (ESI+) m/z 510.1 (M+H)$^+$.

Example 85

(S)-ethyl 4-(4-fluorophenyl)-10-methyl-7-((methylsulfonyl)methyl)-11-oxo-3,4,10,11-tetrahydro-1H-1,4,10-triazadibenzo[cd,f]azulene-3-carboxylate $^1$H NMR (300 MHz, DMSO-d$_6$) δ 11.95-12.00 (m, 1H), 7.85 (d, J=2.0 Hz, 1H), 7.62 (s, 1H), 7.37 (d, J=1.9 Hz, 1H), 7.24 (d, J=8.1 Hz, 1H), 6.87 (t, J=8.7 Hz, 2H), 6.46-6.61 (m, 2H), 6.18-6.29 (m, 1H), 4.44-4.62 (m, 2H), 3.70-4.03 (m, 2H), 3.58 (s, 3H), 2.93 (s, 3H), 0.87-1.03 (m, 3H). MS (ESI+) m/z 510.1 (M+H)$^+$.

Example 86

2-methoxyethyl 10-methyl-7-((methylsulfonyl)methyl)-11-oxo-10,11-dihydro-1H-1,4,10-triazadibenzo[cd,f]azulene-4(3H)-carboxylate Example 86 was prepared according to the procedure used for the preparation of Example 53, substituting 2-methoxyethyl carbonochloridate for 2-ethylhexyl carbonochloridate to provide the title compound. $^1$H NMR (400 MHz, DMSO-d$_6$/D$_2$O) δ 7.78-7.80 (m, 1H), 7.61 (s, 1H), 7.35-7.39 (m, 1H), 7.33 (s, 1H), 7.23 (s, 1H), 5.20-5.30 (m, 1H), 4.49 (d, J=6.8 Hz, 2H), 3.88-4.20 (m, 2H), 3.63 (s, 3H), 3.33-3.39 (m, 1H), 3.12 (s, 2H), 2.94 (s, 3H). MS (ESI+) m/z 446.0 (M+H)$^+$.

Example 87 ethyl 10-methyl-7-((methylsulfonyl)methyl)-11-oxo-10,11-dihydro-1H-1,4,10-triazadibenzo[cd,f]azulene-4(3H)-carboxylate Example 87 was prepared according to the procedure used for the preparation of Example 53, substituting ethyl carbonochloridate for 2-ethylhexyl carbonochloridate to provide the title compound. $^1$H NMR (400 MHz, DMSO-d$_6$/D$_2$O) δ 7.78-7.80 (m, 1H), 7.61 (s, 1H), 7.35-7.39 (m, 1H), 7.32 (s, 1H), 7.23 (s, 1H), 5.21-5.27 (m, 1H), 4.49 (d, J=6.8 Hz, 2H), 4.12-4.17 (m, 1H), 3.85-3.99 (m, 2H), 3.63 (s, 3H), 2.95 (s, 3H), 1.00-1.08 (m, 3H). MS (ESI+) m/z 416.1 (M+H)$^+$.

Example 88 pentyl 10-methyl-7-((methylsulfonyl)methyl)-11-oxo-10,11-dihydro-1H-1,4,10-triazadibenzo[cd,f]azulene-4(3H)-carboxylate Example 88 was prepared according to the procedure used for the preparation of Example 53, substituting pentyl carbonochloridate for 2-ethylhexyl carbonochloridate to provide the title compound. $^1$H NMR (400 MHz, DMSO-d$_6$/D$_2$O) δ 7.79 (d, J=1.9 Hz, 1H), 7.60 (s, 1H), 7.37 (dd, J=8.1, 1.9 Hz, 1H), 7.30 (d, J=8.1 Hz, 1H), 7.22 (s, 1H), 5.22 (d, J=15.5 Hz, 1H), 4.44-4.54 (m, 2H), 4.14 (d, J=15.6 Hz, 1H), 3.91 (dd, J=11.9, 5.4 Hz, 1H), 3.80-3.87 (m, 1H), 3.63 (s, 3H), 2.94 (s, 3H), 1.33-1.41 (m, 2H), 1.03-1.18 (m, 4H), 0.75 (t, J=7.1 Hz, 3H). MS (ESI+) m/z 458.1 (M+H)$^+$.

Example 89

4-chlorobutyl 10-methyl-7-((methylsulfonyl)methyl)-11-oxo-10,11-dihydro-1H-1,4,10-triazadibenzo[cd,f]azulene-4(3H)-carboxylate Example 89 was prepared according to the procedure used for the preparation of Example 53, substituting 4-chlorobutyl carbonochloridate for 2-ethylhexyl carbonochloridate to provide the title compound. $^1$H NMR (400 MHz, DMSO-d$_6$/D$_2$O) δ 7.80 (d, J=1.9 Hz, 1H), 7.61 (s, 1H), 7.36-7.39 (m, 1H), 7.32 (d, J=8.1 Hz, 1H), 7.23 (s, 1H), 5.23 (d, J=15.7 Hz, 1H), 4.45-4.54 (m, 2H), 4.15 (d, J=15.8 Hz, 1H), 3.93-3.99 (m, 1H), 3.83-3.92 (m, 1H), 3.63 (s, 3H), 3.40-3.47 (m, 2H), 2.94 (s, 3H), 1.47-1.58 (m, 4H). MS (ESI+) m/z 478.0 (M+H)$^+$.

Example 90 naphthalen-2-yl 10-methyl-7-((methylsulfonyl)methyl)-11-oxo-10,11-dihydro-1H-1,4,10-triazadibenzo[cd,f]azulene-4(3H)-carboxylate Example 90 was prepared according to the procedure used for the preparation of Example 53, substituting naphthalen-2-yl carbonochloridate for 2-ethylhexyl carbonochloridate to provide the title compound. $^1$H NMR (400 MHz, DMSO-d$_6$/D$_2$O) δ 7.76-7.88 (m, 4H), 7.71 (s, 1H), 7.55-7.63 (m, 1H), 7.39-7.50 (m, 4H), 7.29-7.33 (m, 1H), 7.07 (d, J=8.9 Hz, 1H), 5.33-5.46 (m, 1H), 4.46-4.57 (m, 2H), 4.27-4.38 (m, 1H), 3.67 (s, 3H), 2.96 (s, 3H). MS (ESI+) m/z 513.9 (M+H)$^+$.

Example 91 p-tolyl 10-methyl-7-((methylsulfonyl)methyl)-11-oxo-10,11-dihydro-1H-1,4,10-triazadibenzo[cd,f]azulene-4(3H)-carboxylate Example 91 was prepared according to the procedure used for the preparation of Example 53, substituting p-tolyl carbonochloridate for 2-ethylhexyl carbonochloridate to provide the title compound. $^1$H NMR (400 MHz, DMSO-d$_6$/D$_2$O) δ 7.84 (d, J=1.9 Hz, 1H), 7.68 (s, 1H), 7.47-7.54 (m, 1H), 7.42 (dd, J=8.0, 1.8 Hz, 1H), 7.29 (s, 1H), 7.08 (d, J=8.2 Hz, 2H), 6.77 (d, J=8.5 Hz, 2H), 5.30-5.37 (m, 1H), 4.46-4.56 (m, 2H), 4.22-4.32 (m, 1H), 3.66 (s, 3H), 2.95 (s, 3H), 2.23 (s, 3H). MS (ESI+) m/z 478.2 (M+H)$^+$.

Example 92 neopentyl 10-methyl-7-((methylsulfonyl)methyl)-11-oxo-10,11-dihydro-1H-1,4,10-triazadibenzo[cd,f]azulene-4(3H)-carboxylate Example 92 was prepared according to the procedure used for the preparation of Example 53, substituting neopentyl carbonochloridate for 2-ethylhexyl carbonochloridate to provide the title compound. $^1$H NMR (400 MHz, DMSO-d$_6$/D$_2$O) δ 7.81 (d, J=1.8 Hz, 1H), 7.62 (s, 1H), 7.38 (dd, J=8.1, 1.9 Hz, 1H), 7.32 (d, J=8.1 Hz, 1H), 7.23 (s, 1H), 5.23 (d, J=15.5 Hz, 1H), 4.44-4.54 (m, 2H), 4.18 (d, J=15.6 Hz, 1H), 3.63 (s, 3H), 3.27-3.29 (m, 2H), 2.91 (s, 3H), 0.62-0.79 (m, 9H). MS (ESI+) m/z 458.1 (M+H)$^+$.

Example 93 phenyl 10-methyl-7-((methylsulfonyl)methyl)-11-oxo-10,11-dihydro-1H-1,4,10-triazadibenzo[cd,f]azulene-4(3H)-carboxylate Example 93 was prepared according to the procedure used for the preparation of Example 53, substituting phenyl carbonochloridate for 2-ethylhexyl carbonochloridate to provide the title compound. $^1$H NMR (400 MHz, DMSO-d$_6$/D$_2$O) δ 7.85 (d, J=1.9 Hz, 1H), 7.69 (s, 1H), 7.50-7.55 (m, 1H), 7.42 (dd, J=8.0, 2.0 Hz, 1H), 7.29 (t, J=7.8 Hz, 3H), 7.14 (t, J=7.3 Hz, 1H), 6.89 (dd, J=8.6, 1.1 Hz, 2H), 5.30-5.39 (m, 1H), 4.46-4.57 (m, 2H), 4.26-4.34 (m, 1H), 3.66 (s, 3H), 2.95 (s, 3H). MS (ESI+) m/z 464.1 (M+H)$^+$.

Example 94

4-fluorophenyl 10-methyl-7-((methylsulfonyl)methyl)-11-oxo-10,11-dihydro-1H-1,4,10-triazadibenzo[cd,f]azulene-4(3H)-carboxylate Example 94 was prepared according to the procedure used for the preparation of Example 53, substituting 4-fluorophenyl carbonochloridate for 2-ethylhexyl carbonochloridate to provide the title compound. $^1$H NMR (400 MHz, DMSO-d$_6$/D$_2$O) δ 7.85 (d, J=1.7 Hz, 1H), 7.68 (s, 1H), 7.50-7.57 (m, 1H), 7.42 (dd, J=8.2, 2.0 Hz, 1H), 7.29 (s, 1H), 7.07 (t, J=8.8 Hz, 2H), 6.91-6.96 (m, 2H), 5.31-5.38 (m, 1H), 4.46-4.56 (m, 2H), 4.25-4.34 (m, 1H), 3.66 (s, 3H), 2.95 (s, 3H). MS (ESI+) m/z 482.0 (M+H)$^+$.

Example 95

2-methoxyphenyl 10-methyl-7-((methylsulfonyl)methyl)-11-oxo-10,11-dihydro-1H-1,4,10-triazadibenzo[cd,f]azulene-4(3H)-carboxylate Example 95 was prepared according to the procedure used for the preparation of Example 53, substituting 2-methoxyphenyl carbonochloridate for 2-ethylhexyl carbonochloridate to provide the title compound. $^1$H NMR (400 MHz, DMSO-d$_6$/D$_2$O) δ 7.84 (d, J=1.8 Hz, 1H), 7.68 (s, 1H), 7.49-7.55 (m, 1H), 7.41 (dd, J=8.2, 1.9 Hz, 1H), 7.27 (s, 1H), 7.08-7.14 (m, 1H), 6.97 (d, J=8.2 Hz, 1H), 6.83-6.86 (m, 2H), 5.29-5.36 (m, 1H), 4.45-4.56 (m, 2H), 4.23-4.33 (m, 1H), 3.67 (s, 3H), 3.54 (s, 3H), 2.95 (s, 3H). MS (ESI+) m/z 494.1 (M+H)$^+$.

Example 96

2-fluoroethyl 10-methyl-7-((methylsulfonyl)methyl)-11-oxo-10,11-dihydro-1H-1,4,10-triazadibenzo[cd,f]azulene-4(3H)-carboxylate Example 96 was prepared according to the procedure used for the preparation of Example 53, substituting 2-fluoroethyl carbonochloridate for 2-ethylhexyl carbonochloridate to provide the title compound. $^1$H NMR (400 MHz, DMSO-d$_6$/D$_2$O) δ 7.80 (d, J=1.5 Hz, 1H), 7.62 (s, 1H), 7.38 (dd, J=8.3, 1.7 Hz, 1H), 7.33 (d, J=8.0 Hz, 1H), 7.24 (d, J=0.6 Hz, 1H), 5.27 (d, J=15.6 Hz, 1H), 4.45-4.55 (m, 3H), 4.34-4.39 (m, 1H), 3.99-4.28 (m, 3H), 3.63 (s, 3H), 2.94 (s, 3H). MS (ESI+) m/z 434.0 (M+H)$^+$.

Example 97

4-methoxyphenyl 10-methyl-7-((methylsulfonyl)methyl)-11-oxo-10,11-dihydro-1H-1,4,10-triazadibenzo[cd,f]azulene-4(3H)-carboxylate Example 97 was prepared according to the procedure used for the preparation of Example 53, substituting 4-methoxyphenyl carbonochloridate for 2-ethylhexyl carbonochloridate to provide the title compound. $^1$H NMR (400 MHz, DMSO-d$_6$/D$_2$O) δ 7.84 (d, J=1.8 Hz, 1H), 7.68 (s, 1H), 7.46-7.56 (m, 1H), 7.39-7.44 (m, 1H), 7.25-7.32 (m, 1H), 6.82 (s, 4H), 5.30-5.39 (m, 1H), 4.45-4.56 (m, 2H), 4.21-4.34 (m, 1H), 3.70 (s, 3H), 3.66 (s, 3H), 2.95 (s, 3H). MS (ESI+) m/z 494.0 (M+H)$^+$.

Example 98 but-2-yn-1-yl 10-methyl-7-((methylsulfonyl)methyl)-11-oxo-10,11-dihydro-1H-1,4,10-triazadibenzo[cd,f]azulene-4(3H)-carboxylate Example 98 was prepared according to the procedure used for the preparation of Example 53, substituting but-2-yn-1-yl carbonochloridate for 2-ethylhexyl carbonochloridate to provide the title compound. $^1$H NMR (400 MHz, DMSO-d$_6$/D$_2$O) δ 7.80 (d, J=1.9 Hz, 1H), 7.62 (s, 1H), 7.39 (dd, J=8.3, 1.9 Hz, 1H), 7.31 (d, J=8.1 Hz, 1H), 7.25 (s, 1H), 5.21-5.27 (m, 1H), 4.44-4.55 (m, 4H), 4.13-4.19 (m, 1H), 3.63 (s, 3H), 2.95 (s, 3H), 1.72 (t, J=2.3 Hz, 3H). MS (ESI+) m/z 440.1 (M+H)$^+$.

Example 99

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanamide

Example 99a 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoic acid Example 82 (375 mg, 0.692 mmol) and lithium hydroxide (83 mg, 3.5 mmol) were combined in the mixture of dioxane (6 mL) and water (2 mL). The reaction mixture was stirred at ambient temperature for 5 hours. The reaction mixture was diluted with water, the pH adjusted to 4 by addition of 1M HCl, and extracted by ethyl acetate. The organic layer was washed with saturated aqueous sodium chloride, dried with anhydrous sodium sulfate, filtered and concentrated to afford the title compound (365 mg, 100%).

Example 99b 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanamide Example 99a (31.7 mg, 0.060 mmol), 2-(6-chloro-1H-benzo[d][1,2,3]triazol-1-yl)-1,1,3,3-tetramethylisouronium hexafluorophosphate(V) (49.6 mg, 0.120 mmol) and diisopropylethylamine (0.042 mL, 0.240 mmol) were combined in dimethylformamide (1 mL). To this solution was added 0.5M ammonia in dioxane (0.240 mL, 0.120 mmol). The reaction mixture was stirred at ambient temperature for 2 hours. The reaction mixture was partitioned with ethyl acetate and water. The organic layer was washed with saturated aqueous sodium chloride twice, dried with anhydrous sodium sulfate, filtered and concentrated. The residue was purified by reverse phase HPLC (C18, CH$_3$CN/water (10 mM ammonium acetate), 10-100%) to afford the title compound (18 mg, 57%). $^1$H NMR (400 MHz, DMSO-d$_6$) δ 11.91 (s, 1H) 7.82 (d, J=1.83 Hz, 1H) 7.68 (s, 1H) 7.34 (s, 1H) 7.22 (dd, J=8.24, 1.83 Hz, 1H) 7.01-7.17 (m, 3H) 6.86-6.99 (m, 2H) 6.77 (s, 1H) 5.01 (dd, J=9.00, 5.95 Hz, 1H) 4.38-4.55 (m, 2H) 3.64 (s, 3H) 2.93 (s, 3H) 2.10-2.20 (m, 2H) 1.87-1.98 (m, 1H) 1.31-1.45 (m, 1H). MS (ESI+) m/z 549 (M+Na)$^+$.

Example 100

4-(4-fluorobenzoyl)-10-methyl-7-((methylsulfonyl)methyl)-3,4-dihydro-1H-1,4,10-triazadibenzo[cd,f]azulen-11(10H)-one Example 100 was prepared according to the procedure used for the preparation of Example 54, substituting 4-fluorobenzoyl chloride for isobutyryl chloride to provide the title compound. $^1$H NMR (400 MHz, DMSO-d$_6$/D$_2$O) δ 7.83 (d, J=1.9 Hz, 1H), 7.75 (s, 1H), 7.25-7.33 (m, 1H), 7.10 (ddd, J=13.0, 8.5, 5.9 Hz, 3H), 6.90-7.03 (m, 3H), 5.66-5.88 (m, 1H), 4.33-4.50 (m, 2H), 4.16 (d, J=16.2 Hz, 1H), 3.69 (s, 3H), 2.84 (s, 3H). MS (ESI+) m/z 466.1 (M+H)$^+$.

Example 101

4-(3-methoxypropanoyl)-10-methyl-7-((methylsulfonyl)methyl)-3,4-dihydro-1H-1,4,10-triazadibenzo[cd,f]azulen-11(10H)-one Example 101 was prepared according to the procedure used for the preparation of Example 54, substituting 3-methoxypropanoyl chloride for isobutyryl chloride to provide the title compound. $^1$H NMR (400 MHz, DMSO-d$_6$/D$_2$O) δ 7.86 (s, 1H), 7.67 (s, 1H), 7.38-7.46 (m, 2H), 7.22-7.25 (m, 1H), 5.48-5.61 (m, 1H), 4.52 (q, J=14.0 Hz, 2H), 3.93-4.01 (m, 1H), 3.64 (s, 3H), 3.29-3.43 (m, 3H), 3.00 (s, 2H), 2.95 (s, 3H), 2.33-2.43 (m, 1H), 1.93-2.02 (m, 1H). MS (ESI+) m/z 430.2 (M+H)$^+$.

Example 102

4-([1,1'-biphenyl]-4-carbonyl)-10-methyl-7-((methylsulfonyl)methyl)-3,4-dihydro-1H-1,4,10-triazadibenzo[cd,f]azulen-11(10H)-one Example 102 was prepared according to the procedure used for the preparation of Example 54, substituting [1,1'-biphenyl]-4-carbonyl chloride for isobutyryl chloride to provide the title compound. $^1$H NMR (400 MHz, DMSO-$d_6$/$D_2O$) δ 7.85 (d, J=1.8 Hz, 1H), 7.78 (s, 1H), 7.54 (d, J=7.6 Hz, 2H), 7.39-7.46 (m, 4H), 7.29-7.37 (m, 2H), 7.14 (d, J=8.4 Hz, 3H), 6.99-7.06 (m, 1H), 5.70-5.94 (m, 1H), 4.42 (d, J=5.2 Hz, 2H), 4.14-4.22 (m, 1H), 3.70 (s, 3H), 2.81 (s, 3H). MS (ESI+) m/z 424.0 (M+H)$^+$.

Example 103

4-(3-cyclopentylpropanoyl)-10-methyl-7-((methylsulfonyl)methyl)-3,4-dihydro-1H-1,4,10-triazadibenzo[cd,f]azulen-11(10H)-one Example 103 was prepared according to the procedure used for the preparation of Example 54, substituting 3-cyclopentylpropanoyl chloride for isobutyryl chloride, to provide the title compound. $^1$H NMR (400 MHz, DMSO-$d_6$/$D_2O$) δ 7.86 (s, 1H), 7.65 (s, 1H), 7.41 (dd, J=22.9, 9.0 Hz, 2H), 7.23 (s, 1H), 5.51-5.59 (m, 1H), 4.52 (q, J=13.6 Hz, 2H), 3.89-3.99 (m, 1H), 3.63 (s, 3H), 2.94 (s, 3H), 1.83-2.10 (m, 2H), 1.19-1.40 (m, 9H), 0.66-0.80 (m, 2H). MS (ESI+) m/z 468.2 (M+H)$^+$.

Example 104

4-(2-(3-methoxyphenyl)acetyl)-10-methyl-7-((methylsulfonyl)methyl)-3,4-dihydro-1H-1,4,10-triazadibenzo[cd,f]azulen-11(10H)-one Example 104 was prepared according to the procedure used for the preparation of Example 54, substituting 2-(3-methoxyphenyl)acetyl chloride for isobutyryl chloride to provide the title compound. $^1$H NMR (400 MHz, DMSO-$d_6$/$D_2O$) δ 7.65-7.74 (m, 1H), 7.39-7.49 (m, 2H), 7.16-7.30 (m, 2H), 6.52-6.94 (m, 2H), 6.04-6.18 (m, 1H), 5.49-5.61 (m, 1H), 4.45-4.56 (m, 2H), 3.58 (s, 3H), 3.47 (s, 2H), 2.95 (s, 4H). MS (ESI+) m/z 492.1 (M+H)$^+$.

Example 105

10-methyl-7-((methylsulfonyl)methyl)-4-propionyl-3,4-dihydro-1H-1,4,10-triazadibenzo[cd,f]azulen-11(10H)-one Example 105 was prepared according to the procedure used for the preparation of Example 54, substituting propionyl chloride for isobutyryl chloride to provide the title compound. $^1$H NMR (400 MHz, DMSO-$d_6$/$D_2O$) δ 7.81-7.88 (m, 1H), 7.63-7.69 (m, 1H), 7.37-7.45 (m, 2H), 7.22-7.26 (m, 1H), 5.51-5.61 (m, 1H), 4.52 (q, J=13.8 Hz, 2H), 3.91-3.99 (m, 1H), 3.63 (s, 3H), 2.95 (s, 3H), 2.13 (dq, J=14.8, 7.3 Hz, 1H), 1.64-1.81 (m, 1H), 0.72-0.87 (m, 3H). MS (ESI+) m/z 400.1 (M+H)$^+$.

Example 106

10-methyl-4-(3-methylbutanoyl)-7-((methylsulfonyl)methyl)-3,4-dihydro-1H-1,4,10-triazadibenzo[cd,f]azulen-11(10H)-one Example 106 was prepared according to the procedure used for the preparation of Example 54, substituting 3-methylbutanoyl chloride for isobutyryl chloride to provide the title compound. $^1$H NMR (400 MHz, DMSO-$d_6$/$D_2O$) δ 7.81-7.88 (m, 1H), 7.63-7.69 (m, 1H), 7.32-7.47 (m, 2H), 7.22-7.25 (m, 1H), 5.49-5.62 (m, 1H), 4.47-4.59 (m, 2H), 3.91-3.99 (m, 1H), 3.63 (s, 3H), 2.95 (s, 3H), 1.90-2.01 (m, 1H), 1.66-1.81 (m, 1H), 0.63-0.69 (m, 3H), 0.43-0.51 (m, 4H). MS (ESI+) m/z 428.1 (M+H)$^+$.

Example 107

4-(3,3-dimethylbutanoyl)-10-methyl-7-((methylsulfonyl)methyl)-3,4-dihydro-1H-1,4,10-triazadibenzo[cd,f]azulen-11(10H)-one Example 107 was prepared according to the procedure used for the preparation of Example 54, substituting 3,3-dimethylbutanoyl chloride for isobutyryl chloride to provide the title compound. $^1$H NMR (400 MHz, DMSO-$d_6$/$D_2O$) δ 7.85 (s, 1H), 7.65 (s, 1H), 7.43 (d, J=8.6 Hz, 1H), 7.32 (d, J=8.4 Hz, 1H), 7.23 (s, 1H), 5.57-5.64 (m, 1H), 3.87-3.97 (m, 1H), 4.52 (q, J=13.7 Hz, 2H), 3.63 (s, 3H), 2.94 (s, 3H), 1.84-2.01 (m, 2H), 0.69 (s, 9H). MS (ESI+) m/z 442.2 (M+H)$^+$.

Example 108

10-methyl-7-((methylsulfonyl)methyl)-4-(2-phenylacetyl)-3,4-dihydro-1H-1,4,10-triazadibenzo[cd,f]azulen-11(10H)-one Example 108 was prepared according to the procedure used for the preparation of Example 54, substituting 2-phenylacetyl chloride for isobutyryl chloride to provide the title compound. $^1$H NMR (400 MHz, DMSO-$d_6$/$D_2O$) δ 7.69-7.74 (m, 1H), 7.44 (s, 2H), 7.24-7.28 (m, 2H), 7.19-7.23 (m, 2H), 6.93-7.01 (m, 2H), 6.54-6.62 (m, 1H), 5.49-5.57 (m, 1H), 4.46-4.57 (m, 2H), 3.95-4.01 (m, 1H), 3.58 (s, 3H), 2.96 (s, 5H). MS (ESI+) m/z 462.1 (M+H)$^+$.

Example 109

4-benzoyl-10-methyl-7-((methylsulfonyl)methyl)-3,4-dihydro-1H-1,4,10-triazadibenzo[cd,f]azulen-11(10H)-one Example 109 was prepared according to the procedure used for the preparation of Example 54, substituting benzoyl chloride for isobutyryl chloride to provide the title compound. $^1$H NMR (400 MHz, DMSO-$d_6$/$D_2O$) δ 7.90-7.96 (m, 1H), 7.82 (d, J=2.0 Hz, 1H), 7.75 (s, 1H), 7.20-7.34 (m, 2H), 7.09-7.18 (m, 2H), 7.04 (d, J=7.4 Hz, 2H), 6.92-7.01 (m, 1H), 5.65-5.87 (m, 1H), 4.41 (d, J=5.0 Hz, 2H), 4.11-4.21 (m, 1H), 3.69 (s, 3H), 2.82 (s, 3H). MS (ESI+) m/z 448.0 (M+H)$^+$.

Example 110

4-(4-methoxybenzoyl)-10-methyl-7-((methylsulfonyl)methyl)-3,4-dihydro-1H-1,4,10-triazadibenzo[cd,f]azulen-11(10H)-one Example 110 was prepared according to the procedure used for the preparation of Example 54, substituting 4-methoxybenzoyl chloride for isobutyryl chloride to provide the title compound. $^1$H NMR (400 MHz, DMSO-$d_6$/D$_2$O) δ 7.83 (d, J=1.8 Hz, 1H), 7.75 (s, 1H), 7.27 (s, 1H), 7.14 (dd, J=8.0, 2.1 Hz, 1H), 7.01 (d, J=8.8 Hz, 2H), 6.94 (d, J=8.1 Hz, 1H), 6.68 (d, J=8.8 Hz, 2H), 5.72-5.92 (m, 1H), 4.36-4.49 (m, 2H), 4.12 (d, J=14.4 Hz, 1H), 3.68 (d, J=5.3 Hz, 6H), 2.85 (s, 3H). MS (ESI+) m/z 478.1 (M+H)$^+$.

Example 111 methyl 4-(10-methyl-7-((methylsulfonyl)methyl)-11-oxo-10,11-dihydro-1H-1,4,10-triazadibenzo[cd,f]azulen-4(3H)-yl)-4-oxobutanoate Example 111 was prepared according to the procedure used for the preparation of Example 54, substituting methyl 4-chloro-4-oxobutanoate for isobutyryl chloride, to provide the title compound. $^1$H NMR (400 MHz, DMSO-$d_6$/D$_2$O) δ 7.85-7.89 (m, 1H), 7.66-7.71 (m, 1H), 7.42-7.47 (m, 2H), 7.21-7.25 (m, 1H), 5.49-5.58 (m, 1H), 4.47-4.58 (m, 2H), 3.93-4.01 (m, 1H), 3.64 (s, 3H), 3.40-3.44 (m, 2H), 2.95 (s, 3H), 2.28-2.49 (m, 2H), 1.84-2.00 (m, 1H). MS (ESI+) m/z 458.1 (M+H)$^+$.

Example 112

4-(2,4-difluorobenzoyl)-10-methyl-7-((methylsulfonyl)methyl)-3,4-dihydro-1H-1,4,10-triazadibenzo[cd,f]azulen-11(10H)-one Example 112 was prepared according to the procedure used for the preparation of Example 54, substituting 2,4-difluorobenzoyl chloride for isobutyryl chloride to provide the title compound. $^1$H NMR (400 MHz, DMSO-$d_6$/D$_2$O) δ 7.79 (s, 1H), 7.70 (s, 1H), 7.29-7.38 (m, 1H), 7.00-7.17 (m, 3H), 6.78-6.95 (m, 2H), 5.74-5.85 (m, 1H), 4.33-4.47 (m, 2H), 4.14-4.24 (m, 1H), 3.67 (s, 3H), 2.81 (s, 3H). MS (ESI+) m/z 484.1 (M+H)$^+$.

Example 113

4-(2-fluorobenzoyl)-10-methyl-7-((methylsulfonyl)methyl)-3,4-dihydro-1H-1,4,10-triazadibenzo[cd,f]azulen-11(10H)-one Example 113 was prepared according to the procedure used for the preparation of Example 54, substituting 2-fluorobenzoyl chloride for isobutyryl chloride to provide the title compound. $^1$H NMR (400 MHz, DMSO-$d_6$/D$_2$O) δ 7.80-7.86 (m, 1H), 7.70 (s, 1H), 7.58-7.64 (m, 1H), 7.30-7.40 (m, 1H), 7.17-7.28 (m, 1H), 6.99-7.14 (m, 2H), 6.83-6.99 (m, 2H), 5.72-5.88 (m, 1H), 4.26-4.49 (m, 2H), 4.12-4.25 (m, 1H), 3.68 (s, 3H), 2.77 (s, 3H). MS (ESI+) m/z 466.0 (M+H)$^+$.

Example 114

4-(1-naphthoyl)-10-methyl-7-((methylsulfonyl)methyl)-3,4-dihydro-1H-1,4,10-triazadibenzo[cd,f]azulen-11(10H)-one Example 114 was prepared according to the procedure used for the preparation of Example 54, substituting 1-naphthoyl chloride for isobutyryl chloride to provide the title compound. $^1$H NMR (400 MHz, DMSO-$d_6$/D$_2$O) δ 7.74-7.81 (m, 1H), 7.66-7.73 (m, 1H), 7.60-7.67 (m, 1H), 7.52-7.60 (m, 2H), 7.38-7.49 (m, 2H), 7.16-7.32 (m, 2H), 6.94-7.07 (m, 2H), 6.84-6.92 (m, 1H), 5.89-6.00 (m, 1H), 4.33-4.61 (m, 1H), 4.20-4.30 (m, 2H), 3.69 (s, 3H), 2.59-2.76 (m, 3H). MS (ESI+) m/z 498.1 (M+H)$^+$.

Example 115

4-(cyclopropanecarbonyl)-10-methyl-7-((methylsulfonyl)methyl)-3,4-dihydro-1H-1,4,10-triazadibenzo[cd,f]azulen-11(10H)-one Example 115 was prepared according to the procedure used for the preparation of Example 54, substituting cyclopropanecarbonyl chloride for isobutyryl chloride to provide the title compound. $^1$H NMR (400 MHz, DMSO-$d_6$/D$_2$O) δ 7.83-7.91 (m, 1H), 7.63-7.71 (m, 1H), 7.39-7.47 (m, 2H), 7.18-7.27 (m, 1H), 5.53-5.66 (m, 1H), 4.44-4.61 (m, 2H), 3.89-4.05 (m, 1H), 3.64 (s, 3H), 2.96 (s, 3H), 1.91-1.98 (m, 1H), 1.18-1.32 (m, 1H), 1.04-1.15 (m, 2H), 0.55-0.66 (m, 1H). MS (ESI+) m/z 412.1 (M+H)$^+$.

Example 116

10-methyl-7-((methylsulfonyl)methyl)-4-(3-phenylpropanoyl)-3,4-dihydro-1H-1,4,10-triazadibenzo[cd,f]azulen-11(10H)-one Example 116 was prepared according to the procedure used for the preparation of Example 54, substituting 3-phenylpropanoyl chloride for isobutyryl chloride to provide the title compound. $^1$H NMR (400 MHz, DMSO-$d_6$/D$_2$O) δ 7.83 (d, J=0.6 Hz, 1H), 7.59 (s, 1H), 7.40 (d, J=9.5 Hz, 1H), 7.31 (d, J=8.3 Hz, 1H), 7.23 (s, 1H), 6.97-7.06 (m, 3H), 6.76-6.84 (m, 2H), 5.51-5.63 (m, 1H), 4.51 (q, J=13.9 Hz, 2H), 3.89-4.01 (m, 1H), 3.63 (s, 3H), 2.93 (s, 3H), 2.61 (t, J=7.8 Hz, 2H), 2.33-2.43 (m, 1H), 2.02-2.14 (m, 1H). MS (ESI+) m/z 476.2 (M+H)$^+$.

Example 117

2-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)isoindoline-1,3-dione Example 12d (0.4 g, 0.902 mmol) and 2-(1,3-dioxoisoindolin-2-yl)acetaldehyde (0.683 g, 3.61 mmol) were combined in tetrahydrofuran (9.02 mL) under nitrogen, cooled to 0° C. and treated drop-wise with 1M titanium(IV) chloride in dichloromethane (3.61 mL, 3.61 mmol) to give an opaque red solution. The solution was stirred for 72 hours at ambient temperature and partitioned between ethyl acetate and water. The organic layer was washed with saturated aqueous sodium chloride, dried over anhydrous sodium sulfate, filtered and concentrated. Purification by chromatography (silica gel, 0.5-5% methanol in dichloromethane) afforded the title compound as a yellow powder (0.45 g, 81%). $^1$H NMR (500 MHz, DMSO-d$_6$) δ 11.78 (d, J=1.83 Hz, 1H), 7.93 (d, J=1.53 Hz, 1H), 7.81-7.86 (m, 4H), 7.76 (s, 1H), 7.24-7.30 (m, 1H), 7.21 (dd, J=8.24, 1.83 Hz, 1H), 7.09-7.15 (m, 1H) 6.99-7.05 (m, 1H), 6.96 (d, J=2.44 Hz, 1H), 6.92 (d, J=8.24 Hz, 1H), 5.44 (dd, J=9.92, 5.34 Hz, 1H), 4.51-4.56 (m, 1H), 4.44-4.48 (m, 1H), 3.87 (dd, J=13.28, 5.34 Hz, 1H), 3.66 (s, 3H), 3.52 (dd, J=13.28, 10.22 Hz, 1H), 2.98 (s, 3H). MS (ESI+) m/z 615 (M+H)$^+$.

Example 118

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-methylpropanamide Example 118 was prepared according to the procedure used for the preparation of Example 99b, substituting methanamine for ammonia. Purification by reverse phase HPLC (C18, CH$_3$CN/water (10 mM ammonium acetate), 20-100%) afforded the title compound (22 mg, 68%). $^1$H NMR (400 MHz, DMSO-d$_6$) δ 11.90 (d, J=1.22 Hz, 1H) 7.82 (d, J=1.83 Hz, 1H) 7.77 (q, J=4.48 Hz, 1H) 7.68 (s, 1H) 7.22 (dd, J=8.24, 1.83 Hz, 1H) 7.02-7.12 (m, 3H) 6.87-7.00 (m, 2H) 5.00 (dd, J=9.00, 5.95 Hz, 1H) 4.33-4.58 (m, 2H) 3.64 (s, 3H) 2.93 (s, 3H) 2.55 (d, J=4.58 Hz, 3H) 2.07-2.22 (m, 2H) 1.83-2.00 (m, 1H) 1.31-1.48 (m, 1H). MS (ESI+) m/z 563 (M+Na)$^+$.

Example 119

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N,N-dimethylpropanamide Example 119 was prepared according to the procedure used for the preparation of Example 99b, substituting dimethylamine for ammonia. Purification by reverse phase HPLC (C18, CH$_3$CN/water (10 mM ammonium acetate), 20-100%) afforded the title compound (24 mg, 72%). $^1$H NMR (400 MHz, DMSO-d$_6$) δ 11.89 (s, 1H) 7.83 (d, J=1.83 Hz, 1H) 7.68 (s, 1H) 7.22 (dd, J=8.24, 2.14 Hz, 1H) 7.13-7.20 (m, 1H) 7.11 (s, 1H) 7.02-7.10 (m, 1H) 6.97 (d, J=8.24 Hz, 1H) 6.88-6.96 (m, 1H) 5.03-5.12 (m, 1H) 4.37-4.57 (m, 2H) 3.64 (s, 3H) 2.94 (s, 3H) 2.87 (s, 3H) 2.80 (s, 3H) 2.28-2.46 (m, 2H) 1.85-1.95 (m, 1H) 1.37-1.52 (m, 1H). MS (ESI+) m/z 577 (M+Na)$^+$.

Example 120

4-(2,4-difluorophenyl)-10-methyl-7-((methylsulfonyl)methyl)-3-(3-morpholino-3-oxopropyl)-3,4-dihydro-1H-1,4,10-triazadibenzo[cd,f]azulen-11(10H)-one Example 120 was prepared according to the procedure used for the preparation of Example 99b, substituting morpholine for ammonia. Purification by reverse phase HPLC (C18, CH$_3$CN/water (10 mM ammonium acetate), 20-100%) afforded the title compound (28 mg, 78%). $^1$H NMR (500 MHz, DMSO-d$_6$) δ 11.89 (s, 1H) 7.83 (d, J=1.83 Hz, 1H) 7.68 (s, 1H) 7.22 (d, J=8.24, 1.83 Hz, 1H) 7.03-7.16 (m, 3H) 6.99 (d, J=8.24 Hz, 1H) 6.88-6.94 (m, 1H) 5.08 (t, J=7.63 Hz, 1H) 4.39-4.57 (m, 2H) 3.64 (s, 3H) 3.37-3.55 (m, 8H) 2.94 (s, 3H) 2.40-2.48 (m, 1H) 2.29-2.39 (m, 1H) 1.84-1.94 (m, 1H) 1.38-1.55 (m, 1H). MS (ESI+) m/z 619 (M+Na)$^+$.

Example 121

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-(tetrahydro-2H-pyran-4-yl)propanamide Example 121 was prepared according to the procedure used for the preparation of Example 99b, substituting tetrahydro-2H-pyran-4-amine for ammonia. Purification by reverse phase HPLC (C18, CH$_3$CN/water (10 mM ammonium acetate), 20-100%) afforded the title compound (28 mg, 76%). $^1$H NMR (400 MHz, DMSO-d$_6$) δ 11.90 (s, 1H) 7.86 (d, J=7.63 Hz, 1H) 7.82 (d, J=1.83 Hz, 1H) 7.68 (s, 1H) 7.22 (dd, J=8.24, 1.83 Hz, 1H) 7.02-7.13 (m, 3H) 6.87-6.98 (m, 2H) 5.00 (dd, J=9.16, 5.80 Hz, 1H) 4.36-4.57 (m, 2H) 3.70-3.85 (m, 3H) 3.64 (s, 3H) 2.93 (s, 3H) 2.16 (t, J=7.17 Hz, 2H) 1.89-2.00 (m, 1H) 1.58-1.73 (m, 2H) 1.27-1.45 (m, 3H). MS (ESI+) m/z 633 (M+Na)$^+$.

Example 122

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N'-methyl-N'-phenylpropanehydrazide Example 122 was prepared according to the procedure used for the preparation of Example 99b, substituting 1-methyl-1-phenylhydrazine for ammonia. Purification by reverse phase HPLC (C18, CH$_3$CN/water (10 mM ammonium acetate), 30-100%) afforded the title compound (20 mg, 53%). $^1$H NMR (500 MHz, DMSO-d$_6$) δ 11.95 (d, J=1.83 Hz, 1H) 9.95 (s, 1H) 7.85 (d, J=1.83 Hz, 1H) 7.70 (s, 1H) 7.25 (dd, J=8.24, 1.83 Hz, 1H) 7.13-7.19 (m, 3H) 6.97-7.12 (m, 3H) 6.83-6.92 (m, 1H) 6.64-6.75 (m, 3H) 5.05 (dd, J=8.85, 6.10 Hz, 1H) 4.39-4.56 (m, 2H) 3.65 (s, 3H) 3.05 (s, 3H) 2.93 (s, 3H) 2.22-2.32 (m, 2H) 1.92-2.01 (m, 1H) 1.43-1.54 (m, 1H). MS (ESI+) m/z 654 (M+Na)$^+$.

Example 123

N-benzyl-3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanamide Example 123 was prepared according to the procedure used for the preparation of Example 99b, substituting phenylmethanamine for ammonia. Purification by reverse phase HPLC (C18, CH$_3$CN/water (10 mM ammonium acetate), 30-100%) afforded the title compound (26 mg, 70%). $^1$H NMR (400 MHz, DMSO-d$_6$) δ 11.91 (d, J=2.14 Hz, 1H) 8.39 (t, J=5.95 Hz, 1H) 7.83 (d, J=1.83 Hz, 1H) 7.68 (s, 1H) 7.27-7.33 (m, 2H) 7.19-7.25 (m, 4H) 7.02-7.11 (m, 3H) 6.97 (d, J=7.93 Hz, 1H) 6.81-6.92 (m, 1H) 5.02 (dd, J=9.00, 5.95 Hz, 1H) 4.38-4.57 (m, 2H) 4.25 (d, J=5.80 Hz, 2H) 3.64 (s, 3H) 2.93 (s, 3H) 2.25 (t, J=7.48 Hz, 2H) 1.91-2.02 (m, 1H) 1.35-1.56 (m, 1H). MS (ESI+) m/z 639 (M+Na)$^+$.

Example 124

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-(1,1-dioxidotetrahydrothiophen-3-yl)propanamide Example 124 was prepared according to the procedure used for the preparation of Example 99b, substituting 3-aminotetrahydrothiophene 1,1-dioxide for ammonia. Purification by reverse phase HPLC (C18, CH$_3$CN/water (10 mM ammonium acetate), 20-100%) afforded the title compound (27 mg, 70%). $^1$H NMR (400 MHz, DMSO-d$_6$) δ 11.92 (s, 1H) 8.31 (dd, J=6.71, 3.66 Hz, 1H) 7.83 (s, 1H) 7.68 (s, 1H) 7.22 (dd, J=8.24, 1.83 Hz, 1H) 7.01-7.13 (m, 3H) 6.88-6.98 (m, 2H) 4.95-5.05 (m, 1H) 4.38-4.55 (m, 3H) 3.64 (s, 3H) 3.36-3.44 (m, 1H) 3.23-3.29 (m, 1H) 3.06-3.18 (m, 1H) 2.93 (s, 3H) 2.78-2.92 (m, 1H) 2.27-2.40 (m, 1H) 2.14-2.24 (m, 2H) 1.87-2.05 (m, 2H) 1.37-1.51 (m, 1H). MS (ESI+) m/z 667 (M+Na)$^+$.

Example 125 tert-butyl 4-(3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoyl)piperazine-1-carboxylate Example 125 was prepared according to the procedure used for the preparation of Example 99b, substituting tert-butyl piperazine-1-carboxylate for ammonia. Purification by reverse phase HPLC (C18, CH$_3$CN/water (10 mM ammonium acetate), 30-100%) afforded the title compound (46 mg, 74%). $^1$H NMR (400 MHz, DMSO-d$_6$) δ 11.89 (d, J=1.53 Hz, 1H) 7.83 (d, J=1.83 Hz, 1H) 7.68 (s, 1H) 7.23 (dd, J=8.24, 1.53 Hz, 1H) 7.11-7.19 (m, 2H) 7.03-7.11 (m, 1H) 6.98 (d, J=8.24 Hz, 1H) 6.87-6.95 (m, 1H) 5.08 (t, J=7.63 Hz, 1H) 4.39-4.56 (m, 2H) 3.64 (s, 3H) 3.38-3.44 (m, 2H) 3.24-3.30 (m, 6H) 2.93 (s, 3H) 2.32-2.46 (m, 2H) 1.84-1.98 (m, 1H) 1.43-1.52 (m, 1H) 1.40 (s, 9H). MS (ESI+) m/z 696 (M+H)$^+$.

Example 126 tert-butyl 4-(3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanamido)piperidine-1-carboxylate Example 126 was prepared according to the procedure used for the preparation of Example 99b, substituting tert-butyl 4-aminopiperidine-1-carboxylate for ammonia. Purification by reverse phase HPLC (C18, CH$_3$CN/water (10 mM ammonium acetate), 30-100%) afforded the title compound (48 mg, 75%). NMR (400 MHz, DMSO-d$_6$) δ 11.91 (d, J=2.44 Hz, 1H) 7.80-7.85 (m, 2H) 7.68 (s, 1H) 7.22 (dd, J=8.24, 1.83 Hz, 1H) 7.02-7.13 (m, 3H) 6.88-6.98 (m, 2H) 5.00 (dd, J=9.16, 6.10 Hz, 1H) 4.34-4.55 (m, 2H) 3.76-3.86 (m, 2H) 3.68-3.75 (m, 1H) 3.64 (s, 3H) 2.93 (s, 3H) 2.73-2.88 (m, 2H) 2.15 (t, J=7.02 Hz, 2H) 1.88-1.99 (m, 1H) 1.61-1.73 (m, 2H) 1.34-1.48 (m, 10H) 1.11-1.27 (m, 2H). MS (ESI+) m/z 732 (M+Na)$^+$.

Example 127

4-(4-chlorophenyl)-N-ethyl-10-methyl-11-oxo-3,4,10,11-tetrahydro-1H-1,4,10-triazadibenzo[cd,f]azulene-2-carboxamide

Example 127a 2-bromo-N-(4-chlorophenyl)aniline

Example 127a was prepared according to the procedure used for the preparation of Example 58h, substituting 2-bromoaniline for Example 58g, to provide the title compound.

Example 127b ethyl 1-benzyl-4-(2-((4-chlorophenyl)amino)phenyl)-6-methyl-7-oxo-6,7-dihydro-1H-pyrrolo[2,3-c]pyridine-2-carboxylate Example 127b was prepared according to the procedure used for the preparation of Example 5d, substituting Example 127a for Example 5c, and Example 58f for Example 1f, respectively, to provide the title compound.

Example 127c ethyl 4-(2-((4-chlorophenyl)amino)phenyl)-6-methyl-7-oxo-6,7-dihydro-1H-pyrrolo[2,3-c]pyridine-2-carboxylate Example 127c was prepared according to the procedure used for the preparation of Example 58j, substituting Example 127b for Example 58i, to provide the title compound.

Example 127d ethyl 4-(4-chlorophenyl)-10-methyl-11-oxo-3,4,10,11-tetrahydro-1H-1,4,10-triazadibenzo[cd,f]azulene-2-carboxylate Example 127d was prepared according to the procedure used for the preparation of Example 58k, substituting Example 127c for Example 58j, to provide the title compound.

Example 127e 4-(4-chlorophenyl)-N-ethyl-10-methyl-11-oxo-3,4,10,11-tetrahydro-1H-1,4,10-triazadibenzo[cd,f]azulene-2-carboxamide A mixture of Example 127d (150 mg, 0.346 mmol) and ethanamine (25% in ethanol wt/wt) (5 mL, 0.832 mmol) was sealed and heated at 78° C. for 2 days. The reaction mixture was cooled to ambient temperature and concentrated. The residue was purified by reverse phase HPLC (C18, CH$_3$CN/water (0.1% TFA), 0-100% gradient) to give the title compound (18 mg, 0.042 mmol, 12.03% yield) as pale solid. $^1$H NMR (400 MHz, CDCl$_3$): δ 12.37 (s, 1H), 8.50 (s, 1H), 7.69 (d, J=4.2 Hz, 1H), 7.43 (m, 3H), 7.27 (m, 1H), 6.92 (d, J=8.8 Hz, 2H), 6.46 (d, J=8.3 Hz, 2H), 6.13 (d, J=15.3 Hz, 1H), 4.53 (m, 1H), 3.76 (s, 3H), 3.58 (m, 2H), 1.32 (m, 3H). MS (ESI+) m/z 433.0 (M+H)$^+$

Example 128

6-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)hexyl acetate 7-oxoheptyl acetate (0.155 g, 0.902 mmol) and Example 12d (0.1 g, 0.225 mmol) were combined in tetrahydrofuran (2.255 mL) under nitrogen at 5° C., and treated drop-wise with 1 M titanium(IV) chloride in dichloromethane (0.676 mL, 0.676 mmol) to afford a deep red reaction mixture. The reaction mixture was stirred at ambient temperature for 18 hours and partitioned between ethyl acetate and water. The organic layer was washed with saturated aqueous sodium chloride, dried over anhydrous sodium sulfate, filtered and concentrated. Purification by chromatography (silica gel, 0.5-4% methanol in dichloromethane) afforded the title compound (0.108 g, 80%). $^1$H NMR (500 MHz, DMSO-$d_6$) δ 11.85 (s, 1H), 7.84 (s, 1H), 7.67 (s, 1H), 7.23 (d, J=7.93 Hz, 1H), 7.13 (s, 1H), 7.04-7.10 (m, 1H), 6.98 (d, J=7.93 Hz, 1H), 6.84 (d, J=5.49 Hz, 2H), 5.00 (t, J=6.56 Hz, 1H), 4.40-4.56 (m, 2H), 3.92 (t, J=6.56 Hz, 2H) 3.64 (s, 3H), 2.92 (s, 3H), 1.96 (s, 3H), 1.09-1.67 (m, 10H). MS (ESI+) m/z 598 (M+H)$^+$.

Example 129

3-(aminomethyl)-4-(2,4-difluorophenyl)-10-methyl-7-((methylsulfonyl)methyl)-3,4-dihydro-1H-1,4,10-triazadibenzo[cd,f]azulen-11(10H)-one Example 117 (0.45 g, 0.732 mmol) and hydrazine hydrate (0.733 g, 14.64 mmol) were combined in ethanol (14.64 mL) and stirred at reflux for 2 hours. The solution was allowed to cool to ambient temperature and the resulting white solid was removed by filtration. The filtrate was concentrated to a residue. Purification of the residue by reverse phase HPLC (C18, CH$_3$CN/10 mM ammonium acetate in water, 10-100% gradient) afforded the title compound (0.280 mg, 80%). $^1$H NMR (500 MHz, DMSO-$d_6$) δ 11.84 (s, 1H), 7.82 (d, J=1.83 Hz, 1H), 7.67 (s, 1H), 7.24-7.30 (m, 1H), 7.22 (dd, J=8.09, 1.98 Hz, 1H), 7.15 (s, 1H), 7.00-7.06 (m, 2H), 6.89-6.95 (m, 1H), 5.02 (dd, J=8.24, 6.41 Hz, 1H), 4.41-4.55 (m, 2H), 3.64 (s, 3H), 3.57 (s, 1H), 2.94 (s, 3H), 2.69 (dd, J=12.97, 8.70 Hz, 1H), 2.45 (dd, J=12.97, 6.26 Hz, 1H). MS (ESI+) m/z 485 (M+H)$^+$.

Example 130

N-((((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)amino)(dimethylamino)methylene)-N-methylmethanaminium Example 129 (0.03 g, 0.062 mmol), N-((((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)amino)(dimethylamino)methylene)-N-methylmethanaminium (HCTU, 0.033 g, 0.080 mmol) and N-ethyl-N-isopropylpropan-2-amine (0.032 mL, 0.186 mmol) were combined in DMF (0.619 mL). To the mixture was added acetic acid (10.63 µL, 0.186 mmol) and the mixture was stirred for 1 hour and partitioned between ethyl acetate and water. The organic layer was washed with saturated aqueous sodium chloride, dried over anhydrous sodium sulfate, filtered and concentrated. Purification by reverse phase HPLC (C18, CH$_3$CN/0.1% TFA in water, 10-100% gradient) afforded the title compound as a trifluoroacetate salt (0.03 g, 78%). $^1$H NMR (500 MHz, PYRIDINE-$d_6$) δ 13.11 (s, 1H), 9.84 (s, 1H), 8.08 (d, J=1.47 Hz, 1H), 7.61 (s, 1H), 7.56 (s, 1H), 7.43-7.49 (m, 2H), 7.20 (d, J=8.07 Hz, 1H), 6.82-6.89 (m, 1H), 6.74-6.79 (m, 1H), 5.95-6.00 (m, 1H), 4.65 (s, 2H), 3.73 (dd, J=13.48, 8.71 Hz, 1H), 3.61 (s, 3H), 3.57 (dd, J=13.48, 6.33 Hz, 1H), 3.08 (s, 3H), 2.77 (s, 12H). MS (ESI+) m/z 583 (M)$^+$.

Example 131

4-(2,4-difluorophenyl)-10-methyl-7-((methylsulfonyl)methyl)-3-(3-oxo-3-(piperazin-1-yl)propyl)-3,4-dihydro-1H-1,4,10-triazadibenzo[cd,f]azulen-11(10H)-one To a mixture of Example 125 (40 mg, 0.057 mmol) in dichloromethane (1.5 mL) was added trifluoroacetic acid (0.50 mL, 6.5 mmol). The reaction mixture was stirred at ambient temperature for 30 minutes and concentrated. To the residue was added water, the pH was adjusted to 7 by addition of saturated aqueous sodium bicarbonate, and the mixture was sonicated for 5 minutes, filtered, washed with water, and dried to provide the title compound (18 mg, 53%). $^1$H NMR (500 MHz, DMSO-$d_6$) δ 11.89 (s, 1H) 7.83 (d, J=1.83 Hz, 1H) 7.68 (s, 1H) 7.22 (dd, J=8.24, 1.83 Hz, 1H) 7.03-7.18 (m, 3H) 6.97 (d, J=7.93 Hz, 1H) 6.87-6.94 (m, 1H) 5.08 (t, J=7.63 Hz, 1H) 4.39-4.60 (m, 2H) 3.64 (s, 3H) 3.18-3.25 (m, 2H) 2.94 (s, 3H) 2.55-2.61 (m, 4H) 2.27-2.46 (m, 3H) 1.83-1.94 (m, 1H) 1.38-1.57 (m, 1H). MS (ESI+) m/z 596 (M+H)$^+$.

Example 132

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-(piperidin-4-yl)propanamide To a mixture of Example 126 (42 mg, 0.059 mmol) in dichloromethane (1.5 mL) was added trifluoroacetic acid (0.50 mL, 6.5 mmol). The reaction mixture was stirred at ambient temperature for 30 minutes and concentrated. The residue was purified by reverse phase HPLC (C18, CH$_3$CN/water (10 mM ammonium acetate), 20-100% gradient) to provide the title compound (15 mg, 42%). $^1$H NMR (400 MHz, DMSO-$d_6$) δ 7.77-7.86 (m, 2H) 7.68 (s, 1H) 7.22 (dd, J=8.24, 1.83 Hz, 1H) 7.01-7.13 (m, 3H) 6.85-6.99 (m, 2H) 5.00 (dd, J=9.16, 6.10 Hz, 1H) 4.38-4.56 (m, 2H) 3.57-3.67 (m, 4H) 3.39-3.52 (m, 1H) 2.90-2.99 (m, 5H) 2.51-2.58 (m, 2H) 2.15 (t, J=7.17 Hz, 2H) 1.89-1.97 (m, 1H) 1.62-1.72 (m, 2H) 1.36-1.46 (m, 1H) 1.20-1.35 (m, 2H). MS (ESI+) m/z 610 (M+H)$^+$.

Example 133

4-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)butane-1,2-diyl diacetate 5-Oxopentane-1,2-diyl diacetate (0.182 g, 0.902 mmol) and Example 12d (0.1 g, 0.225 mmol) were combined in tetrahydrofuran (2.2 mL) under nitrogen at 5° C., and treated dropwise with 1 M titanium(IV) chloride in toluene (0.676 mL, 0.676 mmol). The reaction mixture was stirred at ambient temperature for 18 hours and partitioned between ethyl acetate and water. The organic layer was washed with saturated aqueous sodium chloride, dried over anhydrous sodium sulfate, filtered and concentrated. Purification by reverse phase HPLC (C18, CH$_3$CN/0.1% TFA in water, 10-100% gradient) afforded the title compound (0.038 g, 26%). $^1$H NMR (400 MHz, DMSO-d$_6$) δ 11.87 (s, 1H), 7.83-7.87 (m, 1H), 7.69 (s, 1H), 7.22-7.28 (m, 1H), 6.96-7.18 (m, 3H), 6.69-6.87 (m, 2H), 5.01 (t, J=6.71 Hz, 1H), 4.78-4.92 (m, 1H), 4.40-4.56 (m, 2H), 3.85-4.08 (m, 2H), 3.64 (s, 3H), 2.92 (s, 3H), 1.95 (s, 3H), 1.88 (s, 3H), 1.30-1.79 (m, 4H). MS (ESI$^+$) m/z 628 (M+H)$^+$.

Example 134 methyl 5-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)pentanoate Methyl 6-oxohexanoate (0.130 g, 0.902 mmol) and Example 12d (0.1 g, 0.225 mmol) were combined in tetrahydrofuran (2.3 mL) under nitrogen at 5° C., and treated dropwise with 1 M titanium(IV) chloride (0.676 mL, 0.676 mmol) in dichloromethane. The reaction mixture was stirred at ambient temperature for 18 hours and partitioned between ethyl acetate and water. The organic layer was washed with saturated aqueous sodium chloride, dried over anhydrous sodium sulfate, filtered and concentrated. Purification by reverse phase HPLC (C18, CH$_3$CN/0.1% TFA in water, 10-100% gradient) afforded the title compound (0.069 g, 54%). NMR (400 MHz, DMSO-d$_6$) δ 11.84 (d, J=1.83 Hz, 1H), 7.85 (d, J=1.53 Hz, 1H), 7.68 (s, 1H), 7.24 (dd, J=8.24, 1.83 Hz, 1H), 7.13 (d, J=2.44 Hz, 1H), 7.03-7.11 (m, 1H), 6.98 (d, J=8.24 Hz, 1H), 6.76-6.88 (m, 2H), 4.99 (t, J=7.32 Hz, 1H), 4.42-4.55 (m, 2H), 3.64 (s, 3H), 3.54 (s, 3H), 2.92 (s, 3H), 2.19 (t, J=6.71 Hz, 2H), 1.21-1.66 (m, 6H). MS (ESI$^+$) m/z 570 (M+H)$^+$.

Example 135 tert-butyl (2-(((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)amino)-2-oxoethyl)carbamate 2-((Tert-butoxycarbonyl)amino)acetic acid (0.022 g, 0.124 mmol), N-ethyl-N-isopropylpropan-2-amine (0.032 mL, 0.186 mmol) and 2-(6-chloro-1H-benzo[d][1,2,3]triazol-1-yl)-1,1,3,3-tetramethylisouronium hexafluorophosphate(V) (HCTU, 0.028 g, 0.068 mmol) were combined in N,N-dimethylformamide (0.619 mL) and stirred at ambient temperature for 15 minutes. To this solution was added dropwise a solution of Example 129 (0.03 g, 0.062 mmol) dissolved in N,N-dimethylformamide (0.619 mL). The reaction mixture was stirred for 2 hours at ambient temperature and partitioned between ethyl acetate and water. The organic layer was washed with saturated aqueous sodium chloride, dried over anhydrous sodium sulfate, filtered and concentrated. Purification by reverse phase HPLC (C18, CH$_3$CN/10 mM ammonium acetate in water, 10-100% gradient) afforded the title compound (0.02 g, 50%). $^1$H NMR (400 MHz, DMSO-d$_6$) δ 11.93 (s, 1H), 7.82 (m, 1H), 7.81 (d, J=1.83 Hz, 1H), 7.69 (s, 1H), 7.33-7.46 (m, 1H), 7.20 (dd, J=8.24, 1.83 Hz, 1H), 7.12 (s, 1H), 6.93-7.09 (m, 4H), 5.20 (dd, J=8.39, 6.26 Hz, 1H), 4.39-4.53 (m, 2H), 3.65 (s, 3H), 3.53 (d, J=6.10 Hz, 2H), 2.92 (s, 3H), 2.82-2.91 (m, 2H), 2.48-2.51 (m, 9H). MS (ESI$^+$) m/z 640 (M+H)$^+$.

Example 136

4-(2,4-difluorophenyl)-3-(6-hydroxyhexyl)-10-methyl-7-((methylsulfonyl)methyl)-3,4-dihydro-1H-1,4,10-triazadibenzo[cd,f]azulen-11(10H)-one The product from Example 128 (0.08 g, 0.134 mmol) and lithium hydroxide monohydrate (0.056 g, 1.339 mmol) were combined in tetrahydrofuran (1.785 mL)/water (0.892 mL) and the reaction mixture was stirred for 2 hours at 50° C. The reaction mixture was cooled to ambient temperature and partitioned between ethyl acetate and water and the pH was adjusted to 7 by careful addition of aqueous 1 M HCl. The organic layer was washed with saturated aqueous sodium chloride, dried over anhydrous sodium sulfate, filtered and concentrated. Purification by reverse phase HPLC (C18, CH$_3$CN/0.1% TFA in water, 10-100% gradient) afforded the title compound (0.05 g, 67%). $^1$H NMR (400 MHz, DMSO-d$_6$) δ 11.83 (s, 1H), 7.84 (d, J=1.83 Hz, 1H), 7.67 (s, 1H), 7.23 (dd, J=8.09, 1.98 Hz, 1H), 7.12 (d, J=2.44 Hz, 1H), 7.03-7.10 (m, 1H), 6.98 (d, J=8.24 Hz, 1H), 6.78-6.89 (m, 2H), 5.00 (t, J=7.17 Hz, 1H), 4.41-4.54 (m, 2H), 4.32 (t, J=6.56 Hz, 1H), 3.64 (s, 3H), 3.31 (t, J=6.56 Hz, 2H), 2.92 (s, 3H), 1.20-1.67 (m, 10H). MS (ESI+) m/z 556 (M+H)$^+$.

Example 137

N-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)benzamide The product from Example 129 (0.03 g, 0.062 mmol), N-ethyl-N-isopropylpropan-2-amine (0.216 mL, 1.238 mmol) and benzoyl chloride (0.036 mL, 0.310 mmol) were combined in N,N-dimethylformamide (1.238 mL) and heated at 50° C. for 2 hours. The reaction mixture was cooled to ambient temperature and partitioned between ethyl acetate and water. The organic layer was washed with saturated aqueous sodium chloride, dried over anhydrous sodium sulfate, filtered and concentrated. Purification by reverse phase HPLC (C18, CH$_3$CN/0.1% TFA in water, 10-100% gradient) afforded the title compound (0.023 g, 63%). $^1$H NMR (400 MHz, DMSO-d$_6$) δ 11.86 (d, J=2.44 Hz, 1H), 8.55 (t, J=5.49 Hz, 1H), 7.84 (d, J=1.83 Hz, 1H), 7.81 (s, 1H), 7.79 (d, J=1.53 Hz, 1H), 7.72 (s, 1H), 7.44-7.56 (m, 4H), 7.21 (dd, J=8.24, 1.83 Hz, 1H), 7.02-7.12 (m, 2H), 6.99 (d, J=2.75 Hz, 1H), 6.94 (d, J=8.24 Hz, 1H), 5.42 (dd, J=9.61, 5.34 Hz, 1H), 4.40-4.55 (m, 2H), 3.66 (s, 3H), 2.96-3.06 (m, 2H), 2.94 (s, 3H). MS (ESI+) m/z 589 (M+H)$^+$.

Example 138

1-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)-3-phenylurea The product from Example 129 (0.03 g, 0.062 mmol), N-ethyl-N-isopropylpropan-2-amine (0.054 mL, 0.310 mmol) and phenyl isocyanate (6.77 μL, 0.062 mmol) were combined in tetrahydrofuran (1.238 mL) and stirred for 30 minutes at ambient temperature. The reaction mixture was concentrated and the residue was purified by reverse phase HPLC (C18, CH$_3$CN/0.1% TFA in water, 10-100% gradient) to afford the title compound (0.021 g, 56%). $^1$H NMR (400 MHz, DMSO-d$_6$) δ 11.96 (d, J=2.44 Hz, 1H), 8.71 (s, 1H), 7.85 (d, J=1.83 Hz, 1H), 7.72 (s, 1H), 7.41 (d, J=7.63 Hz, 2H), 7.17-7.28 (m, 4H), 7.15 (d, J=2.75 Hz, 1H), 7.03-7.11 (m, 2H), 6.88-6.98 (m, 2H), 6.12 (t, J=5.65 Hz, 1H), 5.25 (t, J=7.48 Hz, 1H), 4.42-4.56 (m, 2H), 3.65 (s, 3H), 3.22-3.31 (m, 1H), 3.00-3.08 (m, 1H), 2.94 (s, 3H). MS (ESI+) m/z 602 (M+H)$^+$.

Example 139

2-amino-N-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)acetamide The product from Example 135 (0.01 g, 0.016 mmol) in a mixture of dichloromethane (2 mL)/TFA (1.0 mL) was stirred at ambient temperature for 1 hour, concentrated and azeotroped three times with toluene to afford the title compound as the TFA salt (0.01 g, 98%). 1H NMR (400 MHz, DMSO-d$_6$) δ 12.03 (d, J=2.44 Hz, 1H), 8.45 (t, J=5.80 Hz, 1H), 8.00 (s, 2H), 8.00 (s, 1H), 7.83 (d, J=1.83 Hz, 1H), 7.72 (s, 1H), 6.92-7.40 (m, 5H) 5.18 (dd, J=9.16, 5.49 Hz, 1H), 4.40-4.55 (m, 2H), 3.65 (s, 3H), 3.43-3.67 (m, 4H), 2.94 (s, 3H). MS (ESI+) m/z 542 (M+H)$^+$.

Example 140

4-(2,4-difluorophenyl)-3-(3,4-dihydroxybutyl)-10-methyl-7-((methylsulfonyl)methyl)-3,4-dihydro-1H-1,4,10-triazadibenzo[cd,f]azulen-11(10H)-one The product from Example 133 (0.038 g, 0.061 mmol) and lithium hydroxide (0.029 g, 1.211 mmol) were combined in tetrahydrofuran (1.614 mL)/water (0.807 mL) and stirred for 2 hours at 50° C. The reaction mixture was cooled to ambient temperature and partitioned between ethyl acetate and water and the pH was adjusted to 7 by careful addition of aqueous 1 M HCl. The organic layer was washed with saturated aqueous sodium chloride, dried over anhydrous sodium sulfate, filtered and concentrated to afford the title compound (0.028 g, 85%). $^1$H NMR (500 MHz, DMSO-d$_6$) δ 11.85 (s, 1H), 7.83 (d, J=1.83 Hz, 1H), 7.67 (s, 1H), 7.19-7.25 (m, 1H), 7.11 (dd, J=5.04, 2.59 Hz, 1H), 7.03-7.09 (m, 1H), 6.84-6.99 (m, 3H), 4.97-5.04 (m, 1H), 4.43-4.53 (m, 2H), 4.34-4.41 (m, J=13.28, 1.98 Hz, 2H), 3.64 (s, 3H), 3.10-3.30 (m, 3H), 2.92 (s, 3H), 1.19-1.86 (m, 4H). MS (ESI+) m/z 544 (M+H)$^+$.

Example 141

4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide

Example 141a ethyl 4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxylate Example 141a was prepared according to the procedure used for the preparation of Example 82, substituting ethyl glyoxalate for methyl 4-oxobutanoate, to provide the title compound as a white solid.

Example 141b 4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxylic acid A 250 mL round-bottomed flask was charged with Example 141a (0.6446 g, 1.222 mmol), dioxane (9.16 mL) and water (3.05 mL) to give a yellow solution. Lithium hydroxide hydrate (0.256 g, 6.11 mmol) was added. The reaction mixture was stirred at ambient temperature for 72 hours. The reaction mixture was quenched with 1N HCl. The resulting suspension was stirred for 15 minutes, and filtered. The solid was rinsed with water, dried overnight at ambient temperature, and then dried in a 60° C. vacuum oven for 72 hours to provide the title compounds as a yellow solid (0.5521 g, 90% yield).

Example 141c 4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide A 250 mL round-bottomed flask was charged with Example 141b (0.0473 g, 0.095 mmol) and dichloromethane (1.894 mL) to give a tan solution. Oxalyl dichloride (0.021 mL, 0.237 mmol) and N,N-dimethylformamide (0.733 μL, 9.47 μmol) were added. The reaction mixture was stirred at ambient temperature for 2 hours and then cooled to 0° C. Ammonium hydroxide (0.186 mL, 4.73 mmol) was added. The reaction mixture was stirred at 0° C. for 15 minutes, and stirred at ambient temperature overnight. The reaction mixture was partitioned between water and ethyl acetate. The organic layer was washed with saturated aqueous sodium chloride, dried over anhydrous magnesium sulfate, filtered, and concentrated. The reaction mixture was purified by HPLC (Phenomenex Luna C8(2) 5 μm 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). Samples were injected in 1.5 mL DMSO:methanol (1:1).)) to provide the title compound as a white solid (7.0 mg, 15% yield). $^1$H NMR (400 MHz, DMSO-d$_6$) δ 11.96-12.01 (m, 1H), 7.75 (d, J=2.0 Hz, 1H), 7.66 (s, 1H), 7.49-7.59 (m, 1H), 7.30 (d, J=2.7 Hz, 1H), 7.10-7.16 (m, 2H), 6.93-7.11 (m, 3H), 6.89 (d, J=8.2 Hz, 1H), 6.68 (bs, 1H), 5.75 (s, 1H), 4.36-4.50 (m, 2H), 2.91 (s, 3H). MS (ESI+) m/z 499.1 (M+H)$^+$.

Example 142

4-(2,4-difluorophenyl)-3-(3-hydroxypropyl)-10-methyl-7-((methylsulfonyl)methyl)-3,4-dihydro-1H-1,4,10-triazadibenzo[cd,f]azulen-11(10H)-one To a solution of Example 82 (542 mg, 1.00 mmol) in tetrahydrofuran (10 mL) was added 1.0 M lithium aluminum hydride in tetrahydrofuran (1.00 mL, 1.00 mmol) dropwise at 0° C. The reaction mixture was stirred at ambient temperature for 2 hours, and quenched by the addition of water (0.04 mL), 15% aqueous sodium hydroxide (0.04 mL) and water (0.12 mL). The resulting mixture was stirred for 20 minutes, diluted with ethyl acetate, filtered through Celite, and concentrated. The residue was triturated with dichloromethane to provide the title compound (413 mg, 80%). $^1$H NMR (500 MHz, DMSO-$d_6$) δ 11.86 (s, 1H), 7.83 (d, J=1.9 Hz, 1H), 7.67 (s, 1H), 7.22 (dd, J=8.2, 1.9 Hz, 1H), 7.13 (s, 1H), 7.11-7.05 (m, 1H), 6.96 (d, J=8.1 Hz, 1H), 6.93-6.84 (m, 2H), 5.05-4.98 (m, 1H), 4.53-4.42 (m, 2H), 4.36 (s, br, 1H), 3.64 (s, 3H), 2.93 (s, 3H), 1.71-1.62 (m, 1H), 1.61-1.54 (m, 1H), 1.50-1.42 (m, 1H), 1.34-1.25 (m, 1H). MS (ESI+) m/z 514 (M+H)$^+$.

Example 143

4-(2,4-difluorophenyl)-10-methyl-7-((methylsulfonyl)methyl)-3-(3-phenoxypropyl)-3,4-dihydro-1H-1,4,10-triazadibenzo[cd,f]azulen-11(10H)-one Example 142 (31 mg, 0.060 mmol), phenol (8.5 mg, 0.090 mmol) and triphenylphosphine (23.6 mg, 0.0900 mmol) were combined in tetrahydrofuran (0.1 mL) and sonicated for 5 minutes. To this reaction mixture was added diisopropyl azodicarboxylate (0.017 mL, 0.090 mmol) and the mixture was sonicated for 6 hours. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 2-4% methanol in dichloromethane). The resulting material from flash chromatography was triturated with 10% dichloromethane in heptanes to provide the title compound (18 mg, 51%). $^1$H NMR (500 MHz, DMSO-$d_6$) δ 11.89 (s, 1H), 7.86 (s, 1H), 7.69 (s, 1H), 7.30-7.15 (m, 4H), 7.12-7.04 (m, 1H), 6.99 (d, J=7.9 Hz, 1H), 6.93-6.77 (m, 5H), 5.13-5.05 (m, 1H), 4.54-4.42 (m, 2H), 3.89 (s, br, 2H), 3.64 (s, 3H), 2.92 (s, 3H), 1.95-1.85 (m, 1H), 1.84-1.71 (m, 2H), 1.49-1.40 (m, 1H). MS (ESI+) m/z 590 (M+H)$^+$.

Example 144

(S)-4-(2,4-difluorophenyl)-10-methyl-7-((methylsulfonyl)methyl)-3-(3-phenoxypropyl)-3,4-dihydro-1H-1,4,10-triazadibenzo[cd,f]azulen-11(10H)-one The product from Example 143 was purified by chiral chromatography on a Chiralpak IB column, eluting with a 4:6 mixture of methanol/carbon dioxide. The fractions containing the first eluted enantiomer were collected and concentrated. The compound was randomly assigned as the (S)-enantiomer. $^1$H NMR (400 MHz, DMSO-$d_6$) δ 11.88 (s, 1H), 7.86 (d, J=1.7 Hz, 1H), 7.69 (s, 1H), 7.28-7.20 (m, 3H), 7.17 (s, 1H), 7.11-7.04 (m, 1H), 6.99 (d, J=8.1 Hz, 1H), 6.92-6.82 (m, 5H), 5.09 (t, J=7.1 Hz, 1H), 4.55-4.42 (m, 2H), 3.89 (t, J=6.0 Hz, 2H), 3.65 (s, 3H), 2.92 (s, 3H), 1.97-1.85 (m, 1H), 1.83-1.72 (m, 2H), 1.49-1.38 (m, 1H). MS (ESI+) m/z 590 (M+H)$^+$.

Example 145

(R)-4-(2,4-difluorophenyl)-10-methyl-7-((methylsulfonyl)methyl)-3-(3-phenoxypropyl)-3,4-dihydro-1H-1,4,10-triazadibenzo[cd,f]azulen-11(10H)-one The product from Example 143 was purified by chiral chromatography on a Chiralpak IB column eluting with a 4:6 mixture of methanol/carbon dioxide. The fractions containing the second eluted enantiomer were collected and concentrated. The compound was randomly assigned as the (R)-enantiomer. $^1$H NMR (400 MHz, DMSO-$d_6$) δ 11.88 (s, 1H), 7.86 (d, J=1.5 Hz, 1H), 7.69 (s, 1H), 7.28-7.20 (m, 3H), 7.17 (s, 1H), 7.11-7.04 (m, 1H), 6.99 (d, J=8.1 Hz, 1H), 6.92-6.80 (m, 5H), 5.09 (t, J=7.1 Hz, 1H), 4.55-4.42 (m, 2H), 3.89 (t, J=6.0 Hz, 2H), 3.64 (s, 3H), 2.92 (s, 3H), 1.95-1.84 (m, 1H), 1.84-1.72 (m, 2H), 1.49-1.39 (m, 1H). MS (ESI+) m/z 590 (M+H)$^+$.

Example 146

4-(4-chlorophenyl)-10-methyl-2-((4-methylpiperazin-1-yl)methyl)-3,4-dihydro-1H-1,4,10-triazadibenzo[cd,f]azulen-11(10H)-one Example 146a 4-(4-chlorophenyl)-10-methyl-11-oxo-3,4,10,11-tetrahydro-1H-1,4,10-triazadibenzo[cd,f]azulene-2-carboxylic acid Example 146a was prepared according to the procedure used for the preparation of Example 58l, substituting Example 127d for Example 58k, to provide the title compound.

Example 146b 4-(4-chlorophenyl)-10-methyl-2-(4-methylpiperazine-1-carbonyl)-3,4-dihydro-1H-1,4,10-triazadibenzo[cd,f]azulen-11(10H)-one To the solution of Example 146a (0.12 g, 0.296 mmol) in anhydrous dichloromethane (5 mL) were added oxalyl chloride (0.052 mL, 0.591 mmol) and dimethylformamide (1.1 µl, 0.015 mmol) and the reaction mixture was stirred at ambient temperature for 2 hours. The reaction mixture was concentrated to dryness and then dried under vacuum for 2 hours. The residue was redissolved in dichloromethane (5 mL) and was treated with 1-methylpiperazine (0.118 g, 1.183 mmol), and the reaction mixture was stirred at ambient temperature overnight. The reaction mixture was concentrated to give the crude title compound, which was taken into next reaction without further purification.

Example 146c 4-(4-chlorophenyl)-10-methyl-2-((4-methylpiperazin-1-yl)methyl)-3,4-dihydro-1H-1,4,10-triazadibenzo[cd,f]azulen-11(10H)-one To a solution of Example 146b (100 mg, 0.133 mmol) in anhydrous tetrahydrofuran (5 mL) were added BH3.tetrahydrofuran (1.332 mL, 1.332 mmol) and the reaction mixture was stirred at 65° C. for 3 hours. After cooling, the reaction mixture was quenched with ethanol (1 mL) and then concentrated. 3N HCl (2 mL) was added and the mixture was heated at 78° C. for 4 hours. The reaction mixture was cooled to ambient temperature and 5 N NaOH (2 mL) was added. The mixture was then extracted with dichlormethane (20 mL×3). The combined organic layers were dried under anhydrous sodium sulfate, filtered, and concentrated. The residue was purified by reverse phase HPLC (C18, CH$_3$CN/water (0.01N ammonium carbonate), 25-55% gradient) to give the title compound (22 mg, 0.044 mmol, 33% yield) as white solid. $^1$H NMR (400 MHz, CDCl$_3$) δ 12.37 (s, 1H), 8.50 (s, 1H), 7.69 (d, J=4.2 Hz, 1H), 7.43 (m, 3H), 7.27 (m, 1H), 6.92 (d, J=8.8 Hz, 2H), 6.46 (d, J=8.3 Hz, 2H), 6.13 (d, J=15.3 Hz, 1H), 4.53 (m, 1H), 3.76 (s, 3H), 3.58 (m, 2H), 1.32 (m, 3H). MS (ESI$^+$) m/z 433.0 (M+H)$^+$.

Example 147

4-(2,4-difluorophenyl)-3-(3-methoxypropyl)-10-methyl-7-((methylsulfonyl)methyl)-3,4-dihydro-1H-1,4,10-triazadibenzo[cd,f]azulen-11(10H)-one

Example 147a 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propyl methanesulfonate Example 142 (103 mg, 0.200 mmol), methanesulfonyl chloride (0.023 mL, 0.30 mmol) and triethylamine (0.056 mL, 0.40 mmol) were combined in N,N-dimethylformamide (2 mL). The reaction mixture was stirred at ambient temperature for 20 hours. To this reaction mixture was added methanesulfonyl chloride (0.023 mL, 0.30 mmol) and triethylamine (0.056 mL, 0.40 mmol) and the mixture was stirred at ambient temperature for another 20 hours. The reaction mixture was partitioned with ethyl acetate and water. The organic layer was washed with saturated aqueous sodium chloride, dried with anhydrous sodium sulfate, filtered, and concentrated to provide the title compound in quantitative yield.

Example 147b 4-(2,4-difluorophenyl)-3-(3-methoxypropyl)-10-methyl-7-((methylsulfonyl)methyl)-3,4-dihydro-1H-1,4,10-triazadibenzo[cd,f]azulen-11(10H)-one Example 147a (35.5 mg, 0.0600 mmol) and 25% sodium methoxide in methanol (0.027 mL, 0.12 mmol) were combined in tetrahydrofuran (1 mL). The reaction mixture was heated at 60° C. for 2 hours, cooled, and concentrated. The residue was purified by flash chromatography (silica gel, 2-4% methanol in dichloromethane) to provide the title compound (10 mg, 32%). $^1$H NMR (400 MHz, DMSO-d$_6$) δ 11.91 (d, J=2.2 Hz, 1H), 7.90 (d, J=1.8 Hz, 1H), 7.74 (s, 1H), 7.29 (dd, J=8.2, 1.8 Hz, 1H), 7.20 (d, J=2.6 Hz, 1H), 7.17-7.10 (m, 1H), 7.03 (d, J=8.1 Hz, 1H), 6.97-6.89 (m, 2H), 5.07 (t, J=7.3 Hz, 1H), 4.59-4.48 (m, 2H), 3.70 (s, 3H), 3.29 (t, J=6.1 Hz, 2H), 3.19 (s, 3H), 2.99 (s, 3H), 1.82-1.67 (m, 2H), 1.65-1.54 (m, 1H), 1.43-1.32 (m, 1H). MS (ESI+) m/z 528 (M+H)$^+$.

Example 148

4-(2,4-difluorophenyl)-3-(3-ethoxypropyl)-10-methyl-7-((methylsulfonyl)methyl)-3,4-dihydro-1H-1,4,10-triazadibenzo[cd,f]azulen-11(10H)-one Example 148 was prepared according to the procedure used for the preparation of Example 147b, substituting 21% sodium ethoxide in ethanol for 25% sodium methoxide in methanol, to provide the title compound (16 mg, 49%). $^1$H NMR (400 MHz, DMSO-d$_6$) δ 11.86 (d, J=2.4 Hz, 1H), 7.84 (d, J=2.0 Hz, 1H), 7.68 (s, 1H), 7.23 (dd, J=8.2, 2.0 Hz, 1H), 7.14 (d, J=2.7 Hz, 1H), 7.11-7.04 (m, 1H), 6.97 (d, J=8.2 Hz, 1H), 6.90-6.84 (m, 2H), 5.08-4.97 (m, 1H), 4.55-4.43 (m, 2H), 3.64 (s, 3H), 3.34-3.25 (m, 4H), 2.93 (s, 3H), 1.72-1.60 (m, 2H), 1.58-1.48 (m, 1H), 1.38-1.25 (m, 1H), 1.03 (t, J=7.0 Hz, 3H). MS (ESI+) m/z 542 (M+H)$^+$.

Example 149

4-isobutyl-10-methyl-7-((methylsulfonyl)methyl)-3,4-dihydro-1H-1,4,10-triazadibenzo[cd,f]azulen-11(10H)-one A 4 mL vial was charged with Example 5f (20 mg, 0.058 mmol), isobutyraldehyde (8.36 mg, 0.116 mmol), acetic acid (0.100 mL, 1.747 mmol) and dichloroethane (2.0 mL). The vial was sealed and the mixture was heated at 80° C. for 1 hour. To this mixture was added silica-supported sodium-cyanoborohydride (200 mg, 0.89 mmol/g, 0.178 mmol) and the mixture was heated at 80° C. for 4 hours. Upon cooling, the reaction mixture was filtered and concentrated. The residue was purified by reverse phase HPLC (C18, CH$_3$CN/water (0.1% TFA), 0-100% gradient) to afford the title compound (16.4 mg, 71%). $^1$H NMR (500 MHz, DMSO-d$_6$) δ 11.80 (s, 1H), 7.68 (s, 1H), 7.56 (s, 1H), 7.25 (p, J=8.4 Hz, 2H), 7.18 (s, 1H), 4.43 (s, 2H), 4.15 (s, 2H), 3.59 (s, 3H), 2.91 (s, 3H), 2.76 (d, J=7.1 Hz, 2H), 1.62 (dt, J=13.4, 6.8 Hz, 1H), 0.69 (d, J=6.6 Hz, 6H). MS (ESI+) m/z 400.1 (M+H)$^+$.

Example 150

4-((1-ethylpiperidin-3-yl)methyl)-10-methyl-7-((methylsulfonyl)methyl)-3,4-dihydro-1H-1,4,10-triazadibenzo[cd,f]azulen-11(10H)-one Example 150 was prepared according to the procedure used for the preparation of Example 149, substituting 1-ethylpiperidine-3-carbaldehyde for isobutyraldehyde to provide the title compound. $^1$H NMR (500 MHz, DMSO-d$_6$) δ 11.85 (s, 1H), 7.66 (d, J=1.7 Hz, 1H), 7.53 (s, 1H), 7.24 (dt, J=17.1, 5.0 Hz, 2H), 7.15 (s, 1H), 4.43 (s, 2H), 4.08 (t, J=15.9 Hz, 2H), 3.59 (s, 3H), 3.19 (d, J=54.0 Hz, 2H), 3.06-2.66 (m, 7H), 2.63 (s, 1H), 2.35 (s, 1H), 1.95-1.35 (m, 4H), 0.93 (s, 4H). MS (ESI+) m/z 469.1 (M+H)$^+$.

Example 151

10-methyl-7-((methylsulfonyl)methyl)-4-(tetrahydro-2H-pyran-4-yl)-3,4-dihydro-1H-1,4,10-triazadibenzo[cd,f]azulen-11(10H)-one Example 151 was prepared according to the procedure used for the preparation of Example 149, substituting dihydro-2H-pyran-4(3H)-one for isobutyraldehyde to provide the title compound. $^1$H NMR (500 MHz, DMSO-d$_6$) δ 11.88 (s, 1H), 7.67 (d, J=1.9 Hz, 1H), 7.58 (s, 1H), 7.27-7.17 (m, 3H), 4.48-4.39 (s, 2H), 3.75-4.3 (m, 2H) 3.73-3.64 (m, 2H), 3.59 (s, 3H), 3.00 (dd, J=11.7, 2.3 Hz, 2H), 2.90 (s, 3H), 2.85-2.77 (m, 1H), 1.80-1.55 (m, 2H), 1.45-1.25 (m, 2H). MS (ESI+) m/z 469.1 (M+H)$^+$. MS (ESI+) m/z 428.1 (M+H)$^+$.

Example 152

4-((2,2-dimethyltetrahydro-2H-pyran-4-yl)methyl)-10-methyl-7-((methylsulfonyl)methyl)-3,4-dihydro-1H-1,4,10-triazadibenzo[cd,f]azulen-11(10H)-one Example 152 was prepared according to the procedure used for the preparation of Example 149, substituting 2,2-dimethyltetrahydro-2H-pyran-4-carbaldehyde for isobutyraldehyde to provide the title compound. $^1$H NMR (500 MHz, DMSO-d$_6$) δ 11.76 (s, 1H), 7.65 (d, J=1.8 Hz, 1H), 7.52 (s, 1H), 7.28-7.13 (m, 3H), 4.41 (s, 2H), 4.07 (s, 2H), 3.57 (d, J=16.4 Hz, 3H), 3.45 (dd, J=11.3, 4.4 Hz, 1H), 3.36 (t, J=11.2 Hz, 1H), 2.90 (s, 3H), 2.83-2.66 (m, 2H), 1.78 (s, 1H), 1.39 (dd, J=26.2, 11.8 Hz, 2H), 0.96 (d, J=6.6 Hz, 6H), 0.91-0.47 (m, 2H). MS (ESI+) m/z 470.1 (M+H)$^+$.

Example 153

4-(4-ethoxybutan-2-yl)-10-methyl-7-((methylsulfonyl)methyl)-3,4-dihydro-1H-1,4,10-triazadibenzo[cd,f]azulen-11(10H)-one Example 153 was prepared according to the procedure used for the preparation of Example 149, substituting 4-ethoxybutan-2-one for isobutyraldehyde to provide the title compound. $^1$H NMR (500 MHz, DMSO-d$_6$) δ 7.65 (s, 1H), 7.49 (s, 1H), 7.20 (d, J=18.5 Hz, 3H), 4.41 (s, 2H), 4.37-4.14 (m, 3H), 3.58 (s, 3H), 3.54-2.95 (m, 4H), 2.90 (s, 3H), 1.63 (dd, J=13.6, 6.7 Hz, 1H), 1.51-1.41 (m, 1H), 1.06 (s, 3H), 0.84 (s, 3H). MS (ESI+) m/z 444.1 (M+H)$^+$.

Example 154

N-(2-cyanoethyl)-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide A stock solution of Example 141b and diiospropylethyl amine (0.13 M and 0.38 M in N,N-dimethylacetamide, respectively, 224 µL, 0.03 mmol 3-aminopropanenitrile (1.0 equivalent) and 0.09 mmol diiospropylethyl amine (3.0 equivalents)), HATU (1-[bis(dimethylamino)methylene]-1H-1,2,3-triazolo[4,5-b]pyridinium 3-oxid hexafluorophosphate), (0.2 M in N,N-dimethylacetamide, 224 µL, 0.045 mmol, 1.5 equivalents), and 3-aminopropanenitrile (0.40 M in N,N-dimethylacetamide, 113 µL, 0.045 mmol, 1.5 equivalents) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL min$^{-1}$ (10 minute residence time). Upon exiting the reactor, the reaction mixture was loaded directly into an injection loop and purified by preperative HPLC (Phenomenex Luna C8(2) 5 µm 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). Samples were injected in 1.5 mL DMSO:methanol (1:1)) to provide the title compound (12.6 mg, 76% yield). NMR (400 MHz, DMSO-d$_6$-D$_2$O) δ 7.72 (d, J=2.0 Hz, 1H), 7.71 (s, 1H), 7.51-7.67 (m, 1H), 7.33 (s, 1H), 7.16 (dd, J=8.2, 2.0 Hz, 1H), 6.98-7.08 (m, 2H), 6.86 (d, J=8.1 Hz, 1H), 5.86 (s, 1H), 4.38-4.51 (m, 2H), 3.67 (s, 3H), 3.14 (ddd, J=13.3, 7.3, 6.0 Hz, 1H), 2.94-3.05 (m, 1H), 2.93 (s, 3H), 1.96-2.16 (m, 2H). MS (ESI+) m/z 551.7 (M+H)$^+$.

Example 155 methyl 2-(4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamido)acetate Example 155 was prepared according to the procedure used for the preparation of Example 154, substituting methyl 2-aminoacetate for 3-aminopropanenitrile, to provide the title compound (12.7 mg, 74% yield). $^1$H NMR (400 MHz, DMSO-d$_6$-D$_2$O) δ 7.75 (d, J=2.1 Hz, 1H), 7.71 (s, 1H), 7.51-7.61 (m, 1H), 7.36 (s, 1H), 7.13 (dd, J=8.3, 2.0 Hz, 1H), 6.99-7.09 (m, 2H), 6.83 (d, J=8.2 Hz, 1H), 5.88 (s, 1H), 4.38-4.49 (m, 1H), 3.67 (s, 3H), 3.60 (s, 1H), 3.48 (s, 2H), 2.90 (s, 2H). MS (ESI+) m/z 571.0 (M+H)$^+$.

Example 156

4-(2,4-difluorophenyl)-10-methyl-7-((methylsulfonyl)methyl)-11-oxo-N-phenethyl-3,4,10,11-tetrahydro-1H-1,4,10-triazadibenzo[cd,f]azulene-3-carboxamide Example 156 was prepared according to the procedure used for the preparation of Example 154, substituting 2-phenylethanamine for 3-aminopropanenitrile, to provide the title compound (15.4 mg, 85% yield). $^1$H NMR (400 MHz, DMSO-d$_6$-D$_2$O) δ 7.75 (d, J=2.1 Hz, 1H), 7.72 (s, 1H), 7.63 (d, J=6.4 Hz, 1H), 7.29 (s, 1H), 7.09-7.22 (m, 4H), 6.98-7.10 (m, 2H), 6.97 (d, J=1.7 Hz, 2H), 6.93-6.97 (m, 2H), 6.83 (d, J=8.2 Hz, 1H), 5.81 (s, 1H), 4.47 (d, J=13.7 Hz, 1H), 4.40 (d, J=13.6 Hz, 1H), 3.68 (s, 3H), 3.12 (ddd, J=12.8, 8.8, 5.8 Hz, 1H), 2.87-2.99 (m, 1H), 2.81 (s, 3H), 2.32 (ddd, J=13.6, 8.2, 5.6 Hz, 1H), 2.15-2.26 (m, 1H). MS (ESI+) m/z 603.0 (M+H)$^+$.

Example 157

N-butyl-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide Example 157 was prepared according to the procedure used for the preparation of Example 154, substituting butan-1-amine for 3-aminopropanenitrile, to provide the title compound (13.8 mg, 83% yield). $^1$H NMR (400 MHz, DMSO-d$_6$-D$_2$O) δ 7.73 (d, J=2.0 Hz, 1H), 7.69 (s, 1H), 7.59-7.68 (m, 1H), 7.32 (s, 1H), 7.18-7.12 (m, 2H), 6.98-7.08 (m, 2H), 6.85 (d, J=8.1 Hz, 1H), 5.79 (s, 1H), 4.36-4.50 (m, 1H), 3.67 (s, 3H), 2.90-3.00 (m, 2H), 2.90 (s, 3H), 2.72 (dd, J=11.6, 4.9 Hz, 1H), 0.81-1.02 (m, 4H), 0.66 (t, J=7.1 Hz, 3H). MS (ESI+) m/z 555.1 (M+H)$^+$.

Example 158

N-cyclohexyl-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide Example 158 was prepared according to the procedure used for the preparation of Example 154, substituting cyclohexanamine for 3-aminopropanenitrile, to provide the title compound (13.1 mg, 75% yield). $^1$H NMR (400 MHz, DMSO-d$_6$-D$_2$O) δ 7.74 (d, J=2.0 Hz, 1H), 7.71 (s, 1H), 7.48-7.58 (m, 1H), 7.32 (s, 1H), 7.16 (dd, J=8.2, 2.0 Hz, 1H), 6.97-7.09 (m, 2H), 6.82 (dd, J=25.9, 8.2 Hz, 2H), 5.78 (s, 1H), 4.36-4.51 (m, 2H), 3.67 (s, 3H), 3.24-3.36 (m, 1H), 2.87 (s, 3H), 1.85 (s, 1H), 1.34-1.55 (m, 4H), 0.86-1.19 (m, 5H), 0.70-0.85 (m, 1H).). MS (ESI+) m/z 581.0 (M+H)+.

Example 159

N-benzyl-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide Example 159 was prepared according to the procedure used for the preparation of Example 154, substituting phenylmethanamine for 3-aminopropanenitrile, to provide the title compound (13.2 mg, 75% yield).). $^1$H NMR (400 MHz, DMSO-$d_6$-$D_2$O) δ 7.66-7.80 (m, 3H), 7.36 (s, 1H), 7.13-7.17 (m, 1H), 7.11 (m, 3H), 7.09-6.99 (m, 2H), 6.87 (d, J=8.2 Hz, 1H), 6.67-6.73 (m, 2H), 5.94 (s, 1H), 4.44-4.57 (m, 2H), 4.27 (d, J=15.3 Hz, 1H), 3.90 (d, J=15.2 Hz, 1H), 3.65 (s, 3H), 2.94 (s, 3H). MS (ESI+) m/z 589.0 (M+H)+.

Example 160

4-(2,4-difluorophenyl)-10-methyl-7-((methylsulfonyl)methyl)-11-oxo-N-(3-phenylpropyl)-3,4,10,11-tetrahydro-1H-1,4,10-triazadibenzo[cd,f]azulene-3-carboxamide Example 160 was prepared according to the procedure used for the preparation of Example 154, substituting 3-phenylpropan-1-amine for 3-aminopropanenitrile, to provide the title compound (10.77 mg, 58% yield). $^1$H NMR (400 MHz, DMSO-$d_6$-$D_2$O) δ 7.61-7.73 (m, 3H), 7.32 (s, 1H), 7.17-7.26 (m, 3H), 7.09-7.17 (m, 2H), 6.97-7.07 (m, 4H), 6.85 (d, J=8.2 Hz, 1H), 5.81 (s, 1H), 4.32 (d, J=13.7 Hz, 1H), 4.18-4.26 (m, 1H), 3.67 (s, 3H), 2.85-3.03 (m, 1H), 2.79 (s, 3H), 2.65-2.76 (m, 1H), 2.20 (t, J=7.6 Hz, 2H), 1.20-1.34 (m, 2H). MS (ESI+) m/z 617.0 (M+H)+.

Example 161

4-(2,4-difluorophenyl)-N-isobutyl-10-methyl-7-((methylsulfonyl)methyl)-11-oxo-3,4,10,11-tetrahydro-1H-1,4,10-triazadibenzo[cd,f]azulene-3-carboxamide Example 161 was prepared according to the procedure used for the preparation of Example 154, substituting 2-methylpropan-1-amine for 3-aminopropanenitrile, to provide the title compound (12.7 mg, 76% yield). $^1$H NMR (400 MHz, DMSO-$d_6$-$D_2$O) δ 7.72-7.76 (m, 1H), 7.71 (s, 1H), 7.66 (dd, J=15.1, 9.1 Hz, 1H), 7.33 (s, 1H), 7.14 (dd, J=8.2, 2.3 Hz, 2H), 6.98-7.09 (m, 2H), 6.84 (d, J=8.2 Hz, 1H), 5.82 (s, 1H), 4.34-4.42 (m, 2H), 3.67 (s, 3H), 2.89 (s, 3H), 2.83 (dd, J=12.8, 7.7 Hz, 1H), 1.84 (s, 2H), 1.27 (dt, J=13.4, 6.8 Hz, 1H), 0.47 (dd, J=6.6, 1.8 Hz, 6H). MS (ESI+) m/z 555.1 (M+H)+.

Example 162

4-(2,4-difluorophenyl)-N-(2-hydroxyethyl)-10-methyl-7-((methylsulfonyl)methyl)-11-oxo-3,4,10,11-tetrahydro-1H-1,4,10-triazadibenzo[cd,f]azulene-3-carboxamide Example 162 was prepared according to the procedure used for the preparation of Example 154, substituting 2-aminoethanol for 3-aminopropanenitrile, to provide the title compound (11.7 mg, 72% yield). $^1$H NMR (400 MHz, DMSO-$d_6$-$D_2$O) δ 7.74 (d, J=2.1 Hz, 1H), 7.70 (s, 1H), 7.54-7.65 (m, 1H), 7.34 (s, 1H), 7.16 (dd, J=8.2, 2.0 Hz, 1H), 6.98-7.08 (m, 2H), 6.85 (d, J=8.2 Hz, 1H), 5.84 (s, 1H), 4.37-4.52 (m, 2H), 3.67 (s, 3H), 2.86-3.08 (m, 7H). MS (ESI+) m/z 543.0 (M+H)+.

Example 163

4-(2,4-difluorophenyl)-10-methyl-7-((methylsulfonyl)methyl)-N-(oxazol-4-ylmethyl)-11-oxo-3,4,10,11-tetrahydro-1H-1,4,10-triazadibenzo[cd,f]azulene-3-carboxamide Example 163 was prepared according to the procedure used for the preparation of Example 154, substituting oxazol-4-ylmethanamine for 3-aminopropanenitrile, to provide the title compound (7.2 mg, 41% yield). $^1$H NMR (400 MHz, DMSO-$d_6$-$D_2$O) δ 8.14 (d, J=0.9 Hz, 1H), 7.75 (d, J=2.0 Hz, 1H), 7.70 (s, 1H), 7.57-7.67 (m, 1H), 7.36 (s, 1H), 7.14 (dd, J=8.2, 2.0 Hz, 1H), 6.96-7.10 (m, 3H), 6.85 (d, J=8.2 Hz, 1H), 5.90 (s, 1H), 4.38-4.52 (m, 2H), 3.84-4.07 (m, 2H), 3.67 (s, 3H), 2.92 (s, 3H). MS (ESI+) m/z 580.0 (M+H)+.

Example 164

N-(cyclopropylmethyl)-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide Example 164 was prepared according to the procedure used for the preparation of Example 154, substituting cyclopropylmethanamine for 3-aminopropanenitrile, to provide the title compound (13.8 mg, 83% yield). $^1$H NMR (400 MHz, DMSO-$d_6$-$D_2$O) δ 7.74 (d, J=2.1 Hz, 1H), 7.71 (s, 1H), 7.54-7.64 (m, 1H), 7.33 (s, 1H), 7.15 (dd, J=8.2, 2.0 Hz, 1H), 6.97-7.08 (m, 2H), 6.87 (d, J=8.2 Hz, 1H), 5.82 (s, 1H), 4.37-4.50 (m, 2H), 3.67 (s, 3H), 2.89 (s, 3H), 2.78-2.87 (m, 1H), 2.60-2.73 (m, 1H), 0.42-0.52 (m, 1H), 0.05-0.18 (m, 2H),−0.21-−0.14 (m, 2H). MS (ESI+) m/z 553.0 (M+H)+.

Example 165

4-(2,4-difluorophenyl)-N-(2-hydroxy-2-methylpropyl)-10-methyl-7-((methylsulfonyl)methyl)-11-oxo-3,4,10,11-tetrahydro-1H-1,4,10-triazadibenzo[cd,f]azulene-3-carboxamide Example 165 was prepared according to the procedure used for the preparation of Example 154, substituting 1-amino-2-methylpropan-2-ol for 3-aminopropanenitrile, to provide the title compound (12.2 mg, 71% yield). $^1$H NMR (400 MHz, DMSO-$d_6$-$D_2$O) δ 7.73-7.77 (m, 1H), 7.72 (s, 1H), 7.67 (dd, J=12.7, 6.5 Hz, 1H), 7.38 (s, 1H), 7.13 (dd, J=8.2, 2.0 Hz, 1H), 6.98-7.10 (m, 2H), 6.83 (d, J=8.2 Hz, 1H), 5.90 (s, 1H), 4.35-4.48 (m, 2H), 3.67 (s, 3H), 2.96 (dd, J=13.2, 5.1 Hz, 1H), 2.88 (s, 3H), 2.74 (d, J=13.1 Hz, 1H), 0.79 (s, 3H), 0.60 (s, 3H). MS (ESI+) m/z 571.0 (M+H)+.

Example 166

4-(2,4-difluorophenyl)-N-(1-(hydroxymethyl)cyclopropyl)-10-methyl-7-((methylsulfonyl)methyl)-11-oxo-3,4,10,11-tetrahydro-1H-1,4,10-triazadibenzo[cd,f]azulene-3-carboxamide Example 166 was prepared according to the procedure used for the preparation of Example 154, substituting (1-aminocyclopropyl)methanol for 3-aminopropanenitrile, to provide the title compound (11.5 mg, 68% yield). $^1$H NMR (400 MHz, DMSO-d$_6$-D$_2$O) δ 7.75 (d, J=2.0 Hz, 1H), 7.70 (s, 1H), 7.43-7.53 (m, 1H), 7.30 (s, 1H), 7.18 (dd, J=8.2, 2.0 Hz, 1H), 6.94-7.08 (m, 2H), 6.87 (d, J=8.1 Hz, 1H), 5.77 (s, 1H), 4.36-4.53 (m, 2H), 3.66 (s, 3H), 3.26 (d, J=11.1 Hz, 1H), 3.08 (d, J=11.1 Hz, 1H), 2.90 (s, 3H), 0.40-0.53 (m, 2H), −0.03-0.13 (m, 2H). MS (ESI+) m/z 569.0 (M+H)$^+$.

Example 167

4-(2,4-difluorophenyl)-10-methyl-N-(1-methylcyclopropyl)-7-((methylsulfonyl)methyl)-11-oxo-3,4,10,11-tetrahydro-1H-1,4,10-triazadibenzo[cd,f]azulene-3-carboxamide Example 167 was prepared according to the procedure used for the preparation of Example 154, substituting 1-methylcyclopropanamine for 3-aminopropanenitrile, to provide the title compound (10.8 mg, 65% yield). $^1$H NMR (400 MHz, DMSO-d$_6$-D$_2$O) δ 7.75 (d, J=2.1 Hz, 1H), 7.70 (s, 1H), 7.50 (d, J=7.3 Hz, 1H), 7.28 (s, 1H), 7.18 (dd, J=8.2, 2.0 Hz, 1H), 6.94-7.08 (m, 2H), 6.88 (d, J=8.1 Hz, 1H), 5.73 (s, 1H), 4.36-4.52 (m, 2H), 3.66 (s, 3H), 2.88 (s, 3H), 0.93 (s, 3H), 0.23-0.34 (m, 2H), 0.13-0.18 (m, 2H). MS (ESI+) m/z 553.0 (M+H)$^+$.

Example 168

4-(2,4-difluorophenyl)-10-methyl-7-((methylsulfonyl)methyl)-11-oxo-N-(4-phenylbutyl)-3,4,10,11-tetrahydro-1H-1,4,10-triazadibenzo[cd,f]azulene-3-carboxamide Example 168 was prepared according to the procedure used for the preparation of Example 154, substituting 4-phenylbutan-1-amine for 3-aminopropanenitrile, to provide the title compound (14.7 mg, 77% yield). $^1$H NMR (400 MHz, DMSO-d$_6$-D$_2$O) δ 7.70-7.72 (m, 1H), 7.69 (s, 1H), 7.57-7.67 (m, 1H), 7.32 (s, 1H), 7.20-7.27 (m, 2H), 6.98-7.19 (m, 6H), 6.84 (d, J=8.2 Hz, 1H), 5.80 (s, 1H), 4.32-4.44 (m, 2H), 3.67 (s, 3H), 2.97 (dt, J=13.2, 6.6 Hz, 1H), 2.87 (s, 3H), 2.68-2.81 (m, 1H), 2.37 (t, J=7.5 Hz, 2H), 1.11-1.25 (m, 2H), 0.96-1.11 (m, 2H). MS (ESI+) m/z 630.9 (M+H)$^+$.

Example 169

4-(3,3-dimethylbutanoyl)-5,7-difluoro-10-methyl-3,4-dihydro-1H-1,4,10-triazadibenzo[cd,f]azulen-11(10H)-one The product from Example 42c (0.05 g, 0.174 mmol), tert-butylacetyl chloride (0.028 g, 0.209 mmol), N,N-dimethylpyridin-4-amine (2.126 mg, 0.017 mmol) and N-ethyl-N-isopropylpropan-2-amine (0.152 mL, 0.870 mmol) were combined in dimethylacetamide (0.870 mL) and stirred at 50° C. for 18 hours. The reaction mixture was cooled to ambient temperature and partitioned between ethyl acetate and water. The organic layer was washed with saturated aqueous sodium chloride, dried over anhydrous sodium sulfate, filtered and concentrated. Purification by reverse phase HPLC (C18, CH$_3$CN/0.1% TFA in water, 10-100% gradient) afforded the title compound (0.012 g, 18%). $^1$H NMR (400 MHz, DMSO-d$_6$) δ 11.60 (s, 1H), 7.83 (s, 1H), 7.53 (d, J=10.38 Hz, 1H), 7.18-7.26 (m, 2H), 5.59 (d, J=14.65 Hz, 1H), 3.87 (d, J=14.95 Hz, 1H), 3.60 (s, 3H), 1.79-1.92 (m, 2H), 0.70 (s, 9H). MS (ESI+) m/z 386 (M+H)$^+$.

Example 170 tert-butyl ((trans)-4-(10-methyl-7-(methylsulfonyl)-11-oxo-10,11-dihydro-1H-1,4,10-triazadibenzo[cd,f]azulen-4(3H)-yl)cyclohexyl)carbamate Example 170a tert-butyl (trans-4-((2-bromo-4-(methylsulfonyl)phenyl)amino)cyclohexyl)carbamate A mixture of 2-bromo-1-fluoro-4-(methylsulfonyl)benzene (0.403 g, 1.592 mmol) and tert-butyl (trans-4-aminocyclohexyl)carbamate (0.352 g, 1.592 mmol) in dimethylsulfoxide (12 mL) and N,N-diisopropylethylamine (0.32 mL, 1.831 mmol) was heated at 100° C. for 4 hours. The reaction mixture was cooled to ambient temperature and partitioned between aqueous ammonium chloride solution and diethyl ether. The organic layer was washed with saturated aqueous sodium chloride, dried over anhydrous magnesium sulfate, filtered and concentrated. The residue was purified by flash column chromatography on silica gel, eluting with 25% ethyl acetate in hexanes to afford the title compound (0.390 g, 0.872 mmol, 55% yield).

Example 170b tert-butyl ((trans)-4-((2-(6-methyl-7-oxo-6,7-dihydro-1H-pyrrolo[2,3-c]pyridin-4-yl)-4-(methylsulfonyl)phenyl)amino)cyclohexyl)carbamate A mixture of Example 170a (0.380 g, 0.849 mmol), Example 1f (0.382 g, 0.892 mmol), cesium fluoride (0.387 g, 2.550 mmol) and tetrakis(triphenylphosphine)palladium (0.098 g, 0.085 mmol) in dimethoxyethane (20 mL) and methanol (10 mL) was stirred under an argon atmosphere at 80° C. for 2 hours. The reaction mixture was cooled to ambient temperature and excess 5N sodium hydroxide solution (8 mL) was added. The reaction mixture was stirred at ambient temperature for 2 hours and then partitioned between aqueous ammonium chloride solution and ethyl acetate. The aqueous layer was extracted with additional ethyl acetate twice. The combined organic layers were washed with saturated aqueous sodium chloride, dried over anhydrous magnesium sulfate, filtered and concentrated. The residue was purified by flash column chromatography on silica gel, eluting with 2% methanol in dichloromethane to afford the title compound (0.279 g, 0.543 mmol, 64% yield).

Example 170c tert-butyl((trans)-4-(10-methyl-7-(methylsulfonyl)-11-oxo-10,11-dihydro-1H-1,4,10-triazadibenzo[cd,f]azulen-4(3H)-yl)cyclohexyl)carbamate To a stirring mixture of Example 170b (0.048 g, 0.093 mmol) and paraformaldehyde (0.048 g, 1.599 mmol) in tetrahydrofuran (1.0 mL) at ambient temperature was added 1M solution of titanium tetrachloride in toluene (0.187 mL, 0.187 mmol). The reaction mixture suspension was stirred at ambient temperature for 1 hour and then partitioned between ethyl acetate and saturated sodium bicarbonate. The aqueous layer was extracted three times with ethyl acetate. The combined organic layers were washed with saturated aqueous sodium chloride, dried over anhydrous magnesium sulfate, filtered, and concentrated. The residue was purified by reverse phase HPLC (C18, CH$_3$CN/water (0.1% TFA), 0-100% gradient) to give the title compound (0.0043 g, 9% yield). $^1$H NMR (400 MHz, DMSO-d$_6$) δ 11.83 (s, 1H), 8.13 (s, 1H), 7.73-7.62 (m, 2H), 7.36 (d, J=8.5 Hz, 1H), 7.20-7.14 (m, 1H), 6.62 (d, J=7.7 Hz, 1H), 4.18 (s, 2H), 3.64 (s, 3H), 3.26 (s, 3H), 3.22-3.14 (m, 1H), 3.02-2.93 (m, 1H), 1.83-1.55 (m, 4H), 1.52-1.25 (m, 11H), 1.16-0.95 (m, 2H). MS (ESI+) m/z 527.1 (M+H)$^+$.

Example 171

4-((trans)-4-aminocyclohexyl)-10-methyl-7-(methylsulfonyl)-3,4-dihydro-1H-1,4,10-triazadibenzo[cd,f]azulen-11(10H)-one Example 170c (0.0114 g, 0.022 mmol) in dichloromethane (1 mL) was treated with trifluoroacetic acid (0.20 mL) and stirred at ambient temperature for 1 hour. The reaction mixture was concentrated and dried under vacuum to afford the title compound as the trifluoracetic acid salt (0.0113 g, 97% yield). $^1$H NMR (400 MHz, DMSO-d$_6$) δ 11.84 (d, J=2.2 Hz, 1H), 8.14 (d, J=2.2 Hz, 1H), 7.68 (dd, J=8.5, 2.3 Hz, 4H), 7.37 (d, J=8.5 Hz, 1H), 7.15 (d, J=2.5 Hz, 1H), 4.12 (bs, 2H), 3.64 (s, 3H), 3.26 (s, 3H), 3.09-2.90 (m, 2H), 1.87 (d, J=10.6 Hz, 2H), 1.72 (d, J=12.6 Hz, 2H), 1.47 (dd, J=23.8, 11.1 Hz, 2H), 1.29-1.18 (m, 2H). MS (ESI+) m/z 427.1 (M+H)$^+$.

Example 172

4-(cyclopropylsulfonyl)-10-methyl-7-((methylsulfonyl)methyl)-3,4-dihydro-1H-1,4,10-triazadibenzo[cd,f]azulen-11(10H)-one Example 172 was prepared according to the procedure used for the preparation of Example 74, substituting cyclopropanesulfonyl chloride for 4-methylbenzene-1-sulfonyl chloride to provide the title compound. $^1$H NMR (400 MHz, DMSO-d$_6$/D$_2$O) δ 7.84 (d, J=2.0 Hz, 1H), 7.75 (s, 1H), 7.44 (d, J=8.1 Hz, 1H), 7.40-7.35 (m, 1H), 7.32 (s, 1H), 5.12 (d, J=16.7 Hz, 1H), 4.54 (dt, J=30.5, 15.1 Hz, 3H), 3.64 (s, 3H), 2.99 (s, 3H), 1.76-1.64 (m, 1H), 0.49 (d, J=5.1 Hz, 3H), 0.35-0.24 (m, 1H). MS (APCI+) m/z 448.0 (M+H)$^+$.

Example 173 ethyl 5,7-difluoro-10-methyl-11-oxo-10,11-dihydro-1H-1,4,10-triazadibenzo[cd,f]azulene-4(3H)-carboxylate

Example 173a tert-butyl 5,7-difluoro-10-methyl-11-oxo-3,4,10,11-tetrahydro-1H-1,4,10-triazadibenzo[cd,f]azulene-1-carboxylate The product from Example 42c (0.86 g, 2.99 mmol), di-tert-butyl dicarbonate (0.98 g, 4.49 mmol), N,N-dimethylpyridin-4-amine (0.018 g, 0.150 mmol) and N-ethyl-N-isopropylpropan-2-amine (1.569 mL, 8.98 mmol) were combined in dimethylacetamide (11.98 mL) and stirred at 50° C. for 1 hour. The reaction mixture was cooled to ambient temperature and partitioned between ethyl acetate and water. The organic layer was washed with saturated aqueous sodium chloride, dried over anhydrous sodium sulfate, filtered, and concentrated to afford the title compound (1.0 g, 86%).

Example 173b 1-tert-butyl 4-ethyl 5,7-difluoro-10-methyl-11-oxo-10,11-dihydro-1H-1,4,10-triazadibenzo[cd,f]azulene-1,4(3H)-dicarboxylate The product from Example 173a (0.7 g, 1.807 mmol), ethyl carbonochloridate (0.7 g, 6.45 mmol), 2-(3H-[1,2,3]triazolo[4,5-b]pyridin-3-yl)-1,1,3,3-tetramethylisouronium hexafluorophosphate(V) (1.0 g, 2.63 mmol) and N-ethyl-N-isopropylpropan-2-amine (1.6 mL, 9.16 mmol) were combined in dimethylacetamide (9 mL) and stirred at 50° C. for 2 hours. The reaction mixture was cooled to ambient temperature and partitioned between ethyl acetate and water. The organic layer was washed with saturated aqueous sodium chloride, dried over anhydrous sodium sulfate, filtered, and concentrated. Purification by chromatography (silica gel, 0-60% ethyl acetate in heptanes) afforded the title compound (0.57 g, 69%).

Example 173c ethyl 5,7-difluoro-10-methyl-11-oxo-10,11-dihydro-1H-1,4,10-triazadibenzo[cd,f]azulene-4(3H)-carboxylate The product from Example 173b (0.57 g, 1.241 mmol) in dichloromethane (5 mL)/TFA (5 mL) was stirred at ambient temperature for 1 hour, concentrated, and azeotroped 3× with dichloromethane. Purification by trituration in a minimal volume of 9:1 dichloromethane/methanol afforded the title compound (0.427 g. 96%). 1H NMR (400 MHz, DMSO-d$_6$) δ 12.00 (s, 1H), 7.90 (s, 1H), 7.53 (dd, J=10.68, 1.53 Hz, 1H), 7.25-7.33 (m, 2H), 5.25 (d, J=15.56 Hz, 1H), 4.13 (d, J=15.56 Hz, 1H), 3.99-4.06 (m, 1H), 3.74-3.84 (m, 1H), 3.61 (s, 3H), 0.99 (t, J=7.17 Hz, 3H). MS (ESI+) m/z 360 (M+H)$^+$.

Example 174

4-(2,4-difluorophenyl)-10-methyl-3-(3-(methylamino)propyl)-7-((methylsulfonyl)methyl)-3,4-dihydro-1H-1,4,10-triazadibenzo[cd,f]azulen-11(10H)-one Example 147a (35.5 mg, 0.0600 mmol), 2.0 M methanamine in tetrahydrofuran (0.150 mL, 0.300 mmol) and potassium carbonate (24.9 mg, 0.180 mmol) were combined in tetrahydrofuran (1 mL). The reaction mixture was heated at 60° C. for 2 hours, cooled, and concentrated. The residue was purified by reverse phase HPLC (C18, CH$_3$CN/water (10 mM ammonium acetate), 20-100% gradient) to provide the title compound (19 mg, 60%). $^1$H NMR (400 MHz, DMSO-d$_6$) δ 7.84 (d, J=1.8 Hz, 1H), 7.68 (s, 1H), 7.23 (dd, J=8.2, 1.8 Hz, 1H), 7.14 (s, 1H), 7.13-7.04 (m, 1H), 6.97 (d, J=8.2 Hz, 1H), 6.93-6.82 (m, 2H), 5.05-4.97 (m, 1H), 4.56-4.42 (m, 2H), 3.64 (s, 3H), 2.92 (s, 3H), 2.45 (t, J=6.1 Hz, 2H), 2.22 (s, 3H), 1.72-1.58 (m, 2H), 1.54-1.42 (m, 1H), 1.36-1.24 (m, 1H). MS (ESI+) m/z 527 (M+H)$^+$.

Example 175

4-(2,4-difluorophenyl)-3-(3-(dimethylamino)propyl)-10-methyl-7-((methylsulfonyl)methyl)-3,4-dihydro-1H-1,4,10-triazadibenzo[cd,f]azulen-11(10H)-one Example 175 was prepared according to the procedure used for the preparation of Example 174, substituting 2.0 M dimethylamine in tetrahydrofuran for 2.0 M methanamine in tetrahydrofuran, to provide the title compound (20 mg, 62%). $^1$H NMR (400 MHz, DMSO-$d_6$) δ 11.84 (s, 1H), 7.84 (d, J=1.8 Hz, 1H), 7.67 (s, 1H), 7.22 (dd, J=8.2, 1.7 Hz, 1H), 7.14 (s, 1H), 7.10-7.05 (m, 1H), 6.96 (d, J=8.1 Hz, 1H), 6.93-6.83 (m, 2H), 5.01 (t, J=7.4 Hz, 1H), 4.53-4.42 (m, 2H), 3.64 (s, 3H), 2.92 (s, 3H), 2.21-2.03 (m, 2H), 2.01 (s, 6H), 1.72-1.60 (m, 1H), 1.59-1.53 (m, 1H), 1.51-1.41 (m, 1H), 1.32-1.22 (m, 1H). MS (ESI+) m/z 541 (M+H)$^+$.

Example 176

4-(4-chlorophenyl)-10-methyl-2-((4-methylpiperazin-1-yl)methyl)-7-((methylsulfonyl)methyl)-3,4-dihydro-1H-1,4,10-triazadibenzo[cd,f]azulen-11(10H)-one To the solution of Example 60 (110 mg, 0.190 mmol) in anhydrous tetrahydrofuran (5 mL) was added BH3.THF (1.896 mL, 1.896 mmol) and the reaction mixture was stirred at 65° C. for 18 hours. The reaction mixture was quenched with ethanol (1 mL), followed by the addition of HCl (3 M, 2 mL). The mixture was stirred at 70° C. for an additional 4 hours. The solvent was evaporated and the residue was treated with 5 N NaOH (2 mL) and the mixture was extracted with dichlorormethane (20 mL×3). The combined organic layers were concentrated and the residue was purified by HPLC (C18, 30%-40% acetonitrile in 0.1% aqueous ammonium hydroxide) to provide the title compound (15 mg, 0.026 mmol, 14% yield). $^1$H NMR (400 MHz, DMSO-$d_6$) δ 11.87 (s, 1H), 7.89 (s, 1H), 7.60 (s, 1H), 7.46 (d, J=7.9 Hz, 1H), 7.34 (d, J=8.0 Hz, 1H), 6.96 (d, J=8.9 Hz, 2H), 6.43 (d, J=8.9 Hz, 2H), 5.22-5.18 (m, 1H), 4.66-4.34 (m, 3H), 3.79-3.73 (m, 1H), 3.66-3.60 (m, 1H), 3.54 (s, 3H), 3.00 (s, 3H), 2.47-2.27 (m, 8H), 2.17 (s, 3H). MS (ESI+) m/z 566.2 (M+H)$^+$.

Example 177

2-(4-(4-fluorophenyl)-10-methyl-11-oxo-3,4,10,11-tetrahydro-1H-1,4,10-triazadibenzo[cd,f]azulen-7-yl)acetonitrile

Example 177a 2-(4-amino-3-bromophenyl)acetonitrile

To a solution of 2-(4-aminophenyl)acetonitrile (3.0 g, 22.70 mmol) in 40 mL dimethylformamide cooled with ice bath was added N-bromosuccinimide (4.04 g, 22.70 mmol) in portions. The mixture was stirred at 0° C. for 30 minutes and then at ambient temperature for 1 hour. Water was added. The precipitate was collected by filtration, washed with water, and dried in a vacuum oven at 40° C. to give the title compound (3.56 g, 16.9 mmol, 74.4% yield).

Example 177b 2-(4-amino-3-(6-methyl-7-oxo-1-tosyl-6,7-dihydro-1H-pyrrolo[2,3-c]pyridin-4-yl)phenyl)acetonitrile A mixture of Example 177a (0.739 g, 3.50 mmol), Example 1f (1.5 g, 3.50 mmol), tris(dibenzylideneacetone)dipalladium(0) (0.080 g, 0.088 mmol), 1,3,5,7-tetramethyl-8-phenyl-2,4,6-trioxa-8-phosphaadamantane (0.051 g, 0.175 mmol) and potassium phosphate (2.230 g, 10.51 mmol) in 30 mL dioxane and 10 mL water was heated at 80° C. under nitrogen for 2 hours. Water was added, and the mixture was extracted with ethyl acetate (3×), washed with saturated aqueous sodium chloride, dried over anhydrous magnesium sulfate, and filtered. The filtrate was concentrated and purified by column chromatography (silica gel, 0-40% ethyl acetate/heptanes gradient) to give the title compound (0.933 g, 2.157 mmol, 61.6% yield).

Example 177c

{4-[(4-fluorophenyl)amino]-3-(6-methyl-7-oxo-6,7-dihydro-1H-pyrrolo[2,3-c]pyridin-4-yl)phenyl}acetonitrile A mixture of Example 177b (120 mg, 0.277 mmol), 1-bromo-4-fluorobenzene (48.6 mg, 0.277 mmol), cesium carbonate (226 mg, 0.694 mmol), and dicyclohexyl(2',4',6'-triisopropylbiphenyl-2-yl)phosphine (X-phos) (13.23 mg, 0.028 mmol) in 4 mL toluene and 1 mL tert-butanol was heated in a Biotage initiator microwave oven at 150° C. for 40 minutes. The reaction mixture was then concentrated. The residue was treated with 1 mL 4N aqueous NaOH solution and 3 mL dioxane. The resulting mixture was heated at 80° C. in the microwave oven for 20 minutes. Water was added, and the mixture was extracted with ethyl acetate (3×), washed with saturated aqueous sodium chloride, dried over anhydrous magnesium sulfate, and filtered. The filtrate was concentrated and the residue was purified by column chromatography (silica gel, 0-10% methanol/dichloromethane gradient) to afford the title compound (43 mg, 0.115 mmol, 41.6% yield).

Example 177d 2-(4-(4-fluorophenyl)-10-methyl-11-oxo-3,4,10,11-tetrahydro-1H-1,4,10-triazadibenzo[cd,f]azulen-7-yl)acetonitrile To a mixture of Example 177c (36 mg, 0.097 mmol) and paraformaldehyde (43.5 mg, 1.450 mmol) in 2 mL tetrahydrofuran was added titanium(IV) chloride (193 μL, 0.193 mmol, 1.0 M toluene solution). The dark red mixture was stirred at ambient temperature for 3 hours. The mixture was cooled with an ice bath and quenched with water, extracted with ethyl acetate (2×), washed with saturated aqueous sodium chloride, dried over anhydrous magnesium sulfate, and filtered. The filtrate was concentrated and the residue was purified by column chromatography (silica gel, 0-10% methanol/dichloromethane gradient) to give the title compound (12 mg, 0.031 mmol, 32% yield). $^1$H NMR (400 MHz, DMSO-$d_6$) δ 11.62-11.28 (m, 1H), 7.82 (d, J=1.7 Hz, 1H), 7.58 (s, 1H), 7.36 (dd, J=8.0, 1.9 Hz, 1H), 7.32-7.26 (m, 2H), 6.79-6.71 (m, 2H), 6.47-6.34 (m, 2H), 4.85-4.62 (m, 2H), 4.05 (s, 2H), 3.56 (s, 3H). MS (ESI+) m/z 385.2 (M+H)$^+$.

Example 178

4-(2,2-dimethyl-3-(pyrrolidin-1-yl)propyl)-10-methyl-7-((methylsulfonyl)methyl)-3,4-dihydro-1H-1,4,10-triazadibenzo[cd,f]azulen-11(10H)-one Example 178 was prepared according to the procedure used for the preparation of Example 149, substituting 2,2-dimethyl-3-(pyrrolidin-1-yl)propanal for isobutyraldehyde to provide the title compound as the trifluoroacetic acid salt. NMR (400 MHz, pyridine-$d_5$) δ 13.69-12.65 (m, 1H), 8.08 (dd, J=10.0, 2.0 Hz, 1H), 7.57 (d, J=3.6 Hz, 2H), 7.42-7.31 (m, 2H), 4.78 (s, 2H), 4.34 (s, 2H), 3.64 (s, 3H), 3.13 (s, 3H), 3.09 (s, 2H), 3.02 (s, 2H), 2.20-2.85 (m, 4H) 1.83-1.68 (m, 4H), 0.99 (s, 6H). MS (ESI+) m/z 483.1 (M+H)$^+$.

Example 179

2-(3-(10-methyl-7-((methylsulfonyl)methyl)-11-oxo-10,11-dihydro-1H-1,4,10-triazadibenzo[cd,f]azulen-4(3H)-yl)pyrrolidin-1-yl)acetic acid Example 179 was prepared according to the procedure used for the preparation of Example 149, substituting 2-(3-oxopyrrolidin-1-yl)acetic acid for isobutyraldehyde to provide the title compound as the trifluoroacetic acid salt. $^1$H NMR (400 MHz, pyridine-$d_5$) δ 13.47-13.38 (m, 1H), 8.10-8.01 (m, 1H), 7.57-7.48 (m, 2H), 7.47-7.29 (m, 2H), 4.73 (s, 2H), 4.39-3.77 (m, 4H), 3.64 (s, 3H), 3.58-3.16 (m, 4H), 3.12 (d, J=6.6 Hz, 3H), 2.50 (s, 1H), 2.22-2.03 (m, 2H), 1.37-1.22 (m, 1H). MS (APCI+) m/z 471.1 (M+H)$^+$.

Example 180

10-methyl-7-((methylsulfonyl)methyl)-4-(2-methyl-tetrahydrofuran-3-yl)-3,4-dihydro-1H-1,4,10-triazadibenzo[cd,f]azulen-11(10H)-one Example 180 was prepared according to the procedure used for the preparation of Example 149, substituting 2-methyldihydrofuran-3(2H)-one for isobutyraldehyde to provide the title compound. $^1$H NMR (400 MHz, pyridine-$d_5$) δ 13.49-13.40 (m, 1H), 8.05 (d, J=2.0 Hz, 1H), 7.60 (dd, J=8.4, 1.9 Hz, 1H), 7.54 (d, J=7.7 Hz, 1H), 7.45-7.27 (m, 2H), 4.82-4.68 (m, 2H), 4.68-3.92 (m, 5H), 3.86-3.40 (m, 4H), 3.12 (s, 3H), 2.25-1.85 (m, 2H), 1.36-1.14 (m, 3H). MS (APCI+) m/z 428.1 (M+H)$^+$.

Example 181

10-methyl-4-(1-methylpiperidin-4-yl)-7-((methylsulfonyl)methyl)-3,4-dihydro-1H-1,4,10-triazadibenzo[cd,f]azulen-11(10H)-one Example 181 was prepared according to the procedure used for the preparation of Example 149, substituting 1-methylpiperidin-4-one for isobutyraldehyde to provide the title compound as the trifluoroacetic acid salt. $^1$H NMR (400 MHz, pyridine-$d_5$) δ 14.00-13.44 (m, 1H), 8.17-7.99 (m, 1H), 7.58-7.42 (m, 1H), 7.42-7.28 (m, 2H), 4.89-4.71 (m, 2H), 4.67-4.11 (m, 3H), 3.65 (s, 3H), 3.53-3.30 (m, 2H), 3.18-3.10 (m, 3H), 2.90-2.6 (m, 2H), 2.69 (s, 3H), 2.27-1.52 (m, 4H). MS (APCI+) m/z 441.1 (M+H)$^+$.

Example 182

10-methyl-7-((methylsulfonyl)methyl)-4-(tetra-hydro-2H-pyran-3-yl)-3,4-dihydro-1H-1,4,10-triazadibenzo[cd,f]azulen-11(10H)-one Example 182 was prepared according to the procedure used for the preparation of Example 149, substituting dihydro-2H-pyran-3(4H)-one for isobutyraldehyde to provide the title compound. $^1$H NMR (400 MHz, pyridine-$d_5$) δ 13.52-13.29 (m, 1H), 8.09-8.01 (m, 1H), 7.55 (d, J=7.6 Hz, 2H), 7.52-7.28 (m, 2H), 4.84-4.69 (m, 2H), 4.60-3.66 (m, 4H), 3.65-3.56 (m, 3H), 3.53-3.16 (m, 2H), 3.16-3.03 (m, 2H), 2.72-2.56 (m, 1H), 2.21-1.19 (m, 5H). MS (APCI+) m/z 428.1 (M+H)$^+$.

Example 183

4-((1-isopropylpiperidin-4-yl)methyl)-10-methyl-7-((methylsulfonyl)methyl)-3,4-dihydro-1H-1,4,10-triazadibenzo[cd,f]azulen-11(10H)-one Example 183 was prepared according to the procedure used for the preparation of Example 149, substituting 1-isopropylpiperidine-4-carbaldehyde for isobutyraldehyde to provide the title compound as the trifluoroacetic acid salt. $^1$H NMR (400 MHz, pyridine-$d_5$) δ 13.69-12.65 (m, 1H), 8.08 (dd, J=10.0, 2.0 Hz, 1H), 7.57 (d, J=3.6 Hz, 2H), 7.42-7.31 (m, 2H), 4.81-4.71 (m, 2H), 4.30-4.19 (m, 2H), 3.64 (d, J=6.9 Hz, 3H), 3.54-3.19 (m, 4H), 3.21 (s, 3H), 3.06-2.88 (m, 2H), 2.78-2.53 (m, 2H), 1.97 (dddd, J=9.6, 8.6, 5.4, 2.1 Hz, 2H), 1.84-1.75 (m, 2H), 1.18-1.02 (m, 6H). MS (APCI+) m/z 483.1 (M+H)$^+$.

Example 184

10-methyl-7-((methylsulfonyl)methyl)-4-(1-(2-oxo-tetrahydrofuran-3-yl)ethyl)-3,4-dihydro-1H-1,4,10-triazadibenzo[cd,f]azulen-11(10H)-one Example 184 was prepared according to the procedure used for the preparation of Example 149, substituting 3-acetyldihydrofuran-2(3H)-one for isobutyraldehyde to provide the title compound. $^1$H NMR (400 MHz, pyridine-$d_5$) δ 13.48-13.34 (m, 1H), 8.10-8.01 (m, J=2.1 Hz, 1H), 7.61-7.53 (m, 2H), 7.50-7.31 (m, 2H), 4.80-4.67 (m, 2H), 4.40-3.98 (m, 4H), 3.62 (s, 3H), 3.10 (s, 3H), 2.80-2.60 (m, 1H), 2.46 (s, 3H), 2.18-1.77 (m, 3H). MS (APCI+) m/z 456.1 (M+H)$^+$.

Example 185

4-(1-methoxypropan-2-yl)-10-methyl-7-((methylsulfonyl)methyl)-3,4-dihydro-1H-1,4,10-triazadibenzo[cd,f]azulen-11(10H)-one Example 185 was prepared according to the procedure used for the preparation of Example 149, substituting 1-methoxypropan-2-one for isobutyraldehyde to provide the title compound. $^1$H NMR (400 MHz, pyridine-$d_5$) δ 13.89-12.95 (m, 1H), 8.05 (d, J=1.3 Hz, 1H), 7.56-7.44 (m, 3H), 7.44-7.34 (m, 1H), 4.71 (d, J=12.4 Hz, 2H), 4.63-4.06 (m, 2H), 3.73-3.64 (m, 1H), 3.64-3.56 (m, 3H), 3.56-3.42 (m, 1H), 3.40-3.27 (m, 1H), 3.17 (s, 3H), 3.09 (d, J=5.1 Hz, 3H), 1.27-1.12 (m, 3H). MS (APCI+) m/z 416.0 (M+H)$^+$.

Example 186

4-(4-methoxybutan-2-yl)-10-methyl-7-((methylsulfonyl)methyl)-3,4-dihydro-1H-1,4,10-triazadibenzo[cd,f]azulen-11(10H)-one Example 186 was prepared according to the procedure used for the preparation of Example 149, substituting 4-methoxybutan-2-one for isobutyraldehyde to provide the title compound. $^1$H NMR (400 MHz, pyridine-d$_5$) δ 13.63-13.11 (m, 1H), 8.04 (d, J=2.0 Hz, 1H), 7.57-7.36 (m, 4H), 4.88-4.51 (m, 2H), 4.51-3.96 (m, 2H), 3.86-3.72 (m, 1H), 3.62 (s, 3H), 3.47-3.34 (m, 1H), 3.33-3.20 (m, 1H), 3.17-2.99 (m, 6H), 2.06-1.87 (m, 1H), 1.80-1.62 (m, 1H), 1.31-1.05 (m, 3H). MS (APCI+) m/z 430.0 (M+H)$^+$.

Example 187

10-methyl-4-(1-methylpyrrolidin-3-yl)-7-((methylsulfonyl)methyl)-3,4-dihydro-1H-1,4,10-triazadibenzo[cd,f]azulen-11(10H)-one Example 187 was prepared according to the procedure used for the preparation of Example 149, substituting 1-methylpyrrolidin-3-one for isobutyraldehyde to provide the title compound as the trifluoroacetic acid salt. $^1$H NMR (400 MHz, pyridine-d$_5$) δ 13.57-13.33 (m, 1H), 8.05 (d, J=1.9 Hz, 1H), 7.57-7.52 (m, 2H), 7.51-7.29 (m, 2H), 4.81-4.69 (m, 2H), 4.69-4.06 (m, 3H), 3.67 (s, 3H), 3.62-3.16 (m, 4H), 3.13 (s, 3H), 2.92-2.74 (m, 3H), 2.35-1.91 (m, 2H). MS (APCI+) m/z 427.1 (M+H)$^+$.

Example 188

10-methyl-7-((methylsulfonyl)methyl)-4-(1-(tetrahydro-2H-pyran-4-yl)ethyl)-3,4-dihydro-1H-1,4,10-triazadibenzo[cd,f]azulen-11(10H)-one Example 188 was prepared according to the procedure used for the preparation of Example 149, substituting 1-(tetrahydro-2H-pyran-4-yl)ethanone for isobutyraldehyde to provide the title compound. $^1$H NMR (400 MHz, pyridine-d$_5$) δ 13.48-13.34 (m, 1H), 8.11-8.02 (m, 1H), 7.67-7.59 (m, 1H), 7.51-7.40 (m, 2H), 7.39-7.29 (m, 1H), 4.90-4.63 (m, 2H), 4.54-3.64 (m, 4H), 3.61 (s, 3H), 3.51-3.15 (m, 3H), 3.11 (s, 3H), 1.83-1.44 (m, 4H), 1.38-1.01 (m, 4H). MS (APCI+) m/z 456.1 (M+H)$^+$.

Example 189

10-methyl-4-(1-methylazepan-4-yl)-7-((methylsulfonyl)methyl)-3,4-dihydro-1H-1,4,10-triazadibenzo[cd,f]azulen-11(10H)-one Example 189 was prepared according to the procedure used for the preparation of Example 149, substituting 1-methylazepan-4-one for isobutyraldehyde to provide the title compound as the trifluoroacetic acid salt. $^1$H NMR (400 MHz, pyridine-d$_5$) δ 13.83-13.26 (m, 1H), 8.07 (dd, J=18.6, 1.9 Hz, 1H), 7.55 (d, J=2.5 Hz, 1H), 7.50-7.27 (m, 3H), 4.82-4.73 (m, 1H), 4.66 (s, 2H), 4.54-4.45 (m, 2H), 3.62 (s, 3H), 3.59-3.20 (m, 4H), 3.06 (s, 3H), 2.80 (s, 3H), 2.39-1.46 (m, 6H). MS (APCI+) m/z 455.2 (M+H)$^+$.

Example 190

4-(1-ethylpiperidin-3-yl)-10-methyl-7-((methylsulfonyl)methyl)-3,4-dihydro-1H-1,4,10-triazadibenzo[cd,f]azulen-11(10H)-one Example 190 was prepared according to the procedure used for the preparation of Example 149, substituting 1-ethylpiperidin-3-one for isobutyraldehyde to provide the title compound as the trifluoroacetic acid salt. $^1$H NMR (400 MHz, pyridine-d$_5$) δ 13.83-12.95 (m, 1H), 8.08-8.00 (m, 1H), 7.75-7.69 (m, 1H), 7.56 (s, 1H), 7.49-7.35 (m, 2H), 4.84-4.58 (m, 2H), 4.65-3.76 (m, 3H), 3.69 (s, 3H), 3.47-3.19 (s, 2H), 3.20-3.14 (m, 3H), 3.11-2.55 (m, 4H), 2.40-1.58 (m, 4H), 1.16-1.02 (m, 3H). MS (APCI+) m/z 455.0 (M+H)$^+$.

Example 191

10-methyl-7-((methylsulfonyl)methyl)-4-(2-(tetrahydro-2H-pyran-4-yl)ethyl)-3,4-dihydro-1H-1,4,10-triazadibenzo[cd,f]azulen-11(10H)-one Example 191 was prepared according to the procedure used for the preparation of Example 149, substituting 2-(tetrahydro-2H-pyran-4-yl)acetaldehyde for isobutyraldehyde to provide the title compound. $^1$H NMR (400 MHz, pyridine-d$_5$) δ 13.45-13.38 (m, 1H), 8.08 (d, J=2.0 Hz, 1H), 7.66-7.60 (m, 1H), 7.56 (s, 1H), 7.50-7.37 (m, 2H), 4.74 (s, 2H), 4.33 (s, 2H), 3.91-3.78 (m, 2H), 3.63 (s, 3H), 3.29-3.13 (m, 4H), 3.11 (s, 3H), 1.56-1.28 (m, 5H), 1.26-1.07 (m, 2H). MS (APCI+) m/z 456.1 (M+H)$^+$.

Example 192

4-(10-methyl-7-((methylsulfonyl)methyl)-11-oxo-10,11-dihydro-1H-1,4,10-triazadibenzo[cd,f]azulen-4(3H)-yl)benzonitrile

Example 192a

4-((4-((methylsulfonyl)methyl)phenyl)amino)benzonitrile

A 20 mL microwave vial was charged with 4-aminobenzonitrile (0.121 g, 1.023 mmol), Example 9a (0.2549 g, 1.023 mmol), diacetoxypalladium (9.19 mg, 0.041 mmol), dicyclohexyl(2',4',6'-triisopropyl-[1,1'-biphenyl]-2-yl)phosphine (0.039 g, 0.082 mmol), cesium carbonate (0.467 g, 1.432 mmol), toluene (8.5 mL) and t-butanol (1.7 mL) to give a yellow suspension. The tube was sealed, and the reaction mixture was heated in a Biotage Creator at 150° C. for 15 minutes fixed hold time. The reaction mixture was filtered through a 2 g Celite SPE column and rinsed with ethyl acetate. The filtrate was washed with saturated aqueous sodium chloride, dried over anhydrous magnesium sulfate, filtered, and concentrated. The residue was purified by flash chromatography (20-100% ethyl acetate/heptanes) to provide the title compound (0.100 g, 34% yield).

Example 192b

4-((2-bromo-4-((methylsulfonyl)methyl)phenyl)amino)benzonitrile

In a 250 mL round-bottomed flask was placed Example 192a (0.100 g, 0.349 mmol) in acetic acid (3.49 mL) to give a white suspension. N-bromosuccinimide (0.062 g, 0.349 mmol) was added in 2 portions 10 minutes apart. After the 1st portion of N-bromosucinimide was added, 3 mL dimethylformamide were added. The reaction mixture was stirred at ambient temperature for 4 hours. The reaction mixture was quenched with 30 mL 10% sodium thiosulfate and diluted with water. The reaction mixture was extracted 2× with ethyl acetate. The combined organic layers were washed 2× with 2N NaOH (until the pH of the aqueous was >7) and 1× with saturated aqueous sodium chloride, dried over anhydrous magnesium sulfate, filtered, and concentrated. The residue was purified by flash chromatography (50-100% ethyl acetate/heptanes) to provide the title compound as a white solid (0.1007 g, 79% yield).

Example 192c 4-((2-(6-methyl-7-oxo-1-tosyl-6,7-dihydro-1H-pyrrolo[2,3-c]pyridin-4-yl)-4-((methylsulfonyl)methyl)phenyl)amino)benzonitrile Example 192c was prepared according to the procedure used for the preparation of Example 6b, substituting Example 192b for Example 6a, to provide the title compound as a white solid (0.115 g, 78% yield).

Example 192d 4-((2-(6-methyl-7-oxo-6,7-dihydro-1H-pyrrolo[2,3-c]pyridin-4-yl)-4-((methylsulfonyl)methyl)phenyl)amino)benzonitrile Example 192d was prepared according to the procedure used for the preparation of Example 12d, substituting Example 192c for Example 12c, to provide the title compound (0.0575 g, 68% yield).

Example 192e 4-(10-methyl-7-((methylsulfonyl)methyl)-11-oxo-10,11-dihydro-1H-1,4,10-triazadibenzo[cd,f]azulen-4(3H)-yl)benzonitrile Example 192e was prepared according to the procedure used for the preparation of Example 82, substituting Example 192d for Example 12d, and paraformaldehyde for methyl 4-oxobutanoate to provide the title compound (0.0277 g, 47% yield). $^1$H NMR (400 MHz, DMSO-$d_6$) δ 11.88-11.93 (m, 1H), 7.95 (d, J=1.9 Hz, 1H), 7.64 (s, 1H), 7.48 (dd, J=8.0, 1.9 Hz, 1H), 7.34-7.46 (m, 4H), 6.48-6.58 (m, 2H), 5.28 (d, J=16.3 Hz, 1H), 4.71-4.42 (m, 3H), 3.56 (s, 3H), 3.01 (s, 3H). MS (ESI+) m/z 445.2 (M+H)$^+$.

Example 193

4-(4-chlorophenyl)-10-methyl-7-((methylsulfonyl)methyl)-2-(morpholinomethyl)-3,4-dihydro-1H-1,4,10-triazadibenzo[cd,f]azulen-11(10H)-one

Example 193a 4-(4-chlorophenyl)-10-methyl-7-((methylsulfonyl)methyl)-2-(morpholine-4-carbonyl)-3,4-dihydro-1H-1,4,10-triazadibenzo[cd,f]azulen-11(10H)-one Example 193a was prepared according to the procedure used for the preparation of Example 58m, substituting morpholine for ammonium hydroxide (25% wt/wt in water), to provide the title compound.

Example 193b 4-(4-chlorophenyl)-10-methyl-7-((methylsulfonyl)methyl)-2-(morpholinomethyl)-3,4-dihydro-1H-1,4,10-triazadibenzo[cd,f]azulen-11(10H)-one Example 193b was prepared according to the procedure used for the preparation of Example 146c, substituting Example 193a for Example 146b, to provide the title compound. $^1$H NMR (400 MHz, DMSO-$d_6$) δ 11.90 (s, 1H), 7.89 (s, 1H), 7.60 (s, 1H), 7.49-7.41 (m, 1H), 7.34 (d, J=8.0 Hz, 1H), 6.96 (d, J=9.0 Hz, 2H), 6.42 (d, J=9.0 Hz, 2H), 5.24-5.20 (m, 1H), 4.61-4.38 (m, 3H), 3.80-3.71 (m, 1H), 3.69-3.57 (m, 5H), 3.54 (s, 3H), 3.00 (s, 3H), 2.46-2.36 (m, 4H). MS (ESI+) m/z 553.2 (M+H)$^+$.

Example 194

N-ethyl-4-(4-fluorophenyl)-10-methyl-7-((methylsulfonyl)methyl)-11-oxo-3,4,10,11-tetrahydro-1H-1,4,10-triazadibenzo[cd,f]azulene-2-carboxamide

Example 194a 2-bromo-N-(4-fluorophenyl)-4-((methylsulfonyl)methyl)aniline

A 100 mL flask was charged with Example 58g (2 g, 7.57 mmol), 1-fluoro-4-iodobenzene (3.36 g, 15.14 mmol), palladium(II) acetate (0.085 g, 0.379 mmol), xantphos (0.219 g, 0.379 mmol), Cs$_2$CO$_3$ (2.52 g, 7.72 mmol) and anhydrous dioxane (40 mL) under argon at room temperature. The mixture was heated at 110° C. for 18 hours. After cooling, the reaction mixture was filtered through a pad of Celite and washed with ethyl acetate. The solvent was removed and the residue was purified by silica gel chromatography, eluting with a gradient of 10/1 to 2/1 petroleum ether/ethyl acetate to provide the title compound (1.1 g, 2.9 mmol, 39% yield) as yellow solid.

Example 194b ethyl 1-benzyl-4-(2-((4-fluorophenyl)amino)-5-((methylsulfonyl)methyl)phenyl)-6-methyl-7-oxo-6,7-dihydro-1H-pyrrolo[2,3-c]pyridine-2-carboxylate A mixture of Example 58f (0.8 g, 1.192 mmol), Example 194a (0.498 g, 1.251 mmol), 1,3,5,7-tetramethyl-6-phenyl-2,4,8-trioxa-6-phosphaadamantane (0.035 g, 0.119 mmol), tris(dibenzylideneacetone)dipalladium(0) (0.055 g, 0.060 mmol) and K$_3$PO$_4$ (0.632 g, 2.98 mmol) were combined and sparged with argon for 30 minutes. A solution of 1,4-dioxane (10 mL) and water (2.500 mL) was sparged with nitrogen for 30 minutes and transferred by syringe into the reaction vessel under argon. The reaction mixture was stirred at 60° C. for 4 hours. The mixture was treated with ethyl acetate (150 mL) and water (50 mL) and the undissolved solid was filtered and washed with ethyl acetate several times. The resulting solid was dried under vacuum to afford the title compound (0.58 g, 0.711 mmol, 59.6% yield).

Example 194c ethyl 4-(2-((4-fluorophenyl)amino)-5-((methylsulfonyl)methyl)phenyl)-6-methyl-7-oxo-6,7-dihydro-1H-pyrrolo[2,3-c]pyridine-2-carboxylate A mixture of Example 194b (0.58 g, 0.987 mmol), anisole (0.216 mL, 1.974 mmol) and concentrated $H_2SO_4$ (0.5 mL, 9.38 mmol) in TFA (10 mL, 130 mmol) was heated at 90° C. for 6 hours. Excess TFA was removed under reduced pressure, and the residue was partitioned between water (10 mL) and ethyl acetate (50 mL). The organic layer was separated, and the aqueous layer was extracted with additional ethyl acetate twice (20 mL). The combined organic layers were washed with saturated aqueous sodium bicarbonate (10 mL), followed by saturated aqueous sodium chloride, (10 mL), dried over anhydrous magnesium sulfate, filtered, and concentrated to give the title compound (0.24 g, 0.241 mmol, 24.4% yield).

Example 194d ethyl 4-(4-fluorophenyl)-10-methyl-7-((methylsulfonyl)methyl)-11-oxo-3,4,10,11-tetrahydro-1H-1,4,10-triazadibenzo[cd,f]azulene-2-carboxylate A mixture of Example 194c (0.31 g, 0.623 mmol), HCl (4 M in dioxane) (4 mL, 16.00 mmol) and paraformaldehyde (0.374 g, 12.46 mmol) in methanol (2.5 mL) was heated at 130° C. for 1.5 hours under microwave. The solvent was removed under reduced pressure to provide the title compound.

Example 194e

N-ethyl-4-(4-fluorophenyl)-10-methyl-7-((methylsulfonyl)methyl)-11-oxo-3,4,10,11-tetrahydro-1H-1,4,10-triazadibenzo[cd,f]azulene-2-carboxamide A mixture of Example 194f (150 mg, 0.294 mmol) and ethylamine (25% in ethanol wt/wt) (5 mL, 0.832 mmol) was sealed and heated at 78° C. for 2 day. The reaction mixture was cooled to ambient temperature and concentrated. The residue was purified by reverse phase preparative HPLC (C18, 30-60% acetonitrile in 0.01 N $NH_4CO_3$/water) to give the title compound (25 mg, 0.049 mmol, 16.7% yield). $^1H$ NMR (400 MHz, DMSO-$d_6$) δ 12.15 (brs, 1H), 8.30 (t, J=5.1 Hz, 1H), 7.94 (t, J=8.2 Hz, 1H), 7.69-7.61 (m, 1H), 7.48-7.46 (m, 1H), 7.38 (d, J=7.9 Hz, 1H), 6.88-6.77 (m, 2H), 6.39-6.29 (m, 2H), 6.33-5.88 (m, 1H), 4.81-4.14 (m, 3H), 3.58 (s, 3H), 3.34-3.32 (m, 2H), 3.01 (s, 3H), 1.24-1.15 (m, 3H). MS (ESI+) m/z 509.2 $(M+H)^+$.

Example 195

5-cyclopropyl-4-(2,4-difluorophenyl)-10-methyl-7-((methylsulfonyl)methyl)-3,4-dihydro-1H-1,4,10-triazadibenzo[cd,f]azulen-11(10H)-one

Example 195a 2-cyclopropyl-N-(2,4-difluorophenyl)-4-((methylsulfonyl)methyl)aniline A 5 mL microwave vial was charged with Example 12b (0.2287 g, 0.608 mmol), cyclopropylboronic acid (0.209 g, 2.432 mmol), cesium carbonate (0.990 g, 3.04 mmol) and dichloropalladium (II)bistriphenylphosphine (0.021 g, 0.030 mmol). The tube was sealed, and the mixture was sparged with nitrogen for 30 minutes. Degassed dioxane (2.53 mL) and water (0.507 mL) were added. The reaction mixture was heated to 100° C. overnight. The reaction mixture was partitioned between ethyl acetate and water. The organic layer was washed with saturated aqueous sodium chloride, dried over anhydrous magnesium sulfate, filtered and concentrated. The reaction mixture was purified by flash chromatography (10-70% ethyl acetate/heptanes) to provide the title compound (0.143 g, 70% yield).

Example 195b 2-bromo-6-cyclopropyl-N-(2,4-difluorophenyl)-4-((methylsulfonyl)methyl)aniline A 250 mL round-bottomed flask was charged with Example 195a and acetic acid (1.41 mL) to give a tan solution. N-bromosuccinimide (0.079 g, 0.445 mmol) was added. The reaction mixture was stirred at room temperature for 1.5 hours. The reaction was quenched with sodium thiosulfate (10 mL 10%) and neutralized with saturated aqueous sodium bicarbonate. The reaction mixture was extracted with ethyl acetate (2×). The combined organic layers were washed with saturated aqueous sodium chloried and concentrated. The residue was purified by flash chromatography (silica gel, 10-70% ethyl acetate/heptanes) to provide the title compound (0.111 g, 63% yield).

Example 195c 4-(3-cyclopropyl-2-((2,4-difluorophenyl)amino)-5-((methylsulfonyl)methyl)phenyl)-6-methyl-1-tosyl-1H-pyrrolo[2,3-c]pyridin-7(6H)-one A 250 mL round-bottomed flask was charged with Example 195b (0.111 g, 0.268 mmol), Example 1f (0.104 g, 0.243 mmol), sodium carbonate (0.090 g, 0.851 mmol), tris(dibenzylideneacetone)dipalladium (0) (0.011 g, 0.012 mmol), and 1,3,5,7-tetramethyl-6-phenyl-2,4,8-trioxa-6-phosphaadamantane (0.012 g, 0.041 mmol). The solids were sparged with nitrogen for 30 minutes. Degassed dioxane (1.946 mL) and water (0.487 mL) were added. The reaction mixture was heated at 60° C. for 3 hours. The reaction mixture was cooled to room temperature and partitioned between ethyl acetate and water. The organic layer was washed with saturated aqueous sodium chloride, dried over anhydrous magnesium sulfate, filtered, and concentrated. The residue was purified by flash chromatography (silica gel, 0-5% methanol/dichloromethane) to provide the title compound. (0.155 g, 100% yield).

Example 195d 4-(3-cyclopropyl-2-((2,4-difluorophenyl)amino)-5-((methylsulfonyl)methyl)phenyl)-6-methyl-1H-pyrrolo[2,3-c]pyridin-7(6H)-one A 100 mL round-bottomed flask was charged with Example 195c (0.1553 g, 0.244 mmol), lithium hydroxide hydrate (0.102 g, 2.435 mmol), dioxane (1.826 mL) and water (0.609 mL). The reaction mixture was heated at 50° C. overnight. The reaction mixture was cooled to room temperature and partitioned between ethyl acetate and water. The aqueous layer was extracted with ethyl acetate. The combined organic layers were washed with saturated aqueous sodium chloride, dried over anhydrous magnesium sulfate, filtered, and concentrated. The residue was purified by flash chromatography (silica gel, 0-5% methanol/dichloromethane) to provide the title compound. (0.0792 g, 67% yield).

Example 195e 5-cyclopropyl-4-(2,4-difluorophenyl)-10-methyl-7-((methylsulfonyl)methyl)-3,4-dihydro-1H-1,4,10-triazadibenzo[cd,f]azulen-11(10H)-one A 250 mL round-bottomed flask was charge with Example 195d (0.0792 g, 0.164 mmol), paraformaldehyde (0.074 g, 0.819 mmol) and tetrahydrofuran (1.638 mL). Titanium (IV) chloride (0.328 mL, 0.328 mmol) was added. The reaction mixture was stirred at room temperature for 1 hour. The reaction mixture was partitioned between ethyl acetate and water. The organic layer was washed with saturated aqueous sodium chloride, and dried over anhydrous magnesium sulfate and mercaptopropyl silica gel for 1 hour. The slurry was filtered through a 10 g Celite SPE column and concentrated. The residue was purified by flash chromatography (silica gel, 0-5% methanol/dichloromethane) to provide the title compound. (0.0609 g, 75% yield). 1H NMR (400 MHz, DMSO-$d_6$) δ 11.79-11.84 (m, 1H), 7.67 (d, J=2.0 Hz, 1H), 7.63 (s, 1H), 7.21 (d, J=2.5 Hz, 1H), 6.96-7.05 (m, 1H), 6.95 (d, J=1.8 Hz, 1H), 6.59-6.68 (m, 1H), 6.24-6.34 (m, 1H), 5.76 (s, 2H), 5.19 (d, J=16.3 Hz, 1H), 4.35-4.56 (m, 3H), 3.59 (s, 3H), 2.95 (s, 3H), 2.07-2.18 (m, 1H), 0.83-0.94 (m, 1H), 0.62-0.72 (m, 2H), 0.28-0.37 (m, 1H). MS (ESI+) m/z 496.1 (M+H)$^+$.

Example 196 tert-butyl (4-(10-methyl-7-((methylsulfonyl)methyl)-11-oxo-10,11-dihydro-1H-1,4,10-triazadibenzo[cd,f]azulen-4(3H)-yl)cyclohexyl)carbamate A mixture of Example 5f (0.262 g, 0.763 mmol) and tert-butyl (4-oxocyclohexyl)carbamate (0.332 g, 1.526 mmol) in dichloromethane (17 mL) was treated with acetic acid (0.437 mL, 7.630 mmol). The reaction mixture was stirred 60° C. for 1.5 hours, and then cooled to 0° C. and treated with sodium triacetoxyborohydride (0.340 g, 1.526 mmol). The reaction mixture was removed from 0° C. ice bath and stirred at ambient temperature for 18 hours. The reaction mixture was quenched by slow addition of saturated sodium bicarbonate solution and then extracted three times with ethyl acetate. The combined organic layers were washed with saturated aqueous sodium chloride, dried over anhydrous magnesium sulfate, filtered and concentrated. The residue was purified by flash column chromatography on silica gel, eluting with 1% methanol in dichloromethane to afford the title compound as a mixture of cis and trans isomers (0.304 g, 0.543 mmol, 74% yield). $^1$H NMR (400 MHz, DMSO-$d_6$) δ 11.87-11.77 (m, 2H), 7.73-7.66 (m, 2H), 7.59-7.52 (m, 2H), 7.31-7.12 (m, 6H), 6.81-6.70 (m, 1H), 6.53-6.48 (m, 1H), 4.54-4.30 (m, 6H), 4.10-3.90 (m, 2H), 3.67-3.57 (m, 6H), 3.30-3.23 (m, 1H), 3.16-3.06 (m, 1H), 2.94 (s, 6H), 2.78-2.68 (m, 1H), 2.62-2.55 (m, 1H), 1.96-1.47 (m, 8H), 1.39-1.32 (m, 18H), 1.26-1.13 (m, 6H), 0.95-0.85 (m, 2H).). MS (ESI+) m/z 541.2 (M+H)$^+$.

Example 197 tert-butyl ((trans)-4-(10-methyl-7-((methylsulfonyl)methyl)-11-oxo-10,11-dihydro-1H-1,4,10-triazadibenzo[cd,f]azulen-4(3H)-yl)cyclohexyl)carbamate Example 196 (0.025 mg, 0.046 mmol), a mixture of cis and trans isomers, was purified by reverse phase HPLC (C18, CH$_3$CN/water (0.1% TFA), 5-70% gradient). Fractions of the first eluted isomer were collected, concentrated, and held under vacuum to remove residual trifluoroacetic acid to give the title compound (0.008 g, 0.015 mmol). $^1$H NMR (500 MHz, DMSO-$d_6$) δ 11.81 (s, 1H), 7.69 (s, 1H), 7.55 (s, 1H), 7.24-7.21 (m, 1H), 7.18-7.12 (m, 2H), 6.51 (d, J=8.0 Hz, 1H), 4.45 (bs, 4H), 3.62 (s, 3H), 3.15-3.06 (m, 1H), 2.94 (s, 3H), 2.58 (t, J=10.9 Hz, 1H), 1.81-1.55 (m, 4H), 1.33 (s, 9H), 1.20-1.16 (m, 2H), 0.94-0.87 (m, 2H). MS (ESI+) m/z 541.0 (M+H)$^+$.

Example 198

4-(4-chlorophenyl)-10-methyl-7-((methylsulfonyl)methyl)-3,4-dihydro-1H-1,4,10-triazadibenzo[cd,f]azulen-11(10H)-one

Example 198a 4-chloro-N-(4-((methylsulfonyl)methyl)phenyl)aniline

A 20 mL microwave vial was charged with 4-chloroaniline (0.129 g, 1.012 mmol), Example 9a (0.2522 g, 1.012 mmol), diacetoxypalladium (9.09 mg, 0.040 mmol), dicyclohexyl(2',4',6'-triisopropyl-[1,1'-biphenyl]-2-yl)phosphine (0.039 g, 0.081 mmol), cesium carbonate (0.462 g, 1.417 mmol), toluene (8.44 mL) and tert-butanol (1.687 mL). The tube was sealed, and the reaction mixture was heated in a Biotage Creator microwave at 150° C. for 15 minutes fixed hold time. The reaction mixture was filtered through a Celite SPE column (2 g) and rinsed with ethyl acetate. The reaction mixture was washed with saturated aqueous sodium chloride, dried over anhydrous magnesium sulfate, filtered, and concentrated. The residue was purified by flash chromatography (silica gel, 20-100% ethyl acetate/heptanes) to provide the title compound. (0.255 g, 85% yield).

Example 198b 2-bromo-N-(4-chlorophenyl)-4-((methylsulfonyl)methyl)aniline

A 250 mL round-bottomed flask was charged with Example 198a (0.2553 g, 0.863 mmol) and acetic acid (8.63 mL). N-bromosuccinimide (0.154 g, 0.863 mmol) was added in 2 portions 10 minutes apart. The reaction mixture was stirred at room temperature for 4 hours. The reaction mixture was quenched with sodium thiosulfate (30 mL, 10%) and diluted with water. The reaction mixture was extracted with ethyl acetate (2×). The combined organic layers were washed with 2N sodium hydroxide until the pH of the aqueous was >7, followed by washing with saturated aqueous sodium chloride, dried over anhydrous magnesium sulfate, filtered, and concentrated. The residue was purified by flash chromatography (silica gel, 50-100% ethyl acetate/heptanes) to provide the title compound. (0.198 g, 61% yield).

Example 198c

4-(2-((4-chlorophenyl)amino)-5-((methylsulfonyl)methyl)phenyl)-6-methyl-1-tosyl-1H-pyrrolo[2,3-c]pyridin-7(6H)-one A 250 mL round-bottomed flask was charged with Example 198b (0.1981 g, 0.529 mmol), Example 1f (0.206 g, 0.481 mmol), sodium carbonate (0.178 g, 1.682 mmol), tris(dibenzylideneacetone)dipalladium (0) (0.022 g, 0.024 mmol), and 1,3,5,7-tetramethyl-6-phenyl-2,4,8-trioxa-6-phosphaadamantane (0.024 g, 0.082 mmol). The solids were flow purged with nitrogen for 1 hour. Degassed dioxane (4.0 mL) and water (1.0 mL) were added. The reaction mixture was heated at 60° C. for 3 hours. The reaction mixture was cooled to room temperature and partitioned between ethyl acetate and water. The organic layer was washed with saturated aqueous sodium chloride, dried over anhydrous magnesium sulfate, filtered and concentrated. The residue was purified by flash chromatography (0-5% methanol/dichloromethane) to provide a tan solid. The solid was triturated with dichloromethane and heptanes and filtered to provide the title compound. (0.167 g, 58% yield).

Example 198d

4-(2-((4-chlorophenyl)amino)-5-((methylsulfonyl)methyl)phenyl)-6-methyl-1H-pyrrolo[2,3-c]pyridin-7(6H)-one A 4 mL vial was charged with Example 198c (0.1673 g, 0.281 mmol), lithium hydroxide hydrate (0.118 g, 2.81 mmol), dioxane (1.40 mL) and water (0.47 mL). The reaction mixture was heated at 50° C. overnight. The reaction mixture was cooled to room temperature and partitioned between water and ethyl acetate. The organic layer was washed with saturated aqueous sodium chloride, dried over anhydrous magnesium sulfate, filtered, and concentrated. The residue was purified by flash chromatography (silica gel, 0-5% methanol/dichloromethane) to provide the title compound. (0.0795 g, 64% yield).

Example 198e

4-(4-chlorophenyl)-10-methyl-7-((methylsulfonyl)methyl)-3,4-dihydro-1H-1,4,10-triazadibenzo[cd,f]azulen-11(10H)-one A 250 mL round-bottomed flask was charged with Example 198d (0.0794 g, 0.180 mmol). paraformaldehyde (0.081 g, 0.898 mmol), and tetrahydrofuran (1.797 mL). Titanium (IV) chloride (0.359 mL, 0.359 mmol) was added. The reaction mixture was stirred at room temperature for 1 hour. The reaction mixture was partitioned between ethyl acetate and water. The organic layer was washed with saturated aqueous sodium chloride, dried over anhydrous magnesium sulfate, filtered, and concentrated. The residue was purified by flash chromatography (silica gel, 0-5% methanol/dichloromethane) to provide the title compound (0.0596 g, 73% yield). $^1$H NMR (400 MHz, DMSO-$d_6$) δ 11.86 (bs, 1H), 7.92 (d, J=2.0 Hz, 1H), 7.61 (s, 1H), 7.45 (dd, J=7.9, 1.9 Hz, 1H), 7.34 (d, J=5.5 Hz, 2H), 6.98 (d, J=9.1 Hz, 2H), 6.42 (d, J=9.0 Hz, 2H), 5.13 (s, 1H), 4.37-4.66 (m, 3H), 3.56 (s, 3H), 3.00 (s, 3H). MS (ESI+) m/z 454.1 (M+H)$^+$.

Example 199

4-(4-chlorophenyl)-10-methyl-7-((methylsulfonyl)methyl)-11-oxo-3,4,10,11-tetrahydro-1H-1,4,10-triazadibenzo[cd,f]azulene-2-carbonitrile To the suspension of Example 58m (50 mg, 0.101 mmol) and triethylamine (0.028 mL, 0.201 mmol) in tetrahydrofuran (1 mL) at 0° C. was added trifluoroacetic anhydride (0.043 mL, 0.302 mmol) dropwise and the reaction mixture was stirred at ambient temperature for further 60 minutes. The solvent was removed and the residue was purified by reverse phase HPLC (C8 column, CH$_3$CN/water (0.01 N ammonium carbonate, 25%-55%) to give the title compound (5 mg, 10.44 μmol, 10% yield) as grey solid. $^1$H NMR (400 MHz, DMSO-$d_6$) δ 13.36 (s, 1H), 7.94 (s, 1H), 7.76 (s, 1H), 7.50 (d, J=9.5 Hz, 1H), 7.39 (d, J=8.1 Hz, 1H), 7.06 (d, J=9.0 Hz, 2H), 6.35 (d, J=9.0 Hz, 2H), 5.23-5.13 (m, 1H), 4.70-4.47 (m, 3H), 3.58 (s, 3H), 3.01 (s, 3H). MS (ESI+) m/z 479.0 (M+H)$^+$.

Example 200

4-(2,4-difluorophenyl)-3-(hydroxymethyl)-10-methyl-7-((methylsulfonyl)methyl)-3,4-dihydro-1H-1,4,10-triazadibenzo[cd,f]azulen-11(10H)-one

Example 200a ethyl 4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxylate Example 12d (89 mg, 0.20 mmol) and ethyl 2-oxoacetate (0.119 mL, 0.600 mmol) were combined in tetrahydrofuran (2 mL). To this suspension was added 1M titanium(IV) chloride in dichloromethane (0.400 mL, 0.400 mmol). The reaction mixture was stirred at ambient temperature for 20 hours, and partitioned with ethyl acetate and water. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (78 mg, 74%).

Example 200b

4-(2,4-difluorophenyl)-3-(hydroxymethyl)-10-methyl-7-((methylsulfonyl)methyl)-3,4-dihydro-1H-1,4,10-triazadibenzo[cd,f]azulen-11(10H)-one To a solution of Example 200a (76.0 mg, 0.144 mmol) in tetrahydrofuran (2 mL) was added 1.0 M lithium aluminum hydride in tetrahydrofuran (0.144 mL, 0.144 mmol) dropwise at 0° C. The reaction mixture was stirred at ambient temperature for 2 hours, and partitioned with ethyl acetate and water. The organic layer was washed with saturated aqueous sodium chloride, dried with anhydrous sodium sulfate, filtered, and concentrated. The residue was purified by flash chromatography (silica gel, 2-5% methanol in dichloromethane) to provide the title compound (45 mg, 64%). $^1$H NMR (400 MHz, DMSO-$d_6$) δ 11.90 (d, J=2.1 Hz, 1H), 7.78 (d, J=1.8 Hz, 1H), 7.66 (s, 1H), 7.60-7.49 (m, 1H), 7.21-7.14 (m, 2H), 7.06-6.96 (m, 2H), 6.90 (d, J=8.8 Hz, 1H), 5.18 (dd, J=9.2, 5.4 Hz, 1H), 4.99 (t, J=4.6 Hz, 1H), 4.52-4.39 (m, 2H), 3.64 (s, 3H), 3.48-3.34 (m, 2H), 2.93 (s, 3H). MS (ESI+) m/z 486 (M+H)+.

Example 201

4-(4-chlorophenyl)-10-methyl-11-oxo-3,4,10,11-tetrahydro-1H-1,4,10-triazadibenzo[cd,f]azulene-2-carbonitrile Example 201a 4-(4-chlorophenyl)-10-methyl-11-oxo-3,4,10,11-tetrahydro-1H-1,4,10-triazadibenzo[cd,f]azulene-2-carboxylic acid Example 201a was prepared according to the procedure used for the preparation of Example 58l, substituting Example 127d for Example 58k, to provide the title compound.

Example 201b 4-(4-chlorophenyl)-10-methyl-11-oxo-3,4,10,11-tetrahydro-1H-1,4,10-triazadibenzo[cd,f]azulene-2-carboxamide Example 201b was prepared according to the procedure used for the preparation of Example 58m, substituting Example 201a for Example 58l, to provide the title compound.

Example 201c 4-(4-chlorophenyl)-10-methyl-11-oxo-3,4,10,11-tetrahydro-1H-1,4,10-triazadibenzo[cd,f]azulene-2-carbonitrile Example 201c was prepared according to the procedure used for the preparation of Example 199, substituting Example 201b for Example 58m, to provide the title compound. $^1$H NMR (400 MHz, DMSO-$d_6$) δ 7.92 (d, J=7.8 Hz, 1H), 7.84 (s, 1H), 7.52-7.47 (m, 2H), 7.36 (d, J=7.6 Hz, 1H), 7.05 (d, J=9.1 Hz, 2H), 6.33 (d, J=9.1 Hz, 2H), 5.20-5.15 (m, 1H), 4.66-4.63 (m, 1H), 3.57 (s, 3H). MS (ESI+) m/z 387.1 (M+H)+.

Example 202

4-(2,4-difluorophenyl)-N-ethyl-10-methyl-7-((methylsulfonyl)methyl)-11-oxo-3,4,10,11-tetrahydro-1H-1,4,10-triazadibenzo[cd,f]azulene-2-carboxamide A mixture of Example 208i (250 mg, 0.289 mmol) and ethylamine (25% in ethanol wt/wt) (5 mL, 1.386 mmol) was sealed and heated at 78° C. for 2 days. The mixture was cooled to ambient temperature and the resulting solid was collected by filtration and washed with methanol several times. The solid was then purified by reverse phase preparative HPLC (C18, 30-60% acetonitrile/0.01 N NH$_4$CO$_3$ in water) to give the title compound (30 mg, 0.057 mmol, 19.71% yield) as white solid. $^1$H NMR (400 MHz, DMSO-$d_6$) δ 12.15 (s, 1H), 8.26 (d, J=4.8 Hz, 1H), 7.82 (d, J=1.7 Hz, 1H), 7.71 (s, 1H), 7.29-7.22 (m, 1H), 7.21-7.07 (m, 1H), 7.02-6.89 (m, 3H), 5.15 (brs, 1H), 4.49 (s, 2H), 3.66 (s, 3H), 3.29-3.26 (m, 3H), 2.96 (s, 3H), 1.14 (t, J=7.3 Hz, 3H). MS (ESI+) m/z 527.2 (M+H)+.

Example 203

4-(4-cyanophenyl)-N-ethyl-10-methyl-7-((methylsulfonyl)methyl)-11-oxo-3,4,10,11-tetrahydro-1H-1,4,10-triazadibenzo[cd,f]azulene-2-carboxamide A mixture of Example 59 (100 mg, 0.190 mmol), potassium hexacyanoferrate(II) trihydrate (17.70 mg, 0.042 mmol), Pd$_2$(dba)$_3$ (8.72 mg, 9.52 μmol), dicyclohexyl(2',4',6'-triisopropyl[1,1'-biphenyl]-2-yl)phosphine (X-Phos) (9.08 mg, 0.019 mmol), palladium(II) acetate (4.28 mg, 0.019 mmol) and Cs$_2$CO$_3$ (93 mg, 0.286 mmol) in dioxane (6 mL) and water (1.5 mL) was sealed and heated at 130° C. under microwave for 3 hours. The reaction mixture was filtered through Celite and washed with ethyl acetate and then concentrated. The residue was purified by reverse phase HPLC (C18, CH$_3$CN/water (0.01N ammonium carbonate), 25-55% gradient) to give the title compound (8.4 mg, 0.016 mmol, 8.55% yield) as pale solid. $^1$H NMR (400 MHz, DMSO-$d_6$) δ 12.28 (s, 1H), 8.35 (t, J=5.0 Hz, 1H), 7.96 (d, J=1.7 Hz, 1H), 7.71 (s, 1H), 7.52-7.49 (m, 1H), 7.45-7.37 (m, 3H), 6.47 (d, J=7.6 Hz, 2H), 5.98 (d, J=17.0 Hz, 1H), 4.67-4.63 (m, 1H), 4.54 (d, J=2.3 Hz, 1H), 4.51-4.50 (m, 1H), 3.59 (s, 3H), 3.42-3.36 (m, 2H), 3.02 (s, 3H), 1.20 (t, J=7.3 Hz, 3H). MS (ESI+) m/z 516.2 (M+H)+.

Example 204

(S)-2-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)isoindoline-1,3-dione Preparatory chiral SFC separation of the product from Example 117 (0.019 g) on an (S,S) WHELK-O 1 column (21 mm×250 mm, 5 micron) eluting with a 4:6 mixture of 0.1% diethylamine in methanol/carbon dioxide afforded the title compound. The stereochemistry was randomly assigned to this first eluted peak (5.004 minutes, 98% ee, 5.1 mg, 64% recovery). %). $^1$H NMR (500 MHz, DMSO-$d_6$) δ 11.78 (d, J=1.83 Hz, 1H), 7.93 (d, J=1.53 Hz, 1H), 7.81-7.86 (m, 4H), 7.76 (s, 1H), 7.24-7.30 (m, 1H), 7.21 (dd, J=8.24, 1.83 Hz, 1H), 7.09-7.15 (m, 1H) 6.99-7.05 (m, 1H), 6.96 (d, J=2.44 Hz, 1H), 6.92 (d, J=8.24 Hz, 1H), 5.44 (dd, J=9.92, 5.34 Hz, 1H), 4.51-4.56 (m, 1H), 4.44-4.48 (m, 1H), 3.87 (dd, J=13.28, 5.34 Hz, 1H), 3.66 (s, 3H), 3.52 (dd, J=13.28, 10.22 Hz, 1H), 2.98 (s, 3H). MS (ESI+) m/z 615 (M+H)+.

Example 205

(R)-2-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)isoindoline-1,3-dione Preparatory chiral SFC separation of the product from Example 117 (0.019 g) on an (S,S) WHELK-O 1 column (21 mm×250 mm, 5 micron) eluting with a 4:6 mixture of 0.1% diethylamine in methanol/carbon dioxide afforded the title compound. The stereochemistry was randomly assigned to this second eluted peak (5.732 minutes, >99% ee, 5.6 mg, 70% recovery). $^1$H NMR (500 MHz, DMSO-$d_6$) δ 11.78 (d, J=1.83 Hz, 1H), 7.93 (d, J=1.53 Hz, 1H), 7.81-7.86 (m, 4H), 7.76 (s, 1H), 7.24-7.30 (m, 1H), 7.21 (dd, J=8.24, 1.83 Hz, 1H), 7.09-7.15 (m, 1H) 6.99-7.05 (m, 1H), 6.96 (d, J=2.44 Hz, 1H), 6.92 (d, J=8.24 Hz, 1H), 5.44 (dd, J=9.92, 5.34 Hz, 1H), 4.51-4.56 (m, 1H), 4.44-4.48 (m, 1H), 3.87 (dd, J=13.28, 5.34 Hz, 1H), 3.66 (s, 3H), 3.52 (dd, J=13.28, 10.22 Hz, 1H), 2.98 (s, 3H). MS (ESI+) m/z 615 (M+H)+.

Example 206

4-(2,4-difluorophenyl)-10-methyl-7-((methylsulfonyl)methyl)-11-oxo-3,4,10,11-tetrahydro-1H-1,4,10-triazadibenzo[cd,f]azulene-5-carbonitrile

Example 206a 2,6-dibromo-N-(2,4-difluorophenyl)-4-((methylsulfonyl)methyl)aniline A 500 mL round-bottomed flask was charged with Example 12a (3.000 g, 7.97 mmol) and trifluoroacetic acid (80 mL) to give a colorless solution. The reaction mixture was cooled to 0° C. N-bromosuccinimide (1.419 g, 7.97 mmol) was added in two portions 10 minutes apart. The cold bath was removed, and the reaction mixture was stirred at ambient temperature for 2 hours. The solvent was removed, and 200 mL 2N sodium hydroxide, 50 mL 10% sodium thiosulfate, and 200 mL ethyl acetate were added. The reaction mixture was stirred for 30 minutes. The layers were separated, and the organic layer was washed with saturated aqueous sodium chloride, dried over anhydrous magnesium sulfate, filtered, and concentrated onto silica gel. The reaction mixture was purified by flash chromatography (20-100% ethyl acetate:heptanes) to provide a white solid (2.48 g, 68%).

Example 206b 4-(3-bromo-2-((2,4-difluorophenyl)amino)-5-((methylsulfonyl)methyl)phenyl)-6-methyl-1-tosyl-1H-pyrrolo[2,3-c]pyridin-7(6H)-one Example 206b was prepared according to the procedure used for the preparation of Example 6b, substituting Example 206a for Example 6a, to provide the title compound as a yellow solid (0.0872 g, 50% yield).

Example 206c 4-(3-bromo-2-((2,4-difluorophenyl)amino)-5-((methylsulfonyl)methyl)phenyl)-6-methyl-1H-pyrrolo[2,3-c]pyridin-7(6H)-one Example 206c was prepared according to the procedure used for the preparation of Example 12d, substituting Example 206b for Example 12c, to provide the title compound as a red oil (0.0552 g, 44% yield).

Example 206d 5-bromo-4-(2,4-difluorophenyl)-10-methyl-7-((methylsulfonyl)methyl)-3,4-dihydro-1H-1,4,10-triazadibenzo[cd,f]azulen-11(10H)-one Example 206d was prepared according to the procedure used for the preparation of Example 82, substituting Example 206c for Example 12d, to provide the title compound as a yellow solid (0.0352 g, 62% yield).

Example 206e 4-(2,4-difluorophenyl)-10-methyl-7-((methylsulfonyl)methyl)-11-oxo-3,4,10,11-tetrahydro-1H-1,4,10-triazadibenzo[cd,f]azulene-5-carbonitrile A 2 mL microwave tube was charged with zinc (II) cyanide (0.012 g, 0.099 mmol) and dichlorobis(triphenylphosphine)palladium(II) (4.62 mg, 6.59 µmol). Example 206d (0.0352 g, 0.066 mmol) and N,N-dimethylformamide (0.659 mL) were added. The tube was sealed, and the reaction mixture was heated in a Biotage Creator at 200° C. for 30 minutes fixed hold time. The reaction mixture was partitioned between ethyl acetate and water. The organic layer was washed with saturated aqueous sodium chloride, dried over anhydrous magnesium sulfate and mercaptopropyl silica gel, filtered and concentrated. The reaction mixture was purified by flash chromatography (0-5% methanol: dichloromethane) to provide a white solid (0.0209 g, 66% yield). $^1$H NMR (500 MHz, DMSO-$d_6$) δ 11.95 (bs, 1H), 8.24 (d, J=2.0 Hz, 1H), 7.81 (s, 1H), 7.78 (d, J=1.9 Hz, 1H), 7.24 (s, 1H), 6.99-7.20 (m, 1H), 6.73 (td, J=8.5, 2.8 Hz, 1H), 6.45 (td, J=9.5, 5.8 Hz, 1H), 5.05-5.14 (m, 1H), 4.43-4.80 (m, 3H), 3.62 (s, 3H), 3.02 (s, 3H). MS (ESI+) m/z 481.0 (M+H)+.

Example 207

10-methyl-7-((methylsulfonyl)methyl)-4-(pyridin-2-yl)-3,4-dihydro-1H-1,4,10-triazadibenzo[cd,f]azulen-11(10H)-one

Example 207a 4-(2-amino-5-((methylsulfonyl)methyl)phenyl)-6-methyl-1-tosyl-1H-pyrrolo[2,3-c]pyridin-7(6H)-one Example 1f (2.0 g, 4.67 mmol), Example 5c (1.6 g, 5.14 mmol), tris(dibenzylideneacetone)dipalladium(0) (0.128 g, 0.14 mmol), 1,3,5,7-tetramethyl-8-phenyl-2,4,6-trioxa-8-phosphaadamantane (0.136 g, 0.467 mmol) and sodium carbonate (2.13 g, 20.1 mmol) were combined and sparged with nitrogen for 30 minutes. To this mixture were added nitrogen-sparged 1,4-dioxane (24 mL) and water (6 mL) via syringe. The reaction mixture was stirred at 60° C. for 5 hours, cooled to ambient temperature and partitioned between ethyl acetate and water. The organic layer was washed with saturated aqueous sodium chloride, treated with 3-mercaptopropyl-functionalized silica gel for 20 minutes, dried over anhydrous magnesium sulfate, filtered through a plug of Celite, and concentrated. The residue was purified by flash chromatography (silica gel, 0-100% ethyl acetate in dichloromethane). The product was further purified by trituration with diethyl ether and then dried in a vacuum oven at 70° C. to give 2.06 g (91%) of the title compound.

Example 207b 6-methyl-4-(5-((methylsulfonyl)methyl)-2-(pyridin-2-ylamino)phenyl)-1-tosyl-1H-pyrrolo[2,3-c]pyridin-7(6H)-one Example 207a (0.4 g, 0.824 mmol), 2-bromopyridine (0.325 g, 2.06 mmol), diacetoxypalladium (0.046 g, 0.206 mmol), dicyclohexyl(2',4',6'-triisopropyl-[1,1'-biphenyl]-2-yl)phosphine (0.196 g, 0.412 mmol) and cesium carbonate (0.537 g, 1.65 mmol) were combined in a 20-mL microwave vial equipped with a magnetic stirbar. Toluene (6.6 mL) and tert-butanol (1.65 mL) were added and the mixture was reacted in a Biotage microwave reactor at 160° C. for 1 hour. The reaction sequence was repeated and then the two reaction mixtures were combined and filtered through a fritted funnel to remove the Pd solids. The filtrate was partitioned between ethyl acetate and water. The organic layer was washed with saturated aqueous sodium chloride, treated with 3-mercaptopropyl-functionalized silica gel for 20 minutes, dried over anhydrous magnesium sulfate, filtered through a plug of Celite, and concentrated. The residue was purified by flash chromatography (silica gel, 0-50% ethyl acetate in dichloromethane and then 5-7% methanol in dichloromethane) to give 0.211 g (23%) of the title compound.

Example 207c 6-methyl-4-(5-((methylsulfonyl)methyl)-2-(pyridin-2-ylamino)phenyl)-1H-pyrrolo[2,3-c]pyridin-7(6H)-one A mixture of Example 207b (0.21 g, 0.373 mmol) in 1,4-dioxane (5 mL) and water (1.7 mL) was treated with lithium hydroxide.H$_2$O (0.157 g, 3.73 mmol) and N,N,N-trimethylhexadecan-1-aminium bromide (0.0041 g, 0.011 mmol) and heated at 63° C. for 3.5 hours, stirred at ambient temperature overnight and then heated at 75° C. for another 1.5 hours. The reaction mixture was cooled to ambient temperature and neutralized with hydrochloric acid solution (2 N aqueous). The resulting mixture was then partitioned between ethyl acetate and water, washed with saturated aqueous sodium chloride, dried over anhydrous magnesium sulfate, filtered and concentrated. The residue was purified by flash chromatography (silica gel, 0-25% methanol in dichloromethane) to give 0.15 g (99%) of the title compound.

Example 207d 10-methyl-7-((methylsulfonyl)methyl)-4-(pyridin-2-yl)-3,4-dihydro-1H-1,4,10-triazadibenzo[cd,f]azulen-11(10H)-one To a 5-mL microwave vial equipped with a magnetic stirbar was added Example 207c (0.15 g, 0.367 mmol), paraformaldehyde (0.033 g, 1.1 mmol), and acetic acid (7.3 mL). The vial was capped and heated at 75° C. for 55 minutes. A second reaction mixture was run as follows. To a 5-mL microwave vial equipped with a magnetic stirbar was added Example 207c (0.082 g, 0.2 mmol), paraformaldehyde (0.018 g, 0.6 mmol), and acetic acid (4 mL). The vial was capped and heated at 75° C. for 45 minutes. The reaction mixtures were combined and concentrated. To the residue was added 1,4-dioxane (5.7 mL) and sodium hydroxide solution (4 N aqueous) (1.4 mL, 5.67 mmol). The reaction mixture heated at 60° C. for 1 hour, cooled to ambient temperature and neutralized with hydrochloric acid solution (2 N aqueous). The resulting mixture was then partitioned between ethyl acetate and water and washed with saturated aqueous sodium chloride. The combined aqueous layers were extracted with ethyl acetate until no product was detected. The organic layers were combined, dried over anhydrous magnesium sulfate, filtered and concentrated. The residue was purified by reverse phase HPLC (C18, acetonitrile/water (0.1% TFA), 10-60%) to provide 0.271 g (89%) of the title compound as the TFA salt. $^1$H NMR (500 MHz, DMSO-d$_6$) δ 11.84 (d, J=1.53 Hz, 1H), 7.98 (dd, J=4.88, 1.22 Hz, 1H), 7.91 (d, J=1.83 Hz, 1H), 7.63 (s, 1H), 7.43 (m, 1H), 7.36 (d, J=7.93 Hz, 1H), 7.29 (m, 2H), 6.51 (ddd, J=7.02, 4.88, 0.61 Hz, 1H), 6.16 (d, J=8.24 Hz, 1H), 5.79 (d, J=15.56 Hz, 1H), 4.62 (d, 1H), 4.52 (d, 1H), 4.24 (d, J=15.56 Hz, 1H), 3.57 (s, 3H), 3.01 (s, 3H). MS (ESI+) m/z 421.1 (M+H)$^+$.

Example 208 ethyl 4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxylate Example 208a 4-bromo-7-methoxy-1H-pyrrolo[2,3-c]pyridine To a solution of 5-bromo-2-methoxy-3-nitropyridine (50 g, 215 mmol) in tetrahydrofuran (2000 mL) was added vinyl-magnesium bromide (800 mL, 644 mmol) dropwise at −70° C., and the mixture was stirred between −70° C. and −60° C. for 2 hours. The reaction mixture was quenched with 20% aqueous NH$_4$Cl, extracted with ethyl acetate, dried over anhydrous Na$_2$SO$_4$, filtered, and concentrated under reduced pressure to get a brown residue. This material was purified by column chromatography on silica gel (eluted with petroleum ether: ethyl acetate=10:1) to give a crude product, which was triturated with dichloromethane and dried under vacuum to give the title compound (20 g, 41.1% yield) as a light yellow solid.

Example 208b 4-bromo-7-methoxy-1-tosyl-1H-pyrrolo[2,3-c]pyridine

To a solution of Example 208a (44 g, 194 mmol) in tetrahydrofuran (600 mL) was added sodium hydride (6.98 g, 290 mmol) portion-wise at 0° C. The mixture was stirred for 1 hour. Then 4-methylbenzene-1-sulfonyl chloride (55.4 g, 290 mmol) was added to the mixture portion-wise at 0° C. After stirring at ambient temperature for 2 hours, the reaction mixture was quenched with 20% aqueous ammonium chloride. The mixture was extracted with ethyl acetate three times and partitioned. The combined organic layers were dried (anhydrouse sodium sulfate), and filtered. The filtrate was concentrated in vacuum to afford a residue which was recrystallized from ethyl acetate and petroleum ether to give the title compound (52 g, 70.4% yield) as light yellow solid.

Example 208c ethyl 4-bromo-7-methoxy-1-tosyl-1H-pyrrolo[2,3-c]pyridine-2-carboxylate To a solution of Example 208b (10.5 g, 27.5 mmol) in tetrahydrofuran (170 mL) was added dropwise lithium diisopropylamide (20.7 mL, 41.40 mmol) at −70° C. and the reaction mixture was stirred between −70° C. and −50° C. for 45 minutes. To the stirred resulting mixture at −70° C. was added ethyl carbonochloridate (4.48 g, 41.3 mmol) dropwise. The reaction mixture was stirred at −70° C. for 1.5 hours, quenched with 20% aqueous ammonium chloride, and extracted with ethyl acetate (150 mL). The combined organic layer was dried over anhydrous sodium sulfate, filtered, and concentrated in vacuum to give the crude product, which was washed with dichloromethane to give the title compound (10 g, 80%) as a white solid.

Example 208d ethyl 4-bromo-7-oxo-1-tosyl-6,7-dihydro-1H-pyrrolo[2,3-c]pyridine-2-carboxylate To a mixture of Example 208c (32.5 g, 71.7 mmol) and sodium iodide (16.12 g, 108 mmol) in acetonitrile (554 mL) was added chlorotrimethylsilane (11.68 g, 108 mmol) dropwise at ambient temperature. The resulting mixture was stirred at ambient temperature for 1 hour. Water (0.685 g, 38.0 mmol) was added dropwise to the reaction mixture and the mixture was stirred at 65° C. for 3 hours. The reaction mixture was cooled to ambient temperature and filtered. The precipitate was dissolved in dichloromethane. The mixture was filtered again and the combined filtrate was concentrated under reduced pressure to give a brown solid which was washed with petroleum and dichloromethane to afford the title compound (23 g, 52.4 mmol, 73.0% yield) as a light yellow solid.

Example 208e ethyl 4-bromo-6-methyl-7-oxo-1-tosyl-6,7-dihydro-1H-pyrrolo[2,3-c]pyridine-2-carboxylate To a solution of Example 208d (7.5 g, 17.07 mmol) in tetrahydrofuran (100 mL) was added sodium hydride (0.520 g, 21.68 mmol) in portions at 0° C., and the reaction mixture was stirred for 30 minutes. Iiodomethane (3.64 g, 25.6 mmol) was added dropwise to the above mixture at 0° C. The resulting mixture was stirred at ambient temperature for 3 hours and another portion of iodomethane (3.64 g, 25.6 mmol) was added at 0° C. The reaction mixture was stirred at ambient temperature for 12 hours, quenched with 20% aqueous ammonium chloride and extracted with ethyl acetate three times. The combined mixtures were dried over anhydrous $Na_2SO_4$, filtered, and concentrated in vacuo. The resulting residue was purified by column chromatography on silica gel, eluting with 1:1 ethyl acetate/hexanes to provide a yellow crude product which was washed with methanol to give the title compound (15.3 g, 80% yield).

Example 208f ethyl 6-methyl-7-oxo-4-(4,4,5,5-tetramethyl-1,3,2-dioxaborolan-2-yl)-1-tosyl-6,7-dihydro-1H-pyrrolo[2,3-c]pyridine-2-carboxylate Example 208f was prepared according to the procedure used for the preparation of Example 1f, substituting Example 208e for Example 1e, to provide the title compound.

Example 208g ethyl 4-(2-((2,4-difluorophenyl)amino)-5-((methylsulfonyl)methyl)phenyl)-6-methyl-7-oxo-1-tosyl-6,7-dihydro-1H-pyrrolo[2,3-c]pyridine-2-carboxylate Example 208g was prepared according to the procedure used for the preparation of Example 5d, substituting Example 12b for Example 5c, and Example 208f for Example 1f, respectively, to provide the title compound.

Example 208h ethyl 4-(2-((2,4-difluorophenyl)amino)-5-((methylsulfonyl)methyl)phenyl)-6-methyl-7-oxo-6,7-dihydro-1H-pyrrolo[2,3-c]pyridine-2-carboxylate A mixture of ethyl Example 208g (0.2 g, 0.299 mmol) in dioxane (2 mL) and ethanol (0.5 mL) was treated with sodium hydroxide (0.747 mL, 1.493 mmol) at ambient temperature. The reaction mixture was heated to 60° C. over 2 minutes. After cooling to ambient temperature, the reaction mixture was partitioned between 1.0 N HCl and ethyl acetate. The organic layer was separated, and the aqueous layer was extracted with additional ethyl acetate twice. The combined organic layers were washed with saturated aqueous sodium chloride, dried over anhydrous magnesium sulfate, filtered, and concentrated to give the title compound (0.15 g, 0.291 mmol, 97% yield).

Example 208i ethyl 4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxylate Example 208i was prepared according to the procedure used for the preparation of Example 58k, substituting Example 208h for Example 58j, to provide the title compound. $^1$H NMR (500 MHz, DMSO-$d_6$) δ 12.67 (s, 1H), 7.84 (d, J=2.14 Hz, 1H), 7.72 (s, 1H), 7.29 (dd, J=8.24, 1.83 Hz, 1H), 7.09-7.13 (m, 1H), 7.03 (d, J=7.93 Hz, 1H), 6.84-6.89 (m, 1H), 6.75-6.81 (m, 1H), 5.09 (s, 2H), 4.49 (s, 2H), 4.29 (q, J=7.02 Hz, 1H), 3.64 (s, 3H), 2.96 (s, 3H), 1.34 (t, J=7.02 Hz, 3H). MS (ESI+) m/z 528.1 (M+H)$^+$.

Example 209

4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxamide Example 209a 4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxylic acid Example 209a was prepared according to the procedure used for the preparation of Example 58l, substituting Example 208i for Example 58k, to provide the title compound.

Example 209b 4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxamide Example 209b was prepared according to the procedure used for the preparation of Example 58m, substituting Example 209a for Example 58l, to provide the title compound. $^1$H NMR (500 MHz, DMSO-$d_6$) δ 12.19 (s, 1H), 7.82 (d, J=2.14 Hz, 1H), 7.72 (s, 2H), 7.70 (s, 1H), 7.53 (s, 1H), 7.26 (dd, J=8.09, 1.98 Hz, 1H), 7.05-7.11 (m, 1H), 6.98 (d, J=7.93 Hz, 1H), 6.90-6.93 (m, 2H), 6.75-6.81 (m, 1H), 5.14 (s, 2H), 4.48 (s, 2H), 3.66 (s, 3H), 2.95 (s, 3H). MS (ESI+) m/z 499.1 (M+H)+.

Example 210

4-(2,4-difluorophenyl)-10-methyl-7-((methylsulfonyl)methyl)-11-oxo-3,4,10,11-tetrahydro-1H-1,4,10-triazadibenzo[cd,f]azulene-2-carbonitrile Example 210 was prepared according to the procedure used for the preparation of Example 199, substituting Example 209b for Example 58m, to provide the title compound. $^1$H NMR (500 MHz, DMSO-d$_6$) δ 13.32 (s, 1H), 7.89 (d, J=1.83 Hz, 1H), 7.82 (s, 1H), 7.32 (dd, J=8.24, 1.83 Hz, 1H), 7.12-7.15 (m, 1H), 7.08 (d, J=8.24 Hz, 1H), 6.83-6.88 (m, 1H), 6.71-6.77 (m, 1H), 4.86 (s, 2H), 4.51 (s, 2H), 3.65 (s, 3H), 2.97 (s, 3H). MS (ESI+) m/z 481.1 (M+H)+.

Example 211

10-methyl-7-((methylsulfonyl)methyl)-4-(3,4,5-trimethoxyphenyl)-3,4-dihydro-1H-1,4,10-triazadibenzo[cd,f]azulen-11(10H)-one Example 211a 6-methyl-4-(5-((methylsulfonyl)methyl)-2-((3,4,5-trimethoxyphenyl)amino)phenyl)-1H-pyrrolo[2,3-c]pyridin-7(6H)-one A mixture of Example 5d (0.075 g, 0.154 mmol), 5-bromo-1,2,3-trimethoxybenzene (0.114 g, 0.463 mmol), cesium carbonate (0.101 g, 0.309 mmol), dicyclohexyl(2',4',6'-triisopropyl-[1,1'-biphenyl]-2-yl)phosphine (XPhos) (0.0368 g, 0.077 mmol), and palladium (II) acetate (0.0087 g, 0.039 mmol) in toluene (3 mL) and tert-butanol (0.75 mL) under argon was heated in a sealed tube in a microwave reactor at 160° C. for 2 hours. The reaction mixture was cooled to ambient temperature and filtered through filter paper. The resulting filtrate was concentrated to near dryness and mixed with ethanol (2 mL), tetrahydrofuran (4 mL), and excess 5N sodium hydroxide solution (2 mL). The reaction mixture was stirred at ambient temperature for 1 hour then concentrated to 5 mL and partitioned between ammonium chloride aqueous solution and ethyl acetate. The aqueous phase was extracted twice more with ethyl acetate. The combined organic layers were washed with saturated aqueous sodium chloride, dried over anhydrous magnesium sulfate, filtered and concentrated. The residue was purified by flash column chromatography on silica gel eluting with 3% methanol in dichloromethane to afford the title compound (0.020 g, 0.040 mmol, 26% yield).

Example 211b 10-methyl-7-((methylsulfonyl)methyl)-4-(3,4,5-trimethoxyphenyl)-3,4-dihydro-1H-1,4,10-triazadibenzo[cd,f]azulen-11(10H)-one A mixture of Example 211a (0.020 g, 0.040 mmol) and paraformaldehyde (0.006 g, 0.201 mmol) in tetrahydrofuran (2 mL) at ambient temperature under argon was treated with a 1M solution of titanium tetrachloride (0.080 mL, 0.080 mmol). The reaction mixture suspension was stirred at ambient temperature for 1 hour and then partitioned between ethyl acetate and saturated sodium bicarbonate. The aqueous layer was extracted three times with ethyl acetate. The combined organic layers were washed with saturated aqueous sodium chloride, dried over anhydrous magnesium sulfate, filtered and concentrated. The residue was triturated with methanol to give the title compound (0.0026 g, 13% yield). $^1$H NMR (500 MHz, DMSO-d$_6$) δ 11.83 (s, 1H), 7.92 (s, 1H), 7.64 (s, 1H), 7.46-7.29 (m, 3H), 5.71 (s, 2H), 5.49-4.66 (m, 2H), 4.56 (s, 2H), 3.57 (s, 3H), 3.51 (s, 6H), 3.45 (s, 3H), 2.96 (s, 3H). MS (ESI+) m/z 510.3 (M+H)+.

Example 212

4-(4-aminocyclohexyl)-10-methyl-7-((methylsulfonyl)methyl)-3,4-dihydro-1H-1,4,10-triazadibenzo[cd,f]azulen-11(10H)-one A mixture of Example 196 (0.240 g, 0.444 mmol) in dichloromethane (10 mL) was treated excess with trifluoroacetic acid (1 mL) and stirred at ambient temperature for 6 hours. The reaction mixture was concentrated and dried under vacuum to afford a solid residue which was partitioned between saturated sodium carbonate solution and ethyl acetate. The aqueous phase was extracted twice more with ethyl acetate and twice with dichloromethane. The combined organic extracts were dried with magnesium sulfate and concentrated. The residue was triturated with ethyl acetate and filtered to give the title compound (0.0066 g, 0.015 mmol, 45% yield). $^1$H NMR (501 MHz, DMSO-d$_6$) δ 11.80 (bs, 1H), 7.68 (s, 1H), 7.51-7.45 (m, 1H), 7.27-7.09 (m, 3H), 4.44-4.39 (m, 2H), 4.18 (s, 2H), 3.10 (bs, 2H), 3.61 (s, 3H), 2.90 (s, 3H), 2.82-2.42 (m, 2H), 1.68-1.45 (m, 4H), 1.36-1.17 (m, 3H), 0.88-0.81 (m, 1H). MS (ESI+) m/z 440.8 (M+H)+.

Example 213

4-(3,5-difluoropyridin-2-yl)-10-methyl-7-((methylsulfonyl)methyl)-3,4-dihydro-1H-1,4,10-triazadibenzo[cd,f]azulen-11(10H)-one Example 213a 4-(2-((3,5-difluoropyridin-2-yl)amino)-5-((methylsulfonyl)methyl)phenyl)-6-methyl-1-tosyl-1H-pyrrolo[2,3-c]pyridin-7(6H)-one Example 207a, 2-bromo-3,5-difluoropyridine (0.245 g, 1.263 mmol), diacetoxypalladium (0.032 g, 0.143 mmol), dicyclohexyl(2',4',6'-triisopropyl-[1,1'-biphenyl]-2-yl)phosphine (0.137 g, 0.287 mmol) and cesium carbonate (0.374 g, 1.148 mmol) were combined in a 20-mL microwave vial equipped with a magnetic stirbar. Toluene (4.4 mL) and tert-butanol (1.1 mL) were added and the reaction mixture was reacted in a Biotage microwave reactor at 160° C. for 1 hour. The reaction mixture was cooled to ambient temperature, diluted with ethyl acetate and water and filtered through a plastic fritted funnel to remove the Pd solids. The filtrate was poured into a separatory funnel and the layers were separated. The organic layer was washed with water and saturated aqueous sodium chloride, dried over anhydrous magnesium sulfate, filtered and concentrated. The residue was purified by flash chromatography (silica gel, 0-70% ethyl acetate in dichloromethane) to give 0.229 g (71%) of the title compound.

Example 213b 4-(2-((3,5-difluoropyridin-2-yl)amino)-5-((methylsulfonyl)methyl)phenyl)-6-methyl-1H-pyrrolo[2,3-c]pyridin-7(6H)-one To Example 213a (0.2129 g, 0.356 mmol) in tetrahydrofuran (8 mL) was added tetrabutylammonium fluoride (0.28 g, 1.07 mmol). The reaction mixture was heated at 60° C. for 45 minutes, cooled to ambient temperature, partitioned between ethyl acetate and water, washed with saturated aqueous sodium chloride, dried over anhydrous magnesium sulfate, filtered, and concentrated. The residue was purified by flash chromatography (silica gel, 0-8% methanol in dichloromethane) to give the title compound as a mixture. It was further purified by flash chromatography (silica gel, 40-75% ethyl acetate in dichloromethane with 2-4% methanol as an additive) to give 0.116 g (73%) of the title compound.

Example 213c 4-(3,5-difluoropyridin-2-yl)-10-methyl-7-((methylsulfonyl)methyl)-3,4-dihydro-1H-1,4,10-triazadibenzo[cd,f]azulen-11(10H)-one To a 5-mL microwave vial equipped with a magnetic stirbar was added Example 213b (0.116 g, 0.261 mmol), paraformaldehyde (0.024 g, 0.783 mmol), and acetic acid (4.5 mL). The vial was capped and heated at 75° C. for 50 minutes. The reaction mixture was cooled to ambient temperature, concentrated under vacuum, diluted with 1,4-dioxane (6 mL), treated with sodium hydroxide solution (4 M aqueous, 1.3 mL, 5.22 mmol) and heated at 75° C. for 1 hour. The reaction mixture was cooled to ambient temperature, concentrated under vacuum, slurried in water and neutralized with hydrochloric acid solution (2 N aqueous). The solid was collected by filtration and rinsed with additional water (20 mL). The solid was purified by reverse phase HPLC (C18, acetonitrile/water (0.1% TFA), 10-70%) to provide 0.09 g (61%) of the title compound as the TFA salt. $^1$H NMR (500 MHz, DMSO-$d_6$) δ 11.87 (s, 1H), 8.06 (d, J=1.83 Hz, 1H), 7.83 (s, 1H), 7.67 (s, 1H), 7.59 (m, 1H), 7.29 (d, J=7.93 Hz, 1H), 7.25 (d, J=1.53 Hz, 1H), 7.13 (d, J=8.24 Hz, 1H), 5.95 (s, 1H), 4.52 (s, 2H), 4.20 (s, 1H), 3.62 (s, 3H), 2.96 (s, 3H). MS (ESI+) m/z 457.1 (M+H)$^+$.

Example 214

4-(2,4-difluorophenyl)-10-methyl-7-((methylsulfonyl)methyl)-3-phenyl-3,4-dihydro-1H-1,4,10-triazadibenzo[cd,f]azulen-11(10H)-one Example 12d (66.5 mg, 0.150 mmol) and benzaldehyde (0.076 mL, 0.75 mmol) were combined in tetrahydrofuran (2 mL). To this suspension was added 1M titanium(IV) chloride in toluene (0.300 mL, 0.300 mmol). The reaction mixture was stirred at ambient temperature for 72 hours, and partitioned with ethyl acetate and water. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (65 mg, 82%). $^1$H NMR (500 MHz, DMSO-$d_6$) δ 12.04 (d, J=2.0 Hz, 1H), 7.71 (d, J=1.8 Hz, 1H), 7.68 (s, 1H), 7.28 (d, J=2.6 Hz, 1H), 7.18-7.00 (m, 7H), 6.89-6.79 (m, 3H), 6.47 (s, 1H), 4.39-4.29 (m, 2H), 3.66 (s, 3H), 2.70 (s, 3H). MS (ESI+) m/z 532 (M+H)$^+$.

Example 215

(R)-4-(2,4-difluorophenyl)-10-methyl-7-((methylsulfonyl)methyl)-3-phenyl-3,4-dihydro-1H-1,4,10-triazadibenzo[cd,f]azulen-11(10H)-one The product from Example 214 was purified by chiral chromatography on a (S,S) WHELK-O 1 column (21×250 mm, 5 micron), eluting with a 4:6 mixture of 0.1% diethylamine in methanol/carbon dioxide. Fractions of the first eluted enantiomer was collected and concentrated. The compound isolated was randomly assigned as (R) enantiomer. $^1$H NMR (500 MHz, DMSO-$d_6$) δ 12.04 (d, J=2.0 Hz, 1H), 7.71 (d, J=1.8 Hz, 1H), 7.68 (s, 1H), 7.28 (d, J=2.6 Hz, 1H), 7.18-7.00 (m, 7H), 6.89-6.79 (m, 3H), 6.47 (s, 1H), 4.39-4.29 (m, 2H), 3.66 (s, 3H), 2.70 (s, 3H). MS (ESI+) m/z 532 (M+H)$^+$.

Example 216

(S)-4-(2,4-difluorophenyl)-10-methyl-7-((methylsulfonyl)methyl)-3-phenyl-3,4-dihydro-1H-1,4,10-triazadibenzo[cd,f]azulen-11(10H)-one The product from Example 214 was purified by chiral chromatography on a (S,S) WHELK-O 1 column (21×250 mm, 5 micron), eluting with a 4:6 mixture of 0.1% diethylamine in methanol/carbon dioxide. Fractions of the second eluted enantiomer was collected and concentrated. The compound isolated was randomly assigned as (S) enantiomer. $^1$H NMR (500 MHz, DMSO-$d_6$) δ 12.04 (d, J=2.0 Hz, 1H), 7.71 (d, J=1.8 Hz, 1H), 7.68 (s, 1H), 7.28 (d, J=2.6 Hz, 1H), 7.18-7.00 (m, 7H), 6.89-6.79 (m, 3H), 6.47 (s, 1H), 4.39-4.29 (m, 2H), 3.66 (s, 3H), 2.70 (s, 3H). MS (ESI+) m/z 532 (M+H)$^+$.

Example 217

4-(2,4-difluorophenyl)-10-methyl-7-((methylsulfonyl)methyl)-3-(naphthalen-1-yl)-3,4-dihydro-1H-1,4,10-triazadibenzo[cd,f]azulen-11(10H)-one Example 12d (0.06 g, 0.135 mmol) and 1-naphthaldehyde (0.148 mL, 1.082 mmol) were combined in tetrahydrofuran (1.353 mL) under nitrogen and treated with 1M titanium(IV) chloride in toluene (1.082 mL, 1.082 mmol). The reaction mixture was heated at 70° C. for 24 hours, cooled to ambient temperature, and partitioned between ethyl acetate and water. The organic layer was washed with saturated aqueous sodium chloride, dried over anhydrous sodium sulfate, filtered, and concentrated. Purification by chromatography (silica gel, 1-5% methanol in dichloromethane) afforded the title compound (0.015 g, 19%). $^1$H NMR (400 MHz, DMSO-$d_6$) δ 12.07 (s, 1H), 8.75 (d, J=8.85 Hz, 1H), 7.86 (d, J=7.93 Hz, 1H), 7.69-7.75 (m, 3H), 7.61 (d, J=8.54 Hz, 1H), 7.55 (t, J=7.32 Hz, 1H), 7.38 (d, J=1.53 Hz, 1H), 7.24 (d, J=2.44 Hz, 1H), 7.11-7.19 (m, 1H), 6.98 (t, J=7.63 Hz, 1H), 6.65-6.73 (m, 2H), 6.60 (d, J=7.02 Hz, 1H), 6.37-6.45 (m, 1H), 6.30 (d, J=7.93 Hz, 1H), 4.20-4.34 (m, 2H), 3.66 (s, 3H), 2.59 (s, 3H). MS (ESI+) m/z 582 (M+H)$^+$.

Example 218

4-(2,4-difluorophenyl)-(3,3-$^2$H$_2$)-10-methyl-7-((methylsulfonyl)methyl)-3,4-dihydro-1H-1,4,10-triazadibenzo[cd,f]azulen-11(10H)-one Example 218 was prepared according to the procedure used for the preparation of Example 82, substituting formaldehyde-d$_2$ for methyl 4-oxobutanoate, to provide the title compound as a yellow solid (0.0352 g, 62% yield). NMR (500 MHz, DMSO-d$_6$) δ 11.85 (s, 1H), 7.86 (d, J=2.0 Hz, 1H), 7.67 (s, 1H), 7.27 (dd, J=8.1, 2.0 Hz, 1H), 7.18 (d, J=2.5 Hz, 1H), 7.08 (ddd, J=12.4, 9.0, 3.1 Hz, 1H), 7.03 (d, J=8.1 Hz, 1H), 6.80-6.88 (m, 1H), 6.76 (td, J=9.4, 5.9 Hz, 1H), 4.50 (bs, 2H), 3.63 (s, 3H), 2.96 (s, 3H). MS (ESI+) m/z 458.1 (M+H)$^+$.

Example 219

4-(2,4-difluorophenyl)-10-methyl-7-((methylsulfonyl)methyl)-3-neopentyl-3,4-dihydro-1H-1,4,10-triazadibenzo[cd,f]azulen-11(10H)-one Example 12d (0.06 g, 0.135 mmol) and 3,3-dimethylbutyraldehyde (0.081 g, 0.812 mmol) were combined in tetrahydrofuran (1.353 mL) under nitrogen and treated dropwise with 1M titanium(IV) chloride in toluene (0.812 mL, 0.812 mmol). The reaction mixture was stirred for 2 hours at 60° C., cooled to ambient temperature, and partitioned between ethyl acetate and water. The organic layer was washed with saturated aqueous sodium chloride, dried over anhydrous sodium sulfate, filtered and concentrated. Purification by chromatography (silica gel, 30-60% of 3:1 ethyl acetate/ethanol in heptanes) afforded the title compound (0.010 g, 14%). NMR (400 MHz, DMSO-d$_6$) δ 11.81 (s, 1H), 7.91 (d, J=1.53 Hz, 1H), 7.68 (s, 1H), 7.25 (dd, J=8.09, 1.68 Hz, 1H), 7.16 (d, J=2.44 Hz, 1H), 7.06-7.13 (m, 1H), 6.98 (d, J=7.93 Hz, 1H), 6.73-6.80 (m, 1H), 6.53-6.60 (m, 1H), 5.19 (dd, J=7.32, 4.88 Hz, 1H), 4.45-4.56 (m, 2H), 3.63 (s, 3H), 2.94 (s, 3H), 1.67 (dd, J=13.73, 4.88 Hz, 1H), 1.20 (dd, J=13.73, 7.63 Hz, 1H), 0.89 (s, 9H). MS (ESI+) m/z 526 (M+H)$^+$.

Example 220

4-(2,4-difluorophenyl)-10-methyl-7-((methylsulfonyl)methyl)-3-((1-oxoisoindolin-2-yl)methyl)-3,4-dihydro-1H-1,4,10-triazadibenzo[cd,f]azulen-11(10H)-one

Example 220a 2-(2,2-dimethoxyethyl)isoindolin-1-one

A 5 mL microwave tube was charged with isoindolin-1-one (0.2544 g, 1.911 mmol), cesium carbonate (1.245 g, 3.82 mmol) and N-methyl-2-pyrrolidinone (9.55 mL) to give a colorless solution. Bromoacetaldehyde dimethyl acetal (1.125 mL, 9.55 mmol) was added. The tube was sealed, and the reaction mixture was heated in a Biotage Creator at 160° C. for 60 minutes fixed hold time. The reaction mixture was partitioned between ethyl acetate and water. The organic layer was washed with saturated aqueous sodium chloride, dried over anhydrous magnesium sulfate, filtered, and concentrated. The reaction mixture was purified by flash chromatography (20-70% ethyl acetate:heptane) to provide a brown oil (0.179 g, 42% yield).

Example 220b 4-(2,4-difluorophenyl)-10-methyl-7-((methylsulfonyl)methyl)-3-((1-oxoisoindolin-2-yl)methyl)-3,4-dihydro-1H-1,4,10-triazadibenzo[cd,f]azulen-11(10H)-one Example 220b was prepared according to the procedure used for the preparation of Example 82, substituting Example 220a for methyl 4-oxobutanoate, to provide the title compound as a white solid (0.0169 g, 29% yield). $^1$H NMR (400 MHz, DMSO-d$_6$) δ 11.84 (m, 1H), 7.91 (d, J=2.0 Hz, 1H), 7.75 (s, 1H), 7.51-7.66 (m, 3H), 7.47 (t, J=6.7 Hz, 1H), 7.18-7.28 (m, 2H), 7.12 (ddd, J=11.9, 8.9, 3.0 Hz, 1H), 6.96 (ddd, J=17.9, 11.7, 5.4 Hz, 3H), 5.46 (dd, J=9.5, 5.8 Hz, 1H), 4.53 (d, J=15.7 Hz, 2H), 4.46 (d, J=13.7 Hz, 1H), 4.17-4.26 (m, 1H), 3.89 (dd, J=13.4, 5.7 Hz, 1H), 3.66 (s, 3H), 3.34-3.44 (m, 1H), 2.97 (s, 3H). MS (ESI−) m/z 599.2 (M−H)$^+$.

Example 221

4-(2,4-difluorophenyl)-3-(2,6-dimethoxyphenyl)-10-methyl-7-((methylsulfonyl)methyl)-3,4-dihydro-1H-1,4,10-triazadibenzo[cd,f]azulen-11(10H)-one Example 12d (53.2 mg, 0.120 mmol) and 2,6-dimethoxybenzaldehyde (100 mg, 0.600 mmol) were combined in tetrahydrofuran (1 mL). To this suspension was added 1M titanium(IV) chloride in toluene (0.240 mL, 0.240 mmol). The reaction mixture was heated at 60° C. for 24 hours, cooled to ambient temperature, and partitioned with ethyl acetate and water. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (8 mg, 11% yield). $^1$H NMR (400 MHz, DMSO-d$_6$) δ 11.62 (d, J=2.0 Hz, 1H), 7.76 (d, J=1.8 Hz, 1H), 7.69 (s, 1H), 7.16-6.73 (m, 7H), 6.60-6.34 (m, 3H), 4.52-4.30 (m, 2H), 3.65 (s, 3H), 3.32 (s, 6H), 2.85 (s, 3H). MS (ESI+) m/z 592 (M+H)$^+$.

Example 222

4-(2,4-difluorophenyl)-3-(3,5-dimethoxyphenyl)-10-methyl-7-((methylsulfonyl)methyl)-3,4-dihydro-1H-1,4,10-triazadibenzo[cd,f]azulen-11(10H)-one Example 222 was prepared according to the procedure used for the preparation of Example 221, substituting 3,5-dimethoxybenzaldehyde for 2,6-dimethoxybenzaldehyde, to provide the title compound (39 mg, 55%). $^1$H NMR (400 MHz, DMSO-d$_6$) δ 12.02 (s, 1H), 7.74 (d, J=1.8 Hz, 1H), 7.69 (s, 1H), 7.26 (d, J=1.7 Hz, 1H), 7.19-7.04 (m, 2H), 6.96-6.81 (m, 3H), 6.34 (s, 1H), 6.27-6.18 (m, 3H), 4.46-4.31 (m, 2H), 3.66 (s, 3H), 3.56 (s, 6H), 2.75 (s, 3H). MS (ESI+) m/z 592 (M+H)$^+$.

Example 223

3-(3,5-di-tert-butylphenyl)-4-(2,4-difluorophenyl)-10-methyl-7-((methylsulfonyl)methyl)-3,4-dihydro-1H-1,4,10-triazadibenzo[cd,f]azulen-11(10H)-one Example 223 was prepared according to the procedure used for the preparation of Example 221, substituting 3,5- di-tert-butylbenzaldehyde for 2,6-dimethoxybenzaldehyde, to provide the title compound (60 mg, 78%). $^1$H NMR (400 MHz, DMSO-d$_6$) δ 11.99 (d, J=1.8 Hz, 1H), 7.70-7.64 (m, 2H), 7.29 (d, J=2.4 Hz, 1H), 7.18-7.09 (m, 1H), 7.07-6.99 (m, 2H), 6.96 (s, 2H), 6.92-6.82 (m, 2H), 6.75 (d, J=8.1 Hz, 1H), 6.44 (s, 1H), 4.41-4.22 (m, 2H), 3.66 (s, 3H), 2.64 (s, 3H), 1.08 (s, 18H). MS (ESI+) m/z 644 (M+H)$^+$.

Example 224 methyl (4-(10-methyl-7-((methylsulfonyl)methyl)-11-oxo-10,11-dihydro-1H-1,4,10-triazadibenzo[cd,f]azulen-4(3H)-yl)cyclohexyl)carbamate A mixture of Example 212 (0.065 g, 0.148 mmol) and N,N-diisopropylethylamine (0.103 mL, 0.590 mmol) in dimethylformamide (5 mL) under argon at ambient temperature was treated with dropwise addition of methyl chloroformate (0.012 mL, 0.148 mmol). The reaction mixture was stirred 2 hours at ambient temperature and then partitioned between aqueous ammonium chloride solution and ethyl acetate. The organic layer was washed with saturated aqueous sodium chloride, dried over anhydrous magnesium sulfate, filtered and concentrated to afford the title compound (0.050 g, 0.100 mmol, 68% yield). $^1$H NMR (400 MHz, DMSO-d$_6$) δ 11.43 (s, 1H), 7.70-7.65 (m, 1H), 7.49-7.43 (m, 1H), 7.28-7.14 (m, 2H), 7.09 (s, 1H), 6.60 (s, 0.5H), 6.37 (d, J=7.0 Hz, 0.5H), 4.43-4.37 (m, 2H), 4.19 (s, 2H), 3.61 (s, 3H), 3.54-3.44 (m, 3H), 3.42-3.10 (m, 1H), 2.89 (s, 3H), 2.85-2.66 (m, 1H), 1.74-1.45 (m, 4H), 1.39-1.18 (m, 3H), 1.04-0.94 (m, 1H). MS (ESI+) m/z 499.1 (M+H)$^+$.

Example 225 methyl ((trans)-4-(10-methyl-7-((methylsulfonyl)methyl)-11-oxo-10,11-dihydro-1H-1,4,10-triazadibenzo[cd,f]azulen-4(3H)-yl)cyclohexyl)carbamate The geometric isomers of Example 224 were separated on reverse phase HPLC (C18, CH$_3$CN/water (0.1% TFA), 5-40% gradient). Fractions of the first eluted isomer was collected and concentrated to provide the title compound (0.008 g, 0.016 mmol, 11% yield). $^1$H NMR (400 MHz, DMSO-d$_6$) δ 11.49 (s, 1H), 7.71 (d, J=1.7 Hz, 1H), 7.49 (s, 1H), 7.28-7.18 (m, 2H), 7.13 (d, J=2.5 Hz, 1H), 6.38 (s, 1H), 4.41 (s, 2H), 4.25 (s, 2H), 3.61 (s, 3H), 3.47 (s, 3H), 3.21-3.11 (m, 1H), 2.89 (s, 3H), 2.79-2.71 (m, 1H), 1.75-1.58 (m, 4H), 1.39-1.25 (m, 3H), 1.02-0.94 (m, 1H). MS (ESI+) m/z 499.1 (M+H)$^+$.

Example 226 methyl ((cis)-4-(10-methyl-7-((methylsulfonyl)methyl)-11-oxo-10,11-dihydro-1H-1,4,10-triazadibenzo[cd,f]azulen-4(3H)-yl)cyclohexyl)carbamate The geometric isomers of Example 224 were separated on reverse phase HPLC (C18, CH$_3$CN/water (0.1% TFA), 5-40% gradient). Fractions of the second eluted isomer was collected and concentrated to provide the title compound (0.0046 g, 0.009 mmol, 6% yield). $^1$H NMR (400 MHz, DMSO-d$_6$) δ 11.47 (s, 1H), 7.69 (d, J=1.7 Hz, 1H), 7.49 (s, 1H), 7.30-7.23 (m, 2H), 7.11 (d, J=2.5 Hz, 1H), 6.60 (s, 1H), 4.42 (s, 2H), 4.23 (s, 2H), 3.61 (s, 3H), 3.51 (s, 3H), 2.89 (s, 3H), 2.87-2.79 (m, 2H), 1.72-1.26 (m, 8H). MS (ESI+) m/z 499.1 (M+H)$^+$.

Example 227

2-(2-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)ethyl)isoindoline-1,3-dione Example 12d (0.06 g, 0.135 mmol) and 3-(1,3-dioxoisoindolin-2-yl)propanal (0.082 g, 0.406 mmol) were combined in tetrahydrofuran (1.353 mL) under nitrogen and treated drop-wise with 1M titanium(IV) chloride in toluene (0.406 mL, 0.406 mmol). The reaction mixture was stirred for 18 hours at 60° C., cooled to ambient temperature, and partitioned between ethyl acetate and water. The organic layer was washed with saturated aqueous sodium chloride, dried over anhydrous sodium sulfate, filtered and concentrated. Purification by reverse phase HPLC (C18, CH$_3$CN/water (0.1% TFA), 0-100% gradient) provided the title compound. (0.018 g, 21%). $^1$H NMR (500 MHz, DMSO-d$_6$) δ11.94 (d, J=2.14 Hz, 1H), 7.88 (d, J=1.53 Hz, 1H), 7.80-7.86 (m, 4H), 7.72 (s, 1H), 7.31 (d, J=2.75 Hz, 1H), 7.28 (dd, J=8.09, 1.98 Hz, 1H), 7.02-7.10 (m, 2H), 6.77-6.83 (m, 1H), 6.65-6.72 (m, 1H), 5.06-5.11 (m, 1H), 4.40-4.57 (m, 2H), 3.70-3.79 (m, 1H), 3.65 (s, 3H), 3.54-3.63 (m, 1H), 2.95 (s, 3H), 1.97-2.07 (m, 1H), 1.62 (dd, J=13.12, 5.19 Hz, 1H). MS (ESI+) m/z 629 (M+H)$^+$.

Example 228

4-(2,4-difluorophenyl)-10-methyl-7-((methylsulfonyl)methyl)-3-(tetrahydro-2H-pyran-4-yl)-3,4-dihydro-1H-1,4,10-triazadibenzo[cd,f]azulen-11(10H)-one Example 12d (0.05 g, 0.113 mmol) and tetrahydropyran-4-carbaldehyde (0.064 g, 0.564 mmol) were combined in tetrahydrofuran (1.127 mL) under nitrogen and treated drop-wise with 1M titanium (IV) chloride in toluene (0.248 mL, 0.248 mmol). The reaction mixture was stirred for 24 hours at 60° C., cooled to ambient temperature and partitioned between ethyl acetate and water. The organic layer was washed with saturated aqueous sodium chloride, dried over anhydrous sodium sulfate, filtered and concentrated. Purification by chromatography (silica gel, 30-60% of 3:1 ethyl acetate/ethanol in heptanes) afforded the title compound (0.028 g, 45%). $^1$H NMR (400 MHz, DMSO-d$_6$) δ 11.88 (d, J=1.22 Hz, 1H), 7.89 (d, J=1.83 Hz, 1H), 7.68 (s, 1H), 7.25 (dd, J=8.24, 1.83 Hz, 1H), 7.02-7.12 (m, 3H), 6.72-6.85 (m, 2H), 4.68 (d, J=9.46 Hz, 1H), 4.49 (q, J=13.73 Hz, 2H), 3.83 (d, J=11.60 Hz, 1H), 3.72 (d, J=9.77 Hz, 1H), 3.64 (s, 3H), 2.91 (s, 3H), 2.81-2.98 (m, 2H), 1.97-2.02 (m, 1H), 1.48-1.60 (m, 1H), 1.32 (t, J=8.70 Hz, 2H), 1.03 (d, J=9.16 Hz, 1H). MS (ESI+) m/z 540 (M+H)$^+$.

Example 229 benzyl (2-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)ethyl)carbamate Example 12d (0.05 g, 0.113 mmol) and 3-[(benzyloxycarbonyl)amino]-1-propanal (0.070 g, 0.338 mmol) were combined in tetrahydrofuran (1.127 mL) under nitrogen and treated drop-wise with 1M titanium (IV) chloride in toluene (0.248 mL, 0.248 mmol). The reaction mixture was stirred for 24 hours at 60° C., cooled to ambient temperature and partitioned between ethyl acetate and water. The organic layer was washed with saturated aqueous sodium chloride, dried over anhydrous sodium sulfate, filtered and concentrated. Purification by chromatography (silica gel, 30-60% of 3:1 ethyl acetate/ethanol in heptanes) afforded the title compound (0.012 g, 17%). $^1$H NMR (500 MHz, DMSO-$d_6$) δ 11.88 (s, 1H), 7.83 (d, J=1.83 Hz, 1H), 7.68 (s, 1H), 7.28-7.42 (m, 6H), 7.23 (d, J=7.93 Hz, 1H), 7.21 (d, J=2.44 Hz, 1H), 7.08 (dd, J=12.66, 9.61 Hz, 1H), 6.95 (d, J=7.93 Hz, 1H), 6.81 (d, J=7.02 Hz, 2H), 5.06 (dd, J=9.16, 5.49 Hz, 1H), 5.03 (s, 2H) 4.40-4.54 (m, 2H), 3.64 (s, 3H), 3.03-3.09 (m, 2H), 2.93 (s, 3H), 1.80-1.92 (m, 1H), 1.30-1.39 (m, 1H). MS (ESI+) m/z 633 (M+H)$^+$.

Example 230

3-([1,1'-biphenyl]-2-yl)-4-(2,4-difluorophenyl)-10-methyl-7-((methylsulfonyl)methyl)-3,4-dihydro-1H-1,4,10-triazadibenzo[cd,f]azulen-11(10H)-one Example 230 was prepared according to the procedure used for the preparation of Example 221, substituting [1,1'-biphenyl]-2-carbaldehyde for 2,6-dimethoxybenzaldehyde and 48 hours for the reaction time instead of 24 hours, to provide the title compound (11 mg, 15%). $^1$H NMR (500 MHz, DMSO-$d_6$) δ 12.00 (d, J=2.3 Hz, 1H), 7.79 (d, J=1.9 Hz, 1H), 7.72 (s, 1H), 7.64 (d, J=7.1 Hz, 2H), 7.52 (t, J=7.5 Hz, 2H), 7.46 (d, J=7.3 Hz, 1H), 7.30 (s, 1H), 7.15-7.04 (m, 3H), 6.81-6.58 (m, 5H), 6.53-6.45 (m, 1H), 6.00-5.85 (m, 1H), 4.48-4.34 (m, 2H), 3.64 (s, 3H), 2.73 (s, 3H). MS (ESI+) m/z 608 (M+H)$^+$.

Example 231

4-(2,4-difluorophenyl)-10-methyl-7-((methylsulfonyl)methyl)-3-(quinolin-8-yl)-3,4-dihydro-1H-1,4,10-triazadibenzo[cd,f]azulen-11(10H)-one Example 12d (53.2 mg, 0.120 mmol) and quinoline-8-carbaldehyde (94.0 mg, 0.600 mmol) were combined in tetrahydrofuran (1 mL). To this suspension was added 1M titanium (IV) chloride in toluene (0.240 mL, 0.240 mmol). The reaction mixture was heated at 60° for 48 hours, cooled, diluted with water, the pH adjusted to 7 by the addition of saturated aqueous sodium bicarbonate, and extracted with ethyl acetate. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (14 mg, 20%). $^1$H NMR (500 MHz, DMSO-$d_6$) δ 12.02 (s, 1H), 9.14 (dd, J=4.2, 1.7 Hz, 1H), 8.34 (dd, J=8.3, 1.7 Hz, 1H), 8.21 (td, J=9.6, 6.2 Hz, 1H), 7.77-7.68 (m, 4H), 7.62 (dd, J=8.3, 4.2 Hz, 1H), 7.29 (d, J=2.1 Hz, 1H), 7.08 (t, J=7.7 Hz, 1H), 7.00 (td, J=8.1, 2.0 Hz, 1H), 6.93-6.84 (m, 2H), 6.71 (dd, J=8.1, 1.8 Hz, 1H), 6.09 (d, J=8.1 Hz, 1H), 4.37-4.23 (m, 2H), 3.69 (s, 3H), 2.64 (s, 3H). MS (ESI+) m/z 583 (M+H)$^+$.

Example 232

4-(2,4-difluorophenyl)-10-methyl-7-((methylsulfonyl)methyl)-3-(pyridin-2-yl)-3,4-dihydro-1H-1,4,10-triazadibenzo[cd,f]azulen-11(10H)-one Example 12d (53.2 mg, 0.12 mmol) and picolinaldehyde (0.057 mL, 0.60 mmol) were combined in tetrahydrofuran (1 mL). To this suspension was added 1M titanium(IV) chloride in toluene (0.240 mL, 0.240 mmol). The mixture was heated at 70° C. for 66 hours, cooled, diluted with water, the pH adjusted to 7 by the addition of saturated aqueous sodium bicarbonate, and extracted with ethyl acetate. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (14 mg, 22%). $^1$H NMR (500 MHz, DMSO-$d_6$) δ 12.04 (d, J=1.8 Hz, 1H), 8.54-8.49 (m, 1H), 8.13 (td, J=9.4, 6.1 Hz, 1H), 7.68 (s, 2H), 7.40 (td, J=7.7, 1.8 Hz, 1H), 7.31 (d, J=2.5 Hz, 1H), 7.15-6.99 (m, 3H), 6.91 (dd, J=8.3, 1.9 Hz, 1H), 6.67 (d, J=7.9 Hz, 1H), 6.61 (s, 1H), 6.50 (d, J=8.2 Hz, 1H), 4.41-4.23 (m, 2H), 3.68 (s, 3H), 2.69 (s, 3H). MS (ESI+) m/z 533 (M+H)$^+$.

Example 233

10-methyl-7-((methylsulfonyl)methyl)-4-(1-((2-(trimethylsilyl)ethoxy)methyl)-1H-indazol-5-yl)-3,4-dihydro-1H-1,4,10-triazadibenzo[cd,f]azulen-11 (10H)-one Example 233a 5-iodo-1-((2-(trimethylsilyl)ethoxy)methyl)-1H-indazole A mixture of 5-iodo-1H-indazole (1.02 g, 4.18 mmol) in tetrahydrofuran (20 mL) at 0° C. under argon was treated with sodium hydride (60% oil dispersion, 0.192 g, 4.81 mmol). The reaction mixture was stirred at 0° C. for 15 minutes. (2-(chloromethoxy)ethyl)trimethylsilane (0.767 g, 4.60 mmol) was added dropwise and the reaction mixture was stirred at ambient temperature for 17 hours. The reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by chromatography on silica gel eluting with 10% ethyl acetate in heptane to give the title compound (0.933 g, 2.49 mmol, 60% yield).

Example 233b

N-(2-bromo-4-((methylsulfonyl)methyl)phenyl)-1-((2-(trimethylsilyl)ethoxy)methyl)-1H-indazol-5-amine A mixture of Example 233a (0.520 g, 1.389 mmol), Example 58g (0.367 g, 1.389 mmol), cesium carbonate (0.905 g, 2.780 mmol), 4,5-bis(diphenylphosphino)-9,9-dimethylxanthene (XantPhos) (0.161 g, 0.278 mmol), and palladium(II)acetate (0.031 g, 0.139 mmol) in dioxane (20 mL) under argon was heated in a sealed tube in a microwave reactor at 130° C. for 4 hours. The reaction mixture was cooled to ambient temperature and partitioned between saturated sodium chloride solution and ethyl acetate. The aqueous layer was extracted with additional ethyl acetate. The combined organic layers were dried over anhydrous magnesium sulfate, filtered, and concentrated. The residue was purified by chromatography on silica gel eluting with 33% ethyl acetate in heptane to give the title compound (0.170 g, 0.333 mmol, 24% yield).

Example 233c 6-methyl-4-(5-((methylsulfonyl)methyl)-2-((1-((2-(trimethylsilyl)ethoxy)methyl)-1H-indazol-5-yl)amino)phenyl)-1H-pyrrolo[2,3-c]pyridin-7(6H)-one A mixture of Example 233b (0.320 g, 0.627 mmol) and Example 1f (0.282 g, 0.658 mmol) in dimethoxyethane (20 mL) and methanol (10 mL) under argon was treated with cesium fluoride (0.286 g, 1.880 mmol) and palladium tetrakis(triphenylphosphine) (0.72 g, 0.063 mmol). The reaction mixture was stirred at 75° C. for 2 hours. The reaction mixture was cooled to ambient temperature and excess 5N sodium hydroxide solution (8 mL) was added. The reaction mixture was stirred at ambient temperature for 2 hours and then partitioned between aqueous ammonium chloride solution and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash column chromatography on silica gel eluting with 1% methanol in dichloromethane to afford the title compound (0.221 g, 0.381 mmol, 61% yield).

Example 233d 10-methyl-7-((methylsulfonyl)methyl)-4-(1-((2-(trimethylsilyl)ethoxy)methyl)-1H-indazol-5-yl)-3,4-dihydro-1H-1,4,10-triazadibenzo[cd,f]azulen-11(10H)-one A mixture of Example 233c (0.221 g, 0.383 mmol) and paraformaldehyde (0.057 g, 1.913 mmol) in tetrahydrofuran (10 mL) under argon was treated with a 1M toluene solution of titanium tetrachloride (0.765 mL, 0.765 mmol). The reaction mixture was stirred at ambient temperature for 3 hours. The reaction mixture was quenched by the slow addition of excess saturated sodium bicarbonate solution and partitioned between water and ethyl acetate. The aqueous layer was extracted with additional ethyl acetate followed by extraction with dichloromethane. The combined organic layers were washed with saturated aqueous sodium chloride, dried over anhydrous magnesium sulfate, filtered, and concentrated. The residue was purified by flash column chromatography on silica gel eluting with 2% methanol in dichloromethane to afford the title compound (0.120 g, 0.203 mmol, 53% yield). $^1$H NMR (500 MHz, DMSO-$d_6$) δ 11.79 (d, J=2.4 Hz, 1H), 7.91 (d, J=1.8 Hz, 1H), 7.74 (d, J=0.5 Hz, 1H), 7.58 (s, 1H), 7.44 (dd, J=8.0, 1.9 Hz, 1H), 7.34 (dd, J=8.8, 4.0 Hz, 3H), 6.79 (dd, J=9.2, 2.2 Hz, 1H), 6.57 (d, J=2.0 Hz, 1H), 5.52 (s, 2H), 4.67 (bs, 2H), 4.57 (s, 2H), 3.51 (s, 3H), 3.41-3.36 (m, 2H), 3.00 (s, 3H), 0.74-0.68 (m, 2H), −0.15--0.21 (m, 9H). MS (ESI−) m/z 588.2 (M−H)$^-$.

Example 234

3-(4-(1H-imidazol-1-yl)phenyl)-4-(2,4-difluorophenyl)-10-methyl-7-((methylsulfonyl)methyl)-3,4-dihydro-1H-1,4,10-triazadibenzo[cd,f]azulen-11(10H)-one Example 234 was prepared according to the procedure used for the preparation of Example 232, substituting 4-(1H-imidazol-1-yl)benzaldehyde for picolinaldehyde and 48 hours for reaction time instead of 66 hours, to provide the title compound (8 mg, 11%). $^1$H NMR (500 MHz, DMSO-$d_6$) δ 12.09 (s, 1H), 8.11 (t, J=1.1 Hz, 1H), 7.73 (d, J=1.8 Hz, 1H), 7.70 (s, 1H), 7.59 (t, J=1.3 Hz, 1H), 7.41 (d, J=8.7 Hz, 2H), 7.32 (d, J=1.7 Hz, 1H), 7.24-7.14 (m, 3H), 7.07-7.02 (m, 2H), 6.91-6.80 (m, 3H), 6.50 (s, 1H), 4.44-4.27 (m, 2H), 3.67 (s, 3H), 2.70 (s, 3H). MS (ESI+) m/z 598 (M+H)$^+$.

Example 235

4-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)benzonitrile Example 235 was prepared according to the procedure used for the preparation of Example 232, substituting 4-formylbenzonitrile for picolinaldehyde and 48 hours for reaction time instead of 66 hours, to provide the title compound (27 mg, 40%). $^1$H NMR (500 MHz, DMSO-$d_6$) δ 12.13 (s, 1H), 7.71 (d, J=9.8 Hz, 2H), 7.60 (d, J=8.2 Hz, 2H), 7.37-7.26 (m, 3H), 7.23-7.15 (m, 1H), 7.05 (d, J=8.2 Hz, 1H), 6.90-6.78 (m, 3H), 6.54 (s, 1H), 4.45-4.26 (m, 2H), 3.66 (s, 3H), 2.73 (s, 3H). MS (ESI+) m/z 557 (M+H)$^+$.

Example 236

4-(2,4-difluorophenyl)-10-methyl-7-((methylsulfonyl)methyl)-3-(3-(pyridin-2-yl)phenyl)-3,4-dihydro-1H-1,4,10-triazadibenzo[cd,f]azulen-11(10H)-one Example 236 was prepared according to the procedure used for the preparation of Example 232, substituting 3-(pyridin-2-yl)benzaldehyde for picolinaldehyde and 48 hours for reaction time instead of 66 hours, to provide the title compound (32 mg, 44%). $^1$H NMR (500 MHz, DMSO-$d_6$) δ 12.07 (d, J=2.3 Hz, 1H), 8.61-8.56 (m, 1H), 7.85-7.79 (m, 2H), 7.76-7.64 (m, 4H), 7.34 (d, J=2.6 Hz, 1H), 7.32-7.27 (m, 1H), 7.24 (t, J=7.7 Hz, 1H), 7.21-7.13 (m, 2H), 7.03 (dd, J=8.2, 1.9 Hz, 1H), 6.94-6.81 (m, 3H), 6.57 (s, 1H), 4.42-4.25 (m, 2H), 3.67 (s, 3H), 2.64 (s, 3H). MS (ESI+) m/z 609 (M+H)$^+$.

Example 237

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)benzonitrile Example 237 was prepared according to the procedure used for the preparation of Example 232, substituting 3-formylbenzonitrile for picolinaldehyde and 48 hours for reaction time instead of 66 hours, to provide the title compound (20 mg, 30%). $^1$H NMR (500 MHz, DMSO-$d_6$) δ 12.13 (s, 1H), 7.73 (d, J=1.8 Hz, 1H), 7.71 (s, 1H), 7.55 (d, J=7.6 Hz, 1H), 7.47-7.40 (m, 2H), 7.39-7.31 (m, 2H), 7.22-7.13 (m, 1H), 7.06 (dd, J=8.2, 1.9 Hz, 1H), 6.93-6.80 (m, 3H), 6.53 (s, 1H), 4.46-4.27 (m, 2H), 3.66 (s, 3H), 2.72 (s, 3H). MS (ESI+) m/z 557 (M+H)$^+$.

Example 238

4-(2,4-difluorophenyl)-10-methyl-7-((methylsulfonyl)methyl)-3-((2-oxopyridin-1(2H)-yl)methyl)-3,4-dihydro-1H-1,4,10-triazadibenzo[cd,f]azulen-11(10H)-one

Example 238a 1-(2,2-dimethoxyethyl)pyridin-2(1H)-one

A 20 mL microwave tube was charged with 2-hydroxypyridine (0.220 g, 2.313 mmol), cesium carbonate (1.507 g, 4.63 mmol) and acetonitrile (11.57 mL) to give a white suspension. Bromoacetaldehyde dimethyl acetal (1.362 mL, 11.57 mmol) was added. The tube was sealed, and the reaction mixture was heated in a Biotage Creator at 120° C. for 30 minutes fixed hold time. The reaction mixture was partitioned between ethyl acetate and water. The organic layer was washed with saturated aqueous sodium chloride, dried over anhydrous magnesium sulfate, filtered, and concentrated. The reaction mixture was purified by flash chromatography (0-5% methanol:dichloromethane) to provide the title compound (0.210 g, 50% yield).

Example 238b 4-(2,4-difluorophenyl)-10-methyl-7-((methylsulfonyl)methyl)-3-((2-oxopyridin-1(2H)-yl)methyl)-3,4-dihydro-1H-1,4,10-triazadibenzo[cd,f]azulen-11(10H)-one Example 238b was prepared according to the procedure used for the preparation of Example 82, substituting Example 238a for methyl 4-oxobutanoate, to provide the title compound as a white solid (0.0884 g, 55% yield). $^1$H NMR (500 MHz, DMSO-$d_6$) δ 11.88-11.93 (m, 1H), 7.89 (d, J=2.0 Hz, 1H), 7.74 (s, 1H), 7.72-7.63 (m, 1H), 7.43 (ddd, J=8.9, 6.7, 2.1 Hz, 1H), 7.21 (dd, J=8.2, 2.0 Hz, 1H), 7.00-7.11 (m, 2H), 6.82-6.89 (m, 2H), 6.67 (d, J=2.6 Hz, 1H), 6.46 (d, J=9.1 Hz, 1H), 6.00 (td, J=6.6, 1.4 Hz, 1H), 5.50 (dd, J=9.1, 5.6 Hz, 1H), 4.54-4.36 (m, 3H), 3.66 (s, 3H), 3.54-3.44 (m, 1H), 2.95 (s, 3H). MS (ESI+) m/z 563.0 (M+H)$^+$.

Example 239 ethyl 4-(2,4-difluorophenyl)-2-(ethylcarbamoyl)-10-methyl-7-((methylsulfonyl)methyl)-11-oxo-3,4,10,11-tetrahydro-1H-1,4,10-triazadibenzo[cd,f]azulene-3-carboxylate Example 239a 4-(2-((2,4-difluorophenyl)amino)-5-((methylsulfonyl)methyl)phenyl)-6-methyl-7-oxo-6,7-dihydro-1H-pyrrolo[2,3-c]pyridine-2-carboxylic acid A suspension of Example 208g (450 mg, 0.672 mmol) in 6 mL tetrahydrofuran was treated with 2N aqueous sodium hydroxide (2016 μL, 4.03 mmol) and heated at 70° C. for 2 hours. Additional 2N sodium hydroxide (2016 μL, 4.03 mmol) and 3 mL ethanol were added. The mixture was heated at 70° C. for another 4 hours. The reaction mixture was concentrated. The residue was taken into water (10 mL), adjusted to pH 2 and the precipitate was collected via filtration to give the title compound, which was used without further purification.

Example 239b 4-(2-((2,4-difluorophenyl)amino)-5-((methylsulfonyl)methyl)phenyl)-N-ethyl-6-methyl-7-oxo-6,7-dihydro-1H-pyrrolo[2,3-c]pyridine-2-carboxamide A solution of Example 239a (270 mg, 0.554 mmol) in 4 mL dichloromethane was treated at 0° C. with 2 drops of dimethylformamide and oxalyl dichloride (242 μL, 2.77 mmol). The mixture was stirred at ambient temperature for 3 hours and then concentrated. The residue was taken into 2 mL tetrahydrofuran and treated with ethylamine (2769 μL, 5.54 mmol, 2.0 M solution in tetrahydrofuran) at 0° C. The mixture was then stirred overnight. Water was added. The mixture was extracted with ethyl acetate (3×) and partitioned. The combined organic layers were washed with water (2×) and saturated aqueous sodium chloride, dried over anhydrous magnesium sulfate, filtered, and concentrated. The residue was purified by column chromatography (silica gel, 0-8% methanol/dichloromethane gradient) to give the title compound (86 mg, 0.167 mmol, 30% yield)

Example 239c ethyl 4-(2,4-difluorophenyl)-2-(ethylcarbamoyl)-10-methyl-7-((methylsulfonyl)methyl)-11-oxo-3,4,10,11-tetrahydro-1H-1,4,10-triazadibenzo[cd,f]azulene-3-carboxylate To a suspension of Example 239b (77 mg, 0.150 mmol) and ethyl 2-oxoacetate (148 μL, 0.748 mmol, 50% solution in toluene) in tetrahydrofuran (2 mL) at ambient temperature was added titanium(IV) chloride (1048 μL, 1.048 mmol, 1.0 M solution in toluene) The mixture was stirred at ambient temperature under nitrogen for 40 hours. The reaction mixture was partitioned between water and ethyl acetate. The aqueous layer was extracted with ethyl acetate. The combined organic layers were washed with saturated aqueous sodium bicarbonate and saturated aqueous sodium chloride, dried over anhydrous magnesium sulfate, and filtered. The filtrate was concentrated and the residue was purified by column chromatography (silica gel, 0-8% methanol/dichloromethane gradient) to give the title compound (46 mg, 0.077 mmol, 51% yield). 1H NMR (400 MHz, DMSO-$d_6$) δ 12.33 (s, 1H), 8.41-8.21 (m, 1H), 7.76 (d, J=1.9 Hz, 1H), 7.74 (s, 1H), 7.64 (td, J=9.4, 5.9 Hz, 1H), 7.20 (dd, J=8.3, 1.9 Hz, 1H), 7.17-7.04 (m, 2H), 6.84 (d, J=8.2 Hz, 1H), 6.78 (s, 1H), 4.49 (d, J=13.7 Hz, 1H), 4.39 (d, J=13.7 Hz, 1H), 3.94 (ddd, J=14.3, 9.0, 5.4 Hz, 1H), 3.85 (dq, J=10.9, 7.1 Hz, 1H), 3.69 (s, 3H), 3.26 (td, J=7.2, 3.7 Hz, 2H), 2.87 (s, 3H), 1.13 (t, J=7.3 Hz, 3H), 0.86 (t, J=7.1 Hz, 3H). MS (ESI+) m/z 599.0 (M+H)$^+$.

Example 240

4-(2,4-difluorophenyl)-10-methyl-7-((methylsulfonyl)methyl)-11-oxo-3,4,10,11-tetrahydro-1H-1,4,10-triazadibenzo[cd,f]azulene-5-carboxamide Example 240a methyl 4-(2,4-difluorophenyl)-10-methyl-7-((methylsulfonyl)methyl)-11-oxo-3,4,10,11-tetrahydro-1H-1,4,10-triazadibenzo[cd,f]azulene-5-carboxylate Example 206d (20 mg, 0.037 mmol) in methanol (20 mL) was added to [1,1'-bis(diphenylphosphino)ferrocene]dichloropalladium(II) (1.369 mg, 1.871 μmol) and triethylamine (10.43 μL, 0.075 mmol) in a 50 mL pressure bottle. The mixture was pressurized with carbon monoxide (60 psi), and stirred 32 hours at 100° C. The solvent was removed. The reaction mixture was purified by flash chromatography (0-5% methanol:dichloromethane) to provide a white solid.

Example 240b 4-(2,4-difluorophenyl)-10-methyl-7-((methylsulfonyl)methyl)-11-oxo-3,4,10,11-tetrahydro-1H-1,4,10-triazadibenzo[cd,f]azulene-5-carboxylic acid A 250 mL round-bottomed flask was charged with Example 240a (0.108 g, 0.210 mmol), lithium hydroxide (0.050 g, 2.103 mmol), tetrahydrofuran (3.00 mL), methanol (1.00 mL) and water (1.00 mL) to give a colorless solution. The reaction mixture was stirred at ambient temperature for 120 hours. The reaction mixture was quenched with 1N HCl. The reaction mixture was filtered, and the solid was rinsed with water and dried in a 60° C. vacuum oven overnight to provide the title compound as a tan solid (0.0695 g, 66% yield).

Example 240c 4-(2,4-difluorophenyl)-10-methyl-7-((methylsulfonyl)methyl)-11-oxo-3,4,10,11-tetrahydro-1H-1,4,10-triazadibenzo[cd,f]azulene-5-carbonyl chloride A 25 mL round-bottomed flask was charged with Example 204b (0.0695 g, 0.139 mmol) and dichloromethane (1.391 mL) to give a tan suspension. Oxalyl dichloride (0.018 mL, 0.209 mmol) and N,N-dimethylformamide (1.077 µL, 0.014 mmol) were added. The reaction mixture was stirred at ambient temperature for 45 minutes. The solvent was removed, dichloromethane and toluene were added, and the solvent was evaporated. This was repeated 3× to provide a tan solid.

Example 240d 4-(2,4-difluorophenyl)-10-methyl-7-((methylsulfonyl)methyl)-11-oxo-3,4,10,11-tetrahydro-1H-1,4,10-triazadibenzo[cd,f]azulene-5-carboxamide A 25 mL round-bottomed flask was charged with Example 240c (0.024 g, 0.046 mmol) and dichloromethane (0.463 mL) to give a tan solution. Ammonium hydroxide (0.027 mL, 0.695 mmol) was added, and the reaction mixture was stirred at ambient temperature for 2 hours. The reaction mixture was partitioned between dichloromethane and saturated aqueous sodium chloride. The organic layer was dried over anhydrous magnesium sulfate, filtered, and concentrated. The reaction mixture was purified by reverse phase HPLC (Phenomenex Luna C8(2) 5 µm 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). Samples were injected in 1.5 mL DMSO:methanol (1:1)) to provide a white solid (0.0010 g, 4% yield). $^1$H NMR (500 MHz, DMSO-d$_6$) δ 11.83 (s, 1H), 7.91 (m, 1H), 7.71 (s, 1H), 7.56 (s, 1H), 7.40 (m, 1H), 7.36 (s, 1H), 7.20 (m, 1H), 6.92 (m, 1H), 6.61 (t, J=7.4 Hz, 1H), 6.30 (dd, J=15.9, 9.4 Hz, 1H), 5.09 (d, J=16.7 Hz, 1H), 4.56 (m, 3H), 3.60 (s, 6H), 3.01 (s, 6H). MS (ESI+) m/z 499.1 (M+H)$^+$.

Example 241

4-(2,4-difluorophenyl)-N,10-dimethyl-7-((methylsulfonyl)methyl)-11-oxo-3,4,10,11-tetrahydro-1H-1,4,10-triazadibenzo[cd,f]azulene-5-carboxamide Example 241 was prepared according to the procedure used for the preparation of Example 240d, substituting methylamine for ammonium hydroxide, to provide the title compound as a white solid (0.0091 g, 38% yield). NMR (500 MHz, DMSO-d$_6$) δ 11.83 (m, 1H), 7.96 (q, J=4.6 Hz, 1H), 7.91 (d, J=2.0 Hz, 1H), 7.73 (d, J=2.0 Hz, 1H), 7.18 (d, J=2.6 Hz, 1H), 6.93 (m, 1H), 6.64 (td, J=8.6, 3.0 Hz, 1H), 6.38 (td, J=9.6, 5.8 Hz, 1H), 5.01 (m, 1H), 4.55 (m, 3H), 3.61 (s, 3H), 2.99 (s, 3H), 2.62 (d, J=4.6 Hz, 3H). MS (ESI+) m/z 513.1 (M+H)$^+$.

Example 242

4-(2,4-difluorophenyl)-N,N,10-trimethyl-7-((methylsulfonyl)methyl)-11-oxo-3,4,10,11-tetrahydro-1H-1,4,10-triazadibenzo[cd,f]azulene-5-carboxamide Example 242 was prepared according to the procedure used for the preparation of Example 240d, substituting N,N-dimethylamine for ammonium hydroxide, to provide the title compound as a white solid (0.0076 g, 31% yield). $^1$H NMR (500 MHz, DMSO-d$_6$) δ 11.82 (s, 1H), 7.93 (d, J=5.9 Hz, 1H), 7.75 (d, J=15.6 Hz, 1H), 7.18 (t, J=3.5 Hz, 1H), 7.21-7.11 (m, 2H), 7.11-6.92 (m, 1H), 6.72 (s, 1H), 6.58 (s, 1H), 6.31 (s, 1H), 4.93 (dd, J=16.1, 10.8 Hz, 1H), 4.66-4.42 (m, 2H), 4.34 (d, J=16.5 Hz, 1H), 3.63 (s, 4H), 2.98 (s, 3H), 2.88 (s, 3H), 2.72 (s, 2H), 2.22 (s, 2H). MS (ESI+) m/z 527.0 (M+H)$^+$.

Example 243

N-(4-(10-methyl-7-((methylsulfonyl)methyl)-11-oxo-10,11-dihydro-1H-1,4,10-triazadibenzo[cd,f]azulen-4(3H)-yl)cyclohexyl)acetamide A mixture of Example 212 (0.062 g, 0.079 mmol) in dimethylformamide (5 mL) was treated with N,N-diisopropylethylamine (0.062 mL, 0.356 mmol) and acetyl chloride (0.0062 g, 0.079 mmol) at ambient temperature under argon. The reaction mixture was stirred at ambient temperature for 2 hours and then partitioned between aqueous ammonium chloride solution and ethyl acetate. The aqueous layer was extracted 4 times with additional ethyl acetate and then extracted three times with dichloromethane. The combined organic layers were dried over anhydrous magnesium sulfate, filtered, and concentrated to afford the title compound (0.017 g, 0.035 mmol, 45% yield). $^1$H NMR (400 MHz, DMSO-d$_6$) δ 11.48 (s, 1H), 7.70 (s, 1H), 7.52-7.46 (m, 1H), 7.40-7.15 (m, 3H), 7.12 (s, 1H), 4.45-4.38 (m, 2H), 4.22 (s, 2H), 3.68-3.54 (m, 3.5H), 3.44-3.35 (m, 0.5H), 3.17-3.09 (m, 0.5H), 2.90-2.88 (m, 3H), 2.83-2.79 (m, 0.5H), 1.81-1.44 (m, 5H), 1.30 (m, 4H), 1.06-0.86 (m, 2H). MS (ESI+) m/z 483.1 (M+H)$^+$.

Example 244

10-methyl-7-((methylsulfonyl)methyl)-4-(pyridin-3-yl)-3,4-dihydro-1H-1,4,10-triazadibenzo[cd,f]azulen-11(10H)-one Example 244a 6-methyl-4-(5-((methylsulfonyl)methyl)-2-(pyridin-3-ylamino)phenyl)-1-tosyl-1H-pyrrolo[2,3-c]pyridin-7(6H)-one A suspension of Example 5d (200 mg, 0.412 mmol), 3-bromopyridine (65.1 mg, 0.412 mmol), cesium carbonate (335 mg, 1.030 mmol), and dicyclohexyl(2',4',6'-triisopropylbiphenyl-2-yl)phosphine (X-phos) (39.3 mg, 0.082 mmol) in toluene (4 mL) and tert-butanol (1 mL) was purged with nitrogen and then heated in Biotage Initiator microwave oven at 150° C. for 45 minutes. Water was added. The mixture was extracted with ethyl acetate (3×). The combined organic layers were washed with saturated aqueous sodium chloride, dried over anhydrous magnesium sulfate, and filtered. The filtrate was concentrated and the residue was purified by column chromatography (silica gel, 0-8% methanol/dichloromethane gradient) to give the title compound (74 mg, 0.132 mmol, 31.9% yield).

Example 244b 6-methyl-4-(5-((methylsulfonyl)methyl)-2-(pyridin-3-ylamino)phenyl)-1H-pyrrolo[2,3-c]pyridin-7(6H)-one Example 244a (55 mg, 0.098 mmol) and lithium hydroxide monohydrate (20.51 mg, 0.489 mmol) in dioxane (1.5 mL) and water (0.5 mL) was stirred at 60° C. for 6 hours. The mixture was partitioned between water and ethyl acetate. The aqueous layer was extracted with ethyl acetate (3×). The combined organic layers were washed with saturated aqueous sodium chloride, dried over anhydrous magnesium sulfate, filtered, and concentrated. The residue was purified by column chromatography (silica gel, 0-8% methanol/dichloromethane gradient) to give the title compound (33 mg, 0.081 mmol, 83% yield) as an off-white solid.

Example 244c 10-methyl-7-((methylsulfonyl)methyl)-4-(pyridin-3-yl)-3,4-dihydro-1H-1,4,10-triazadibenzo[cd,f]azulen-11(10H)-one A suspension of Example 244b (27 mg, 0.066 mmol) and paraformaldehyde (19.85 mg, 0.661 mmol) in acetic acid (1 mL) was stirred at 75° C. for 1.5 hours. Acetic acid was evaporated under reduced pressure and the residue was taken into dichloromethane and washed with 1N NaOH solution. The aqueous phase was back extracted with dichloromethane. The combined organic phases were dried over anhydrous magnesium sulfate, and filtered. The filtrate was concentrated and the residue was purified by column chromatography (silica gel, 0-8% methanol/dichloromethane gradient) to give the title compound (15 mg, 0.036 mmol, 54.0% yield) as a white solid. 1H NMR (500 MHz, DMSO-$d_6$) δ 11.88 (s, 1H), 7.94 (d, J=1.8 Hz, 1H), 7.78 (d, J=2.9 Hz, 1H), 7.73 (dd, J=4.5, 1.1 Hz, 1H), 7.63 (s, 1H), 7.47 (dd, J=8.0, 1.8 Hz, 1H), 7.38 (d, J=8.0 Hz, 2H), 6.97 (dd, J=8.5, 4.5 Hz, 1H), 6.82-6.76 (m, 1H), 5.24 (d, J=14.3 Hz, 1H), 4.52 (dd, J=60.4, 26.1 Hz, 3H), 3.55 (s, 3H), 3.01 (s, 3H). MS ESI (+) 421.1 (M+H)$^+$.

Example 245

4-(5-chloropyridin-2-yl)-10-methyl-7-((methylsulfonyl)methyl)-3,4-dihydro-1H-1,4,10-triazadibenzo[cd,f]azulen-11(10H)-one Example 245a 4-(2-((5-chloropyridin-2-yl)amino)-5-((methylsulfonyl)methyl)phenyl)-6-methyl-1-tosyl-1H-pyrrolo[2,3-c]pyridin-7(6H)-one Example 245a was prepared according to the procedure used for the preparation of Example 244a, substituting 2-bromo-5-chloropyridine for 3-bromopyridine to provide the title compound Example 245b 4-(2-((5-chloropyridin-2-yl)amino)-5-((methylsulfonyl)methyl)phenyl)-6-methyl-1H-pyrrolo[2,3-c]pyridin-7(6H)-one Example 245b was prepared according to the procedure used for the preparation of Example 244b, substituting example 245a for example 244a to provide the title compound Example 245c 4-(5-chloropyridin-2-yl)-10-methyl-7-((methylsulfonyl)methyl)-3,4-dihydro-1H-1,4,10-triazadibenzo[cd,f]azulen-11(10H)-one Example 245c was prepared according to the procedure used for the preparation of Example 244c, substituting example 245b for example 244b to provide the title compound. 1H NMR (400 MHz, DMSO-$d_6$) δ 16.38-16.29 (m, 1H), 11.86 (s, 1H), 7.95 (d, J=25.9 Hz, 2H), 7.64 (s, 1H), 7.49-7.27 (m, 4H), 6.19 (d, J=8.3 Hz, 1H), 5.69 (d, J=15.8 Hz, 1H), 4.62 (d, J=13.5 Hz, 1H), 4.51 (d, J=13.5 Hz, 1H), 4.29 (d, J=15.6 Hz, 1H), 3.58 (s, 3H), 3.01 (s, 3H). MS (ESI+) m/z 455.1.

Example 246

4-(1H-indazol-5-yl)-10-methyl-7-((methylsulfonyl)methyl)-3,4-dihydro-1H-1,4,10-triazadibenzo[cd,f]azulen-11(10H)-one A mixture of Example 233d (0.058 g, 0.098 mmol) in dioxane (2 mL) at ambient temperature under argon was treated with excess 4N HCl in dioxane (7 mL). The reaction mixture was stirred at ambient temperature for 16 hours and then quenched with the slow addition of saturated sodium bicarbonate solution until pH=8. The mixture was partitioned between aqueous sodium bicarbonate solution and ethyl acetate. The aqueous layer was extracted with additional ethyl acetate. The combined organic layers were washed with saturated aqueous sodium chloride, dried over anhydrous magnesium sulfate, filtered, and concentrated. The residue was purified by reverse phase HPLC (C18, $CH_3CN$/water (0.1% TFA), 0-100% gradient) to afford the title compound as the trifluoroacetate salt (0.024 g, 0.042 mmol, 43% yield). $^1$H NMR (400 MHz, DMSO-$d_6$) δ 11.79 (s, 1H), 7.91 (s, 1H), 7.70 (s, 1H), 7.59 (s, 1H), 7.39 (dd, J=40.3, 7.9 Hz, 3H), 7.18 (d, J=9.0 Hz, 1H), 6.72 (d, J=9.1 Hz, 1H), 6.62 (s, 1H), 4.72 (s, 2H), 4.57 (s, 2H), 3.53 (s, 3H), 3.50 (bs, 1H), 3.01 (s, 3H). MS (ESI+) m/z 460.1 (M+H)$^+$.

Example 247

4-benzyl-10-methyl-7-((methylsulfonyl)methyl)-3,4-dihydro-1H-1,4,10-triazadibenzo[cd,f]azulen-11(10H)-one A mixture of Example 5f (0.0515 g, 0.150 mmol) and benzaldehyde (0.0318 g, 0.300 mmol) in dichloromethane (6 mL) was treated with acetic acid (0.086 mL, 1.500 mmol). The reaction mixture was stirred at 60° C. for 1 hour then cooled to 0° C. (ice bath) and treated with sodium triacetoxyborohydride (0.0669 g, 0.300 mmol). The reaction mixture was removed from 0° C. ice bath and stirred at ambient temperature for 16 hours. The reaction mixture was quenched by the slow addition of saturated sodium bicarbonate solution and then extracted twice with dichloromethane. The combined organic layers were washed with saturated aqueous sodium chloride, dried over anhydrous magnesium sulfate, filtered, and concentrated. The residue was purified by recrystallization from methanol and dimethylsulfoxide to afford the title compound (0.0145 g, 0.033 mmol, 22% yield). $^1$H NMR (500 MHz, DMSO-$d_6$) δ 11.80 (s, 1H), 7.71 (d, J=1.3 Hz, 1H), 7.56 (s, 1H), 7.27-7.16 (m, 7H), 6.99 (d, J=2.2 Hz, 1H), 4.43 (s, 2H), 4.25 (s, 2H), 4.05 (s, 2H), 3.65 (s, 3H), 2.93 (s, 3H). MS (ESI+) m/z 434.1 (M+H)$^+$.

Example 248

10-methyl-7-((methylsulfonyl)methyl)-4-(pyrimidin-5-yl)-3,4-dihydro-1H-1,4,10-triazadibenzo[cd,f]azulen-11(10H)-one Example 248a 6-methyl-4-(5-((methylsulfonyl)methyl)-2-(pyrimidin-5-ylamino)phenyl)-1H-pyrrolo[2,3-c]pyridin-7(6H)-one A mixture of Example 5d (0.300 g, 0.618 mmol), 5-iodopyrimidine (0.382 g, 1.853 mmol), cesium carbonate (0.403 g, 1.236 mmol), dicyclohexyl(2',4',6'-triisopropyl-[1,1'-biphenyl]-2-yl)phosphine (XPhos)(0.147 g, 0.309 mmol), and palladium (II) acetate (0.035 g, 0.154 mmol) in toluene (12 mL) and tert-butanol (3 mL) under argon was heated in a sealed tube in a microwave reactor at 160° C. for 1 hour. The reaction mixture was cooled to ambient temperature and filtered through filter paper. The resulting filtrate was concentrated to near dryness and mixed with ethanol (10 mL), dioxane (20 mL), and excess 5N sodium hydroxide solution (10 mL). The reaction mixture was stirred at ambient temperature for 1 hour and then concentrated to 5 mL and partitioned between saturated ammonium chloride aqueous solution and ethyl acetate. The aqueous phase was extracted once more with ethyl acetate. The combined organic layers were washed with saturated aqueous sodium chloride, dried over anhydrous magnesium sulfate, filtered, and concentrated. The residue was purified by flash column chromatography on silica gel eluting with 5% methanol in dichloromethane to afford the title compound (0.066 g, 0.161 mmol, 26% yield).

Example 248b 10-methyl-7-((methylsulfonyl)methyl)-4-(pyrimidin-5-yl)-3,4-dihydro-1H-1,4,10-triazadibenzo[cd,f]azulen-11(10H)-one A mixture of Example 248a (0.040 g, 0.098 mmol) and paraformaldehyde (0.015 g, 0.488 mmol) in acetic acid (10 mL) under argon was stirred at 75° C. for 2 hours. The reaction mixture was concentrated to a semi-solid and purified by reverse phase HPLC (C18, CH$_3$CN/water (0.1% TFA), 0-100% gradient) and dried under vacuum to afford the title compound (0.0065 g, 0.015 mmol, 15% yield). $^1$H NMR (400 MHz, DMSO-$d_6$) δ 11.59 (s, 1H), 8.31 (s, 1H), 7.95 (s, 3H), 7.59 (s, 1H), 7.51-7.46 (m, 1H), 7.40-7.35 (m, 2H), 4.87 (s, 2H), 4.54 (s, 2H), 3.56 (s, 3H), 2.96 (s, 3H). MS (ESI+) m/z 422.1 (M+H)$^+$.

Example 249

10-methyl-7-((methylsulfonyl)methyl)-4-(pyridin-2-ylmethyl)-3,4-dihydro-1H-1,4,10-triazadibenzo[cd,f]azulen-11(10H)-one A mixture of Example 5f (208 mg, 0.606 mmol), picolinaldehyde (0.116 mL, 1.211 mmol) and acetic acid (0.347 mL, 6.06 mmol) in dichloromethane (12 mL) was heated under reflux, for 2 hours. The reaction mixture was cooled to ice/water bath temperature for 15 minutes and then sodium triaceteoxyborohydride (297 mg, 1.333 mmol) was added to the reaction mixture under argon. The mixture was stirred at 0° C. for 15 minutes, allowed to warm slowly to ambient temperature over 2 hours, and then stirred at ambient temperature for 16 hours. The pH of the mixture was adjusted to pH=6-7 by the addition of saturated aqueous bicarbonate solution, and the mixture was then extracted with dichloromethane. The organic layers were combined, dried over anhydrous magnesium sulfate, filter, and concentrated. The residue was triturated with methanol and dimethylsulfoxide, and the resulting solid was collected and dried to provide the title compound (108 mg, 41% yield). $^1$H NMR (500 MHz, DMSO-$d_6$) δ 11.80 (bs, 1H), 8.46 (ddd, J=4.8, 1.8, 0.9 Hz, 1H), 7.72 (d, J=1.9 Hz, 1H), 7.64 (td, J=7.6, 1.8 Hz, 1H), 7.56 (s, 1H), 7.29-7.15 (m, 4H), 7.03 (d, J=2.5 Hz, 1H), 4.45-4.39 (m, 4H), 4.13 (s, 2H), 3.65 (s, 3H), 2.92 (s, 3H). (ESI+) m/z 435.1 (M+H)$^+$.

Example 250

10-methyl-7-((methylsulfonyl)methyl)-4-(pyridazin-3-ylmethyl)-3,4-dihydro-1H-1,4,10-triazadibenzo[cd,f]azulen-11(10H)-one Example 250 was prepared according to the procedure used for the preparation of Example 249, substituting pyridazine-3-carbaldehyde for picolinaldehyde to provide the title compound. $^1$H NMR (400 MHz, DMSO-$d_6$) δ 11.82 (bs, 1H), 9.08 (dd, J=4.7, 1.8 Hz, 1H), 7.73 (d, J=1.9 Hz, 1H), 7.62-7.51 (m, 3H), 7.30-7.19 (m, 2H), 7.03 (d, J=2.6 Hz, 1H), 4.56 (s, 2H), 4.43 (s, 2H), 4.15 (s, 2H), 3.65 (s, 3H), 2.92 (s, 3H). (ESI+) m/z 436.4 (M+H)$^+$.

Example 251

(S)-4-(2,4-difluorophenyl)-10-methyl-7-((methylsulfonyl)methyl)-3-((2-oxopyridin-1(2H)-yl)methyl)-3,4-dihydro-1H-1,4,10-triazadibenzo[cd,f]azulen-11(10H)-one Preparatory chiral SFC separation of the product from Example 238 (0.0204 g) on a WHELK-O S.S column. (21×250 mm, 5 micron column, eluting with 30% methanol in supercritical CO$_2$ at 70 mL/min for 20 minutes) afforded the title compound as the first eluted peak. The stereochemistry was randomly assigned to this first eluted peak (8.6 mg, 84% recovery). 1H NMR (500 MHz, DMSO-$d_6$) δ 11.90 (bs, 1H), 7.89 (d, J=2.0 Hz, 1H), 7.74 (s, 1H), 7.64-7.72 (m, 1H), 7.43 (ddd, J=8.9, 6.7, 2.1 Hz, 1H), 7.21 (dd, J=8.2, 2.0 Hz, 1H), 7.00-7.11 (m, 2H), 6.82-6.89 (m, 2H), 6.67 (s, 1H), 6.46 (dd, J=9.1, 1.3 Hz, 1H), 6.00 (td, J=6.6, 1.4 Hz, 1H), 5.50 (dd, J=9.1, 5.6 Hz, 1H), 4.37-4.55 (m, 3H), 3.66 (s, 3H), 3.44-3.54 (m, 1H), 2.95 (s, 3H). MS (ESI+) m/z 563.1 (M+H)$^+$.

Example 252

(R)-4-(2,4-difluorophenyl)-10-methyl-7-((methylsulfonyl)methyl)-3-((2-oxopyridin-1(2H)-yl)methyl)-3,4-dihydro-1H-1,4,10-triazadibenzo[cd,f]azulen-11(10H)-one Preparatory chiral SFC separation of the product from Example 238 (0.0204 g) on a WHELK-O S.S column. (21×250 mm, 5 micron column, eluting with 30% methanol in supercritical $CO_2$ at 70 mL/min for 20 minutes) afforded the title compound as the second eluted peak. The stereochemistry was randomly assigned to this second eluted peak (7.9 mg, 77% recovery). 1H NMR (500 MHz, DMSO-$d_6$) δ 11.90 (bs, 1H), 7.89 (d, J=2.0 Hz, 1H), 7.74 (s, 1H), 7.68 (d, J=6.3 Hz, 1H), 7.43 (ddd, J=8.9, 6.7, 2.1 Hz, 1H), 7.21 (dd, J=8.2, 2.0 Hz, 1H), 7.00-7.11 (m, 2H), 6.82-6.89 (m, 2H), 6.67 (s, 1H), 6.46 (d, J=9.1 Hz, 1H), 6.00 (td, J=6.6, 1.3 Hz, 1H), 5.50 (dd, J=9.1, 5.6 Hz, 1H), 4.36-4.55 (m, 3H), 3.66 (s, 3H), 3.44-3.51 (m, 1H), 2.95 (s, 3H). MS (ESI+) m/z 563.1 $(M+H)^+$.

Example 253

10-methyl-7-((methylsulfonyl)methyl)-4-(5-(trifluoromethyl)pyridin-2-yl)-3,4-dihydro-1H-1,4,10-triazadibenzo[cd,f]azulen-11(10H)-one

Example 253a 6-methyl-4-(5-((methylsulfonyl)methyl)-2-((5-(trifluoromethyl)pyridin-2-yl)amino)phenyl)-1-tosyl-1H-pyrrolo[2,3-c]pyridin-7(6H)-one Example 207a (0.16 g, 0.33 mmol), 2-bromo-5-(trifluoromethyl)pyridine (0.112 g, 0.495 mmol), diacetoxypalladium (0.019 g, 0.083 mmol), dicyclohexyl(2',4',6'-triisopropyl-[1,1'-biphenyl]-2-yl)phosphine (0.079 g, 0.165 mmol) and cesium carbonate (0.215 g, 0.66 mmol) were combined in a 20-mL microwave vial and sparged with nitrogen for 30 minutes. To this were added nitrogen-sparged anhydrous toluene (2.4 mL) and tert-butanol (0.6 mL). The reaction mixture was heated at 105° C. overnight, then cooled to ambient temperature and partitioned between ethyl acetate and water. The organic layer was washed with brine, treated with 3-mercaptopropyl-functionalized silica gel for 20 minutes, dried over anhydrous magnesium sulfate, filtered through a plug of Celite and concentrated. The residue was purified by flash chromatography (silica gel, 25-100% ethyl acetate in dichloromethane, then 5-15% methanol in dichloromethane) to give 0.077 g (37%) of the title compound and 0.0245 g (16%) of Example 253b.

Example 253b 6-methyl-4-(5-((methylsulfonyl)methyl)-2-((5-(trifluoromethyl)pyridin-2-yl)amino)phenyl)-1H-pyrrolo[2,3-c]pyridin-7(6H)-one A mixture of Example 253a (0.077 g, 0.122 mmol) in tetrahydrofuran (1.5 mL) was treated with tetrabutylammonium fluoride (0.028 g, 0.107 mmol), heated at 50° C. for 50 minutes and then at 60° C. for one hour. It was then stirred at ambient temperature overnight. Additional tetrabutylammonium fluoride (0.028 g, 0.107 mmol) was added and heating was continued at 60° C. for 3 hours. The reaction mixture was concentrated to dryness, triturated with ethyl acetate and then dried in a vacuum oven at 70° C. to give 0.054 g (93%) of the title compound.

Example 253c 10-methyl-7-((methylsulfonyl)methyl)-4-(5-(trifluoromethyl)pyridin-2-yl)-3,4-dihydro-1H-1,4,10-triazadibenzo[cd,f]azulen-11(10H)-one To a 5-mL microwave vial equipped with a magnetic stirbar were added Example 253b (0.025 g, 0.052 mmol), paraformaldehyde (0.006 g, 0.207 mmol), and acetic acid (1.2 mL). The vial was capped and heated at 75° C. for 45 minutes. Additional paraformaldehyde (0.006 g, 0.207 mmol) was added and heating was continued for 1 hour at 75° C. The reaction mixture was then concentrated. The residue was dissolved in acetonitrile (3 mL) and water (0.75 mL), treated with sodium acetate (0.043 g, 0.518 mmol) and heated at 50° C. for 1 hour. The reaction mixture was cooled to ambient temperature, partitioned between ethyl acetate and water, washed with brine, dried over anhydrous magnesium sulfate, filtered and concentrated. The residue was purified by flash chromatography (silica gel, 0-8% methanol in dichloromethane) to give 0.026 g (103%) of the title compound. $^1$H NMR (400 MHz, DMSO-$d_6$) δ 11.91 (s, 1H), 8.33 (s, 1H), 7.95 (s, 1H), 7.67 (s, 1H), 7.62 (d, J=7.63 Hz, 1H), 7.44 (m, 2H), 7.34 (s, 1H), 6.29 (s, 1H), 5.83 (s, 1H), 4.64 (m, 1H), 4.53 (m, 1H), 4.35 (d, J=14.95 Hz, 1H), 3.58 (s, 3H), 3.02 (s, 3H). MS (ESI+) m/z 489.1 $(M+H)^+$.

Example 254

4-(2-fluoropyridin-4-yl)-10-methyl-7-((methylsulfonyl)methyl)-3,4-dihydro-1H-1,4,10-triazadibenzo[cd,f]azulen-11(10H)-one

Example 254a

A mixture of Example 207a (0.146 g, 0.3 mmol), 4-bromo-2-fluoropyridine (0.069 g, 0.390 mmol), 2-(dicyclohexylphosphino)-2',4',6'-triisopropylbiphenyl (0.072 g, 0.150 mmol), palladium(II) acetate (0.017 g, 0.075 mmol), and cesium carbonate (0.244 g, 0.750 mmol) in toluene (3 mL) and tert-butanol (0.750 mL) was heated at 160° C. for 1 hour. Two more identical runs were conducted, and the combined reaction mixtures were partitioned between water and ethyl acetate. The aqueous layer was extracted with additional ethyl acetate several times. The combined organic layers were washed with saturated aqueous sodium chloride, dried over anhydrous magnesium sulfate, filtered, and concentrated. The residue was purified by flash chromatography on silica gel eluting with 100:10:1 ethyl acetate/methanol/ $NH_4OH$ to afford 0.14 g (36%) of the title compound.

Example 254b 4-(2-fluoropyridin-4-yl)-10-methyl-7-((methylsulfonyl)methyl)-3,4-dihydro-1H-1,4,10-triazadibenzo[cd,f]azulen-11(10H)-one A mixture of Example 254a (0.13 g, 0.305 mmol) and paraformaldehyde (0.027 g, 0.914 mmol) in acetic acid (6 mL) was heated at 75° C. for 4 hours. The solvent was evaporated, and the residue was purified by reverse phase preparative HPLC (C18, $CH_3CN$/water (0.1% trifluoroacetic acid), 0-100% gradient) to afford the title compound as trifluoroacetic acid salt (0.085 g, 0.154 mmol, 50.5% yield).

$^1$H NMR (400 MHz, DMSO-d$_6$) δ 11.94 (s, 1H), 7.96 (d, J=1.9 Hz, 1H), 7.65 (d, J=17.7 Hz, 2H), 7.55-7.34 (m, 4H), 5.27 (d, J=16.3 Hz, 1H), 4.64 (d, J=13.6 Hz, 1H), 4.60-4.46 (m, 2H), 3.57 (s, 3H), 3.01 (s, 3H). MS (ESI+) m/z 438.9 [M+H]$^+$.

Example 255

10-methyl-4-((1-methyl-1H-pyrazol-3-yl)methyl)-7-((methylsulfonyl)methyl)-3,4-dihydro-1H-1,4,10-triazadibenzo[cd,f]azulen-11(10H)-one Example 255 was prepared according to the procedure used for the preparation of Example 249, substituting 1-methyl-1H-pyrazole-3-carbaldehyde for picolinaldehyde, and the residue was recrystallized from dichloromethane, to provide the title compound. $^1$H NMR (400 MHz, DMSO-d$_6$) δ11.75 (bs, 1H), 7.69 (d, J=2.0 Hz, 1H), 7.54-7.48 (m, 2H), 7.29 (d, J=8.2 Hz, 1H), 7.23 (dd, J=8.2, 2.0 Hz, 1H), 7.15-6.97 (m, 1H), 5.96 (d, J=2.1 Hz, 1H), 4.43 (bs, 2H), 4.23-4.04 (m, 4H), 3.75 (s, 2H), 3.63 (s, 3H), 2.92 (s, 3H). (ESI+) m/z 438.1 (M+H)$^+$.

Example 256

4-(6-methoxypyridin-2-yl)-10-methyl-7-((methylsulfonyl)methyl)-3,4-dihydro-1H-1,4,10-triazadibenzo[cd,f]azulen-11(10H)-one Example 256a 4-(2-((6-methoxypyridin-2-yl)amino)-5-((methylsulfonyl)methyl)phenyl)-6-methyl-1-tosyl-1H-pyrrolo[2,3-c]pyridin-7(6H)-one Example 207a (0.243 g, 0.5 mmol), 2-bromo-6-methoxypyridine (0.188 g, 1 mmol), diacetoxypalladium (0.028 g, 0.125 mmol), dicyclohexyl(2',4',6'-triisopropyl-[1,1'-biphenyl]-2-yl)phosphine (0.12 g, 0.25 mmol), and cesium carbonate (0.326 g, 1 mmol) were combined in a 5-mL microwave vial. Anhydrous toluene (4 mL) and tert-butanol (1 mL) were added. The vial was capped and the mixture was heated at 160° C. for 1 hour in a Biotage microwave reactor. The reaction mixture was filtered through a fritted funnel to remove the palladium solids. The filtrate was partitioned between ethyl acetate and water. The organic layer was washed with saturated aqueous sodium chloride, treated with 3-mercaptopropyl-functionalized silica gel for 20 minutes, dried over anhydrous magnesium sulfate, filtered through a plug of Celite, and concentrated. The residue was purified by flash chromatography (silica gel, 0-100% ethyl acetate in dichloromethane, then 5-10% methanol in ethyl acetate) to give 0.15 g (51%) of the title compound and 0.08 g (37%) of Example 256b.

Example 256b 4-(2-((6-methoxypyridin-2-yl)amino)-5-((methylsulfonyl)methyl)phenyl)-6-methyl-1H-pyrrolo[2,3-c]pyridin-7(6H)-one A mixture of Example 256a (0.122 g, 0.206 mmol) and tetrabutylammonium fluoride (0.108 g, 0.412 mmol) in tetrahydrofuran (3.5 mL) was heated at 60° C. for 50 minutes and then concentrated. The residue was purified by flash chromatography (silica gel, 0-20% methanol in dichloromethane) and trituration in dichloromethane to give 0.077 g (71%) of the title compound. A portion of this material was then combined with a portion of the deprotected material obtained in Example 256a (0.133 g total) and purified by reverse phase HPLC (C18, acetonitrile/water (0.1% trifluoroacetic acid), 5-70%) to provide 0.071 g (43% recovery) of the title compound as the trifluoroacetic acid salt.

Example 256c 4-(6-methoxypyridin-2-yl)-10-methyl-7-((methylsulfonyl)methyl)-3,4-dihydro-1H-1,4,10-triazadibenzo[cd,f]azulen-11(10H)-one A mixture of Example 256b (0.043 g, 0.077 mmol) and paraformaldehyde (0.005 g, 0.155 mmol) were combined in a 5-mL microwave vial. The vial was capped and the mixture was sparged with nitrogen for 30 minutes. To this was added nitrogen-sparged acetic acid (3 mL). The resulting mixture was stirred at ambient temperature for 4 hours. The reaction mixture was then quenched with methanol and concentrated to dryness keeping the bath temperature below 30° C. The residue was purified by reverse phase HPLC (C18, acetonitrile/water (0.1% trifluoroacetic acid), 5-75%) to provide 0.019 g (43%) of the title compound as the trifluoroacetic acid salt. 1H NMR (400 MHz, DMSO-d$_6$) δ 11.85 (d, J=1.83 Hz, 1H), 7.93 (d, J=1.53 Hz, 1H), 7.64 (s, 1H), 7.44 (m, 1H), 7.39 (m, 1H), 7.31 (d, J=2.44 Hz, 1H), 7.17 (t, J=7.93 Hz, 1H), 5.90 (d, J=7.63 Hz, 1H), 5.78 (d, J=15.56 Hz, 1H), 5.58 (d, J=7.93 Hz, 1H), 4.62 (m, 1H), 4.52 (m, 1H), 4.22 (d, J=15.26 Hz, 1H), 3.74 (s, 3H), 3.58 (s, 3H), 2.99 (m, 3H). MS (ESI+) m/z 451.1 (M+H)$^+$.

Example 257

4-(2,2-dimethyl-3-morpholinopropyl)-10-methyl-7-((methylsulfonyl)methyl)-3,4-dihydro-1H-1,4,10-triazadibenzo[cd,f]azulen-11(10H)-one Example 257a 4-(2-((2,2-dimethyl-3-morpholinopropyl)amino)-5-((methylsulfonyl)methyl)phenyl)-6-methyl-1H-pyrrolo[2,3-c]pyridin-7(6H)-one A mixture of Example 5d (77 mg, 0.159 mmol) and 2,2-dimethyl-3-morpholinopropanal (0.056 mL, 0.317 mmol) was stirred in dichloromethane (5 mL). To this mixture was added acetic acid (0.045 mL, 0.793 mmol). The resulting partial suspension was heated under reflux for 1.5 hour. The reaction mixture was cooled in an ice/water bath for 15 minutes and then sodium triacetoxyborohydride (106 mg, 0.476 mmol) was added to the mixture under argon. The mixture was stirred at 0° C. for 15 minutes and then allowed to warm slowly to ambient temperature over 1 hour. The mixture was then stirred at ambient temperature for 16 hours. Saturated aqueous sodium bicarbonate solution was added followed by addition of saturated aqueous ammonium chloride and water. The mixture was extracted with dichloromethane and the layers separated. The organic layer was dried over anhydrous magnesium sulfate, filtered, and concentrated to provide the title compound.

Example 257b 4-(2-((2,2-dimethyl-3-morpholinopropyl)amino)-5-((methylsulfonyl)methyl)phenyl)-6-methyl-1H-pyrrolo[2,3-c]pyridin-7(6H)-one Example 257a (130 mg, 0.203 mmol) was dissolved in dioxane (8 mL) and ethanol (4 mL). To this mixture was added 5N aqueous sodium hydroxide solution (5 mL) and the mixture was stirred at ambient temperature for 4 hours. The mixture was concentrated to approximately ⅓ of the volume and then partitioned between saturated aqueous ammonium chloride and ethyl acetate. The organic layer was dried over anhydrous magnesium sulfate, filtered, and concentrated. The residue was triturated with a mixture of ethyl ether and ethyl acetate, filtered, and dried, to provide the title compound.

Example 257c 4-(2,2-dimethyl-3-morpholinopropyl)-10-methyl-7-((methylsulfonyl)methyl)-3,4-dihydro-1H-1,4,10-triazadibenzo[cd,f]azulen-11(10H)-one A mixture of Example 257b (38 mg, 0.077 mmol) and paraformaldehyde (12.5 mg, 0.411 mmol) in tetrahydrofuran (10 mL) was stirred at ambient temperature. To resulting suspension was added 1M solution of titanium tetrachloride (0.82 mL). The reaction mixture was stirred for 24 hours at ambient temperature and then added to a mixture of saturated aqueous sodium bicarbonate and ethyl acetate. The organic layer was separated and the aqueous layer extracted with ethyl acetate. The combined organic layers were dried over anhydrous magnesium sulfate, filtered, and concentrated. The residue was purified by flash chromatography (silica gel, 2% methanol/dichloromethane) to provide the title compound (10.8 mg, 28% yield). $^1$H NMR (400 MHz, DMSO-$d_6$) δ 11.75 (bs, 1H), 7.63 (d, J=2.1 Hz, 1H), 7.51 (s, 1H), 7.38 (d, J=8.2 Hz, 1H), 7.24 (dd, J=8.2, 2.0 Hz, 1H), 7.10 (d, J=2.5 Hz, 1H), 4.42 (s, 2H), 4.13 (s, 2H), 3.63 (s, 3H), 3.37 (m, 4H), 2.91 (s, 3H), 2.13 (bs, 4H), 1.88 (bs, 2H), 0.63 (s, 6H). (ESI+) m/z 499.2 (M+H)$^+$.

Example 258

4-(5-fluoropyrimidin-2-yl)-10-methyl-7-((methylsulfonyl)methyl)-3,4-dihydro-1H-1,4,10-triazadibenzo[cd,f]azulen-11(10H)-one Example 258a 4-(2-((5-fluoropyrimidin-2-yl)amino)-5-((methylsulfonyl)methyl)phenyl)-6-methyl-1-tosyl-1H-pyrrolo[2,3-c]pyridin-7(6H)-one Example 207a (0.243 g, 0.5 mmol), 2-bromo-5-fluoropyrimidine (0.177 g, 1 mmol), diacetoxypalladium (0.028 g, 0.125 mmol), dicyclohexyl(2',4',6'-triisopropyl-[1,1'-biphenyl]-2-yl)phosphine (0.12 g, 0.25 mmol), and cesium carbonate (0.326 g, 1 mmol) were combined in a 5-mL microwave vial and sparged with nitrogen for 30 minutes. A nitrogen-sparged solution of anhydrous toluene (3.2 mL) and tert-butanol (0.8 mL) was added. The reaction mixture was heated at 110° C. for 3 hours, cooled to ambient temperature, and filtered through a fritted funnel to remove the palladium solids. The filtrate was partitioned between ethyl acetate and water. The organic layer was washed with saturated aqueous sodium chloride, treated with 3-mercaptopropyl-functionalized silica gel for 20 minutes, dried over anhydrous magnesium sulfate, filtered through a plug of Celite, and concentrated. The residue was triturated with methanol, filtered, and dried in a vacuum oven at 70° C. to give 0.215 (74%) of the title compound.

Example 258b 4-(2-((5-fluoropyrimidin-2-yl)amino)-5-((methylsulfonyl)methyl)phenyl)-6-methyl-1H-pyrrolo[2,3-c]pyridin-7(6H)-one A mixture of Example 258a (0.215 g, 0.37 mmol) in tetrahydrofuran (15 mL) was treated with tetrabutylammonium fluoride (0.145 g, 0.554 mmol) and stirred at 60° C. for 1 hour and 40 minutes. The reaction mixture was cooled to ambient temperature and concentrated. The concentrate was slurried in dichloromethane and the solid was collected by filtration and dried in a vacuum oven at 70° C. to give 0.068 g (43%) of the title compound.

Example 258c 4-(5-fluoropyrimidin-2-yl)-10-methyl-7-((methylsulfonyl)methyl)-3,4-dihydro-1H-1,4,10-triazadibenzo[cd,f]azulen-11(10H)-one A mixture of Example 258b (0.059 g, 0.137 mmol) and paraformaldehyde (0.016 g, 0.548 mmol) were combined in a 5-mL microwave vial. The vial was capped and sparged with nitrogen for 30 minutes. Nitrogen-sparged acetic acid (5 mL) was added and the mixture was heated at 75° C. for 3 hours and 40 minutes. The reaction mixture was concentrated to dryness, slurried in water and treated with sodium acetate until basic. The resulting mixture was heated at 50° C. for 2 hours and then cooled to ambient temperature. The solid was collected by filtration, rinsed with 300 mL of water and dried in a vacuum oven at 70° C. overnight. The solid was then slurried in ethyl acetate, stirred for 1 hour and filtered. To this solid (0.04 g, 0.091 mmol) in methanol (0.25 mL) was added hydrogen chloride solution (4 M in 1,4-dioxane) (0.3 mL, 1 mmol). The resulting mixture was stirred at ambient temperature for 30 minutes. The solid was collected by filtration and dried in a vacuum oven at 70° C. to give 0.0354 (54%) of the title compound as the HCl salt. $^1$H NMR (400 MHz, DMSO-$d_6$) δ 11.87 (d, J=2.14 Hz, 1H), 8.31 (s, 2H), 7.83 (d, J=1.53 Hz, 1H), 7.60 (s, 1H), 7.37 (m, 2H), 7.30 (d, J=2.44 Hz, 1H), 5.70 (d, J=15.56 Hz, 1H), 4.60 (m, 1H), 4.49 (m, 1H), 4.34 (d, J=15.56 Hz, 1H), 3.58 (s, 3H), 3.01 (s, 3H). MS (ESI+) m/z 440.1 (M+H)$^+$.

Example 259

10-methyl-7-((methylsulfonyl)methyl)-4-(pyrimidin-4-yl)-3,4-dihydro-1H-1,4,10-triazadibenzo[cd,f]azulen-11(10H)-one Example 259a 6-methyl-4-(5-((methylsulfonyl)methyl)-2-(pyrimidin-4-ylamino)phenyl)-1-tosyl-1H-pyrrolo[2,3-c]pyridin-7(6H)-one Example 207a (0.243 g, 0.5 mmol), 4-bromopyrimidine (0.159 g, 1 mmol), diacetoxypalladium (0.028 g, 0.125 mmol), dicyclohexyl(2',4',6'-triisopropyl-[1,1'-biphenyl]-2-yl)phosphine (0.12 g, 0.25 mmol), and cesium carbonate (0.326 g, 1 mmol) were combined in a 5-mL microwave vial and sparged with nitrogen for 30 minutes. A nitrogen-sparged solution of anhydrous toluene (3.2 mL) and tert-butanol (0.8 mL) was added. The reaction mixture was heated at 110° C. for 16.5 hours, cooled to ambient temperature and filtered through a fritted funnel to remove the palladium solids. The filtrate was partitioned between ethyl acetate and water. The organic layer was washed with saturated aqueous sodium chloride, treated with 3-mercaptopropyl-functionalized silica gel for 20 minutes, dried over anhydrous magnesium sulfate, filtered through a plug of Celite, and concentrated. The residue was purified by flash chromatography (silica gel, 20 to 100% of a 3:1 mixture of ethyl acetate/ethanol in heptanes) to provide an impure mixture. The material was subjected to a second flash chromatography (silica gel, 45 to 50% of a 3:1 mixture of ethyl acetate/ethanol in heptanes) to provide 0.042 g (15%) of the title compound.

Example 259b 6-methyl-4-(5-((methylsulfonyl)methyl)-2-(pyrimidin-4-ylamino)phenyl)-1H-pyrrolo[2,3-c]pyridin-7(6H)-one A mixture of Example 259a (0.042 g, 0.075 mmol) in tetrahydrofuran (2 mL) was treated with tetrabutylammonium fluoride (0.02 g, 0.075 mmol) and heated at 60° C. for 45 minutes. Additional tetrabutylammonium fluoride (0.02 g, 0.075 mmol) was added and heating was continued for another 1.25 hours. The reaction mixture was cooled to ambient temperature, concentrated, and slurried in ethyl acetate. The solid was collected by filtration and then purified by reverse phase HPLC (C18, acetonitrile/water (0.1% trifluoroacetic acid), 5-70%) to provide 0.039 g (99%) of the title compound.

Example 259c 10-methyl-7-((methylsulfonyl)methyl)-4-(pyrimidin-4-yl)-3,4-dihydro-1H-1,4,10-triazadibenzo[cd,f]azulen-11(10H)-one To a 5-mL microwave vial equipped with a magnetic stirbar were added Example 259b (0.039 g, 0.075 mmol), paraformaldehyde (0.011 g, 0.375 mmol) and acetic acid (1.3 mL). The vial was capped and heated at 75° C. for 40 minutes. The reaction mixture was concentrated. The residue was dissolved in acetonitrile (3 mL) and water (0.75 mL) and treated with sodium acetate until basic. The resulting mixture was heated at 50° C. for one hour and then cooled to ambient temperature. The reaction mixture was partitioned between ethyl acetate and water, washed with saturated aqueous sodium chloride, dried over anhydrous magnesium sulfate, filtered, and concentrated. The residue was purified by reverse phase HPLC (C18, acetonitrile/water (0.1% trifluoroacetic acid), 10-60%) to provide 0.004 g (9%) of the title compound as the trifluoroacetic acid salt. $^1$H NMR (500 MHz, DMSO-$d_6$) δ 11.87 (d, J=0.61 Hz, 1H), 8.24 (m, 2H), 7.82 (s, 1H), 7.60 (s, 1H), 7.35 (m, 3H), 6.60 (t, J=4.73 Hz, 1H), 5.79 (d, J=15.56 Hz, 1H), 4.60 (m, 1H), 4.49 (d, J=13.43 Hz, 1H), 4.30 (d, J=15.26 Hz, 1H), 3.58 (s, 3H), 3.01 (s, 3H). MS (ESI+) m/z 422.1 (M+H)$^+$.

Example 260

4-(2-(3-(dimethylamino)propoxy)benzyl)-10-methyl-7-((methylsulfonyl)methyl)-3,4-dihydro-1H-1,4,10-triazadibenzo[cd,f]azulen-11(10H)-one Example 260a 4-(2-((2-(3-(dimethylamino)propoxy)benzyl)amino)-5-((methylsulfonyl)methyl)phenyl)-6-methyl-1-tosyl-1H-pyrrolo[2,3-c]pyridin-7(6H)-one A mixture of Example 5d (106 mg, 0.218 mmol) and 2-(3-(dimethylamino)propoxy)benzaldehyde (0.067 mL, 0.314 mmol) was stirred in dichloroethane (5 mL). To this mixture was added acetic acid (0.062 mL, 1.091 mmol). The resulting partial suspension was heated under reflux for 1.5 hour. The reaction mixture was cooled in an ice/water bath for 15 minutes and then sodium triacetoxyborohydride (146 mg, 0.655 mmol) was added to the mixture under argon. The mixture was stirred at 0° C. for 15 minutes and then allowed to warm slowly to ambient temperature over 1 hour. The mixture was then stirred at ambient temperature for 16 hours. Saturated aqueous sodium bicarbonate solution was added followed by saturated aqueous sodium carbonate and water. The mixture was extracted with dichloromethane and the layers separated. The organic layer was dried over anhydrous magnesium sulfate, filtered, and concentrated. The residue was purified by flash chromatography (silica gel, 4-10% methanol in dichloromethane) to provide the title compound.

Example 260b 4-(2-((2-(3-(dimethylamino)propoxy)benzyl)amino)-5-((methylsulfonyl)methyl)phenyl)-6-methyl-1H-pyrrolo[2,3-c]pyridin-7(6H)-one Example 260a (101 mg, 0.149 mmol) was dissolved in dioxane (5 mL). To this mixture was added 5N aqueous sodium hydroxide solution (5 mL) and the mixture was stirred at 80° C. for 4 hours. The mixture was partitioned between saturated aqueous ammonium chloride and ethyl acetate. The organic layer was dried over anhydrous magnesium sulfate, filtered, and concentrated. The residue was purified by flash chromatography (silica gel, 10% methanol in dichloromethane) to provide the title compound.

Example 260c 4-(2-(3-(dimethylamino)propoxy)benzyl)-10-methyl-7-((methylsulfonyl)methyl)-3,4-dihydro-1H-1,4,10-triazadibenzo[cd,f]azulen-11(10H)-one A mixture of Example 260b (43 mg, 0.082 mmol) and paraformaldehyde (10 mg, 0.329 mmol) in tetrahydrofuran (10 mL) was stirred at ambient temperature. To resulting suspension was added 1M solution of titanium tetrachloride (0.66 mL). The reaction mixture was stirred for 24 hours at ambient temperature and then added to a mixture of saturated aqueous sodium bicarbonate and ethyl acetate. The organic layer was separated and the aqueous layer extracted with ethyl acetate. The combined organic layers were dried over anhydrous magnesium sulfate, filtered, and concentrated. The residue was purified by reverse phase HPLC (C18, CH$_3$CN/water (0.1% trifluoroacetic acid), 0-100% gradient) to afford the title compound (16.5 mg, 38%) as the trifluoroacetic acid salt. $^1$H NMR (400 MHz, DMSO-$d_6$) δ 11.83 (s, 1H), 9.41 (s, 1H), 7.74 (s, 1H), 7.57 (s, 1H), 7.25-7.15 (m, 3H), 7.11 (d, J=7.3 Hz, 1H), 7.06 (d, J=2.7 Hz, 1H), 6.95 (d, J=8.2 Hz, 1H), 6.83 (t, J=7.4 Hz, 1H), 4.44 (s, 2H), 4.25 (s, 2H), 4.12 (s, 2H), 4.00 (t, J=5.9 Hz, 2H), 3.57 (s, 3H), 3.16 (dt, J=9.7, 5.3 Hz, 2H), 2.94 (s, 3H), 2.77 (d, J=4.5 Hz, 6H), 2.05 (d$_q$, J=11.6, 5.9 Hz, 2H). (ESI+) m/z 535.1 (M+H)$^+$.

Example 261

2-(10-methyl-7-((methylsulfonyl)methyl)-11-oxo-10,11-dihydro-1H-1,4,10-triazadibenzo[cd,f]azulen-4(3H)-yl)-2-phenylacetonitrile A mixture of Example 5f (57.7 mg, 0.168 mmol), benzaldehyde (19.6 mg, 0.185 mmol), and sodium cyanide (9.3 mg, 0.185 mmol) in methanol (8 mL) was heated to 60° C. over 30 minutes. Acetic acid (0.481 mL, 8.40 mmol) was added, and the partial suspension was heated at 60° C. for 18 hours. To the cooled reaction mixture was added water (10 mL) and the resulting precipitate collected by filtration. The precipitate was purified by reverse phase HPLC (C18, $CH_3CN$/water (0.1% trifluoroacetic acid), 0-100% gradient) to afford the title compound (20 mg, 26%). $^1$H NMR (400 MHz, 90° C., DMSO-$d_6$) δ 11.53 (s, 1H), 7.76 (d, J=2.0 Hz, 1H), 7.54 (s, 1H), 7.31 (d, J=12.7 Hz, 7H), 6.93 (d, J=2.7 Hz, 1H), 5.64 (s, 1H), 4.43 (d, J=1.6 Hz, 2H), 4.19 (s, 2H), 3.64 (s, 3H), 2.88 (s, 3H). (ESI+) m/z 459.1 $(M+H)^+$.

Example 262

2-(2-((10-methyl-7-((methylsulfonyl)methyl)-11-oxo-10,11-dihydro-1H-1,4,10-triazadibenzo[cd,f]azulen-4(3H)-yl)methyl)phenoxy)acetamide Example 262a 2-(2-(((2-(6-methyl-7-oxo-1-tosyl-6,7-dihydro-1H-pyrrolo[2,3-c]pyridin-4-yl)-4-((methylsulfonyl)methyl)phenyl)amino)methyl)phenoxy)acetamide A mixture of Example 5d (260 mg, 0.536 mmol) and 2-(2-formylphenoxy)acetamide (80 mg, 0.446 mmol) was stirred in dichloroethane (7 mL). To this mixture was added acetic acid (0.128 mL, 2.232 mmol). The resulting partial suspension was heated at 80° C. for 2.5 hours. The reaction mixture was cooled in an ice/water bath for 15 minutes and then sodium triacetoxyborohydride (299 mg, 1.34 mmol) was added to the mixture under argon. The mixture was stirred at 0° C. for 15 minutes and then allowed to warm slowly to ambient temperature over 1 hour. The mixture was then stirred at ambient temperature for 16 hours. Saturated aqueous sodium bicarbonate solution was added followed by addition of water. The mixture was extracted with dichloromethane and the layers separated. The organic layer was dried over anhydrous magnesium sulfate, filtered and concentrated. The residue was purified by flash chromatography (silica gel, 1-3% methanol in dichloromethane) to provide the title compound.

Example 262b 2-(2-(((2-(6-methyl-7-oxo-6,7-dihydro-1H-pyrrolo[2,3-c]pyridin-4-yl)-4-((methylsulfonyl)methyl)phenyl)amino)methyl)phenoxy)acetamide Example 262a (170 mg, 0.262 mmol) was dissolved in dioxane (10 mL). To this mixture was added 5N aqueous sodium hydroxide solution (3 mL) and the mixture was stirred at 80° C. for 6 hours. The mixture was partitioned between saturated aqueous ammonium chloride and ethyl acetate. The organic layer was dried over anhydrous magnesium sulfate, filtered, and concentrated to provide the title compound.

Example 262c 2-(2-((10-methyl-7-((methylsulfonyl)methyl)-11-oxo-10,11-dihydro-1H-1,4,10-triazadibenzo[cd,f]azulen-4(3H)-yl)methyl)phenoxy)acetamide A mixture of Example 262b (49 mg, 0.099 mmol) and paraformaldehyde (12 mg, 0.396 mmol) in tetrahydrofuran (10 mL) was stirred at ambient temperature. To the resulting suspension was added a 1M solution of titanium tetrachloride (0.79 mL). The reaction mixture was stirred for 16 hours at ambient temperature and then added to a mixture of saturated aqueous sodium bicarbonate and ethyl acetate. The organic layer was separated and the aqueous layer extracted with ethyl acetate. The combined organic layers were dried over anhydrous magnesium sulfate, filtered, and concentrated. The residue was purified by reverse phase HPLC (C18, $CH_3CN$/water (0.1% trifluoroacetic acid), 0-70% gradient) to afford the title compound (3.4 mg, 7%) $^1$H NMR (400 MHz, DMSO-$d_6$) δ 11.51 (s, 1H), 7.73 (s, 1H), 7.52 (s, 1H), 7.21 (s, 2H), 7.16 (t, J=7.9 Hz, 1H), 7.12-6.96 (m, 4H), 6.89 (d, J=8.3 Hz, 1H), 6.81 (t, J=7.4 Hz, 1H), 4.41 (d, J=5.6 Hz, 4H), 4.28 (s, 2H), 4.17 (s, 2H), 3.65 (s, 3H), 2.89 (s, 3H). (ESI+) m/z 507.2 $(M+H)^+$.

Example 263

4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxylic acid The preparation of Example 263 was described in Example 209a. $^1$H NMR (500 MHz, DMSO-$d_6$) δ 13.21 (s, 1H), 12.44 (s, 1H), 7.83 (d, J=1.22 Hz, 1H), 7.71 (s, 1H), 7.28 (dd, J=8.24, 1.53 Hz, 1H), 7.10 (m, 1H), 7.01 (d, J=7.93 Hz, 1H), 6.88 (td, J=8.54, 2.44 Hz, 1H), 6.82 (td, J=9.23, 5.95 Hz, 1H), 5.09 (s, 2H), 4.49 (s, 2H), 3.63 (s, 3H), 2.96 (s, 3H). MS (ESI+) m/z 500.1 $(M+H)^+$.

Example 264

10-methyl-7-((methylsulfonyl)methyl)-4-(2-(pyridin-2-ylmethoxy)benzyl)-3,4-dihydro-1H-1,4,10-triazadibenzo[cd,f]azulen-11(10H)-one Example 264a 6-methyl-4-(5-((methylsulfonyl)methyl)-2-((2-(pyridin-2-ylmethoxy)benzyl)amino)phenyl)-1-tosyl-1H-pyrrolo[2,3-c]pyridin-7(6H)-one A mixture of Example 5d (72.4 mg, 0.149 mmol) and 2-(pyridin-2-ylmethoxy)benzaldehyde (0.027 mL, 0.124 mmol) was stirred in dichloroethane (5 mL). To this mixture was added acetic acid (0.036 mL, 0.621 mmol). The resulting partial suspension was heated at 80° C. for 2.5 hour. The reaction mixture was cooled in an ice/water bath for 15 minutes and then sodium triacetoxyborohydride (83 mg, 0.373 mmol) was added to the mixture under argon. The mixture was stirred at 0° C. for 15 minutes and then allowed to warm slowly to ambient temperature over 1 hour. The mixture was then stirred at ambient temperature for 18 hours. Saturated aqueous sodium bicarbonate solution was added followed by the addition of water. The mixture was extracted with dichloromethane and the layers separated. The organic layer was dried over anhydrous magnesium sulfate, filtered, and concentrated. The residue was purified by flash chromatography (silica gel, 1-2% methanol in dichloromethane) to provide the title compound.

Example 264b 6-methyl-4-(5-((methylsulfonyl)methyl)-2-((2-(pyridin-2-ylmethoxy)benzyl)amino)phenyl)-1H-pyrrolo[2,3-c]pyridin-7(6H)-one Example 264a (90 mg, 0.132 mmol) was dissolved in dioxane (8 mL). To this mixture was added 5N aqueous sodium hydroxide solution (2 mL) and the mixture was stirred at 85° C. for 4 hours. The mixture was partitioned between saturated aqueous ammonium chloride and ethyl acetate. The organic layer was dried over anhydrous magnesium sulfate, filtered, and concentrated to provide the title compound.

Example 264c 10-methyl-7-((methylsulfonyl)methyl)-4-(2-(pyridin-2-ylmethoxy)benzyl)-3,4-dihydro-1H-1,4,10-triazadibenzo[cd,f]azulen-11(10H)-one A mixture of Example 264b (44 mg, 0.083 mmol) and paraformaldehyde (10 mg, 0.333 mmol) in tetrahydrofuran (10 mL) was stirred at ambient temperature. To resulting suspension was added a 1M solution of titanium tetrachloride (0.67 mL). The reaction mixture was stirred for 7 hours at ambient temperature and then added to a mixture of saturated aqueous sodium bicarbonate and ethyl acetate. The organic layer was separated and the aqueous layer extracted with ethyl acetate. The combined organic layers were dried over anhydrous magnesium sulfate, filtered, and concentrated. The residue was purified by reverse phase HPLC (C18, CH$_3$CN/water (0.1% trifluoroacetic acid), 0-100% gradient) to afford the title compound (19.7 mg, 44%) $^1$H NMR (500 MHz, DMSO-d$_6$) δ 11.97 (d, J=2.9 Hz, 1H), 8.63 (dd, J=5.0, 1.6 Hz, 1H), 7.88 (td, J=7.7, 1.7 Hz, 1H), 7.77 (d, J=2.0 Hz, 1H), 7.59 (s, 1H), 7.50-7.37 (m, 2H), 7.28-7.12 (m, 5H), 7.01 (d, J=8.2 Hz, 1H), 6.87 (t, J=7.5 Hz, 1H), 5.20 (s, 2H), 4.46 (s, 2H), 4.34 (s, 2H), 4.31 (s, 2H), 3.62 (s, 3H), 2.94 (s, 3H). (ESI+) m/z 541.1 (M+H)$^+$.

Example 265

(R)-7-(ethylsulfonyl)-10-methyl-4-(1-phenylethyl)-3,4-dihydro-1H-1,4,10-triazadibenzo[cd,f]azulen-11(10H)-one Example 265a (R)-2-bromo-4-(ethylsulfonyl)-N-(1-phenylethyl) aniline A mixture of Example 2b (661 mg, 2.476 mmol), (R)-1-phenylethanamine (526 mg, 4.340 mmol), and N-ethyl-N-isopropylpropan-2-amine (1.12 mL, 6.420 mmol) in dimethylsulfoxide (12 mL) was heated at 100° C. for 16 hours. The mixture was cooled to ambient temperature and partitioned between saturated aqueous ammonium chloride and ethyl acetate. The organic layer was dried over anhydrous magnesium sulfate, filtered, and concentrated. The residue was purified by flash chromatography (silica gel, 2% ethanol and 6% ethyl acetate in heptane) to provide the title compound.

Example 265b (R)-4-(5-(ethylsulfonyl)-2-((1-phenylethyl)amino) phenyl)-6-methyl-1-tosyl-1H-pyrrolo[2,3-c]pyridin-7(6H)-one A mixture of Example 265a (320 mg, 0.869 mmol), Example 1f (558 mg, 1.30 mmol), cesium fluoride (528 mg, 3.480 mmol) and tetrakis(triphenylphosphine)palladium(0) (100 mg, 0.087 mmol) was sparged with argon for 15 minutes followed by the addition of a degassed dimethoxyethane (20 mL) and methanol (10 mL) mixture. The reaction mixture was heated at 85° C. for 2.5 hours. The mixture was cooled to ambient temperature and partitioned between saturated aqueous sodium chloride and ethyl acetate. The organic layer was dried over anhydrous magnesium sulfate, filtered, and concentrated to provide the title compound.

Example 265c (R)-4-(5-(ethylsulfonyl)-2-((1-phenylethyl)amino) phenyl)-6-methyl-1H-pyrrolo[2,3-c]pyridin-7(6H)-one Example 265b (170 mg, 0.262 mmol) was dissolved in dioxane (20 mL). To this mixture was added 5N aqueous sodium hydroxide solution (5 mL) and the mixture was stirred at 85° C. for 4 hours. The mixture was partitioned between saturated aqueous ammonium chloride and ethyl acetate. The organic layer was dried over anhydrous magnesium sulfate, filtered, and concentrated. The residue was purified by flash chromatography (silica gel, 1-2% methanol in dichloromethane) to provide the title compound.

Example 265d (R)-7-(ethylsulfonyl)-10-methyl-4-(1-phenylethyl)-3,4-dihydro-1H-1,4,10-triazadibenzo[cd,f]azulen-11 (10H)-one A mixture of Example 265c (140 mg, 0.321 mmol) and paraformaldehyde (39 mg, 1.286 mmol) in tetrahydrofuran (10 mL) was stirred at ambient temperature. To resulting suspension was added 1M solution of titanium tetrachloride (2.57 mL). The reaction mixture was stirred for 4 hours at ambient temperature and then added to a mixture of saturated aqueous sodium bicarbonate and ethyl acetate. The organic layer was separated and the aqueous layer extracted with ethyl acetate. The combined organic layers were dried over anhydrous magnesium sulfate, filtered, and concentrated. The residue was purified by recrystallization from methanol and dimethysulfoxide to provide the title compound (109 mg, 76%) NMR (400 MHz, 90° C., DMSO-d$_6$) δ 11.50 (s, 1H), 8.09 (d, J=2.3 Hz, 1H), 7.64 (s, 1H), 7.60 (dd, J=8.3, 2.2 Hz, 1H), 7.41 (d, J=8.3 Hz, 1H), 7.29-7.12 (m, 5H), 6.91 (s, 1H), 4.38 (q, J=6.7 Hz, 1H), 4.23-4.01 (m, 2H), 3.67 (s, 3H), 3.28 (q, J=7.4 Hz, 2H), 1.22 (d, J=6.6 Hz, 3H), 1.16 (t, J=7.3 Hz, 3H). (ESI+) m/z 448.0 (M+H)$^+$.

Example 266

10-methyl-4-(pyridin-2-yl)-7-(pyrrolidin-1-ylsulfonyl)-3,4-dihydro-1H-1,4,5,10-tetraazadibenzo[cd,f] azulen-11(10H)-one Example 266a 3-bromo-2-chloro-5-(pyrrolidin-1-ylsulfonyl)pyridine 5-bromo-6-chloropyridine-3-sulfonyl chloride (4.7 g, 16.2 mmol) in dichloromethane (60 mL) at 0° C. was treated drop-wise with pyrrolidine (2.7 mL, 32.3 mmol) and stirred for 20 minutes at 0° C. The ice bath was removed and stirring was continued at ambient temperature for 45 minutes. The reaction mixture was concentrated, slurried in water and filtered. The solid was then slurried in diethyl ether and filtered to give 4.66 g (88%) of the title compound.

Example 266b

To a mixture of Example 266a (1 g, 3.1 mmol) and pyridin-2-amine (0.36 g, 3.8 mmol) in dimethyl sulfoxide (10 mL) was added sodium hydride (0.25 g, 6.2 mmol). The mixture was stirred at ambient temperature for 1.5 hours and then at 50° C. for 1 hour. The reaction mixture was cooled to ambient temperature and water was added to induce precipitation. The solid was collected by filtration, rinsed with additional water and dried by pulling air through. The solid was then slurried in diethyl ether, stirred for 1 hour, and filtered. The diethyl ether filtrate was concentrated. Both the solid as well as the residue from the concentration were purified individually by flash chromatography (silica gel, 5 to 60% ethyl acetate in heptanes) and then combined to give 0.785 g (67%) of the title compound.

Example 266c 6-methyl-4-(2-(pyridin-2-ylamino)-5-(pyrrolidin-1-ylsulfonyl)pyridin-3-yl)-1-tosyl-1H-pyrrolo[2,3-c]pyridin-7(6H)-one Example 266b (0.066 g, 0.173 mmol), Example 1f (0.064 g, 0.15 mmol), tris(dibenzylideneacetone)dipalladium(0) (0.004 g, 4.5 µmol), 1,3,5,7-tetramethyl-8-phenyl-2,4,6-trioxa-8-phosphaadamantane (0.004 g, 0.015 mmol) and sodium carbonate (0.068 g, 0.645 mmol) were combined and sparged with nitrogen for 30 minutes. To this were added nitrogen-sparged 1,4-dioxane (0.8 mL) and water (0.2 mL). The reaction mixture was stirred at 60° C. for 4 hours and then partitioned between ethyl acetate and water. The organic layer was washed with saturated aqueous sodium chloride, treated with 3-mercaptopropyl-functionalized silica gel for 20 minutes, dried over anhydrous magnesium sulfate, filtered through a plug of Celite, and concentrated. The residue was purified by flash chromatography (silica gel, 0 to 100% ethyl acetate in heptanes) to provide 0.049 g (54%) of the title compound.

Example 266d 6-methyl-4-(2-(pyridin-2-ylamino)-5-(pyrrolidin-1-ylsulfonyl)pyridin-3-yl)-1H-pyrrolo[2,3-c]pyridin-7(6H)-one A mixture of Example 266c (0.047 g, 0.078 mmol) in 1,4-dioxane (0.75 mL) and ethanol (0.25 mL) was treated with sodium hydroxide solution (4 M aqueous, 0.1 mL, 0.4 mmol) and heated at 60° C. for 30 minutes. The reaction mixture was cooled to ambient temperature and neutralized with hydrochloric acid solution (2 M aqueous). The resulting mixture was partitioned between ethyl acetate and water, washed with saturated aqueous sodium chloride, dried over anhydrous magnesium sulfate, filtered, and concentrated. The residue was purified by reverse phase HPLC (C18, acetonitrile/water (0.1% trifluoroacetic acid), 20-90%) to provide 0.04 g (92%) of the title compound as the trifluoroacetic acid salt.

Example 266e 10-methyl-4-(pyridin-2-yl)-7-(pyrrolidin-1-ylsulfonyl)-3,4-dihydro-1H-1,4,5,10-tetraazadibenzo[cd,f]azulen-11(10H)-one To a 5-mL microwave vial equipped with a magnetic stirbar were added Example 266d (0.031 g, 0.055 mmol), paraformaldehyde (0.008 g, 0.275 mmol) and acetic acid (1 mL). The vial was capped and heated at 70° C. for 45 minutes. Additional paraformaldehyde (0.008 g, 0.275 mmol) was added and heating was continued at 80° C. for 90 minutes. Additional paraformaldehyde (0.016 g, 0.55 mmol) was again added and heating was continued overnight at 80° C. The reaction mixture was concentrated and then taken up in acetonitrile (3 mL). Saturated sodium bicarbonate solution was added to achieve pH=10. Water (0.5 mL) was added to provide a homogeneous solution. The mixture was heated at 50° C. overnight. The reaction mixture was cooled to ambient temperature, diluted with water (5 mL) and neutralized with hydrochloric acid solution (2 M aqueous). The layers were separated. The aqueous layer was extracted with ethyl acetate. The organic layers were combined and concentrated. The residue was purified by reverse phase HPLC (C18, acetonitrile/water (0.1% trifluoroacetic acid), 15-90%) to provide 0.007 g (21%) of the title compound as the trifluoroacetic acid salt. $^1$H NMR (500 MHz, DMSO-$d_6$) δ 11.97 (d, J=1.83 Hz, 1H), 8.75 (d, J=2.14 Hz, 1H), 8.62 (d, J=2.14 Hz, 1H), 8.09 (dd, J=5.04, 1.07 Hz, 1H), 7.92 (s, 1H), 7.46 (m, 1H), 7.34 (d, J=2.75 Hz, 1H), 6.73 (dd, J=6.71, 5.49 Hz, 1H), 6.57 (d, J=8.54 Hz, 1H), 5.15 (s, 2H), 3.64 (s, 3H), 3.31 (m, 4H), 1.74 (m, 4H). LCMS m/z 463.21.

Example 267

(S)-7-(ethylsulfonyl)-10-methyl-4-(1-phenylethyl)-3,4-dihydro-1H-1,4,10-triazadibenzo[cd,f]azulen-11(10H)-one Example 267 was prepared according to the procedure used for the preparation of Example 265, substituting (S)-1-phenylethanamine for (R)-1-phenylethanamine to provide the title compound. $^1$H NMR (400 MHz, 90° C., DMSO-$d_6$) δ 11.52 (s, 1H), 8.09 (d, J=2.2 Hz, 1H), 7.65 (s, 1H), 7.60 (dd, J=8.4, 2.2 Hz, 1H), 7.41 (d, J=8.4 Hz, 1H), 7.29-7.12 (m, 5H), 6.91 (d, J=2.6 Hz, 1H), 4.38 (q, J=6.6 Hz, 1H), 4.22-4.01 (m, 2H), 3.67 (s, 3H), 3.29 (q, J=7.4 Hz, 2H), 3.19 (s, 2H), 1.22 (d, J=6.6 Hz, 3H), 1.16 (t, J=7.3 Hz, 3H). (ESI+) m/z 448.0 (M+H)$^+$.

Example 268

(R)-methyl 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoate The product from Example 82 was purified by chiral chromatography on a Chiralpak OJ-H column (21×250 mm, 5 micron) eluting with a 7:13 mixture of methanol/carbon dioxide. Fractions of the first eluted enantiomer were collected and concentrated. The compound isolated was randomly assigned as the (R) enantiomer. $^1$H NMR (500 MHz, DMSO-$d_6$) δ 11.91 (s, 1H), 7.85 (d, J=1.5 Hz, 1H), 7.70 (s, 1H), 7.24 (dd, J=8.2, 1.7 Hz, 1H), 7.13 (s, 1H), 7.11-7.06 (m, 1H), 6.99 (d, J=8.2 Hz, 1H), 6.97-6.85 (m, 2H), 5.04 (t, J=7.6 Hz, 1H), 4.57-4.42 (m, 2H), 3.64 (s, 3H), 3.55 (s, 3H), 2.93 (s, 3H), 2.46-2.36 (m, 2H), 1.96-1.85 (m, 1H), 1.59-1.48 (m, 1H). (ESI+) m/z 542 (M+H)$^+$.

Example 269

(S)-methyl 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoate The product from Example 82 was purified by chiral chromatography on a Chiralpak OJ-H column (21×250 mm, 5 micron) eluting with a 7:13 mixture of methanol/carbon dioxide. Fractions of the second eluted enantiomer were collected and concentrated. The compound isolated was randomly assigned as the (S) enantiomer. NMR (400 MHz, DMSO-$d_6$) δ 11.89 (s, 1H), 7.85 (d, J=1.6 Hz, 1H), 7.69 (s, 1H), 7.24 (dd, J=8.2, 1.7 Hz, 1H), 7.12 (s, 1H), 7.11-7.04 (m, 1H), 6.99 (d, J=8.2 Hz, 1H), 6.96-6.84 (m, 2H), 5.03 (t, J=7.6 Hz, 1H), 4.57-4.40 (m, 2H), 3.64 (s, 3H), 3.55 (s, 3H), 2.93 (s, 3H), 2.46-2.37 (m, 2H), 1.97-1.84 (m, 1H), 1.60-1.47 (m, 1H). (ESI+) m/z 542 (M+H)$^+$.

Example 270

4-(2,4-difluorophenyl)-10-methyl-2-(1-methyl-1H-pyrazol-4-yl)-7-(methylsulfonyl)-3,4-dihydro-1H-1,4,10-triazadibenzo[cd,f]azulen-11(10H)-one Example 270a 4-bromo-2-iodo-7-methoxy-1-tosyl-1H-pyrrolo[2,3-c]pyridine To a solution of n-butyl lithium (2.5 M, 36 mL, 90 mmol in tetrahydrofuran) in anhydrous tetrahydrofuran (200 mL) was added diisopropylamine (7.33 g, 72.4 mmol) dropwise at −70° C. and then the reaction mixture was stirred at −70° C. to −50° C. for 45 minutes. To the solution of Example 1c (23.0 g, 60.3 mmol) in anhydrous tetrahydrofuran (400 mL) was added the above lithium diisopropylamide solution dropwise at −70° C. and then stirred for 1.5 hours. Then the solution of iodine (35.2 g, 139 mmol) in anhydrous tetrahydrofuran (300 mL) was added dropwise to the above mixture at −70° C. The reaction mixture was stirred at −70° C. for another 3 hours and poured into aqueous $Na_2S_2O_3$ solution. The suspension was filtered and the filter cake was washed with dichloromethane and then dried to give the title compound (20 g, 39.4 mmol, 65.4% yield) as white solid.

Example 270b 4-bromo-2-iodo-1-tosyl-1H-pyrrolo[2,3-c]pyridin-7(6H)-one

To the reaction mixture of Example 270a (15 g, 29.6 mmol) and sodium iodide (7.09 g, 47.3 mmol) in acetonitrile (300 mL) was added chlorotrimethylsilane (5.88 mL, 46.0 mmol) dropwise at room temperature. The reaction mixture was stirred at room temperature for 1 hour. Water (0.266 mL, 14.79 mmol) was added dropwise to the reaction mixture and the reaction mixture was stirred at 65° C. for 4 hours. After cooling to room temperature, the reaction mixture was filtered to give crude product, which was then re-dissolved in dichloromethane. The solid was filtered off and the filtrate was concentrated under reduced pressure to give title compound (11 g, 22.31 mmol, 75% yield) as white solid.

Example 270c 4-bromo-2-iodo-6-methyl-1-tosyl-1H-pyrrolo[2,3-c]pyridin-7(6H)-one

To a solution of Example 270b in dimethylformamide (51.7 mL) was added sodium hydride (0.538 g, 13.45 mmol) in portions at 0° C., and the mixture was stirred for 30 minutes, followed by the dropwise addition of iodomethane (0.839 mL, 13.45 mmol). The resulting mixture was stirred at room temperature overnight. The reaction mixture was quenched with saturated aqueous ammonium chloride solution. The resulting suspension was filtered and the filter cake was dissolved in dichloromethane, dried over anhydrous sodium sulfate, filtered, and concentrated under reduced pressure. The residue was washed with ethyl acetate and then dried to afford the title compound (5 g, 9.86 mmol, 95% yield).

Example 270d 4-bromo-6-methyl-2-(1-methyl-1H-pyrazol-4-yl)-1-tosyl-1H-pyrrolo[2,3-c]pyridin-7(6H)-one A mixture of Example 270c (0.431 g, 0.85 mmol), 1-methyl-4-(4,4,5,5-tetramethyl-1,3,2-dioxaborolan-2-yl)-1H-pyrazole (0.177 g, 0.850 mmol), tris(dibenzylideneacetone)dipalladium(0) (0.019 g, 0.021 mmol), 1,3,5,7-tetramethyl-8-phenyl-2,4,6-trioxa-8-phosphaadamantane (0.025 g, 0.085 mmol), and sodium carbonate (0.135 g, 1.275 mmol) in dioxane (5 mL) and water (1.25 mL) was stirred at 50° C. for 3 hours. The mixture was concentrated to dryness and extracted with ethyl acetate (20 mL). The filtrate was concentrated and the residue purified by silica gel flash chromatography (petroleum ether/ethyl acetate 1:1-0:1) to give the title compound (0.353 g, 0.697 mmol, 82% yield).

Example 270e 6-methyl-2-(1-methyl-1H-pyrazol-4-yl)-4-(4,4,5,5-tetramethyl-1,3,2-dioxaborolan-2-yl)-1-tosyl-1H-pyrrolo[2,3-c]pyridin-7(6H)-one A mixture of Example 270d (0.5 g, 1.084 mmol), 4,4,4',4',5,5,5',5'-octamethyl-2,2'-bi(1,3,2-dioxaborolane) (0.330 g, 1.301 mmol), [1,1'-bis(diphenylphosphino)ferrocene]dichloropalladium(II) (0.079 g, 0.108 mmol), and potassium acetate (0.160 g, 1.626 mmol) in 1,4-dioxane (5 mL) was stirred at 100° C. for 16 hours. The mixture was filtered and concentrated. The residue was purified by silica gel flash chromatography (petroleum ether/ethyl acetate 1:1-0:1) to give the title compound (0.3 g, 0.395 mmol, 36.5% yield).

Example 270f 2-bromo-N-(2,4-difluorophenyl)-4-(methylsulfonyl) aniline

A mixture of 2-bromo-4-(methylsulfonyl) aniline (0.8 g, 3.20 mmol), 2,4-difluoro-1-iodobenzene (0.768 g, 3.20 mmol), tris(dibenzylideneacetone)dipalladium(0) (0.146 g, 0.160 mmol), X-phos (2.78 g, 4.80 mmol), and cesium carbonate (0.104 g, 0.320 mmol) in 1,4-dioxane (10 mL) was stirred at 100° C. for 16 hours. The mixture was filtered and the filtrate was concentrated to dryness. The residue was washed with petroleum ether/ethyl acetate 1:1 to the title compound (0.9 g, 2.485 mmol, 78% yield).

Example 270g 4-(2-((2,4-difluorophenyl)amino)-5-(methylsulfonyl) phenyl)-6-methyl-2-(1-methyl-1H-pyrazol-4-yl)-1-tosyl-1H-pyrrolo[2,3-c]pyridin-7(6H)-one A mixture of Example 270e (150 mg, 0.295 mmol), Example 270f (107 mg, 0.295 mmol), tris(dibenzylideneacetone)dipalladium(0) (6.75 mg, 7.38 μmol), potassium phosphate, dibasic (77 mg, 0.443 mmol), and 1,3,5,7-tetramethyl-8-phenyl-2,4,6-trioxa-8-phosphaadamantane (8.62 mg, 0.030 mmol) in 1,4-dioxane (12 mL) and water (3.00 mL) was stirred at 60° C. for 3 hours. The mixture was concentrated to dryness and extracted with ethyl acetate (20 mL). The filtrate was concentrated and the residue was purified by flash chromatography (silica gel, petroleum ether/ethyl acetate 1:1-0:1) to provide the title compound (150 mg, 0.158 mmol, 53.6% yield).

Example 270h 4-(2-((2,4-difluorophenyl)amino)-5-(methylsulfonyl)phenyl)-6-methyl-2-(1-methyl-1H-pyrazol-4-yl)-1H-pyrrolo[2,3-c]pyridin-7(6H)-one To a solution of Example 270g (50 mg, 0.075 mmol) in 1,4-dioxane (10 mL) was added sodium hydroxide (50 mg, 1.250 mmol) and water (2 mL). The mixture was stirred at 80° C. for 5 hours. The mixture was adjusted to pH 5 by 1N HCl and then extracted with ethyl acetate. The organic phase was dried over anhydrous saturated sodium sulfate, filtered, and concentrated to give the crude product (50 mg, 0.041 mmol, 54.7% yield) as a yellow solid, which was used in the next step without further purification.

Example 270i 4-(2,4-difluorophenyl)-10-methyl-2-(1-methyl-1H-pyrazol-4-yl)-7-(methylsulfonyl)-3,4-dihydro-1H-1,4,10-triazadibenzo[cd,f]azulen-11(10H)-one To a solution of Example 270h (100 mg, 0.196 mmol) in tetrahydrofuran (5 mL) was added paraformaldehyde (5.89 mg, 0.196 mmol) and TiCl$_3$ (0.022 mL, 0.196 mmol) at 0° C., and the mixture was stirred at ambient temperature for 3 hours. The mixture was diluted with water (10 mL) and ethyl acetate (10 mL). It was then extracted with ethyl acetate three times. The combined organic layer was dried over anhydrous sodium sulfate and then concentrated, and the residue was purified by reverse phase preparative HPLC (C18, CH$_3$CN/water (0.1% trifluoroacetic acid), 0-100% gradient) to afford the title compound (25 mg, 0.047 mmol, 23.94% yield). 1H NMR (400 MHz, DMSO-d$_6$) δ 12.12 (s, 1H), 8.26 (s, 1H), 8.15 (s, 1H), 7.91 (d, J=14.6 Hz, 2H), 7.70 (d, J=8.4 Hz, 1H), 7.35-6.91 (m, 4H), 4.85 (s, 2H), 3.90 (s, 3H), 3.68 (s, 3H), 3.31 (s, 3H). MS (ESI+) m/z 522.0 [M+H]$^+$.

Example 271

4-(4-chlorophenyl)-10-methyl-2-(1-methyl-1H-pyrazol-4-yl)-7-(methylsulfonyl)-3,4-dihydro-1H-1,4,10-triazadibenzo[cd,f]azulen-11(10H)-one Example 271a 2-bromo-N-(4-chlorophenyl)-4-(methylsulfonyl)aniline A mixture of 2-bromo-4-(methylsulfonyl)aniline (0.8 g, 3.20 mmol), 1-chloro-4-iodobenzene (0.763 g, 3.20 mmol), tris(dibenzylideneacetone)dipalladium (0.293 g, 0.320 mmol), cesium carbonate (0.052 g, 0.160 mmol) and Xantphos (2.78 g, 4.80 mmol) was stirred at 90° C. for 16 hours under nitrogen. The reaction mixture cooled to ambient temperature and was filtered and the filtrated was concentrated. The residue was washed with petroleum ether/ethyl acetate (3:1) to provide the title compound (0.8 g, 1.996 mmol, 62.4% yield).

Example 271b 4-(2-((4-chlorophenyl)amino)-5-(methylsulfonyl)phenyl)-6-methyl-2-(1-methyl-1H-pyrazol-4-yl)-1-tosyl-1H-pyrrolo[2,3-c]pyridin-7(6H)-one A mixture of Example 270e (150 mg, 0.295 mmol), Example 271a (106 mg, 0.295 mmol), tris(dibenzylideneacetone)dipalladium (6.75 mg, 7.38 μmol), potassium phosphate, dibasic (77 mg, 0.443 mmol), and 1,3,5,7-tetramethyl-8-phenyl-2,4,6-trioxa-8-phosphaadamantane (8.62 mg, 0.030 mmol) in dioxane (12 mL) and water (3 mL) was stirred at 50° C. for 3 hours. The mixture was concentrated and extracted with ethyl acetate (20 mL). The filtrate was concentrated and the solid was washed with petroleum ether/ethyl acete (1:1) to give the title compound (0.15 g, 0.161 mmol, 54.5% yield).

Example 271c 4-(2-((4-chlorophenyl)amino)-5-(methylsulfonyl)phenyl)-6-methyl-2-(1-methyl-1H-pyrazol-4-yl)-1H-pyrrolo[2,3-c]pyridin-7(6H)-one To a solution of Example 271b (150 mg, 0.227 mmol) in 1,4-dioxane (10 mL) was added sodium hydroxide (80 mg, 2.000 mmol) and water (2 mL). The reaction mixture was stirred at 60° C. for 3 hours. The mixture cooled to ambient temperature and the pH was adjusted to pH=5 by the addition of 1N HCl. The mixture was then extracted with ethyl acetate, dried over anhydrous sodium sulfate, filtered, and concentrated to give the title compound (80 mg, 0.079 mmol, 34.8% yield).

Example 271d 4-(4-chlorophenyl)-10-methyl-2-(1-methyl-1H-pyrazol-4-yl)-7-(methylsulfonyl)-3,4-dihydro-1H-1,4,10-triazadibenzo[cd,f]azulen-11(10H)-one To a 5-mL microwave vial equipped with a magnetic stir bar was added Example 271c (70 mg, 0.134 mmol), paraformaldehyde (12.08 mg, 0.402 mmol), and acetic acid (2 mL). The vial was capped and heated at 75° C. for 1 hour. The mixture was concentrated in vacuo. The residue was suspended in methanol (10 mL) and acetic acid (1 mL) and heated at 85° C. for 20 minutes and then allowed to cool to ambient temperature. The resulting solid was collected by filtration and washed with methanol to give the title compound as an off white solid. $^1$H NMR (300 MHz, DMSO-d$_6$) δ 12.12 (s, 1H), 8.38 (s, 1H), 8.31 (s, 1H), 8.07 (s, 1H), 7.97-7.82 (m, 2H), 7.58 (d, J=8.3 Hz, 1H), 6.98 (d, J=8.8 Hz, 2H), 6.18 (d, J=8.6 Hz, 2H), 5.12 (s, 1H), 4.61 (s, 1H), 3.94 (s, 3H), 3.60 (s, 3H), 3.34-3.09 (m, 3H). MS (ESI+) m/z 518.0 [M+H]$^+$.

Example 272

(R)—N-ethyl-7-(ethylsulfonyl)-10-methyl-11-oxo-4-(1-phenylpropyl)-3,4,10,11-tetrahydro-1H-1,4,10-triazadibenzo[cd,f]azulene-2-carboxamide

Example 272a 4-bromo-6-methyl-7-oxo-6,7-dihydro-1H-pyrrolo[2,3-c]pyridine-2-carboxylic acid Example 208e (7.25 g, 24.2 mmol) in tetrahydrofuran/ethanol (1:2, 210 mL) was heated at 75° C. to dissolve the solid. The mixture was then cooled to 35° C. To this solution was added 1M aqueous lithium hydroxide (97 mL). The mixture was heated at 75° C. for 2 hours and then cooled to ambient temperature. The reaction mixture was then mixed with 1N HCl (100 mL) and water (300 mL) and allowed to stir at ambient temperature overnight. The resulting precipitate was collected by filtration, rinsed with water, and then dried to provide the title compound (6.41 gm. 98%).

Example 272b 4-bromo-N-ethyl-6-methyl-7-oxo-6,7-dihydro-1H-pyrrolo[2,3-c]pyridine-2-carboxamide A mixture of Example 272a (5.4 g, 19.9 mmol) in dimethyl sulfoxide (100 mL) was treated with 2-(3H-[1,2,3]triazolo[4,5-b]pyridin-3-yl)-1,1,3,3-tetramethylisouronium hexafluorophosphate(V) (8.33 g, 21.91 mmol) and N-ethyl-N-isopropylpropan-2-amine (10.5 mL, 60.1 mmol) and stirred for 5 minutes. Ethylamine solution (2 M in tetrahydrofuran) (11 mL, 22.00 mmol) was added and stirring was continued at ambient temperature for 7 hours. The reaction mixture was then diluted with 600 mL of water and stirred overnight at ambient temperature. The resulting solid was collected by filtration and rinsed with 1 L of water. The solid was dried to provide the title compound (5.54 g, 93%).

Example 272c

N-ethyl-6-methyl-7-oxo-4-(4,4,5,5-tetramethyl-1,3,2-dioxaborolan-2-yl)-6,7-dihydro-1H-pyrrolo[2,3-c]pyridine-2-carboxamide A mixture of Example 272b (5.4 g, 18.11 mmol), 4,4,4',4',5,5,5',5'-octamethyl-2,2'-bi(1,3,2-dioxaborolane) (13.80 g, 54.3 mmol), X-Phos (0.363 g, 0.761 mmol), tris(dibenzylideneacetone)dipalladium (0.166 g, 0.181 mmol), and oven dried potassium acetate (5.33 g, 54.3 mmol) was degassed with a stream of nitrogen blowing into the flask and over the solids to purge the flask for about 1 hour. To this mixture was then added via cannula degassed, anhydrous dioxane (60 mL) and the mixture was heated at 75° C. overnight. The reaction mixture was cooled to ambient temperature and then diluted with water and ethyl acetate and stirred for 30 minutes. The mixture was diluted further with ethyl acetate and methanol was added to help the solids dissolve. The mixture was partitioned. The resulting organic layer was washed with saturated aqueous sodium chloride, and the combined aqueous washes were back extracted with 10% methanol/ethyl acetate. The combined organic extracts were stirred with 10 g. SiliaMetS® Thiol palladium scavenger (Silicycle) for one hour. Anhydrous sodium sulfate was added directly to this mixture and stirring continued for another 30 minutes. The entire mixture was then filtered through a Buchner funnel, rinsed with ethyl acetate, and the resulting filtrate concentrated under reduced pressure. The resulting residue was mixed with 200 mL of 10% diethyl ether/heptane and sonicated for 30 minutes. The resulting solid was collected by vacuum filtration, washed with 100 mL of 10% % diethyl ether/heptane followed by 200 mL of heptane, and dried to provide the title compound (5.1 g, 82% yield).

Example 272d (R)-2-bromo-4-(ethylsulfonyl)-N-(1-phenylpropyl)aniline

A mixture of Example 2b (522 mg, 1.954 mmol), (R)-1-phenylpropan-1-amine (801 mg, 5.860 mmol), and N-ethyl-N-isopropylpropan-2-amine (0.683 mL, 3.910 mmol) in dimethylsulfoxide (10 mL) was heated at 120° C. for 18 hours. The mixture was cooled to ambient temperature and partitioned between saturated aqueous ammonium chloride and ethyl acetate. The organic layer was dried over anhydrous magnesium sulfate, filtered, and concentrated. The residue was purified by flash chromatography (silica gel, 2% ethanol and 6% ethyl acetate in heptane) to provide the title compound.

Example 272e (R)—N-ethyl-4-(5-(ethylsulfonyl)-2-((1-phenylpropyl)amino)phenyl)-6-methyl-7-oxo-6,7-dihydro-1H-pyrrolo[2,3-c]pyridine-2-carboxamide A mixture of Example 272d (288 mg, 0.753 mmol), Example 272c (200 mg, 0.579 mmol), potassium phosphate (369 mg, 1.738 mmol), 1,3,5,7-tetramethyl-6-phenyl-2,4,8-trioxa-6-phosphaadamantane (20.3 mg, 0.070 mmol) and tris(dibenzylideneacetone)dipalladium(0) (21.2 mg, 0.023 mmol) was sparged with argon for 15 minutes followed by addition of degassed tetrahydofuran (6 mL) and water (1.5 mL) mixture. The reaction mixture was heated at 60° C. for 3 hours. The mixture was cooled to ambient temperature and partitioned between saturated aqueous sodium chloride and ethyl acetate. The organic layer was dried over anhydrous magnesium sulfate, filtered, and concentrated. The residue was purified by flash chromatography (silica gel, 8% ethanol and 25% ethyl acetate in heptane) to provide the title compound.

Example 272f (R)—N-ethyl-7-(ethylsulfonyl)-10-methyl-11-oxo-4-(1-phenylpropyl)-3,4,10,11-tetrahydro-1H-1,4,10-triazadibenzo[cd,f]azulene-2-carboxamide A mixture of Example 272e (100 mg, 0.192 mmol) and paraformaldehyde (23 mg, 0.768 mmol) in tetrahydrofuran (6 mL) was stirred at ambient temperature. To resulting suspension was added 1M solution of titanium tetrachloride (0.39 mL). The reaction mixture was stirred for 1 hour at ambient temperature and then at 60° C. for 2 hours. The mixture was cooled to ambient temperature and partitioned between saturated aqueous sodium chloride and ethyl acetate. The organic layer was dried over anhydrous magnesium sulfate, filtered, and concentrated. The residue was purified by recrystallization from methanol to provide the title compound (87 mg, 85%) $^1$H NMR (400 MHz, 90° C., DMSO-d$_6$) δ 11.79 (s, 1H), 8.07 (d, J=2.2 Hz, 1H), 7.94 (t, J=5.4 Hz, 1H), 7.64-7.54 (m, 2H), 7.34 (d, J=8.4 Hz, 1H), 7.27-7.12 (m, 5H), 4.76 (d, J=16.5 Hz, 1H), 4.48 (d, J=16.5 Hz, 1H), 4.27 (t, J=7.1 Hz, 1H), 3.68 (s, 3H), 3.21-3.32 (m, 4H), 1.76 (p, J=7.2 Hz, 2H), 1.15 (dt, J=16.7, 7.3 Hz, 6H), 0.52 (t, J=7.2 Hz, 3H). (ESI+) m/z 532.9 (M+H)$^+$.

Example 273

10-methyl-2-(1-methyl-1H-pyrazol-4-yl)-7-((methylsulfonyl)methyl)-4-(pyridin-2-yl)-3,4-dihydro-1H-1,4,10-triazadibenzo[cd,f]azulen-11(10H)-one Example 273a N-(2-bromo-4-((methylsulfonyl)methyl)phenyl)pyridin-2-amine Example 273a was prepared according to the procedure used for the preparation of Example 58h, substituting 2-iodopyridine for 1-chloro-4-iodobenzene, to give the title compound.

Example 273b 6-methyl-2-(1-methyl-1H-pyrazol-4-yl)-4-(5-((methylsulfonyl)methyl)-2-(pyridin-2-ylamino)phenyl)-1-tosyl-1H-pyrrolo[2,3-c]pyridin-7(6H)-one Example 273b was prepared according to the procedure used for the preparation of Example 270g, substituting Example 273a for Example 270f, to give the title compound.

Example 273c 6-methyl-2-(1-methyl-1H-pyrazol-4-yl)-4-(5-((methylsulfonyl)methyl)-2-(pyridin-2-ylamino)phenyl)-1H-pyrrolo[2,3-c]pyridin-7(6H)-one Example 273c was prepared according to the procedure used for the preparation of Example 270h, substituting Example 273b for Example 270g, to give the title compound.

Example 273d 10-methyl-2-(1-methyl-1H-pyrazol-4-yl)-7-((methylsulfonyl)methyl)-4-(pyridin-2-yl)-3,4-dihydro-1H-1,4,10-triazadibenzo[cd,f]azulen-11(10H)-one Example 273d was prepared according to the procedure used for the preparation of Example 270i, substituting Example 273c for Example 270h, to give the title compound. $^1$H NMR (400 MHz, DMSO-d$_6$): δ 11.99 (s, 1H), 8.23 (s, 1H), 8.02 (s, 1H), 7.92 (m, 2H), 7.63 (s, 1H), 7.46 (dd, J=8.0, 1.6 Hz, 1H), 7.37 (d, J=8.0 Hz, 1H), 7.28-7.24 (m, 1H), 6.47 (dd, J=6.7, 5.2 Hz, 1H), 6.01 (d, J=8.4 Hz, 1H), 5.94 (d, J=15.6 Hz, 1H), 4.63 (d, J=13.6 Hz, 1H), 4.52 (d, J=13.6 Hz, 1H), 4.33 (d, J=15.7 Hz, 1H), 3.94 (s, 3H), 3.59 (s, 3H), 3.01 (s, 3H). MS (ESI+) m/z 501.0 [M+H]$^+$.

Example 274

10-methyl-2-(1-methyl-1H-pyrazol-4-yl)-7-(methylsulfonyl)-4-phenyl-3,4-dihydro-1H-1,4,10-triazadibenzo[cd,f]azulen-11(10H)-one Example 274a 2-bromo-4-(methylsulfonyl)-N-phenylaniline Example 274a was prepared according to the procedure used for the preparation of Example 270f, substituting iodobenzene for 2,4-difluoro-1-iodobenzene, to give the title compound.

Example 274b 6-methyl-2-(1-methyl-1H-pyrazol-4-yl)-4-(5-(methylsulfonyl)-2-(phenylamino)phenyl)-1-tosyl-1H-pyrrolo[2,3-c]pyridin-7(6H)-one Example 274b was prepared according to the procedure used for the preparation of Example 270g, substituting Example 274a for Example 270f, to give the title compound.

Example 274c 6-methyl-2-(1-methyl-1H-pyrazol-4-yl)-4-(5-(methylsulfonyl)-2-(phenylamino)phenyl)-1H-pyrrolo[2,3-c]pyridin-7(6H)-one Example 274c was prepared according to the procedure used for the preparation of Example 270h, substituting Example 274b for Example 270g, to give the title compound.

Example 274d 10-methyl-2-(1-methyl-1H-pyrazol-4-yl)-7-(methylsulfonyl)-4-phenyl-3,4-dihydro-1H-1,4,10-triazadibenzo[cd,f]azulen-11(10H)-one Example 274d was prepared according to the procedure used for the preparation of Example 270i, substituting Example 274c for Example 270h, to give the title compound. $^1$H NMR (400 MHz, DMSO-d$_6$) δ 12.06 (s, 1H), 8.37 (d, J=2.1 Hz, 1H), 8.31 (s, 1H), 8.06 (s, 1H), 7.92 (dd, J=8.2, 2.2 Hz, 1H), 7.85 (s, 1H), 7.56 (d, J=8.2 Hz, 1H), 6.98-6.90 (m, 2H), 6.51 (s, 1H), 6.23 (d, J=8.0 Hz, 2H), 3.95 (s, 3H), 3.59 (s, 3H), 3.38 (s, 3H). MS (ESI+) m/z 486.0 [M+H]$^+$.

Example 275

10-methyl-2-(1-methyl-1H-pyrazol-4-yl)-7-(methylsulfonyl)-4-(pyridin-2-yl)-3,4-dihydro-1H-1,4,10-triazadibenzo[cd,f]azulen-11(10H)-one Example 275a N-(2-bromo-4-(methylsulfonyl)phenyl)pyridin-2-amine Example 274a was prepared according to the procedure used for the preparation of Example 270f, substituting 2-iodopyridine for 2,4-difluoro-1-iodobenzene, to give the title compound.

Example 275b 6-methyl-2-(1-methyl-1H-pyrazol-4-yl)-4-(5-(methylsulfonyl)-2-(pyridin-2-ylamino)phenyl)-1-tosyl-1H-pyrrolo[2,3-c]pyridin-7(6H)-one Example 275b was prepared according to the procedure used for the preparation of Example 270g, substituting Example 275a for Example 270f, to give the title compound.

Example 275c 6-methyl-2-(1-methyl-1H-pyrazol-4-yl)-4-(5-(methylsulfonyl)-2-(pyridin-2-ylamino)phenyl)-1H-pyrrolo[2,3-c]pyridin-7(6H)-one Example 275c was prepared according to the procedure used for the preparation of Example 270h, substituting Example 275b for Example 270g, to give the title compound.

Example 275d 10-methyl-2-(1-methyl-1H-pyrazol-4-yl)-7-(methylsulfonyl)-4-(pyridin-2-yl)-3,4-dihydro-1H-1,4,10-triazadibenzo[cd,f]azulen-11(10H)-one Example 275d was prepared according to the procedure used for the preparation of Example 270i, substituting Example 275c for Example 270h, to give the title compound. $^1$H NMR (400 MHz, DMSO-$d_6$) δ 12.06 (s, 1H), 8.37 (d, J=2.0 Hz, 1H), 8.26 (s, 1H), 8.04 (s, 1H), 7.97-7.85 (m, 3H), 7.61 (d, J=8.3 Hz, 1H), 7.35 (s, 1H), 6.56 (d, J=6.1 Hz, 1H), 6.13 (d, J=8.5 Hz, 1H), 5.88 (d, J=16.1 Hz, 1H), 4.37 (s, 1H), 3.95 (s, 3H), 3.61 (s, 3H), 3.37 (s, 3H). MS (ESI+) m/z 487.0 [M+H]$^+$.

Example 276

4-(4-fluorophenyl)-10-methyl-2-(1-methyl-1H-pyrazol-4-yl)-7-((methylsulfonyl)methyl)-3,4-dihydro-1H-1,4,10-triazadibenzo[cd,f]azulen-11(10H)-one

Example 276a 2-bromo-N-(4-fluorophenyl)-4-((methylsulfonyl)methyl)aniline

Example 276a was prepared according to the procedure used for the preparation of Example 58h, substituting 1-fluoro-4-iodobenzene for 1-chloro-4-iodobenzene, to give the title compound.

Example 276b 4-(2-((4-fluorophenyl)amino)-5-((methylsulfonyl)methyl)phenyl)-6-methyl-2-(1-methyl-1H-pyrazol-4-yl)-1-tosyl-1H-pyrrolo[2,3-c]pyridin-7(6H)-one Example 276b was prepared according to the procedure used for the preparation of Example 270g, substituting Example 276a for Example 270f, to give the title compound.

Example 276c 4-(2-((4-fluorophenyl)amino)-5-((methylsulfonyl)methyl)phenyl)-6-methyl-2-(1-methyl-1H-pyrazol-4-yl)-1H-pyrrolo[2,3-c]pyridin-7(6H)-one Example 276c was prepared according to the procedure used for the preparation of Example 270h, substituting Example 276b for Example 270g, to give the title compound.

Example 276d 4-(4-fluorophenyl)-10-methyl-2-(1-methyl-1H-pyrazol-4-yl)-7-((methylsulfonyl)methyl)-3,4-dihydro-1H-1,4,10-triazadibenzo[cd,f]azulen-11(10H)-one Example 276d was prepared according to the procedure used for the preparation of Example 270i, substituting Example 276c for Example 270h, to give the title compound. $^1$H NMR (400 MHz, DMSO-$d_6$) δ 12.02 (s, 1H), 8.29 (s, 1H), 8.05 (s, 1H), 7.90 (s, 1H), 7.60 (s, 1H), 7.47 (d, J=8.0 Hz, 1H), 7.35 (d, J=7.9 Hz, 1H), 6.75 (t, J=8.9 Hz, 2H), 6.13 (dd, J=9.2, 4.4 Hz, 2H), 4.57 (s, 2H), 3.94 (s, 3H), 3.57 (s, 3H), 3.00 (s, 3H). MS (ESI+) m/z 518.0 [M+H]$^+$.

BIOLOGICAL EXAMPLES

Bromodomain Domain Binding Assay

A time-resolved fluorescence resonance energy transfer (TR-FRET) assay was used to determine the affinities of compounds of the Examples listed in Table 1 for each bromodomain of BRD4. His-tagged first (BD1: amino acids K57-E168) and second (BD2: amino acids E352-E168) bromodomains of BRD4 were expressed and purified. An Alexa647-labeled BET-inhibitor was used as the fluorescent probe in the assay.

Synthesis of Alexa647-Labeled Bromodomain Inhibitor Compound 2-((6S,Z)-4-(4-chlorophenyl)-2,3,9-trimethyl-6H-thieno[3,2-f][1,2,4]triazolo[4,3-a][1,4]diazepin-6-yl)acetic acid Methyl 2-((6S,Z)-4-(4-chlorophenyl)-2,3,9-trimethyl-6H-thieno[3,2-f][1,2,4]triazolo[4,3-a][1,4]diazepin-6-yl)acetate (WO 2006129623)(100.95 mg, 0.243 mmol was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and evaporated to afford 2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 87.0%); ESI-MS m/z=401.1 [(M+H)$^+$] which was used directly in the next reaction.

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis (2,2,2-trifluoroacetate)

2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 0.213 mmol) was combined with 2,2'-(ethane-1,2-diylbis(oxy))diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction was diluted to 6 mL with dimethylsulfoxide:water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)$^+$]; 529.1 [(M−H)$^−$] and (S,Z)—N,N'-(2,2'-(ethane-1,2-diylbis(oxy))bis(ethane-2,1-diyl))bis(2-((6S,Z)-4-((4-chlorophenyl)-2,3,9-trimethyl-6H-thieno[3,2-f][1,2,4]triazolo[4,3-a][1,4]diazepin-6-yl)acetamide) bis(2,2,2-trifluoroacetate) (3.0 mg, 1.5%); ESI-MS m/z=913.2 [(M+H)$^+$]; 911.0 [(M−H)$^−$].

N-(2-(2-(2-amido-(Alexa647)-ethoxy)ethoxy)ethyl)-2-((6S,Z)-4-((4-chlorophenyl)-2,3,9-trimethyl-6H-thieno[3,2-f][1,2,4]triazolo[4,3-a][1,4]diazepin-6-yl) acetamide(2,2,2-trifluoroacetate)

N-(2-(2-(2-aminoethoxy)ethoxy)ethyl)-2-((6S,Z)-4-((4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) was combined with Alexa Fluor® 647 carboxylic Acid, succinimidyl ester (Life Technologies, Grand Island, N.Y.; 3 mg, 0.0024 mmol) were combined in 1 mL anhydrous dimethylsulfoxide containing diisopropylethylamine (1% v/v) and shaken at ambient temperature for 16 hours. The reaction was diluted to 3 mL with dimethylsulfoxide:water (9:1, v:v) and purified in one injection with time collection Waters Deltapak C18 200×25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((6S,Z)-4-((4-chlorophenyl)-2,3,9-trimethyl-6H-thieno[3,2-f][1,2,4]triazolo[4,3-a][1,4]diazepin-6-yl)acetamide(2,2,2-trifluoroacetate) (1.8 mg); MALDI-MS m/z=1371.1, 1373.1 [(M+H)$^+$] as a dark blue powder.

Assay

Compound dilution series were prepared in DMSO via an approximately 3-fold serial dilution from one of the following:
Assay method C: 1250 µM-21 nM
Assay method D: 500 µM-8.5 nM
Assay method E: 0.47 mM to 7.8 nM
Assay method F: 250 µM-4.2 nM
Assay method G: 0.047 mM to 0.78 nM
or 5-fold serial dilution from one of the following:
Assay method A: 2.5 mM-800 nM
Assay method B: 2.5 mM-797 nM For Assay methods A, C, D, and F: Compounds were then diluted 6:100 in assay buffer (20 mM Sodium Phosphate, pH 6.0, 50 mM NaCl, 1 mM Ethylenediaminetetraacetic acid, 0.01% Triton X-100, 1 mM DL-Dithiothreitol) to yield 3× working solutions. Six microliters (4) of the working solution was then transferred to white, low-volume assay plates (Costar #3673). A 1.5× assay mixture containing His-tagged bromodomain, Europium-conjugated anti-His antibody (Invitrogen PV5596) and the Alexa-647-conjugated probe molecule was also prepared. Twelve µL of this solution were added to the assay plate to reach a final volume of 18 µL.

For Assay methods B, E, and G: Compound dilutions were added directly into white, low-volume assay plates (Perkin Elmer Proxiplate 384 Plus#6008280) using a Labcyte Echo in conjunction with Labcyte Access and Thermo Multidrop CombinL robotics. Compounds were then suspended in eight microliters (µL) of assay buffer (20 mM Sodium Phosphate, pH 6.0, 50 mM NaCl, 1 mM Ethylenediaminetetraacetic acid disodium salt dihydrate, 0.01% Triton X-100, 1 mM DL-Dithiothreitol) containing His-tagged bromodomain, Europium-conjugated anti-His antibody (Invitrogen PV5596) and Alexa-647-conjugated probe.

The final concentration of 1× assay mixture for assay methods A, B, C, D, E, F, and G contains 2% DMSO, 8 nM His-tagged bromodomain, 1 nM Europium-conjugated anti-His-tag antibody and 100 nM or 30 nM probe (for BDI or BDII, respectively) and compound concentration in the range of: 50 µM-16 nM for method A, 49.02 µM-15.63 nM for method B, 25 µM-423 pM for method C, 10 µM-169 pM for method D, 9.19 µM-150 pM for method E, 5 µM-85 pM for method F, and 0.92 µM-15 pM for method G.

After a one-hour equilibration at room temperature, TR-FRET ratios were determined using an Envision multilabel plate reader (Ex 340, Em 495/520).

TR-FRET data were normalized to the means of 24 no-compound controls ("high") and 8 controls containing 1 µM un-labeled probe ("low"). Percent inhibition was plotted as a function of compound concentration and the data were fit with the 4 parameter logistic equation to obtain IC$_{50}$s. Inhibition constants ($K_i$) were calculated from the IC$_{50}$s, probe $K_d$ and probe concentration. Typical Z' values were between 0.65 and 0.75. The minimum significant ratio was determined to evaluate assay reproducibility (Eastwood et al., (2006) J Biomol Screen, 11: 253-261). The MSR was determined to be 2.03 for BDI and 1.93 for BDII, and a moving MSR (last six run MSR overtime) for both BDI and BDII was typically <3. The $K_i$ values are reported in Table 1.

MX-1 Cell Line Proliferation Assay

The impact of compounds of the Examples on cancer cell proliferation was determined using the breast cancer cell line MX-1 (ATCC) in a 3-day proliferation assay and the data are reported in Table 1. MX-1 cells were maintained in RPMI 1640 medium (Sigma) supplemented with 10% FBS at 37 C.° and an atmosphere of 5% CO$_2$. For compound testing, MX-1 cells were plated in 96-well black bottom plates at a density of 5000 cells/well in 90 µL of culture media and incubated at 37° overnight to allow cell adhesion and spreading. Compound dilution series were prepared in DMSO via a 3-fold serial dilution from 3 mM to 0.1 µM. The DMSO dilution series were then diluted 1:100 in phosphate buffered saline, and 10 µL of the resulted solution were added to the appropriate wells of the MX-1 cell plate. The final compound concentrations in the wells were 3, 1, 0.3, 0.1, 0.03, 0.01, 0.003, 0.001, 0.0003, and 0.0001 µM or 1, 0.3, 0.1, 0.03, 0.01, 0.003, 0.001, 0.0003, 0.0001, and 0.00003 µM. After the addition of compounds, the cells were incubated for 72 more hours and the amounts of viable cells were determined using the Cell Titer Glo assay kit (Promega) according to manufacturer suggested protocol.

Luminescence readings from the Cell Titer Glo assay were normalized to the DMSO treated cells and analyzed using the GraphPad Prism software with sigmoidal curve fitting to obtain EC$_{50}$s. The minimum significant ratio (MSR) was determined to evaluate assay reproducibility (Eastwood et al., (2006) J Biomol Screen, 11: 253-261). The overall MSR was determined to be 2.1 and a moving MSR (last six run MSR overtime) has been <2.

TABLE 1

| Compound of Example # | TR-FRET assay protocol | TR-FRET Binding Ki: BRD4 (BDI_K57-E168) (μM) | TR-FRET Binding Ki: BRD4 (BDII_E352-M457) (μM) | Cellular proliferation: $EC_{50}$ (μM) |
|---|---|---|---|---|
| 1 | E | 0.0327 | 0.0105 | 0.0272 |
| 2 | E | 0.0246 | 0.00836 | 0.0192 |
| 3 | E | 0.046 | 0.00891 | 0.0487 |
| 4 | E | 2 | 3.09 | ND |
| 5 | E | 0.765 | 0.758 | ND |
| 6 | E | 0.00108 | 0.00171 | 0.00201 |
| 7 | B | 0.0511 | 0.0267 | 0.0145 |
| 8 | E | 0.000646 | 0.00377 | 0.00568 |
| 9 | G | 0.000453 | 0.00111 | 0.000721 |
| 10 | E | 0.00694 | 0.00599 | 0.0608 |
| 11 | G | 0.00161 | 0.00257 | 0.00164 |
| 12 | G | 0.00134 | 0.000472 | 0.0040 |
| 13 | G | 0.00484 | 0.00768 | 0.00726 |
| 14 | E | 0.0069 | 0.000882 | 0.0146 |
| 15 | E | 0.00522 | 0.000631 | 0.00875 |
| 16 | E | 0.0926 | 0.0189 | 0.337 |
| 17 | E | 0.165 | 0.0539 | ND |
| 18 | E | 0.145 | 0.0241 | 0.343 |
| 19 | E | 0.246 | 0.0438 | 0.37 |
| 20 | E | 0.158 | 0.0245 | 0.544 |
| 21 | G | 0.00443 | 0.003 | 0.00105 |
| 22 | G | 0.000875 | 0.00095 | 0.00171 |
| 23 | E | 0.0017 | 0.000783 | 0.0070 |
| 24 | E | 0.000963 | 0.000801 | 0.00107 |
| 25 | E | 0.00174 | 0.000847 | 0.0087 |
| 26 | G | 0.000701 | 0.000719 | 0.00103 |
| 27 | E | 0.00119 | 0.00101 | 0.00127 |
| 28 | E | 0.0011 | 0.00117 | 0.0137 |
| 29 | E | 0.00695 | 0.00274 | 0.00103 |
| 30 | E | 0.00498 | 0.00136 | 0.00139 |
| 31 | G | 0.00167 | 0.00118 | 0.000752 |
| 32 | G | 0.00101 | 0.00114 | 0.00138 |
| 33 | G | 0.0383 | 0.0228 | 0.495 |
| 34 | G | 0.00245 | 0.00389 | 0.0147 |
| 35 | G | 0.0355 | 0.0951 | 0.331 |
| 36 | G | 0.00505 | 0.00625 | >1 |
| 37 | G | 0.00336 | 0.0024 | >1 |
| 38 | G | >0.238 | >0.408 | ND |
| 39 | G | >0.238 | >0.408 | ND |
| 40 | G | 0.0294 | 0.136 | 0.398 |
| 41 | G | 0.0495 | 0.0578 | >1 |
| 42 | G | 0.00156 | 0.00203 | 0.00544 |
| 43 | G | 0.00729 | 0.0247 | ND |
| 44 | G | 0.00261 | 0.00247 | 0.0487 |
| 45 | G | 0.00392 | 0.00375 | 0.141 |
| 46 | G | 0.0137 | 0.00748 | 0.152 |
| 47 | G | 0.00137 | 0.00127 | 0.00833 |
| 48 | G | 0.00112 | 0.000855 | 0.00441 |
| 49 | G | 0.00199 | 0.00221 | 0.00863 |
| 50 | G | 0.00344 | 0.00551 | 0.0422 |
| 51 | G | 0.00443 | 0.0132 | 0.174 |
| 52 | G | 0.0174 | 0.00499 | 0.247 |
| 53 | G | 0.00478 | 0.0219 | ND |
| 54 | G | 0.00585 | 0.00145 | ND |
| 55 | G | 0.00896 | 0.0159 | 0.146 |
| 56 | G | 0.0144 | 0.0353 | 0.197 |
| 57 | G | 0.0647 | 0.0906 | ND |
| 58 | G | 0.00202 | 0.000617 | 0.00538 |
| 59 | G | 0.0031 | 0.000972 | 0.0038 |
| 60 | G | 0.00255 | 0.0331 | 0.115 |
| 61 | G | 0.0211 | 0.00374 | >1 |
| 62 | G | 0.00723 | 0.00473 | 0.91 |
| 63 | G | 0.0822 | 0.0736 | ND |
| 64 | G | 0.00269 | 0.00285 | 0.0846 |
| 65 | G | >0.238 | 0.238 | ND |
| 66 | G | >0.238 | >0.408 | ND |
| 67 | G | >0.238 | >0.408 | ND |
| 68 | G | 0.0127 | 0.00422 | 0.0401 |
| 69 | G | 0.00325 | 0.00324 | 0.0431 |
| 70 | G | 0.00741 | 0.00188 | 0.131 |
| 71 | G | 0.0304 | 0.0267 | ND |
| 72 | G | 0.0262 | 0.037 | ND |
| 73 | G | 0.0165 | 0.0194 | ND |
| 74 | G | >0.238 | 0.369 | ND |
| 75 | G | >0.238 | >0.408 | ND |
| 76 | G | >0.238 | >0.408 | ND |
| 77 | G | >0.238 | 0.275 | ND |
| 78 | G | 0.216 | 0.126 | ND |
| 79 | G | >0.238 | >0.408 | ND |
| 80 | G | >0.238 | >0.408 | ND |
| 81 | G | 0.0517 | 0.0323 | ND |
| 82 | G | 0.0133 | 0.00112 | 0.979 |
| 83 | G | >0.238 | >0.408 | ND |
| 84 | G | 0.00224 | 0.00386 | 0.0177 |
| 85 | G | 0.0108 | 0.0111 | 0.0489 |
| 86 | G | 0.0103 | 0.0139 | ND |
| 87 | G | 0.00254 | 0.0021 | 0.00469 |
| 88 | G | 0.00346 | 0.00176 | ND |
| 89 | G | 0.00577 | 0.00453 | ND |
| 90 | G | 0.00132 | 0.00201 | 0.0306 |
| 91 | G | 0.00327 | 0.00115 | 0.00181 |
| 92 | G | 0.00374 | 0.00558 | ND |
| 93 | G | 0.00284 | 0.00163 | 0.00259 |
| 94 | G | 0.00603 | 0.00349 | 0.00602 |
| 95 | G | 0.00218 | 0.00253 | 0.0141 |
| 96 | G | 0.00346 | 0.00161 | ND |
| 97 | G | 0.00321 | 0.00135 | ND |
| 98 | G | 0.00234 | 0.00315 | 0.00441 |
| 99 | G | 0.0155 | 0.00166 | 0.165 |
| 100 | G | 0.0298 | 0.00741 | ND |
| 101 | G | 0.00483 | 0.00277 | ND |
| 102 | G | 0.00941 | 0.0269 | 0.151 |
| 103 | G | 0.00812 | 0.00471 | ND |
| 104 | G | 0.0347 | 0.0262 | ND |
| 105 | G | 0.00549 | 0.00268 | 0.0162 |
| 106 | G | 0.00589 | 0.00191 | 0.0192 |
| 107 | G | 0.00642 | 0.00379 | 0.00704 |
| 108 | G | 0.0139 | 0.00211 | 0.165 |
| 109 | G | 0.0641 | 0.0156 | ND |
| 110 | G | 0.0417 | 0.0199 | ND |
| 111 | G | 0.0077 | 0.00331 | 0.084 |
| 112 | G | 0.0532 | 0.0152 | ND |
| 113 | G | 0.0856 | 0.0109 | ND |
| 114 | G | 0.112 | 0.0255 | ND |
| 115 | G | 0.0087 | 0.00271 | 0.00783 |
| 116 | G | 0.016 | 0.0112 | ND |
| 117 | G | 0.0723 | 0.00127 | >1 |
| 118 | G | 0.0126 | 0.00138 | 0.174 |
| 119 | G | 0.0119 | 0.000602 | 0.134 |
| 120 | G | 0.00928 | 0.00159 | >1 |
| 121 | G | 0.00665 | 0.000799 | >1 |
| 122 | G | 0.0108 | 0.000922 | >1 |
| 123 | G | 0.00995 | 0.000983 | >1 |
| 124 | G | 0.00884 | 0.00278 | 0.944 |
| 125 | G | 0.00926 | 0.00236 | 0.342 |
| 126 | G | 0.0536 | 0.08 | ND |
| 127 | G | 0.00268 | 0.00135 | 0.0417 |
| 128 | G | 0.0291 | 0.002 | 0.0729 |
| 129 | G | 0.0162 | 0.0025 | 0.25 |
| 130 | G | 0.215 | 0.0146 | ND |
| 131 | G | 0.0107 | 0.00235 | >1 |
| 132 | G | 0.0113 | 0.00314 | >1 |
| 133 | G | 0.00929 | 0.0014 | 0.204 |
| 134 | G | 0.0144 | 0.00111 | 0.182 |
| 135 | G | 0.0114 | 0.00214 | 0.51 |
| 136 | G | 0.0132 | 0.00133 | 0.0492 |
| 137 | G | 0.0517 | 0.00387 | 0.24 |
| 138 | G | 0.0225 | 0.00194 | 0.256 |
| 139 | G | 0.0175 | 0.00233 | 0.627 |
| 140 | G | 0.00999 | 0.00224 | 0.936 |
| 141 | G | 0.0208 | 0.0109 | 0.319 |
| 142 | G | 0.00861 | 0.00060 | 0.0518 |
| 143 | G | 0.0549 | 0.00306 | 0.175 |
| 144 | G | >0.238 | 0.0188 | 0.318 |

TABLE 1-continued

| Compound of Example # | TR-FRET assay protocol | TR-FRET Binding Ki: BRD4 (BDI_K57-E168) (µM) | TR-FRET Binding Ki: BRD4 (BDII_E352-M457) (µM) | Cellular proliferation: EC$_{50}$ (µM) |
|---|---|---|---|---|
| 145 | G | 0.0551 | 0.00138 | 0.0806 |
| 146 | G | 0.00142 | 0.017 | 0.124 |
| 147 | G | 0.00702 | 0.00097 | 0.0203 |
| 148 | G | 0.00677 | 0.00054 | 0.0319 |
| 149 | G | 0.00178 | 0.00082 | 0.00193 |
| 150 | G | 0.00405 | 0.0108 | ND |
| 151 | G | 0.00114 | 0.0023 | 0.00426 |
| 152 | G | 0.00718 | 0.011 | ND |
| 153 | G | 0.00372 | 0.00918 | ND |
| 154 | G | 0.0507 | 0.0531 | ND |
| 155 | G | 0.0427 | 0.0478 | 0.349 |
| 156 | G | 0.0468 | 0.0421 | 0.214 |
| 157 | G | 0.0396 | 0.0239 | 0.0774 |
| 158 | G | 0.0603 | 0.0773 | ND |
| 159 | G | 0.0386 | 0.0198 | 0.0578 |
| 160 | G | 0.125 | 0.118 | ND |
| 161 | G | 0.0321 | 0.0214 | 0.0416 |
| 162 | G | 0.0471 | 0.0604 | ND |
| 163 | G | 0.0574 | 0.0454 | ND |
| 164 | G | 0.0417 | 0.030 | 0.0725 |
| 165 | G | 0.0814 | 0.0796 | ND |
| 166 | G | 0.060 | 0.0733 | ND |
| 167 | G | 0.0692 | 0.0763 | ND |
| 168 | G | 0.0932 | 0.124 | ND |
| 169 | G | 0.0124 | 0.00467 | 0.0699 |
| 170 | G | 0.00707 | 0.0252 | 0.0576 |
| 171 | G | 0.0164 | 0.0292 | ND |
| 172 | G | 0.0578 | 0.0128 | 0.551 |
| 173 | G | 0.00672 | 0.00314 | 0.0199 |
| 174 | G | 0.0126 | 0.00153 | 0.239 |
| 175 | G | 0.015 | 0.0019 | 0.0999 |
| 176 | G | 0.00101 | 0.00355 | 0.0142 |
| 177 | G | 0.00202 | 0.00127 | 0.00372 |
| 178 | G | 0.00436 | 0.00438 | 0.123 |
| 179 | G | 0.0201 | 0.0807 | ND |
| 180 | G | 0.00151 | 0.0027 | ND |
| 181 | G | 0.00333 | 0.0171 | ND |
| 182 | G | 0.00131 | 0.0020 | 0.00108 |
| 183 | G | 0.00384 | 0.0155 | ND |
| 184 | G | 0.00434 | 0.00682 | ND |
| 185 | G | 0.00419 | 0.0102 | 0.0283 |
| 186 | G | 0.00421 | 0.0092 | ND |
| 187 | G | 0.00574 | 0.050 | ND |
| 188 | G | 0.00364 | 0.00462 | ND |
| 189 | G | 0.00582 | 0.0223 | ND |
| 190 | G | 0.0267 | 0.0309 | ND |
| 191 | G | 0.00100 | 0.00338 | 0.0107 |
| 192 | G | 0.00165 | 0.00108 | 0.00125 |
| 193 | G | 0.00185 | 0.0124 | 0.0317 |
| 194 | G | 0.00133 | 0.00038 | 0.00147 |
| 195 | G | 0.00266 | 0.00062 | 0.00377 |
| 196 | G | 0.00114 | 0.00172 | 0.00382 |
| 197 | G | 0.00152 | 0.00265 | 0.00266 |
| 198 | G | 0.00159 | 0.00063 | 0.00069 |
| 199 | G | 0.00081 | 0.00121 | 0.0108 |
| 200 | G | 0.00818 | 0.00205 | 0.0342 |
| 201 | G | 0.00085 | 0.0032 | 0.0278 |
| 202 | G | 0.00079 | 0.00035 | 0.0043 |
| 203 | G | 0.00099 | 0.00071 | 0.00543 |
| 204 | G | 0.0461 | 0.00122 | >1 |
| 205 | G | 0.20 | 0.0291 | >1 |
| 206 | G | 0.00096 | 0.00051 | 0.00141 |
| 207 | G | 0.00092 | 0.00209 | 0.00133 |
| 208 | G | 0.00341 | 0.00115 | 0.0107 |
| 209 | G | 0.0012 | 0.00086 | 0.00654 |
| 210 | G | 0.00172 | 0.00080 | 0.0133 |
| 211 | G | 0.00567 | 0.00747 | 0.118 |
| 212 | G | 0.00239 | 0.0050 | 0.155 |
| 213 | G | 0.00065 | 0.00042 | 0.0014 |
| 214 | G | 0.0408 | 0.00325 | 0.431 |
| 215 | G | 0.0657 | 0.00587 | 0.454 |
| 216 | G | 0.0573 | 0.0658 | 0.603 |
| 217 | G | 0.193 | 0.0426 | >1 |
| 218 | G | 0.00064 | 0.00064 | 0.00136 |
| 219 | G | 0.0399 | 0.00476 | 0.301 |
| 220 | G | 0.0516 | 0.00261 | 0.285 |
| 221 | G | 0.0316 | 0.0123 | 0.033 |
| 222 | G | 0.17 | 0.0294 | 0.16 |
| 223 | G | >0.238 | >0.408 | ND |
| 224 | G | 0.00164 | 0.0014 | 0.00584 |
| 225 | G | 0.00325 | 0.00239 | 0.0122 |
| 226 | G | 0.00384 | 0.00186 | 0.00782 |
| 227 | G | 0.00794 | 0.00118 | 0.134 |
| 228 | G | 0.0245 | 0.00222 | 0.0849 |
| 229 | G | 0.00411 | 0.00196 | 0.0412 |
| 230 | G | >0.238 | 0.0581 | 0.528 |
| 231 | G | 0.039 | 0.00542 | 0.149 |
| 232 | G | 0.108 | 0.00848 | 0.363 |
| 233 | G | 0.00615 | 0.00377 | ND |
| 234 | G | 0.0103 | 0.0094 | >1 |
| 235 | G | 0.0161 | 0.00651 | 0.162 |
| 236 | G | 0.0859 | 0.030 | >1 |
| 237 | G | 0.0218 | 0.0121 | 0.313 |
| 238 | G | 0.0621 | 0.0046 | 0.275 |
| 239 | G | 0.0319 | 0.00212 | 0.294 |
| 240 | G | 0.00314 | 0.00193 | 0.0859 |
| 241 | G | 0.00307 | 0.00176 | 0.0515 |
| 242 | G | 0.0126 | 0.00378 | >1 |
| 243 | G | 0.00185 | 0.00347 | 0.153 |
| 244 | G | 0.00043 | 0.00102 | 0.00213 |
| 245 | G | 0.00054 | 0.00094 | 0.00109 |
| 246 | G | 0.00432 | 0.0036 | 0.0117 |
| 247 | G | 0.00222 | 0.00242 | 0.00494 |
| 248 | G | 0.00339 | 0.00329 | 0.0256 |
| 249 | G | 0.0061 | 0.0191 | 0.0177 |
| 250 | G | 0.0088 | 0.0225 | 0.845 |
| 251 | G | >0.238 | 0.142 | ND |
| 252 | G | 0.0161 | 0.00224 | 0.108 |
| 253 | G | 0.00070 | 0.00118 | 0.0013 |
| 254 | G | 0.00112 | 0.00071 | 0.0039 |
| 255 | G | 0.00453 | 0.00733 | 0.0343 |
| 256 | G | 0.00059 | 0.00054 | 0.00035 |
| 257 | G | 0.00234 | 0.00919 | 0.0211 |
| 258 | G | 0.00092 | 0.00239 | 0.00443 |
| 259 | G | 0.0034 | 0.00305 | 0.019 |
| 260 | G | 0.00726 | 0.0034 | 0.219 |
| 261 | G | 0.00932 | 0.00778 | >1.0 |
| 262 | G | 0.00937 | 0.0132 | ND |
| 263 | G | 0.00704 | 0.00807 | >1.0 |
| 264 | G | 0.00697 | 0.00153 | 0.899 |
| 265 | G | 0.0256 | 0.00421 | 0.17 |
| 266 | G | 0.0178 | 0.00815 | 0.0427 |
| 267 | G | 0.0727 | 0.0947 | ND |
| 268 | G | 0.0828 | 0.0164 | ND |
| 269 | G | 0.00569 | 0.00092 | ND |
| 270 | G | 0.011 | 0.00335 | 0.0807 |
| 271 | G | 0.00391 | 0.00164 | 0.0852 |
| 272 | G | 0.0589 | 0.00635 | ND |
| 273 | G | 0.00112 | 0.00088 | ND |
| 274 | G | 0.00283 | 0.00156 | ND |
| 275 | G | 0.00209 | 0.00085 | ND |
| 276 | G | 0.00119 | 0.00118 | ND |

ND = not determined.

LPS (Lipopolysaccharide) Induced IL-6 Production Mouse Assay

Compounds of the Examples listed in Table 2 were assayed for their ability to inhibit LPS (lipopolysaccharide) induced IL-6 (Interleukin-6) production in mice. Fox Chase SCID® female mice (Charles Rivers Labs, 5 per group) or CD1 female mice (5 per group) received an intraperitoneal challenge of lipopolysaccharide (2.5 mg/kg, L2630 E. coli 0111:B4) one hour after oral administration of compounds. Mice were euthanized 2 hours after lipopolysaccharide injection, blood was removed by cardiac puncture, and then the serum harvested from the blood samples was frozen at −80° C. On the day of the assay the serum samples were brought to room temperature and then diluted 1:20 in phosphate-buffered saline containing 2% bovine serum albumin. Interleukin-6 measurements were performed using a cytokine assay from Meso Scale Discovery (Gaithersburg, Md.) for mouse serum analysis according to the manufacturer's protocol and read on a SECTOR Imager 6000 (Meso Scale Discovery, Gaithersburg, Md.) instrument. Statistical analysis was performed using Prism software (version 5.0) incorporating Dunnett's one way ANOVA. The IL-6 mean and standard deviation of the group of vehicle treated animals were compared with the IL-6 mean and standard deviation of the group treated with drug. A p value <0.05 means that there is less than a 5% probability that the mean values in the two groups are equal. The % inhibition values in Table 2 all exhibited a p value less than 0.05.

TABLE 2

Inhibition of LPS induced IL-6 production

| Compound of Example # | % inhibition | Mouse strain |
|---|---|---|
| 6 | 64 | SCID |
| 7 | 53 | SCID |
| 8 | 53 | SCID |
| 9 | 79 | SCID |
| 12 | 90 | SCID |
| 15 | 68 | SCID |
| 23 | 54 | SCID |
| 24 | 78 | SCID |
| 26 | 88 | SCID |
| 27 | 79 | SCID |
| 29 | 76 | SCID |
| 30 | 81 | SCID |
| 31 | 83 | SCID |
| 42 | 86 | CD1 |
| 58 | 39 | CD1 |
| 59 | 68 | CD1 |
| 60 | 44 | CD1 |
| 149 | 86 | CD1 |
| 151 | 57 | CD1 |
| 173 | 87 | CD1 |
| 182 | 77 | CD1 |
| 191 | 60 | CD1 |
| 192 | 73 | CD1 |
| 194 | 53 | CD1 |
| 195 | 85 | CD1 |
| 196 | 79 | CD1 |
| 198 | 86 | CD1 |
| 199 | 90 | CD1 |
| 202 | 47 | CD1 |
| 206 | 76 | CD1 |
| 207 | 65 | CD1 |

Xenograft Tumor Growth Inhibition Assay

The effect of compounds of the examples to inhibit the growth of OPM-2 xenograft tumors implanted in mice was evaluated. A suspension of cancer cells ($5\times10^6$ per 0.1 mL) prepared in RPMI culture medium (Invitrogen, Carlsbad, Calif.) was diluted 1:1 with a solution of Matrigel™ (BD Biosciences, Franklin Lakes, N.J.) and inoculated subcutaneously into the right hind flank of female SCID-beige (Charles River Labs) mice. Randomization into treatment and vehicle control groups (8-10/group) occurred when the mean tumor volume reached approximately 250 mm$^3$. Compounds were formulated in 2.5% DMSO, 10% ethanol, 27.5% PEG 400, 60% Phosol 53 MCT. Administration of compound or vehicle was initiated on the day following randomization and continued for 21 days. Tumors were measured twice a week throughout the treatment period using a pair of calipers and tumor volumes were calculated according to the formula $V = L \times W^2/2$ (V: volume, mm$^3$; L: length, mm. W: width, mm). Tumor growth inhibition was calculated based on the mean tumor volume measured on the first day that the mean volume of the vehicle group exceeded 2000 mm$^3$ according to the formula:

% TGI=100−(100×(mean tumor volume of treatment group/mean tumor volume of control group))

Results are shown in Table 3.

TABLE 3

OPM-2 human multiple myeloma cancer xenograft model

| Compound of Example # | Dose mg/kg | route, regimen | % TGI[a] | % removed from study[b] |
|---|---|---|---|---|
| 9 | 1.85 | PO, QD x21 | 87*** | 56 |
| 9 | 3.75 | PO, QD x21 | nd[c] | 100 |
| 12 | 1.5 | IP, QD x21 | 82** | 11 |
| 12 | 1.5 | IP, QD x21 | 91*** | 22 |
| 12 | 3 | IP, QD x21 | 89** | 11 |
| 12 | 3 | IP, QD x21 | nd[c] | 100 |
| 12 | 3 | PO, 3 on 4 off x3 weeks | 81*** | 0 |
| 12 | 3 | PO, QD x11 | 72*** | 0 |
| 12 | 1.5 | PO, QD x21 | 87*** | 22 |
| 12 | 3 | PO, QD x21 | 94*** | 56 |
| 173 | 1.25 | PO, QD x21 | 49** | 0 |
| 173 | 2.5 | PO, QD x21 | nd[c] | 67 |
| 196 | 2.5 | PO, QD x21 | 84*** | 0 |
| 196 | 5 | PO, QD x21 | 92*** | 44 |
| 199 | 1.25 | PO, QD x21 | 91*** | 38 |
| 199 | 2.5 | PO, QD x21 | nd[c] | 50 |
| 199 | 5 | PO, QD x21 | nd[c] | 50 |
| 207 | 0.25 | PO, QD x21 | 60*** | 0 |
| 207 | 0.5 | PO, QD x21 | 93*** | 11 |
| 207 | 0.5 | PO, QD x21 | 94*** | 13 |
| 207 | 1.0 | PO, QD x21 | 97*** | 44 |
| 213 | 0.5 | PO, QD x21 | 82*** | 13 |
| 213 | 1 | PO, QD x21 | 96*** | 25 |
| 213 | 1 | PO, QD x21 | 95*** | 13 |
| 213 | 2 | PO, QD x21 | nd[c] | 63 |

[a]The p values (as indicated by asterisks) are derived from Student's T test comparison of treatment group vs. control group. *p < 0.001, p < 0.01, *p < 0.05.

[b]Percentage of treatment group that were removed from study due to morbidity or weight loss in excess of 20%.

[c]Not determined.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:
1. A compound of formula (I),

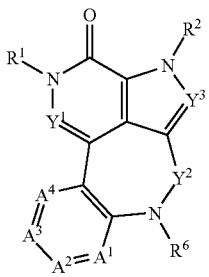

or a pharmaceutically acceptable salt thereof,
wherein:
formula (I) is selected from the group consisting of:

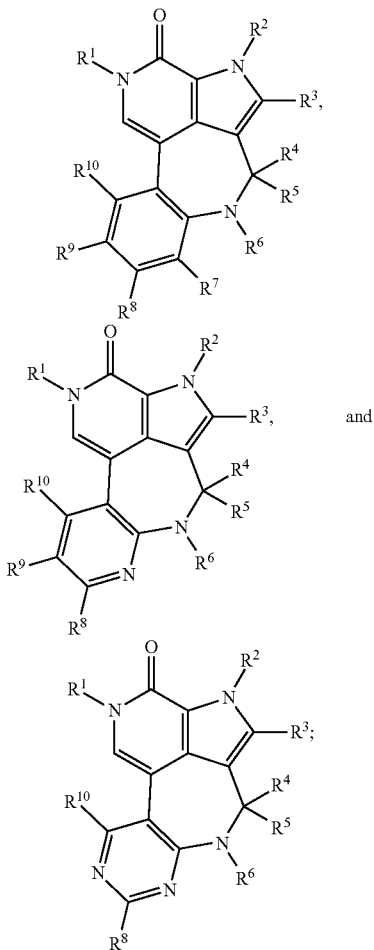

wherein:
$R^1$ is $CD_3$, $C_1$-$C_3$ alkyl or $C_1$-$C_3$ haloalkyl;
$R^2$ is H or $C_1$-$C_3$ alkyl;
$R^3$ is H, $C_1$-$C_6$ alkyl, $C_2$-$C_6$ alkenyl, $C_2$-$C_6$ alkynyl, halogen, $C_1$-$C_6$ haloalkyl, CN, C(O)$R^{3a}$, C(O)O$R^{3a}$, C(O)N$R^{3b}R^{3c}$, S(O)$R^{3d}$, S(O)$_2R^{3a}$, S(O)$_2$N$R^{3b}R^{3c}$ or $G^1$, wherein the $C_1$-$C_6$ alkyl, $C_2$-$C_6$ alkenyl and $C_2$-$C_6$ alkynyl are each optionally and independently substituted with one or two substituents independently selected from the group consisting of $G^1$, CN, C(O)$R^{3a}$, C(O)O$R^{3a}$, C(O)N$R^{3b}R^{3c}$, C(O)N($R^{3b}$)N$R^{3b}R^{3c}$, S(O)$R^{3d}$, S(O)$_2R^{3a}$, S(O)$_2$N$R^{3b}R^{3c}$, O$R^{3a}$, OC(O)$R^{3d}$, N$R^{3b}R^{3c}$, N($R^{3b}$)C(O)$R^{3d}$, N($R^{3b}$)S(O)$_2R^{3d}$, N($R^{3b}$)C(O)O$R^{3d}$, N($R^{3b}$)C(O)N$R^{3b}R^{3c}$, N($R^{3b}$)S(O)$_2$N$R^{3b}R^{3c}$ and N($R^{3b}$)C(N$R^{3b}R^{3c}$)=N$R^{3b}R^{3c}$;

$R^4$ is H, deuterium, $C_1$-$C_6$ alkyl, halogen or $C_1$-$C_6$ haloalkyl;

$R^5$ is H, deuterium, $C_1$-$C_6$ alkyl, $C_2$-$C_6$ alkenyl, $C_2$-$C_6$ alkynyl, halogen, $C_1$-$C_6$ haloalkyl, C(O)$R^{5a}$, C(O)O$R^{5a}$, C(O)N$R^{5b}R^{5c}$, S(O)$R^{5d}$, S(O)$_2R^{5a}$, S(O)$_2$N$R^{5b}R^{5c}$ or $G^1$, wherein the $C_1$-$C_6$ alkyl, $C_2$-$C_6$ alkenyl and $C_2$-$C_6$ alkynyl are each optionally and independently substituted with one or two substituents independently selected from the group consisting of $G^1$, CN, C(O)$R^{5a}$, C(O)O$R^{5a}$, C(O)N$R^{5b}R^{5c}$, C(O)N($R^{5b}$)N$R^{5b}R^{5c}$, S(O)$R^{5d}$, S(O)$_2R^{5a}$, S(O)$_2$N$R^{5b}R^{5c}$, O$R^{5a}$, OC(O)$R^{5d}$, N$R^{5b}R^{5c}$, N($R^{5b}$)C(O)$R^{5d}$, N($R^{5b}$)S(O)$_2R^{5d}$, N($R^{5b}$)C(O)O$R^{5d}$, N($R^{5b}$)C(O)N$R^{5b}R^{5c}$, N($R^{5b}$)S(O)$_2$N$R^{5b}R^{5c}$ and N($R^{5b}$)C(N$R^{5b}R^{5c}$)=N$R^{5b}R^{5c}$;

$R^{3a}$, $R^{3b}$, $R^{3c}$, $R^{5a}$ and $R^{5b}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^1$ or ($C_1$-$C_6$ alkylenyl)-$G^1$;

$R^{5c}$, at each occurrence, is independently H, $C_1$-$C_6$ alkyl, $C_2$-$C_6$ alkenyl, $C_2$-$C_6$ alkynyl, $C_1$-$C_6$ haloalkyl, $G^1$, ($C_1$-$C_6$ alkylenyl)-$G^1$, ($C_1$-$C_6$ alkylenyl)-CN, ($C_1$-$C_6$ alkylenyl)-O$R^a$ or ($C_1$-$C_6$ alkylenyl)-C(O)O$R^a$;

$R^{3d}$, at each occurrence, is independently $C_1$-$C_6$ alkyl, $C_2$-$C_6$ alkenyl, $C_2$-$C_6$ alkynyl, $C_1$-$C_6$ haloalkyl, $G^1$ or ($C_1$-$C_6$ alkylenyl)-$G^1$;

$R^{5d}$, at each occurrence, is independently $C_1$-$C_6$ alkyl, $C_2$-$C_6$ alkenyl, $C_2$-$C_6$ alkynyl, $C_1$-$C_6$ haloalkyl, $G^1$, ($C_1$-$C_6$ alkylenyl)-$G^1$, ($C_1$-$C_6$ alkylenyl)-N$R^cR^d$ or ($C_1$-$C_6$ alkylenyl)-N($R^e$)C(O)O($R^b$);

$G^1$, at each occurrence, is independently aryl, heteroaryl, heterocyclyl, cycloalkyl or cycloalkenyl, wherein each $G^1$ is optionally substituted with one, two, three, four or five $R^{1g}$ groups;

$R^6$ is H, $C_1$-$C_6$ alkyl, $C_2$-$C_6$ alkenyl, $C_2$-$C_6$ alkynyl, halogen, $C_1$-$C_6$ haloalkyl, C(O)$R^{6a}$, C(O)O$R^{6a}$, C(O)N$R^{6b}R^{6c}$, S(O)$_2R^{6a}$, S(O)$_2$N$R^{6b}R^{6c}$ or $G^2$, wherein the $C_1$-$C_6$ alkyl, $C_2$-$C_6$ alkenyl, and $C_2$-$C_6$ alkynyl are each optionally and independently substituted with one or two substituents independently selected from the group consisting of $G^2$, CN, C(O)$R^{6a}$, C(O)O$R^{6a}$, C(O)N$R^{6b}R^{6c}$, C(O)N($R^{6b}$)N$R^{6b}R^{6c}$, S(O)$R^{6d}$, S(O)$_2R^{6a}$, S(O)$_2$N$R^{6b}R^{6c}$, O$R^{6a}$, OC(O)$R^{6d}$, N$R^{6b}R^{6c}$, N($R^{6b}$)C(O)$R^{6d}$, N($R^{6b}$)S(O)$_2R^{6d}$, N($R^{6b}$)C(O)O$R^{6d}$, N($R^{6b}$)C(O)N$R^{6b}R^{6c}$, N($R^{6b}$)S(O)$_2$N$R^{6b}R^{6c}$ and N($R^{6b}$)C(N$R^{6b}R^{6c}$)=N$R^{6b}R^{6c}$;

$R^{6a}$, $R^{6b}$ and $R^{6c}$, at each occurrence, are each independently H, alkyl, $C_2$-$C_6$ alkenyl, $C_2$-$C_6$ alkynyl, haloalkyl, $G^2$, ($C_1$-$C_6$ alkylenyl)-$G^2$, ($C_1$-$C_6$ alkylenyl)-O$R^a$, ($C_1$-$C_6$ alkylenyl)-S(O)$_2R^a$, ($C_1$-$C_6$ alkylenyl)-S(O)$_2$N$R^cR^d$, ($C_1$-$C_6$ alkylenyl)-C(O)$R^a$, ($C_1$-$C_6$ alkylenyl)-C(O)O$R^a$, ($C_1$-$C_6$ alkylenyl)-C(O)N$R^cR^d$, ($C_1$-$C_6$ alkylenyl)-N$R^cR^d$, ($C_1$-$C_6$ alkylenyl)-N($R^e$)C(O)$R^b$, ($C_1$-$C_6$ alkylenyl)-N($R^e$)S(O)$_2R^b$, ($C_1$-$C_6$ alkylenyl)-N($R^e$)C(O)O($R^b$), ($C_1$-$C_6$ alkylenyl)-N($R^e$)C(O)N$R^cR^d$ or ($C_1$-$C_6$ alkylenyl)-N($R^e$)S(O)$_2$N$R^cR^d$;

$R^{6d}$, at each occurrence, is independently alkyl, $C_2$-$C_6$ alkenyl, $C_2$-$C_6$ alkynyl, haloalkyl, $G^2$, ($C_1$-$C_6$ alkylenyl)-$G^2$, ($C_1$-$C_6$ alkylenyl)-$OR^a$, ($C_1$-$C_6$ alkylenyl)-$S(O)_2R^a$, ($C_1$-$C_6$ alkylenyl)-$S(O)_2NR^cR^d$, ($C_1$-$C_6$ alkylenyl)-$C(O)R^a$, ($C_1$-$C_6$ alkylenyl)-$C(O)OR^a$, ($C_1$-$C_6$ alkylenyl)-$C(O)NR^cR^d$, ($C_1$-$C_6$ alkylenyl)-$NR^cR^d$, ($C_1$-$C_6$ alkylenyl)-$N(R^e)C(O)R^b$, ($C_1$-$C_6$ alkylenyl)-$N(R^e)S(O)_2R^b$, ($C_1$-$C_6$ alkylenyl)-$N(R^e)C(O)O(R^b)$, ($C_1$-$C_6$ alkylenyl)-$N(R^e)C(O)NR^cR^d$ or ($C_1$-$C_6$ alkylenyl)-$N(R^e)S(O)_2NR^cR^d$;

$G^2$, at each occurrence, is independently aryl, heteroaryl, heterocyclyl, cycloalkyl or cycloalkenyl, wherein each $G^2$ is optionally substituted with one, two, three, four or five $R^{2g}$ groups;

$R^7$, $R^8$ and $R^9$ are each independently H, $C_1$-$C_6$ alkyl, $C_2$-$C_6$ alkenyl, $C_2$-$C_6$ alkynyl, halogen, $C_1$-$C_6$ haloalkyl, CN, $NO_2$, $OR^{y1}$, $OC(O)R^{y2}$, $OC(O)NR^{y3}R^{y4}$, $SR^{y1}$, $S(O)_2R^{y1}$, $S(O)_2NR^{y3}R^{y4}$, $C(O)R^{y1}$, $C(O)OR^{y1}$, $C(O)NR^{y3}R^{y4}$, $NR^{y3}R^{y4}$, $N(R^{y3})C(O)R^{y2}$, $N(R^{y3})S(O)_2R^{y2}$, $N(R^{y3})C(O)O(R^{y2})$, $N(R^{y3})C(O)NR^{y3}R^{y4}$, $N(R^{y3})S(O)_2NR^{y3}R^{y4}$, $G^3$, ($C_1$-$C_6$ alkylenyl)-CN, ($C_1$-$C_6$ alkylenyl)-$OR^{y1}$, ($C_1$-$C_6$ alkylenyl)-$OC(O)R^{y2}$, ($C_1$-$C_6$ alkylenyl)-$OC(O)NR^{y3}R^{y4}$, ($C_1$-$C_6$ alkylenyl)-$S(O)_2R^{y1}$, ($C_1$-$C_6$ alkylenyl)-$S(O)_2NR^{y3}R^{y4}$, ($C_1$-$C_6$ alkylenyl)-$C(O)R^{y1}$, ($C_1$-$C_6$ alkylenyl)-$C(O)OR^{y1}$, ($C_1$-$C_6$ alkylenyl)-$C(O)NR^{y3}R^{y4}$, ($C_1$-$C_6$ alkylenyl)-$NR^{y3}R^{y4}$, ($C_1$-$C_6$ alkylenyl)-$N(R^{y3})C(O)R^{y2}$, ($C_1$-$C_6$ alkylenyl)-$N(R^{y3})S(O)_2R^{y2}$, ($C_1$-$C_6$ alkylenyl)-$N(R^{y3})C(O)O(R^{y2})$, ($C_1$-$C_6$ alkylenyl)-$N(R^{y3})C(O)NR^{y3}R^{y4}$, ($C_1$-$C_6$ alkylenyl)-$N(R^{y3})S(O)_2NR^{y3}R^{y4}$, ($C_1$-$C_6$ alkylenyl)-CN or ($C_1$-$C_6$ alkylenyl)-$G^3$;

$R^{y1}$, $R^{y3}$ and $R^{y4}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^3$, ($C_1$-$C_6$ alkylenyl)-$G^3$, ($C_1$-$C_6$ alkylenyl)-$OR^a$, ($C_1$-$C_6$ alkylenyl)-$S(O)_2R^a$, ($C_1$-$C_6$ alkylenyl)-$S(O)_2NR^cR^d$, ($C_1$-$C_6$ alkylenyl)-$C(O)R^a$, ($C_1$-$C_6$ alkylenyl)-$C(O)OR^a$, ($C_1$-$C_6$ alkylenyl)-$C(O)NR^cR^d$, ($C_1$-$C_6$ alkylenyl)-$NR^cR^d$, ($C_1$-$C_6$ alkylenyl)-$N(R^e)C(O)R^b$, ($C_1$-$C_6$ alkylenyl)-$N(R^e)S(O)_2R^b$, ($C_1$-$C_6$ alkylenyl)-$N(R^e)C(O)O(R^b)$, ($C_1$-$C_6$ alkylenyl)-$N(R^e)C(O)NR^cR^d$ or ($C_1$-$C_6$ alkylenyl)-$N(R^e)S(O)_2NR^cR^d$;

$R^{y2}$, at each occurrence, is independently $C_1$-$C_6$ alkyl, $C_2$-$C_6$ alkenyl, $C_2$-$C_6$ alkynyl, $C_1$-$C_6$ haloalkyl, $G^3$, ($C_1$-$C_6$ alkylenyl)-$G^3$, ($C_1$-$C_6$ alkylenyl)-$OR^a$, ($C_1$-$C_6$ alkylenyl)-$S(O)_2R^a$, ($C_1$-$C_6$ alkylenyl)-$S(O)_2NR^cR^d$, ($C_1$-$C_6$ alkylenyl)-$C(O)R^a$, ($C_1$-$C_6$ alkylenyl)-$C(O)OR^a$, ($C_1$-$C_6$ alkylenyl)-$C(O)NR^cR^d$, ($C_1$-$C_6$ alkylenyl)-$NR^cR^d$, ($C_1$-$C_6$ alkylenyl)-$N(R^e)C(O)R^b$, ($C_1$-$C_6$ alkylenyl)-$N(R^e)S(O)_2R^b$, ($C_1$-$C_6$ alkylenyl)-$N(R^e)C(O)O(R^b)$, ($C_1$-$C_6$ alkylenyl)-$N(R^e)C(O)NR^cR^d$ or ($C_1$-$C_6$ alkylenyl)-$N(R^e)S(O)_2NR^cR^d$;

$G^3$, at each occurrence, is independently aryl, heteroaryl, heterocyclyl, cycloalkyl or cycloalkenyl, wherein each $G^3$ group is optionally substituted with one, two, three, four or five $R^{4g}$ groups;

$R^{10}$ is H, $C_1$-$C_3$ alkyl, halogen, $C_1$-$C_3$ haloalkyl or CN;

$R^{1g}$, $R^{2g}$ and $R^{4g}$, at each occurrence, is independently selected from the group consisting of oxo, $C_1$-$C_6$ alkyl, $C_2$-$C_6$ alkenyl, $C_2$-$C_6$ alkynyl, halogen, $C_1$-$C_6$ haloalkyl, CN, $NO_2$, $G^{2a}$, $OR^a$, $OC(O)R^b$, $OC(O)NR^cR^d$, $SR^a$, $S(O)_2R^a$, $S(O)_2NR^cR^d$, $C(O)R^a$, $C(O)OR^a$, $C(O)NR^cR^d$, $NR^cR^d$, $N(R^e)C(O)R^b$, $N(R^e)S(O)_2R^b$, $N(R^e)C(O)O(R^b)$, $N(R^e)C(O)NR^cR^d$, $N(R^e)S(O)_2NR^cR^d$, ($C_1$-$C_6$ alkylenyl)-CN, ($C_1$-$C_6$ alkylenyl)-$G^{2a}$, ($C_1$-$C_6$ alkylenyl)-$OR^a$, ($C_1$-$C_6$ alkylenyl)-$OC(O)R^b$, ($C_1$-$C_6$ alkylenyl)-$OC(O)NR^cR^d$, ($C_1$-$C_6$ alkylenyl)-$S(O)_2R^a$, ($C_1$-$C_6$ alkylenyl)-$S(O)_2NR^cR^d$, ($C_1$-$C_6$ alkylenyl)-$C(O)R^a$, ($C_1$-$C_6$ alkylenyl)-$C(O)OR^a$, ($C_1$-$C_6$ alkylenyl)-$C(O)NR^cR^d$, ($C_1$-$C_6$ alkylenyl)-$NR^cR^d$, ($C_1$-$C_6$ alkylenyl)-$N(R^e)C(O)R^b$, ($C_1$-$C_6$ alkylenyl)-$N(R^e)S(O)_2R^b$, ($C_1$-$C_6$ alkylenyl)-$N(R^e)C(O)O(R^b)$, ($C_1$-$C_6$ alkylenyl)-$N(R^e)C(O)NR^cR^d$, ($C_1$-$C_6$ alkylenyl)-$N(R^e)S(O)_2NR^cR^d$ or ($C_1$-$C_6$ alkylenyl)-CN;

$R^a$, $R^c$, $R^d$ and $R^e$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^{2a}$, ($C_1$-$C_6$ alkylenyl)-$OR^{z1}$, ($C_1$-$C_6$ alkylenyl)-$NR^{z3}R^{z4}$, ($C_1$-$C_6$ alkylenyl)-$C(O)NR^{z3}R^{z4}$ or ($C_1$-$C_6$ alkylenyl)-$G^{2a}$;

$R^b$, at each occurrence, is independently $C_1$-$C_6$ alkyl, $C_2$-$C_6$ alkenyl, $C_2$-$C_6$ alkynyl, $C_1$-$C_6$ haloalkyl, $G^{2a}$ or ($C_1$-$C_6$ alkylenyl)-$G^{2a}$;

$G^{2a}$, at each occurrence, is independently aryl, heteroaryl, heterocyclyl, cycloalkyl or cycloalkenyl, wherein each $G^{2a}$ group is optionally substituted with one, two, three, four or five $R^{3g}$ groups;

$R^{3g}$, at each occurrence, is independently oxo, $C_1$-$C_6$ alkyl, $C_2$-$C_6$ alkenyl, $C_2$-$C_6$ alkynyl, halogen, $C_1$-$C_6$ haloalkyl, CN, $NO_2$, $OR^{z1}$, $OC(O)R^{z2}$, $OC(O)NR^{z3}R^{z4}$, $SR^{z1}$, $S(O)_2R^{z1}$, $S(O)_2NR^{z3}R^{z4}$, $C(O)R^{z1}$, $C(O)OR^{z1}$, $C(O)NR^{z3}R^{z4}$, $NR^{z3}R^{z4}$, $N(R^{z3})C(O)R^{z2}$, $N(R^{z3})S(O)_2R^{z2}$, $N(R^{z3})C(O)O(R^{z2})$, $N(R^{z3})C(O)NR^{z3}R^{z4}$, $N(R^{z3})S(O)_2NR^{z3}R^{z4}$, ($C_1$-$C_6$ alkylenyl)-$OR^{z1}$, ($C_1$-$C_6$ alkylenyl)-$OC(O)R^{z2}$, ($C_1$-$C_6$ alkylenyl)-$OC(O)NR^{z3}R^{z4}$, ($C_1$-$C_6$ alkylenyl)-$S(O)_2R^{z1}$, ($C_1$-$C_6$ alkylenyl)-$S(O)_2NR^{z3}R^{z4}$, ($C_1$-$C_6$ alkylenyl)-$C(O)R^{z1}$, ($C_1$-$C_6$ alkylenyl)-$C(O)OR^{z1}$, ($C_1$-$C_6$ alkylenyl)-$C(O)NR^{z3}R^{z4}$, ($C_1$-$C_6$ alkylenyl)-$NR^{z3}R^{z4}$, ($C_1$-$C_6$ alkylenyl)-$N(R^{z3})C(O)R^{z2}$, ($C_1$-$C_6$ alkylenyl)-$N(R^{z3})S(O)_2R^{z2}$, ($C_1$-$C_6$ alkylenyl)-$N(R^{z3})C(O)O(R^{z2})$, ($C_1$-$C_6$ alkylenyl)-$N(R^{z3})C(O)NR^{z3}R^{z4}$, ($C_1$-$C_6$ alkylenyl)-$N(R^{z3})S(O)_2NR^{z3}R^{z4}$ or ($C_1$-$C_6$ alkylenyl)-CN;

$R^{z1}$, $R^{z3}$ and $R^{z4}$, at each occurrence, are each independently H, $C_1$-$C_6$ alkyl, $C_2$-$C_6$ alkenyl, $C_2$-$C_6$ alkynyl or $C_1$-$C_6$ haloalkyl; and $R^{z2}$, at each occurrence, is independently $C_1$-$C_6$ alkyl, $C_2$-$C_6$ alkenyl, $C_2$-$C_6$ alkynyl or $C_1$-$C_6$ haloalkyl.

2. The compound of claim 1, or a pharmaceutically acceptable salt thereof, wherein $R^1$ is $C_1$-$C_3$ alkyl.

3. The compound of claim 1, or a pharmaceutically acceptable salt thereof, wherein $R^2$ is H.

4. The compound of claim 1, or a pharmaceutically acceptable salt thereof, wherein $R^3$ is H, $C_1$-$C_6$ alkyl, CN, $C(O)R^{3a}$, $C(O)OR^{3a}$ or $C(O)NR^{3b}R^{3c}$, wherein the $C_1$-$C_6$ alkyl is optionally substituted with one substituent selected from the group consisting of $G^1$, $NR^{3b}R^{3c}$, $N(R^{3b})C(O)R^{3d}$, $N(R^{3b})S(O)_2R^{3d}$, $N(R^{3b})C(O)OR^{3d}$, $N(R^{3b})C(O)NR^{3b}R^{3c}$ and $N(R^{3b})S(O)_2NR^{3b}R^{3c}$.

5. The compound of claim 1, or a pharmaceutically acceptable salt thereof, wherein $R^4$ is H or deuterium; and $R^5$ is H, deuterium, $C_1$-$C_6$ alkyl, $C_2$-$C_6$ alkenyl, $C_2$-$C_6$ alkynyl, $C_1$-$C_6$ haloalkyl, $C(O)R^{5a}$, $C(O)OR^{5a}$ or $G^1$, wherein the $C_1$-$C_6$ alkyl, $C_2$-$C_6$ alkenyl and $C_2$-$C_6$ alkynyl are each optionally and independently substituted with one or two substituents independently selected from the group consisting of $G^1$, $C(O)R^{5a}$, C(O)OR$^{5a}$, C(O)NR$^{5b}$R$^{5c}$, C(O)N(R$^{5b}$)NR$^{5b}$R$^{5c}$, OR$^{5a}$, OC(O)R$^{5d}$, NR$^{5b}$R$^{5c}$, N(R$^{5b}$)C(O)R$^{5d}$, N(R$^{5b}$)S(O)$_2$R$^{5d}$, N(R$^{5b}$)C(O)OR$^{5d}$, N(R$^{5b}$)C(O)NR$^{5b}$R$^{5c}$ and N(R$^{5b}$)S(O)$_2$NR$^{5b}$R$^{5c}$.

6. The compound of claim 1, or a pharmaceutically acceptable salt thereof, wherein R$^6$ is H, C$_1$-C$_6$ alkyl, C$_2$-C$_6$ alkenyl, C(O)R$^{6a}$, C(O)OR$^{6a}$, C(O)NR$^{6b}$R$^{6c}$, S(O)$_2$R$^{6a}$ or G$^2$, wherein the C$_1$-C$_6$ alkyl and C$_2$-C$_6$ alkenyl are each optionally and independently substituted with one or two substituents independently selected from the group consisting of G$^2$, CN, C(O)OR$^{6a}$, NR$^{6b}$R$^{6c}$, N(R$^{6b}$)C(O)R$^{6d}$, N(R$^{6b}$)S(O)$_2$R$^{6d}$, N(R$^{6b}$)C(O)OR$^{6d}$, N(R$^{6b}$)C(O)NR$^{6b}$R$^{6c}$ and N(R$^{6b}$)S(O)$_2$NR$^{6b}$R$^{6c}$.

7. The compound of claim 1, or a pharmaceutically acceptable salt thereof, wherein R$^9$ is H, C$_1$-C$_6$ alkyl, halogen, C$_1$-C$_6$ haloalkyl, CN, S(O)$_2$R$^{y1}$, S(O)$_2$NR$^{y3}$R$^{y4}$, C(O)NR$^{y3}$R$^{y4}$, NR$^{y3}$R$^{y4}$, N(R$^{y3}$)C(O)R$^{y2}$, N(R$^{y3}$)S(O)$_2$R$^{y2}$, N(R$^{y3}$)C(O)O(R$^{y2}$), N(R$^{y3}$)C(O)NR$^{y3}$R$^{y4}$, N(R$^{y3}$)S(O)$_2$NR$^{y3}$R$^{y4}$, (C$_1$-C$_6$ alkylenyl)-S(O)$_2$R$^{y1}$, (C$_1$-C$_6$ alkylenyl)-S(O)$_2$NR$^{y3}$R$^{y4}$, (C$_1$-C$_6$ alkylenyl)-C(O)NR$^{y3}$R$^{y4}$, (C$_1$-C$_6$ alkylenyl)-NR$^{y3}$R$^{y4}$, (C$_1$-C$_6$ alkylenyl)-N(R$^{y3}$)C(O)R$^{y2}$, (C$_1$-C$_6$ alkylenyl)-N(R$^{y3}$)S(O)$_2$R$^{y2}$, (C$_1$-C$_6$ alkylenyl)-N(R$^{y3}$)C(O)O(R$^{y2}$), (C$_1$-C$_6$ alkylenyl)-N(R$^{y3}$)C(O)NR$^{y3}$R$^{y4}$ or (C$_1$-C$_6$ alkylenyl)-N(R$^{y3}$)S(O)$_2$NR$^{y3}$R$^{y4}$.

8. The compound of claim 1, or a pharmaceutically acceptable salt thereof, wherein R$^1$ is C$_1$-C$_3$ alkyl; and
R$^2$ is H.

9. The compound of claim 8, or a pharmaceutically acceptable salt thereof, wherein R$^4$ is H or deuterium; and
R$^5$ is C$_2$-C$_6$ alkenyl, optionally substituted with one G$^1$; or
R$^5$ is H, deuterium, C$_1$-C$_6$ alkyl, C(O)R$^{5a}$, C(O)OR$^{5a}$ or G$^1$, wherein the C$_1$-C$_6$ alkyl is optionally substituted with one substituent selected from the group consisting of G$^1$, C(O)R$^{5a}$, C(O)OR$^{5a}$, C(O)NR$^{5b}$R$^{5c}$, C(O)N(R$^{5b}$)NR$^{5b}$R$^{5c}$, OR$^{5a}$, OC(O)R$^{5d}$, NR$^{5b}$R$^{5c}$ and N(R$^{5b}$)C(NR$^{5b}$R$^{5c}$)=NR$^{5b}$R$^{5c}$.

10. The compound of claim 8, or a pharmaceutically acceptable salt thereof, wherein R$^3$ is H, —C(O)R$^{3a}$, or —C(O)NR$^{3b}$R$^{3c}$.

11. The compound of claim 8, or a pharmaceutically acceptable salt thereof, wherein R$^6$ is H, C$_1$-C$_6$ alkyl, —C(O)R$^{6a}$, —C(O)OR$^{6a}$, —C(O)NR$^{6b}$R$^{6c}$, —S(O)$_2$R$^{6a}$, or G$^2$; wherein the C$_1$-C$_6$ alkyl is unsubstituted or substituted with a substituent selected from the group consisting of G$^2$ and —C(O)OR$^{6a}$.

12. The compound of claim 8, or a pharmaceutically acceptable salt thereof, wherein R$^9$ is H, C$_1$-C$_6$ alkyl, halogen, —S(O)$_2$R$^{y1}$, —S(O)$_2$NR$^{y3}$R$^{y4}$, —NR$^{y3}$R$^{y4}$, —N(R$^{y3}$)S(O)$_2$R$^{y2}$, or —(C$_1$-C$_6$ alkylenyl)-S(O)$_2$R$^{y1}$.

13. The compound of claim 8, or a pharmaceutically acceptable salt thereof, wherein R$^1$ is CH$_3$;
R$^4$ is H or deuterium;
R$^7$ is H, C$_1$-C$_3$ alkyl, halogen or cyclopropyl, wherein cyclopropyl is optionally substituted with one, two, three, four or five R$^{4g}$ groups;
R$^8$ is H, C$_1$-C$_6$ alkyl, halogen, C$_1$-C$_6$ haloalkyl, CN, C(O)NR$^{y3}$R$^{y4}$, (C$_1$-C$_6$ alkylenyl)-NR$^{y3}$R$^{y4}$, (C$_1$-C$_6$ alkylenyl)-N(R$^{y3}$)C(O)R$^{y2}$, (C$_1$-C$_6$ alkylenyl)-N(R$^{y3}$)S(O)$_2$R$^{y2}$, (C$_1$-C$_6$ alkylenyl)-N(R$^{y3}$)C(O)O(R$^{y2}$), (C$_1$-C$_6$ alkylenyl)-N(R$^{y3}$)C(O)NR$^{y3}$R$^{y4}$, (C$_1$-C$_6$ alkylenyl)-N(R$^{y3}$)S(O)$_2$NR$^{y3}$R$^{y4}$, G$^3$ or (C$_1$-C$_6$ alkylenyl)-G$^3$, wherein each G$^3$ is heterocyclyl, optionally and independently substituted with one, two, three, four or five R$^{4g}$ groups; and R$^{10}$ is H, C$_1$-C$_3$ alkyl or halogen.

14. The compound of claim 13, or a pharmaceutically acceptable salt thereof, wherein R$^3$ is H or —C(O)NR$^{3b}$R$^{3c}$.

15. The compound of claim 13, or a pharmaceutically acceptable salt thereof, wherein R$^5$ is H, deuterium, or C$_1$-C$_6$ alkyl optionally substituted with a substituent selected from the group consisting of —C(O)OR$^{5a}$ and OR$^{5a}$.

16. The compound of claim 13, or a pharmaceutically acceptable salt thereof, wherein R$^6$ is —C(O)R$^{6a}$, —C(O)OR$^{6a}$, —C(O)NR$^{6b}$R$^{6c}$, G$^2$, or C$_1$-C$_6$ alkyl which is unsubstituted or substituted with a G$^2$ group.

17. The compound of claim 13, or a pharmaceutically acceptable salt thereof, wherein R$^9$ is halogen, —NR$^{y3}$R$^{y4}$, —N(R$^{y3}$)C(O)R$^{y2}$, —N(R$^{y3}$)S(O)$_2$R$^{y2}$, or —(C$_1$-C$_6$ alkylenyl)-S(O)$_2$R$^{y1}$.

18. The compound of claim 13, or a pharmaceutically acceptable salt thereof, wherein R$^7$ is H or halogen;
R$^8$ is H; and
R$^{10}$ is H.

19. The compound of claim 18, or a pharmaceutically acceptable salt thereof, wherein R$^9$ is halogen, —N(R$^{y3}$)S(O)$_2$R$^{y2}$, or —(C$_1$-C$_6$ alkylenyl)-S(O)$_2$R$^{y1}$.

20. The compound of claim 19, or a pharmaceutically acceptable salt thereof, wherein R$^6$ is —C(O)R$^{6a}$, —C(O)OR$^{6a}$, —C(O)NR$^{6b}$R$^{6c}$, G$^2$, or C$_1$-C$_6$ alkyl which is unsubstituted or substituted with a G$^2$ group.

21. The compound of claim 20, or a pharmaceutically acceptable salt thereof, wherein R$^5$ is H, deuterium, or C$_1$-C$_6$ alkyl optionally substituted with a substituent selected from the group consisting of —C(O)OR$^{5a}$ and OR$^{5a}$.

22. The compound of claim 21, or a pharmaceutically acceptable salt thereof, wherein R$^3$ is H or —C(O)NR$^{3b}$R$^{3c}$.

23. The compound of claim 22, or a pharmaceutically acceptable salt thereof, wherein R$^{3b}$ and R$^{3c}$ are each independently H or C$_1$-C$_6$ alkyl;
R$^{5a}$ is C$_1$-C$_6$ alkyl;
R$^{y1}$ and R$^{y2}$ are each independently C$_1$-C$_6$ alkyl; and
R$^{y3}$ is H.

24. The compound of claim 8, or a pharmaceutically acceptable salt thereof, wherein R$^1$ is CH$_3$;
R$^3$ is H, C$_1$-C$_6$ alkyl, CN or C(O)NR$^{3b}$R$^{3c}$, wherein the C$_1$-C$_6$ alkyl is substituted with one G$^1$, wherein G$^1$ is C$_4$-C$_6$ heterocyclyl, optionally substituted with one, two, three, four or five R$^1$ groups;
R$^4$ is H or deuterium;
R$^7$ is H, C$_1$-C$_3$ alkyl, halogen, CN or cyclopropyl, wherein cyclopropyl is optionally substituted with one, two, three, four or five R$^{4g}$ groups;
R$^8$ is H;
R$^9$ is halogen, N(R$^{y3}$)S(O)$_2$R$^{y2}$ or (C$_1$-C$_6$ alkylenyl)-S(O)$_2$R$^{y1}$; and
R$^{10}$ is H.

25. The compound of claim 24, or a pharmaceutically acceptable salt thereof, wherein R⁵ is H; and
R⁶ is phenyl, pyridinyl, or cyclohexyl; each of which is optionally substituted; or R⁶ is —C(O)O(C₁-C₆ alkyl); or R⁶ is —CH₂-(optionally substituted tetrahydropyranyl).

26. The compound of claim 8, or a pharmaceutically acceptable salt thereof, wherein
R¹ is CH₃;
R³ is G¹;
R⁴ is H or deuterium;
R⁷ is H, C₁-C₃ alkyl, halogen, CN or cyclopropyl, wherein cyclopropyl is optionally substituted with one, two, three, four or five R⁴ᵍ groups;
R⁸ is H;
R⁹ is S(O)₂Rʸ¹, N(Rʸ³)S(O)₂Rʸ² or (C₁-C₆ alkylenyl)-S(O)₂Rʸ¹; and
R¹⁰ is H.

27. The compound of claim 8, or a pharmaceutically acceptable salt thereof, wherein
R¹ is CH₃;
R³ is G¹, wherein G¹ is heteroaryl, optionally substituted with one, two, three, four or five R¹ᵍ groups;
R⁴ is H or deuterium;
R⁵ is H;
R⁷ is H, C₁-C₃ alkyl, halogen, CN or cyclopropyl, wherein cyclopropyl is optionally substituted with one, two, three, four or five R⁴ᵍ groups;
R⁸ is H;
R⁹ is S(O)₂Rʸ¹, N(Rʸ³)S(O)₂Rʸ² or (C₁-C₆ alkylenyl)-S(O)₂Rʸ¹; and
R¹⁰ is H.

28. The compound of claim 1, or a pharmaceutically acceptable salt thereof, wherein the compound is selected from the group consisting of:
4-(cyclopropylmethyl)-7-(isopropylsulfonyl)-10-methyl-3,4-dihydro-1H-1,4,10-triazadibenzo[cd,f]azulen-11(10H)-one;
4-(cyclopropylmethyl)-7-(ethylsulfonyl)-10-methyl-3,4-dihydro-1H-1,4,10-triazadibenzo[cd,f]azulen-11(10H)-one;
4-(cyclopropylmethyl)-3-ethyl-7-(ethylsulfonyl)-10-methyl-3,4-dihydro-1H-1,4,10-triazadibenzo[cd,f]azulen-11(10H)-one;
10-methyl-7-(methylsulfonyl)-3,4-dihydro-1H-1,4,10-triazadibenzo[cd,f]azulen-11(10H)-one;
10-methyl-7-((methylsulfonyl)methyl)-3,4-dihydro-1H-1,4,10-triazadibenzo[cd,f]azulen-11(10H)-one;
4-(cyclopropylmethyl)-10-methyl-7-((methylsulfonyl)methyl)-3,4-dihydro-1H-1,4,10-triazadibenzo[cd,f]azulen-11(10H)-one;
ethyl 4-(cyclopropylmethyl)-10-methyl-7-((methylsulfonyl)methyl)-11-oxo-3,4,10,11-tetrahydro-1H-1,4,10-triazadibenzo[cd,f]azulene-3-carboxylate;
4-(4-fluorophenyl)-10-methyl-7-(methylsulfonyl)-3,4-dihydro-1H-1,4,10-triazadibenzo[cd,f]azulen-11(10H)-one;
4-(4-fluorophenyl)-10-methyl-7-((methylsulfonyl)methyl)-3,4-dihydro-1H-1,4,10-triazadibenzo[cd,f]azulen-11(10H)-one;
4-(2,4-difluorophenyl)-10-methyl-7-((methylsulfonyl)methyl)-3,4-dihydro-1H-1,4,10-triazadibenzo[cd,f]azulen-11(10H)-one;
4-(cyclopropylmethyl)-10-methyl-3,4-dihydro-1H-1,4,10-triazadibenzo[cd,f]azulen-11(10H)-one;
methyl 3-(4-(cyclopropylmethyl)-10-methyl-7-((methylsulfonyl)methyl)-11-oxo-3,4,10,11-tetrahydro-1H-1,4,10-triazadibenzo[cd,f]azulen-3-yl)propanoate;
4-(cyclopropylmethyl)-3-(2-methoxyethyl)-10-methyl-7-((methylsulfonyl)methyl)-3,4-dihydro-1H-1,4,10-triazadibenzo[cd,f]azulen-11(10H)-one;
3-benzyl-10-methyl-7-((methylsulfonyl)methyl)-3,4-dihydro-1H-1,4,10-triazadibenzo[cd,f]azulen-11(10H)-one;
methyl 3-(10-methyl-7-((methylsulfonyl)methyl)-11-oxo-3,4,10,11-tetrahydro-1H-1,4,10-triazadibenzo[cd,f]azulen-3-yl)propanoate;
10-methyl-7-((methylsulfonyl)methyl)-3-phenethyl-3,4-dihydro-1H-1,4,10-triazadibenzo[cd,f]azulen-11(10H)-one;
3-isobutyl-10-methyl-7-((methylsulfonyl)methyl)-3,4-dihydro-1H-1,4,10-triazadibenzo[cd,f]azulen-11(10H)-one;
(E)-3-(4-fluorostyryl)-10-methyl-7-((methylsulfonyl)methyl)-3,4-dihydro-1H-1,4,10-triazadibenzo[cd,f]azulen-11(10H)-one;
4-butyl-10-methyl-7-((methylsulfonyl)methyl)-3,4-dihydro-1H-1,4,10-triazadibenzo[cd,f]azulen-11(10H)-one;
tert-butyl 3-((10-methyl-7-((methylsulfonyl)methyl)-11-oxo-10,11-dihydro-1H-1,4,10-triazadibenzo[cd,f]azulen-4(3H)-yl)methyl)pyrrolidine-1-carboxylate;
10-methyl-7-((methylsulfonyl)methyl)-4-((tetrahydrofuran-3-yl)methyl)-3,4-dihydro-1H-1,4,10-triazadibenzo[cd,f]azulen-11(10H)-one;
4-((4,4-difluorocyclohexyl)methyl)-10-methyl-7-((methylsulfonyl)methyl)-3,4-dihydro-1H-1,4,10-triazadibenzo[cd,f]azulen-11(10H)-one;
tert-butyl 4-((10-methyl-7-((methylsulfonyl)methyl)-11-oxo-10,11-dihydro-1H-1,4,10-triazadibenzo[cd,f]azulen-4(3H)-yl)methyl)piperidine-1-carboxylate;
10-methyl-7-((methylsulfonyl)methyl)-4-((tetrahydro-2H-pyran-3-yl)methyl)-3,4-dihydro-1H-1,4,10-triazadibenzo[cd,f]azulen-11(10H)-one;
4-(4,4-difluorocyclohexyl)-10-methyl-7-((methylsulfonyl)methyl)-3,4-dihydro-1H-1,4,10-triazadibenzo[cd,f]azulen-11(10H)-one;
4-(4-fluorophenyl)-(3,3-²H₂)-10-methyl-7-((methylsulfonyl)methyl)-3,4-dihydro-1H-1,4,10-triazadibenzo[cd,f]azulen-11(10H)-one;
ethyl 4-(4-fluorophenyl)-10-methyl-7-((methylsulfonyl)methyl)-11-oxo-3,4,10,11-tetrahydro-1H-1,4,10-triazadibenzo[cd,f]azulene-3-carboxylate;
tert-butyl 4-(4-(4-fluorophenyl)-10-methyl-7-((methylsulfonyl)methyl)-11-oxo-3,4,10,11-tetrahydro-1H-1,4,10-triazadibenzo[cd,f]azulene-3-carbonyl)piperazine-1-carboxylate;
10-methyl-7-((methylsulfonyl)methyl)-4-(pyrrolidin-3-ylmethyl)-3,4-dihydro-1H-1,4,10-triazadibenzo[cd,f]azulen-11(10H)-one;
10-methyl-7-((methylsulfonyl)methyl)-4-(piperidin-4-ylmethyl)-3,4-dihydro-1H-1,4,10-triazadibenzo[cd,f]azulen-11(10H)-one;
4-(4-fluorophenyl)-3-(4-methoxypiperidine-1-carbonyl)-10-methyl-7-((methylsulfonyl)methyl)-3,4-dihydro-1H-1,4,10-triazadibenzo[cd,f]azulen-11(10H)-one;
4-(4-fluorophenyl)-10-methyl-3-(4-methylpiperazine-1-carbonyl)-7-((methylsulfonyl)methyl)-3,4-dihydro-1H-1,4,10-triazadibenzo[cd,f]azulen-11(10H)-one;
5,7-difluoro-10-methyl-4-((tetrahydrofuran-3-yl)methyl)-3,4-dihydro-1H-1,4,10-triazadibenzo[cd,f]azulen-11(10H)-one;
N-cyclopentyl-10-methyl-7-((methylsulfonyl)methyl)-11-oxo-10,11-dihydro-1H-1,4,10-triazadibenzo[cd,f]azulene-4(3H)-carboxamide;

N-ethyl-10-methyl-7-((methylsulfonyl)methyl)-11-oxo-10,11-dihydro-1H-1,4,10-triazadibenzo[cd,f]azulene-4(3H)-carboxamide;

N-(4-fluorophenyl)-10-methyl-7-((methylsulfonyl)methyl)-11-oxo-10,11-dihydro-1H-1,4,10-triazadibenzo[cd,f]azulene-4(3H)-carboxamide;

4-butyl-5,7-difluoro-10-methyl-3,4-dihydro-1H-1,4,10-triazadibenzo[cd,f]azulen-11(10H)-one;

5,7-difluoro-10-methyl-4-propyl-3,4-dihydro-1H-1,4,10-triazadibenzo[cd,f]azulen-11(10H)-one;

4-(cyclopropylmethyl)-5,7-difluoro-10-methyl-3,4-dihydro-1H-1,4,10-triazadibenzo[cd,f]azulen-11(10H)-one;

methyl 4-(5,7-difluoro-10-methyl-11-oxo-10,11-dihydro-1H-1,4,10-triazadibenzo[cd,f]azulen-4(3H)-yl)butanoate;

5,7-difluoro-10-methyl-4-(3-phenylpropyl)-3,4-dihydro-1H-1,4,10-triazadibenzo[cd,f]azulen-11(10H)-one;

10-methyl-7-((methylsulfonyl)methyl)-11-oxo-N-(o-tolyl)-10,11-dihydro-1H-1,4,10-triazadibenzo[cd,f]azulene-4(3H)-carboxamide;

2-ethylhexyl 10-methyl-7-((methylsulfonyl)methyl)-11-oxo-10,11-dihydro-1H-1,4,10-triazadibenzo[cd,f]azulene-4(3H)-carboxylate;

4-isobutyryl-10-methyl-7-((methylsulfonyl)methyl)-3,4-dihydro-1H-1,4,10-triazadibenzo[cd,f]azulen-11(10H)-one;

5,7-difluoro-10-methyl-4-phenethyl-3,4-dihydro-1H-1,4,10-triazadibenzo[cd,f]azulen-11(10H)-one;

4-(2-(benzo[d][1,3]dioxol-5-yl)ethyl)-5,7-difluoro-10-methyl-3,4-dihydro-1H-1,4,10-triazadibenzo[cd,f]azulen-11(10H)-one;

4-((1Z,3E)-2,4-diphenylbuta-1,3-dien-1-yl)-5,7-difluoro-10-methyl-3,4-dihydro-1H-1,4,10-triazadibenzo[cd,f]azulen-11(10H)-one;

4-(4-chlorophenyl)-10-methyl-7-((methylsulfonyl)methyl)-11-oxo-3,4,10,11-tetrahydro-1H-1,4,10-triazadibenzo[cd,f]azulene-2-carboxamide;

4-(4-chlorophenyl)-N-ethyl-10-methyl-7-((methylsulfonyl)methyl)-11-oxo-3,4,10,11-tetrahydro-1H-1,4,10-triazadibenzo[cd,f]azulene-2-carboxamide;

4-(4-chlorophenyl)-10-methyl-2-(4-methylpiperazine-1-carbonyl)-7-((methylsulfonyl)methyl)-3,4-dihydro-1H-1,4,10-triazadibenzo[cd,f]azulen-11(10H)-one;

N-(2,6-dimethylphenyl)-10-methyl-7-((methylsulfonyl)methyl)-11-oxo-10,11-dihydro-1H-1,4,10-triazadibenzo[cd,f]azulene-4(3H)-carboxamide;

N-(4-methoxyphenyl)-10-methyl-7-((methylsulfonyl)methyl)-11-oxo-10,11-dihydro-1H-1,4,10-triazadibenzo[cd,f]azulene-4(3H)-carboxamide;

N-(4-ethylphenethyl)-10-methyl-7-((methylsulfonyl)methyl)-11-oxo-10,11-dihydro-1H-1,4,10-triazadibenzo[cd,f]azulene-4(3H)-carboxamide;

10-methyl-7-((methylsulfonyl)methyl)-11-oxo-N-propyl-10,11-dihydro-1H-1,4,10-triazadibenzo[cd,f]azulene-4(3H)-carboxamide;

N-(3-methoxybenzyl)-10-methyl-7-((methylsulfonyl)methyl)-11-oxo-10,11-dihydro-1H-1,4,10-triazadibenzo[cd,f]azulene-4(3H)-carboxamide;

N-(2-chloroethyl)-10-methyl-7-((methylsulfonyl)methyl)-11-oxo-10,11-dihydro-1H-1,4,10-triazadibenzo[cd,f]azulene-4(3H)-carboxamide;

N-(cyclohexylmethyl)-10-methyl-7-((methylsulfonyl)methyl)-11-oxo-10,11-dihydro-1H-1,4,10-triazadibenzo[cd,f]azulene-4(3H)-carboxamide;

N-(2,4-difluorophenyl)-10-methyl-7-((methylsulfonyl)methyl)-11-oxo-10,11-dihydro-1H-1,4,10-triazadibenzo[cd,f]azulene-4(3H)-carboxamide;

N-(4-isopropylphenyl)-10-methyl-7-((methylsulfonyl)methyl)-11-oxo-10,11-dihydro-1H-1,4,10-triazadibenzo[cd,f]azulene-4(3H)-carboxamide;

N-(2,6-difluorophenyl)-10-methyl-7-((methylsulfonyl)methyl)-11-oxo-10,11-dihydro-1H-1,4,10-triazadibenzo[cd,f]azulene-4(3H)-carboxamide;

N-(4-fluoro-3-(trifluoromethyl)phenyl)-10-methyl-7-((methylsulfonyl)methyl)-11-oxo-10,11-dihydro-1H-1,4,10-triazadibenzo[cd,f]azulene-4(3H)-carboxamide;

ethyl 4-(((10-methyl-7-((methylsulfonyl)methyl)-11-oxo-3,4,10,11-tetrahydro-1H-1,4,10-triazadibenzo[cd,f]azulene-4-carboxamido)methyl)cyclohexanecarboxylate;

N-(3-methoxypropyl)-10-methyl-7-((methylsulfonyl)methyl)-11-oxo-10,11-dihydro-1H-1,4,10-triazadibenzo[cd,f]azulene-4(3H)-carboxamide;

10-methyl-7-((methylsulfonyl)methyl)-4-tosyl-3,4-dihydro-1H-1,4,10-triazadibenzo[cd,f]azulen-11(10H)-one;

4-([1,1'-biphenyl]-4-ylsulfonyl)-10-methyl-7-((methylsulfonyl)methyl)-3,4-dihydro-1H-1,4,10-triazadibenzo[cd,f]azulen-11(10H)-one;

4-((4-methoxyphenyl)sulfonyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(phenylsulfonyl)-3,4-dihydro-1H-1,4,10-triazadibenzo[cd,f]azulen-11(10H)-one;

4-((2-methoxyphenyl)sulfonyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-((4-phenoxyphenyl)sulfonyl)-3,4-dihydro-1H-1,4,10-triazadibenzo[cd,f]azulen-11(10H)-one;

4-((4-fluorophenyl)sulfonyl)-10-methyl-7-((methylsulfonyl)methyl)-3,4-dihydro-1H-1,4,10-triazadibenzo[cd,f]azulen-11(10H)-one;

4-(2-naphthoyl)-10-methyl-7-((methylsulfonyl)methyl)-3,4-dihydro-1H-1,4,10-triazadibenzo[cd,f]azulen-11(10H)-one;

methyl 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoate;

(R)-ethyl 4-(4-fluorophenyl)-10-methyl-7-((methylsulfonyl)methyl)-11-oxo-3,4,10,11-tetrahydro-1H-1,4,10-triazadibenzo[cd,f]azulene-3-carboxylate;

(S)-ethyl 4-(4-fluorophenyl)-10-methyl-7-((methylsulfonyl)methyl)-11-oxo-3,4,10,11-tetrahydro-1H-1,4,10-triazadibenzo[cd,f]azulene-3-carboxylate;

2-methoxyethyl 10-methyl-7-((methylsulfonyl)methyl)-11-oxo-10,11-dihydro-1H-1,4,10-triazadibenzo[cd,f]azulene-4(3H)-carboxylate;

ethyl 10-methyl-7-((methylsulfonyl)methyl)-11-oxo-10,11-dihydro-1H-1,4,10-triazadibenzo[cd,f]azulene-4(3H)-carboxylate;

pentyl 10-methyl-7-((methylsulfonyl)methyl)-11-oxo-10,11-dihydro-1H-1,4,10-triazadibenzo[cd,f]azulene-4(3H)-carboxylate;

4-chlorobutyl 10-methyl-7-((methylsulfonyl)methyl)-11-oxo-10,11-dihydro-1H-1,4,10-triazadibenzo[cd,f]azulene-4(3H)-carboxylate;

naphthalen-2-yl 10-methyl-7-((methylsulfonyl)methyl)-11-oxo-10,11-dihydro-1H-1,4,10-triazadibenzo[cd,f]azulene-4(3H)-carboxylate;

p-tolyl 10-methyl-7-((methylsulfonyl)methyl)-11-oxo-10,11-dihydro-1H-1,4,10-triazadibenzo[cd,f]azulene-4(3H)-carboxylate;

neopentyl 10-methyl-7-((methylsulfonyl)methyl)-11-oxo-10,11-dihydro-1H-1,4,10-triazadibenzo[cd,f]azulene-4(3H)-carboxylate;

phenyl 10-methyl-7-((methylsulfonyl)methyl)-11-oxo-10,11-dihydro-1H-1,4,10-triazadibenzo[cd,f]azulene-4(3H)-carboxylate;

4-fluorophenyl 10-methyl-7-((methylsulfonyl)methyl)-11-oxo-10,11-dihydro-1H-1,4,10-triazadibenzo[cd,f]azulene-4(3H)-carboxylate;

2-methoxyphenyl 10-methyl-7-((methylsulfonyl)methyl)-11-oxo-10,11-dihydro-1H-1,4,10-triazadibenzo[cd,f]azulene-4(3H)-carboxylate;

2-fluoroethyl 10-methyl-7-((methylsulfonyl)methyl)-11-oxo-10,11-dihydro-1H-1,4,10-triazadibenzo[cd,f]azulene-4(3H)-carboxylate;

4-methoxyphenyl 10-methyl-7-((methylsulfonyl)methyl)-11-oxo-10,11-dihydro-1H-1,4,10-triazadibenzo[cd,f]azulene-4(3H)-carboxylate;

but-2-yn-1-yl 10-methyl-7-((methylsulfonyl)methyl)-11-oxo-10,11-dihydro-1H-1,4,10-triazadibenzo[cd,f]azulene-4(3H)-carboxylate;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanamide;

4-(4-fluorobenzoyl)-10-methyl-7-((methylsulfonyl)methyl)-3,4-dihydro-1H-1,4,10-triazadibenzo[cd,f]azulen-11(10H)-one;

4-(3-methoxypropanoyl)-10-methyl-7-((methylsulfonyl)methyl)-3,4-dihydro-1H-1,4,10-triazadibenzo[cd,f]azulen-11(10H)-one;

4-([1,1'-biphenyl]-4-carbonyl)-10-methyl-7-((methylsulfonyl)methyl)-3,4-dihydro-1H-1,4,10-triazadibenzo[cd,f]azulen-11(10H)-one;

4-(3-cyclopentylpropanoyl)-10-methyl-7-((methylsulfonyl)methyl)-3,4-dihydro-1H-1,4,10-triazadibenzo[cd,f]azulen-11(10H)-one;

4-(2-(3-methoxyphenyl)acetyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-propionyl-3,4-dihydro-1H-1,4,10-triazadibenzo[cd,f]azulen-11(10H)-one;

10-methyl-4-(3-methylbutanoyl)-7-((methylsulfonyl)methyl)-3,4-dihydro-1H-1,4,10-triazadibenzo[cd,f]azulen-11(10H)-one;

4-(3,3-dimethylbutanoyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(2-phenylacetyl)-3,4-dihydro-1H-1,4,10-triazadibenzo[cd,f]azulen-11(10H)-one;

4-benzoyl-10-methyl-7-((methylsulfonyl)methyl)-3,4-dihydro-1H-1,4,10-triazadibenzo[cd,f]azulen-11(10H)-one;

4-(4-methoxybenzoyl)-10-methyl-7-((methylsulfonyl)methyl)-3,4-dihydro-1H-1,4,10-triazadibenzo[cd,f]azulen-11(10H)-one;

methyl 4-(10-methyl-7-((methylsulfonyl)methyl)-11-oxo-10,11-dihydro-1H-1,4,10-triazadibenzo[cd,f]azulen-4(3H)-yl)-4-oxobutanoate;

4-(2,4-difluorobenzoyl)-10-methyl-7-((methylsulfonyl)methyl)-3,4-dihydro-1H-1,4,10-triazadibenzo[cd,f]azulen-11(10H)-one;

4-(2-fluorobenzoyl)-10-methyl-7-((methylsulfonyl)methyl)-3,4-dihydro-1H-1,4,10-triazadibenzo[cd,f]azulen-11(10H)-one;

4-(1-naphthoyl)-10-methyl-7-((methylsulfonyl)methyl)-3,4-dihydro-1H-1,4,10-triazadibenzo[cd,f]azulen-11(10H)-one;

4-(cyclopropanecarbonyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(3-phenylpropanoyl)-3,4-dihydro-1H-1,4,10-triazadibenzo[cd,f]azulen-11(10H)-one;

2-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)isoindoline-1,3-dione;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-methylpropanamide;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N,N-dimethylpropanamide;

4-(2,4-difluorophenyl)-10-methyl-7-((methylsulfonyl)methyl)-3-(3-morpholino-3-oxopropyl)-3,4-dihydro-1H-1,4,10-triazadibenzo[cd,f]azulen-11(10H)-one;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-(tetrahydro-2H-pyran-4-yl)propanamide;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N'-methyl-N'-phenylpropanehydrazide;

N-benzyl-3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanamide;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-(1,1-dioxidotetrahydrothiophen-3-yl)propanamide;

tert-butyl 4-(3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoyl)piperazine-1-carboxylate;

tert-butyl 4-(3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanamido)piperidine-1-carboxylate;

4-(4-chlorophenyl)-N-ethyl-10-methyl-11-oxo-3,4,10,11-tetrahydro-1H-1,4,10-triazadibenzo[cd,f]azulene-2-carboxamide;

6-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)hexyl acetate;

3-(aminomethyl)-4-(2,4-difluorophenyl)-10-methyl-7-((methylsulfonyl)methyl)-3,4-dihydro-1H-1,4,10-triazadibenzo[cd,f]azulen-11(10H)-one;

N-((((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)amino)(dimethylamino)methylene)-N-methylmethanaminium;

4-(2,4-difluorophenyl)-10-methyl-7-((methylsulfonyl)methyl)-3-(3-oxo-3-(piperazin-1-yl)propyl)-3,4-dihydro-1H-1,4,10-triazadibenzo[cd,f]azulen-11(10H)-one;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)-N-(piperidin-4-yl)propanamide;

4-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)butane-1,2-diyl diacetate;

methyl 5-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)pentanoate;

tert-butyl (2-(((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)amino)-2-oxoethyl)carbamate;

4-(2,4-difluorophenyl)-3-(6-hydroxyhexyl)-10-methyl-7-((methylsulfonyl)methyl)-3,4-dihydro-1H-1,4,10-triazadibenzo[cd,f]azulen-11(10H)-one;

N-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)benzamide;

1-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)-3-phenylurea;

2-amino-N-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)acetamide;

4-(2,4-difluorophenyl)-3-(3,4-dihydroxybutyl)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-3-(3-hydroxypropyl)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-3-(3-phenoxypropyl)-3,4-dihydro-1H-1,4,10-triazadibenzo[cd,f]azulen-11(10H)-one;

(S)-4-(2,4-difluorophenyl)-10-methyl-7-((methylsulfonyl)methyl)-3-(3-phenoxypropyl)-3,4-dihydro-1H-1,4,10-triazadibenzo[cd,f]azulen-11(10H)-one;

(R)-4-(2,4-difluorophenyl)-10-methyl-7-((methylsulfonyl)methyl)-3-(3-phenoxypropyl)-3,4-dihydro-1H-1,4,10-triazadibenzo[cd,f]azulen-11(10H)-one;

4-(4-chlorophenyl)-10-methyl-2-(4-methylpiperazin-1-yl)methyl)-3,4-dihydro-1H-1,4,10-triazadibenzo[cd,f]azulen-11(10H)-one;

4-(2,4-difluorophenyl)-3-(3-methoxypropyl)-10-methyl-7-((methylsulfonyl)methyl)-3,4-dihydro-1H-1,4,10-triazadibenzo[cd,f]azulen-11(10H)-one;

4-(2,4-difluorophenyl)-3-(3-ethoxypropyl)-10-methyl-7-((methylsulfonyl)methyl)-3,4-dihydro-1H-1,4,10-triazadibenzo[cd,f]azulen-11(10H)-one;

4-isobutyl-10-methyl-7-((methylsulfonyl)methyl)-3,4-dihydro-1H-1,4,10-triazadibenzo[cd,f]azulen-11(10H)-one;

4-((1-ethylpiperidin-3-yl)methyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(tetrahydro-2H-pyran-4-yl)-3,4-dihydro-1H-1,4,10-triazadibenzo[cd,f]azulen-11(10H)-one;

4-((2,2-dimethyltetrahydro-2H-pyran-4-yl)methyl)-10-methyl-7-((methylsulfonyl)methyl)-3,4-dihydro-1H-1,4,10-triazadibenzo[cd,f]azulen-11(10H)-one;

4-(4-ethoxybutan-2-yl)-10-methyl-7-((methylsulfonyl)methyl)-3,4-dihydro-1H-1,4,10-triazadibenzo[cd,f]azulen-11(10H)-one;

N-(2-cyanoethyl)-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

methyl 2-(4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamido)acetate;

4-(2,4-difluorophenyl)-10-methyl-7-((methylsulfonyl)methyl)-11-oxo-N-phenethyl-3,4,10,11-tetrahydro-1H-1,4,10-triazadibenzo[cd,f]azulene-3-carboxamide;

N-butyl-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

N-cyclohexyl-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

N-benzyl-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-10-methyl-7-((methylsulfonyl)methyl)-11-oxo-N-(3-phenylpropyl)-3,4,10,11-tetrahydro-1H-1,4,10-triazadibenzo[cd,f]azulene-3-carboxamide;

4-(2,4-difluorophenyl)-N-isobutyl-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-N-(2-hydroxyethyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-10-methyl-7-((methylsulfonyl)methyl)-N-(oxazol-4-ylmethyl)-11-oxo-3,4,10,11-tetrahydro-1H-1,4,10-triazadibenzo[cd,f]azulene-3-carboxamide;

N-(cyclopropylmethyl)-4-(2,4-difluorophenyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-N-(2-hydroxy-2-methylpropyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-N-(1-(hydroxymethyl)cyclopropyl)-10-methyl-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-10-methyl-N-(1-methylcyclopropyl)-7-((methylsulfonyl)methyl)-11-oxo-3,4,10,11-tetrahydro-1H-1,4,10-triazadibenzo[cd,f]azulene-3-carboxamide;

4-(2,4-difluorophenyl)-10-methyl-7-((methylsulfonyl)methyl)-11-oxo-N-(4-phenylbutyl)-3,4,10,11-tetrahydro-1H-1,4,10-triazadibenzo[cd,f]azulene-3-carboxamide;

4-(3,3-dimethylbutanoyl)-5,7-difluoro-10-methyl-3,4-dihydro-1H-1,4,10-triazadibenzo[cd,f]azulen-11(10H)-one;

tert-butyl ((trans)-4-(10-methyl-7-(methylsulfonyl)-11-oxo-10,11-dihydro-1H-1,4,10-triazadibenzo[cd,f]azulen-4(3H)-yl)cyclohexyl)carbamate;

4-((trans)-4-aminocyclohexyl)-10-methyl-7-(methylsulfonyl)-3,4-dihydro-1H-1,4,10-triazadibenzo[cd,f]azulen-11(10H)-one;

4-(cyclopropylsulfonyl)-10-methyl-7-((methylsulfonyl)methyl)-3,4-dihydro-1H-1,4,10-triazadibenzo[cd,f]azulen-11(10H)-one;

ethyl 5,7-difluoro-10-methyl-11-oxo-10,11-dihydro-1H-1,4,10-triazadibenzo[cd,f]azulene-4(3H)-carboxylate;

4-(2,4-difluorophenyl)-10-methyl-3-(3-(methylamino)propyl)-7-((methylsulfonyl)methyl)-3,4-dihydro-1H-1,4,10-triazadibenzo[cd,f]azulen-11(10H)-one;

4-(2,4-difluorophenyl)-3-(3-(dimethylamino)propyl)-10-methyl-7-((methylsulfonyl)methyl)-3,4-dihydro-1H-1,4,10-triazadibenzo[cd,f]azulen-11(10H)-one;

4-(4-chlorophenyl)-10-methyl-2-((4-methylpiperazin-1-yl)methyl)-7-((methylsulfonyl)methyl)-3,4-dihydro-1H-1,4,10-triazadibenzo[cd,f]azulen-11(10H)-one;

2-(4-(4-fluorophenyl)-10-methyl-11-oxo-3,4,10,11-tetrahydro-1H-1,4,10-triazadibenzo[cd,f]azulen-7-yl)acetonitrile;

4-(2,2-dimethyl-3-(pyrrolidin-1-yl)propyl)-10-methyl-7-((methylsulfonyl)methyl)-3,4-dihydro-1H-1,4,10-triazadibenzo[cd,f]azulen-11(10H)-one;

2-(3-(10-methyl-7-((methylsulfonyl)methyl)-11-oxo-10,11-dihydro-1H-1,4,10-triazadibenzo[cd,f]azulen-4(3H)-yl)pyrrolidin-1-yl)acetic acid;

10-methyl-7-((methylsulfonyl)methyl)-4-(2-methyltetrahydrofuran-3-yl)-3,4-dihydro-1H-1,4,10-triazadibenzo[cd,f]azulen-11(10H)-one;

10-methyl-4-(1-methylpiperidin-4-yl)-7-((methylsulfonyl)methyl)-3,4-dihydro-1H-1,4,10-triazadibenzo[cd,f]azulen-11(10H)-one;

10-methyl-7-((methylsulfonyl)methyl)-4-(tetrahydro-2H-pyran-3-yl)-3,4-dihydro-1H-1,4,10-triazadibenzo[cd,f]azulen-11(10H)-one;

4-((1-isopropylpiperidin-4-yl)methyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(1-(2-oxotetrahydrofuran-3-yl)ethyl)-3,4-dihydro-1H-1,4,10-triazadibenzo[cd,f]azulen-11(10H)-one;

4-(1-methoxypropan-2-yl)-10-methyl-7-((methylsulfonyl)methyl)-3,4-dihydro-1H-1,4,10-triazadibenzo[cd,f]azulen-11(10H)-one;

4-(4-methoxybutan-2-yl)-10-methyl-7-((methylsulfonyl)methyl)-3,4-dihydro-1H-1,4,10-triazadibenzo[cd,f]azulen-11(10H)-one;

10-methyl-4-(1-methylpyrrolidin-3-yl)-7-((methylsulfonyl)methyl)-3,4-dihydro-1H-1,4,10-triazadibenzo[cd,f]azulen-11(10H)-one;

10-methyl-7-((methylsulfonyl)methyl)-4-(1-(tetrahydro-2H-pyran-4-yl)ethyl)-3,4-dihydro-1H-1,4,10-triazadibenzo[cd,f]azulen-11(10H)-one;

10-methyl-4-(1-methylazepan-4-yl)-7-((methylsulfonyl)methyl)-3,4-dihydro-1H-1,4,10-triazadibenzo[cd,f]azulen-11(10H)-one;

4-(1-ethylpiperidin-3-yl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(2-(tetrahydro-2H-pyran-4-yl)ethyl)-3,4-dihydro-1H-1,4,10-triazadibenzo[cd,f]azulen-11(10H)-one;

4-(10-methyl-7-((methylsulfonyl)methyl)-11-oxo-10,11-dihydro-1H-1,4,10-triazadibenzo[cd,f]azulen-4(3H)-yl)benzonitrile;

4-(4-chlorophenyl)-10-methyl-7-((methylsulfonyl)methyl)-2-(morpholinomethyl)-3,4-dihydro-1H-1,4,10-triazadibenzo[cd,f]azulen-11(10H)-one;

N-ethyl-4-(4-fluorophenyl)-10-methyl-7-((methylsulfonyl)methyl)-11-oxo-3,4,10,11-tetrahydro-1H-1,4,10-triazadibenzo[cd,f]azulene-2-carboxamide;

5-cyclopropyl-4-(2,4-difluorophenyl)-10-methyl-7-((methylsulfonyl)methyl)-3,4-dihydro-1H-1,4,10-triazadibenzo[cd,f]azulen-11(10H)-one;

tert-butyl (4-(10-methyl-7-((methylsulfonyl)methyl)-11-oxo-10,11-dihydro-1H-1,4,10-triazadibenzo[cd,f]azulen-4(3H)-yl)cyclohexyl)carbamate;

tert-butyl ((trans)-4-(10-methyl-7-((methylsulfonyl)methyl)-11-oxo-10,11-dihydro-1H-1,4,10-triazadibenzo[cd,f]azulen-4(3H)-yl)cyclohexyl)carbamate;

4-(4-chlorophenyl)-10-methyl-7-((methylsulfonyl)methyl)-3,4-dihydro-1H-1,4,10-triazadibenzo[cd,f]azulen-11(10H)-one;

4-(4-chlorophenyl)-10-methyl-7-((methylsulfonyl)methyl)-11-oxo-3,4,10,11-tetrahydro-1H-1,4,10-triazadibenzo[cd,f]azulene-2-carbonitrile;

4-(2,4-difluorophenyl)-3-(hydroxymethyl)-10-methyl-7-((methylsulfonyl)methyl)-3,4-dihydro-1H-1,4,10-triazadibenzo[cd,f]azulen-11(10H)-one;

4-(4-chlorophenyl)-10-methyl-11-oxo-3,4,10,11-tetrahydro-1H-1,4,10-triazadibenzo[cd,f]azulene-2-carbonitrile;

4-(2,4-difluorophenyl)-N-ethyl-10-methyl-7-((methylsulfonyl)methyl)-11-oxo-3,4,10,11-tetrahydro-1H-1,4,10-triazadibenzo[cd,f]azulene-2-carboxamide;

4-(4-cyanophenyl)-N-ethyl-10-methyl-7-((methylsulfonyl)methyl)-11-oxo-3,4,10,11-tetrahydro-1H-1,4,10-triazadibenzo[cd,f]azulene-2-carboxamide;

(S)-2-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)isoindoline-1,3-dione;

(R)-2-((4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)methyl)isoindoline-1,3-dione;

4-(2,4-difluorophenyl)-10-methyl-7-((methylsulfonyl)methyl)-11-oxo-3,4,10,11-tetrahydro-1H-1,4,10-triazadibenzo[cd,f]azulene-5-carbonitrile;

10-methyl-7-((methylsulfonyl)methyl)-4-(pyridin-2-yl)-3,4-dihydro-1H-1,4,10-triazadibenzo[cd,f]azulen-11(10H)-one;

ethyl 4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxylate;

4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxamide;

4-(2,4-difluorophenyl)-10-methyl-7-((methylsulfonyl)methyl)-11-oxo-3,4,10,11-tetrahydro-1H-1,4,10-triazadibenzo[cd,f]azulene-2-carbonitrile;

10-methyl-7-((methylsulfonyl)methyl)-4-(3,4,5-trimethoxyphenyl)-3,4-dihydro-1H-1,4,10-triazadibenzo[cd,f]azulen-11(10H)-one;

4-(4-aminocyclohexyl)-10-methyl-7-((methylsulfonyl)methyl)-3,4-dihydro-1H-1,4,10-triazadibenzo[cd,f]azulen-11(10H)-one;

4-(3,5-difluoropyridin-2-yl)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-3-phenyl-3,4-dihydro-1H-1,4,10-triazadibenzo[cd,f]azulen-11(10H)-one;

(R)-4-(2,4-difluorophenyl)-10-methyl-7-((methylsulfonyl)methyl)-3-phenyl-3,4-dihydro-1H-1,4,10-triazadibenzo[cd,f]azulen-11(10H)-one;

(S)-4-(2,4-difluorophenyl)-10-methyl-7-((methylsulfonyl)methyl)-3-phenyl-3,4-dihydro-1H-1,4,10-triazadibenzo[cd,f]azulen-11(10H)-one;

4-(2,4-difluorophenyl)-10-methyl-7-((methylsulfonyl)methyl)-3-(naphthalen-1-yl)-3,4-dihydro-1H-1,4,10-triazadibenzo[cd,f]azulen-11(10H)-one;

4-(2,4-difluorophenyl)-(3,3-$^2$H$_2$)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-3-neopentyl-3,4-dihydro-1H-1,4,10-triazadibenzo[cd,f]azulen-11(10H)-one;

4-(2,4-difluorophenyl)-10-methyl-7-((methylsulfonyl)methyl)-3-((1-oxoisoindolin-2-yl)methyl)-3,4-dihydro-1H-1,4,10-triazadibenzo[cd,f]azulen-11(10H)-one;

4-(2,4-difluorophenyl)-3-(2,6-dimethoxyphenyl)-10-methyl-7-((methylsulfonyl)methyl)-3,4-dihydro-1H-1,4,10-triazadibenzo[cd,f]azulen-11(10H)-one;

4-(2,4-difluorophenyl)-3-(3,5-dimethoxyphenyl)-10-methyl-7-((methylsulfonyl)methyl)-3,4-dihydro-1H-1,4,10-triazadibenzo[cd,f]azulen-11(10H)-one;

3-(3,5-di-tert-butylphenyl)-4-(2,4-difluorophenyl)-10-methyl-7-((methylsulfonyl)methyl)-3,4-dihydro-1H-1,4,10-triazadibenzo[cd,f]azulen-11(10H)-one;

methyl (4-(10-methyl-7-((methylsulfonyl)methyl)-11-oxo-10,11-dihydro-1H-1,4,10-triazadibenzo[cd,f]azulen-4(3H)-yl)cyclohexyl)carbamate;

methyl ((trans)-4-(10-methyl-7-((methylsulfonyl)methyl)-11-oxo-10,11-dihydro-1H-1,4,10-triazadibenzo[cd,f]azulen-4(3H)-yl)cyclohexyl)carbamate;

methyl ((cis)-4-(10-methyl-7-((methylsulfonyl)methyl)-11-oxo-10,11-dihydro-1H-1,4,10-triazadibenzo[cd,f]azulen-4(3H)-yl)cyclohexyl)carbamate;

2-(2-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)ethyl)isoindoline-1,3-dione;

4-(2,4-difluorophenyl)-10-methyl-7-((methylsulfonyl)methyl)-3-(tetrahydro-2H-pyran-4-yl)-3,4-dihydro-1H-1,4,10-triazadibenzo[cd,f]azulen-11(10H)-one;

benzyl (2-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)ethyl)carbamate;

3-([1,1'-biphenyl]-2-yl)-4-(2,4-difluorophenyl)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-3-(quinolin-8-yl)-3,4-dihydro-1H-1,4,10-triazadibenzo[cd,f]azulen-11(10H)-one;

4-(2,4-difluorophenyl)-10-methyl-7-((methylsulfonyl)methyl)-3-(pyridin-2-yl)-3,4-dihydro-1H-1,4,10-triazadibenzo[cd,f]azulen-11(10H)-one;

3-(4-(1H-imidazol-1-yl)phenyl)-4-(2,4-difluorophenyl)-10-methyl-7-((methylsulfonyl)methyl)-3,4-dihydro-1H-1,4,10-triazadibenzo[cd,f]azulen-11(10H)-one;

4-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)benzonitrile;

4-(2,4-difluorophenyl)-10-methyl-7-((methylsulfonyl)methyl)-3-(3-(pyridin-2-yl)phenyl)-3,4-dihydro-1H-1,4,10-triazadibenzo[cd,f]azulen-11(10H)-one;

3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)benzonitrile;

4-(2,4-difluorophenyl)-10-methyl-7-((methylsulfonyl)methyl)-3-((2-oxopyridin-1(2H)-yl)methyl)-3,4-dihydro-1H-1,4,10-triazadibenzo[cd,f]azulen-11(10H)-one;

ethyl 4-(2,4-difluorophenyl)-2-(ethylcarbamoyl)-10-methyl-7-((methylsulfonyl)methyl)-11-oxo-3,4,10,11-tetrahydro-1H-1,4,10-triazadibenzo[cd,f]azulene-3-carboxylate;

4-(2,4-difluorophenyl)-10-methyl-7-((methylsulfonyl)methyl)-11-oxo-3,4,10,11-tetrahydro-1H-1,4,10-triazadibenzo[cd,f]azulene-5-carboxamide;

4-(2,4-difluorophenyl)-N,10-dimethyl-7-((methylsulfonyl)methyl)-11-oxo-3,4,10,11-tetrahydro-1H-1,4,10-triazadibenzo[cd,f]azulene-5-carboxamide;

4-(2,4-difluorophenyl)-N,N,10-trimethyl-7-((methylsulfonyl)methyl)-11-oxo-3,4,10,11-tetrahydro-1H-1,4,10-triazadibenzo[cd,f]azulene-5-carboxamide;

N-(4-(10-methyl-7-((methylsulfonyl)methyl)-11-oxo-10,11-dihydro-1H-1,4,10-triazadibenzo[cd,f]azulen-4(3H)-yl)cyclohexyl)acetamide;

10-methyl-7-((methylsulfonyl)methyl)-4-(pyridin-3-yl)-3,4-dihydro-1H-1,4,10-triazadibenzo[cd,f]azulen-11(10H)-one;

4-(5-chloropyridin-2-yl)-10-methyl-7-((methylsulfonyl)methyl)-3,4-dihydro-1H-1,4,10-triazadibenzo[cd,f]azulen-11(10H)-one;

4-(1H-indazol-5-yl)-10-methyl-7-((methylsulfonyl)methyl)-3,4-dihydro-1H-1,4,10-triazadibenzo[cd,f]azulen-11(10H)-one;

4-benzyl-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(pyrimidin-5-yl)-3,4-dihydro-1H-1,4,10-triazadibenzo[cd,f]azulen-11(10H)-one;

10-methyl-7-((methylsulfonyl)methyl)-4-(pyridin-2-ylmethyl)-3,4-dihydro-1H-1,4,10-triazadibenzo[cd,f]azulen-11(10H)-one;

10-methyl-7-((methylsulfonyl)methyl)-4-(pyridazin-3-ylmethyl)-3,4-dihydro-1H-1,4,10-triazadibenzo[cd,f]azulen-11(10H)-one;

(S)-4-(2,4-difluorophenyl)-10-methyl-7-((methylsulfonyl)methyl)-3-((2-oxopyridin-1(2H)-yl)methyl)-3,4-dihydro-1H-1,4,10-triazadibenzo[cd,f]azulen-11(10H)-one;

(R)-4-(2,4-difluorophenyl)-10-methyl-7-((methylsulfonyl)methyl)-3-((2-oxopyridin-1(2H)-yl)methyl)-3,4-dihydro-1H-1,4,10-triazadibenzo[cd,f]azulen-11(10H)-one;

10-methyl-7-((methylsulfonyl)methyl)-4-(5-(trifluoromethyl)pyridin-2-yl)-3,4-dihydro-1H-1,4,10-triazadibenzo[cd,f]azulen-11(10H)-one;

4-(2-fluoropyridin-4-yl)-10-methyl-7-((methylsulfonyl)methyl)-3,4-dihydro-1H-1,4,10-triazadibenzo[cd,f]azulen-11(10H)-one;

10-methyl-4-((1-methyl-1H-pyrazol-3-yl)methyl)-7-((methylsulfonyl)methyl)-3,4-dihydro-1H-1,4,10-triazadibenzo[cd,f]azulen-11(10H)-one;

4-(6-methoxypyridin-2-yl)-10-methyl-7-((methylsulfonyl)methyl)-3,4-dihydro-1H-1,4,10-triazadibenzo[cd,f]azulen-11(10H)-one;

4-(2,2-dimethyl-3-morpholinopropyl)-10-methyl-7-((methylsulfonyl)methyl)-3,4-dihydro-1H-1,4,10-triazadibenzo[cd,f]azulen-11(10H)-one;

4-(5-fluoropyrimidin-2-yl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(pyrimidin-4-yl)-3,4-dihydro-1H-1,4,10-triazadibenzo[cd,f]azulen-11(10H)-one;

4-(2-(3-(dimethylamino)propoxy)benzyl)-10-methyl-7-((methylsulfonyl)methyl)-3,4-dihydro-1H-1,4,10-triazadibenzo[cd,f]azulen-11(10H)-one;

2-(10-methyl-7-((methylsulfonyl)methyl)-11-oxo-10,11-dihydro-1H-1,4,10-triazadibenzo[cd,f]azulen-4(3H)-yl)-2-phenylacetonitrile;

2-(2-((10-methyl-7-((methylsulfonyl)methyl)-11-oxo-10,11-dihydro-1H-1,4,10-triazadibenzo[cd,f]azulen-4(3H)-yl)methyl)phenoxy)acetamide;

4-(2,4-difluorophenyl)-10-methyl-7-((methylsulfonyl)methyl)-11-oxo-3,4,10,11-tetrahydro-1H-1,4,10-triazadibenzo[cd,f]azulene-2-carboxylic acid;

10-methyl-7-((methylsulfonyl)methyl)-4-(2-(pyridin-2-ylmethoxy)benzyl)-3,4-dihydro-1H-1,4,10-triazadibenzo[cd,f]azulen-11(10H)-one;

(R)-7-(ethylsulfonyl)-10-methyl-4-(1-phenylethyl)-3,4-dihydro-1H-1,4,10-triazadibenzo[cd,f]azulen-11(10H)-one;

(S)-7-(ethylsulfonyl)-10-methyl-4-(1-phenylethyl)-3,4-dihydro-1H-1,4,10-triazadibenzo[cd,f]azulen-11(10H)-one;

(R)-methyl 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoate;

(S)-methyl 3-(4-(2,4-difluorophenyl)-10-methyl-7-((methylsulfonyl)methyl)-11-oxo-3,4,10,11-tetrahydro-1H-1,4,10-triazadibenzo[cd,f]azulen-3-yl)propanoate;

4-(2,4-difluorophenyl)-10-methyl-2-(1-methyl-1H-pyrazol-4-yl)-7-(methylsulfonyl)-3,4-dihydro-1H-1,4,10-triazadibenzo[cd,f]azulen-11(10H)-one;

4-(4-chlorophenyl)-10-methyl-2-(1-methyl-1H-pyrazol-4-yl)-7-(methylsulfonyl)-3,4-dihydro-1H-1,4,10-triazadibenzo[cd,f]azulen-11(10H)-one;

(R)—N-ethyl-7-(ethylsulfonyl)-10-methyl-11-oxo-4-(1-phenylpropyl)-3,4,10,11-tetrahydro-1H-1,4,10-triazadibenzo[cd,f]azulene-2-carboxamide;

10-methyl-2-(1-methyl-1H-pyrazol-4-yl)-7-((methylsulfonyl)methyl)-4-(pyridin-2-yl)-3,4-dihydro-1H-1,4,10-triazadibenzo[cd,f]azulen-11(10H)-one;

10-methyl-2-(1-methyl-1H-pyrazol-4-yl)-7-(methylsulfonyl)-4-phenyl-3,4-dihydro-1H-1,4,10-triazadibenzo[cd,f]azulen-11(10H)-one;

10-methyl-2-(1-methyl-1H-pyrazol-4-yl)-7-(methylsulfonyl)-4-(pyridin-2-yl)-3,4-dihydro-1H-1,4,10-triazadibenzo[cd,f]azulen-11(10H)-one; and 4-(4-fluorophenyl)-10-methyl-2-(1-methyl-1H-pyrazol-4-yl)-7-((methylsulfonyl)methyl)-3,4-dihydro-1H-1,4,10-triazadibenzo[cd,f]azulen-11(10H)-one.

29. The compound of claim 1, or a pharmaceutically acceptable salt thereof, wherein the compound is selected from the group consisting of:

4-(cyclopropylmethyl)-10-methyl-7-((methylsulfonyl)methyl)-3,4-dihydro-1H-1,4,10-triazadibenzo[cd,f]azulen-11(10H)-one;

4-(4-fluorophenyl)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-3,4-dihydro-1H-1,4,10-triazadibenzo[cd,f]azulen-11(10H)-one;

methyl 3-(4-(cyclopropylmethyl)-10-methyl-7-((methylsulfonyl)methyl)-11-oxo-3,4,10,11-tetrahydro-1H-1,4,10-triazadibenzo[cd,f]azulen-3-yl)propanoate;

4-(cyclopropylmethyl)-3-(2-methoxyethyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-((tetrahydrofuran-3-yl)methyl)-3,4-dihydro-1H-1,4,10-triazadibenzo[cd,f]azulen-11(10H)-one;

4-(4,4-difluorocyclohexyl)-10-methyl-7-((methylsulfonyl)methyl)-3,4-dihydro-1H-1,4,10-triazadibenzo[cd,f]azulen-11(10H)-one;

4-(4-fluorophenyl)-(3,3-$^2$H$_2$)-10-methyl-7-((methylsulfonyl)methyl)-3,4-dihydro-1H-1,4,10-triazadibenzo[cd,f]azulen-11(10H)-one;

5,7-difluoro-10-methyl-4-((tetrahydrofuran-3-yl)methyl)-3,4-dihydro-1H-1,4,10-triazadibenzo[cd,f]azulen-11(10H)-one;

5,7-difluoro-10-methyl-4-propyl-3,4-dihydro-1H-1,4,10-triazadibenzo[cd,f]azulen-11(10H)-one;

4-(4-chlorophenyl)-10-methyl-7-((methylsulfonyl)methyl)-11-oxo-3,4,10,11-tetrahydro-1H-1,4,10-triazadibenzo[cd,f]azulene-2-carboxamide;

4-(4-chlorophenyl)-N-ethyl-10-methyl-7-((methylsulfonyl)methyl)-11-oxo-3,4,10,11-tetrahydro-1H-1,4,10-triazadibenzo[cd,f]azulene-2-carboxamide;

10-methyl-7-((methylsulfonyl)methyl)-11-oxo-N-propyl-10,11-dihydro-1H-1,4,10-triazadibenzo[cd,f]azulene-4(3H)-carboxamide;

ethyl 10-methyl-7-((methylsulfonyl)methyl)-11-oxo-10,11-dihydro-1H-1,4,10-triazadibenzo[cd,f]azulene-4(3H)-carboxylate;

p-tolyl 10-methyl-7-((methylsulfonyl)methyl)-11-oxo-10,11-dihydro-1H-1,4,10-triazadibenzo[cd,f]azulene-4(3H)-carboxylate;

4-fluorophenyl 10-methyl-7-((methylsulfonyl)methyl)-11-oxo-10,11-dihydro-1H-1,4,10-triazadibenzo[cd,f]azulene-4(3H)-carboxylate; and 4-(3,3-dimethylbutanoyl)-10-methyl-7-((methylsulfonyl)methyl)-3,4-dihydro-1H-1,4,10-triazadibenzo[cd,f]azulen-11(10H)-one.

30. The compound of claim 1, or a pharmaceutically acceptable salt thereof, wherein the compound is selected from the group consisting of:

4-(4-fluorophenyl)-10-methyl-7-((methylsulfonyl)methyl)-3,4-dihydro-1H-1,4,10-triazadibenzo[cd,f]azulen-11(10H)-one;

4-(2,4-difluorophenyl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-((tetrahydrofuran-3-yl)methyl)-3,4-dihydro-1H-1,4,10-triazadibenzo[cd,f]azulen-11(10H)-one;

ethyl 5,7-difluoro-10-methyl-11-oxo-10,11-dihydro-1H-1,4,10-triazadibenzo[cd,f]azulene-4(3H)-carboxylate;

4-(4-chlorophenyl)-10-methyl-2-((4-methylpiperazin-1-yl)methyl)-7-((methylsulfonyl)methyl)-3,4-dihydro-1H-1,4,10-triazadibenzo[cd,f]azulen-11(10H)-one;

N-ethyl-4-(4-fluorophenyl)-10-methyl-7-((methylsulfonyl)methyl)-11-oxo-3,4,10,11-tetrahydro-1H-1,4,10-triazadibenzo[cd,f]azulene-2-carboxamide;

5-cyclopropyl-4-(2,4-difluorophenyl)-10-methyl-7-((methylsulfonyl)methyl)-3,4-dihydro-1H-1,4,10-triazadibenzo[cd,f]azulen-11(10H)-one;

tert-butyl (4-(10-methyl-7-((methylsulfonyl)methyl)-11-oxo-10,11-dihydro-1H-1,4,10-triazadibenzo[cd,f]azulen-4(3H)-yl)cyclohexyl)carbamate;

4-(4-chlorophenyl)-10-methyl-7-((methylsulfonyl)methyl)-3,4-dihydro-1H-1,4,10-triazadibenzo[cd,f]azulen-11(10H)-one;

4-(4-chlorophenyl)-10-methyl-7-((methylsulfonyl)methyl)-11-oxo-3,4,10,11-tetrahydro-1H-1,4,10-triazadibenzo[cd,f]azulene-2-carbonitrile;

4-(2,4-difluorophenyl)-N-ethyl-10-methyl-7-((methylsulfonyl)methyl)-11-oxo-3,4,10,11-tetrahydro-1H-1,4,10-triazadibenzo[cd,f]azulene-2-carboxamide;

4-(2,4-difluorophenyl)-10-methyl-7-((methylsulfonyl)methyl)-11-oxo-3,4,10,11-tetrahydro-1H-1,4,10-triazadibenzo[cd,f]azulene-5-carbonitrile;

10-methyl-7-((methylsulfonyl)methyl)-4-(pyridin-2-yl)-3,4-dihydro-1H-1,4,10-triazadibenzo[cd,f]azulen-11(10H)-one;

4-(3,5-difluoropyridin-2-yl)-10-methyl-7-((methylsulfonyl)methyl)-3,4-dihydro-1H-1,4,10-triazadibenzo[cd,f]azulen-11(10H)-one;

10-methyl-7-((methylsulfonyl)methyl)-4-(5-(trifluoromethyl)pyridin-2-yl)-3,4-dihydro-1H-1,4,10-triazadibenzo[cd,f]azulen-11(10H)-one;

4-(6-methoxypyridin-2-yl)-10-methyl-7-((methylsulfonyl)methyl)-3,4-dihydro-1H-1,4,10-triazadibenzo[cd,f]azulen-11(10H)-one; and 4-(4-chlorophenyl)-10-methyl-2-(1-methyl-1H-pyrazol-4-yl)-7-(methylsulfonyl)-3,4-dihydro-1H-1,4,10-triazadibenzo[cd,f]azulen-11(10H)-one.

31. The compound of claim 1, or a pharmaceutically acceptable sale thereof, wherein the compound is
4-(cyclopropylmethyl)-10-methyl-11-oxo-3,4,10,11-tetrahydro-1H-1,4,5,10-tetraazadibenzo[cd,f]azulene-7-sulfonamide;

4-(4-fluorophenyl)-7,10-dimethyl-3,4-dihydro-1H-1,4,5,10-tetraazadibenzo[cd,f]azulen-11(10H)-one;

7-amino-4-(4-fluorophenyl)-10-methyl-3,4-dihydro-1H-1,4,5,10-tetraazadibenzo[cd,f]azulen-11(10H)-one;

N-(4-(4-fluorophenyl)-10-methyl-11-oxo-3,4,10,11-tetrahydro-1H-1,4,5,10-tetraazadibenzo[cd,f]azulen-7-yl)ethanesulfonamide;

N-(4-(2,4-difluorophenyl)-10-methyl-11-oxo-3,4,10,11-tetrahydro-1H-1,4,5,10-tetraazadibenzo[cd,f]azulen-7-yl)ethanesulfonamide;

7-fluoro-4-(4-fluorophenyl)-10-methyl-3,4-dihydro-1H-1,4,5,10-tetraazadibenzo[cd,f]azulen-11(10H)-one;

4-(4-fluorophenyl)-7,10-dimethyl-3-phenyl-3,4-dihydro-1H-1,4,5,10-tetraazadibenzo[cd,f]azulen-11(10H)-one;

7-fluoro-10-methyl-3,4-dihydro-1H-1,4,5,10-tetraazadibenzo[cd,f]azulen-11(10H)-one;

ethyl 7-fluoro-10-methyl-11-oxo-3,4,10,11-tetrahydro-1H-1,4,5,10-tetraazadibenzo[cd,f]azulene-3-carboxylate;

ethyl 4-(4-fluorophenyl)-7,10-dimethyl-11-oxo-3,4,10,11-tetrahydro-1H-1,4,5,10-tetraazadibenzo[cd,f]azulene-3-carboxylate;

4-(2,4-difluorophenyl)-10-methyl-3,4-dihydro-1H-1,4,5,7,10-pentaazadibenzo[cd,f]azulen-11(10H)-one;

10-methyl-4-(pyridin-2-yl)-7-(pyrrolidin-1-ylsulfonyl)-3,4-dihydro-1H-1,4,5,10-tetraazadibenzo[cd,f]azulen-11(10H)-one;

N-(4-(4-fluorophenyl)-10-methyl-11-oxo-3,4,10,11-tetrahydro-1H-1,4,5,10-tetraazadibenzo[cd,f]azulen-7-yl)ethanesulfonamide;

N-(4-(2,4-difluorophenyl)-10-methyl-11-oxo-3,4,10,11-tetrahydro-1H-1,4,5,10-tetraazadibenzo[cd,f]azulen-7-yl)ethanesulfonamide;

7-fluoro-4-(4-fluorophenyl)-10-methyl-3,4-dihydro-1H-1,4,5,10-tetraazadibenzo[cd,f]azulen-11(10H)-one; and N-(4-(4-fluorophenyl)-10-methyl-11-oxo-3,4,10,11-tetrahydro-1H-1,4,5,10-tetraazadibenzo[cd,f]azulen-7-yl)ethanesulfonamide.

32. The compound of claim 1, or a pharmaceutically acceptable salt thereof, wherein the compound is selected from the group consisting of:
4-(4-fluorophenyl)-10-methyl-7-((methylsulfonyl)methyl)-3,4-dihydro-1H-1,4,10-triazadibenzo[cd,f]azulen-11(10H)-one; and 4-(2,4-difluorophenyl)-10-methyl-7-((methylsulfonyl)methyl)-3,4-dihydro-1H-1,4,10-triazadibenzo[cd,f]azulen-11(10H)-one.

33. The compound of claim 1, or a pharmaceutically acceptable sale thereof, wherein the compound is 4-(4-fluorophenyl)-10-methyl-7-((methylsulfonyl)methyl)-3,4-dihydro-1H-1,4,10-triazadibenzo[cd,f]azulen-11(10H)-one.

34. The compound of claim 1, or a pharmaceutically acceptable sale thereof, wherein the compound is 4-(2,4-difluorophenyl)-10-methyl-7-((methylsulfonyl)methyl)-3,4-dihydro-1H-1,4,10-triazadibenzo[cd,f]azulen-11(10H)-one.

35. A pharmaceutical composition comprising a therapeutically effective amount of a compound according to claim 1, or a pharmaceutically acceptable salt thereof, and a pharmaceutically acceptable carrier.

36. A pharmaceutical composition comprising a therapeutically effective amount of a compound according to claim 32, or a pharmaceutically acceptable salt thereof, and a pharmaceutically acceptable carrier.

37. A pharmaceutical composition comprising a therapeutically effective amount of a compound according to claim 33, or a pharmaceutically acceptable salt thereof, and a pharmaceutically acceptable carrier.

38. A pharmaceutical composition comprising a therapeutically effective amount of a compound according to claim 34, or a pharmaceutically acceptable salt thereof, and a pharmaceutically acceptable carrier.

39. A method for inhibiting bromodomain activity in a subject, comprising administering to a subject in need thereof, a therapeutically effective amount of a compound according to claim 1, or a pharmaceutically acceptable salt thereof.

40. The method of claim 39, wherein the subject suffers from a cancer selected from the group consisting of acoustic neuroma, acute leukemia, acute lymphocytic leukemia, acute myelocytic leukemia, acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, Hodgkin's lymphoma, non-Hodgkin's lymphoma; a malignancy of the bladder breast, colon, lung, ovaries, pancreas, prostate, skin and uterus; a hyperproliferative disorder of the bladder, breast, colon, lung, ovaries, pancreas, prostate, skin and uterus; a lymphoid malignancy of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, a solid tumor, small cell lung cancer, stomach cancer, squamous cell carcinoma, synovioma, sweat gland carcinoma, thyroid cancer, Waldenstrom's macroglobulinemia, a testicular tumor, uterine cancer and Wilms' tumor.

41. The method of claim 39, wherein the subject suffers from a disease or condition selected from the group consisting of Addison's disease, acute gout, ankylosing spondylitis, asthma, atherosclerosis, Behcet's disease, a bullous skin disease, cardiac myopathy, cardiac hypertrophy, chronic obstructive pulmonary disease, Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's arteritis, toxic shock, thyroiditis, type I diabetes, ulcerative colitis, uveitis, vitiligo, vasculitis and Wegener's granulomatosis.

42. The method of claim 39, wherein the subject suffers from a disease or condition selected from the group consisting of diabetic nephropathy, hypertensive nephropathy, human immunodeficiency virus-associated nephropathy, glomerulonephritis, lupus nephritis, immunoglobulin A nephropathy, focal segmental glomerulosclerosis, membranous glomerulonephritis, minimal change disease, polycystic kidney disease and tubular interstitial nephritis.

43. The method of claim 39, wherein the subject suffers from a disease or condition selected from the group consisting of ischemia-reperfusion induced kidney disease, cardiac induced kidney disease, cardiac major surgery induced kidney disease, percutaneous coronary intervention induced kidney disease, radio-contrast agent induced kidney disease, sepsis induced kidney disease, pneumonia induced kidney disease, and drug toxicity induced kidney disease.

44. The method of claim 39, wherein the subject suffers from acquired immunodeficiency syndrome.

45. The method of claim 39, wherein the subject suffers from a disease or condition selected from the group consisting of obesity, dyslipidemia, hypercholesterolemia, Alzheimer's disease, metabolic syndrome, hepatic steatosis, type II diabetes, insulin resistance, diabetic retinopathy and diabetic neuropathy.

46. A method for contraception in a male subject, comprising administering to a male subject in need thereof, a therapeutically effective amount of a compound according to claim 1, or a pharmaceutically acceptable salt thereof.

47. A compound of formula (I),

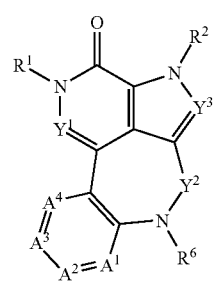

(I)

or a pharmaceutically acceptable salt thereof,
wherein:
  formula (I) is selected from the group consisting of:

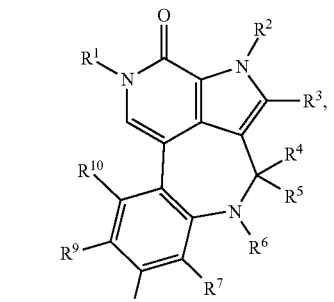

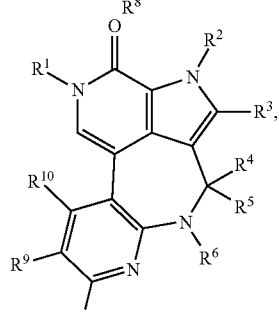

and

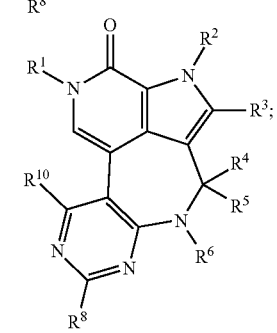

wherein:
  $R^1$ is $CD_3$, $C_1$-$C_3$ alkyl or $C_1$-$C_3$ haloalkyl;
  $R^2$ is H or $C_1$-$C_3$ alkyl;
  $R^3$ is H, $C_1$-$C_6$ alkyl, $C_2$-$C_6$ alkenyl, $C_2$-$C_6$ alkynyl, halogen, $C_1$-$C_6$ haloalkyl, $C(O)R^{3a}$, $C(O)OR^{3a}$, $C(O)NR^{3b}R^{3c}$, $S(O)R^{3d}$, $S(O)_2R^{3a}$, $S(O)_2NR^{3b}R^{3c}$ or $G^1$, wherein the $C_1$-$C_6$ alkyl, $C_2$-$C_6$ alkenyl and $C_2$-$C_6$ alkynyl are each optionally and independently substituted with one or two substituents independently selected from the group consisting of $G^1$, $C(O)R^{3a}$, $C(O)OR^{3a}$, $C(O)NR^{3b}R^{3c}$, $C(O)N(R^{3b})$ NR$^{3b}$R$^{3c}$, S(O)R$^{3d}$, S(O)$_2$R$^{3a}$, S(O)$_2$NR$^{3b}$R$^{3c}$, OR$^{3a}$, OC(O)R$^{3d}$, NR$^{3b}$R$^{3c}$, N(R$^{3b}$)C(O)R$^{3d}$, N(R$^{3b}$)S(O)$_2$R$^{3d}$, N(R$^{3b}$)C(O)OR$^{3d}$, N(R$^{3b}$)C(O)NR$^{3b}$R$^{3c}$, N(R$^{3b}$)S(O)$_2$NR$^{3b}$R$^{3c}$ and N(R$^{3b}$)C(NR$^{3b}$R$^{3c}$)=NR$^{3b}$R$^{3c}$;

R$^4$ is H, deuterium, C$_1$-C$_6$ alkyl, halogen or C$_1$-C$_6$ haloalkyl;

R$^5$ is H, deuterium, C$_1$-C$_6$ alkyl, C$_2$-C$_6$ alkenyl, C$_2$-C$_6$ alkynyl, halogen, C$_1$-C$_6$ haloalkyl, C(O)R$^{5a}$, C(O)OR$^{5a}$, C(O)NR$^{5b}$R$^{5c}$, S(O)R$^{5d}$, S(O)$_2$R$^{5a}$, S(O)$_2$NR$^{5b}$R$^{5c}$ or G$^1$, wherein the C$_1$-C$_6$ alkyl, C$_2$-C$_6$ alkenyl and C$_2$-C$_6$ alkynyl are each optionally and independently substituted with one or two substituents independently selected from the group consisting of G$^1$, C(O)R$^{5a}$, C(O)OR$^{5a}$, C(O)NR$^{5b}$R$^{5c}$, C(O)N(R$^{5b}$)NR$^{5b}$R$^{5c}$, S(O)R$^{5d}$, S(O)$_2$R$^{5a}$, S(O)$_2$NR$^{5b}$R$^{5c}$, OR$^{5a}$, OC(O)R$^{5d}$, NR$^{5b}$R$^{5c}$, N(R$^{5b}$)C(O)R$^{5d}$, N(R$^{5b}$)S(O)$_2$R$^{5d}$, N(R$^{5b}$)C(O)OR$^{5d}$, N(R$^{5b}$)C(O)NR$^{5b}$R$^{5c}$, N(R$^{5b}$)S(O)$_2$NR$^{5b}$R$^{5c}$ and N(R$^{5b}$)C(NR$^{5b}$R$^{5c}$)=NR$^{5b}$R$^{5c}$;

R$^{3a}$, R$^{3b}$, R$^{3c}$, R$^{5a}$, R$^{5b}$ and R$^{5c}$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^1$ or (C$_1$-C$_6$ alkylenyl)-G$^1$;

R$^{3d}$ and R$^{5d}$, at each occurrence, are each independently C$_1$-C$_6$ alkyl, C$_2$-C$_6$ alkenyl, C$_2$-C$_6$ alkynyl, C$_1$-C$_6$ haloalkyl, G$^1$ or (C$_1$-C$_6$ alkylenyl)-G$^1$;

G$^1$, at each occurrence, is independently aryl, heteroaryl, heterocyclyl, cycloalkyl or cycloalkenyl, wherein each G$^1$ is optionally substituted with one, two, three, four or five R$^{1g}$ groups;

R$^6$ is H, C$_1$-C$_6$ alkyl, C$_2$-C$_6$ alkenyl, C$_2$-C$_6$ alkynyl, halogen, C$_1$-C$_6$ haloalkyl, C(O)R$^{6a}$, C(O)OR$^{6a}$, C(O)NR$^{6b}$R$^{6c}$, S(O)$_2$R$^{6a}$, S(O)$_2$NR$^{6b}$R$^{6c}$ or G$^2$, wherein the C$_1$-C$_6$ alkyl, C$_2$-C$_6$ alkenyl, and C$_2$-C$_6$ alkynyl are each optionally and independently substituted with one or two substituents independently selected from the group consisting of G$^2$, C(O)R$^{6a}$, C(O)OR$^{6a}$, C(O)NR$^{6b}$R$^{6c}$, C(O)N(R$^{6b}$)NR$^{6b}$R$^{6c}$, S(O)R$^{6d}$, S(O)$_2$R$^{6a}$, S(O)$_2$NR$^{6b}$R$^{6c}$, OR$^{6a}$, OC(O)R$^{6d}$, NR$^{6b}$R$^{6c}$, N(R$^{6b}$)C(O)R$^{6d}$, N(R$^{6b}$)S(O)$_2$R$^{6d}$, N(R$^{6b}$)C(O)OR$^{6d}$, N(R$^{6b}$)C(O)NR$^{6b}$R$^{6c}$, N(R$^{6b}$)S(O)$_2$NR$^{6b}$R$^{6c}$ and N(R$^{6b}$)C(NR$^{6b}$R$^{6c}$)=NR$^{6b}$R$^{6c}$;

R$^{6a}$, R$^{6b}$ and R$^{6c}$, at each occurrence, are each independently H, alkyl, C$_2$-C$_6$ alkenyl, C$_2$-C$_6$ alkynyl, haloalkyl, G$^2$, (C$_1$-C$_6$ alkylenyl)-G$^2$, (C$_1$-C$_6$ alkylenyl)-OR$^a$, (C$_1$-C$_6$ alkylenyl)-S(O)$_2$R$^a$, (C$_1$-C$_6$ alkylenyl)-S(O)$_2$NR$^c$R$^d$, (C$_1$-C$_6$ alkylenyl)-C(O)R$^a$, (C$_1$-C$_6$ alkylenyl)-C(O)OR$^a$, (C$_1$-C$_6$ alkylenyl)-C(O)NR$^c$R$^d$, (C$_1$-C$_6$ alkylenyl)-NR$^c$R$^d$, (C$_1$-C$_6$ alkylenyl)-N(R$^e$)C(O)R$^b$, (C$_1$-C$_6$ alkylenyl)-N(R$^e$)S(O)$_2$R$^b$, (C$_1$-C$_6$ alkylenyl)-N(R$^e$)C(O)O(R$^b$), (C$_1$-C$_6$ alkylenyl)-N(R$^e$)C(O)NR$^c$R$^d$ or (C$_1$-C$_6$ alkylenyl)-N(R$^e$)S(O)$_2$NR$^c$R$^d$;

R$^{6d}$, at each occurrence, is independently alkyl, C$_2$-C$_6$ alkenyl, C$_2$-C$_6$ alkynyl, haloalkyl, G$^2$, (C$_1$-C$_6$ alkylenyl)-G$^2$, (C$_1$-C$_6$ alkylenyl)-OR$^a$, (C$_1$-C$_6$ alkylenyl)-S(O)$_2$R$^a$, (C$_1$-C$_6$ alkylenyl)-S(O)$_2$NR$^c$R$^d$, (C$_1$-C$_6$ alkylenyl-C(O)R$^a$, (C$_1$-C$_6$ alkylenyl)-C(O)OR$^a$, (C$_1$-C$_6$ alkylenyl)-C(O)NR$^c$R$^d$, (C$_1$-C$_6$ alkylenyl)-NR$^c$R$^d$, (C$_1$-C$_6$ alkylenyl)-N(R$^e$)C(O)R$^b$, (C$_1$-C$_6$ alkylenyl)-N(R$^e$)S(O)$_2$R$^b$, (C$_1$-C$_6$ alkylenyl)-N(R$^e$)C(O)O(R$^b$), (C$_1$-C$_6$ alkylenyl)-N(R$^e$)C(O)NR$^c$R$^d$ or (C$_1$-C$_6$ alkylenyl)-N(R$^e$)S(O)$_2$NR$^c$R$^d$;

G$^2$, at each occurrence, is independently aryl, heteroaryl, heterocyclyl, cycloalkyl or cycloalkenyl, wherein each G$^2$ is optionally substituted with one, two, three, four or five R$^{2g}$ groups;

R$^7$, R$^8$ and R$^9$ are each independently H, C$_1$-C$_6$ alkyl, C$_2$-C$_6$ alkenyl, C$_2$-C$_6$ alkynyl, halogen, C$_1$-C$_6$ haloalkyl, CN, NO$_2$, OR$^{y1}$, OC(O)R$^{y2}$, OC(O)NR$^{y3}$R$^{y4}$, SR$^{y1}$, S(O)$_2$R$^{y1}$, S(O)$_2$NR$^{y3}$R$^{y4}$, C(O)R$^{y1}$, C(O)OR$^{y1}$, C(O)NR$^{y3}$R$^{y4}$, NR$^{y3}$R$^{y4}$, N(R$^{y3}$)C(O)R$^{y2}$, N(R$^{y3}$)S(O)$_2$R$^{y2}$, N(R$^{y3}$)C(O)O(R$^{y2}$), N(R$^{y3}$)C(O)NR$^{y3}$R$^{y4}$, N(R$^{y3}$)S(O)$_2$NR$^{y3}$R$^{y4}$, G$^3$, (C$_1$-C$_6$ alkylenyl)-CN, (C$_1$-C$_6$ alkylenyl)-OR$^{y1}$, (C$_1$-C$_6$ alkylenyl)-OC(O)R$^{y2}$, (C$_1$-C$_6$ alkylenyl)-OC(O)NR$^{y3}$R$^{y4}$, (C$_1$-C$_6$ alkylenyl)-S(O)$_2$R$^{y1}$, (C$_1$-C$_6$ alkylenyl)-S(O)$_2$NR$^{y3}$R$^{y4}$, (C$_1$-C$_6$ alkylenyl)-C(O)R$^{y1}$, (C$_1$-C$_6$ alkylenyl)-C(O)OR$^{y1}$, (C$_1$-C$_6$ alkylenyl)-C(O)NR$^{y3}$R$^{y4}$, (C$_1$-C$_6$ alkylenyl)-NR$^{y3}$R$^{y4}$, (C$_1$-C$_6$ alkylenyl)-N(R$^{y3}$)C(O)R$^{y2}$, (C$_1$-C$_6$ alkylenyl)-N(R$^{y3}$)S(O)$_2$R$^{y2}$, (C$_1$-C$_6$ alkylenyl)-N(R$^{y3}$)C(O)O(R$^{y2}$), (C$_1$-C$_6$ alkylenyl)-N(R$^{y3}$)C(O)NR$^{y3}$R$^{y4}$, (C$_1$-C$_6$ alkylenyl)-N(R$^{y3}$)S(O)$_2$NR$^{y3}$R$^{y4}$, (C$_1$-C$_6$ alkylenyl)-CN or (C$_1$-C$_6$ alkylenyl)-G$^3$;

R$^{y1}$, R$^{y3}$ and R$^{y4}$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^3$, (C$_1$-C$_6$ alkylenyl)-G$^3$, (C$_1$-C$_6$ alkylenyl)-OR$^a$, (C$_1$-C$_6$ alkylenyl)-S(O)$_2$R$^a$, (C$_1$-C$_6$ alkylenyl)-S(O)$_2$NR$^c$R$^d$, (C$_1$-C$_6$ alkylenyl)-C(O)R$^a$, (C$_1$-C$_6$ alkylenyl)-C(O)OR$^a$, (C$_1$-C$_6$ alkylenyl)-C(O)NR$^c$R$^d$, (C$_1$-C$_6$ alkylenyl)-NR$^c$R$^d$, (C$_1$-C$_6$ alkylenyl)-N(R$^e$)C(O)R$^b$, (C$_1$-C$_6$ alkylenyl)-N(R$^e$)S(O)$_2$R$^b$, (C$_1$-C$_6$ alkylenyl)-N(R$^e$)C(O)O(R$^b$), (C$_1$-C$_6$ alkylenyl)-N(R$^e$)C(O)NR$^c$R$^d$ or (C$_1$-C$_6$ alkylenyl)-N(R$^e$)S(O)$_2$NR$^c$R$^d$;

R$^{y2}$, at each occurrence, is independently C$_1$-C$_6$ alkyl, C$_2$-C$_6$ alkenyl, C$_2$-C$_6$ alkynyl, C$_1$-C$_6$ haloalkyl, G$^3$, (C$_1$-C$_6$ alkylenyl)-G$^3$, (C$_1$-C$_6$ alkylenyl)-OR$^a$, (C$_1$-C$_6$ alkylenyl)-S(O)$_2$R$^a$, (C$_1$-C$_6$ alkylenyl)-S(O)$_2$NR$^c$R$^d$, (C$_1$-C$_6$ alkylenyl)-C(O)R$^a$, (C$_1$-C$_6$ alkylenyl)-C(O)OR$^a$, (C$_1$-C$_6$ alkylenyl)-C(O)NR$^c$R$^d$, (C$_1$-C$_6$ alkylenyl)-NR$^c$R$^d$, (C$_1$-C$_6$ alkylenyl)-N(R$^e$)C(O)R$^b$, (C$_1$-C$_6$ alkylenyl)-N(R$^e$)S(O)$_2$R$^b$, (C$_1$-C$_6$ alkylenyl)-N(R$^e$)C(O)O(R$^b$), (C$_1$-C$_6$ alkylenyl)-N(R$^e$)C(O)NR$^c$R$^d$ or (C$_1$-C$_6$ alkylenyl)-N(R$^e$)S(O)$_2$NR$^c$R$^d$;

G$^3$, at each occurrence, is independently aryl, heteroaryl, heterocyclyl, cycloalkyl or cycloalkenyl, wherein each G$^3$ group is optionally substituted with one, two, three, four or five R$^{4g}$ groups;

R$^{10}$ is H, C$_1$-C$_3$ alkyl, halogen, C$_1$-C$_3$ haloalkyl or CN;

R$^{2g}$ and R$^{4g}$, at each occurrence, is independently selected from the group consisting of oxo, C$_1$-C$_6$ alkyl, C$_2$-C$_6$ alkenyl, C$_2$-C$_6$ alkynyl, halogen, C$_1$-C$_6$ haloalkyl, CN, NO$_2$, G$^{2a}$, OR$^a$, OC(O)R$^b$, OC(O)NR$^c$R$^d$, SR$^a$, S(O)$_2$R$^a$, S(O)$_2$NR$^c$R$^d$, C(O)R$^a$, C(O)OR$^a$, C(O)NR$^c$R$^d$, NR$^c$R$^d$, N(R$^e$)C(O)R$^b$, N(R$^e$)S(O)$_2$R$^b$, N(R$^e$)C(O)O(R$^b$), N(R$^e$)C(O)NR$^c$R$^d$, N(R$^e$)S(O)$_2$NR$^c$R$^d$, (C$_1$-C$_6$ alkylenyl)-CN, (C$_1$-C$_6$ alkylenyl)-G$^{2a}$, (C$_1$-C$_6$ alkylenyl)-OR$^a$, (C$_1$-C$_6$ alkylenyl)-OC(O)R$^b$, (C$_1$-C$_6$ alkylenyl)-OC(O)NR$^c$R$^d$, (C$_1$-C$_6$ alkylenyl)-S(O)$_2$R$^a$, (C$_1$-C$_6$ alkylenyl)-S(O)$_2$NR$^c$R$^d$, (C$_1$-C$_6$ alkylenyl)-C(O)R$^a$, (C$_1$-C$_6$ alkylenyl)-C(O)OR$^a$, (C$_1$-C$_6$ alkylenyl)-C(O)NR$^c$R$^d$, (C$_1$-C$_6$ alkylenyl)-NR$^c$R$^d$, (C$_1$-C$_6$ alkylenyl)-N(R$^e$)C(O)R$^b$, (C$_1$-C$_6$ alkylenyl)-N(R$^e$)S(O)$_2$R$^b$, (C$_1$-C$_6$ alkylenyl)-N(R$^e$)C(O)O(R$^b$), (C$_1$-C$_6$ alkylenyl)-N(R$^e$)C(O)NR$^c$R$^d$, (C$_1$-C$_6$ alkylenyl)-N(R$^e$)S(O)$_2$NR$^c$R$^d$ or (C$_1$-C$_6$ alkylenyl)-CN;

R$^a$, R$^c$, R$^d$ and R$^e$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^{2a}$, (C$_1$-C$_6$ alkylenyl)-OR$^{z1}$, (C$_1$-C$_6$ alkylenyl)-NR$^{z3}$R$^{z4}$, (C$_1$-C$_6$ alkylenyl)-C(O)NR$^{z3}$R$^{z4}$ or (C$_1$-C$_6$ alkylenyl)-G$^{2a}$;

R$^b$, at each occurrence, is independently C$_1$-C$_6$ alkyl, C$_2$-C$_6$ alkenyl, C$_2$-C$_6$ alkynyl, C$_1$-C$_6$ haloalkyl, G$^{2a}$ or (C$_1$-C$_6$ alkylenyl)-G$^{2a}$;

G$^{2a}$, at each occurrence, is independently aryl, heteroaryl, heterocyclyl, cycloalkyl or cycloalkenyl, wherein each G$^{2a}$ group is optionally substituted with one, two, three, four or five R$^{3g}$ groups;

R$^{3g}$, at each occurrence, is independently oxo, C$_1$-C$_6$ alkyl, C$_2$-C$_6$ alkenyl, C$_2$-C$_6$ alkynyl, halogen, C$_1$-C$_6$ haloalkyl, CN, NO$_2$, OR$^{z1}$, OC(O)R$^{z2}$, OC(O)NR$^{z3}$R$^{z4}$, SR$^{z1}$, S(O)$_2$R$^{z1}$, S(O)$_2$NR$^{z3}$R$^{z4}$, C(O)R$^{z1}$, C(O)OR$^{z1}$, C(O)NR$^{z3}$R$^{z4}$, NR$^{z3}$R$^{z4}$, N(R$^{z3}$)C(O)R$^{z2}$, N(R$^{z3}$)S(O)$_2$R$^{z2}$, N(R$^{z3}$)C(O)O(R$^{z2}$), N(R$^{z3}$)C(O)NR$^{z3}$R$^{z4}$, N(R$^{z3}$)S(O)$_2$NR$^{z3}$R$^{z4}$, (C$_1$-C$_6$ alkylenyl)-OR$^{z1}$, (C$_1$-C$_6$ alkylenyl)-OC(O)R$^{z2}$, (C$_1$-C$_6$ alkylenyl)-OC(O)NR$^{z3}$R$^{z4}$, (C$_1$-C$_6$ alkylenyl)-S(O)$_2$R$^{z1}$, (C$_1$-C$_6$ alkylenyl)-S(O)$_2$NR$^{z3}$R$^{z4}$, (C$_1$-C$_6$ alkylenyl)-C(O)R$^{z1}$, (C$_1$-C$_6$ alkylenyl)-C(O)OR$^{z1}$, (C$_1$-C$_6$ alkylenyl)-C(O)NR$^{z3}$R$^{z4}$, (C$_1$-C$_6$ alkylenyl)-NR$^{z3}$R$^{z4}$, (C$_1$-C$_6$ alkylenyl)-N(R$^{z3}$)C(O)R$^{z2}$, (C$_1$-C$_6$ alkylenyl)-N(R$^{z3}$)S(O)$_2$R$^{z2}$, (C$_1$-C$_6$ alkylenyl)-N(R$^{z3}$)C(O)O(R$^{z2}$), (C$_1$-C$_6$ alkylenyl)-N(R$^{z3}$)C(O)NR$^{z3}$R$^{z4}$, (C$_1$-C$_6$ alkylenyl)-N(R$^{z3}$)S(O)$_2$NR$^{z3}$R$^{z4}$ or (C$_1$-C$_6$ alkylenyl)-CN;

R$^{z1}$, R$^{z3}$ and R$^{z4}$, at each occurrence, are each independently H, C$_1$-C$_6$ alkyl, C$_2$-C$_6$ alkenyl, C$_2$-C$_6$ alkynyl or C$_1$-C$_6$ haloalkyl; and R$^{z2}$, at each occurrence, is independently C$_1$-C$_6$ alkyl, C$_2$-C$_6$ alkenyl, C$_2$-C$_6$ alkynyl or C$_1$-C$_6$ haloalkyl.

48. A compound of formula (I),

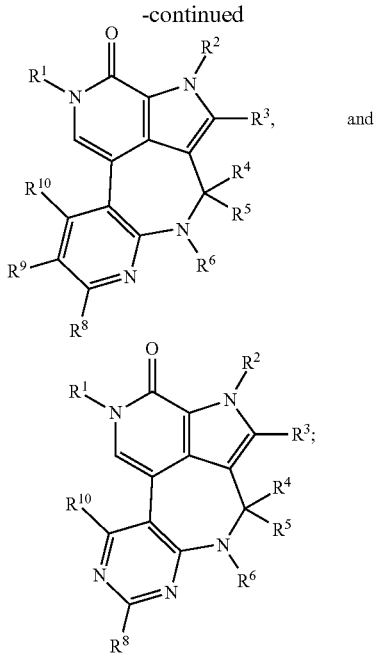

(I)

or a pharmaceutically acceptable salt thereof, wherein:

formula (I) is selected from the group consisting of:

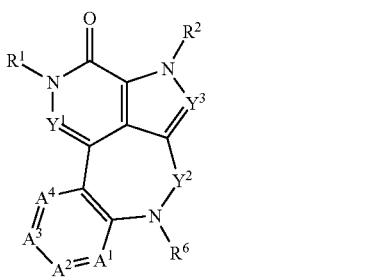

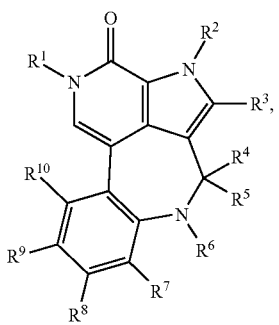

wherein:

R$^1$ is CD$_3$, C$_1$-C$_3$ alkyl or C$_1$-C$_3$ haloalkyl;

R$^2$ is H or C$_1$-C$_3$ alkyl;

R$^3$ is H, C$_1$-C$_6$ alkyl, C$_2$-C$_6$ alkenyl, C$_2$-C$_6$ alkynyl, halogen, C$_1$-C$_6$ haloalkyl, CN, C(O)R$^{3a}$, C(O)OR$^{3a}$, C(O)NR$^{3b}$R$^{3c}$, S(O)R$^{3d}$, S(O)$_2$R$^{3a}$, S(O)$_2$NR$^{3b}$R$^{3c}$ or G$^1$, wherein the C$_1$-C$_6$ alkyl, C$_2$-C$_6$ alkenyl and C$_2$-C$_6$ alkynyl are each optionally and independently substituted with one or two substituents independently selected from the group consisting of G$^1$, CN, C(O)R$^{3a}$, C(O)OR$^{3a}$, C(O)NR$^{3b}$R$^{3c}$, C(O)N(R$^{3b}$)NR$^{3b}$R$^{3c}$, S(O)R$^{3d}$, S(O)$_2$R$^{3a}$, S(O)$_2$NR$^{3b}$R$^{3c}$, OR$^{3a}$, OC(O)R$^{3d}$, NR$^{3b}$R$^{3c}$, N(R$^{3b}$)C(O)R$^{3d}$, N(R$^{3b}$)S(O)$_2$R$^{3d}$, N(R$^{3b}$)C(O)OR$^{3d}$, N(R$^{3b}$)C(O)NR$^{3b}$R$^{3c}$, N(R$^{3b}$)S(O)$_2$NR$^{3b}$R$^{3c}$ and N(R$^{3b}$)C(NR$^{3b}$R$^{3c}$)=NR$^{3b}$R$^{3c}$;

R$^4$ is H, deuterium, C$_1$-C$_6$ alkyl, halogen or C$_1$-C$_6$ haloalkyl;

R$^5$ is H, deuterium, C$_1$-C$_6$ alkyl, C$_2$-C$_6$ alkenyl, C$_2$-C$_6$ alkynyl, halogen, C$_1$-C$_6$ haloalkyl, C(O)R$^{5a}$, C(O)OR$^{5a}$, C(O)NR$^{5b}$R$^{5c}$, S(O)R$^{5d}$, S(O)$_2$R$^{5a}$, S(O)$_2$NR$^{5b}$R$^{5c}$ or G$^1$, wherein the C$_1$-C$_6$ alkyl, C$_2$-C$_6$ alkenyl and C$_2$-C$_6$ alkynyl are each optionally and independently substituted with one or two substituents independently selected from the group consisting of G$^1$, C(O)R$^{5a}$, C(O)OR$^{5a}$, C(O)NR$^{5b}$R$^{5c}$, C(O)N(R$^{5b}$)NR$^{5b}$R$^{5c}$, S(O)R$^{5d}$, S(O)$_2$R$^{5a}$, S(O)$_2$NR$^{5b}$R$^{5c}$, OR$^{5a}$, OC(O)R$^{5d}$, NR$^{5b}$R$^{5c}$, N(R$^{5b}$)C(O)R$^{5d}$, N(R$^{5b}$)S(O)$_2$R$^{5d}$, N(R$^{5b}$)C(O)OR$^{5d}$, N(R$^{5b}$)C(O)NR$^{5b}$R$^{5c}$, N(R$^{5b}$)S(O)$_2$NR$^{5b}$R$^{5c}$ and N(R$^{5b}$)C(NR$^{5b}$R$^{5c}$)=NR$^{5b}$R$^{5c}$;

R$^{3a}$, R$^{3b}$, R$^{3c}$, R$^{5a}$ and R$^{5b}$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^1$ or (C$_1$-C$_6$ alkylenyl)-G$^1$;

R$^{5c}$, at each occurrence, is independently H, C$_1$-C$_6$ alkyl, C$_2$-C$_6$ alkenyl, C$_2$-C$_6$ alkynyl, C$_1$-C$_6$ haloalkyl, G$^1$, (C$_1$-C$_6$ alkylenyl)-G$^1$, (C$_1$-C$_6$ alkylenyl)-CN, (C$_1$-C$_6$ alkylenyl)-OR$^a$ or (C$_1$-C$_6$ alkylenyl)-C(O)OR$^a$;

$R^{3d}$, at each occurrence, is independently $C_1$-$C_6$ alkyl, $C_2$-$C_6$ alkenyl, $C_2$-$C_6$ alkynyl, $C_1$-$C_6$ haloalkyl, $G^1$ or ($C_1$-$C_6$ alkylenyl)-$G^1$;

$R^{5d}$, at each occurrence, is independently $C_1$-$C_6$ alkyl, $C_2$-$C_6$ alkenyl, $C_2$-$C_6$ alkynyl, $C_1$-$C_6$ haloalkyl, $G^1$, ($C_1$-$C_6$ alkylenyl)-$G^1$, ($C_1$-$C_6$ alkylenyl)-$NR^cR^d$ or ($C_1$-$C_6$ alkylenyl)-$N(R^e)C(O)O(R^b)$;

$G^1$, at each occurrence, is independently aryl, heteroaryl, heterocyclyl, cycloalkyl or cycloalkenyl, wherein each $G^1$ is optionally substituted with one, two, three, four or five $R^{1g}$ groups;

$R^6$ is H, $C_1$-$C_6$ alkyl, $C_2$-$C_6$ alkenyl, $C_2$-$C_6$ alkynyl, halogen, $C_1$-$C_6$ haloalkyl, $C(O)R^{6a}$, $C(O)OR^{6a}$, $C(O)NR^{6b}R^{6c}$, $S(O)_2R^{6a}$, $S(O)_2NR^{6b}R^{6c}$ or $G^2$, wherein the $C_1$-$C_6$ alkyl, $C_2$-$C_6$ alkenyl, and $C_2$-$C_6$ alkynyl are each optionally and independently substituted with one or two substituents independently selected from the group consisting of $G^2$, $C(O)R^{6a}$, $C(O)OR^{6a}$, $C(O)NR^{6b}R^{6c}$, $C(O)N(R^{6b})NR^{6b}R^{6c}$, $S(O)R^{6d}$, $S(O)_2R^{6a}$, $S(O)_2NR^{6b}R^{6c}$, $OR^{6a}$, $OC(O)R^{6d}$, $NR^{6b}R^{6c}$, $N(R^{6b})C(O)R^{6d}$, $N(R^{6b})S(O)_2R^{6d}$, $N(R^{6b})C(O)OR^{6d}$, $N(R^{6b})C(O)NR^{6b}R^{6c}$, $N(R^{6b})S(O)_2NR^{6b}R^{6c}$ and $N(R^{6b})C(NR^{6b}R^{6c})=NR^{6b}R^{6c}$;

$R^{6a}$, $R^{6b}$ and $R^{6c}$, at each occurrence, are each independently H, alkyl, $C_2$-$C_6$ alkenyl, $C_2$-$C_6$ alkynyl, haloalkyl, $G^2$, ($C_1$-$C_6$ alkylenyl)-$G^2$, ($C_1$-$C_6$ alkylenyl)-$OR^a$, ($C_1$-$C_6$ alkylenyl)-$S(O)_2R^a$, ($C_1$-$C_6$ alkylenyl)-$S(O)_2NR^cR^d$, ($C_1$-$C_6$ alkylenyl)-$C(O)R^a$, ($C_1$-$C_6$ alkylenyl)-$C(O)OR^a$, ($C_1$-$C_6$ alkylenyl)-$C(O)NR^cR^d$, ($C_1$-$C_6$ alkylenyl)-$NR^cR^d$, ($C_1$-$C_6$ alkylenyl)-$N(R^e)C(O)R^b$, ($C_1$-$C_6$ alkylenyl)-$N(R^e)S(O)_2R^b$, ($C_1$-$C_6$ alkylenyl)-$N(R^e)C(O)O(R^b)$, ($C_1$-$C_6$ alkylenyl)-$N(R^e)C(O)NR^cR^d$ or ($C_1$-$C_6$ alkylenyl)-$N(R^e)S(O)_2NR^cR^d$;

$R^{6d}$, at each occurrence, is independently alkyl, $C_2$-$C_6$ alkenyl, $C_2$-$C_6$ alkynyl, haloalkyl, $G^2$, ($C_1$-$C_6$ alkylenyl)-$G^2$, ($C_1$-$C_6$ alkylenyl)-$OR^a$, ($C_1$-$C_6$ alkylenyl)-$S(O)_2R^a$, ($C_1$-$C_6$ alkylenyl)-$S(O)_2NR^cR^d$, ($C_1$-$C_6$ alkylenyl)-$C(O)R^a$, ($C_1$-$C_6$ alkylenyl)-$C(O)OR^a$, ($C_1$-$C_6$ alkylenyl)-$C(O)NR^cR^d$, ($C_1$-$C_6$ alkylenyl)-$NR^cR^d$, ($C_1$-$C_6$ alkylenyl)-$N(R^e)C(O)R^b$, ($C_1$-$C_6$ alkylenyl)-$N(R^e)S(O)_2R^b$, ($C_1$-$C_6$ alkylenyl)-$N(R^e)C(O)O(R^b)$, ($C_1$-$C_6$ alkylenyl)-$N(R^e)C(O)NR^cR^d$ or ($C_1$-$C_6$ alkylenyl)-$N(R^e)S(O)_2NR^cR^d$;

$G^2$, at each occurrence, is independently aryl, heteroaryl, heterocyclyl, cycloalkyl or cycloalkenyl, wherein each $G^2$ is optionally substituted with one, two, three, four or five $R^{2g}$ groups;

$R^7$, $R^8$ and $R^9$ are each independently H, $C_1$-$C_6$ alkyl, $C_2$-$C_6$ alkenyl, $C_2$-$C_6$ alkynyl, halogen, $C_1$-$C_6$ haloalkyl, CN, $NO_2$, $OR^{y1}$, $OC(O)R^{y2}$, $OC(O)NR^{y3}R^{y4}$, $SR^{y1}$, $S(O)_2R^{y1}$, $S(O)_2NR^{y3}R^{y4}$, $C(O)R^{y1}$, $C(O)OR^{y1}$, $C(O)NR^{y3}R^{y4}$, $NR^{y3}R^{y4}$, $N(R^{y3})C(O)R^{y2}$, $N(R^{y3})S(O)_2R^{y2}$, $N(R^{y3})C(O)O(R^{y2})$, $N(R^{y3})C(O)NR^{y3}R^{y4}$, $N(R^{y3})S(O)_2NR^{y3}R^{y4}$, $G^3$, ($C_1$-$C_6$ alkylenyl)-CN, ($C_1$-$C_6$ alkylenyl)-$OR^{y1}$, ($C_1$-$C_6$ alkylenyl)-$OC(O)R^{y2}$, ($C_1$-$C_6$ alkylenyl)-$OC(O)NR^{y3}R^{y4}$, ($C_1$-$C_6$ alkylenyl)-$S(O)_2R^{y1}$, ($C_1$-$C_6$ alkylenyl)-$S(O)_2NR^{y3}R^{y4}$, ($C_1$-$C_6$ alkylenyl)-$C(O)R^{y1}$, ($C_1$-$C_6$ alkylenyl)-$C(O)OR^{y1}$, ($C_1$-$C_6$ alkylenyl)-$C(O)NR^{y3}R^{y4}$, ($C_1$-$C_6$ alkylenyl)-$NR^{y3}R^{y4}$, ($C_1$-$C_6$ alkylenyl)-$N(R^{y3})C(O)R^{y2}$, ($C_1$-$C_6$ alkylenyl)-$N(R^{y3})S(O)_2R^{y2}$, ($C_1$-$C_6$ alkylenyl)-$N(R^{y3})C(O)O(R^{y2})$, ($C_1$-$C_6$ alkylenyl)-$N(R^{y3})C(O)NR^{y3}R^{y4}$, ($C_1$-$C_6$ alkylenyl)-$N(R^{y3})S(O)_2NR^{y3}R^{y4}$, ($C_1$-$C_6$ alkylenyl)-CN or ($C_1$-$C_6$ alkylenyl)-$G^3$;

$R^{y1}$, $R^{y3}$ and $R^{y4}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^3$, ($C_1$-$C_6$ alkylenyl)-$G^3$, ($C_1$-$C_6$ alkylenyl)-$OR^a$, ($C_1$-$C_6$ alkylenyl)-$S(O)_2R^a$, ($C_1$-$C_6$ alkylenyl)-$S(O)_2NR^cR^d$, ($C_1$-$C_6$ alkylenyl)-$C(O)R^a$, ($C_1$-$C_6$ alkylenyl)-$C(O)OR^a$, ($C_1$-$C_6$ alkylenyl)-$C(O)NR^cR^d$, ($C_1$-$C_6$ alkylenyl)-$NR^cR^d$, ($C_1$-$C_6$ alkylenyl)-$N(R^e)C(O)R^b$, ($C_1$-$C_6$ alkylenyl)-$N(R^e)S(O)_2R^b$, ($C_1$-$C_6$ alkylenyl)-$N(R^e)C(O)O(R^b)$, ($C_1$-$C_6$ alkylenyl)-$N(R^e)C(O)NR^cR^d$ or ($C_1$-$C_6$ alkylenyl)-$N(R^e)S(O)_2NR^cR^d$;

$R^{y2}$, at each occurrence, is independently $C_1$-$C_6$ alkyl, $C_2$-$C_6$ alkenyl, $C_2$-$C_6$ alkynyl, $C_1$-$C_6$ haloalkyl, $G^3$, ($C_1$-$C_6$ alkylenyl)-$G^3$, ($C_1$-$C_6$ alkylenyl)-$OR^a$, ($C_1$-$C_6$ alkylenyl)-$S(O)_2R^a$, ($C_1$-$C_6$ alkylenyl)-$S(O)_2NR^cR^d$, ($C_1$-$C_6$ alkylenyl)-$C(O)R^a$, ($C_1$-$C_6$ alkylenyl)-$C(O)OR^a$, ($C_1$-$C_6$ alkylenyl)-$C(O)NR^cR^d$, ($C_1$-$C_6$ alkylenyl)-$NR^cR^d$, ($C_1$-$C_6$ alkylenyl)-$N(R^e)C(O)R^b$, ($C_1$-$C_6$ alkylenyl)-$N(R^e)S(O)_2R^b$, ($C_1$-$C_6$ alkylenyl)-$N(R^e)C(O)O(R^b)$, ($C_1$-$C_6$ alkylenyl)-$N(R^e)C(O)NR^cR^d$ or ($C_1$-$C_6$ alkylenyl)-$N(R^e)S(O)_2NR^cR^d$;

$G^3$, at each occurrence, is independently aryl, heteroaryl, heterocyclyl, cycloalkyl or cycloalkenyl, wherein each $G^3$ group is optionally substituted with one, two, three, four or five $R^{4g}$ groups;

$R^{10}$ is H, $C_1$-$C_3$ alkyl, halogen, $C_1$-$C_3$ haloalkyl or CN;

$R^{1g}$, $R^{2g}$ and $R^{4g}$, at each occurrence, is independently selected from the group consisting of oxo, $C_1$-$C_6$ alkyl, $C_2$-$C_6$ alkenyl, $C_2$-$C_6$ alkynyl, halogen, $C_1$-$C_6$ haloalkyl, CN, $NO_2$, $G^{2a}$, $OR^a$, $OC(O)R^b$, $OC(O)NR^cR^d$, SW, $S(O)_2R^a$, $S(O)_2NR^cR^d$, $C(O)R^a$, $C(O)OR^a$, $C(O)NR^cR^d$, $NR^cR^d$, $N(R^e)C(O)R^b$, $N(R^e)S(O)_2R^b$, $N(R^e)C(O)O(R^b)$, $N(R^e)C(O)NR^cR^d$, $N(R^e)S(O)_2NR^cR^d$, ($C_1$-$C_6$ alkylenyl)-CN, ($C_1$-$C_6$ alkylenyl)-$G^{2a}$, ($C_1$-$C_6$ alkylenyl)-$OR^a$, ($C_1$-$C_6$ alkylenyl)-$OC(O)R^b$, ($C_1$-$C_6$ alkylenyl)-$OC(O)NR^cR^d$, ($C_1$-$C_6$ alkylenyl)-$S(O)_2R^a$, ($C_1$-$C_6$ alkylenyl)-$S(O)_2NR^cR^d$, ($C_1$-$C_6$ alkylenyl)-$C(O)R^a$, ($C_1$-$C_6$ alkylenyl)-$C(O)OR^a$, ($C_1$-$C_6$ alkylenyl)-$C(O)NR^cR^d$, ($C_1$-$C_6$ alkylenyl)-$NR^cR^d$, ($C_1$-$C_6$ alkylenyl)-$N(R^e)C(O)R^b$, ($C_1$-$C_6$ alkylenyl)-$N(R^e)S(O)_2R^b$, ($C_1$-$C_6$ alkylenyl)-$N(R^e)C(O)O(R^b)$, ($C_1$-$C_6$ alkylenyl)-$N(R^e)C(O)NR^cR^d$, ($C_1$-$C_6$ alkylenyl)-$N(R^e)S(O)_2NR^cR^d$ or ($C_1$-$C_6$ alkylenyl)-CN;

$R^a$, $R^c$, $R^d$ and $R^e$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^{2a}$ or ($C_1$-$C_6$ alkylenyl)-$G^{2a}$;

$R^b$, at each occurrence, is independently $C_1$-$C_6$ alkyl, $C_2$-$C_6$ alkenyl, $C_2$-$C_6$ alkynyl, $C_1$-$C_6$ haloalkyl, $G^{2a}$ or ($C_1$-$C_6$ alkylenyl)-$G^{2a}$;

$G^{2a}$, at each occurrence, is independently aryl, heteroaryl, heterocyclyl, cycloalkyl or cycloalkenyl, wherein each $G^{2a}$ group is optionally substituted with one, two, three, four or five $R^{3g}$ groups;

$R^{3g}$, at each occurrence, is independently oxo, $C_1$-$C_6$ alkyl, $C_2$-$C_6$ alkenyl, $C_2$-$C_6$ alkynyl, halogen, $C_1$-$C_6$ haloalkyl, CN, $NO_2$, $OR^{z1}$, $OC(O)R^{z2}$, $OC(O)NR^{z3}R^{z4}$, $SR^{z1}$, $S(O)_2R^{z1}$, $S(O)_2NR^{z3}R^{z4}$, $C(O)R^{z1}$, $C(O)OR^{z1}$, $C(O)NR^{z3}R^{z4}$, $NR^{z3}R^{z4}$, $N(R^{z3})C(O)R^{z2}$, $N(R^{z3})S(O)_2R^{z2}$, $N(R^{z3})C(O)O(R^{z2})$, $N(R^{z3})C(O)NR^{z3}R^{z4}$, $N(R^{z3})S(O)_2NR^{z3}R^{z4}$, ($C_1$-$C_6$ alkylenyl), ($C_1$-$C_6$ alkylenyl)-$OC(O)R^{z2}$, ($C_1$-$C_6$ alkylenyl)-$OC(O)NR^{z3}R^{z4}$, ($C_1$-$C_6$ alkylenyl)-$S(O)_2R^{z1}$, ($C_1$-$C_6$ alkylenyl)-$S(O)_2NR^{z3}R^{z4}$, ($C_1$-$C_6$ alkylenyl)-$C(O)R^{z1}$, ($C_1$-$C_6$ alkylenyl)-$C(O)OR^{z1}$, ($C_1$-$C_6$ alkylenyl)-C(O)NR$^{z3}$R$^{z4}$, (C$_1$-C$_6$ alkylenyl)-NR$^{z3}$R$^{z4}$, (C$_1$-C$_6$ alkylenyl)-N(R$^{z3}$)C(O)R$^{z2}$, (C$_1$-C$_6$ alkylenyl)-N(R$^{z3}$)S(O)$_2$R$^{z2}$, (C$_1$-C$_6$ alkylenyl)-N(R$^{z3}$)C(O)O(R$^{z2}$), (C$_1$-C$_6$ alkylenyl)-N(R$^{z3}$)C(O)NR$^{z3}$R$^{z4}$, (C$_1$-C$_6$ alkylenyl)-N(R$^{z3}$)S(O)$_2$NR$^{z3}$R$^{z4}$ or (C$_1$-C$_6$ alkylenyl)-CN;

R$^{z1}$, R$^{z3}$ and R$^{z4}$, at each occurrence, are each independently H, C$_1$-C$_6$ alkyl, C$_2$-C$_6$ alkenyl, C$_2$-C$_6$ alkynyl or C$_1$-C$_6$ haloalkyl; and R$^{z2}$, at each occurrence, is independently C$_1$-C$_6$ alkyl, C$_2$-C$_6$ alkenyl, C$_2$-C$_6$ alkynyl or C$_1$-C$_6$ haloalkyl.

\* \* \* \* \*